US009685617B2

(12) United States Patent
Beers et al.

(10) Patent No.: US 9,685,617 B2
(45) Date of Patent: *Jun. 20, 2017

(54) ORGANIC ELECTRONUMINESCENT MATERIALS AND DEVICES

(71) Applicant: Universal Display Corporation, Ewing, NJ (US)

(72) Inventors: Scott Beers, Flemington, NJ (US); Chuanjun Xia, Lawrenceville, NJ (US); Lichang Zeng, Lawrenceville, NJ (US); Vadim Adamovich, Yardley, PA (US); Michael S. Weaver, Princeton, NJ (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 266 days.

This patent is subject to a terminal disclaimer.

(21) Appl. No.: 13/928,456

(22) Filed: Jun. 27, 2013

(65) Prior Publication Data

US 2014/0131676 A1 May 15, 2014

Related U.S. Application Data

(63) Continuation-in-part of application No. 13/673,338, filed on Nov. 9, 2012.

(51) Int. Cl.

*H01L 51/50* (2006.01)
*H01L 51/00* (2006.01)
(Continued)

(52) U.S. Cl.

CPC ...... *H01L 51/0085* (2013.01); *C07F 15/0033* (2013.01); *C09K 11/06* (2013.01);
(Continued)

(58) Field of Classification Search

CPC ............. H01L 51/0084; H01L 51/0085; H01L 51/0086; H01L 51/0087; H01L 51/0088;
(Continued)

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Wong et al., "Multifunctional Iridium Complexes Based on Carbazole Modules as Highly Efficient Electrophosphors", 2006, Angew. Chem. Int. Ed., vol. 45, pp. 7800-7803.*

(Continued)

*Primary Examiner* — Jennifer Chriss
*Assistant Examiner* — Dylan Kershner
(74) *Attorney, Agent, or Firm* — Duane Morris LLP

(57) ABSTRACT

Novel iridium complexes containing phenylpyridine and pyridyl aza-benzo fused ligands are described. These complexes are useful as light emitters when incorporated into OLEDs.

31 Claims, 3 Drawing Sheets

Formula I

Formula II

(51) Int. Cl.
*C07F 15/00* (2006.01)
*C09K 11/06* (2006.01)

(52) U.S. Cl.
CPC .... *C09K 2211/185* (2013.01); *H01L 51/0054* (2013.01); *H01L 51/0074* (2013.01); *H01L 51/50* (2013.01); *H01L 51/5016* (2013.01)

(58) Field of Classification Search
CPC . H01L 51/50; H01L 51/5016; H01L 51/0054; H01L 51/0074; C07F 15/0033; C09K 11/06; C09K 2211/185; C09K 2211/1018; C09K 2211/1029; C09K 2211/1033; C09K 2211/1037; C09K 2211/104; C09K 2211/1088; C09K 2211/1092; C09K 2211/1096
USPC ....... 548/103, 108, 402; 546/4, 10; 428/690, 428/917; 257/40, E51.041, E51.043, 257/E51.044; 313/504, 506; 252/301.16
See application file for complete search history.

(56) References Cited

U.S. PATENT DOCUMENTS

| | | | | |
|---|---|---|---|---|
| 5,247,190 | A | 9/1993 | Friend et al. | |
| 5,703,436 | A | 12/1997 | Forrest et al. | |
| 5,707,745 | A | 1/1998 | Forrest et al. | |
| 5,834,893 | A | 11/1998 | Bulovic et al. | |
| 5,844,363 | A | 12/1998 | Gu et al. | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A | 8/2000 | Baldo et al. | |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 8,722,205 | B2 * | 5/2014 | Xia et al. | 428/690 |
| 8,946,697 | B1 * | 2/2015 | Ma et al. | 257/40 |
| 2002/0034656 | A1 | 3/2002 | Thompson et al. | |
| 2002/0134984 | A1 | 9/2002 | Igarashi | |
| 2002/0158242 | A1 | 10/2002 | Son et al. | |
| 2003/0068535 | A1 | 4/2003 | Takiguchi et al. | |
| 2003/0138657 | A1 | 7/2003 | Li et al. | |
| 2003/0151042 | A1 | 8/2003 | Hueschen | |
| 2003/0152802 | A1 | 8/2003 | Tsuboyama et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0137267 | A1 | 7/2004 | Igarashi et al. | |
| 2004/0137268 | A1 | 7/2004 | Igarashi et al. | |
| 2004/0174116 | A1 | 9/2004 | Lu et al. | |
| 2005/0025993 | A1 | 2/2005 | Thompson et al. | |
| 2005/0112407 | A1 | 5/2005 | Ogasawara et al. | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong et al. | |
| 2007/0128466 | A1 | 6/2007 | Nomura et al. | |
| 2007/0190359 | A1 | 8/2007 | Knowles et al. | |
| 2007/0196691 | A1 | 8/2007 | Ikemizu et al. | |
| 2007/0247061 | A1 * | 10/2007 | Adamovich et al. | 313/504 |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0233433 | A1 * | 9/2008 | Igarashi et al. | 428/704 |
| 2008/0261076 | A1 | 10/2008 | Kwong et al. | |
| 2008/0297033 | A1 | 12/2008 | Knowles et al. | |
| 2008/0297038 | A1 | 12/2008 | Yagi | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0101870 | A1 | 4/2009 | Prakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2009/0315454 | A1 * | 12/2009 | Igarashi | 313/504 |
| 2010/0187984 | A1 * | 7/2010 | Lin et al. | 313/504 |
| 2010/0237334 | A1 | 9/2010 | Ma et al. | |
| 2010/0244004 | A1 * | 9/2010 | Xia et al. | 257/40 |
| 2010/0270916 | A1 | 10/2010 | Xia et al. | |
| 2011/0227049 | A1 | 9/2011 | Xia et al. | |
| 2012/0061654 | A1 | 3/2012 | Rayabarapu et al. | |
| 2013/0092905 | A1 * | 4/2013 | Numata et al. | 257/40 |

FOREIGN PATENT DOCUMENTS

| | | | |
|---|---|---|---|
| EP | 2034538 | | 3/2009 |
| JP | 2002-332291 | | 11/2002 |
| JP | 200511610 | | 1/2005 |
| JP | 2007123392 | | 5/2007 |
| JP | 2007254297 | | 10/2007 |
| JP | 2008-074939 | | 4/2008 |
| JP | 2008074939 | | 4/2008 |
| JP | 2008074939 | A * | 4/2008 |
| JP | 2009-013366 | | 1/2009 |
| TW | 201100384 | | 1/2011 |
| WO | 0139234 | | 5/2001 |
| WO | 0202714 | | 1/2002 |
| WO | 0215645 | | 2/2002 |
| WO | 03040257 | | 5/2003 |
| WO | 03060956 | | 7/2003 |
| WO | 2004093207 | | 10/2004 |
| WO | 2004107822 | | 12/2004 |
| WO | 2005014551 | | 2/2005 |
| WO | 2005019373 | | 3/2005 |
| WO | 2005030900 | | 4/2005 |
| WO | 2005089025 | | 9/2005 |
| WO | 2005123873 | | 12/2005 |
| WO | 2006009024 | | 1/2006 |
| WO | 2006056418 | | 6/2006 |
| WO | 2006072002 | | 7/2006 |
| WO | 2006082742 | | 8/2006 |
| WO | 2006098120 | | 9/2006 |
| WO | 2006100298 | | 9/2006 |
| WO | 2006103874 | | 10/2006 |
| WO | 2006114966 | | 11/2006 |
| WO | 2006132173 | | 12/2006 |
| WO | 2007002683 | | 1/2007 |
| WO | 2007004380 | | 1/2007 |
| WO | 2007063754 | | 6/2007 |
| WO | 2007063796 | | 6/2007 |
| WO | 2008044723 | | 4/2008 |

(56) References Cited

FOREIGN PATENT DOCUMENTS

| | | |
|---|---|---|
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010/111175 | 9/2010 |
| WO | 2010/118029 | 10/2010 |
| WO | 2011122133 | 10/2011 |
| WO | WO 2011122133 A1 * | 10/2011 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett, 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

(56) References Cited

OTHER PUBLICATIONS

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Rayabararu, Dinesh et al., "Metal complexes and light-emitting devices using them", XP002718489 retrieved from STN Database accession No. 2010:1282120.

European Search Report dated Jan. 27, 2014 for corresponding EP Application No. 13191819.5.

Search Report issued Jul. 5, 2016 for corresponding ROC (Taiwan) Application No. 102140557.

Tomohiro Oshiyama, WO2008044723 A1, Date of Japanese language publication: Apr. 17, 2008, Date of machine translation: May 21, 2016, pp. 1-195.

Wang et al., "Multifunctional Iridium Complexes Based on Carbazole Modules as Highly Efficient Electrophosphors," Angew. Chem. Int. Ed. 2006, 45, 7800-7803.

* cited by examiner

Formula I

Formula II

ORGANIC ELECTRONUMINESCENT MATERIALS AND DEVICES

CROSS-REFERENCE TO RELATED APPLICATIONS

This application is a continuation-in-part application of U.S. application Ser. No. 13/673,338, filed Nov. 9, 2012, the disclosure of which is expressly incorporated herein by reference in its entirety.

JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to iridium complexes containing aza-benzo fused ligands. In particular, iridium complexes containing both phenylpyridine ligands and aza-benzo fused ligands were found to be useful as phosphorescent emitters when used in OLED devices. Additionally, iridium complexes containing both phenylpyridine ligands and aza-benzo fused ligands where an alkyl group is bonded to the pyridine ring of the aza-dibenzofuran moiety of the ligand were also found to be useful as phosphorescent emitters.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

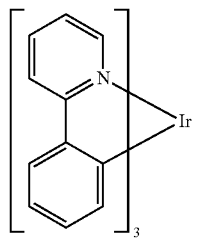

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound having the formula $Ir(L_A)_n(L_B)_{3-n}$, and having the structure:

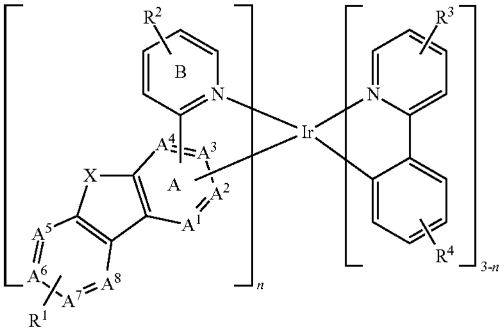

with Formula I is provided. In the compound of Formula I, $A^1$, $A^2$, $A^3$, $A^4$, $A^5$, $A^6$, $A^7$, and $A^8$ comprise carbon or nitrogen, and at least one of $A^1$, $A^2$, $A^3$, $A^4$, $A^5$, $A^6$, $A^7$, and $A^8$ is nitrogen. Ring B is bonded to ring A through a C—C bond, the iridium is bonded to ring A through a Ir—C bond. X is O, S, or Se. $R^1$, $R^2$, $R^3$, and $R^4$ independently represent mono-, di-, tri-, tetra-substitution, or no substitution, and any adjacent substitutions in $R^1$, $R^2$, $R^3$, and $R^4$ are optionally linked together to form a ring. $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and n is an integer from 1 to 3.

In one aspect, n is 1. In one aspect, the compound has the formula:

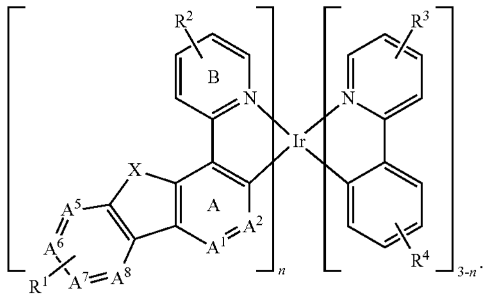

In one aspect, the compound has the formula:

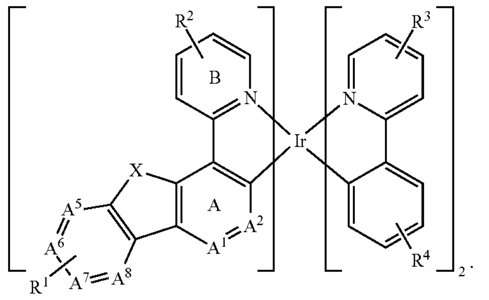

In one aspect, only one of $A^1$ to $A^8$ is nitrogen. In one aspect, only one of $A^5$ to $A^8$ is nitrogen. In one aspect, X is O.

In one aspect, $R^1$, $R^2$, $R^3$, and $R^4$ are independently selected from the group consisting of hydrogen, deuterium, alkyl, and combinations thereof. In one aspect, $R^2$ is alkyl.

In one aspect, the alkyl is deuterated or partially deuterated. In one aspect, $R^3$ is alkyl.

In one aspect, the alkyl is deuterated or partially deuterated.

In one embodiment, a first device comprising a first organic light emitting device is provided. The first device further comprises an anode, a cathode, and an organic layer, disposed between the anode and the cathode. The organic layer comprises a compound having the formula $Ir(L_A)_n(L_B)_{3-n}$, having the structure according to Formula I.

The inventors have found that iridium complexes containing aza-benzo fused ligands, I particular iridium complexes containing both phenylpyridine ligands and aza-benzo fused ligands are useful as phosphorescent emitters useful for OLED devices.

According to another aspect of the present disclosure, a compound having the formula $Ir(L_A)_n(L_B)_{3-n}$, and having the structure:

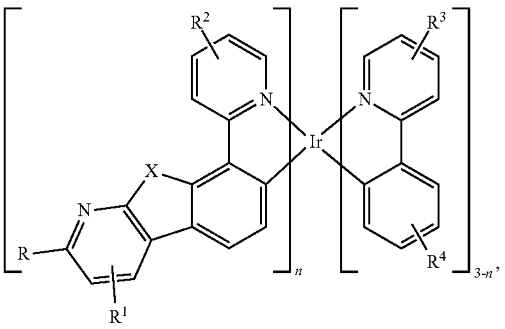

Formula II, is provided. In the compound of Formula II, X is O, S, or Se; R is selected from the group consisting of alkyl, cycloalkyl, and combinations thereof; $R^1$ represent mono-, di-substitution, or no substitution; $R^2$, $R^3$, and $R^4$ independently represent mono-, di-, tri-, tetra-substitution, or no substitution; any adjacent substitutions in $R^1$, $R^2$, $R^3$, and $R^4$ are optionally linked together to form a ring; $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and n is an integer from 1 to 3.

According to an embodiment, a first device comprising a first organic light emitting device, further comprising an anode, a cathode, and an organic layer, disposed between the anode and the cathode, comprising a compound having the formula $Ir(L_A)_n(L_B)_{3-n}$, and having the structure according to Formula II is disclosed.

The inventors have discovered that addition of an alkyl group to the aza ring of the specific aza-dibenzofuran ring system in the iridium complexes containing aza-benzo fused ligands results in the formation of green phosphorescent compounds with superior device stability.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
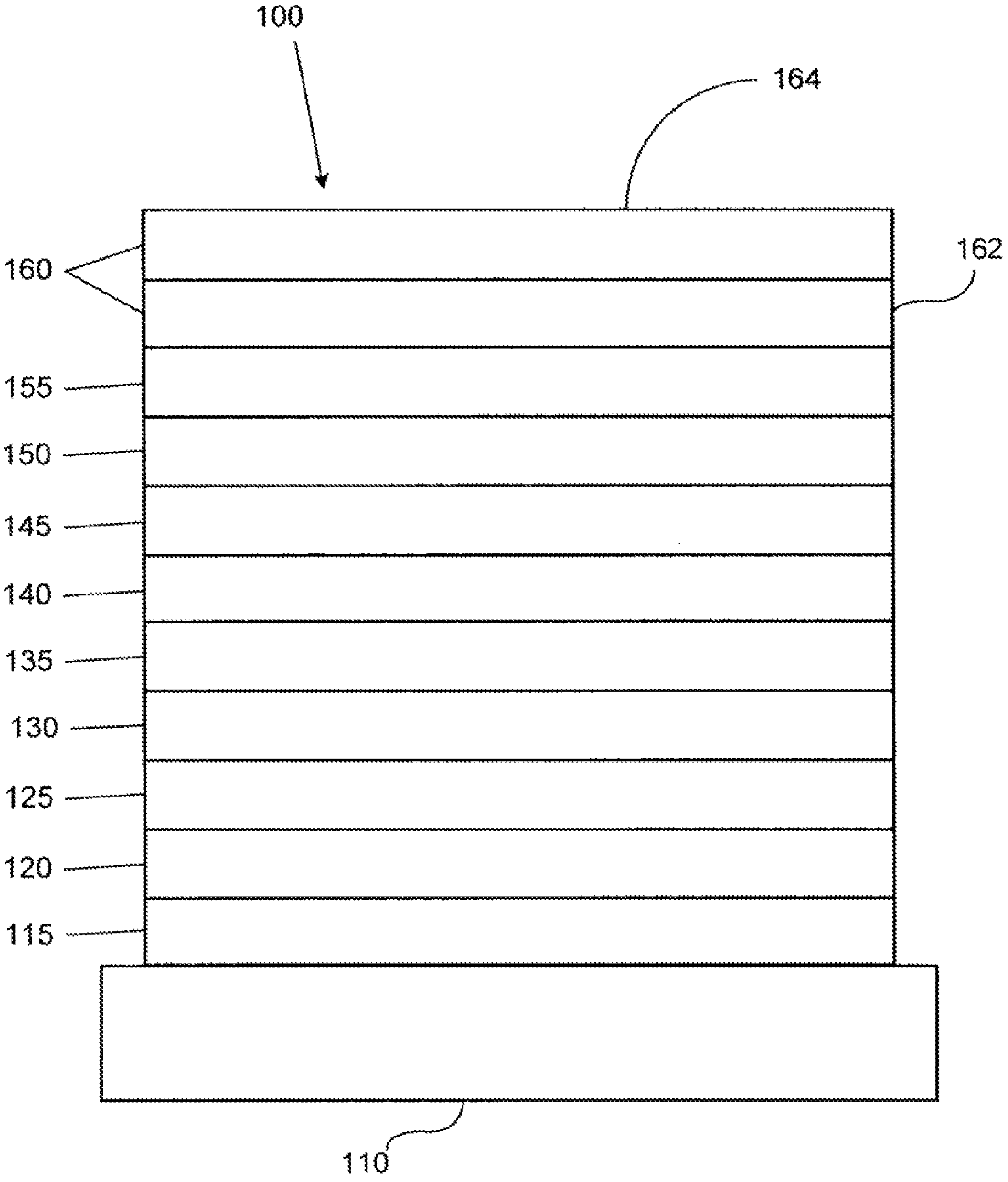
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
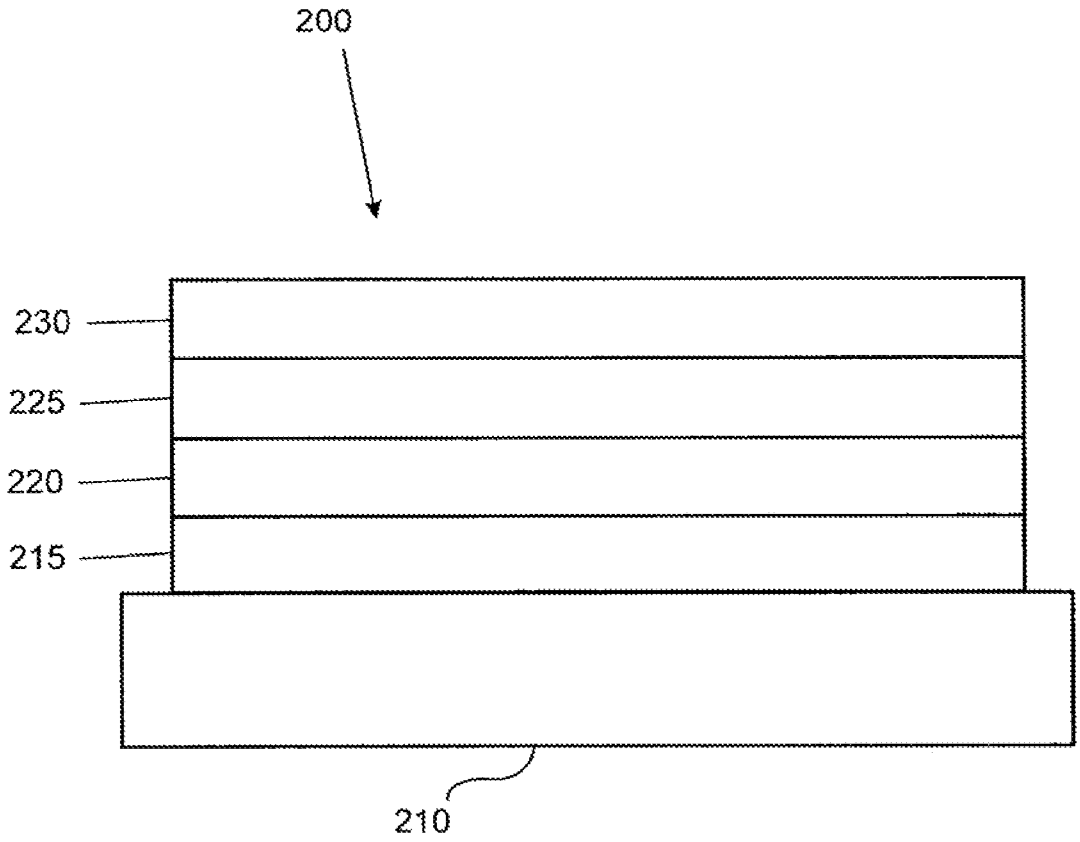
FIG. 2 shows an inverted organic light emitting device that does not have a separate electron transport layer.
Figure 3:
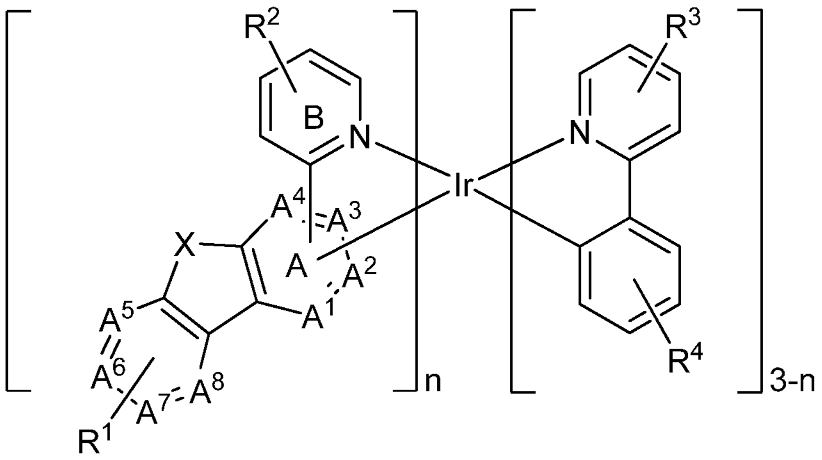
FIG. 3 show structural Formula I and Formula II.
Figure 3:
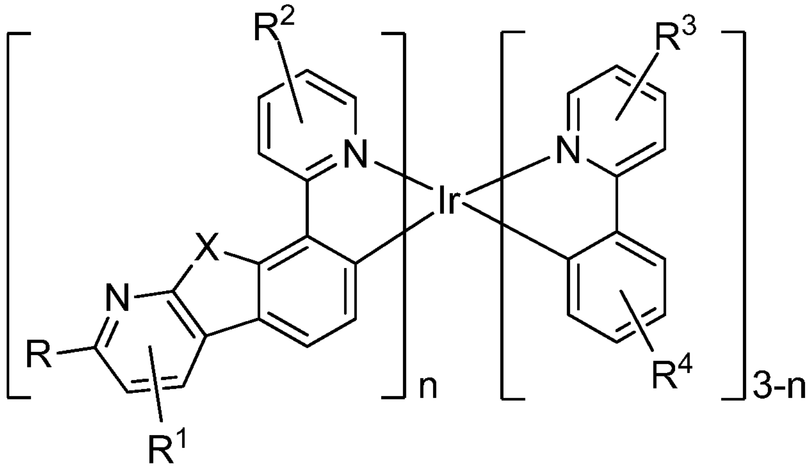

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound having the formula $Ir(L_A)_n(L_B)_{3-n}$, and having the structure:

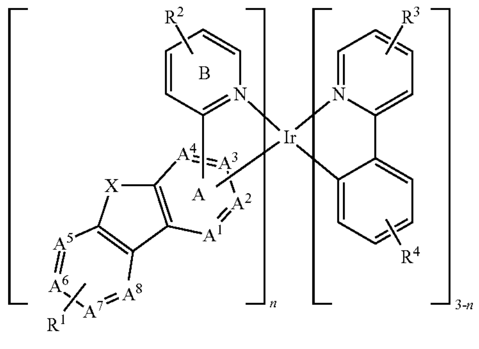

with Formula I is provided. In the compound of Formula I, $A^1$, $A^2$, $A^3$, $A^4$, $A^5$, $A^6$, $A^7$, and $A^8$ comprise carbon or nitrogen, and at least one of $A^1$, $A^2$, $A^3$, $A^4$, $A^5$, $A^6$, $A^7$, and $A^8$ is nitrogen. Ring B is bonded to ring A through a C—C bond, the iridium is bonded to ring A through a Ir—C bond. X is O, S, or Se. $R^1$, $R^2$, $R^3$, and $R^4$ independently represent mono-, di-, tri-, tetra-substitution, or no substitution, and any adjacent substitutions in $R^1$, $R^2$, $R^3$, and $R^4$ are optionally linked together to form a ring. $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and n is an integer from 1 to 3.

Heteroleptic iridium complexes with 2-phenylpyridine and 2-(4-dibenzofuran)-pyridine ligands have been previously disclosed. The dibenzofuran substitution extends the conjugation of the ligand and lowers the LUMO of the complex, resulting in a slight red shifted emission and less saturated green color. For example, Compound A has a $\lambda_{max}$ of 528 nm in 2-methyl-tetrahydrofuran at room temperature, compared to around 516 nm for tris(2-phenylpyridine) iridium. The compounds of Formula I introduce an azadibenzofuran substitution, as in, for example, Compound 1, which further lowers the LUMO of the complex due to the electron deficient nature of the azadibenzofuran group. The reduction potential was measured at −2.55 V versus −2.60 V for Compound A. Based on these results, it was expected that the emission of Compound 1 will be further red shifted. Surprisingly, the PL of compounds of Formula I such as Compound 1, measured under the same condition as Compound A, showed a $\lambda_{max}$ of 523 nm, which is 5 nm blue shifted compared to Compound A. Similarly, the $\lambda_{max}$ of Compound 4 is 524 nm which is 4 nm blue shifted compared to Compound A. The results are summarized in Table 1. Thus, compounds of Formula I unexpectedly have blue shifted emission spectra, which makes compounds of Formula I more suitable for use as a saturated green color in display applications.

TABLE 1

| Compound | Structure | Redox Potential vs. Fc/Fc+ | PL (phosphorescent luminescence) in 2-methyl-THF |
|---|---|---|---|
| $Ir(PPy)_3$ | 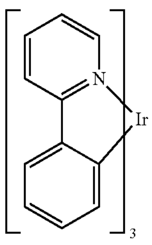 | $E_{Red}$: −2.70 V<br>$E_{Ox}$: 0.31 V | R.T.: 516 nm<br>77 K: 493 nm |
| Compound A | 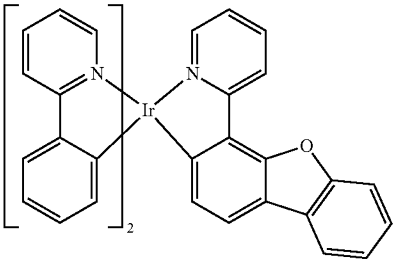 | $E_{Red}$: −2.60 V<br>$E_{Ox}$: 0.35 V | R.T.: 528 nm<br>77 K: 512 nm |
| Compound 1 | 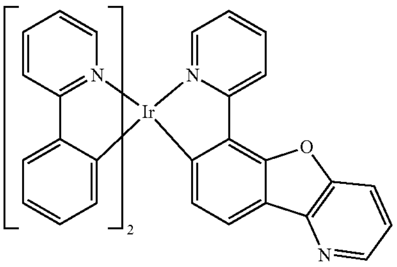 | $E_{Red}$: −2.55 V<br>$E_{Ox}$: 0.40 V | R.T.: 523 nm<br>77 K: 510 nm |

TABLE 1-continued

| Compound | Structure | Redox Potential vs. Fc/Fc+ | PL (phosphorescent luminescence) in 2-methyl-THF |
|---|---|---|---|
| Compound 4 | 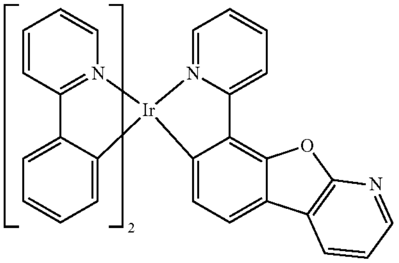 | ERed: −2.55 V<br>Eox: 0.37 V | R.T.: 524 nm<br>77 K: 510 |

In one embodiment, n is 1. In one embodiment, the compound has the formula:

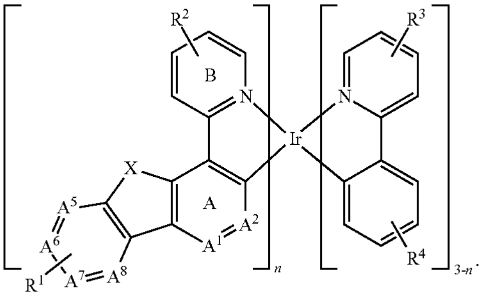

In one embodiment, the compound has the formula:

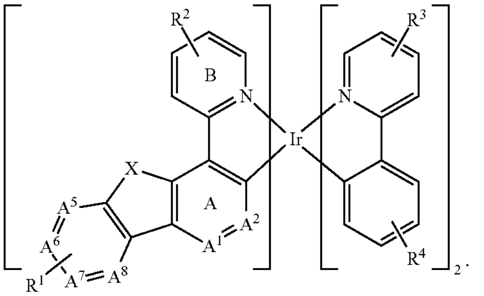

In one embodiment, only one of $A^1$ to $A^8$ is nitrogen. In one embodiment, only one of $A^5$ to $A^8$ is nitrogen. In one embodiment, X is O.

In one embodiment, $R^1$, $R^2$, $R^3$, and $R^4$ are independently selected from the group consisting of hydrogen, deuterium, alkyl, and combinations thereof. In one embodiment, $R^2$ is alkyl.

In one embodiment, the alkyl is deuterated or partially deuterated. In one embodiment, $R^3$ is alkyl.

In one embodiment, the alkyl is deuterated or partially deuterated.

In one embodiment, $L_A$ is selected from the group consisting of:

$L_{A1}$

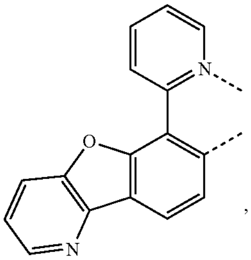

, $L_{A2}$

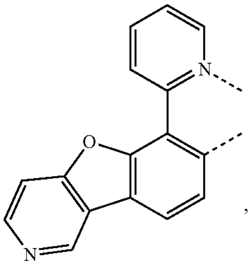

, $L_{A3}$

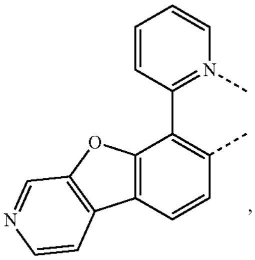

, $L_{A4}$

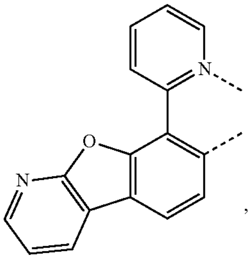

,

-continued
$L_{A5}$
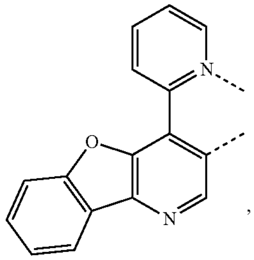
,
$L_{A6}$
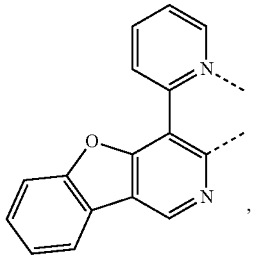
,
$L_{A7}$
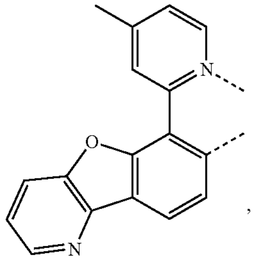
,
$L_{A8}$
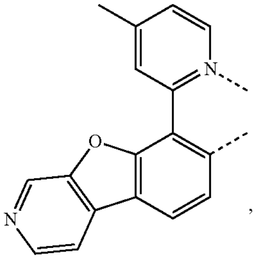
,
$L_{A9}$
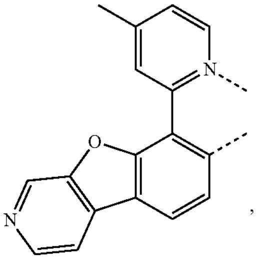
,
$L_{A10}$
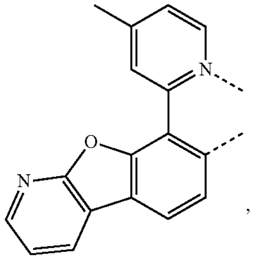
,
-continued
$L_{A11}$
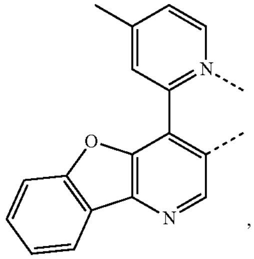
,
$L_{A12}$
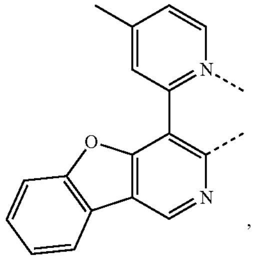
,
$L_{A13}$
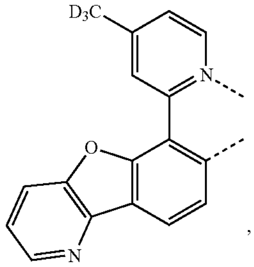
,
$L_{A14}$
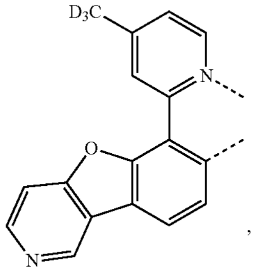
,
$L_{A15}$
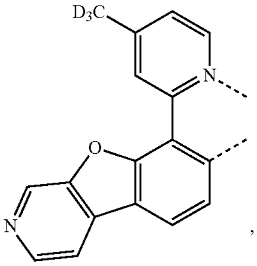
,
$L_{A16}$
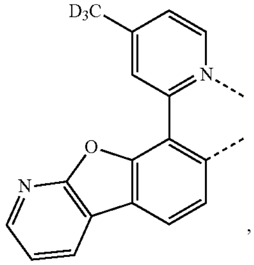
, -continued
L$_{A17}$
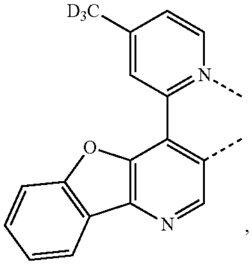
,
L$_{A48}$
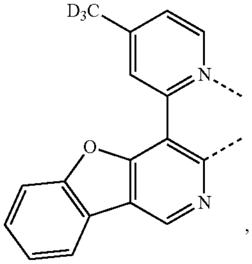
,
L$_{A19}$
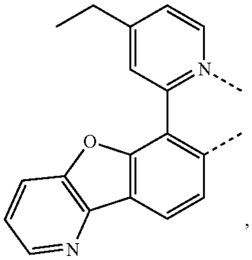
,
L$_{A20}$
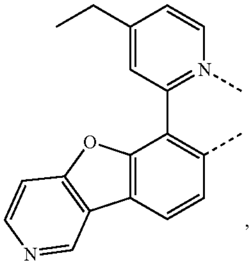
,
L$_{A21}$
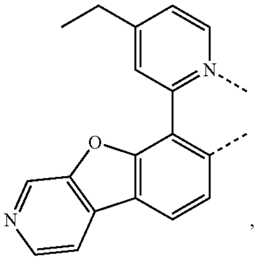
,
L$_{A22}$
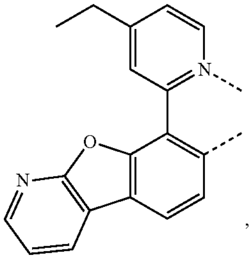
,
-continued
L$_{A23}$
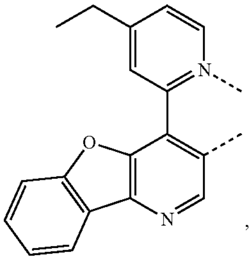
,
L$_{A24}$
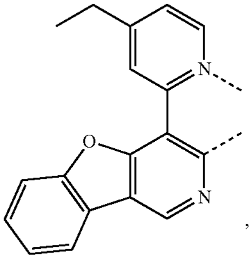
,
L$_{A25}$
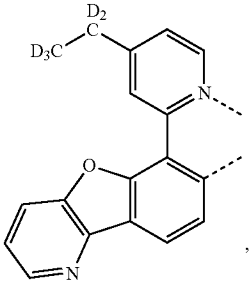
,
L$_{A26}$
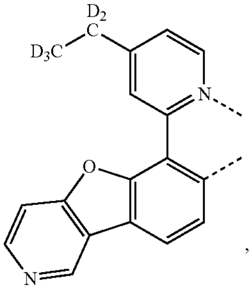
,
L$_{A27}$
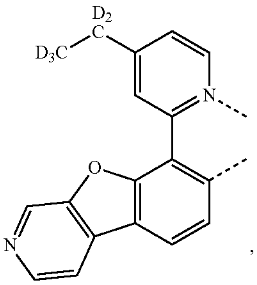
, -continued
L$_{A28}$
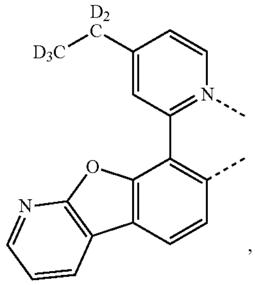
,
L$_{A29}$
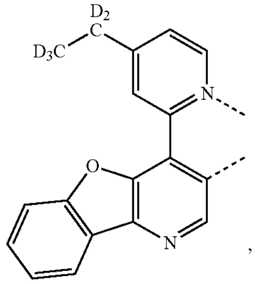
,
L$_{A30}$
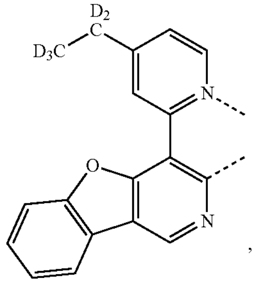
,
L$_{A31}$
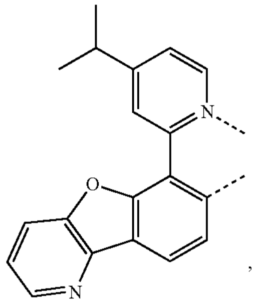
,
L$_{A32}$
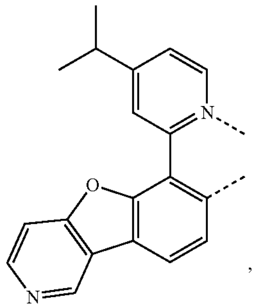
,
-continued
L$_{A33}$
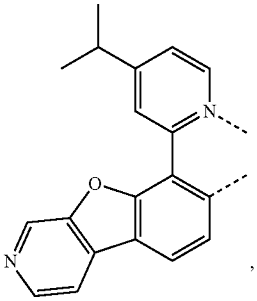
,
L$_{A34}$
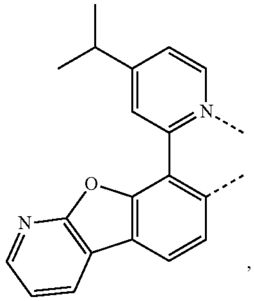
,
L$_{A35}$
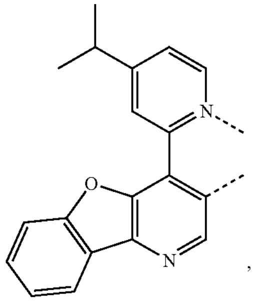
,
L$_{A36}$
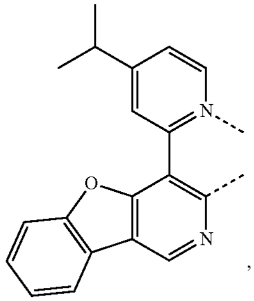
,
L$_{A37}$
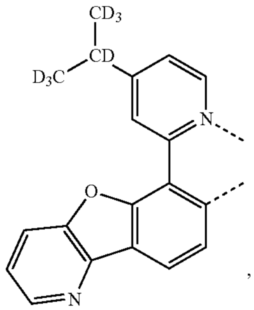
, -continued
L_{A38}
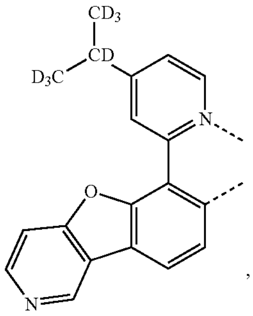
,
L_{A39}
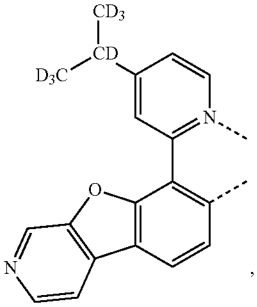
,
L_{A40}
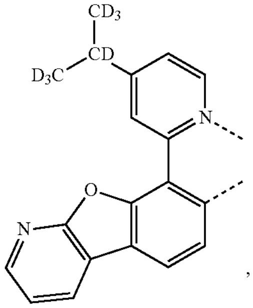
,
L_{A41}
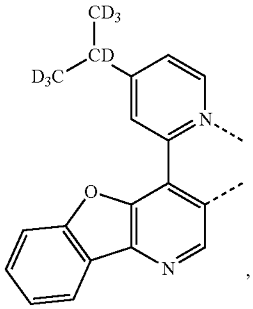
,
L_{A42}
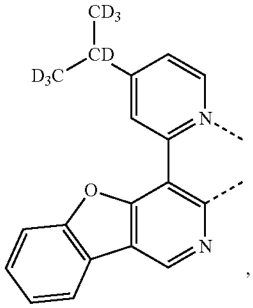
,
-continued
L_{A43}
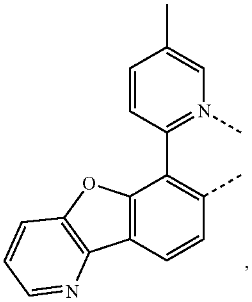
,
L_{A44}
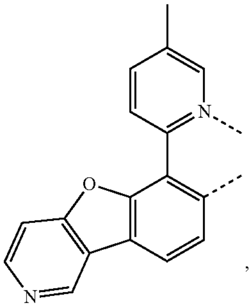
,
L_{A45}
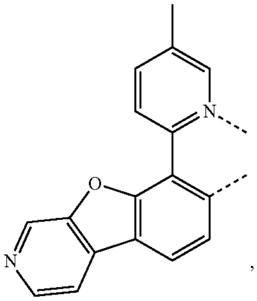
,
L_{A46}
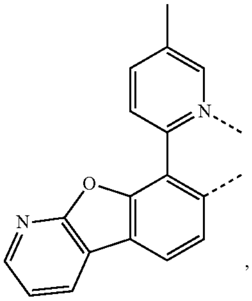
,
L_{A47}
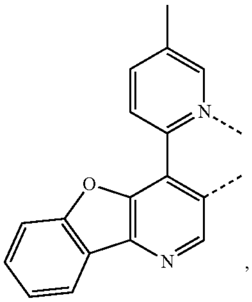
, -continued
$L_{A18}$
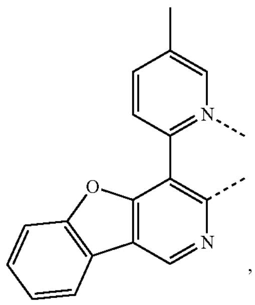
,
$L_{A49}$
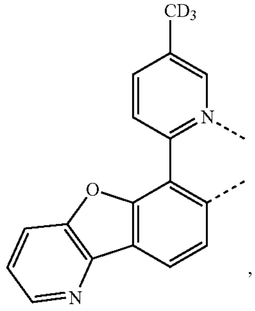
,
$L_{A50}$
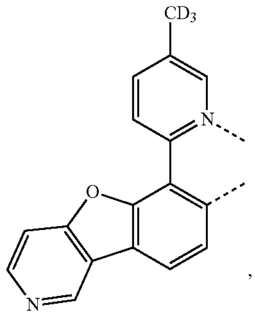
,
$L_{A51}$
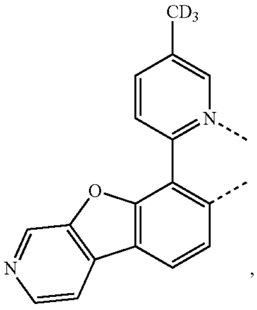
,
$L_{A52}$
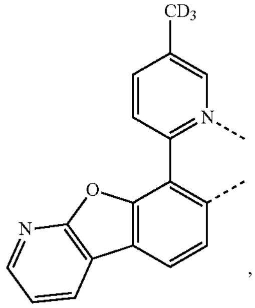
,
-continued
$L_{A53}$
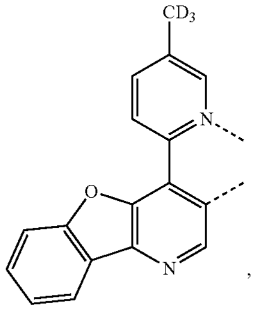
,
$L_{A54}$
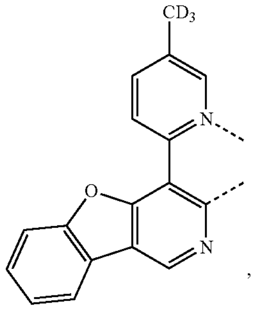
,
$L_{A55}$
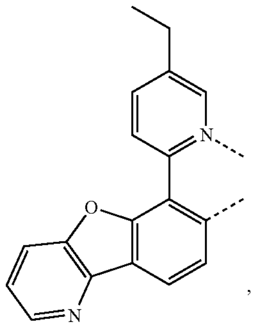
,
$L_{A56}$
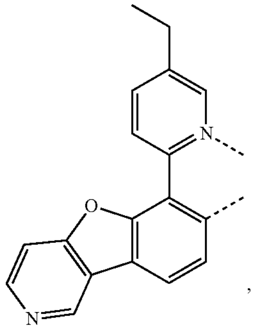
,
$L_{A57}$
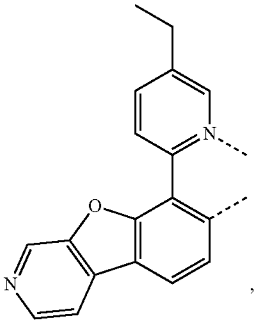
, -continued
L_A58
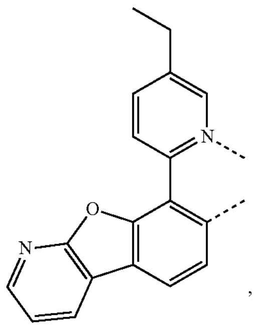
,
L_A59
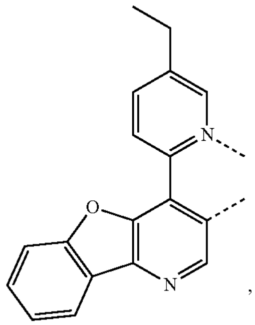
,
L_A60
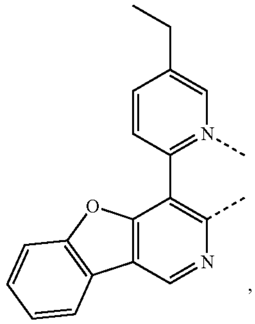
,
L_A61
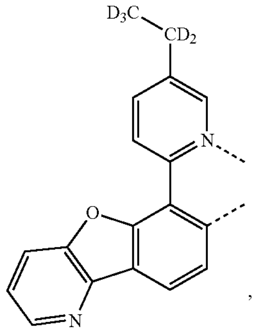
,
-continued
L_A62
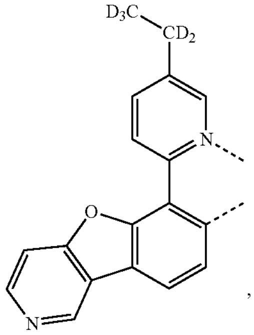
,
L_A63
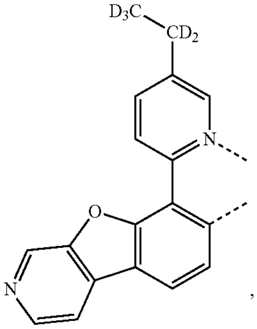
,
L_A64
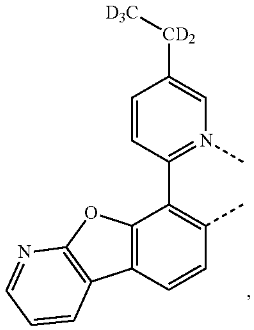
,
L_A65
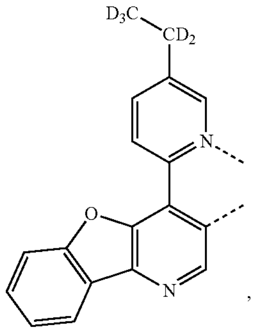
, $L_{A66}$
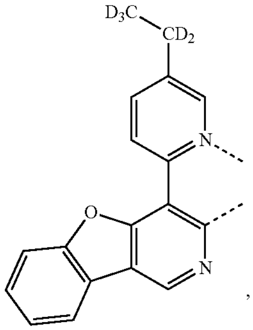
,
$L_{A67}$
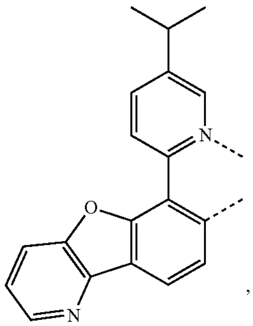
,
$L_{A68}$
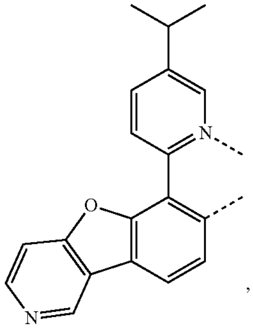
,
$L_{A69}$
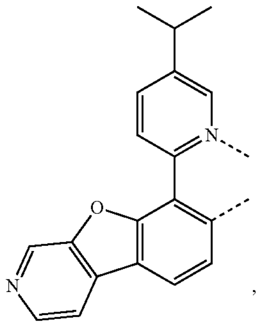
,
$L_{A70}$
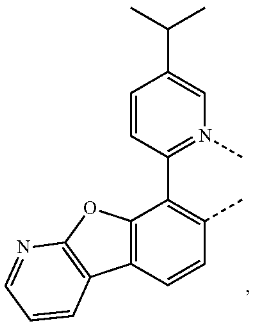
,
$L_{A71}$
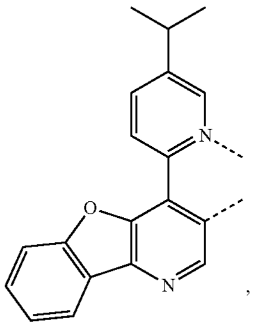
,
$L_{A72}$
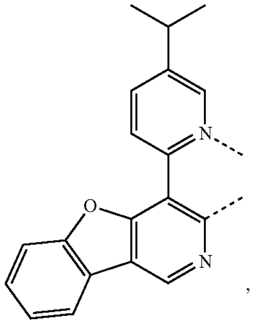
,
$L_{A73}$
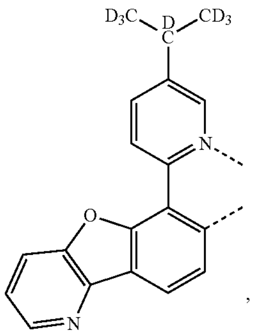
, -continued
L$_{A74}$
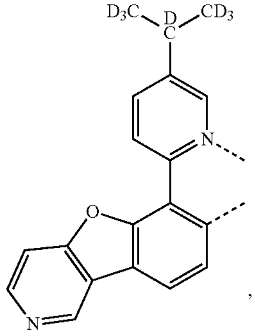
,
L$_{A75}$
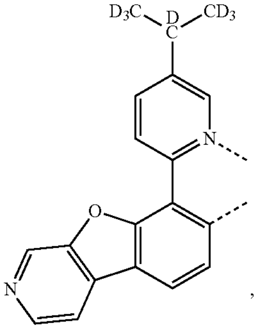
,
L$_{A76}$
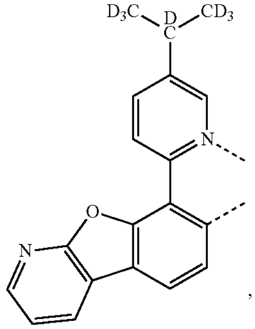
,
L$_{A77}$
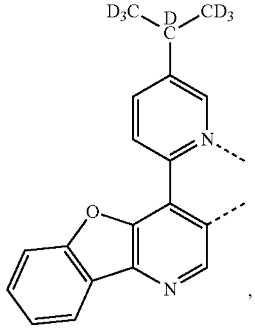
,
-continued
L$_{A78}$
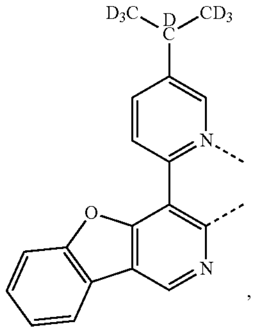
,
L$_{A79}$
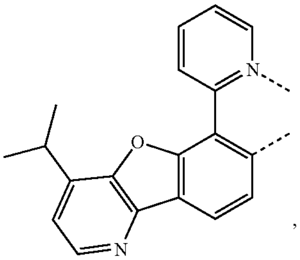
,
L$_{A80}$
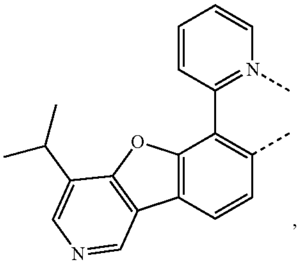
,
L$_{A81}$
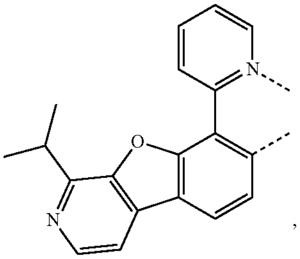
,
L$_{A82}$
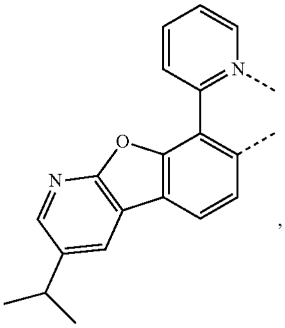
, -continued
$L_{A83}$
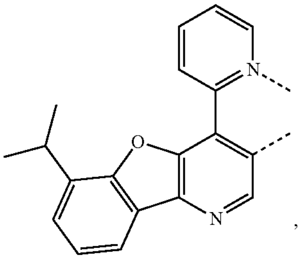,
$L_{A84}$
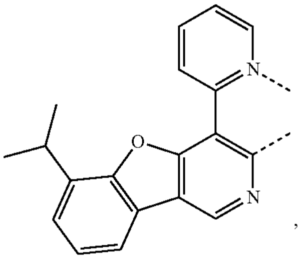,
$L_{A85}$
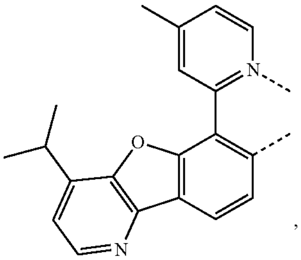,
$L_{A86}$
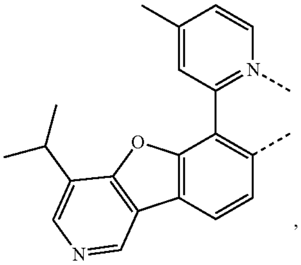,
$L_{A87}$
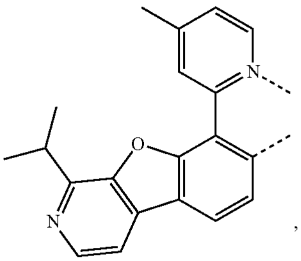,
-continued
$L_{A88}$
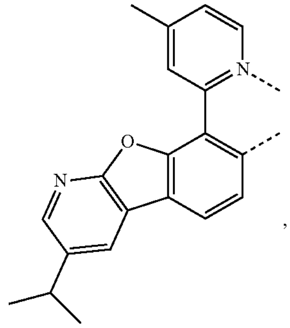,
$L_{A89}$
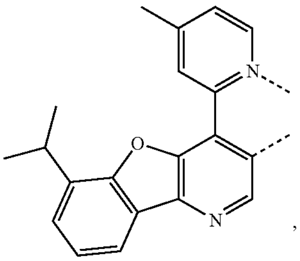,
$L_{A90}$
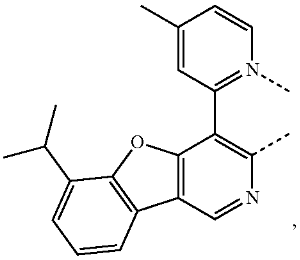,
$L_{A91}$
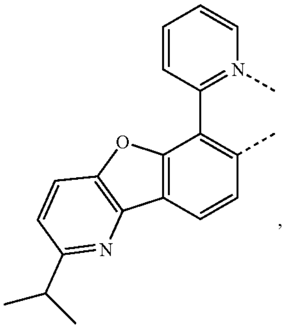,
$L_{A92}$
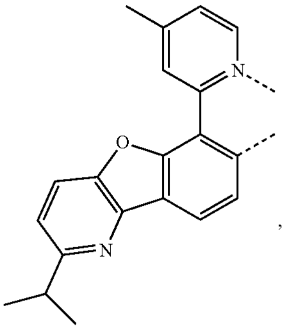, -continued
$L_{A93}$
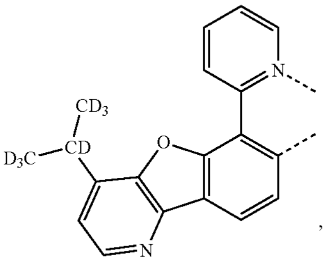
,
$L_{A94}$
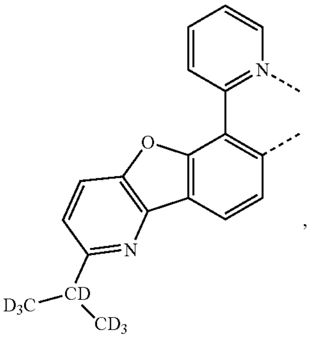
,
$L_{A95}$
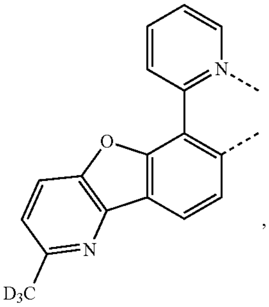
,
$L_{A96}$
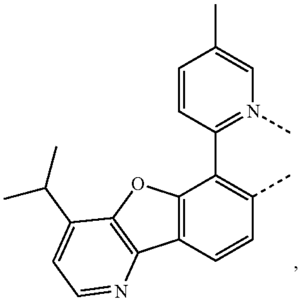
,
$L_{A97}$
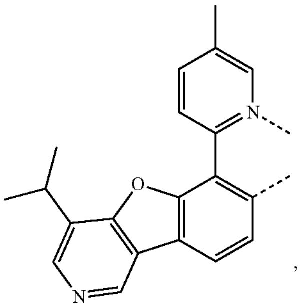
,
-continued
$L_{A98}$
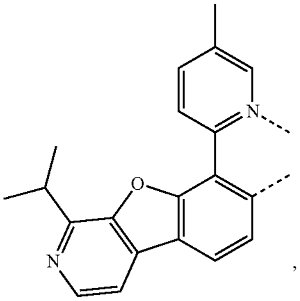
,
$L_{A99}$
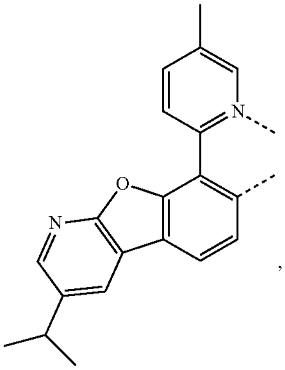
,
$L_{A100}$
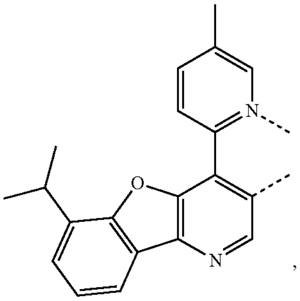
, and
$L_{A101}$
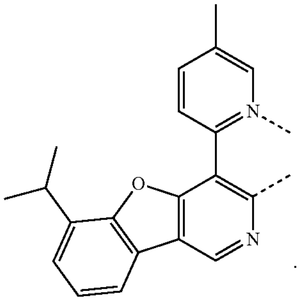
.
In one embodiment, $L_A$ is selected from the group consisting of:

-continued
L$_{A102}$
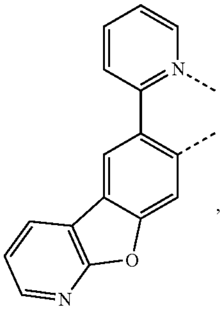
,
L$_{A103}$
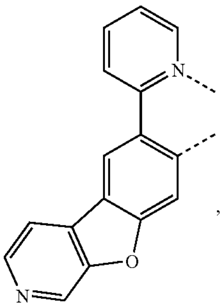
,
L$_{A104}$
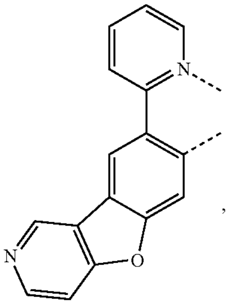
,
L$_{A105}$
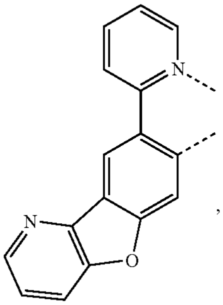
,
L$_{A106}$
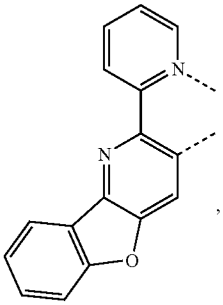
,
L$_{A107}$
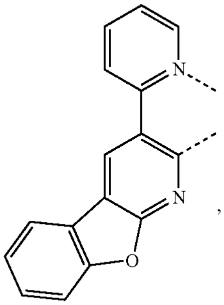
,
L$_{A108}$
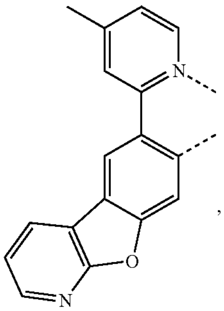
,
L$_{A109}$
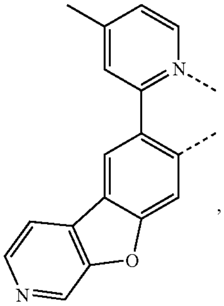
,
L$_{A110}$
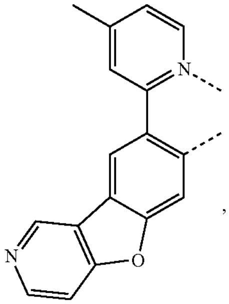
,
L$_{A111}$
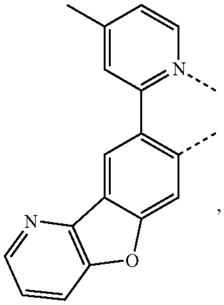
, -continued
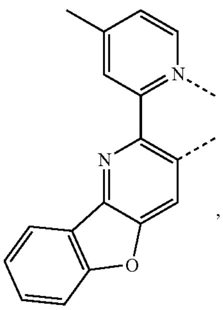
, $L_{A112}$
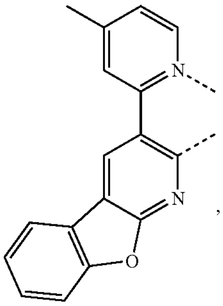
, $L_{A113}$
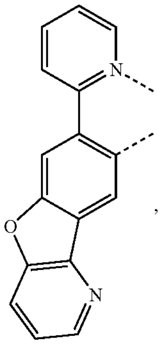
, $L_{A114}$
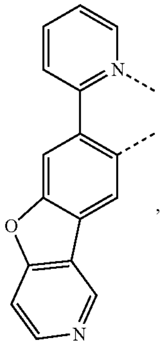
, $L_{A115}$
-continued
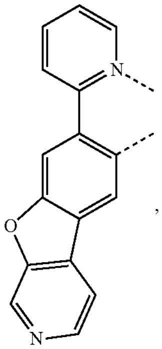
, $L_{A116}$
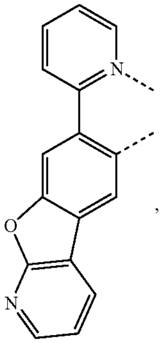
, $L_{A117}$
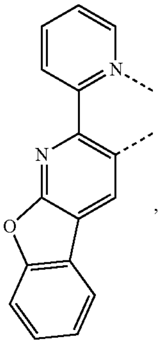
, and $L_{A118}$
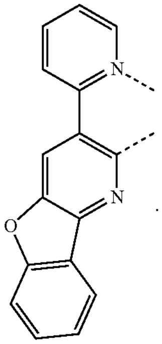
. $L_{A119}$
In one embodiment, $L_B$ is selected from the group consisting of:

-continued
$L_{B1}$
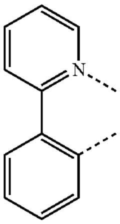
$L_{B2}$
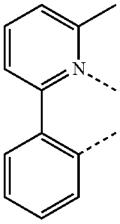
$L_{B3}$
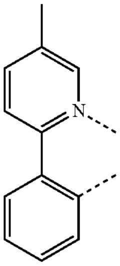
$L_{B4}$
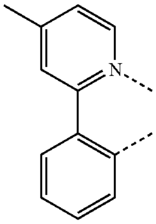
$L_{B5}$
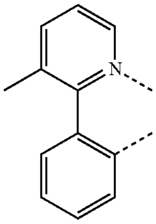
$L_{B6}$
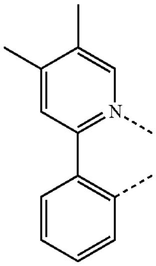
$L_{B7}$
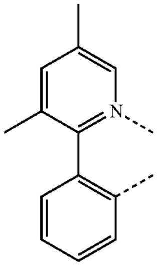
$L_{B8}$
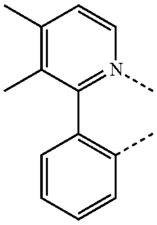
$L_{B9}$
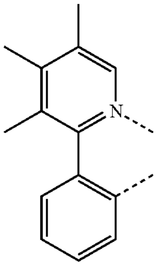
$L_{B10}$
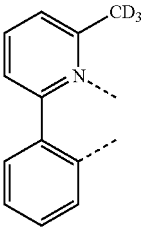
$L_{B11}$
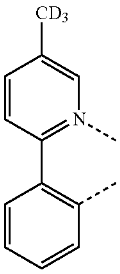
$L_{B12}$
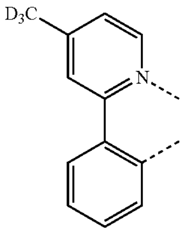

-continued $L_{B13}$

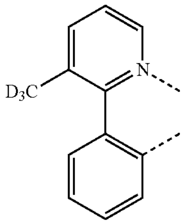

$L_{B14}$

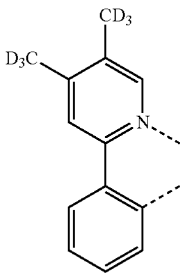

$L_{B15}$

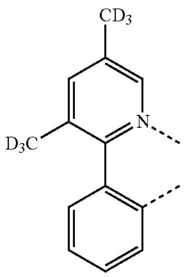

$L_{B16}$

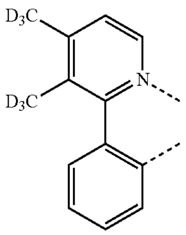

$L_{B17}$

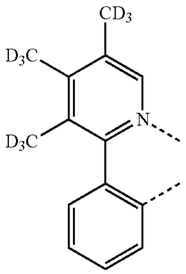

$L_{B18}$

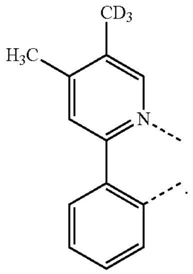

In one embodiment, the compound of formula $Ir(L_A)(L_B)_2$ has one of the formulas listed in the table below:

| Compound Number | $L_A$ | $L_B$ |
|---|---|---|
| 1. | $L_{A1}$ | $L_{B1}$ |
| 2. | $L_{A2}$ | $L_{B1}$ |
| 3. | $L_{A3}$ | $L_{B1}$ |
| 4. | $L_{A4}$ | $L_{B1}$ |
| 5. | $L_{A5}$ | $L_{B1}$ |
| 6. | $L_{A6}$ | $L_{B1}$ |
| 7. | $L_{A7}$ | $L_{B1}$ |
| 8. | $L_{A8}$ | $L_{B1}$ |
| 9. | $L_{A9}$ | $L_{B1}$ |
| 10. | $L_{A10}$ | $L_{B1}$ |
| 11. | $L_{A11}$ | $L_{B1}$ |
| 12. | $L_{A12}$ | $L_{B1}$ |
| 13. | $L_{A13}$ | $L_{B1}$ |
| 14. | $L_{A14}$ | $L_{B1}$ |
| 15. | $L_{A15}$ | $L_{B1}$ |
| 16. | $L_{A16}$ | $L_{B1}$ |
| 17. | $L_{A17}$ | $L_{B1}$ |
| 18. | $L_{A18}$ | $L_{B1}$ |
| 19. | $L_{A19}$ | $L_{B1}$ |
| 20. | $L_{A10}$ | $L_{B1}$ |
| 21. | $L_{A21}$ | $L_{B1}$ |
| 22. | $L_{A22}$ | $L_{B1}$ |
| 23. | $L_{A23}$ | $L_{B1}$ |
| 24. | $L_{A24}$ | $L_{B1}$ |
| 25. | $L_{A25}$ | $L_{B1}$ |
| 26. | $L_{A26}$ | $L_{B1}$ |
| 27. | $L_{A27}$ | $L_{B1}$ |
| 28. | $L_{A28}$ | $L_{B1}$ |
| 29. | $L_{A29}$ | $L_{B1}$ |
| 30. | $L_{A30}$ | $L_{B1}$ |
| 31. | $L_{A31}$ | $L_{B1}$ |
| 32. | $L_{A32}$ | $L_{B1}$ |
| 33. | $L_{A33}$ | $L_{B1}$ |
| 34. | $L_{A34}$ | $L_{B1}$ |
| 35. | $L_{A35}$ | $L_{B1}$ |
| 36. | $L_{A36}$ | $L_{B1}$ |
| 37. | $L_{A37}$ | $L_{B1}$ |
| 38. | $L_{A38}$ | $L_{B1}$ |
| 39. | $L_{A39}$ | $L_{B1}$ |
| 40. | $L_{A40}$ | $L_{B1}$ |
| 41. | $L_{A41}$ | $L_{B1}$ |
| 42. | $L_{A42}$ | $L_{B1}$ |
| 43. | $L_{A43}$ | $L_{B1}$ |
| 44. | $L_{A44}$ | $L_{B1}$ |
| 45. | $L_{A45}$ | $L_{B1}$ |
| 46. | $L_{A46}$ | $L_{B1}$ |
| 47. | $L_{A47}$ | $L_{B1}$ |
| 48. | $L_{A48}$ | $L_{B1}$ |
| 49. | $L_{A49}$ | $L_{B1}$ |
| 50. | $L_{A50}$ | $L_{B1}$ |
| 51. | $L_{A51}$ | $L_{B1}$ |
| 52. | $L_{A52}$ | $L_{B1}$ |
| 53. | $L_{A53}$ | $L_{B1}$ |
| 54. | $L_{A54}$ | $L_{B1}$ |
| 55. | $L_{A55}$ | $L_{B1}$ |
| 56. | $L_{A56}$ | $L_{B1}$ |
| 57. | $L_{A57}$ | $L_{B1}$ |
| 58. | $L_{A58}$ | $L_{B1}$ |
| 59. | $L_{A59}$ | $L_{B1}$ |
| 60. | $L_{A60}$ | $L_{B1}$ |
| 61. | $L_{A61}$ | $L_{B1}$ |
| 62. | $L_{A62}$ | $L_{B1}$ |
| 63. | $L_{A63}$ | $L_{B1}$ |
| 64. | $L_{A64}$ | $L_{B1}$ |
| 65. | $L_{A65}$ | $L_{B1}$ |
| 66. | $L_{A66}$ | $L_{B1}$ |
| 67. | $L_{A67}$ | $L_{B1}$ |
| 68. | $L_{A68}$ | $L_{B1}$ |
| 69. | $L_{A69}$ | $L_{B1}$ |
| 70. | $L_{A70}$ | $L_{B1}$ |
| 71. | $L_{A71}$ | $L_{B1}$ |
| 72. | $L_{A72}$ | $L_{B1}$ |
| 73. | $L_{A73}$ | $L_{B1}$ |
| 74. | $L_{A74}$ | $L_{B1}$ |

-continued

| Compound Number | $L_A$ | $L_B$ |
|---|---|---|
| 75. | $L_{A75}$ | $L_{B1}$ |
| 76. | $L_{A76}$ | $L_{B1}$ |
| 77. | $L_{A77}$ | $L_{B1}$ |
| 78. | $L_{A78}$ | $L_{B1}$ |
| 79. | $L_{A79}$ | $L_{B1}$ |
| 80. | $L_{A80}$ | $L_{B1}$ |
| 81. | $L_{A81}$ | $L_{B1}$ |
| 82. | $L_{A82}$ | $L_{B1}$ |
| 83. | $L_{A83}$ | $L_{B1}$ |
| 84. | $L_{A84}$ | $L_{B1}$ |
| 85. | $L_{A85}$ | $L_{B1}$ |
| 86. | $L_{A86}$ | $L_{B1}$ |
| 87. | $L_{A87}$ | $L_{B1}$ |
| 88. | $L_{A88}$ | $L_{B1}$ |
| 89. | $L_{A89}$ | $L_{B1}$ |
| 90. | $L_{A90}$ | $L_{B1}$ |
| 91. | $L_{A91}$ | $L_{B1}$ |
| 92. | $L_{A92}$ | $L_{B1}$ |
| 93. | $L_{A93}$ | $L_{B1}$ |
| 94. | $L_{A94}$ | $L_{B1}$ |
| 95. | $L_{A95}$ | $L_{B1}$ |
| 96. | $L_{A96}$ | $L_{B1}$ |
| 97. | $L_{A97}$ | $L_{B1}$ |
| 98. | $L_{A98}$ | $L_{B1}$ |
| 99. | $L_{A99}$ | $L_{B1}$ |
| 100. | $L_{A100}$ | $L_{B1}$ |
| 101. | $L_{A101}$ | $L_{B1}$ |
| 102. | $L_{A102}$ | $L_{B1}$ |
| 103. | $L_{A103}$ | $L_{B1}$ |
| 104. | $L_{A104}$ | $L_{B1}$ |
| 105. | $L_{A105}$ | $L_{B1}$ |
| 106. | $L_{A106}$ | $L_{B1}$ |
| 107. | $L_{A107}$ | $L_{B1}$ |
| 108. | $L_{A108}$ | $L_{B1}$ |
| 109. | $L_{A109}$ | $L_{B1}$ |
| 110. | $L_{A110}$ | $L_{B1}$ |
| 111. | $L_{A111}$ | $L_{B1}$ |
| 112. | $L_{A112}$ | $L_{B1}$ |
| 113. | $L_{A113}$ | $L_{B1}$ |
| 114. | $L_{A114}$ | $L_{B1}$ |
| 115. | $L_{A115}$ | $L_{B1}$ |
| 116. | $L_{A116}$ | $L_{B1}$ |
| 117. | $L_{A117}$ | $L_{B1}$ |
| 118. | $L_{A118}$ | $L_{B1}$ |
| 119. | $L_{A119}$ | $L_{B1}$ |
| 120. | $L_{A1}$ | $L_{B2}$ |
| 121. | $L_{A2}$ | $L_{B2}$ |
| 122. | $L_{A3}$ | $L_{B2}$ |
| 123. | $L_{A4}$ | $L_{B2}$ |
| 124. | $L_{A5}$ | $L_{B2}$ |
| 125. | $L_{A6}$ | $L_{B2}$ |
| 126. | $L_{A7}$ | $L_{B2}$ |
| 127. | $L_{A8}$ | $L_{B2}$ |
| 128. | $L_{A9}$ | $L_{B2}$ |
| 129. | $L_{A10}$ | $L_{B2}$ |
| 130. | $L_{A11}$ | $L_{B2}$ |
| 131. | $L_{A12}$ | $L_{B2}$ |
| 132. | $L_{A13}$ | $L_{B2}$ |
| 133. | $L_{A14}$ | $L_{B2}$ |
| 134. | $L_{A15}$ | $L_{B2}$ |
| 135. | $L_{A16}$ | $L_{B2}$ |
| 136. | $L_{A17}$ | $L_{B2}$ |
| 137. | $L_{A18}$ | $L_{B2}$ |
| 138. | $L_{A19}$ | $L_{B2}$ |
| 139. | $L_{A10}$ | $L_{B2}$ |
| 140. | $L_{A21}$ | $L_{B2}$ |
| 141. | $L_{A22}$ | $L_{B2}$ |
| 142. | $L_{A23}$ | $L_{B2}$ |
| 143. | $L_{A24}$ | $L_{B2}$ |
| 144. | $L_{A25}$ | $L_{B2}$ |
| 145. | $L_{A26}$ | $L_{B2}$ |
| 146. | $L_{A27}$ | $L_{B2}$ |
| 147. | $L_{A28}$ | $L_{B2}$ |
| 148. | $L_{A29}$ | $L_{B2}$ |
| 149. | $L_{A30}$ | $L_{B2}$ |
| 150. | $L_{A31}$ | $L_{B2}$ |

-continued

| Compound Number | $L_A$ | $L_B$ |
|---|---|---|
| 151. | $L_{A32}$ | $L_{B2}$ |
| 152. | $L_{A33}$ | $L_{B2}$ |
| 153. | $L_{A34}$ | $L_{B2}$ |
| 154. | $L_{A35}$ | $L_{B2}$ |
| 155. | $L_{A36}$ | $L_{B2}$ |
| 156. | $L_{A37}$ | $L_{B2}$ |
| 157. | $L_{A38}$ | $L_{B2}$ |
| 158. | $L_{A39}$ | $L_{B2}$ |
| 159. | $L_{A40}$ | $L_{B2}$ |
| 160. | $L_{A41}$ | $L_{B2}$ |
| 161. | $L_{A42}$ | $L_{B2}$ |
| 162. | $L_{A43}$ | $L_{B2}$ |
| 163. | $L_{A44}$ | $L_{B2}$ |
| 164. | $L_{A45}$ | $L_{B2}$ |
| 165. | $L_{A46}$ | $L_{B2}$ |
| 166. | $L_{A47}$ | $L_{B2}$ |
| 167. | $L_{A48}$ | $L_{B2}$ |
| 168. | $L_{A49}$ | $L_{B2}$ |
| 169. | $L_{A50}$ | $L_{B2}$ |
| 170. | $L_{A51}$ | $L_{B2}$ |
| 171. | $L_{A52}$ | $L_{B2}$ |
| 172. | $L_{A53}$ | $L_{B2}$ |
| 173. | $L_{A54}$ | $L_{B2}$ |
| 174. | $L_{A55}$ | $L_{B2}$ |
| 175. | $L_{A56}$ | $L_{B2}$ |
| 176. | $L_{A57}$ | $L_{B2}$ |
| 177. | $L_{A58}$ | $L_{B2}$ |
| 178. | $L_{A59}$ | $L_{B2}$ |
| 179. | $L_{A60}$ | $L_{B2}$ |
| 180. | $L_{A61}$ | $L_{B2}$ |
| 181. | $L_{A62}$ | $L_{B2}$ |
| 182. | $L_{A63}$ | $L_{B2}$ |
| 183. | $L_{A64}$ | $L_{B2}$ |
| 184. | $L_{A65}$ | $L_{B2}$ |
| 185. | $L_{A66}$ | $L_{B2}$ |
| 186. | $L_{A67}$ | $L_{B2}$ |
| 187. | $L_{A68}$ | $L_{B2}$ |
| 188. | $L_{A69}$ | $L_{B2}$ |
| 189. | $L_{A70}$ | $L_{B2}$ |
| 190. | $L_{A71}$ | $L_{B2}$ |
| 191. | $L_{A72}$ | $L_{B2}$ |
| 192. | $L_{A73}$ | $L_{B2}$ |
| 193. | $L_{A74}$ | $L_{B2}$ |
| 194. | $L_{A75}$ | $L_{B2}$ |
| 195. | $L_{A76}$ | $L_{B2}$ |
| 196. | $L_{A77}$ | $L_{B2}$ |
| 197. | $L_{A78}$ | $L_{B2}$ |
| 198. | $L_{A79}$ | $L_{B2}$ |
| 199. | $L_{A80}$ | $L_{B2}$ |
| 200. | $L_{A81}$ | $L_{B2}$ |
| 201. | $L_{A82}$ | $L_{B2}$ |
| 202. | $L_{A83}$ | $L_{B2}$ |
| 203. | $L_{A84}$ | $L_{B2}$ |
| 204. | $L_{A85}$ | $L_{B2}$ |
| 205. | $L_{A86}$ | $L_{B2}$ |
| 206. | $L_{A87}$ | $L_{B2}$ |
| 207. | $L_{A88}$ | $L_{B2}$ |
| 208. | $L_{A89}$ | $L_{B2}$ |
| 209. | $L_{A90}$ | $L_{B2}$ |
| 210. | $L_{A91}$ | $L_{B2}$ |
| 211. | $L_{A92}$ | $L_{B2}$ |
| 212. | $L_{A93}$ | $L_{B2}$ |
| 213. | $L_{A94}$ | $L_{B2}$ |
| 214. | $L_{A95}$ | $L_{B2}$ |
| 215. | $L_{A96}$ | $L_{B2}$ |
| 216. | $L_{A97}$ | $L_{B2}$ |
| 217. | $L_{A98}$ | $L_{B2}$ |
| 218. | $L_{A99}$ | $L_{B2}$ |
| 219. | $L_{A100}$ | $L_{B2}$ |
| 220. | $L_{A101}$ | $L_{B2}$ |
| 221. | $L_{A102}$ | $L_{B2}$ |
| 222. | $L_{A103}$ | $L_{B2}$ |
| 223. | $L_{A104}$ | $L_{B2}$ |
| 224. | $L_{A105}$ | $L_{B2}$ |
| 225. | $L_{A106}$ | $L_{B2}$ |
| 226. | $L_{A107}$ | $L_{B2}$ |

-continued

| Compound Number | $L_A$ | $L_B$ |
|---|---|---|
| 227. | $L_{A108}$ | $L_{B2}$ |
| 228. | $L_{A109}$ | $L_{B2}$ |
| 229. | $L_{A110}$ | $L_{B2}$ |
| 230. | $L_{A111}$ | $L_{B2}$ |
| 231. | $L_{A112}$ | $L_{B2}$ |
| 232. | $L_{A113}$ | $L_{B2}$ |
| 233. | $L_{A114}$ | $L_{B2}$ |
| 234. | $L_{A115}$ | $L_{B2}$ |
| 235. | $L_{A116}$ | $L_{B2}$ |
| 236. | $L_{A117}$ | $L_{B2}$ |
| 237. | $L_{A118}$ | $L_{B2}$ |
| 238. | $L_{A119}$ | $L_{B2}$ |
| 239. | $L_{A1}$ | $L_{B3}$ |
| 240. | $L_{A2}$ | $L_{B3}$ |
| 241. | $L_{A3}$ | $L_{B3}$ |
| 242. | $L_{A4}$ | $L_{B3}$ |
| 243. | $L_{A5}$ | $L_{B3}$ |
| 244. | $L_{A6}$ | $L_{B3}$ |
| 245. | $L_{A7}$ | $L_{B3}$ |
| 246. | $L_{A8}$ | $L_{B3}$ |
| 247. | $L_{A9}$ | $L_{B3}$ |
| 248. | $L_{A10}$ | $L_{B3}$ |
| 249. | $L_{A11}$ | $L_{B3}$ |
| 250. | $L_{A12}$ | $L_{B3}$ |
| 251. | $L_{A13}$ | $L_{B3}$ |
| 252. | $L_{A14}$ | $L_{B3}$ |
| 253. | $L_{A15}$ | $L_{B3}$ |
| 254. | $L_{A16}$ | $L_{B3}$ |
| 255. | $L_{A17}$ | $L_{B3}$ |
| 256. | $L_{A18}$ | $L_{B3}$ |
| 257. | $L_{A19}$ | $L_{B3}$ |
| 258. | $L_{A10}$ | $L_{B3}$ |
| 259. | $L_{A21}$ | $L_{B3}$ |
| 260. | $L_{A22}$ | $L_{B3}$ |
| 261. | $L_{A23}$ | $L_{B3}$ |
| 262. | $L_{A24}$ | $L_{B3}$ |
| 263. | $L_{A25}$ | $L_{B3}$ |
| 264. | $L_{A26}$ | $L_{B3}$ |
| 265. | $L_{A27}$ | $L_{B3}$ |
| 266. | $L_{A28}$ | $L_{B3}$ |
| 267. | $L_{A29}$ | $L_{B3}$ |
| 268. | $L_{A30}$ | $L_{B3}$ |
| 269. | $L_{A31}$ | $L_{B3}$ |
| 270. | $L_{A32}$ | $L_{B3}$ |
| 271. | $L_{A33}$ | $L_{B3}$ |
| 272. | $L_{A34}$ | $L_{B3}$ |
| 273. | $L_{A35}$ | $L_{B3}$ |
| 274. | $L_{A36}$ | $L_{B3}$ |
| 275. | $L_{A37}$ | $L_{B3}$ |
| 276. | $L_{A38}$ | $L_{B3}$ |
| 277. | $L_{A39}$ | $L_{B3}$ |
| 278. | $L_{A40}$ | $L_{B3}$ |
| 279. | $L_{A41}$ | $L_{B3}$ |
| 280. | $L_{A42}$ | $L_{B3}$ |
| 281. | $L_{A43}$ | $L_{B3}$ |
| 282. | $L_{A44}$ | $L_{B3}$ |
| 283. | $L_{A45}$ | $L_{B3}$ |
| 284. | $L_{A46}$ | $L_{B3}$ |
| 285. | $L_{A47}$ | $L_{B3}$ |
| 286. | $L_{A48}$ | $L_{B3}$ |
| 287. | $L_{A49}$ | $L_{B3}$ |
| 288. | $L_{A50}$ | $L_{B3}$ |
| 289. | $L_{A51}$ | $L_{B3}$ |
| 290. | $L_{A52}$ | $L_{B3}$ |
| 291. | $L_{A53}$ | $L_{B3}$ |
| 292. | $L_{A54}$ | $L_{B3}$ |
| 293. | $L_{A55}$ | $L_{B3}$ |
| 294. | $L_{A56}$ | $L_{B3}$ |
| 295. | $L_{A57}$ | $L_{B3}$ |
| 296. | $L_{A58}$ | $L_{B3}$ |
| 297. | $L_{A59}$ | $L_{B3}$ |
| 298. | $L_{A60}$ | $L_{B3}$ |
| 299. | $L_{A61}$ | $L_{B3}$ |
| 300. | $L_{A62}$ | $L_{B3}$ |
| 301. | $L_{A63}$ | $L_{B3}$ |
| 302. | $L_{A64}$ | $L_{B3}$ |

-continued

| Compound Number | $L_A$ | $L_B$ |
|---|---|---|
| 303. | $L_{A65}$ | $L_{B3}$ |
| 304. | $L_{A66}$ | $L_{B3}$ |
| 305. | $L_{A67}$ | $L_{B3}$ |
| 306. | $L_{A68}$ | $L_{B3}$ |
| 307. | $L_{A69}$ | $L_{B3}$ |
| 308. | $L_{A70}$ | $L_{B3}$ |
| 309. | $L_{A71}$ | $L_{B3}$ |
| 310. | $L_{A72}$ | $L_{B3}$ |
| 311. | $L_{A73}$ | $L_{B3}$ |
| 312. | $L_{A74}$ | $L_{B3}$ |
| 313. | $L_{A75}$ | $L_{B3}$ |
| 314. | $L_{A76}$ | $L_{B3}$ |
| 315. | $L_{A77}$ | $L_{B3}$ |
| 316. | $L_{A78}$ | $L_{B3}$ |
| 317. | $L_{A79}$ | $L_{B3}$ |
| 318. | $L_{A80}$ | $L_{B3}$ |
| 319. | $L_{A81}$ | $L_{B3}$ |
| 320. | $L_{A82}$ | $L_{B3}$ |
| 321. | $L_{A83}$ | $L_{B3}$ |
| 322. | $L_{A84}$ | $L_{B3}$ |
| 323. | $L_{A85}$ | $L_{B3}$ |
| 324. | $L_{A86}$ | $L_{B3}$ |
| 325. | $L_{A87}$ | $L_{B3}$ |
| 326. | $L_{A88}$ | $L_{B3}$ |
| 327. | $L_{A89}$ | $L_{B3}$ |
| 328. | $L_{A90}$ | $L_{B3}$ |
| 329. | $L_{A91}$ | $L_{B3}$ |
| 330. | $L_{A92}$ | $L_{B3}$ |
| 331. | $L_{A93}$ | $L_{B3}$ |
| 332. | $L_{A94}$ | $L_{B3}$ |
| 333. | $L_{A95}$ | $L_{B3}$ |
| 334. | $L_{A96}$ | $L_{B3}$ |
| 335. | $L_{A97}$ | $L_{B3}$ |
| 336. | $L_{A98}$ | $L_{B3}$ |
| 337. | $L_{A99}$ | $L_{B3}$ |
| 338. | $L_{A100}$ | $L_{B3}$ |
| 339. | $L_{A101}$ | $L_{B3}$ |
| 340. | $L_{A102}$ | $L_{B3}$ |
| 341. | $L_{A103}$ | $L_{B3}$ |
| 342. | $L_{A104}$ | $L_{B3}$ |
| 343. | $L_{A105}$ | $L_{B3}$ |
| 344. | $L_{A106}$ | $L_{B3}$ |
| 345. | $L_{A107}$ | $L_{B3}$ |
| 346. | $L_{A108}$ | $L_{B3}$ |
| 347. | $L_{A109}$ | $L_{B3}$ |
| 348. | $L_{A110}$ | $L_{B3}$ |
| 349. | $L_{A111}$ | $L_{B3}$ |
| 350. | $L_{A112}$ | $L_{B3}$ |
| 351. | $L_{A113}$ | $L_{B3}$ |
| 352. | $L_{A114}$ | $L_{B3}$ |
| 353. | $L_{A115}$ | $L_{B3}$ |
| 354. | $L_{A116}$ | $L_{B3}$ |
| 355. | $L_{A117}$ | $L_{B3}$ |
| 356. | $L_{A118}$ | $L_{B3}$ |
| 357. | $L_{A119}$ | $L_{B3}$ |
| 358. | $L_{A1}$ | $L_{B4}$ |
| 359. | $L_{A2}$ | $L_{B4}$ |
| 360. | $L_{A3}$ | $L_{B4}$ |
| 361. | $L_{A4}$ | $L_{B4}$ |
| 362. | $L_{A5}$ | $L_{B4}$ |
| 363. | $L_{A6}$ | $L_{B4}$ |
| 364. | $L_{A7}$ | $L_{B4}$ |
| 365. | $L_{A8}$ | $L_{B4}$ |
| 366. | $L_{A9}$ | $L_{B4}$ |
| 367. | $L_{A10}$ | $L_{B4}$ |
| 368. | $L_{A11}$ | $L_{B4}$ |
| 369. | $L_{A12}$ | $L_{B4}$ |
| 370. | $L_{A13}$ | $L_{B4}$ |
| 371. | $L_{A14}$ | $L_{B4}$ |
| 372. | $L_{A15}$ | $L_{B4}$ |
| 373. | $L_{A16}$ | $L_{B4}$ |
| 374. | $L_{A17}$ | $L_{B4}$ |
| 375. | $L_{A18}$ | $L_{B4}$ |
| 376. | $L_{A19}$ | $L_{B4}$ |
| 377. | $L_{A10}$ | $L_{B4}$ |
| 378. | $L_{A21}$ | $L_{B4}$ |

-continued

| Compound Number | $L_A$ | $L_B$ |
|---|---|---|
| 379. | $L_{A22}$ | $L_{B4}$ |
| 380. | $L_{A23}$ | $L_{B4}$ |
| 381. | $L_{A24}$ | $L_{B4}$ |
| 382. | $L_{A25}$ | $L_{B4}$ |
| 383. | $L_{A26}$ | $L_{B4}$ |
| 384. | $L_{A27}$ | $L_{B4}$ |
| 385. | $L_{A28}$ | $L_{B4}$ |
| 386. | $L_{A29}$ | $L_{B4}$ |
| 387. | $L_{A30}$ | $L_{B4}$ |
| 388. | $L_{A31}$ | $L_{B4}$ |
| 389. | $L_{A32}$ | $L_{B4}$ |
| 390. | $L_{A33}$ | $L_{B4}$ |
| 391. | $L_{A34}$ | $L_{B4}$ |
| 392. | $L_{A35}$ | $L_{B4}$ |
| 393. | $L_{A36}$ | $L_{B4}$ |
| 394. | $L_{A37}$ | $L_{B4}$ |
| 395. | $L_{A38}$ | $L_{B4}$ |
| 396. | $L_{A39}$ | $L_{B4}$ |
| 397. | $L_{A40}$ | $L_{B4}$ |
| 398. | $L_{A41}$ | $L_{B4}$ |
| 399. | $L_{A42}$ | $L_{B4}$ |
| 400. | $L_{A43}$ | $L_{B4}$ |
| 401. | $L_{A44}$ | $L_{B4}$ |
| 402. | $L_{A45}$ | $L_{B4}$ |
| 403. | $L_{A46}$ | $L_{B4}$ |
| 404. | $L_{A47}$ | $L_{B4}$ |
| 405. | $L_{A48}$ | $L_{B4}$ |
| 406. | $L_{A49}$ | $L_{B4}$ |
| 407. | $L_{A50}$ | $L_{B4}$ |
| 408. | $L_{A51}$ | $L_{B4}$ |
| 409. | $L_{A52}$ | $L_{B4}$ |
| 410. | $L_{A53}$ | $L_{B4}$ |
| 411. | $L_{A54}$ | $L_{B4}$ |
| 412. | $L_{A55}$ | $L_{B4}$ |
| 413. | $L_{A56}$ | $L_{B4}$ |
| 414. | $L_{A57}$ | $L_{B4}$ |
| 415. | $L_{A58}$ | $L_{B4}$ |
| 416. | $L_{A59}$ | $L_{B4}$ |
| 417. | $L_{A60}$ | $L_{B4}$ |
| 418. | $L_{A61}$ | $L_{B4}$ |
| 419. | $L_{A62}$ | $L_{B4}$ |
| 420. | $L_{A63}$ | $L_{B4}$ |
| 421. | $L_{A64}$ | $L_{B4}$ |
| 422. | $L_{A65}$ | $L_{B4}$ |
| 423. | $L_{A66}$ | $L_{B4}$ |
| 424. | $L_{A67}$ | $L_{B4}$ |
| 425. | $L_{A68}$ | $L_{B4}$ |
| 426. | $L_{A69}$ | $L_{B4}$ |
| 427. | $L_{A70}$ | $L_{B4}$ |
| 428. | $L_{A71}$ | $L_{B4}$ |
| 429. | $L_{A72}$ | $L_{B4}$ |
| 430. | $L_{A73}$ | $L_{B4}$ |
| 431. | $L_{A74}$ | $L_{B4}$ |
| 432. | $L_{A75}$ | $L_{B4}$ |
| 433. | $L_{A76}$ | $L_{B4}$ |
| 434. | $L_{A77}$ | $L_{B4}$ |
| 435. | $L_{A78}$ | $L_{B4}$ |
| 436. | $L_{A79}$ | $L_{B4}$ |
| 437. | $L_{A80}$ | $L_{B4}$ |
| 438. | $L_{A81}$ | $L_{B4}$ |
| 439. | $L_{A82}$ | $L_{B4}$ |
| 440. | $L_{A83}$ | $L_{B4}$ |
| 441. | $L_{A84}$ | $L_{B4}$ |
| 442. | $L_{A85}$ | $L_{B4}$ |
| 443. | $L_{A86}$ | $L_{B4}$ |
| 444. | $L_{A87}$ | $L_{B4}$ |
| 445. | $L_{A88}$ | $L_{B4}$ |
| 446. | $L_{A89}$ | $L_{B4}$ |
| 447. | $L_{A90}$ | $L_{B4}$ |
| 448. | $L_{A91}$ | $L_{B4}$ |
| 449. | $L_{A92}$ | $L_{B4}$ |
| 450. | $L_{A93}$ | $L_{B4}$ |
| 451. | $L_{A94}$ | $L_{B4}$ |
| 452. | $L_{A95}$ | $L_{B4}$ |
| 453. | $L_{A96}$ | $L_{B4}$ |
| 454. | $L_{A97}$ | $L_{B4}$ |

-continued

| Compound Number | $L_A$ | $L_B$ |
|---|---|---|
| 455. | $L_{A98}$ | $L_{B4}$ |
| 456. | $L_{A99}$ | $L_{B4}$ |
| 457. | $L_{A100}$ | $L_{B4}$ |
| 458. | $L_{A101}$ | $L_{B4}$ |
| 459. | $L_{A102}$ | $L_{B4}$ |
| 460. | $L_{A103}$ | $L_{B4}$ |
| 461. | $L_{A104}$ | $L_{B4}$ |
| 462. | $L_{A105}$ | $L_{B4}$ |
| 463. | $L_{A106}$ | $L_{B4}$ |
| 464. | $L_{A107}$ | $L_{B4}$ |
| 465. | $L_{A108}$ | $L_{B4}$ |
| 466. | $L_{A109}$ | $L_{B4}$ |
| 467. | $L_{A110}$ | $L_{B4}$ |
| 468. | $L_{A111}$ | $L_{B4}$ |
| 469. | $L_{A112}$ | $L_{B4}$ |
| 470. | $L_{A113}$ | $L_{B4}$ |
| 471. | $L_{A114}$ | $L_{B4}$ |
| 472. | $L_{A115}$ | $L_{B4}$ |
| 473. | $L_{A116}$ | $L_{B4}$ |
| 474. | $L_{A117}$ | $L_{B4}$ |
| 475. | $L_{A118}$ | $L_{B4}$ |
| 476. | $L_{A119}$ | $L_{B4}$ |
| 477. | $L_{A1}$ | $L_{B5}$ |
| 478. | $L_{A2}$ | $L_{B5}$ |
| 479. | $L_{A3}$ | $L_{B5}$ |
| 480. | $L_{A4}$ | $L_{B5}$ |
| 481. | $L_{A5}$ | $L_{B5}$ |
| 482. | $L_{A6}$ | $L_{B5}$ |
| 483. | $L_{A7}$ | $L_{B5}$ |
| 484. | $L_{A8}$ | $L_{B5}$ |
| 485. | $L_{A9}$ | $L_{B5}$ |
| 486. | $L_{A10}$ | $L_{B5}$ |
| 487. | $L_{A11}$ | $L_{B5}$ |
| 488. | $L_{A12}$ | $L_{B5}$ |
| 489. | $L_{A13}$ | $L_{B5}$ |
| 490. | $L_{A14}$ | $L_{B5}$ |
| 491. | $L_{A15}$ | $L_{B5}$ |
| 492. | $L_{A16}$ | $L_{B5}$ |
| 493. | $L_{A17}$ | $L_{B5}$ |
| 494. | $L_{A18}$ | $L_{B5}$ |
| 495. | $L_{A19}$ | $L_{B5}$ |
| 496. | $L_{A10}$ | $L_{B5}$ |
| 497. | $L_{A21}$ | $L_{B5}$ |
| 498. | $L_{A22}$ | $L_{B5}$ |
| 499. | $L_{A23}$ | $L_{B5}$ |
| 500. | $L_{A24}$ | $L_{B5}$ |
| 501. | $L_{A25}$ | $L_{B5}$ |
| 502. | $L_{A26}$ | $L_{B5}$ |
| 503. | $L_{A27}$ | $L_{B5}$ |
| 504. | $L_{A28}$ | $L_{B5}$ |
| 505. | $L_{A29}$ | $L_{B5}$ |
| 506. | $L_{A30}$ | $L_{B5}$ |
| 507. | $L_{A31}$ | $L_{B5}$ |
| 508. | $L_{A32}$ | $L_{B5}$ |
| 509. | $L_{A33}$ | $L_{B5}$ |
| 510. | $L_{A34}$ | $L_{B5}$ |
| 511. | $L_{A35}$ | $L_{B5}$ |
| 512. | $L_{A36}$ | $L_{B5}$ |
| 513. | $L_{A37}$ | $L_{B5}$ |
| 514. | $L_{A38}$ | $L_{B5}$ |
| 515. | $L_{A39}$ | $L_{B5}$ |
| 516. | $L_{A40}$ | $L_{B5}$ |
| 517. | $L_{A41}$ | $L_{B5}$ |
| 518. | $L_{A42}$ | $L_{B5}$ |
| 519. | $L_{A43}$ | $L_{B5}$ |
| 520. | $L_{A44}$ | $L_{B5}$ |
| 521. | $L_{A45}$ | $L_{B5}$ |
| 522. | $L_{A46}$ | $L_{B5}$ |
| 523. | $L_{A47}$ | $L_{B5}$ |
| 524. | $L_{A48}$ | $L_{B5}$ |
| 525. | $L_{A49}$ | $L_{B5}$ |
| 526. | $L_{A50}$ | $L_{B5}$ |
| 527. | $L_{A51}$ | $L_{B5}$ |
| 528. | $L_{A52}$ | $L_{B5}$ |
| 529. | $L_{A53}$ | $L_{B5}$ |
| 530. | $L_{A54}$ | $L_{B5}$ |

-continued

| Compound Number | $L_A$ | $L_B$ |
|---|---|---|
| 531. | $L_{A55}$ | $L_{B5}$ |
| 532. | $L_{A56}$ | $L_{B5}$ |
| 533. | $L_{A57}$ | $L_{B5}$ |
| 534. | $L_{A58}$ | $L_{B5}$ |
| 535. | $L_{A59}$ | $L_{B5}$ |
| 536. | $L_{A60}$ | $L_{B5}$ |
| 537. | $L_{A61}$ | $L_{B5}$ |
| 538. | $L_{A62}$ | $L_{B5}$ |
| 539. | $L_{A63}$ | $L_{B5}$ |
| 540. | $L_{A64}$ | $L_{B5}$ |
| 541. | $L_{A65}$ | $L_{B5}$ |
| 542. | $L_{A66}$ | $L_{B5}$ |
| 543. | $L_{A67}$ | $L_{B5}$ |
| 544. | $L_{A68}$ | $L_{B5}$ |
| 545. | $L_{A69}$ | $L_{B5}$ |
| 546. | $L_{A70}$ | $L_{B5}$ |
| 547. | $L_{A71}$ | $L_{B5}$ |
| 548. | $L_{A72}$ | $L_{B5}$ |
| 549. | $L_{A73}$ | $L_{B5}$ |
| 550. | $L_{A74}$ | $L_{B5}$ |
| 551. | $L_{A75}$ | $L_{B5}$ |
| 552. | $L_{A76}$ | $L_{B5}$ |
| 553. | $L_{A77}$ | $L_{B5}$ |
| 554. | $L_{A78}$ | $L_{B5}$ |
| 555. | $L_{A79}$ | $L_{B5}$ |
| 556. | $L_{A80}$ | $L_{B5}$ |
| 557. | $L_{A81}$ | $L_{B5}$ |
| 558. | $L_{A82}$ | $L_{B5}$ |
| 559. | $L_{A83}$ | $L_{B5}$ |
| 560. | $L_{A84}$ | $L_{B5}$ |
| 561. | $L_{A85}$ | $L_{B5}$ |
| 562. | $L_{A86}$ | $L_{B5}$ |
| 563. | $L_{A87}$ | $L_{B5}$ |
| 564. | $L_{A88}$ | $L_{B5}$ |
| 565. | $L_{A89}$ | $L_{B5}$ |
| 566. | $L_{A90}$ | $L_{B5}$ |
| 567. | $L_{A91}$ | $L_{B5}$ |
| 568. | $L_{A92}$ | $L_{B5}$ |
| 569. | $L_{A93}$ | $L_{B5}$ |
| 570. | $L_{A94}$ | $L_{B5}$ |
| 571. | $L_{A95}$ | $L_{B5}$ |
| 572. | $L_{A96}$ | $L_{B5}$ |
| 573. | $L_{A97}$ | $L_{B5}$ |
| 574. | $L_{A98}$ | $L_{B5}$ |
| 575. | $L_{A99}$ | $L_{B5}$ |
| 576. | $L_{A100}$ | $L_{B5}$ |
| 577. | $L_{A101}$ | $L_{B5}$ |
| 578. | $L_{A102}$ | $L_{B5}$ |
| 579. | $L_{A103}$ | $L_{B5}$ |
| 580. | $L_{A104}$ | $L_{B5}$ |
| 581. | $L_{A105}$ | $L_{B5}$ |
| 582. | $L_{A106}$ | $L_{B5}$ |
| 583. | $L_{A107}$ | $L_{B5}$ |
| 584. | $L_{A108}$ | $L_{B5}$ |
| 585. | $L_{A109}$ | $L_{B5}$ |
| 586. | $L_{A110}$ | $L_{B5}$ |
| 587. | $L_{A111}$ | $L_{B5}$ |
| 588. | $L_{A112}$ | $L_{B5}$ |
| 589. | $L_{A113}$ | $L_{B5}$ |
| 590. | $L_{A114}$ | $L_{B5}$ |
| 591. | $L_{A115}$ | $L_{B5}$ |
| 592. | $L_{A116}$ | $L_{B5}$ |
| 593. | $L_{A117}$ | $L_{B5}$ |
| 594. | $L_{A118}$ | $L_{B5}$ |
| 595. | $L_{A119}$ | $L_{B5}$ |
| 596. | $L_{A1}$ | $L_{B6}$ |
| 597. | $L_{A2}$ | $L_{B6}$ |
| 598. | $L_{A3}$ | $L_{B6}$ |
| 599. | $L_{A4}$ | $L_{B6}$ |
| 600. | $L_{A5}$ | $L_{B6}$ |
| 601. | $L_{A6}$ | $L_{B6}$ |
| 602. | $L_{A7}$ | $L_{B6}$ |
| 603. | $L_{A8}$ | $L_{B6}$ |
| 604. | $L_{A9}$ | $L_{B6}$ |
| 605. | $L_{A10}$ | $L_{B6}$ |
| 606. | $L_{A11}$ | $L_{B6}$ |

-continued

| Compound Number | $L_A$ | $L_B$ |
|---|---|---|
| 607. | $L_{A12}$ | $L_{B6}$ |
| 608. | $L_{A13}$ | $L_{B6}$ |
| 609. | $L_{A14}$ | $L_{B6}$ |
| 610. | $L_{A15}$ | $L_{B6}$ |
| 611. | $L_{A16}$ | $L_{B6}$ |
| 612. | $L_{A17}$ | $L_{B6}$ |
| 613. | $L_{A18}$ | $L_{B6}$ |
| 614. | $L_{A19}$ | $L_{B6}$ |
| 615. | $L_{A10}$ | $L_{B6}$ |
| 616. | $L_{A21}$ | $L_{B6}$ |
| 617. | $L_{A22}$ | $L_{B6}$ |
| 618. | $L_{A23}$ | $L_{B6}$ |
| 619. | $L_{A24}$ | $L_{B6}$ |
| 620. | $L_{A25}$ | $L_{B6}$ |
| 621. | $L_{A26}$ | $L_{B6}$ |
| 622. | $L_{A27}$ | $L_{B6}$ |
| 623. | $L_{A28}$ | $L_{B6}$ |
| 624. | $L_{A29}$ | $L_{B6}$ |
| 625. | $L_{A30}$ | $L_{B6}$ |
| 626. | $L_{A31}$ | $L_{B6}$ |
| 627. | $L_{A32}$ | $L_{B6}$ |
| 628. | $L_{A33}$ | $L_{B6}$ |
| 629. | $L_{A34}$ | $L_{B6}$ |
| 630. | $L_{A35}$ | $L_{B6}$ |
| 631. | $L_{A36}$ | $L_{B6}$ |
| 632. | $L_{A37}$ | $L_{B6}$ |
| 633. | $L_{A38}$ | $L_{B6}$ |
| 634. | $L_{A39}$ | $L_{B6}$ |
| 635. | $L_{A40}$ | $L_{B6}$ |
| 636. | $L_{A41}$ | $L_{B6}$ |
| 637. | $L_{A42}$ | $L_{B6}$ |
| 638. | $L_{A43}$ | $L_{B6}$ |
| 639. | $L_{A44}$ | $L_{B6}$ |
| 640. | $L_{A45}$ | $L_{B6}$ |
| 641. | $L_{A46}$ | $L_{B6}$ |
| 642. | $L_{A47}$ | $L_{B6}$ |
| 643. | $L_{A48}$ | $L_{B6}$ |
| 644. | $L_{A49}$ | $L_{B6}$ |
| 645. | $L_{A50}$ | $L_{B6}$ |
| 646. | $L_{A51}$ | $L_{B6}$ |
| 647. | $L_{A52}$ | $L_{B6}$ |
| 648. | $L_{A53}$ | $L_{B6}$ |
| 649. | $L_{A54}$ | $L_{B6}$ |
| 650. | $L_{A55}$ | $L_{B6}$ |
| 651. | $L_{A56}$ | $L_{B6}$ |
| 652. | $L_{A57}$ | $L_{B6}$ |
| 653. | $L_{A58}$ | $L_{B6}$ |
| 654. | $L_{A59}$ | $L_{B6}$ |
| 655. | $L_{A60}$ | $L_{B6}$ |
| 656. | $L_{A61}$ | $L_{B6}$ |
| 657. | $L_{A62}$ | $L_{B6}$ |
| 658. | $L_{A63}$ | $L_{B6}$ |
| 659. | $L_{A64}$ | $L_{B6}$ |
| 660. | $L_{A65}$ | $L_{B6}$ |
| 661. | $L_{A66}$ | $L_{B6}$ |
| 662. | $L_{A67}$ | $L_{B6}$ |
| 663. | $L_{A68}$ | $L_{B6}$ |
| 664. | $L_{A69}$ | $L_{B6}$ |
| 665. | $L_{A70}$ | $L_{B6}$ |
| 666. | $L_{A71}$ | $L_{B6}$ |
| 667. | $L_{A72}$ | $L_{B6}$ |
| 668. | $L_{A73}$ | $L_{B6}$ |
| 669. | $L_{A74}$ | $L_{B6}$ |
| 670. | $L_{A75}$ | $L_{B6}$ |
| 671. | $L_{A76}$ | $L_{B6}$ |
| 672. | $L_{A77}$ | $L_{B6}$ |
| 673. | $L_{A78}$ | $L_{B6}$ |
| 674. | $L_{A79}$ | $L_{B6}$ |
| 675. | $L_{A80}$ | $L_{B6}$ |
| 676. | $L_{A81}$ | $L_{B6}$ |
| 677. | $L_{A82}$ | $L_{B6}$ |
| 678. | $L_{A83}$ | $L_{B6}$ |
| 679. | $L_{A84}$ | $L_{B6}$ |
| 680. | $L_{A85}$ | $L_{B6}$ |
| 681. | $L_{A86}$ | $L_{B6}$ |
| 682. | $L_{A87}$ | $L_{B6}$ |

-continued

| Compound Number | $L_A$ | $L_B$ |
|---|---|---|
| 683. | $L_{A88}$ | $L_{B6}$ |
| 684. | $L_{A89}$ | $L_{B6}$ |
| 685. | $L_{A90}$ | $L_{B6}$ |
| 686. | $L_{A91}$ | $L_{B6}$ |
| 687. | $L_{A92}$ | $L_{B6}$ |
| 688. | $L_{A93}$ | $L_{B6}$ |
| 689. | $L_{A94}$ | $L_{B6}$ |
| 690. | $L_{A95}$ | $L_{B6}$ |
| 691. | $L_{A96}$ | $L_{B6}$ |
| 692. | $L_{A97}$ | $L_{B6}$ |
| 693. | $L_{A98}$ | $L_{B6}$ |
| 694. | $L_{A99}$ | $L_{B6}$ |
| 695. | $L_{A100}$ | $L_{B6}$ |
| 696. | $L_{A101}$ | $L_{B6}$ |
| 697. | $L_{A102}$ | $L_{B6}$ |
| 698. | $L_{A103}$ | $L_{B6}$ |
| 699. | $L_{A104}$ | $L_{B6}$ |
| 700. | $L_{A105}$ | $L_{B6}$ |
| 701. | $L_{A106}$ | $L_{B6}$ |
| 702. | $L_{A107}$ | $L_{B6}$ |
| 703. | $L_{A108}$ | $L_{B6}$ |
| 704. | $L_{A109}$ | $L_{B6}$ |
| 705. | $L_{A110}$ | $L_{B6}$ |
| 706. | $L_{A111}$ | $L_{B6}$ |
| 707. | $L_{A112}$ | $L_{B6}$ |
| 708. | $L_{A113}$ | $L_{B6}$ |
| 709. | $L_{A114}$ | $L_{B6}$ |
| 710. | $L_{A115}$ | $L_{B6}$ |
| 711. | $L_{A116}$ | $L_{B6}$ |
| 712. | $L_{A117}$ | $L_{B6}$ |
| 713. | $L_{A118}$ | $L_{B6}$ |
| 714. | $L_{A119}$ | $L_{B6}$ |
| 715. | $L_{A1}$ | $L_{B7}$ |
| 716. | $L_{A2}$ | $L_{B7}$ |
| 717. | $L_{A3}$ | $L_{B7}$ |
| 718. | $L_{A4}$ | $L_{B7}$ |
| 719. | $L_{A5}$ | $L_{B7}$ |
| 720. | $L_{A6}$ | $L_{B7}$ |
| 721. | $L_{A7}$ | $L_{B7}$ |
| 722. | $L_{A8}$ | $L_{B7}$ |
| 723. | $L_{A9}$ | $L_{B7}$ |
| 724. | $L_{A10}$ | $L_{B7}$ |
| 725. | $L_{A11}$ | $L_{B7}$ |
| 726. | $L_{A12}$ | $L_{B7}$ |
| 727. | $L_{A13}$ | $L_{B7}$ |
| 728. | $L_{A14}$ | $L_{B7}$ |
| 729. | $L_{A15}$ | $L_{B7}$ |
| 730. | $L_{A16}$ | $L_{B7}$ |
| 731. | $L_{A17}$ | $L_{B7}$ |
| 732. | $L_{A18}$ | $L_{B7}$ |
| 733. | $L_{A19}$ | $L_{B7}$ |
| 734. | $L_{A10}$ | $L_{B7}$ |
| 735. | $L_{A21}$ | $L_{B7}$ |
| 736. | $L_{A22}$ | $L_{B7}$ |
| 737. | $L_{A23}$ | $L_{B7}$ |
| 738. | $L_{A24}$ | $L_{B7}$ |
| 739. | $L_{A25}$ | $L_{B7}$ |
| 740. | $L_{A26}$ | $L_{B7}$ |
| 741. | $L_{A27}$ | $L_{B7}$ |
| 742. | $L_{A28}$ | $L_{B7}$ |
| 743. | $L_{A29}$ | $L_{B7}$ |
| 744. | $L_{A30}$ | $L_{B7}$ |
| 745. | $L_{A31}$ | $L_{B7}$ |
| 746. | $L_{A32}$ | $L_{B7}$ |
| 747. | $L_{A33}$ | $L_{B7}$ |
| 748. | $L_{A34}$ | $L_{B7}$ |
| 749. | $L_{A35}$ | $L_{B7}$ |
| 750. | $L_{A36}$ | $L_{B7}$ |
| 751. | $L_{A37}$ | $L_{B7}$ |
| 752. | $L_{A38}$ | $L_{B7}$ |
| 753. | $L_{A39}$ | $L_{B7}$ |
| 754. | $L_{A40}$ | $L_{B7}$ |
| 755. | $L_{A41}$ | $L_{B7}$ |
| 756. | $L_{A42}$ | $L_{B7}$ |
| 757. | $L_{A43}$ | $L_{B7}$ |
| 758. | $L_{A44}$ | $L_{B7}$ |

-continued

| Compound Number | $L_A$ | $L_B$ |
|---|---|---|
| 759. | $L_{A45}$ | $L_{B7}$ |
| 760. | $L_{A46}$ | $L_{B7}$ |
| 761. | $L_{A47}$ | $L_{B7}$ |
| 762. | $L_{A48}$ | $L_{B7}$ |
| 763. | $L_{A49}$ | $L_{B7}$ |
| 764. | $L_{A50}$ | $L_{B7}$ |
| 765. | $L_{A51}$ | $L_{B7}$ |
| 766. | $L_{A52}$ | $L_{B7}$ |
| 767. | $L_{A53}$ | $L_{B7}$ |
| 768. | $L_{A54}$ | $L_{B7}$ |
| 769. | $L_{A55}$ | $L_{B7}$ |
| 770. | $L_{A56}$ | $L_{B7}$ |
| 771. | $L_{A57}$ | $L_{B7}$ |
| 772. | $L_{A58}$ | $L_{B7}$ |
| 773. | $L_{A59}$ | $L_{B7}$ |
| 774. | $L_{A60}$ | $L_{B7}$ |
| 775. | $L_{A61}$ | $L_{B7}$ |
| 776. | $L_{A62}$ | $L_{B7}$ |
| 777. | $L_{A63}$ | $L_{B7}$ |
| 778. | $L_{A64}$ | $L_{B7}$ |
| 779. | $L_{A65}$ | $L_{B7}$ |
| 780. | $L_{A66}$ | $L_{B7}$ |
| 781. | $L_{A67}$ | $L_{B7}$ |
| 782. | $L_{A68}$ | $L_{B7}$ |
| 783. | $L_{A69}$ | $L_{B7}$ |
| 784. | $L_{A70}$ | $L_{B7}$ |
| 785. | $L_{A71}$ | $L_{B7}$ |
| 786. | $L_{A72}$ | $L_{B7}$ |
| 787. | $L_{A73}$ | $L_{B7}$ |
| 788. | $L_{A74}$ | $L_{B7}$ |
| 789. | $L_{A75}$ | $L_{B7}$ |
| 790. | $L_{A76}$ | $L_{B7}$ |
| 791. | $L_{A77}$ | $L_{B7}$ |
| 792. | $L_{A78}$ | $L_{B7}$ |
| 793. | $L_{A79}$ | $L_{B7}$ |
| 794. | $L_{A80}$ | $L_{B7}$ |
| 795. | $L_{A81}$ | $L_{B7}$ |
| 796. | $L_{A82}$ | $L_{B7}$ |
| 797. | $L_{A83}$ | $L_{B7}$ |
| 798. | $L_{A84}$ | $L_{B7}$ |
| 799. | $L_{A85}$ | $L_{B7}$ |
| 800. | $L_{A86}$ | $L_{B7}$ |
| 801. | $L_{A87}$ | $L_{B7}$ |
| 802. | $L_{A88}$ | $L_{B7}$ |
| 803. | $L_{A89}$ | $L_{B7}$ |
| 804. | $L_{A90}$ | $L_{B7}$ |
| 805. | $L_{A91}$ | $L_{B7}$ |
| 806. | $L_{A92}$ | $L_{B7}$ |
| 807. | $L_{A93}$ | $L_{B7}$ |
| 808. | $L_{A94}$ | $L_{B7}$ |
| 809. | $L_{A95}$ | $L_{B7}$ |
| 810. | $L_{A96}$ | $L_{B7}$ |
| 811. | $L_{A97}$ | $L_{B7}$ |
| 812. | $L_{A98}$ | $L_{B7}$ |
| 813. | $L_{A99}$ | $L_{B7}$ |
| 814. | $L_{A100}$ | $L_{B7}$ |
| 815. | $L_{A101}$ | $L_{B7}$ |
| 816. | $L_{A102}$ | $L_{B7}$ |
| 817. | $L_{A103}$ | $L_{B7}$ |
| 818. | $L_{A104}$ | $L_{B7}$ |
| 819. | $L_{A105}$ | $L_{B7}$ |
| 820. | $L_{A106}$ | $L_{B7}$ |
| 821. | $L_{A107}$ | $L_{B7}$ |
| 822. | $L_{A108}$ | $L_{B7}$ |
| 823. | $L_{A109}$ | $L_{B7}$ |
| 824. | $L_{A110}$ | $L_{B7}$ |
| 825. | $L_{A111}$ | $L_{B7}$ |
| 826. | $L_{A112}$ | $L_{B7}$ |
| 827. | $L_{A113}$ | $L_{B7}$ |
| 828. | $L_{A114}$ | $L_{B7}$ |
| 829. | $L_{A115}$ | $L_{B7}$ |
| 830. | $L_{A116}$ | $L_{B7}$ |
| 831. | $L_{A117}$ | $L_{B7}$ |
| 832. | $L_{A118}$ | $L_{B7}$ |
| 833. | $L_{A119}$ | $L_{B7}$ |
| 834. | $L_{A1}$ | $L_{B8}$ |

-continued

| Compound Number | $L_A$ | $L_B$ |
|---|---|---|
| 835. | $L_{A2}$ | $L_{B8}$ |
| 836. | $L_{A3}$ | $L_{B8}$ |
| 837. | $L_{A4}$ | $L_{B8}$ |
| 838. | $L_{A5}$ | $L_{B8}$ |
| 839. | $L_{A6}$ | $L_{B8}$ |
| 840. | $L_{A7}$ | $L_{B8}$ |
| 841. | $L_{A8}$ | $L_{B8}$ |
| 842. | $L_{A9}$ | $L_{B8}$ |
| 843. | $L_{A10}$ | $L_{B8}$ |
| 844. | $L_{A11}$ | $L_{B8}$ |
| 845. | $L_{A12}$ | $L_{B8}$ |
| 846. | $L_{A13}$ | $L_{B8}$ |
| 847. | $L_{A14}$ | $L_{B8}$ |
| 848. | $L_{A15}$ | $L_{B8}$ |
| 849. | $L_{A16}$ | $L_{B8}$ |
| 850. | $L_{A17}$ | $L_{B8}$ |
| 851. | $L_{A18}$ | $L_{B8}$ |
| 852. | $L_{A19}$ | $L_{B8}$ |
| 853. | $L_{A10}$ | $L_{B8}$ |
| 854. | $L_{A21}$ | $L_{B8}$ |
| 855. | $L_{A22}$ | $L_{B8}$ |
| 856. | $L_{A23}$ | $L_{B8}$ |
| 857. | $L_{A24}$ | $L_{B8}$ |
| 858. | $L_{A25}$ | $L_{B8}$ |
| 859. | $L_{A26}$ | $L_{B8}$ |
| 860. | $L_{A27}$ | $L_{B8}$ |
| 861. | $L_{A28}$ | $L_{B8}$ |
| 862. | $L_{A29}$ | $L_{B8}$ |
| 863. | $L_{A30}$ | $L_{B8}$ |
| 864. | $L_{A31}$ | $L_{B8}$ |
| 865. | $L_{A32}$ | $L_{B8}$ |
| 866. | $L_{A33}$ | $L_{B8}$ |
| 867. | $L_{A34}$ | $L_{B8}$ |
| 868. | $L_{A35}$ | $L_{B8}$ |
| 869. | $L_{A36}$ | $L_{B8}$ |
| 870. | $L_{A37}$ | $L_{B8}$ |
| 871. | $L_{A38}$ | $L_{B8}$ |
| 872. | $L_{A39}$ | $L_{B8}$ |
| 873. | $L_{A40}$ | $L_{B8}$ |
| 874. | $L_{A41}$ | $L_{B8}$ |
| 875. | $L_{A42}$ | $L_{B8}$ |
| 876. | $L_{A43}$ | $L_{B8}$ |
| 877. | $L_{A44}$ | $L_{B8}$ |
| 878. | $L_{A45}$ | $L_{B8}$ |
| 879. | $L_{A46}$ | $L_{B8}$ |
| 880. | $L_{A47}$ | $L_{B8}$ |
| 881. | $L_{A48}$ | $L_{B8}$ |
| 882. | $L_{A49}$ | $L_{B8}$ |
| 883. | $L_{A50}$ | $L_{B8}$ |
| 884. | $L_{A51}$ | $L_{B8}$ |
| 885. | $L_{A52}$ | $L_{B8}$ |
| 886. | $L_{A53}$ | $L_{B8}$ |
| 887. | $L_{A54}$ | $L_{B8}$ |
| 888. | $L_{A55}$ | $L_{B8}$ |
| 889. | $L_{A56}$ | $L_{B8}$ |
| 890. | $L_{A57}$ | $L_{B8}$ |
| 891. | $L_{A58}$ | $L_{B8}$ |
| 892. | $L_{A59}$ | $L_{B8}$ |
| 893. | $L_{A60}$ | $L_{B8}$ |
| 894. | $L_{A61}$ | $L_{B8}$ |
| 895. | $L_{A62}$ | $L_{B8}$ |
| 896. | $L_{A63}$ | $L_{B8}$ |
| 897. | $L_{A64}$ | $L_{B8}$ |
| 898. | $L_{A65}$ | $L_{B8}$ |
| 899. | $L_{A66}$ | $L_{B8}$ |
| 900. | $L_{A67}$ | $L_{B8}$ |
| 901. | $L_{A68}$ | $L_{B8}$ |
| 902. | $L_{A69}$ | $L_{B8}$ |
| 903. | $L_{A70}$ | $L_{B8}$ |
| 904. | $L_{A71}$ | $L_{B8}$ |
| 905. | $L_{A72}$ | $L_{B8}$ |
| 906. | $L_{A73}$ | $L_{B8}$ |
| 907. | $L_{A74}$ | $L_{B8}$ |
| 908. | $L_{A75}$ | $L_{B8}$ |
| 909. | $L_{A76}$ | $L_{B8}$ |
| 910. | $L_{A77}$ | $L_{B8}$ |

-continued

| Compound Number | $L_A$ | $L_B$ |
|---|---|---|
| 911. | $L_{A78}$ | $L_{B8}$ |
| 912. | $L_{A79}$ | $L_{B8}$ |
| 913. | $L_{A80}$ | $L_{B8}$ |
| 914. | $L_{A81}$ | $L_{B8}$ |
| 915. | $L_{A82}$ | $L_{B8}$ |
| 916. | $L_{A83}$ | $L_{B8}$ |
| 917. | $L_{A84}$ | $L_{B8}$ |
| 918. | $L_{A85}$ | $L_{B8}$ |
| 919. | $L_{A86}$ | $L_{B8}$ |
| 920. | $L_{A87}$ | $L_{B8}$ |
| 921. | $L_{A88}$ | $L_{B8}$ |
| 922. | $L_{A89}$ | $L_{B8}$ |
| 923. | $L_{A90}$ | $L_{B8}$ |
| 924. | $L_{A91}$ | $L_{B8}$ |
| 925. | $L_{A92}$ | $L_{B8}$ |
| 926. | $L_{A93}$ | $L_{B8}$ |
| 927. | $L_{A94}$ | $L_{B8}$ |
| 928. | $L_{A95}$ | $L_{B8}$ |
| 929. | $L_{A96}$ | $L_{B8}$ |
| 930. | $L_{A97}$ | $L_{B8}$ |
| 931. | $L_{A98}$ | $L_{B8}$ |
| 932. | $L_{A99}$ | $L_{B8}$ |
| 933. | $L_{A100}$ | $L_{B8}$ |
| 934. | $L_{A101}$ | $L_{B8}$ |
| 935. | $L_{A102}$ | $L_{B8}$ |
| 936. | $L_{A103}$ | $L_{B8}$ |
| 937. | $L_{A104}$ | $L_{B8}$ |
| 938. | $L_{A105}$ | $L_{B8}$ |
| 939. | $L_{A106}$ | $L_{B8}$ |
| 940. | $L_{A107}$ | $L_{B8}$ |
| 941. | $L_{A108}$ | $L_{B8}$ |
| 942. | $L_{A109}$ | $L_{B8}$ |
| 943. | $L_{A110}$ | $L_{B8}$ |
| 944. | $L_{A111}$ | $L_{B8}$ |
| 945. | $L_{A112}$ | $L_{B8}$ |
| 946. | $L_{A113}$ | $L_{B8}$ |
| 947. | $L_{A114}$ | $L_{B8}$ |
| 948. | $L_{A115}$ | $L_{B8}$ |
| 949. | $L_{A116}$ | $L_{B8}$ |
| 950. | $L_{A117}$ | $L_{B8}$ |
| 951. | $L_{A118}$ | $L_{B8}$ |
| 952. | $L_{A119}$ | $L_{B8}$ |
| 953. | $L_{A1}$ | $L_{B9}$ |
| 954. | $L_{A2}$ | $L_{B9}$ |
| 955. | $L_{A3}$ | $L_{B9}$ |
| 956. | $L_{A4}$ | $L_{B9}$ |
| 957. | $L_{A5}$ | $L_{B9}$ |
| 958. | $L_{A6}$ | $L_{B9}$ |
| 959. | $L_{A7}$ | $L_{B9}$ |
| 960. | $L_{A8}$ | $L_{B9}$ |
| 961. | $L_{A9}$ | $L_{B9}$ |
| 962. | $L_{A10}$ | $L_{B9}$ |
| 963. | $L_{A11}$ | $L_{B9}$ |
| 964. | $L_{A12}$ | $L_{B9}$ |
| 965. | $L_{A13}$ | $L_{B9}$ |
| 966. | $L_{A14}$ | $L_{B9}$ |
| 967. | $L_{A15}$ | $L_{B9}$ |
| 968. | $L_{A16}$ | $L_{B9}$ |
| 969. | $L_{A17}$ | $L_{B9}$ |
| 970. | $L_{A18}$ | $L_{B9}$ |
| 971. | $L_{A19}$ | $L_{B9}$ |
| 972. | $L_{A10}$ | $L_{B9}$ |
| 973. | $L_{A21}$ | $L_{B9}$ |
| 974. | $L_{A22}$ | $L_{B9}$ |
| 975. | $L_{A23}$ | $L_{B9}$ |
| 976. | $L_{A24}$ | $L_{B9}$ |
| 977. | $L_{A25}$ | $L_{B9}$ |
| 978. | $L_{A26}$ | $L_{B9}$ |
| 979. | $L_{A27}$ | $L_{B9}$ |
| 980. | $L_{A28}$ | $L_{B9}$ |
| 981. | $L_{A29}$ | $L_{B9}$ |
| 982. | $L_{A30}$ | $L_{B9}$ |
| 983. | $L_{A31}$ | $L_{B9}$ |
| 984. | $L_{A32}$ | $L_{B9}$ |
| 985. | $L_{A33}$ | $L_{B9}$ |
| 986. | $L_{A34}$ | $L_{B9}$ |

-continued

| Compound Number | $L_A$ | $L_B$ |
|---|---|---|
| 987. | $L_{A35}$ | $L_{B9}$ |
| 988. | $L_{A36}$ | $L_{B9}$ |
| 989. | $L_{A37}$ | $L_{B9}$ |
| 990. | $L_{A38}$ | $L_{B9}$ |
| 991. | $L_{A39}$ | $L_{B9}$ |
| 992. | $L_{A40}$ | $L_{B9}$ |
| 993. | $L_{A41}$ | $L_{B9}$ |
| 994. | $L_{A42}$ | $L_{B9}$ |
| 995. | $L_{A43}$ | $L_{B9}$ |
| 996. | $L_{A44}$ | $L_{B9}$ |
| 997. | $L_{A45}$ | $L_{B9}$ |
| 998. | $L_{A46}$ | $L_{B9}$ |
| 999. | $L_{A47}$ | $L_{B9}$ |
| 1000. | $L_{A48}$ | $L_{B9}$ |
| 1001. | $L_{A49}$ | $L_{B9}$ |
| 1002. | $L_{A50}$ | $L_{B9}$ |
| 1003. | $L_{A51}$ | $L_{B9}$ |
| 1004. | $L_{A52}$ | $L_{B9}$ |
| 1005. | $L_{A53}$ | $L_{B9}$ |
| 1006. | $L_{A54}$ | $L_{B9}$ |
| 1007. | $L_{A55}$ | $L_{B9}$ |
| 1008. | $L_{A56}$ | $L_{B9}$ |
| 1009. | $L_{A57}$ | $L_{B9}$ |
| 1010. | $L_{A58}$ | $L_{B9}$ |
| 1011. | $L_{A59}$ | $L_{B9}$ |
| 1012. | $L_{A60}$ | $L_{B9}$ |
| 1013. | $L_{A61}$ | $L_{B9}$ |
| 1014. | $L_{A62}$ | $L_{B9}$ |
| 1015. | $L_{A63}$ | $L_{B9}$ |
| 1016. | $L_{A64}$ | $L_{B9}$ |
| 1017. | $L_{A65}$ | $L_{B9}$ |
| 1018. | $L_{A66}$ | $L_{B9}$ |
| 1019. | $L_{A67}$ | $L_{B9}$ |
| 1020. | $L_{A68}$ | $L_{B9}$ |
| 1021. | $L_{A69}$ | $L_{B9}$ |
| 1022. | $L_{A70}$ | $L_{B9}$ |
| 1023. | $L_{A71}$ | $L_{B9}$ |
| 1024. | $L_{A72}$ | $L_{B9}$ |
| 1025. | $L_{A73}$ | $L_{B9}$ |
| 1026. | $L_{A74}$ | $L_{B9}$ |
| 1027. | $L_{A75}$ | $L_{B9}$ |
| 1028. | $L_{A76}$ | $L_{B9}$ |
| 1029. | $L_{A77}$ | $L_{B9}$ |
| 1030. | $L_{A78}$ | $L_{B9}$ |
| 1031. | $L_{A79}$ | $L_{B9}$ |
| 1032. | $L_{A80}$ | $L_{B9}$ |
| 1033. | $L_{A81}$ | $L_{B9}$ |
| 1034. | $L_{A82}$ | $L_{B9}$ |
| 1035. | $L_{A83}$ | $L_{B9}$ |
| 1036. | $L_{A84}$ | $L_{B9}$ |
| 1037. | $L_{A85}$ | $L_{B9}$ |
| 1038. | $L_{A86}$ | $L_{B9}$ |
| 1039. | $L_{A87}$ | $L_{B9}$ |
| 1040. | $L_{A88}$ | $L_{B9}$ |
| 1041. | $L_{A89}$ | $L_{B9}$ |
| 1042. | $L_{A90}$ | $L_{B9}$ |
| 1043. | $L_{A91}$ | $L_{B9}$ |
| 1044. | $L_{A92}$ | $L_{B9}$ |
| 1045. | $L_{A93}$ | $L_{B9}$ |
| 1046. | $L_{A94}$ | $L_{B9}$ |
| 1047. | $L_{A95}$ | $L_{B9}$ |
| 1048. | $L_{A96}$ | $L_{B9}$ |
| 1049. | $L_{A97}$ | $L_{B9}$ |
| 1050. | $L_{A98}$ | $L_{B9}$ |
| 1051. | $L_{A99}$ | $L_{B9}$ |
| 1052. | $L_{A100}$ | $L_{B9}$ |
| 1053. | $L_{A101}$ | $L_{B9}$ |
| 1054. | $L_{A102}$ | $L_{B9}$ |
| 1055. | $L_{A103}$ | $L_{B9}$ |
| 1056. | $L_{A104}$ | $L_{B9}$ |
| 1057. | $L_{A105}$ | $L_{B9}$ |
| 1058. | $L_{A106}$ | $L_{B9}$ |
| 1059. | $L_{A107}$ | $L_{B9}$ |
| 1060. | $L_{A108}$ | $L_{B9}$ |
| 1061. | $L_{A109}$ | $L_{B9}$ |
| 1062. | $L_{A110}$ | $L_{B9}$ |

-continued

| Compound Number | $L_A$ | $L_B$ |
|---|---|---|
| 1063. | $L_{A111}$ | $L_{B9}$ |
| 1064. | $L_{A112}$ | $L_{B9}$ |
| 1065. | $L_{A113}$ | $L_{B9}$ |
| 1066. | $L_{A114}$ | $L_{B9}$ |
| 1067. | $L_{A115}$ | $L_{B9}$ |
| 1068. | $L_{A116}$ | $L_{B9}$ |
| 1069. | $L_{A117}$ | $L_{B9}$ |
| 1070. | $L_{A118}$ | $L_{B9}$ |
| 1071. | $L_{A119}$ | $L_{B9}$ |
| 1072. | $L_{A1}$ | $L_{B10}$ |
| 1073. | $L_{A2}$ | $L_{B10}$ |
| 1074. | $L_{A3}$ | $L_{B10}$ |
| 1075. | $L_{A4}$ | $L_{B10}$ |
| 1076. | $L_{A5}$ | $L_{B10}$ |
| 1077. | $L_{A6}$ | $L_{B10}$ |
| 1078. | $L_{A7}$ | $L_{B10}$ |
| 1079. | $L_{A8}$ | $L_{B10}$ |
| 1080. | $L_{A9}$ | $L_{B10}$ |
| 1081. | $L_{A10}$ | $L_{B10}$ |
| 1082. | $L_{A11}$ | $L_{B10}$ |
| 1083. | $L_{A12}$ | $L_{B10}$ |
| 1084. | $L_{A13}$ | $L_{B10}$ |
| 1085. | $L_{A14}$ | $L_{B10}$ |
| 1086. | $L_{A15}$ | $L_{B10}$ |
| 1087. | $L_{A16}$ | $L_{B10}$ |
| 1088. | $L_{A17}$ | $L_{B10}$ |
| 1089. | $L_{A18}$ | $L_{B10}$ |
| 1090. | $L_{A19}$ | $L_{B10}$ |
| 1091. | $L_{A10}$ | $L_{B10}$ |
| 1092. | $L_{A21}$ | $L_{B10}$ |
| 1093. | $L_{A22}$ | $L_{B10}$ |
| 1094. | $L_{A23}$ | $L_{B10}$ |
| 1095. | $L_{A24}$ | $L_{B10}$ |
| 1096. | $L_{A25}$ | $L_{B10}$ |
| 1097. | $L_{A26}$ | $L_{B10}$ |
| 1098. | $L_{A27}$ | $L_{B10}$ |
| 1099. | $L_{A28}$ | $L_{B10}$ |
| 1100. | $L_{A29}$ | $L_{B10}$ |
| 1101. | $L_{A30}$ | $L_{B10}$ |
| 1102. | $L_{A31}$ | $L_{B10}$ |
| 1103. | $L_{A32}$ | $L_{B10}$ |
| 1104. | $L_{A33}$ | $L_{B10}$ |
| 1105. | $L_{A34}$ | $L_{B10}$ |
| 1106. | $L_{A35}$ | $L_{B10}$ |
| 1107. | $L_{A36}$ | $L_{B10}$ |
| 1108. | $L_{A37}$ | $L_{B10}$ |
| 1109. | $L_{A38}$ | $L_{B10}$ |
| 1110. | $L_{A39}$ | $L_{B10}$ |
| 1111. | $L_{A40}$ | $L_{B10}$ |
| 1112. | $L_{A41}$ | $L_{B10}$ |
| 1113. | $L_{A42}$ | $L_{B10}$ |
| 1114. | $L_{A43}$ | $L_{B10}$ |
| 1115. | $L_{A44}$ | $L_{B10}$ |
| 1116. | $L_{A45}$ | $L_{B10}$ |
| 1117. | $L_{A46}$ | $L_{B10}$ |
| 1118. | $L_{A47}$ | $L_{B10}$ |
| 1119. | $L_{A48}$ | $L_{B10}$ |
| 1120. | $L_{A49}$ | $L_{B10}$ |
| 1121. | $L_{A50}$ | $L_{B10}$ |
| 1122. | $L_{A51}$ | $L_{B10}$ |
| 1123. | $L_{A52}$ | $L_{B10}$ |
| 1124. | $L_{A53}$ | $L_{B10}$ |
| 1125. | $L_{A54}$ | $L_{B10}$ |
| 1126. | $L_{A55}$ | $L_{B10}$ |
| 1127. | $L_{A56}$ | $L_{B10}$ |
| 1128. | $L_{A57}$ | $L_{B10}$ |
| 1129. | $L_{A58}$ | $L_{B10}$ |
| 1130. | $L_{A59}$ | $L_{B10}$ |
| 1131. | $L_{A60}$ | $L_{B10}$ |
| 1132. | $L_{A61}$ | $L_{B10}$ |
| 1133. | $L_{A62}$ | $L_{B10}$ |
| 1134. | $L_{A63}$ | $L_{B10}$ |
| 1135. | $L_{A64}$ | $L_{B10}$ |
| 1136. | $L_{A65}$ | $L_{B10}$ |
| 1137. | $L_{A66}$ | $L_{B10}$ |
| 1138. | $L_{A67}$ | $L_{B10}$ |

-continued

| Compound Number | $L_A$ | $L_B$ |
|---|---|---|
| 1139. | $L_{A68}$ | $L_{B10}$ |
| 1140. | $L_{A69}$ | $L_{B10}$ |
| 1141. | $L_{A70}$ | $L_{B10}$ |
| 1142. | $L_{A71}$ | $L_{B10}$ |
| 1143. | $L_{A72}$ | $L_{B10}$ |
| 1144. | $L_{A73}$ | $L_{B10}$ |
| 1145. | $L_{A74}$ | $L_{B10}$ |
| 1146. | $L_{A75}$ | $L_{B10}$ |
| 1147. | $L_{A76}$ | $L_{B10}$ |
| 1148. | $L_{A77}$ | $L_{B10}$ |
| 1149. | $L_{A78}$ | $L_{B10}$ |
| 1150. | $L_{A79}$ | $L_{B10}$ |
| 1151. | $L_{A80}$ | $L_{B10}$ |
| 1152. | $L_{A81}$ | $L_{B10}$ |
| 1153. | $L_{A82}$ | $L_{B10}$ |
| 1154. | $L_{A83}$ | $L_{B10}$ |
| 1155. | $L_{A84}$ | $L_{B10}$ |
| 1156. | $L_{A85}$ | $L_{B10}$ |
| 1157. | $L_{A86}$ | $L_{B10}$ |
| 1158. | $L_{A87}$ | $L_{B10}$ |
| 1159. | $L_{A88}$ | $L_{B10}$ |
| 1160. | $L_{A89}$ | $L_{B10}$ |
| 1161. | $L_{A90}$ | $L_{B10}$ |
| 1162. | $L_{A91}$ | $L_{B10}$ |
| 1163. | $L_{A92}$ | $L_{B10}$ |
| 1164. | $L_{A93}$ | $L_{B10}$ |
| 1165. | $L_{A94}$ | $L_{B10}$ |
| 1166. | $L_{A95}$ | $L_{B10}$ |
| 1167. | $L_{A96}$ | $L_{B10}$ |
| 1168. | $L_{A97}$ | $L_{B10}$ |
| 1169. | $L_{A98}$ | $L_{B10}$ |
| 1170. | $L_{A99}$ | $L_{B10}$ |
| 1171. | $L_{A100}$ | $L_{B10}$ |
| 1172. | $L_{A101}$ | $L_{B10}$ |
| 1173. | $L_{A102}$ | $L_{B10}$ |
| 1174. | $L_{A103}$ | $L_{B10}$ |
| 1175. | $L_{A104}$ | $L_{B10}$ |
| 1176. | $L_{A105}$ | $L_{B10}$ |
| 1177. | $L_{A106}$ | $L_{B10}$ |
| 1178. | $L_{A107}$ | $L_{B10}$ |
| 1179. | $L_{A108}$ | $L_{B10}$ |
| 1180. | $L_{A109}$ | $L_{B10}$ |
| 1181. | $L_{A110}$ | $L_{B10}$ |
| 1182. | $L_{A111}$ | $L_{B10}$ |
| 1183. | $L_{A112}$ | $L_{B10}$ |
| 1184. | $L_{A113}$ | $L_{B10}$ |
| 1185. | $L_{A114}$ | $L_{B10}$ |
| 1186. | $L_{A115}$ | $L_{B10}$ |
| 1187. | $L_{A116}$ | $L_{B10}$ |
| 1188. | $L_{A117}$ | $L_{B10}$ |
| 1189. | $L_{A118}$ | $L_{B10}$ |
| 1190. | $L_{A119}$ | $L_{B10}$ |
| 1191. | $L_{A1}$ | $L_{B11}$ |
| 1192. | $L_{A2}$ | $L_{B11}$ |
| 1193. | $L_{A3}$ | $L_{B11}$ |
| 1194. | $L_{A4}$ | $L_{B11}$ |
| 1195. | $L_{A5}$ | $L_{B11}$ |
| 1196. | $L_{A6}$ | $L_{B11}$ |
| 1197. | $L_{A7}$ | $L_{B11}$ |
| 1198. | $L_{A8}$ | $L_{B11}$ |
| 1199. | $L_{A9}$ | $L_{B11}$ |
| 1200. | $L_{A10}$ | $L_{B11}$ |
| 1201. | $L_{A11}$ | $L_{B11}$ |
| 1202. | $L_{A12}$ | $L_{B11}$ |
| 1203. | $L_{A13}$ | $L_{B11}$ |
| 1204. | $L_{A14}$ | $L_{B11}$ |
| 1205. | $L_{A15}$ | $L_{B11}$ |
| 1206. | $L_{A16}$ | $L_{B11}$ |
| 1207. | $L_{A17}$ | $L_{B11}$ |
| 1208. | $L_{A18}$ | $L_{B11}$ |
| 1209. | $L_{A19}$ | $L_{B11}$ |
| 1210. | $L_{A10}$ | $L_{B11}$ |
| 1211. | $L_{A21}$ | $L_{B11}$ |
| 1212. | $L_{A22}$ | $L_{B11}$ |
| 1213. | $L_{A23}$ | $L_{B11}$ |
| 1214. | $L_{A24}$ | $L_{B11}$ |

-continued

| Compound Number | $L_A$ | $L_B$ |
|---|---|---|
| 1215. | $L_{A25}$ | $L_{B11}$ |
| 1216. | $L_{A26}$ | $L_{B11}$ |
| 1217. | $L_{A27}$ | $L_{B11}$ |
| 1218. | $L_{A28}$ | $L_{B11}$ |
| 1219. | $L_{A29}$ | $L_{B11}$ |
| 1220. | $L_{A30}$ | $L_{B11}$ |
| 1221. | $L_{A31}$ | $L_{B11}$ |
| 1222. | $L_{A32}$ | $L_{B11}$ |
| 1223. | $L_{A33}$ | $L_{B11}$ |
| 1224. | $L_{A34}$ | $L_{B11}$ |
| 1225. | $L_{A35}$ | $L_{B11}$ |
| 1226. | $L_{A36}$ | $L_{B11}$ |
| 1227. | $L_{A37}$ | $L_{B11}$ |
| 1228. | $L_{A38}$ | $L_{B11}$ |
| 1229. | $L_{A39}$ | $L_{B11}$ |
| 1230. | $L_{A40}$ | $L_{B11}$ |
| 1231. | $L_{A41}$ | $L_{B11}$ |
| 1232. | $L_{A42}$ | $L_{B11}$ |
| 1233. | $L_{A43}$ | $L_{B11}$ |
| 1234. | $L_{A44}$ | $L_{B11}$ |
| 1235. | $L_{A45}$ | $L_{B11}$ |
| 1236. | $L_{A46}$ | $L_{B11}$ |
| 1237. | $L_{A47}$ | $L_{B11}$ |
| 1238. | $L_{A48}$ | $L_{B11}$ |
| 1239. | $L_{A49}$ | $L_{B11}$ |
| 1240. | $L_{A50}$ | $L_{B11}$ |
| 1241. | $L_{A51}$ | $L_{B11}$ |
| 1242. | $L_{A52}$ | $L_{B11}$ |
| 1243. | $L_{A53}$ | $L_{B11}$ |
| 1244. | $L_{A54}$ | $L_{B11}$ |
| 1245. | $L_{A55}$ | $L_{B11}$ |
| 1246. | $L_{A56}$ | $L_{B11}$ |
| 1247. | $L_{A57}$ | $L_{B11}$ |
| 1248. | $L_{A58}$ | $L_{B11}$ |
| 1249. | $L_{A59}$ | $L_{B11}$ |
| 1250. | $L_{A60}$ | $L_{B11}$ |
| 1251. | $L_{A61}$ | $L_{B11}$ |
| 1252. | $L_{A62}$ | $L_{B11}$ |
| 1253. | $L_{A63}$ | $L_{B11}$ |
| 1254. | $L_{A64}$ | $L_{B11}$ |
| 1255. | $L_{A65}$ | $L_{B11}$ |
| 1256. | $L_{A66}$ | $L_{B11}$ |
| 1257. | $L_{A67}$ | $L_{B11}$ |
| 1258. | $L_{A68}$ | $L_{B11}$ |
| 1259. | $L_{A69}$ | $L_{B11}$ |
| 1260. | $L_{A70}$ | $L_{B11}$ |
| 1261. | $L_{A71}$ | $L_{B11}$ |
| 1262. | $L_{A72}$ | $L_{B11}$ |
| 1263. | $L_{A73}$ | $L_{B11}$ |
| 1264. | $L_{A74}$ | $L_{B11}$ |
| 1265. | $L_{A75}$ | $L_{B11}$ |
| 1266. | $L_{A76}$ | $L_{B11}$ |
| 1267. | $L_{A77}$ | $L_{B11}$ |
| 1268. | $L_{A78}$ | $L_{B11}$ |
| 1269. | $L_{A79}$ | $L_{B11}$ |
| 1270. | $L_{A80}$ | $L_{B11}$ |
| 1271. | $L_{A81}$ | $L_{B11}$ |
| 1272. | $L_{A82}$ | $L_{B11}$ |
| 1273. | $L_{A83}$ | $L_{B11}$ |
| 1274. | $L_{A84}$ | $L_{B11}$ |
| 1275. | $L_{A85}$ | $L_{B11}$ |
| 1276. | $L_{A86}$ | $L_{B11}$ |
| 1277. | $L_{A87}$ | $L_{B11}$ |
| 1278. | $L_{A88}$ | $L_{B11}$ |
| 1279. | $L_{A89}$ | $L_{B11}$ |
| 1280. | $L_{A90}$ | $L_{B11}$ |
| 1281. | $L_{A91}$ | $L_{B11}$ |
| 1282. | $L_{A92}$ | $L_{B11}$ |
| 1283. | $L_{A93}$ | $L_{B11}$ |
| 1284. | $L_{A94}$ | $L_{B11}$ |
| 1285. | $L_{A95}$ | $L_{B11}$ |
| 1286. | $L_{A96}$ | $L_{B11}$ |
| 1287. | $L_{A97}$ | $L_{B11}$ |
| 1288. | $L_{A98}$ | $L_{B11}$ |
| 1289. | $L_{A99}$ | $L_{B11}$ |
| 1290. | $L_{A100}$ | $L_{B11}$ |

-continued

| Compound Number | $L_A$ | $L_B$ |
|---|---|---|
| 1291. | $L_{A101}$ | $L_{B11}$ |
| 1292. | $L_{A102}$ | $L_{B11}$ |
| 1293. | $L_{A103}$ | $L_{B11}$ |
| 1294. | $L_{A104}$ | $L_{B11}$ |
| 1295. | $L_{A105}$ | $L_{B11}$ |
| 1296. | $L_{A106}$ | $L_{B11}$ |
| 1297. | $L_{A107}$ | $L_{B11}$ |
| 1298. | $L_{A108}$ | $L_{B11}$ |
| 1299. | $L_{A109}$ | $L_{B11}$ |
| 1300. | $L_{A110}$ | $L_{B11}$ |
| 1301. | $L_{A111}$ | $L_{B11}$ |
| 1302. | $L_{A112}$ | $L_{B11}$ |
| 1303. | $L_{A113}$ | $L_{B11}$ |
| 1304. | $L_{A114}$ | $L_{B11}$ |
| 1305. | $L_{A115}$ | $L_{B11}$ |
| 1306. | $L_{A116}$ | $L_{B11}$ |
| 1307. | $L_{A117}$ | $L_{B11}$ |
| 1308. | $L_{A118}$ | $L_{B11}$ |
| 1309. | $L_{A119}$ | $L_{B11}$ |
| 1310. | $L_{A1}$ | $L_{B12}$ |
| 1311. | $L_{A2}$ | $L_{B12}$ |
| 1312. | $L_{A3}$ | $L_{B12}$ |
| 1313. | $L_{A4}$ | $L_{B12}$ |
| 1314. | $L_{A5}$ | $L_{B12}$ |
| 1315. | $L_{A6}$ | $L_{B12}$ |
| 1316. | $L_{A7}$ | $L_{B12}$ |
| 1317. | $L_{A8}$ | $L_{B12}$ |
| 1318. | $L_{A9}$ | $L_{B12}$ |
| 1319. | $L_{A10}$ | $L_{B12}$ |
| 1320. | $L_{A11}$ | $L_{B12}$ |
| 1321. | $L_{A12}$ | $L_{B12}$ |
| 1322. | $L_{A13}$ | $L_{B12}$ |
| 1323. | $L_{A14}$ | $L_{B12}$ |
| 1324. | $L_{A15}$ | $L_{B12}$ |
| 1325. | $L_{A16}$ | $L_{B12}$ |
| 1326. | $L_{A17}$ | $L_{B12}$ |
| 1327. | $L_{A18}$ | $L_{B12}$ |
| 1328. | $L_{A19}$ | $L_{B12}$ |
| 1329. | $L_{A10}$ | $L_{B12}$ |
| 1330. | $L_{A21}$ | $L_{B12}$ |
| 1331. | $L_{A22}$ | $L_{B12}$ |
| 1332. | $L_{A23}$ | $L_{B12}$ |
| 1333. | $L_{A24}$ | $L_{B12}$ |
| 1334. | $L_{A25}$ | $L_{B12}$ |
| 1335. | $L_{A26}$ | $L_{B12}$ |
| 1336. | $L_{A27}$ | $L_{B12}$ |
| 1337. | $L_{A28}$ | $L_{B12}$ |
| 1338. | $L_{A29}$ | $L_{B12}$ |
| 1339. | $L_{A30}$ | $L_{B12}$ |
| 1340. | $L_{A31}$ | $L_{B12}$ |
| 1341. | $L_{A32}$ | $L_{B12}$ |
| 1342. | $L_{A33}$ | $L_{B12}$ |
| 1343. | $L_{A34}$ | $L_{B12}$ |
| 1344. | $L_{A35}$ | $L_{B12}$ |
| 1345. | $L_{A36}$ | $L_{B12}$ |
| 1346. | $L_{A37}$ | $L_{B12}$ |
| 1347. | $L_{A38}$ | $L_{B12}$ |
| 1348. | $L_{A39}$ | $L_{B12}$ |
| 1349. | $L_{A40}$ | $L_{B12}$ |
| 1350. | $L_{A41}$ | $L_{B12}$ |
| 1351. | $L_{A42}$ | $L_{B12}$ |
| 1352. | $L_{A43}$ | $L_{B12}$ |
| 1353. | $L_{A44}$ | $L_{B12}$ |
| 1354. | $L_{A45}$ | $L_{B12}$ |
| 1355. | $L_{A46}$ | $L_{B12}$ |
| 1356. | $L_{A47}$ | $L_{B12}$ |
| 1357. | $L_{A48}$ | $L_{B12}$ |
| 1358. | $L_{A49}$ | $L_{B12}$ |
| 1359. | $L_{A50}$ | $L_{B12}$ |
| 1360. | $L_{A51}$ | $L_{B12}$ |
| 1361. | $L_{A52}$ | $L_{B12}$ |
| 1362. | $L_{A53}$ | $L_{B12}$ |
| 1363. | $L_{A54}$ | $L_{B12}$ |
| 1364. | $L_{A55}$ | $L_{B12}$ |
| 1365. | $L_{A56}$ | $L_{B12}$ |
| 1366. | $L_{A57}$ | $L_{B12}$ |
| 1367. | $L_{A58}$ | $L_{B12}$ |
| 1368. | $L_{A59}$ | $L_{B12}$ |
| 1369. | $L_{A60}$ | $L_{B12}$ |
| 1370. | $L_{A61}$ | $L_{B12}$ |
| 1371. | $L_{A62}$ | $L_{B12}$ |
| 1372. | $L_{A63}$ | $L_{B12}$ |
| 1373. | $L_{A64}$ | $L_{B12}$ |
| 1374. | $L_{A65}$ | $L_{B12}$ |
| 1375. | $L_{A66}$ | $L_{B12}$ |
| 1376. | $L_{A67}$ | $L_{B12}$ |
| 1377. | $L_{A68}$ | $L_{B12}$ |
| 1378. | $L_{A69}$ | $L_{B12}$ |
| 1379. | $L_{A70}$ | $L_{B12}$ |
| 1380. | $L_{A71}$ | $L_{B12}$ |
| 1381. | $L_{A72}$ | $L_{B12}$ |
| 1382. | $L_{A73}$ | $L_{B12}$ |
| 1383. | $L_{A74}$ | $L_{B12}$ |
| 1384. | $L_{A75}$ | $L_{B12}$ |
| 1385. | $L_{A76}$ | $L_{B12}$ |
| 1386. | $L_{A77}$ | $L_{B12}$ |
| 1387. | $L_{A78}$ | $L_{B12}$ |
| 1388. | $L_{A79}$ | $L_{B12}$ |
| 1389. | $L_{A80}$ | $L_{B12}$ |
| 1390. | $L_{A81}$ | $L_{B12}$ |
| 1391. | $L_{A82}$ | $L_{B12}$ |
| 1392. | $L_{A83}$ | $L_{B12}$ |
| 1393. | $L_{A84}$ | $L_{B12}$ |
| 1394. | $L_{A85}$ | $L_{B12}$ |
| 1395. | $L_{A86}$ | $L_{B12}$ |
| 1396. | $L_{A87}$ | $L_{B12}$ |
| 1397. | $L_{A88}$ | $L_{B12}$ |
| 1398. | $L_{A89}$ | $L_{B12}$ |
| 1399. | $L_{A90}$ | $L_{B12}$ |
| 1400. | $L_{A91}$ | $L_{B12}$ |
| 1401. | $L_{A92}$ | $L_{B12}$ |
| 1402. | $L_{A93}$ | $L_{B12}$ |
| 1403. | $L_{A94}$ | $L_{B12}$ |
| 1404. | $L_{A95}$ | $L_{B12}$ |
| 1405. | $L_{A96}$ | $L_{B12}$ |
| 1406. | $L_{A97}$ | $L_{B12}$ |
| 1407. | $L_{A98}$ | $L_{B12}$ |
| 1408. | $L_{A99}$ | $L_{B12}$ |
| 1409. | $L_{A100}$ | $L_{B12}$ |
| 1410. | $L_{A101}$ | $L_{B12}$ |
| 1411. | $L_{A102}$ | $L_{B12}$ |
| 1412. | $L_{A103}$ | $L_{B12}$ |
| 1413. | $L_{A104}$ | $L_{B12}$ |
| 1414. | $L_{A105}$ | $L_{B12}$ |
| 1415. | $L_{A106}$ | $L_{B12}$ |
| 1416. | $L_{A107}$ | $L_{B12}$ |
| 1417. | $L_{A108}$ | $L_{B12}$ |
| 1418. | $L_{A109}$ | $L_{B12}$ |
| 1419. | $L_{A110}$ | $L_{B12}$ |
| 1420. | $L_{A111}$ | $L_{B12}$ |
| 1421. | $L_{A112}$ | $L_{B12}$ |
| 1422. | $L_{A113}$ | $L_{B12}$ |
| 1423. | $L_{A114}$ | $L_{B12}$ |
| 1424. | $L_{A115}$ | $L_{B12}$ |
| 1425. | $L_{A116}$ | $L_{B12}$ |
| 1426. | $L_{A117}$ | $L_{B12}$ |
| 1427. | $L_{A118}$ | $L_{B12}$ |
| 1428. | $L_{A119}$ | $L_{B12}$ |
| 1429. | $L_{A1}$ | $L_{B13}$ |
| 1430. | $L_{A2}$ | $L_{B13}$ |
| 1431. | $L_{A3}$ | $L_{B13}$ |
| 1432. | $L_{A4}$ | $L_{B13}$ |
| 1433. | $L_{A5}$ | $L_{B13}$ |
| 1434. | $L_{A6}$ | $L_{B13}$ |
| 1435. | $L_{A7}$ | $L_{B13}$ |
| 1436. | $L_{A8}$ | $L_{B13}$ |
| 1437. | $L_{A9}$ | $L_{B13}$ |
| 1438. | $L_{A10}$ | $L_{B13}$ |
| 1439. | $L_{A11}$ | $L_{B13}$ |
| 1440. | $L_{A12}$ | $L_{B13}$ |
| 1441. | $L_{A13}$ | $L_{B13}$ |
| 1442. | $L_{A14}$ | $L_{B13}$ |

-continued

| Compound Number | $L_A$ | $L_B$ |
|---|---|---|
| 1443. | $L_{A15}$ | $L_{B13}$ |
| 1444. | $L_{A16}$ | $L_{B13}$ |
| 1445. | $L_{A17}$ | $L_{B13}$ |
| 1446. | $L_{A18}$ | $L_{B13}$ |
| 1447. | $L_{A19}$ | $L_{B13}$ |
| 1448. | $L_{A10}$ | $L_{B13}$ |
| 1449. | $L_{A21}$ | $L_{B13}$ |
| 1450. | $L_{A22}$ | $L_{B13}$ |
| 1451. | $L_{A23}$ | $L_{B13}$ |
| 1452. | $L_{A24}$ | $L_{B13}$ |
| 1453. | $L_{A25}$ | $L_{B13}$ |
| 1454. | $L_{A26}$ | $L_{B13}$ |
| 1455. | $L_{A27}$ | $L_{B13}$ |
| 1456. | $L_{A28}$ | $L_{B13}$ |
| 1457. | $L_{A29}$ | $L_{B13}$ |
| 1458. | $L_{A30}$ | $L_{B13}$ |
| 1459. | $L_{A31}$ | $L_{B13}$ |
| 1460. | $L_{A32}$ | $L_{B13}$ |
| 1461. | $L_{A33}$ | $L_{B13}$ |
| 1462. | $L_{A34}$ | $L_{B13}$ |
| 1463. | $L_{A35}$ | $L_{B13}$ |
| 1464. | $L_{A36}$ | $L_{B13}$ |
| 1465. | $L_{A37}$ | $L_{B13}$ |
| 1466. | $L_{A38}$ | $L_{B13}$ |
| 1467. | $L_{A39}$ | $L_{B13}$ |
| 1468. | $L_{A40}$ | $L_{B13}$ |
| 1469. | $L_{A41}$ | $L_{B13}$ |
| 1470. | $L_{A42}$ | $L_{B13}$ |
| 1471. | $L_{A43}$ | $L_{B13}$ |
| 1472. | $L_{A44}$ | $L_{B13}$ |
| 1473. | $L_{A45}$ | $L_{B13}$ |
| 1474. | $L_{A46}$ | $L_{B13}$ |
| 1475. | $L_{A47}$ | $L_{B13}$ |
| 1476. | $L_{A48}$ | $L_{B13}$ |
| 1477. | $L_{A49}$ | $L_{B13}$ |
| 1478. | $L_{A50}$ | $L_{B13}$ |
| 1479. | $L_{A51}$ | $L_{B13}$ |
| 1480. | $L_{A52}$ | $L_{B13}$ |
| 1481. | $L_{A53}$ | $L_{B13}$ |
| 1482. | $L_{A54}$ | $L_{B13}$ |
| 1483. | $L_{A55}$ | $L_{B13}$ |
| 1484. | $L_{A56}$ | $L_{B13}$ |
| 1485. | $L_{A57}$ | $L_{B13}$ |
| 1486. | $L_{A58}$ | $L_{B13}$ |
| 1487. | $L_{A59}$ | $L_{B13}$ |
| 1488. | $L_{A60}$ | $L_{B13}$ |
| 1489. | $L_{A61}$ | $L_{B13}$ |
| 1490. | $L_{A62}$ | $L_{B13}$ |
| 1491. | $L_{A63}$ | $L_{B13}$ |
| 1492. | $L_{A64}$ | $L_{B13}$ |
| 1493. | $L_{A65}$ | $L_{B13}$ |
| 1494. | $L_{A66}$ | $L_{B13}$ |
| 1495. | $L_{A67}$ | $L_{B13}$ |
| 1496. | $L_{A68}$ | $L_{B13}$ |
| 1497. | $L_{A69}$ | $L_{B13}$ |
| 1498. | $L_{A70}$ | $L_{B13}$ |
| 1499. | $L_{A71}$ | $L_{B13}$ |
| 1500. | $L_{A72}$ | $L_{B13}$ |
| 1501. | $L_{A73}$ | $L_{B13}$ |
| 1502. | $L_{A74}$ | $L_{B13}$ |
| 1503. | $L_{A75}$ | $L_{B13}$ |
| 1504. | $L_{A76}$ | $L_{B13}$ |
| 1505. | $L_{A77}$ | $L_{B13}$ |
| 1506. | $L_{A78}$ | $L_{B13}$ |
| 1507. | $L_{A79}$ | $L_{B13}$ |
| 1508. | $L_{A80}$ | $L_{B13}$ |
| 1509. | $L_{A81}$ | $L_{B13}$ |
| 1510. | $L_{A82}$ | $L_{B13}$ |
| 1511. | $L_{A83}$ | $L_{B13}$ |
| 1512. | $L_{A84}$ | $L_{B13}$ |
| 1513. | $L_{A85}$ | $L_{B13}$ |
| 1514. | $L_{A86}$ | $L_{B13}$ |
| 1515. | $L_{A87}$ | $L_{B13}$ |
| 1516. | $L_{A88}$ | $L_{B13}$ |
| 1517. | $L_{A89}$ | $L_{B13}$ |
| 1518. | $L_{A90}$ | $L_{B13}$ |
| 1519. | $L_{A91}$ | $L_{B13}$ |
| 1520. | $L_{A92}$ | $L_{B13}$ |
| 1521. | $L_{A93}$ | $L_{B13}$ |
| 1522. | $L_{A94}$ | $L_{B13}$ |
| 1523. | $L_{A95}$ | $L_{B13}$ |
| 1524. | $L_{A96}$ | $L_{B13}$ |
| 1525. | $L_{A97}$ | $L_{B13}$ |
| 1526. | $L_{A98}$ | $L_{B13}$ |
| 1527. | $L_{A99}$ | $L_{B13}$ |
| 1528. | $L_{A100}$ | $L_{B13}$ |
| 1529. | $L_{A101}$ | $L_{B13}$ |
| 1530. | $L_{A102}$ | $L_{B13}$ |
| 1531. | $L_{A103}$ | $L_{B13}$ |
| 1532. | $L_{A104}$ | $L_{B13}$ |
| 1533. | $L_{A105}$ | $L_{B13}$ |
| 1534. | $L_{A106}$ | $L_{B13}$ |
| 1535. | $L_{A107}$ | $L_{B13}$ |
| 1536. | $L_{A108}$ | $L_{B13}$ |
| 1537. | $L_{A109}$ | $L_{B13}$ |
| 1538. | $L_{A110}$ | $L_{B13}$ |
| 1539. | $L_{A111}$ | $L_{B13}$ |
| 1540. | $L_{A112}$ | $L_{B13}$ |
| 1541. | $L_{A113}$ | $L_{B13}$ |
| 1542. | $L_{A114}$ | $L_{B13}$ |
| 1543. | $L_{A115}$ | $L_{B13}$ |
| 1544. | $L_{A116}$ | $L_{B13}$ |
| 1545. | $L_{A117}$ | $L_{B13}$ |
| 1546. | $L_{A118}$ | $L_{B13}$ |
| 1547. | $L_{A119}$ | $L_{B13}$ |
| 1548. | $L_{A1}$ | $L_{B14}$ |
| 1549. | $L_{A2}$ | $L_{B14}$ |
| 1550. | $L_{A3}$ | $L_{B14}$ |
| 1551. | $L_{A4}$ | $L_{B14}$ |
| 1552. | $L_{A5}$ | $L_{B14}$ |
| 1553. | $L_{A6}$ | $L_{B14}$ |
| 1554. | $L_{A7}$ | $L_{B14}$ |
| 1555. | $L_{A8}$ | $L_{B14}$ |
| 1556. | $L_{A9}$ | $L_{B14}$ |
| 1557. | $L_{A10}$ | $L_{B14}$ |
| 1558. | $L_{A11}$ | $L_{B14}$ |
| 1559. | $L_{A12}$ | $L_{B14}$ |
| 1560. | $L_{A13}$ | $L_{B14}$ |
| 1561. | $L_{A14}$ | $L_{B14}$ |
| 1562. | $L_{A15}$ | $L_{B14}$ |
| 1563. | $L_{A16}$ | $L_{B14}$ |
| 1564. | $L_{A17}$ | $L_{B14}$ |
| 1565. | $L_{A18}$ | $L_{B14}$ |
| 1566. | $L_{A19}$ | $L_{B14}$ |
| 1567. | $L_{A10}$ | $L_{B14}$ |
| 1568. | $L_{A21}$ | $L_{B14}$ |
| 1569. | $L_{A22}$ | $L_{B14}$ |
| 1570. | $L_{A23}$ | $L_{B14}$ |
| 1571. | $L_{A24}$ | $L_{B14}$ |
| 1572. | $L_{A25}$ | $L_{B14}$ |
| 1573. | $L_{A26}$ | $L_{B14}$ |
| 1574. | $L_{A27}$ | $L_{B14}$ |
| 1575. | $L_{A28}$ | $L_{B14}$ |
| 1576. | $L_{A29}$ | $L_{B14}$ |
| 1577. | $L_{A30}$ | $L_{B14}$ |
| 1578. | $L_{A31}$ | $L_{B14}$ |
| 1579. | $L_{A32}$ | $L_{B14}$ |
| 1580. | $L_{A33}$ | $L_{B14}$ |
| 1581. | $L_{A34}$ | $L_{B14}$ |
| 1582. | $L_{A35}$ | $L_{B14}$ |
| 1583. | $L_{A36}$ | $L_{B14}$ |
| 1584. | $L_{A37}$ | $L_{B14}$ |
| 1585. | $L_{A38}$ | $L_{B14}$ |
| 1586. | $L_{A39}$ | $L_{B14}$ |
| 1587. | $L_{A40}$ | $L_{B14}$ |
| 1588. | $L_{A41}$ | $L_{B14}$ |
| 1589. | $L_{A42}$ | $L_{B14}$ |
| 1590. | $L_{A43}$ | $L_{B14}$ |
| 1591. | $L_{A44}$ | $L_{B14}$ |
| 1592. | $L_{A45}$ | $L_{B14}$ |
| 1593. | $L_{A46}$ | $L_{B14}$ |
| 1594. | $L_{A47}$ | $L_{B14}$ |

-continued

| Compound Number | $L_A$ | $L_B$ |
|---|---|---|
| 1595. | $L_{A48}$ | $L_{B14}$ |
| 1596. | $L_{A49}$ | $L_{B14}$ |
| 1597. | $L_{A50}$ | $L_{B14}$ |
| 1598. | $L_{A51}$ | $L_{B14}$ |
| 1599. | $L_{A52}$ | $L_{B14}$ |
| 1600. | $L_{A53}$ | $L_{B14}$ |
| 1601. | $L_{A54}$ | $L_{B14}$ |
| 1602. | $L_{A55}$ | $L_{B14}$ |
| 1603. | $L_{A56}$ | $L_{B14}$ |
| 1604. | $L_{A57}$ | $L_{B14}$ |
| 1605. | $L_{A58}$ | $L_{B14}$ |
| 1606. | $L_{A59}$ | $L_{B14}$ |
| 1607. | $L_{A60}$ | $L_{B14}$ |
| 1608. | $L_{A61}$ | $L_{B14}$ |
| 1609. | $L_{A62}$ | $L_{B14}$ |
| 1610. | $L_{A63}$ | $L_{B14}$ |
| 1611. | $L_{A64}$ | $L_{B14}$ |
| 1612. | $L_{A65}$ | $L_{B14}$ |
| 1613. | $L_{A66}$ | $L_{B14}$ |
| 1614. | $L_{A67}$ | $L_{B14}$ |
| 1615. | $L_{A68}$ | $L_{B14}$ |
| 1616. | $L_{A69}$ | $L_{B14}$ |
| 1617. | $L_{A70}$ | $L_{B14}$ |
| 1618. | $L_{A71}$ | $L_{B14}$ |
| 1619. | $L_{A72}$ | $L_{B14}$ |
| 1620. | $L_{A73}$ | $L_{B14}$ |
| 1621. | $L_{A74}$ | $L_{B14}$ |
| 1622. | $L_{A75}$ | $L_{B14}$ |
| 1623. | $L_{A76}$ | $L_{B14}$ |
| 1624. | $L_{A77}$ | $L_{B14}$ |
| 1625. | $L_{A78}$ | $L_{B14}$ |
| 1626. | $L_{A79}$ | $L_{B14}$ |
| 1627. | $L_{A80}$ | $L_{B14}$ |
| 1628. | $L_{A81}$ | $L_{B14}$ |
| 1629. | $L_{A82}$ | $L_{B14}$ |
| 1630. | $L_{A83}$ | $L_{B14}$ |
| 1631. | $L_{A84}$ | $L_{B14}$ |
| 1632. | $L_{A85}$ | $L_{B14}$ |
| 1633. | $L_{A86}$ | $L_{B14}$ |
| 1634. | $L_{A87}$ | $L_{B14}$ |
| 1635. | $L_{A88}$ | $L_{B14}$ |
| 1636. | $L_{A89}$ | $L_{B14}$ |
| 1637. | $L_{A90}$ | $L_{B14}$ |
| 1638. | $L_{A91}$ | $L_{B14}$ |
| 1639. | $L_{A92}$ | $L_{B14}$ |
| 1640. | $L_{A93}$ | $L_{B14}$ |
| 1641. | $L_{A94}$ | $L_{B14}$ |
| 1642. | $L_{A95}$ | $L_{B14}$ |
| 1643. | $L_{A96}$ | $L_{B14}$ |
| 1644. | $L_{A97}$ | $L_{B14}$ |
| 1645. | $L_{A98}$ | $L_{B14}$ |
| 1646. | $L_{A99}$ | $L_{B14}$ |
| 1647. | $L_{A100}$ | $L_{B14}$ |
| 1648. | $L_{A101}$ | $L_{B14}$ |
| 1649. | $L_{A102}$ | $L_{B14}$ |
| 1650. | $L_{A103}$ | $L_{B14}$ |
| 1651. | $L_{A104}$ | $L_{B14}$ |
| 1652. | $L_{A105}$ | $L_{B14}$ |
| 1653. | $L_{A106}$ | $L_{B14}$ |
| 1654. | $L_{A107}$ | $L_{B14}$ |
| 1655. | $L_{A108}$ | $L_{B14}$ |
| 1656. | $L_{A109}$ | $L_{B14}$ |
| 1657. | $L_{A110}$ | $L_{B14}$ |
| 1658. | $L_{A111}$ | $L_{B14}$ |
| 1659. | $L_{A112}$ | $L_{B14}$ |
| 1660. | $L_{A113}$ | $L_{B14}$ |
| 1661. | $L_{A114}$ | $L_{B14}$ |
| 1662. | $L_{A115}$ | $L_{B14}$ |
| 1663. | $L_{A116}$ | $L_{B14}$ |
| 1664. | $L_{A117}$ | $L_{B14}$ |
| 1665. | $L_{A118}$ | $L_{B14}$ |
| 1666. | $L_{A119}$ | $L_{B14}$ |
| 1667. | $L_{A1}$ | $L_{B15}$ |
| 1668. | $L_{A2}$ | $L_{B15}$ |
| 1669. | $L_{A3}$ | $L_{B15}$ |
| 1670. | $L_{A4}$ | $L_{B15}$ |

-continued

| Compound Number | $L_A$ | $L_B$ |
|---|---|---|
| 1671. | $L_{A5}$ | $L_{B15}$ |
| 1672. | $L_{A6}$ | $L_{B15}$ |
| 1673. | $L_{A7}$ | $L_{B15}$ |
| 1674. | $L_{A8}$ | $L_{B15}$ |
| 1675. | $L_{A9}$ | $L_{B15}$ |
| 1676. | $L_{A10}$ | $L_{B15}$ |
| 1677. | $L_{A11}$ | $L_{B15}$ |
| 1678. | $L_{A12}$ | $L_{B15}$ |
| 1679. | $L_{A13}$ | $L_{B15}$ |
| 1680. | $L_{A14}$ | $L_{B15}$ |
| 1681. | $L_{A15}$ | $L_{B15}$ |
| 1682. | $L_{A16}$ | $L_{B15}$ |
| 1683. | $L_{A17}$ | $L_{B15}$ |
| 1684. | $L_{A18}$ | $L_{B15}$ |
| 1685. | $L_{A19}$ | $L_{B15}$ |
| 1686. | $L_{A10}$ | $L_{B15}$ |
| 1687. | $L_{A21}$ | $L_{B15}$ |
| 1688. | $L_{A22}$ | $L_{B15}$ |
| 1689. | $L_{A23}$ | $L_{B15}$ |
| 1690. | $L_{A24}$ | $L_{B15}$ |
| 1691. | $L_{A25}$ | $L_{B15}$ |
| 1692. | $L_{A26}$ | $L_{B15}$ |
| 1693. | $L_{A27}$ | $L_{B15}$ |
| 1694. | $L_{A28}$ | $L_{B15}$ |
| 1695. | $L_{A29}$ | $L_{B15}$ |
| 1696. | $L_{A30}$ | $L_{B15}$ |
| 1697. | $L_{A31}$ | $L_{B15}$ |
| 1698. | $L_{A32}$ | $L_{B15}$ |
| 1699. | $L_{A33}$ | $L_{B15}$ |
| 1700. | $L_{A34}$ | $L_{B15}$ |
| 1701. | $L_{A35}$ | $L_{B15}$ |
| 1702. | $L_{A36}$ | $L_{B15}$ |
| 1703. | $L_{A37}$ | $L_{B15}$ |
| 1704. | $L_{A38}$ | $L_{B15}$ |
| 1705. | $L_{A39}$ | $L_{B15}$ |
| 1706. | $L_{A40}$ | $L_{B15}$ |
| 1707. | $L_{A41}$ | $L_{B15}$ |
| 1708. | $L_{A42}$ | $L_{B15}$ |
| 1709. | $L_{A43}$ | $L_{B15}$ |
| 1710. | $L_{A44}$ | $L_{B15}$ |
| 1711. | $L_{A45}$ | $L_{B15}$ |
| 1712. | $L_{A46}$ | $L_{B15}$ |
| 1713. | $L_{A47}$ | $L_{B15}$ |
| 1714. | $L_{A48}$ | $L_{B15}$ |
| 1715. | $L_{A49}$ | $L_{B15}$ |
| 1716. | $L_{A50}$ | $L_{B15}$ |
| 1717. | $L_{A51}$ | $L_{B15}$ |
| 1718. | $L_{A52}$ | $L_{B15}$ |
| 1719. | $L_{A53}$ | $L_{B15}$ |
| 1720. | $L_{A54}$ | $L_{B15}$ |
| 1721. | $L_{A55}$ | $L_{B15}$ |
| 1722. | $L_{A56}$ | $L_{B15}$ |
| 1723. | $L_{A57}$ | $L_{B15}$ |
| 1724. | $L_{A58}$ | $L_{B15}$ |
| 1725. | $L_{A59}$ | $L_{B15}$ |
| 1726. | $L_{A60}$ | $L_{B15}$ |
| 1727. | $L_{A61}$ | $L_{B15}$ |
| 1728. | $L_{A62}$ | $L_{B15}$ |
| 1729. | $L_{A63}$ | $L_{B15}$ |
| 1730. | $L_{A64}$ | $L_{B15}$ |
| 1731. | $L_{A65}$ | $L_{B15}$ |
| 1732. | $L_{A66}$ | $L_{B15}$ |
| 1733. | $L_{A67}$ | $L_{B15}$ |
| 1734. | $L_{A68}$ | $L_{B15}$ |
| 1735. | $L_{A69}$ | $L_{B15}$ |
| 1736. | $L_{A70}$ | $L_{B15}$ |
| 1737. | $L_{A71}$ | $L_{B15}$ |
| 1738. | $L_{A72}$ | $L_{B15}$ |
| 1739. | $L_{A73}$ | $L_{B15}$ |
| 1740. | $L_{A74}$ | $L_{B15}$ |
| 1741. | $L_{A75}$ | $L_{B15}$ |
| 1742. | $L_{A76}$ | $L_{B15}$ |
| 1743. | $L_{A77}$ | $L_{B15}$ |
| 1744. | $L_{A78}$ | $L_{B15}$ |
| 1745. | $L_{A79}$ | $L_{B15}$ |
| 1746. | $L_{A80}$ | $L_{B15}$ |

-continued

| Compound Number | $L_A$ | $L_B$ |
|---|---|---|
| 1747. | $L_{A81}$ | $L_{B15}$ |
| 1748. | $L_{A82}$ | $L_{B15}$ |
| 1749. | $L_{A83}$ | $L_{B15}$ |
| 1750. | $L_{A84}$ | $L_{B15}$ |
| 1751. | $L_{A85}$ | $L_{B15}$ |
| 1752. | $L_{A86}$ | $L_{B15}$ |
| 1753. | $L_{A87}$ | $L_{B15}$ |
| 1754. | $L_{A88}$ | $L_{B15}$ |
| 1755. | $L_{A89}$ | $L_{B15}$ |
| 1756. | $L_{A90}$ | $L_{B15}$ |
| 1757. | $L_{A91}$ | $L_{B15}$ |
| 1758. | $L_{A92}$ | $L_{B15}$ |
| 1759. | $L_{A93}$ | $L_{B15}$ |
| 1760. | $L_{A94}$ | $L_{B15}$ |
| 1761. | $L_{A95}$ | $L_{B15}$ |
| 1762. | $L_{A96}$ | $L_{B15}$ |
| 1763. | $L_{A97}$ | $L_{B15}$ |
| 1764. | $L_{A98}$ | $L_{B15}$ |
| 1765. | $L_{A99}$ | $L_{B15}$ |
| 1766. | $L_{A100}$ | $L_{B15}$ |
| 1767. | $L_{A101}$ | $L_{B15}$ |
| 1768. | $L_{A102}$ | $L_{B15}$ |
| 1769. | $L_{A103}$ | $L_{B15}$ |
| 1770. | $L_{A104}$ | $L_{B15}$ |
| 1771. | $L_{A105}$ | $L_{B15}$ |
| 1772. | $L_{A106}$ | $L_{B15}$ |
| 1773. | $L_{A107}$ | $L_{B15}$ |
| 1774. | $L_{A108}$ | $L_{B15}$ |
| 1775. | $L_{A109}$ | $L_{B15}$ |
| 1776. | $L_{A110}$ | $L_{B15}$ |
| 1777. | $L_{A111}$ | $L_{B15}$ |
| 1778. | $L_{A112}$ | $L_{B15}$ |
| 1779. | $L_{A113}$ | $L_{B15}$ |
| 1780. | $L_{A114}$ | $L_{B15}$ |
| 1781. | $L_{A115}$ | $L_{B15}$ |
| 1782. | $L_{A116}$ | $L_{B15}$ |
| 1783. | $L_{A117}$ | $L_{B15}$ |
| 1784. | $L_{A118}$ | $L_{B15}$ |
| 1785. | $L_{A119}$ | $L_{B15}$ |
| 1786. | $L_{A1}$ | $L_{B16}$ |
| 1787. | $L_{A2}$ | $L_{B16}$ |
| 1788. | $L_{A3}$ | $L_{B16}$ |
| 1789. | $L_{A4}$ | $L_{B16}$ |
| 1790. | $L_{A5}$ | $L_{B16}$ |
| 1791. | $L_{A6}$ | $L_{B16}$ |
| 1792. | $L_{A7}$ | $L_{B16}$ |
| 1793. | $L_{A8}$ | $L_{B16}$ |
| 1794. | $L_{A9}$ | $L_{B16}$ |
| 1795. | $L_{A10}$ | $L_{B16}$ |
| 1796. | $L_{A11}$ | $L_{B16}$ |
| 1797. | $L_{A12}$ | $L_{B16}$ |
| 1798. | $L_{A13}$ | $L_{B16}$ |
| 1799. | $L_{A14}$ | $L_{B16}$ |
| 1800. | $L_{A15}$ | $L_{B16}$ |
| 1801. | $L_{A16}$ | $L_{B16}$ |
| 1802. | $L_{A17}$ | $L_{B16}$ |
| 1803. | $L_{A18}$ | $L_{B16}$ |
| 1804. | $L_{A19}$ | $L_{B16}$ |
| 1805. | $L_{A10}$ | $L_{B16}$ |
| 1806. | $L_{A21}$ | $L_{B16}$ |
| 1807. | $L_{A22}$ | $L_{B16}$ |
| 1808. | $L_{A23}$ | $L_{B16}$ |
| 1809. | $L_{A24}$ | $L_{B16}$ |
| 1810. | $L_{A25}$ | $L_{B16}$ |
| 1811. | $L_{A26}$ | $L_{B16}$ |
| 1812. | $L_{A27}$ | $L_{B16}$ |
| 1813. | $L_{A28}$ | $L_{B16}$ |
| 1814. | $L_{A29}$ | $L_{B16}$ |
| 1815. | $L_{A30}$ | $L_{B16}$ |
| 1816. | $L_{A31}$ | $L_{B16}$ |
| 1817. | $L_{A32}$ | $L_{B16}$ |
| 1818. | $L_{A33}$ | $L_{B16}$ |
| 1819. | $L_{A34}$ | $L_{B16}$ |
| 1820. | $L_{A35}$ | $L_{B16}$ |
| 1821. | $L_{A36}$ | $L_{B16}$ |
| 1822. | $L_{A37}$ | $L_{B16}$ |

-continued

| Compound Number | $L_A$ | $L_B$ |
|---|---|---|
| 1823. | $L_{A38}$ | $L_{B16}$ |
| 1824. | $L_{A39}$ | $L_{B16}$ |
| 1825. | $L_{A40}$ | $L_{B16}$ |
| 1826. | $L_{A41}$ | $L_{B16}$ |
| 1827. | $L_{A42}$ | $L_{B16}$ |
| 1828. | $L_{A43}$ | $L_{B16}$ |
| 1829. | $L_{A44}$ | $L_{B16}$ |
| 1830. | $L_{A45}$ | $L_{B16}$ |
| 1831. | $L_{A46}$ | $L_{B16}$ |
| 1832. | $L_{A47}$ | $L_{B16}$ |
| 1833. | $L_{A48}$ | $L_{B16}$ |
| 1834. | $L_{A49}$ | $L_{B16}$ |
| 1835. | $L_{A50}$ | $L_{B16}$ |
| 1836. | $L_{A51}$ | $L_{B16}$ |
| 1837. | $L_{A52}$ | $L_{B16}$ |
| 1838. | $L_{A53}$ | $L_{B16}$ |
| 1839. | $L_{A54}$ | $L_{B16}$ |
| 1840. | $L_{A55}$ | $L_{B16}$ |
| 1841. | $L_{A56}$ | $L_{B16}$ |
| 1842. | $L_{A57}$ | $L_{B16}$ |
| 1843. | $L_{A58}$ | $L_{B16}$ |
| 1844. | $L_{A59}$ | $L_{B16}$ |
| 1845. | $L_{A60}$ | $L_{B16}$ |
| 1846. | $L_{A61}$ | $L_{B16}$ |
| 1847. | $L_{A62}$ | $L_{B16}$ |
| 1848. | $L_{A63}$ | $L_{B16}$ |
| 1849. | $L_{A64}$ | $L_{B16}$ |
| 1850. | $L_{A65}$ | $L_{B16}$ |
| 1851. | $L_{A66}$ | $L_{B16}$ |
| 1852. | $L_{A67}$ | $L_{B16}$ |
| 1853. | $L_{A68}$ | $L_{B16}$ |
| 1854. | $L_{A69}$ | $L_{B16}$ |
| 1855. | $L_{A70}$ | $L_{B16}$ |
| 1856. | $L_{A71}$ | $L_{B16}$ |
| 1857. | $L_{A72}$ | $L_{B16}$ |
| 1858. | $L_{A73}$ | $L_{B16}$ |
| 1859. | $L_{A74}$ | $L_{B16}$ |
| 1860. | $L_{A75}$ | $L_{B16}$ |
| 1861. | $L_{A76}$ | $L_{B16}$ |
| 1862. | $L_{A77}$ | $L_{B16}$ |
| 1863. | $L_{A78}$ | $L_{B16}$ |
| 1864. | $L_{A79}$ | $L_{B16}$ |
| 1865. | $L_{A80}$ | $L_{B16}$ |
| 1866. | $L_{A81}$ | $L_{B16}$ |
| 1867. | $L_{A82}$ | $L_{B16}$ |
| 1868. | $L_{A83}$ | $L_{B16}$ |
| 1869. | $L_{A84}$ | $L_{B16}$ |
| 1870. | $L_{A85}$ | $L_{B16}$ |
| 1871. | $L_{A86}$ | $L_{B16}$ |
| 1872. | $L_{A87}$ | $L_{B16}$ |
| 1873. | $L_{A88}$ | $L_{B16}$ |
| 1874. | $L_{A89}$ | $L_{B16}$ |
| 1875. | $L_{A90}$ | $L_{B16}$ |
| 1876. | $L_{A91}$ | $L_{B16}$ |
| 1877. | $L_{A92}$ | $L_{B16}$ |
| 1878. | $L_{A93}$ | $L_{B16}$ |
| 1879. | $L_{A94}$ | $L_{B16}$ |
| 1880. | $L_{A95}$ | $L_{B16}$ |
| 1881. | $L_{A96}$ | $L_{B16}$ |
| 1882. | $L_{A97}$ | $L_{B16}$ |
| 1883. | $L_{A98}$ | $L_{B16}$ |
| 1884. | $L_{A99}$ | $L_{B16}$ |
| 1885. | $L_{A100}$ | $L_{B16}$ |
| 1886. | $L_{A101}$ | $L_{B16}$ |
| 1887. | $L_{A102}$ | $L_{B16}$ |
| 1888. | $L_{A103}$ | $L_{B16}$ |
| 1889. | $L_{A104}$ | $L_{B16}$ |
| 1890. | $L_{A105}$ | $L_{B16}$ |
| 1891. | $L_{A106}$ | $L_{B16}$ |
| 1892. | $L_{A107}$ | $L_{B16}$ |
| 1893. | $L_{A108}$ | $L_{B16}$ |
| 1894. | $L_{A109}$ | $L_{B16}$ |
| 1895. | $L_{A110}$ | $L_{B16}$ |
| 1896. | $L_{A111}$ | $L_{B16}$ |
| 1897. | $L_{A112}$ | $L_{B16}$ |
| 1898. | $L_{A113}$ | $L_{B16}$ |

-continued

| Compound Number | $L_A$ | $L_B$ |
|---|---|---|
| 1899. | $L_{A114}$ | $L_{B16}$ |
| 1900. | $L_{A115}$ | $L_{B16}$ |
| 1901. | $L_{A116}$ | $L_{B16}$ |
| 1902. | $L_{A117}$ | $L_{B16}$ |
| 1903. | $L_{A118}$ | $L_{B16}$ |
| 1904. | $L_{A119}$ | $L_{B16}$ |
| 1905. | $L_{A1}$ | $L_{B17}$ |
| 1906. | $L_{A2}$ | $L_{B17}$ |
| 1907. | $L_{A3}$ | $L_{B17}$ |
| 1908. | $L_{A4}$ | $L_{B17}$ |
| 1909. | $L_{A5}$ | $L_{B17}$ |
| 1910. | $L_{A6}$ | $L_{B17}$ |
| 1911. | $L_{A7}$ | $L_{B17}$ |
| 1912. | $L_{A8}$ | $L_{B17}$ |
| 1913. | $L_{A9}$ | $L_{B17}$ |
| 1914. | $L_{A10}$ | $L_{B17}$ |
| 1915. | $L_{A11}$ | $L_{B17}$ |
| 1916. | $L_{A12}$ | $L_{B17}$ |
| 1917. | $L_{A13}$ | $L_{B17}$ |
| 1918. | $L_{A14}$ | $L_{B17}$ |
| 1919. | $L_{A15}$ | $L_{B17}$ |
| 1920. | $L_{A16}$ | $L_{B17}$ |
| 1921. | $L_{A17}$ | $L_{B17}$ |
| 1922. | $L_{A18}$ | $L_{B17}$ |
| 1923. | $L_{A19}$ | $L_{B17}$ |
| 1924. | $L_{A10}$ | $L_{B17}$ |
| 1925. | $L_{A21}$ | $L_{B17}$ |
| 1926. | $L_{A22}$ | $L_{B17}$ |
| 1927. | $L_{A23}$ | $L_{B17}$ |
| 1928. | $L_{A24}$ | $L_{B17}$ |
| 1929. | $L_{A25}$ | $L_{B17}$ |
| 1930. | $L_{A26}$ | $L_{B17}$ |
| 1931. | $L_{A27}$ | $L_{B17}$ |
| 1932. | $L_{A28}$ | $L_{B17}$ |
| 1933. | $L_{A29}$ | $L_{B17}$ |
| 1934. | $L_{A30}$ | $L_{B17}$ |
| 1935. | $L_{A31}$ | $L_{B17}$ |
| 1936. | $L_{A32}$ | $L_{B17}$ |
| 1937. | $L_{A33}$ | $L_{B17}$ |
| 1938. | $L_{A34}$ | $L_{B17}$ |
| 1939. | $L_{A35}$ | $L_{B17}$ |
| 1940. | $L_{A36}$ | $L_{B17}$ |
| 1941. | $L_{A37}$ | $L_{B17}$ |
| 1942. | $L_{A38}$ | $L_{B17}$ |
| 1943. | $L_{A39}$ | $L_{B17}$ |
| 1944. | $L_{A40}$ | $L_{B17}$ |
| 1945. | $L_{A41}$ | $L_{B17}$ |
| 1946. | $L_{A42}$ | $L_{B17}$ |
| 1947. | $L_{A43}$ | $L_{B17}$ |
| 1948. | $L_{A44}$ | $L_{B17}$ |
| 1949. | $L_{A45}$ | $L_{B17}$ |
| 1950. | $L_{A46}$ | $L_{B17}$ |
| 1951. | $L_{A47}$ | $L_{B17}$ |
| 1952. | $L_{A48}$ | $L_{B17}$ |
| 1953. | $L_{A49}$ | $L_{B17}$ |
| 1954. | $L_{A50}$ | $L_{B17}$ |
| 1955. | $L_{A51}$ | $L_{B17}$ |
| 1956. | $L_{A52}$ | $L_{B17}$ |
| 1957. | $L_{A53}$ | $L_{B17}$ |
| 1958. | $L_{A54}$ | $L_{B17}$ |
| 1959. | $L_{A55}$ | $L_{B17}$ |
| 1960. | $L_{A56}$ | $L_{B17}$ |
| 1961. | $L_{A57}$ | $L_{B17}$ |
| 1962. | $L_{A58}$ | $L_{B17}$ |
| 1963. | $L_{A59}$ | $L_{B17}$ |
| 1964. | $L_{A60}$ | $L_{B17}$ |
| 1965. | $L_{A61}$ | $L_{B17}$ |
| 1966. | $L_{A62}$ | $L_{B17}$ |
| 1967. | $L_{A63}$ | $L_{B17}$ |
| 1968. | $L_{A64}$ | $L_{B17}$ |
| 1969. | $L_{A65}$ | $L_{B17}$ |
| 1970. | $L_{A66}$ | $L_{B17}$ |
| 1971. | $L_{A67}$ | $L_{B17}$ |
| 1972. | $L_{A68}$ | $L_{B17}$ |
| 1973. | $L_{A69}$ | $L_{B17}$ |
| 1974. | $L_{A70}$ | $L_{B17}$ |

-continued

| Compound Number | $L_A$ | $L_B$ |
|---|---|---|
| 1975. | $L_{A71}$ | $L_{B17}$ |
| 1976. | $L_{A72}$ | $L_{B17}$ |
| 1977. | $L_{A73}$ | $L_{B17}$ |
| 1978. | $L_{A74}$ | $L_{B17}$ |
| 1979. | $L_{A75}$ | $L_{B17}$ |
| 1980. | $L_{A76}$ | $L_{B17}$ |
| 1981. | $L_{A77}$ | $L_{B17}$ |
| 1982. | $L_{A78}$ | $L_{B17}$ |
| 1983. | $L_{A79}$ | $L_{B17}$ |
| 1984. | $L_{A80}$ | $L_{B17}$ |
| 1985. | $L_{A81}$ | $L_{B17}$ |
| 1986. | $L_{A82}$ | $L_{B17}$ |
| 1987. | $L_{A83}$ | $L_{B17}$ |
| 1988. | $L_{A84}$ | $L_{B17}$ |
| 1989. | $L_{A85}$ | $L_{B17}$ |
| 1990. | $L_{A86}$ | $L_{B17}$ |
| 1991. | $L_{A87}$ | $L_{B17}$ |
| 1992. | $L_{A88}$ | $L_{B17}$ |
| 1993. | $L_{A89}$ | $L_{B17}$ |
| 1994. | $L_{A90}$ | $L_{B17}$ |
| 1995. | $L_{A91}$ | $L_{B17}$ |
| 1996. | $L_{A92}$ | $L_{B17}$ |
| 1997. | $L_{A93}$ | $L_{B17}$ |
| 1998. | $L_{A94}$ | $L_{B17}$ |
| 1999. | $L_{A95}$ | $L_{B17}$ |
| 2000. | $L_{A96}$ | $L_{B17}$ |
| 2001. | $L_{A97}$ | $L_{B17}$ |
| 2002. | $L_{A98}$ | $L_{B17}$ |
| 2003. | $L_{A99}$ | $L_{B17}$ |
| 2004. | $L_{A100}$ | $L_{B17}$ |
| 2005. | $L_{A101}$ | $L_{B17}$ |
| 2006. | $L_{A102}$ | $L_{B17}$ |
| 2007. | $L_{A103}$ | $L_{B17}$ |
| 2008. | $L_{A104}$ | $L_{B17}$ |
| 2009. | $L_{A105}$ | $L_{B17}$ |
| 2010. | $L_{A106}$ | $L_{B17}$ |
| 2011. | $L_{A107}$ | $L_{B17}$ |
| 2012. | $L_{A108}$ | $L_{B17}$ |
| 2013. | $L_{A109}$ | $L_{B17}$ |
| 2014. | $L_{A110}$ | $L_{B17}$ |
| 2015. | $L_{A111}$ | $L_{B17}$ |
| 2016. | $L_{A112}$ | $L_{B17}$ |
| 2017. | $L_{A113}$ | $L_{B17}$ |
| 2018. | $L_{A114}$ | $L_{B17}$ |
| 2019. | $L_{A115}$ | $L_{B17}$ |
| 2020. | $L_{A116}$ | $L_{B17}$ |
| 2021. | $L_{A117}$ | $L_{B17}$ |
| 2022. | $L_{A118}$ | $L_{B17}$ |
| 2023. | $L_{A119}$ | $L_{B17}$ |
| 2024. | $L_{A1}$ | $L_{B18}$ |
| 2025. | $L_{A2}$ | $L_{B18}$ |
| 2026. | $L_{A3}$ | $L_{B18}$ |
| 2027. | $L_{A4}$ | $L_{B18}$ |
| 2028. | $L_{A5}$ | $L_{B18}$ |
| 2029. | $L_{A6}$ | $L_{B18}$ |
| 2030. | $L_{A7}$ | $L_{B18}$ |
| 2031. | $L_{A8}$ | $L_{B18}$ |
| 2032. | $L_{A9}$ | $L_{B18}$ |
| 2033. | $L_{A10}$ | $L_{B18}$ |
| 2034. | $L_{A11}$ | $L_{B18}$ |
| 2035. | $L_{A12}$ | $L_{B18}$ |
| 2036. | $L_{A13}$ | $L_{B18}$ |
| 2037. | $L_{A14}$ | $L_{B18}$ |
| 2038. | $L_{A15}$ | $L_{B18}$ |
| 2039. | $L_{A16}$ | $L_{B18}$ |
| 2040. | $L_{A17}$ | $L_{B18}$ |
| 2041. | $L_{A18}$ | $L_{B18}$ |
| 2042. | $L_{A19}$ | $L_{B18}$ |
| 2043. | $L_{A10}$ | $L_{B18}$ |
| 2044. | $L_{A21}$ | $L_{B18}$ |
| 2045. | $L_{A22}$ | $L_{B18}$ |
| 2046. | $L_{A23}$ | $L_{B18}$ |
| 2047. | $L_{A24}$ | $L_{B18}$ |
| 2048. | $L_{A25}$ | $L_{B18}$ |
| 2049. | $L_{A26}$ | $L_{B18}$ |
| 2050. | $L_{A27}$ | $L_{B18}$ |

-continued

| Compound Number | $L_A$ | $L_B$ |
|---|---|---|
| 2051. | $L_{A28}$ | $L_{B18}$ |
| 2052. | $L_{A29}$ | $L_{B18}$ |
| 2053. | $L_{A30}$ | $L_{B18}$ |
| 2054. | $L_{A31}$ | $L_{B18}$ |
| 2055. | $L_{A32}$ | $L_{B18}$ |
| 2056. | $L_{A33}$ | $L_{B18}$ |
| 2057. | $L_{A34}$ | $L_{B18}$ |
| 2058. | $L_{A35}$ | $L_{B18}$ |
| 2059. | $L_{A36}$ | $L_{B18}$ |
| 2060. | $L_{A37}$ | $L_{B18}$ |
| 2061. | $L_{A38}$ | $L_{B18}$ |
| 2062. | $L_{A39}$ | $L_{B18}$ |
| 2063. | $L_{A40}$ | $L_{B18}$ |
| 2064. | $L_{A41}$ | $L_{B18}$ |
| 2065. | $L_{A42}$ | $L_{B18}$ |
| 2066. | $L_{A43}$ | $L_{B18}$ |
| 2067. | $L_{A44}$ | $L_{B18}$ |
| 2068. | $L_{A45}$ | $L_{B18}$ |
| 2069. | $L_{A46}$ | $L_{B18}$ |
| 2070. | $L_{A47}$ | $L_{B18}$ |
| 2071. | $L_{A48}$ | $L_{B18}$ |
| 2072. | $L_{A49}$ | $L_{B18}$ |
| 2073. | $L_{A50}$ | $L_{B18}$ |
| 2074. | $L_{A51}$ | $L_{B18}$ |
| 2075. | $L_{A52}$ | $L_{B18}$ |
| 2076. | $L_{A53}$ | $L_{B18}$ |
| 2077. | $L_{A54}$ | $L_{B18}$ |
| 2078. | $L_{A55}$ | $L_{B18}$ |
| 2079. | $L_{A56}$ | $L_{B18}$ |
| 2080. | $L_{A57}$ | $L_{B18}$ |
| 2081. | $L_{A58}$ | $L_{B18}$ |
| 2082. | $L_{A59}$ | $L_{B18}$ |
| 2083. | $L_{A60}$ | $L_{B18}$ |
| 2084. | $L_{A61}$ | $L_{B18}$ |
| 2085. | $L_{A62}$ | $L_{B18}$ |
| 2086. | $L_{A63}$ | $L_{B18}$ |
| 2087. | $L_{A64}$ | $L_{B18}$ |
| 2088. | $L_{A65}$ | $L_{B18}$ |
| 2089. | $L_{A66}$ | $L_{B18}$ |
| 2090. | $L_{A67}$ | $L_{B18}$ |
| 2091. | $L_{A68}$ | $L_{B18}$ |
| 2092. | $L_{A69}$ | $L_{B18}$ |
| 2093. | $L_{A70}$ | $L_{B18}$ |
| 2094. | $L_{A71}$ | $L_{B18}$ |
| 2095. | $L_{A72}$ | $L_{B18}$ |
| 2096. | $L_{A73}$ | $L_{B18}$ |
| 2097. | $L_{A74}$ | $L_{B18}$ |
| 2098. | $L_{A75}$ | $L_{B18}$ |
| 2099. | $L_{A76}$ | $L_{B18}$ |
| 2100. | $L_{A77}$ | $L_{B18}$ |
| 2101. | $L_{A78}$ | $L_{B18}$ |
| 2102. | $L_{A79}$ | $L_{B18}$ |
| 2103. | $L_{A80}$ | $L_{B18}$ |
| 2104. | $L_{A81}$ | $L_{B18}$ |
| 2105. | $L_{A82}$ | $L_{B18}$ |
| 2106. | $L_{A83}$ | $L_{B18}$ |
| 2107. | $L_{A84}$ | $L_{B18}$ |
| 2108. | $L_{A85}$ | $L_{B18}$ |
| 2109. | $L_{A86}$ | $L_{B18}$ |
| 2110. | $L_{A87}$ | $L_{B18}$ |
| 2111. | $L_{A88}$ | $L_{B18}$ |
| 2112. | $L_{A89}$ | $L_{B18}$ |
| 2113. | $L_{A90}$ | $L_{B18}$ |
| 2114. | $L_{A91}$ | $L_{B18}$ |
| 2115. | $L_{A92}$ | $L_{B18}$ |
| 2116. | $L_{A93}$ | $L_{B18}$ |
| 2117. | $L_{A94}$ | $L_{B18}$ |
| 2118. | $L_{A95}$ | $L_{B18}$ |
| 2119. | $L_{A96}$ | $L_{B18}$ |
| 2120. | $L_{A97}$ | $L_{B18}$ |
| 2121. | $L_{A98}$ | $L_{B18}$ |
| 2122. | $L_{A99}$ | $L_{B18}$ |
| 2123. | $L_{A100}$ | $L_{B18}$ |
| 2124. | $L_{A101}$ | $L_{B18}$ |
| 2125. | $L_{A102}$ | $L_{B18}$ |
| 2126. | $L_{A103}$ | $L_{B18}$ |
| 2127. | $L_{A104}$ | $L_{B18}$ |
| 2128. | $L_{A105}$ | $L_{B18}$ |
| 2129. | $L_{A106}$ | $L_{B18}$ |
| 2130. | $L_{A107}$ | $L_{B18}$ |
| 2131. | $L_{A108}$ | $L_{B18}$ |
| 2132. | $L_{A109}$ | $L_{B18}$ |
| 2133. | $L_{A110}$ | $L_{B18}$ |
| 2134. | $L_{A111}$ | $L_{B18}$ |
| 2135. | $L_{A112}$ | $L_{B18}$ |
| 2136. | $L_{A113}$ | $L_{B18}$ |
| 2137. | $L_{A114}$ | $L_{B18}$ |
| 2138. | $L_{A115}$ | $L_{B18}$ |
| 2139. | $L_{A116}$ | $L_{B18}$ |
| 2140. | $L_{A117}$ | $L_{B18}$ |
| 2141. | $L_{A118}$ | $L_{B18}$ |
| 2142. | $L_{A119}$ | $L_{B18}$ |

In one embodiment, the compound is selected from the group consisting of:

Compound 1

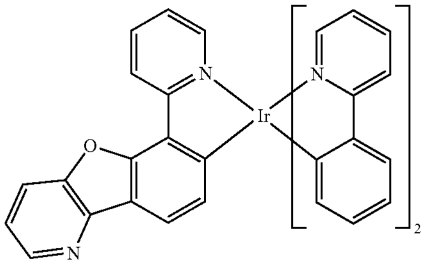

Compound 2

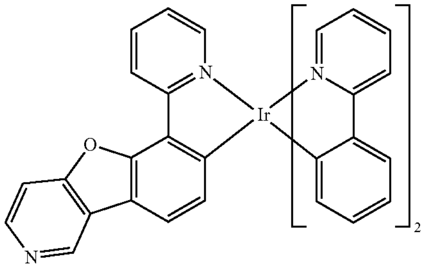

Compound 3

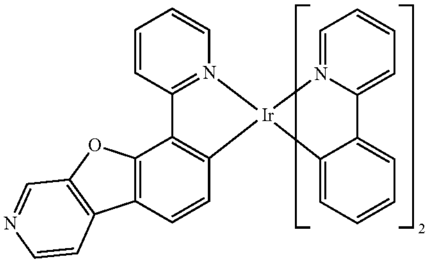

Compound 4

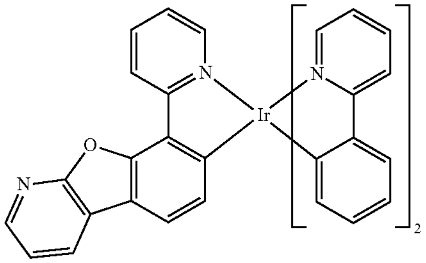

-continued
Compound 5
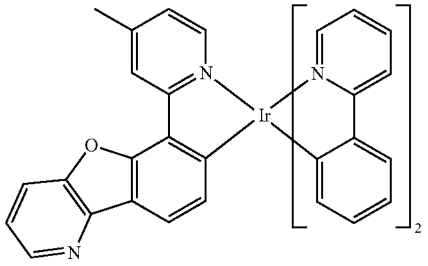
Compound 144
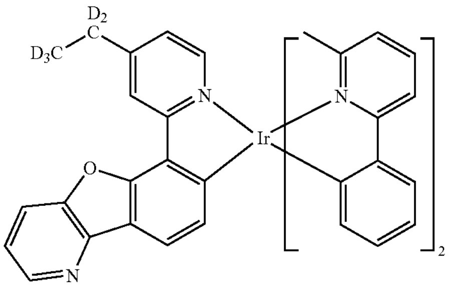
Compound 715
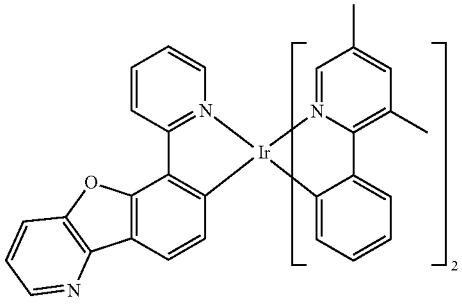
Compound 1596
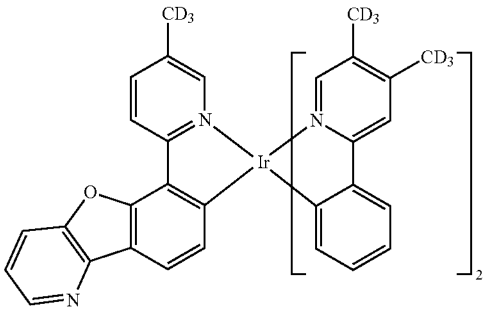
Compound 81
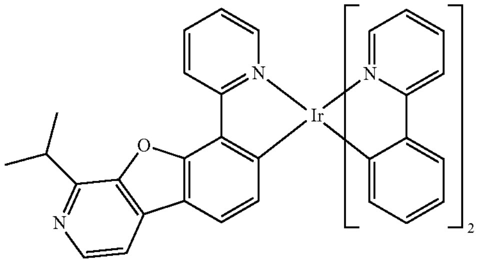
-continued
Compound 319
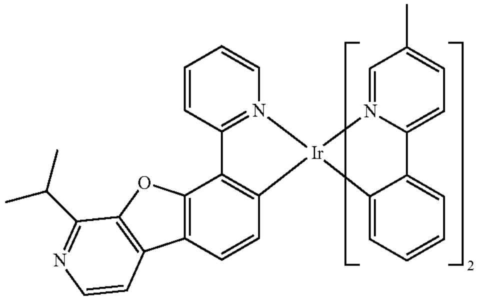
Compound 80
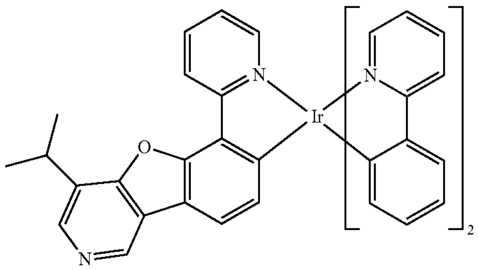
Compound 123
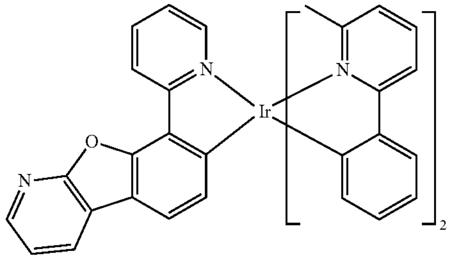
Compound 1194
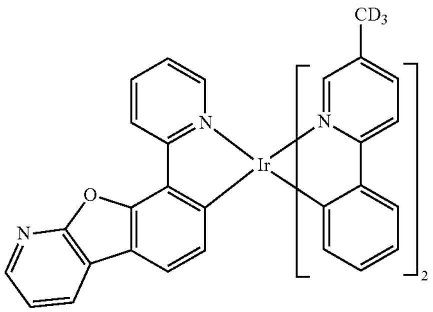
Compound 28
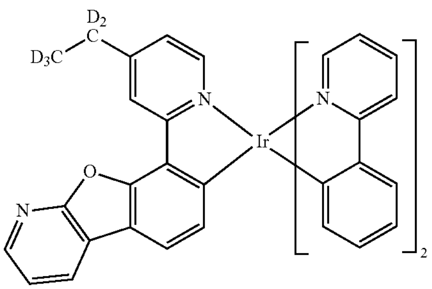

-continued
Compound 391
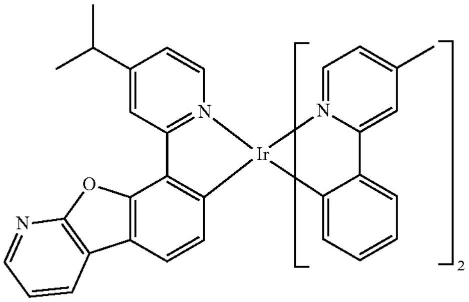
Compound 272
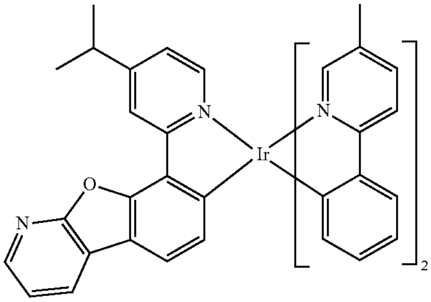
Compound 102
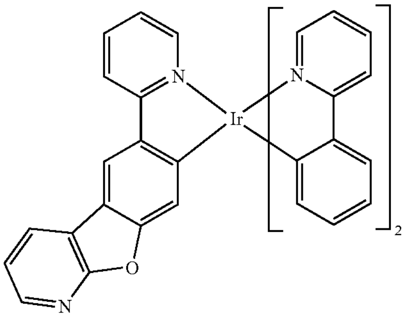
Compound 1649
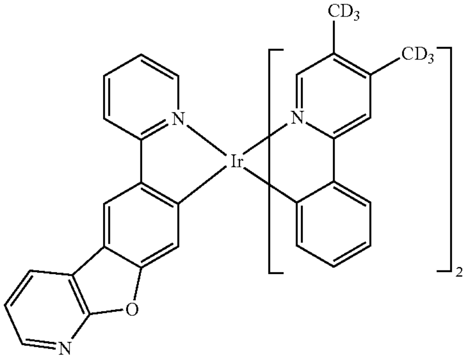
-continued
Compound 105
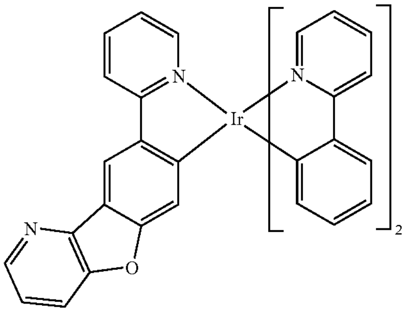
Compound 343
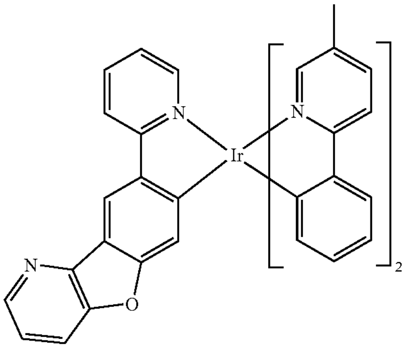
Compound 706
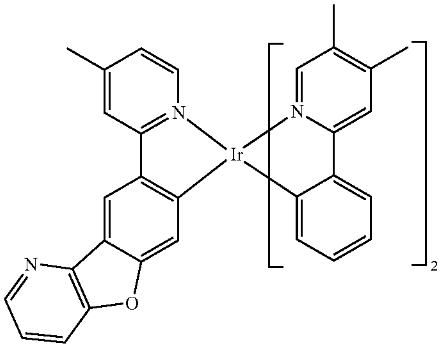
Compound 1658
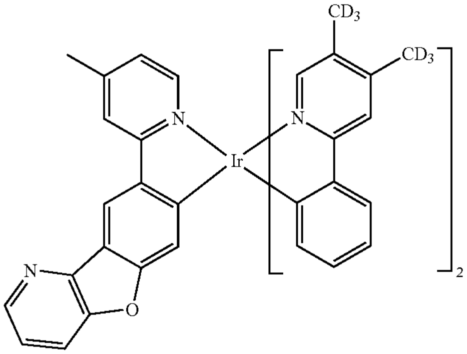

-continued
Compound 106
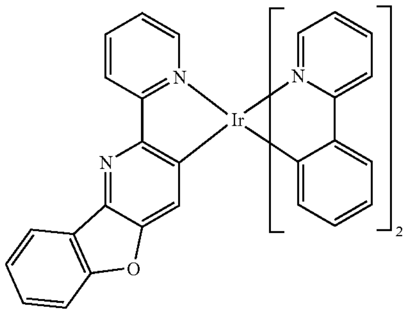
Compound 112
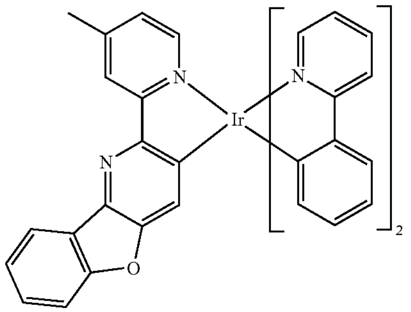
Compound 113
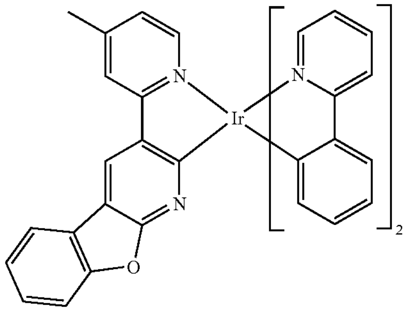
Compound 709
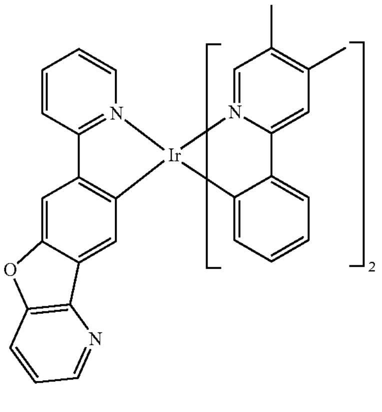
-continued
Compound 117
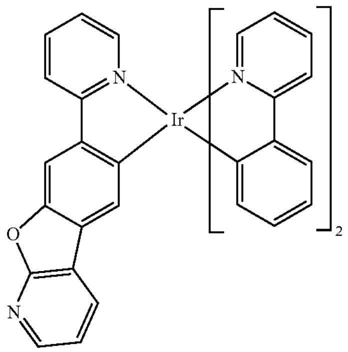
Compound 118
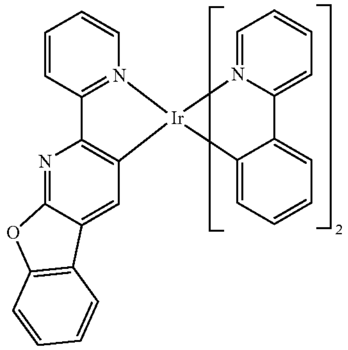
Compound 119
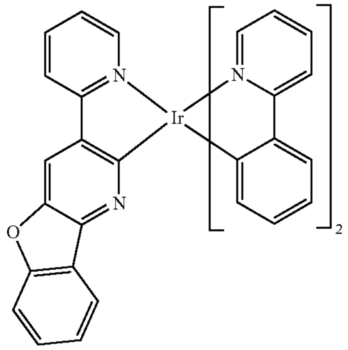
Compound 1304
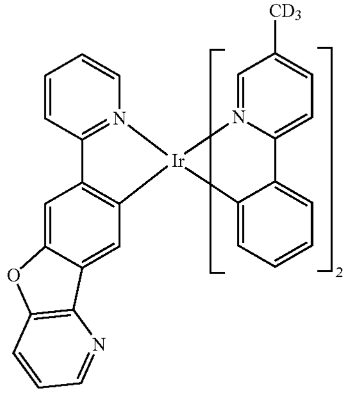

-continued

Compound 1664

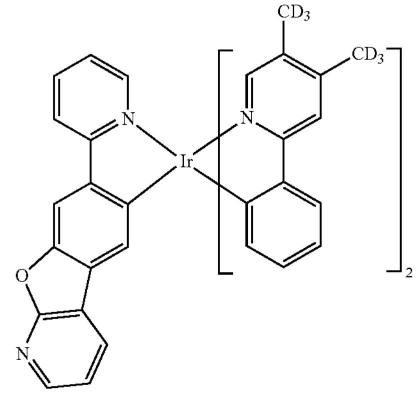

Compound 1632

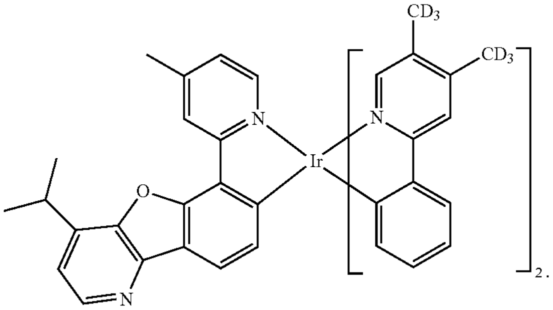

In one embodiment, a first device comprising a first organic light emitting device is disclosed. The first organic light emitting device comprises an anode, a cathode, and an organic layer, disposed between the anode and the cathode, comprising a compound having the formula $Ir(L_A)_n(L_B)_{3-n}$, having the structure according to Formula I

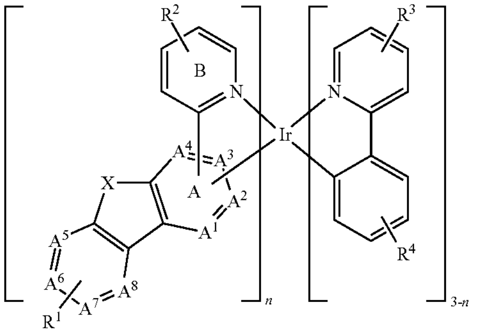

is provided. In the compound of Formula I, $A^1$, $A^2$, $A^3$, $A^4$, $A^5$, $A^6$, $A^7$, and $A^8$ comprise carbon or nitrogen, and at least one of $A^1$, $A^2$, $A^3$, $A^4$, $A^5$, $A^6$, $A^7$, and $A^8$ is nitrogen. Ring B is bonded to ring A through a C—C bond, the iridium is bonded to ring A through a Ir—C bond. X is O, S, or Se. $R^1$, $R^2$, $R^3$, and $R^4$ independently represent mono-, di-, tri-, tetra-substitution, or no substitution, and any adjacent substitutions in $R^1$, $R^2$, $R^3$, and $R^4$ are optionally linked together to form a ring. $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and n is an integer from 1 to 3.

In one embodiment, the first device is a consumer product. In one embodiment, the first device is an organic light-emitting device. In one embodiment, the first device comprises a lighting panel.

In another embodiment, the organic layer in the first organic light emitting device is an emissive layer and the compound is an emissive dopant. In one embodiment, the organic layer is an emissive layer and the compound is a non-emissive dopant.

In one embodiment, the organic layer further comprises a host. In one embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}CHC_nH_{2n+1}$, $Ar_1$, $Ar_1$-$Ar_2$, $C_nH_{2n}{-}Ar_1$, or no substitution, wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In one embodiment, the host comprises at least one chemical group selected from the group consisting of carbazole, dibenzothiphene, dibenzofuran, dibenzoselenophene, azacarbazole, aza-dibenzothiophene, aza-dibenzofuran, and aza-dibenzoselenophene.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

In one embodiment, the host is selected from a group of compounds, the Host Group, consisting of:

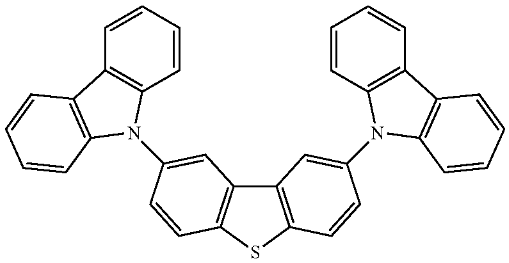

,

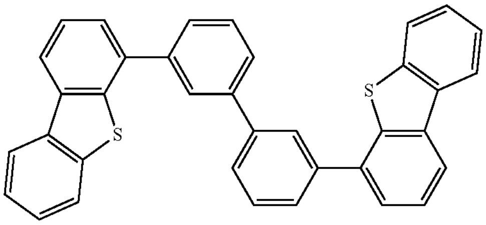

,

-continued

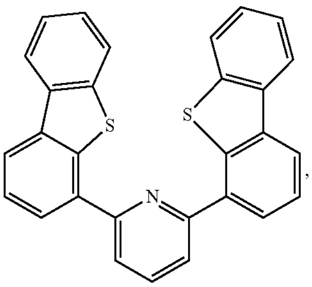

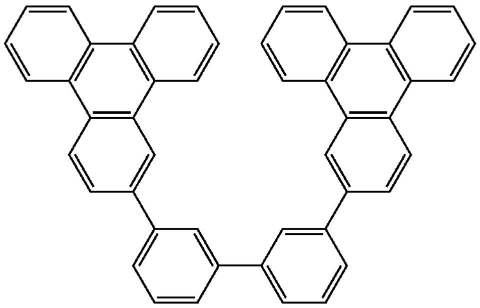

,

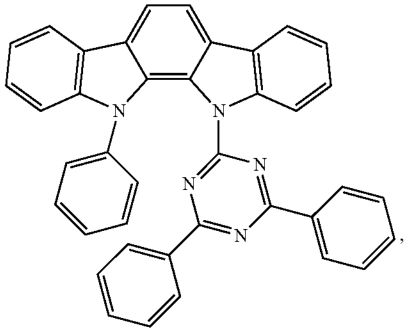

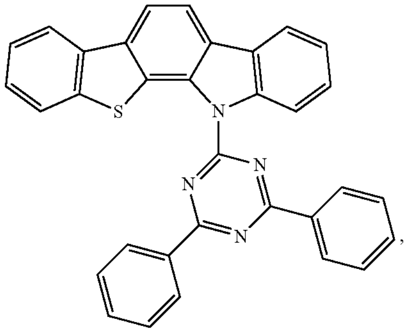

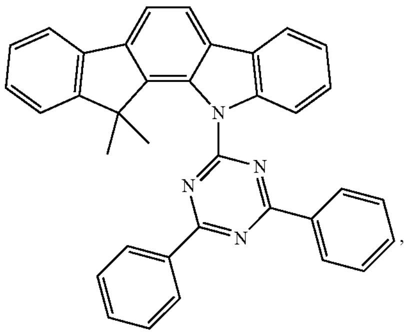

-continued

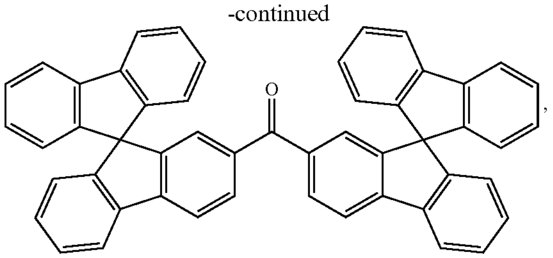

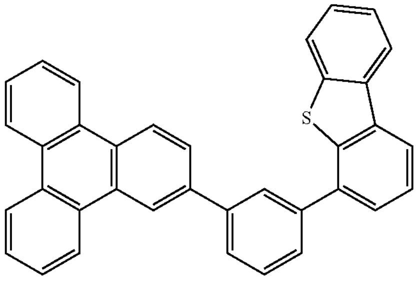

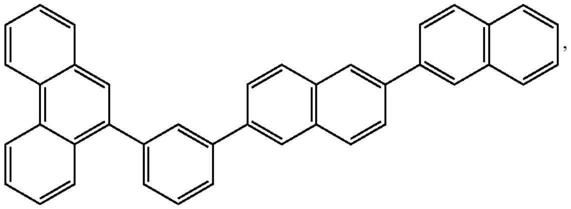

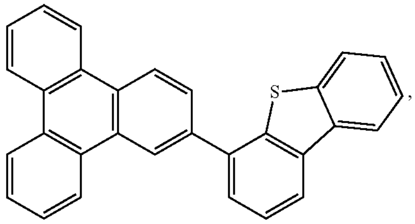 [SMILES: c1ccc2c(c1)sc1c(-c3ccc4c5ccccc5c5ccccc5c4c3)cccc12]

and combinations thereof.

In one embodiment, the host comprises a metal complex.

According to an aspect of the present disclosure, the compound according to Formula I wherein $A^1$-$A^4$ and $A^6$-$A^8$ are C and $A^5$ is N and having a structure according to Formula II

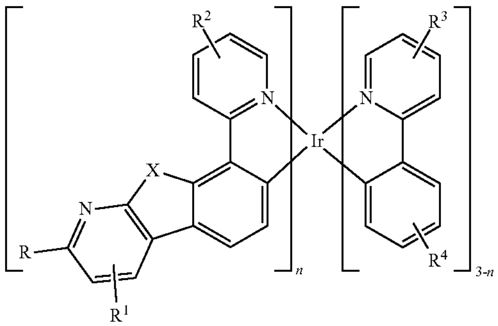

is also provided. In the compound of Formula II, X, $R^1$, $R^2$, $R^3$, and $R^4$, and n are as defined for Formula I. R is selected from the group consisting of alkyl, cycloalkyl, and combinations thereof; $R^1$ represent mono-, di-substitution, or no substitution.

In one embodiment, n in the compound of Formula II is 1. In one embodiment, X is O. In one embodiment, R is alkyl. In one embodiment, R is cycloalkyl. In one embodiment, R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof. In one embodiment, $R^1$, $R^2$, $R^3$, and $R^4$ can be independently selected from the group consisting of hydrogen, deuterium, alkyl, and combinations thereof. In one embodiment, $R^2$ is alkyl, or partially or fully deuterated alkyl. In one embodiment, $R^3$ is alkyl, or partially or fully deuterated alkyl.

In one embodiment, $L_A$ in Formula II is selected from the group consisting of $L_{A120}$

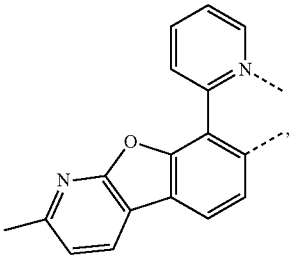

$L_{A121}$

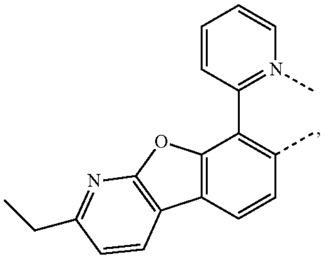

$L_{A122}$

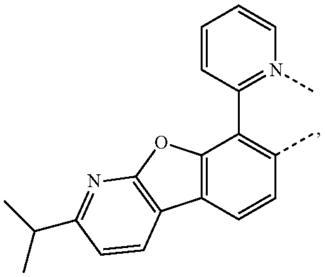

$L_{A123}$

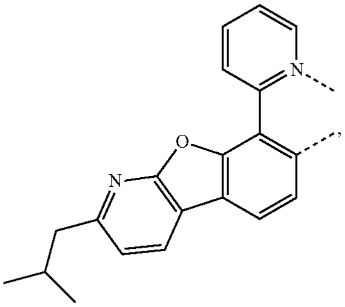

-continued $L_{A124}$

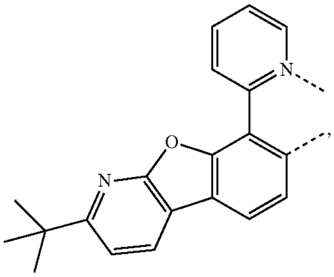

$L_{A125}$

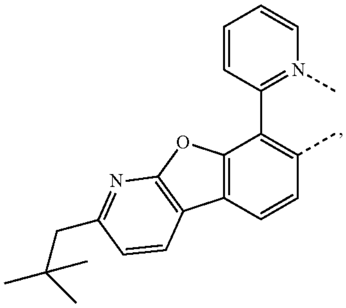

$L_{A126}$

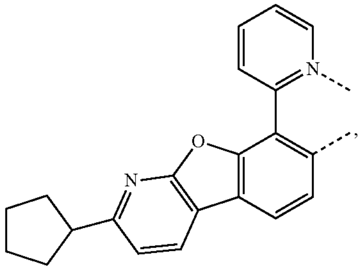

$L_{A127}$

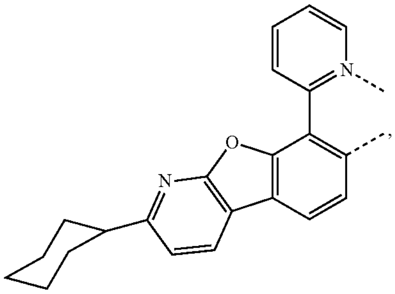

$L_{A128}$

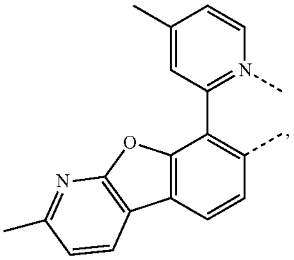

-continued
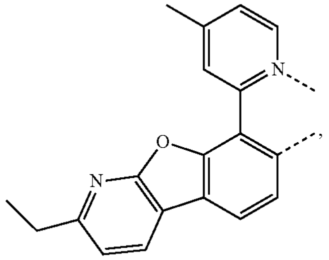
$L_{A129}$
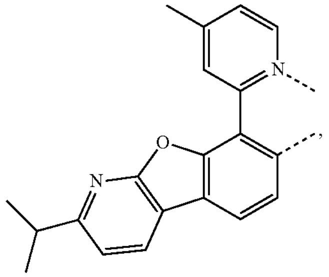
$L_{A130}$
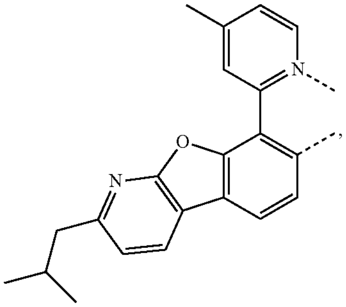
$L_{A131}$
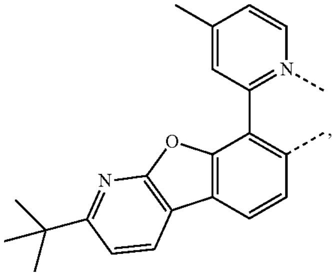
$L_{A132}$
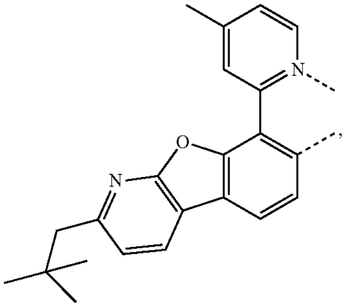
$L_{A133}$
-continued
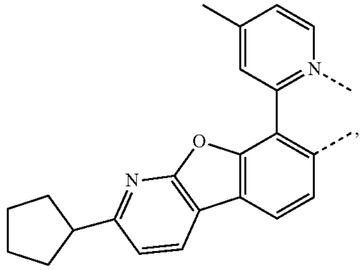
$L_{A134}$
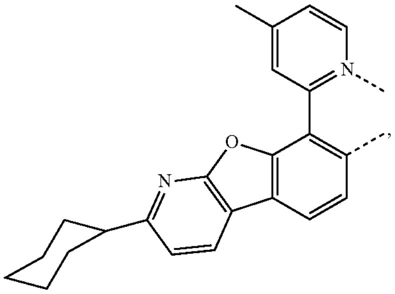
$L_{A135}$
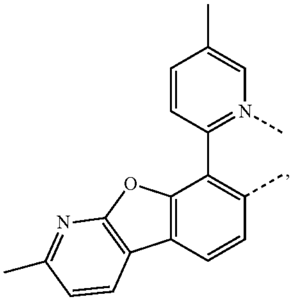
$L_{A136}$
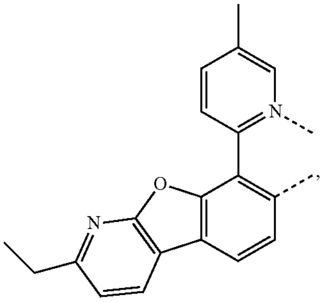
$L_{A137}$
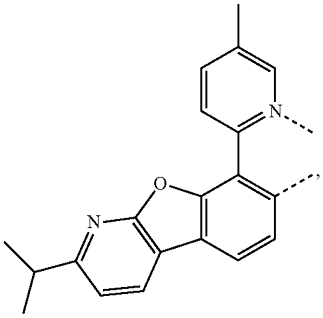
$L_{A138}$ $L_{A139}$
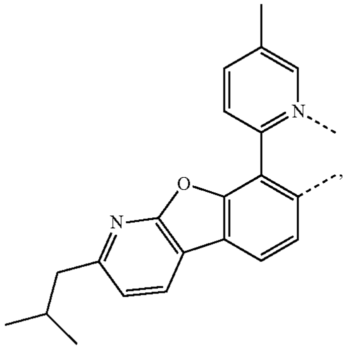
$L_{A140}$
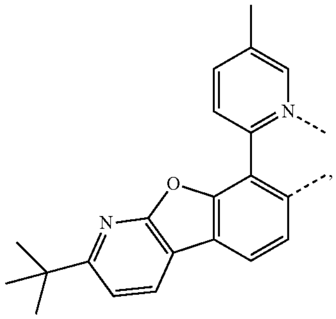
$L_{A141}$
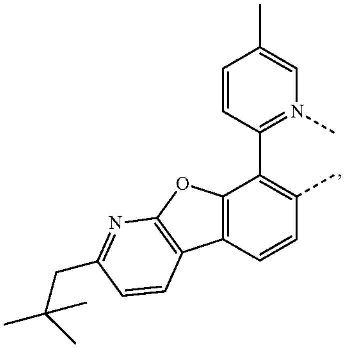
$L_{A142}$
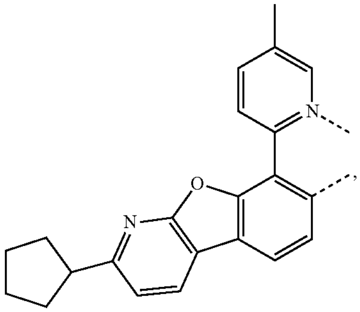
$L_{A143}$
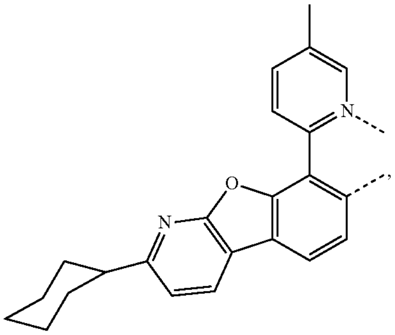
$L_{A144}$
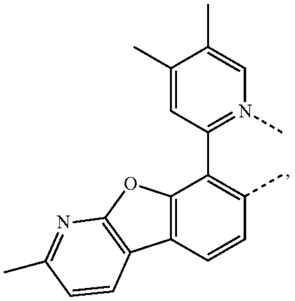
$L_{A145}$
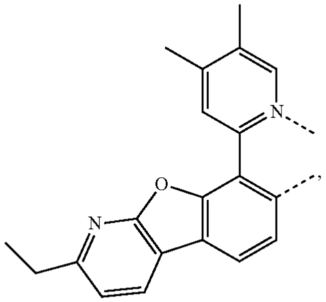
$L_{A146}$
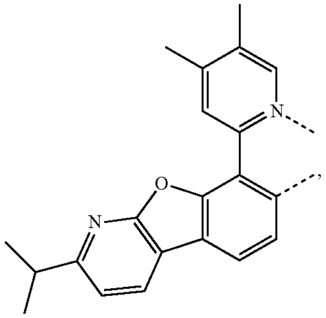
$L_{A147}$
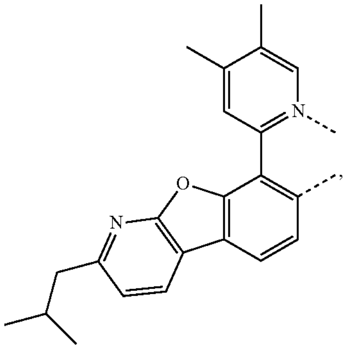

-continued
L$_{A148}$
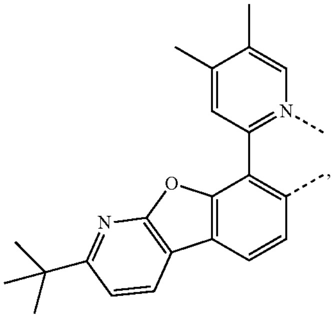
L$_{A149}$
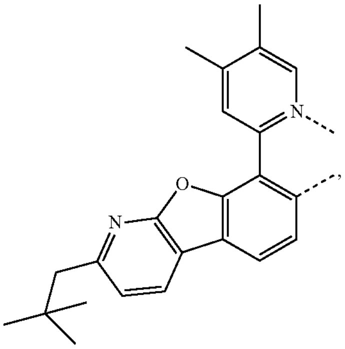
L$_{A150}$
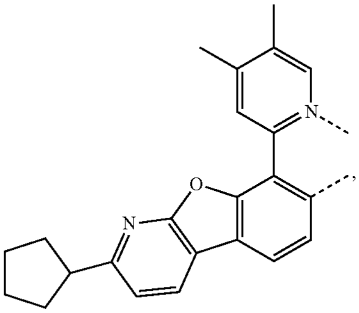
L$_{A151}$
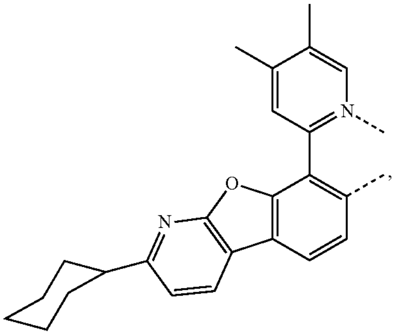
L$_{A152}$
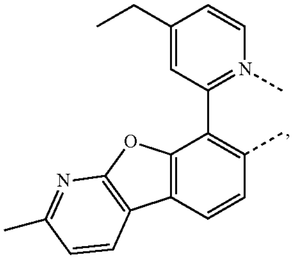
-continued
L$_{A153}$
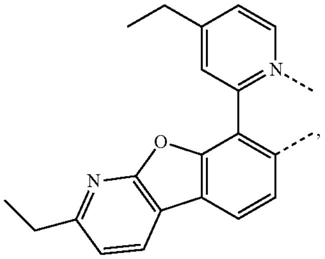
L$_{A154}$
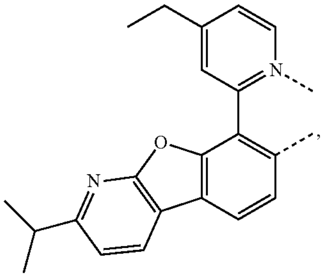
L$_{A155}$
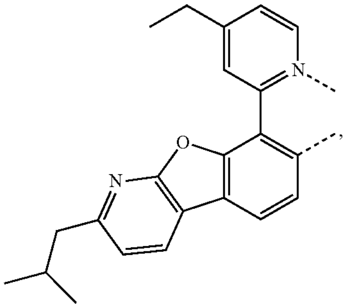
L$_{A156}$
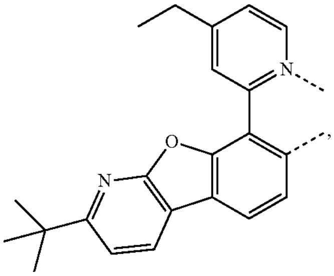
L$_{A157}$
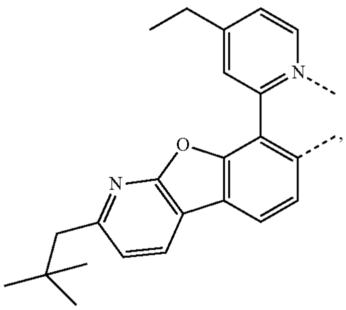

-continued
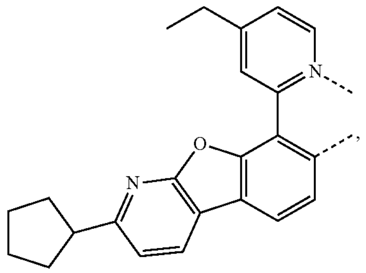
$L_{A158}$
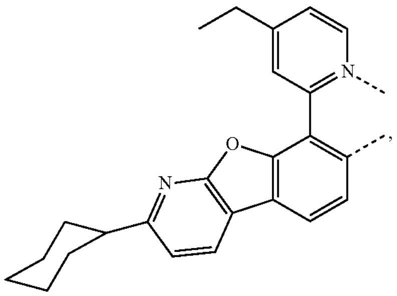
$L_{A159}$
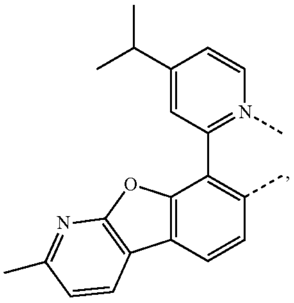
$L_{A160}$
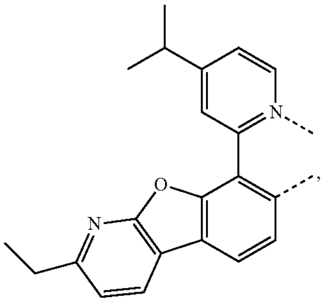
$L_{A161}$
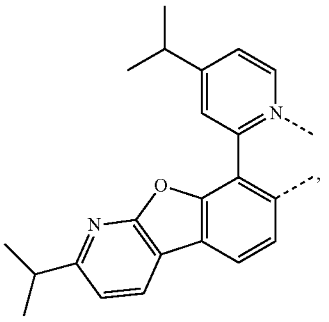
$L_{A162}$
-continued
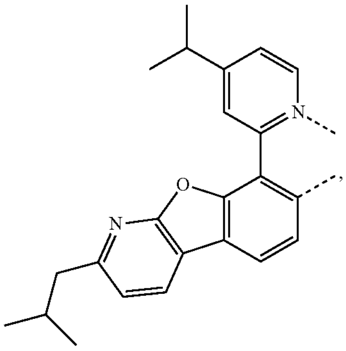
$L_{A163}$
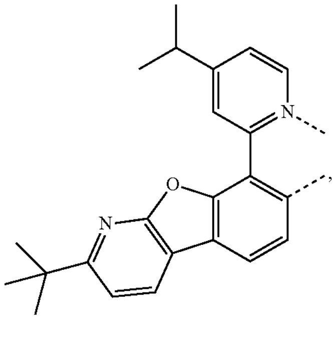
$L_{A164}$
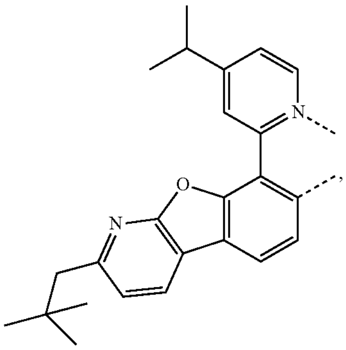
$L_{A165}$
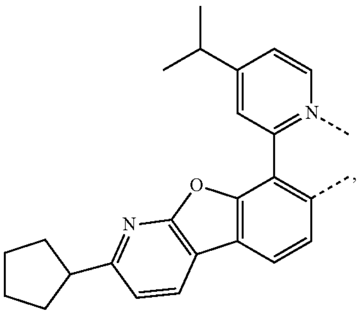
$L_{A166}$ -continued
L$_{A167}$
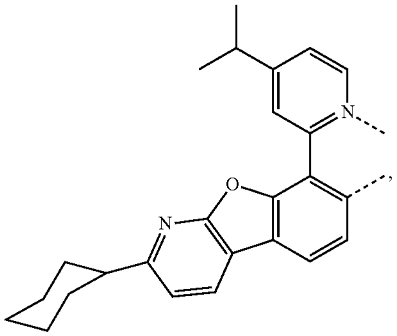
L$_{A168}$
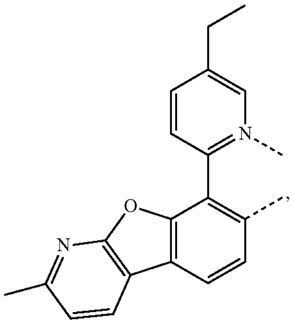
L$_{A169}$
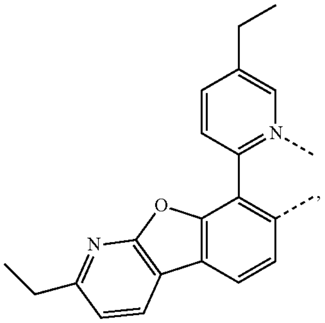
L$_{A170}$
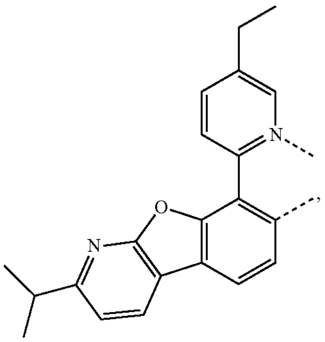
-continued
L$_{A171}$
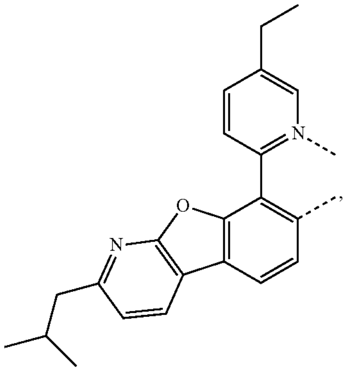
L$_{A172}$
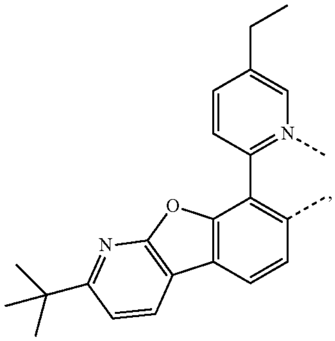
L$_{A173}$
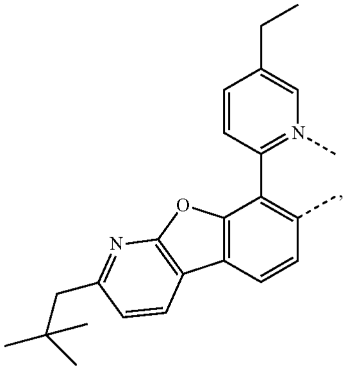
L$_{A174}$
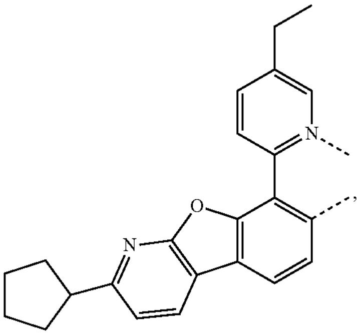

L$_{A175}$
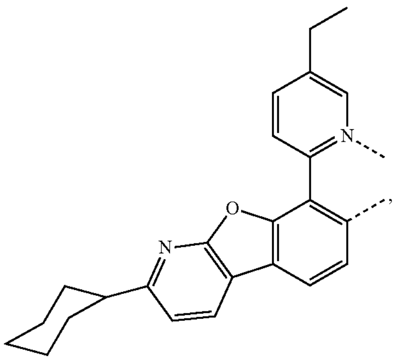
L$_{A176}$
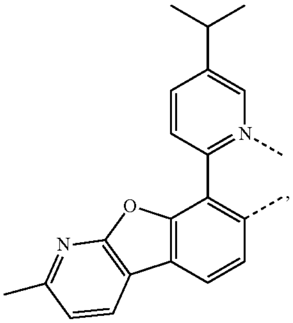
L$_{A177}$
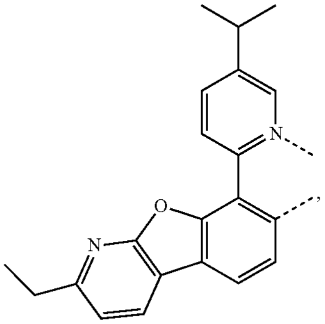
L$_{A178}$
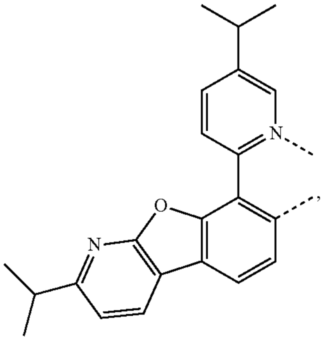
L$_{A179}$
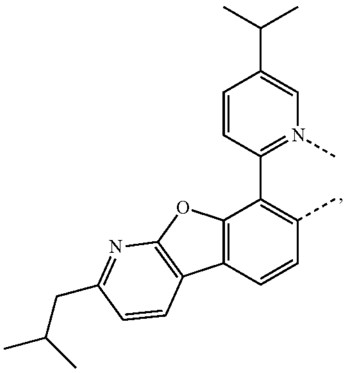
L$_{A180}$
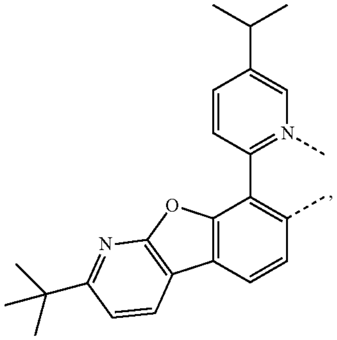
L$_{A181}$
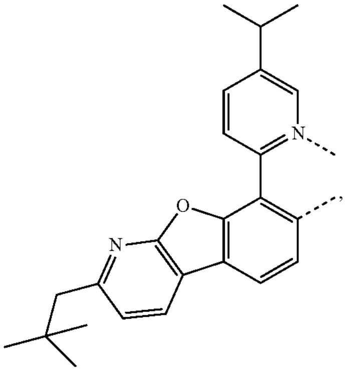
L$_{A182}$
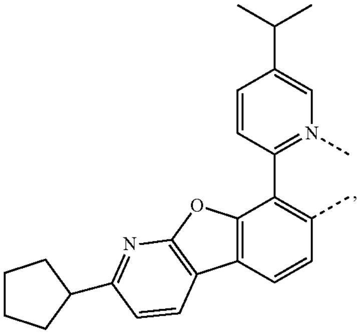

-continued
$L_{A183}$
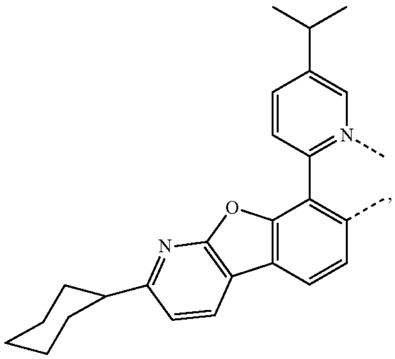
$L_{A184}$
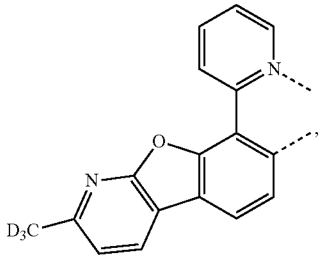
$L_{A185}$
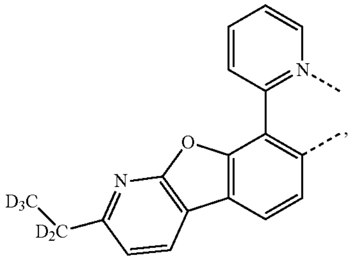
$L_{A186}$
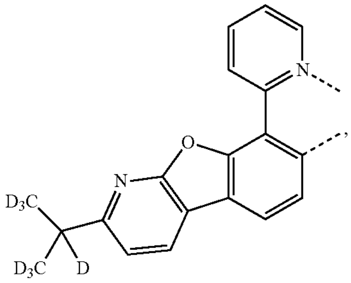
$L_{A187}$
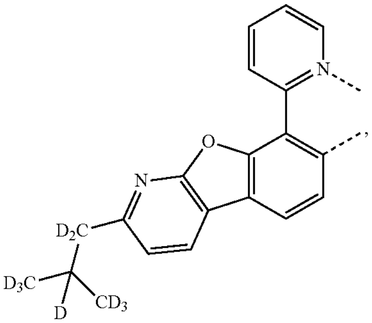
-continued
$L_{A188}$
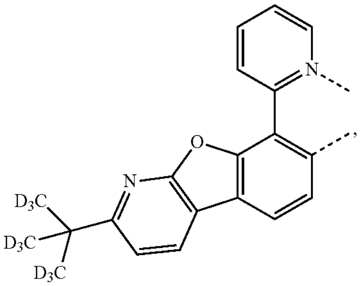
$L_{A189}$
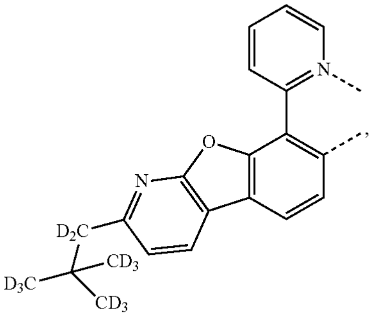
$L_{A190}$
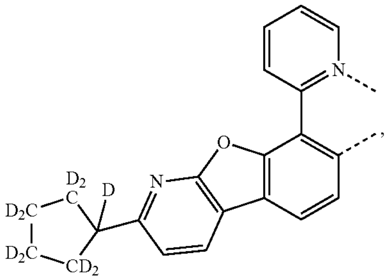
$L_{A191}$
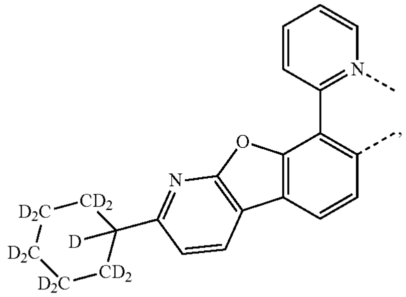
$L_{A192}$
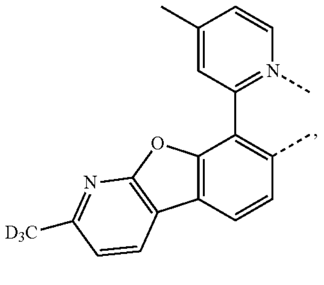

-continued
$L_{A193}$
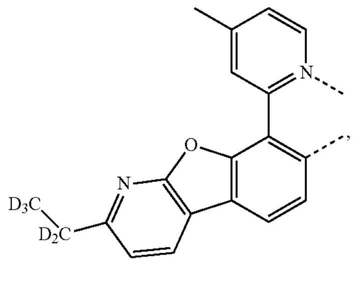
$L_{A194}$
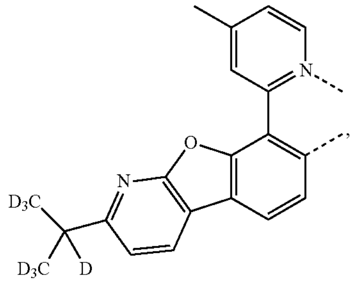
$L_{A195}$
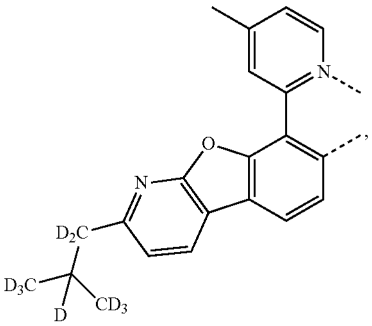
$L_{A196}$
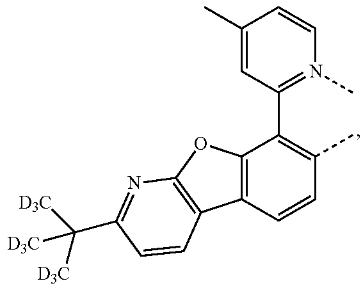
$L_{A197}$
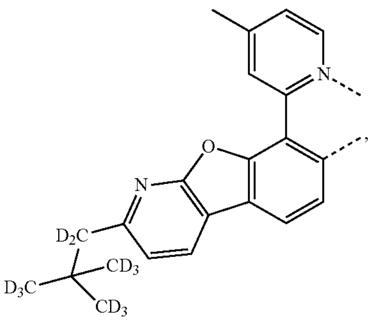
-continued
$L_{A198}$
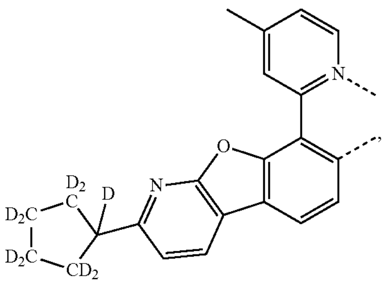
$L_{A199}$
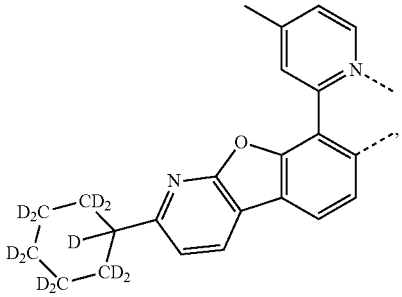
$L_{A200}$
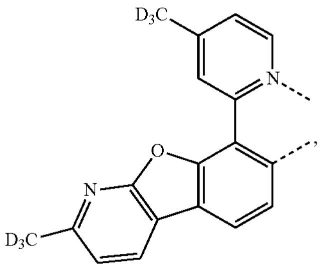
$L_{A201}$
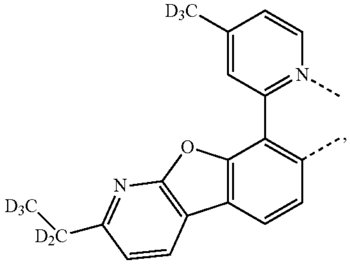
$L_{A202}$
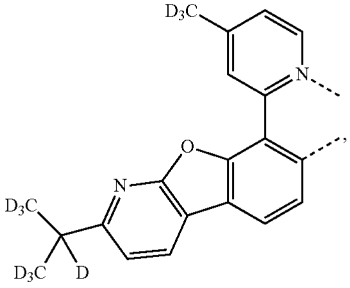

-continued
$L_{A203}$
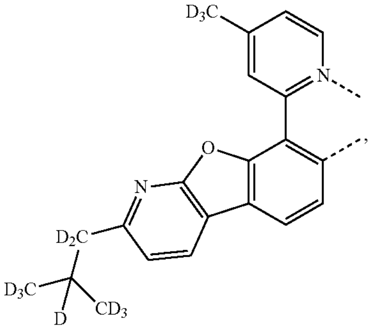
$L_{A204}$
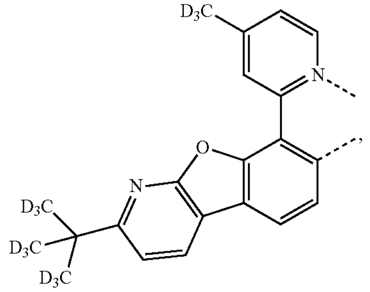
$L_{A205}$
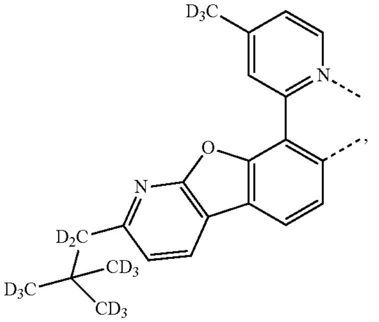
$L_{A206}$
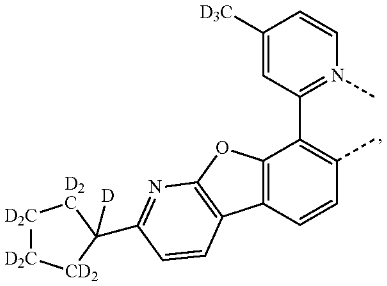
$L_{A207}$
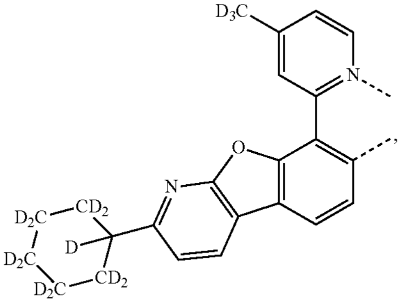
-continued
$L_{A208}$
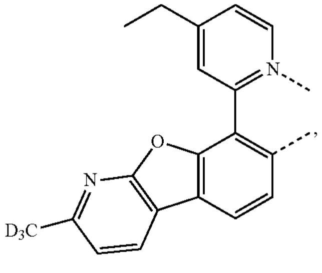
$L_{A209}$
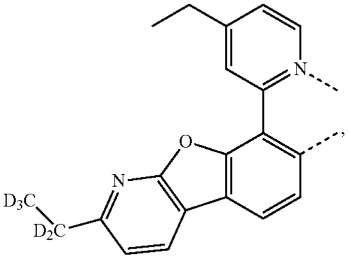
$L_{A210}$
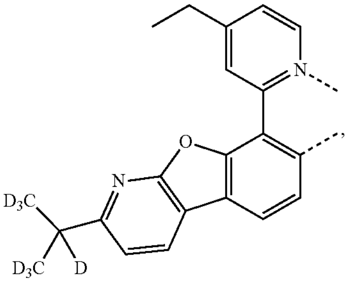
$L_{A211}$
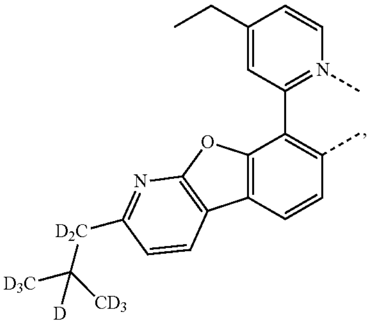
$L_{A212}$
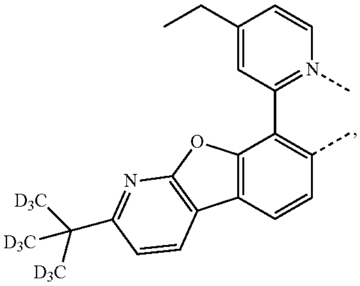

-continued
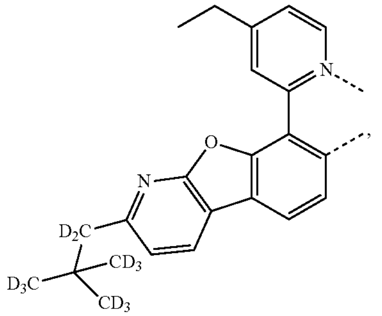
$L_{A213}$
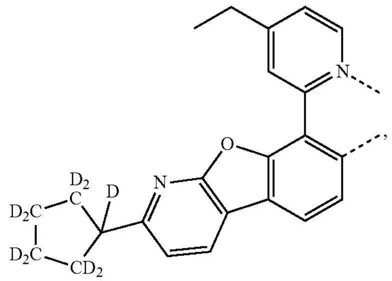
$L_{A214}$
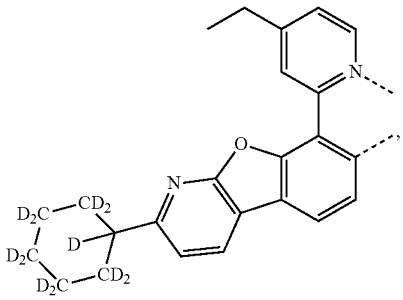
$L_{A215}$
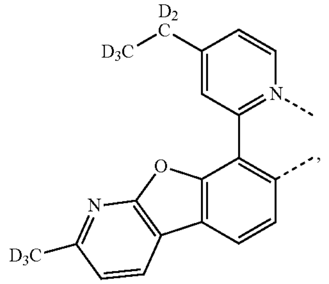
$L_{A216}$
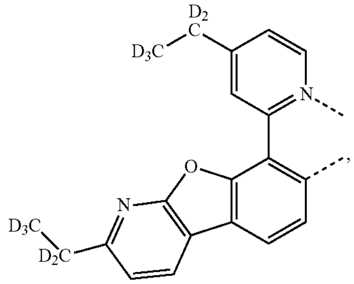
$L_{A217}$
-continued
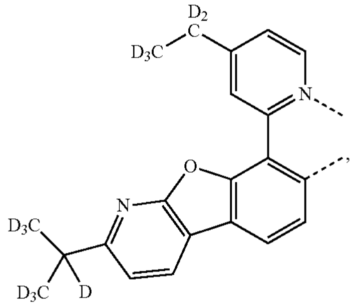
$L_{A218}$
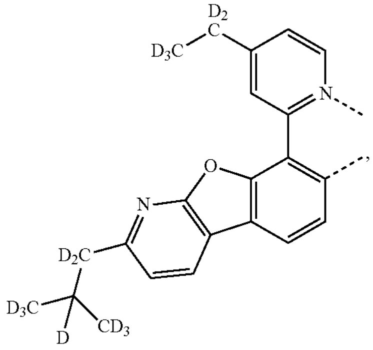
$L_{A219}$
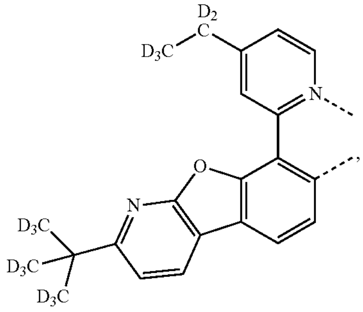
$L_{A220}$
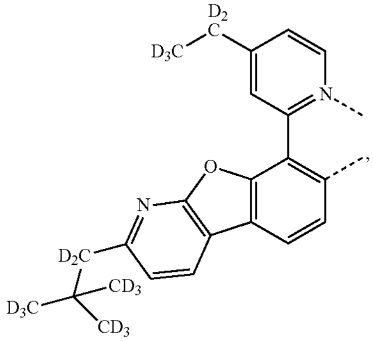
$L_{A221}$ -continued
$L_{A222}$
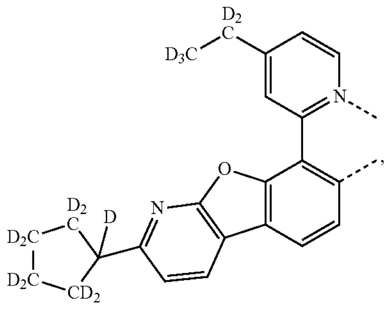
$L_{A223}$
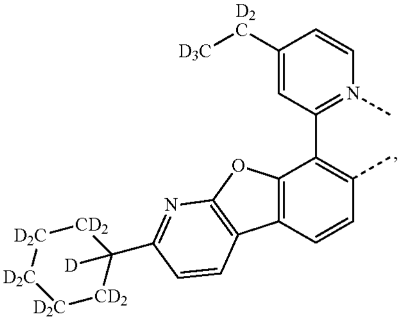
$L_{A224}$
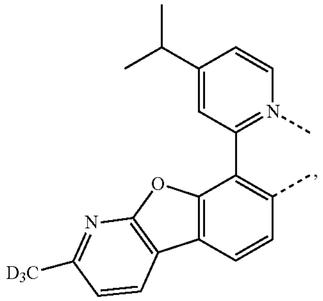
$L_{A225}$
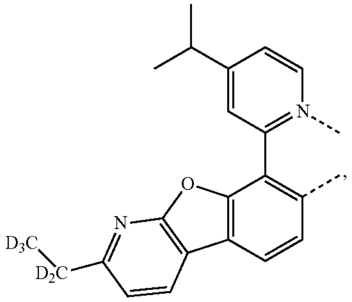
$L_{A226}$
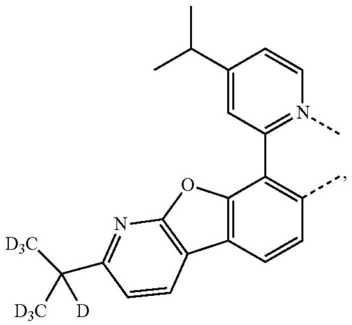
-continued
$L_{A227}$
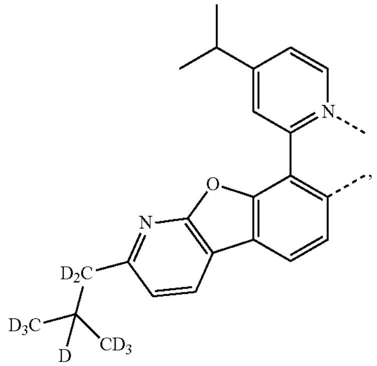
$L_{A228}$
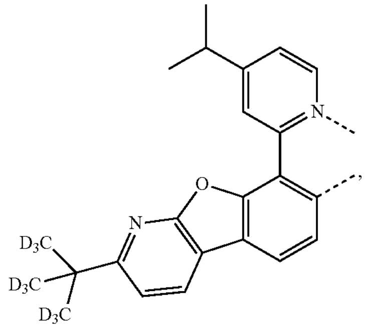
$L_{A229}$
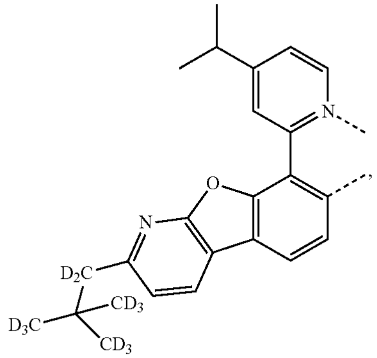
$L_{A230}$
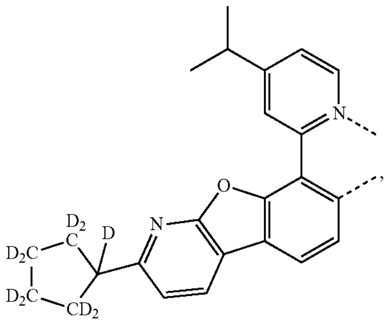

L_A231
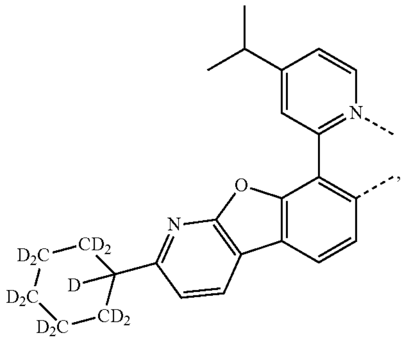
L_A232
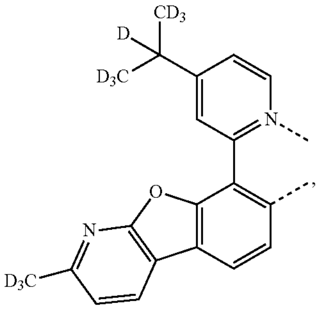
L_A233
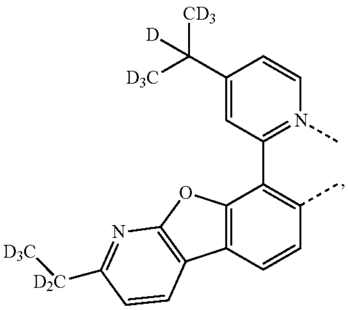
L_A234
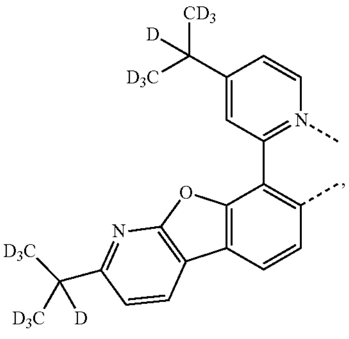
L_A235
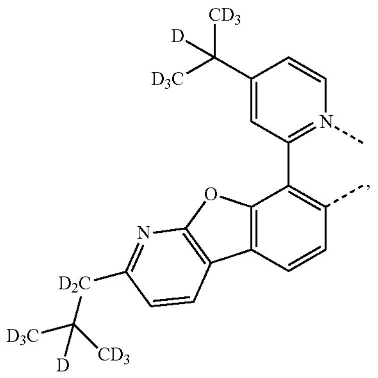
L_A236
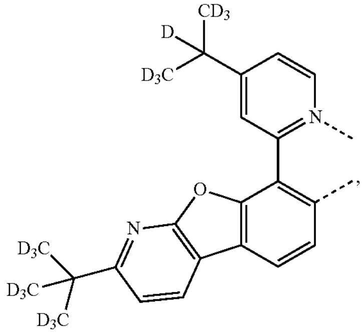
L_A237
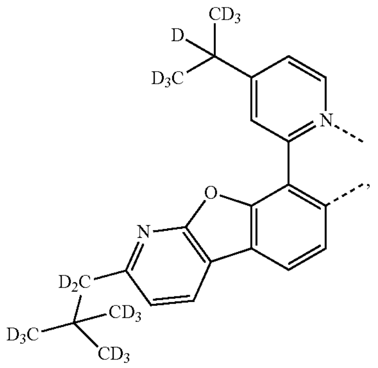
L_A238
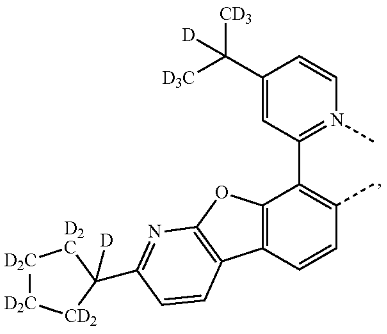

-continued
$L_{A239}$
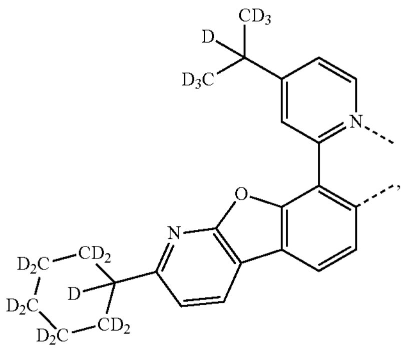
$L_{A240}$
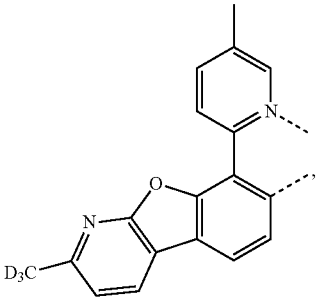
$L_{A241}$
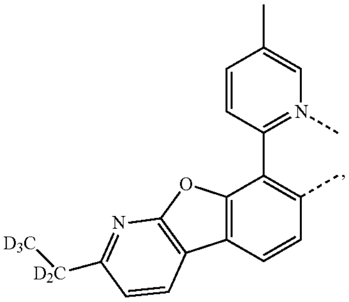
$L_{A242}$
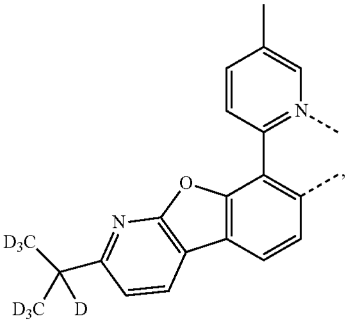
-continued
$L_{A243}$
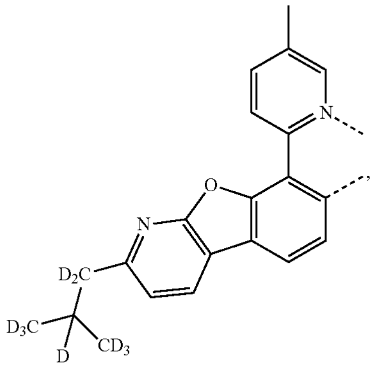
$L_{A244}$
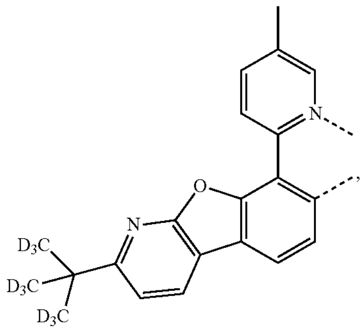
$L_{A245}$
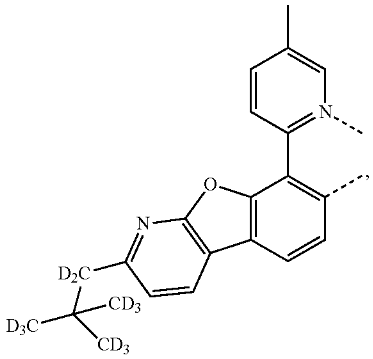
$L_{A246}$
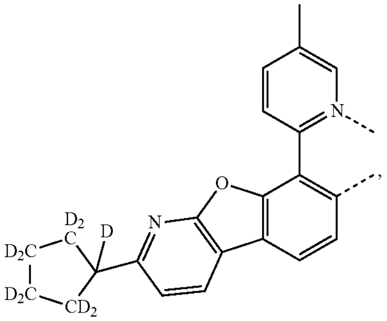

-continued
L$_{A247}$
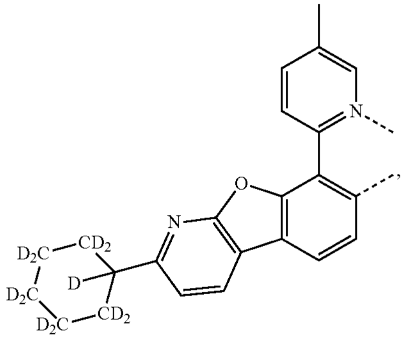
L$_{A248}$
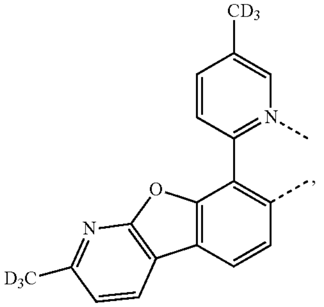
L$_{A249}$
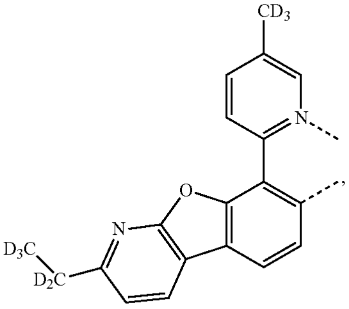
L$_{A250}$
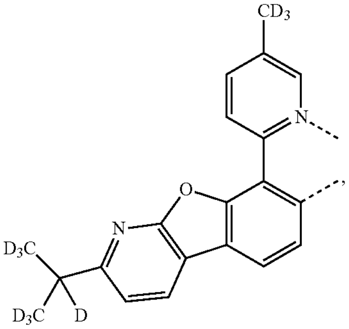
-continued
L$_{A251}$
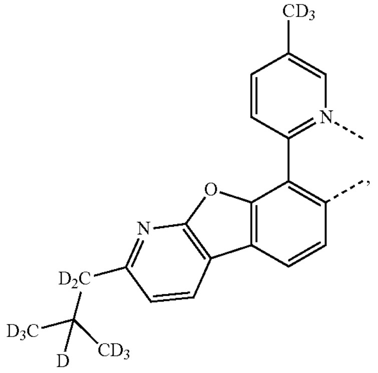
L$_{A252}$
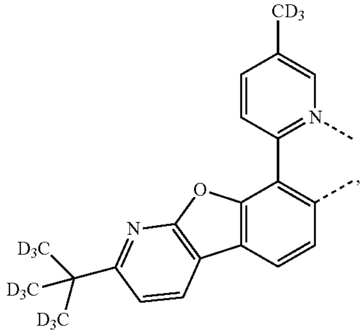
L$_{A253}$
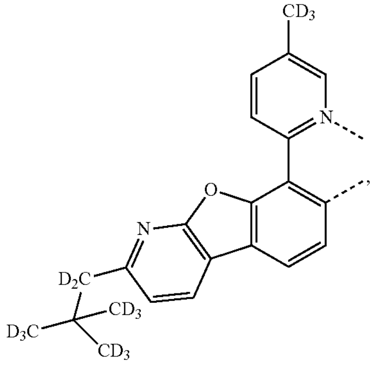
L$_{A254}$
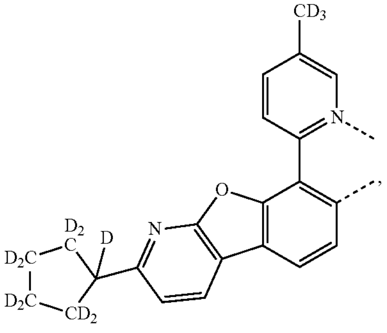

-continued
L$_{A255}$
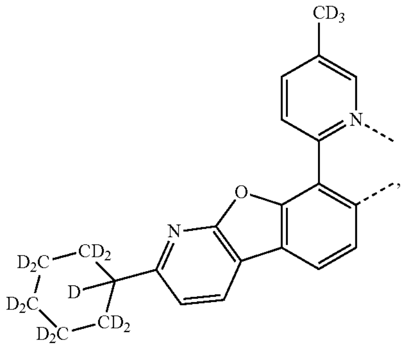
L$_{A256}$
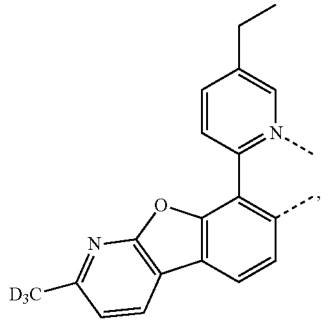
L$_{A257}$
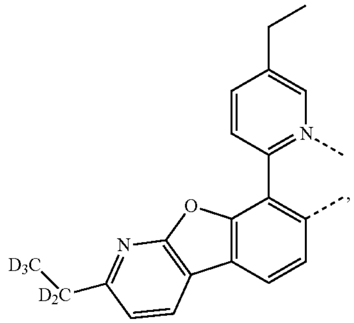
L$_{A258}$
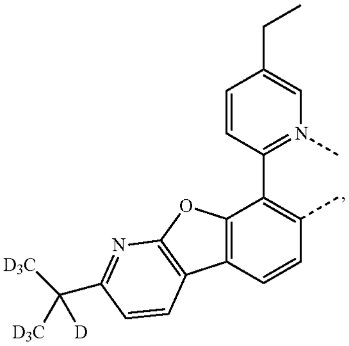
-continued
L$_{A259}$
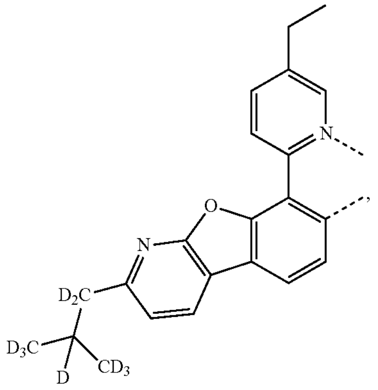
L$_{A260}$
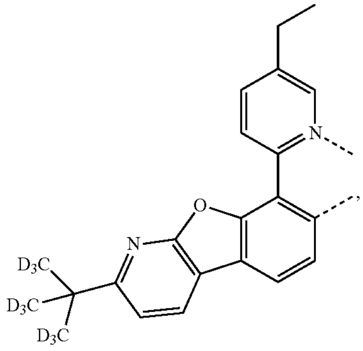
L$_{A261}$
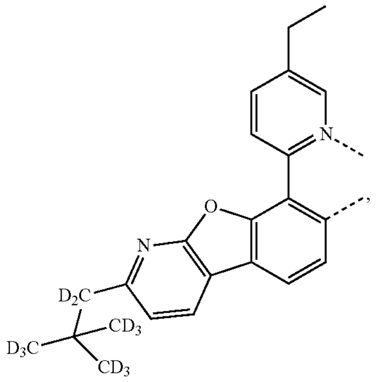
L$_{A262}$
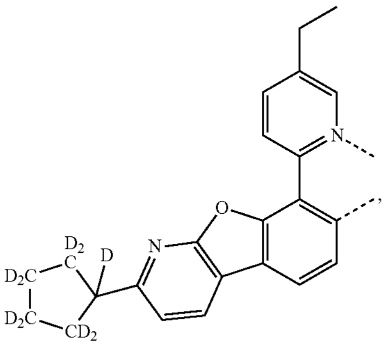

-continued
$L_{A263}$
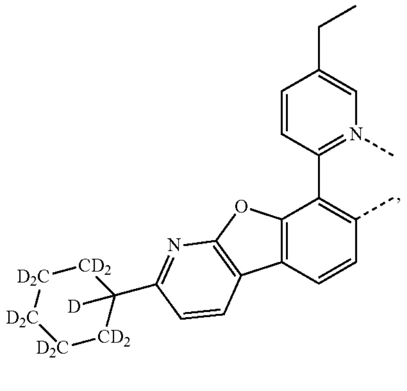
$L_{A264}$
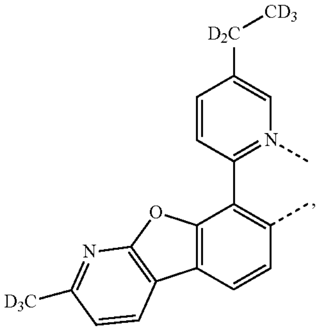
$L_{A265}$
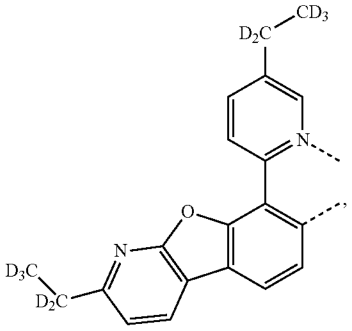
$L_{A266}$
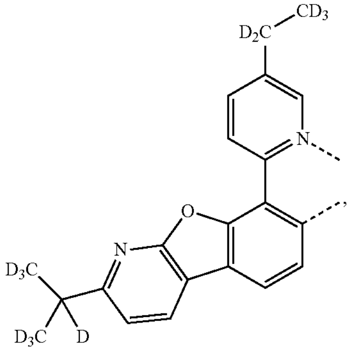
-continued
$L_{A267}$
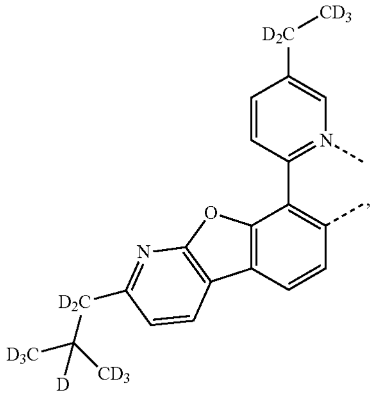
$L_{A268}$
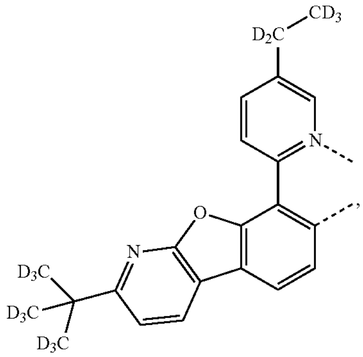
$L_{A269}$
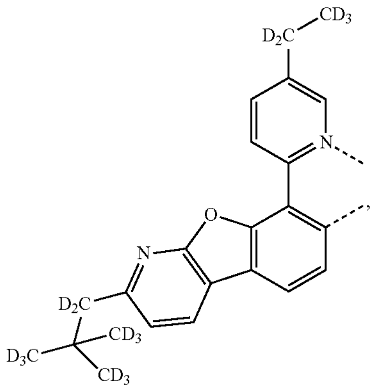
$L_{A270}$
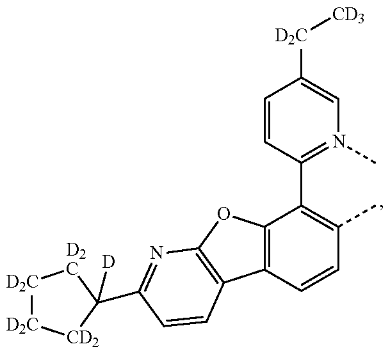

-continued
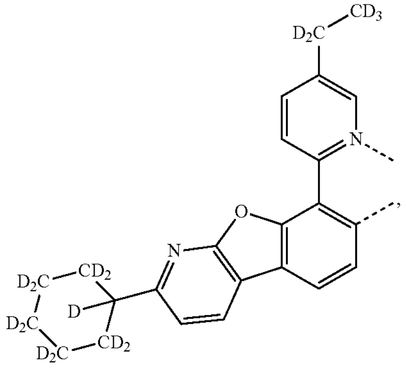
$L_{A271}$
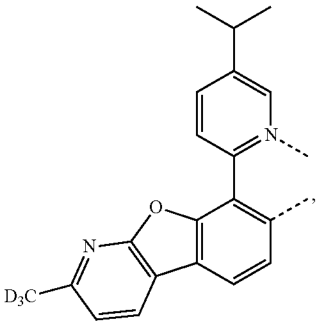
$L_{A272}$
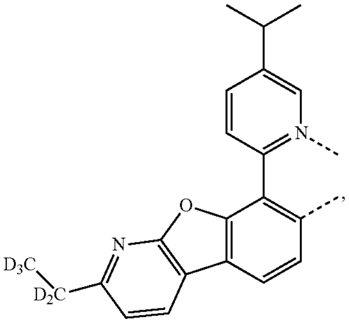
$L_{A273}$
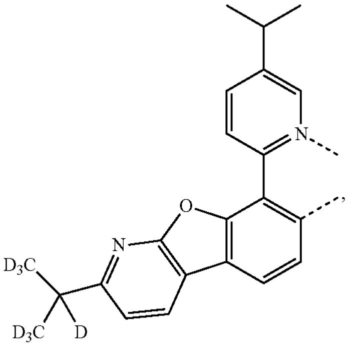
$L_{A274}$
-continued
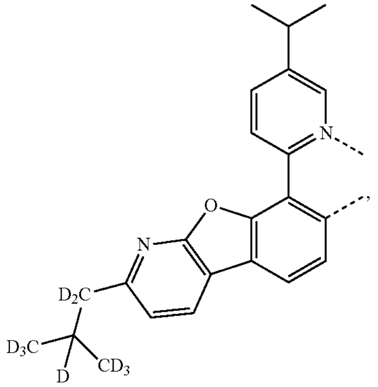
$L_{A275}$
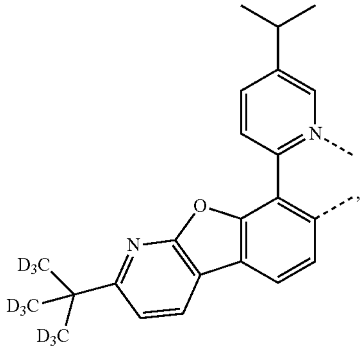
$L_{A276}$
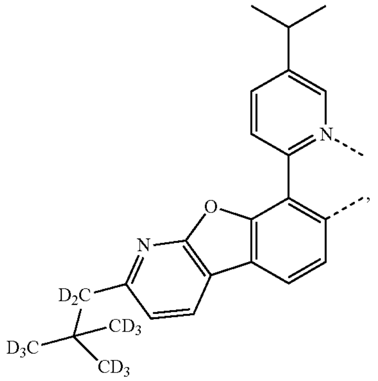
$L_{A277}$
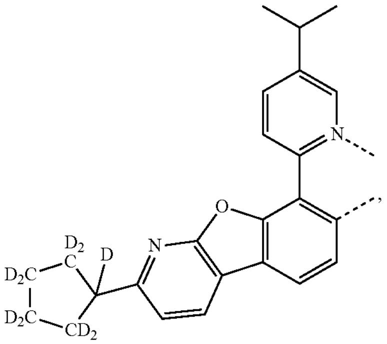
$L_{A278}$ -continued
$L_{A279}$
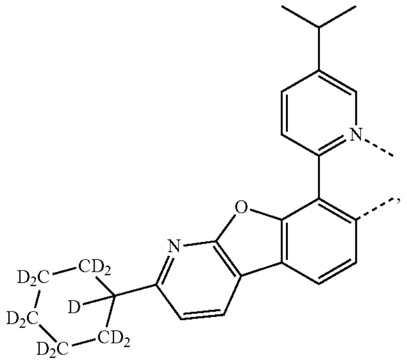
$L_{A280}$
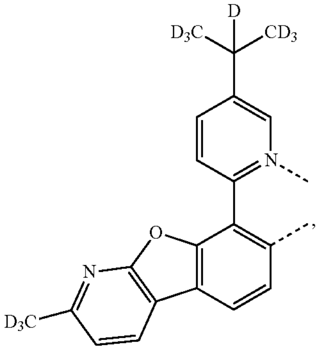
$L_{A281}$
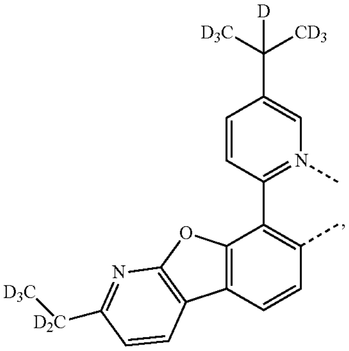
$L_{A282}$
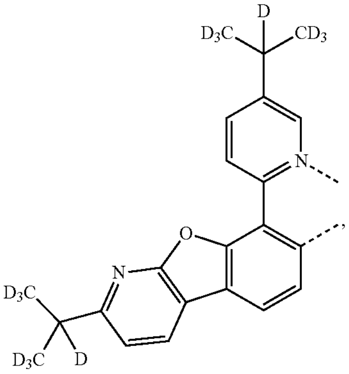
-continued
$L_{A283}$
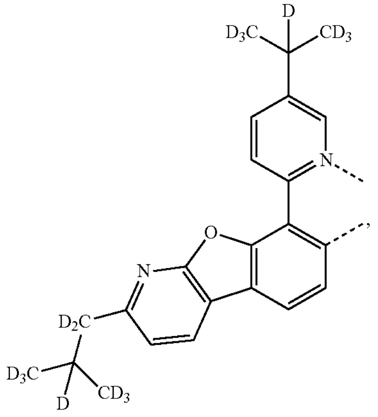
$L_{A284}$
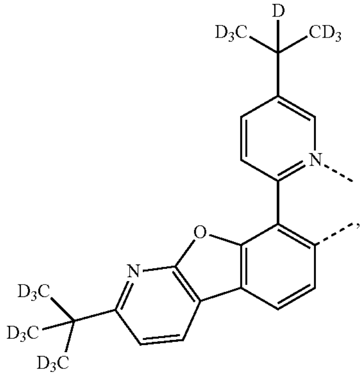
$L_{A285}$
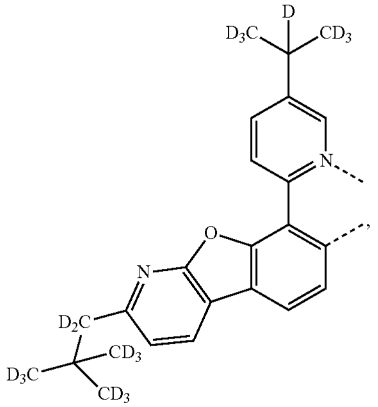
$L_{A286}$
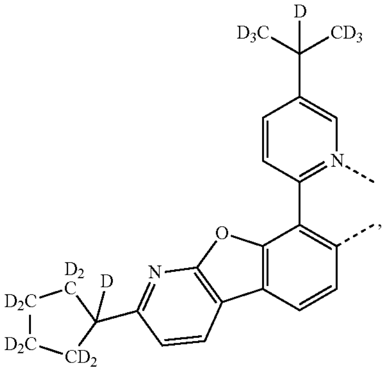

-continued
L_{A287}
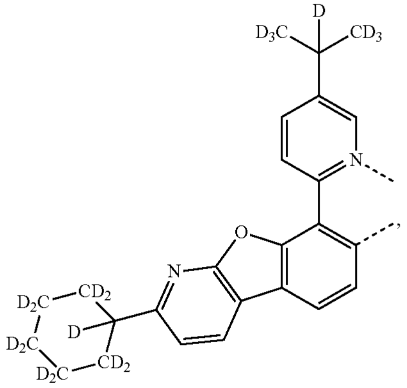
L_{A288}
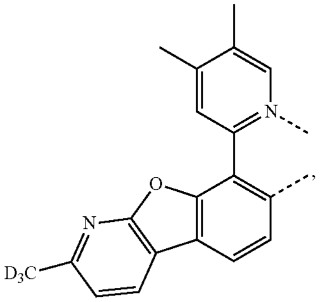
L_{A289}
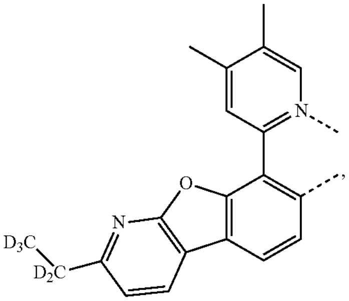
L_{A290}
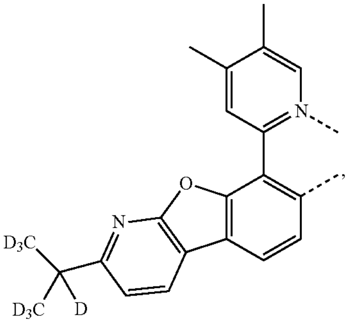
-continued
L_{A291}
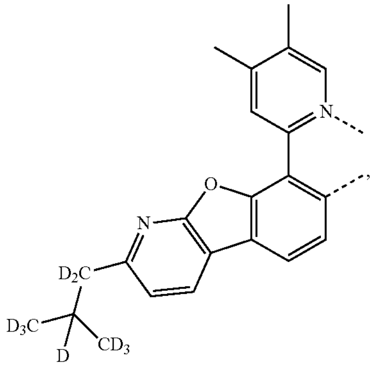
L_{A292}
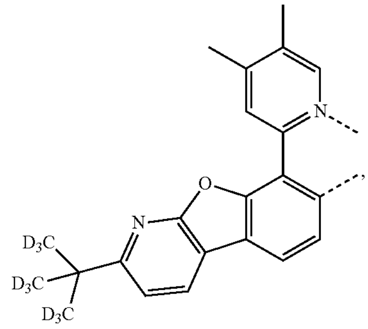
L_{A293}
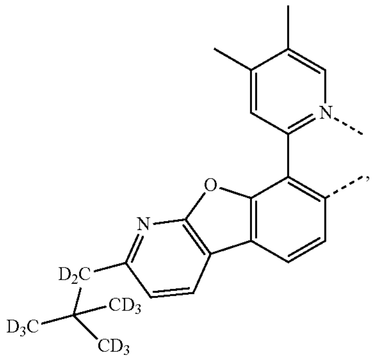
L_{A294}
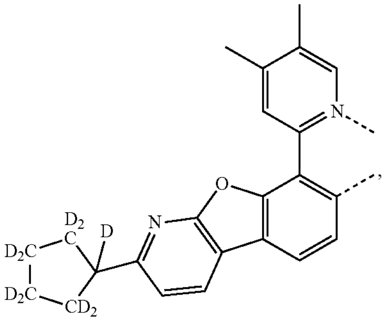

-continued
L$_{A295}$
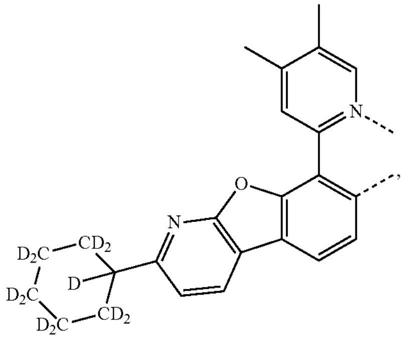
L$_{A296}$
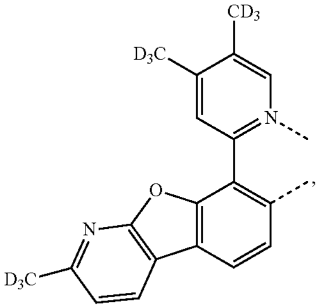
L$_{A297}$
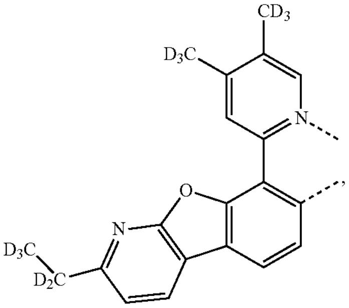
L$_{A298}$
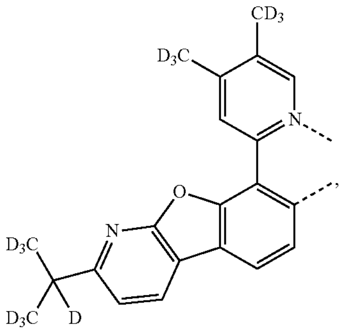
-continued
L$_{A299}$
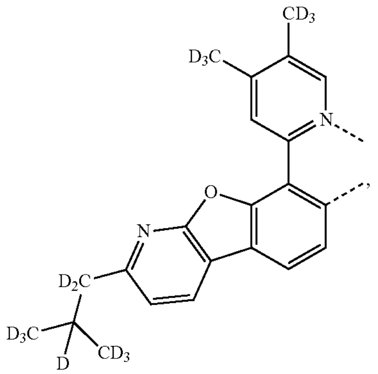
L$_{A300}$
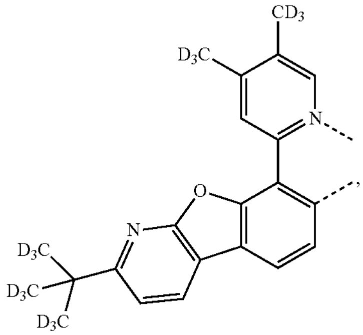
L$_{A301}$
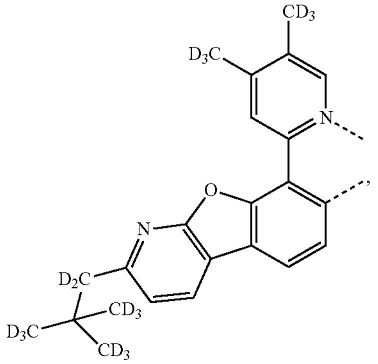
L$_{A302}$
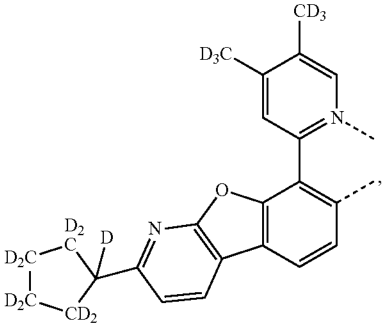

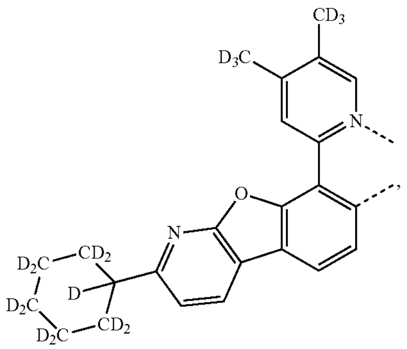
$L_{A303}$
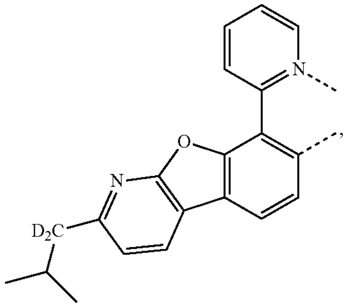
$L_{A304}$
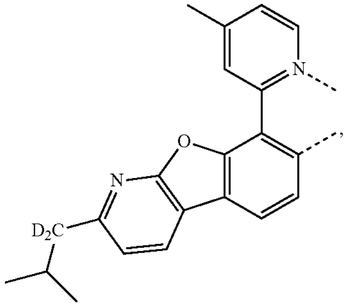
$L_{A305}$
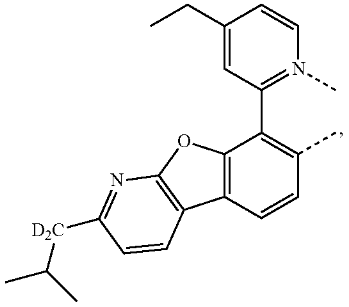
$L_{A306}$
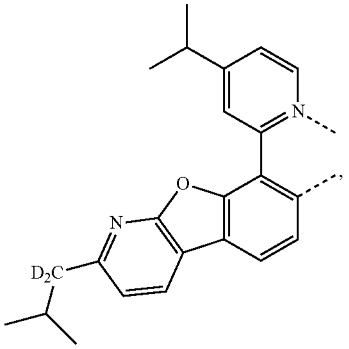
$L_{A307}$
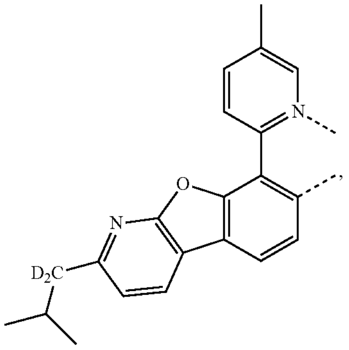
$L_{A308}$
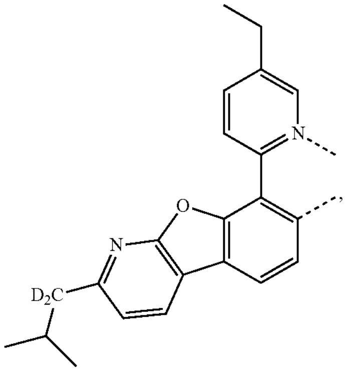
$L_{A309}$
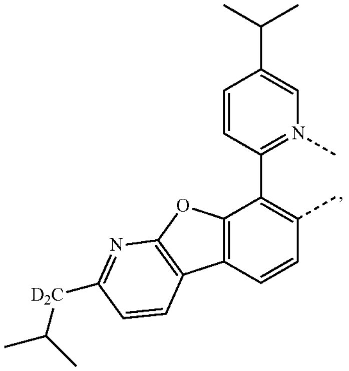
$L_{A310}$ -continued
$L_{A311}$
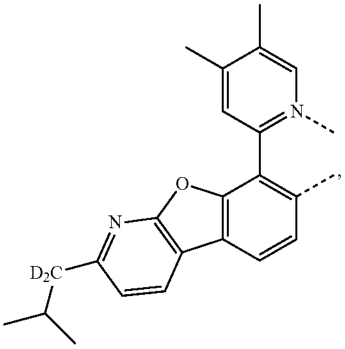
$L_{A312}$
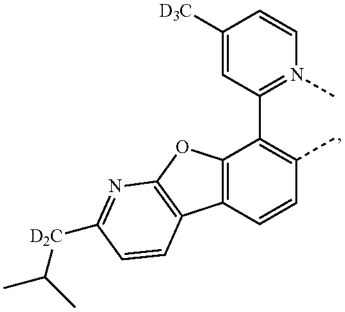
$L_{A313}$
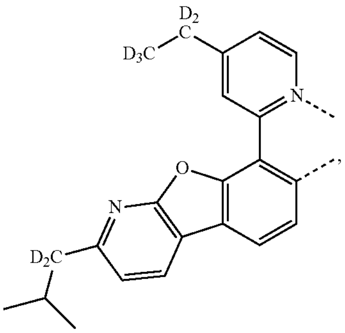
$L_{A314}$
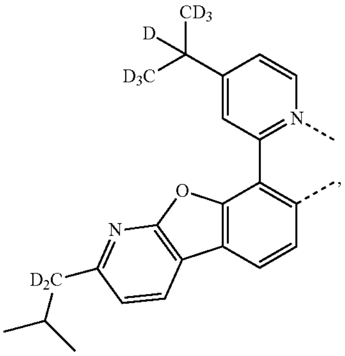
-continued
$L_{A315}$
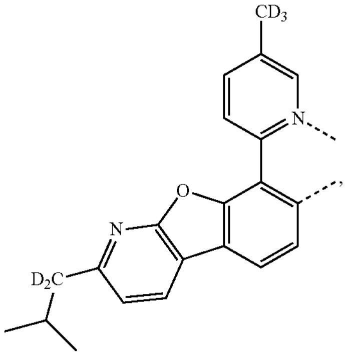
$L_{A316}$
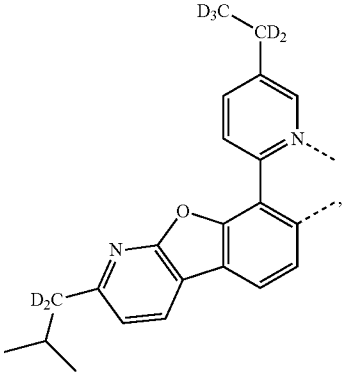
and
$L_{A317}$
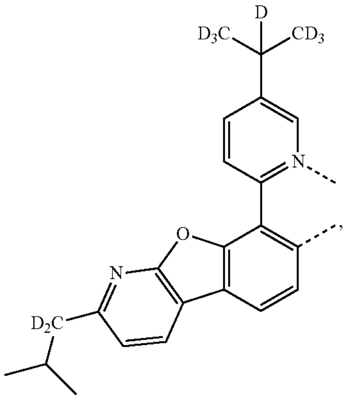
The $L_B$ in Formula II is selected from the group consisting of:
$L_{B1}$
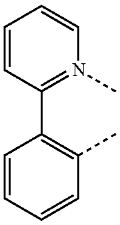

-continued
$L_{B2}$
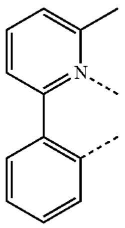
$L_{B3}$
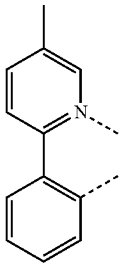
$L_{B4}$
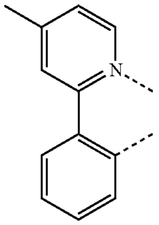
$L_{B5}$
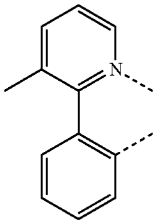
$L_{B6}$
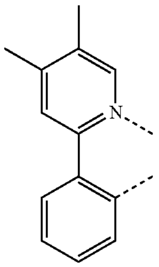
$L_{B7}$
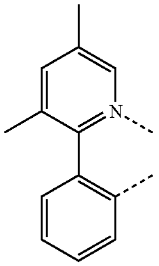
-continued
$L_{B8}$
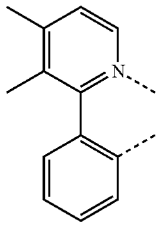
$L_{B9}$
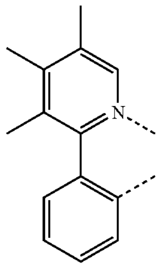
$L_{B10}$
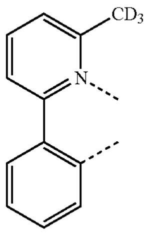
$L_{B11}$
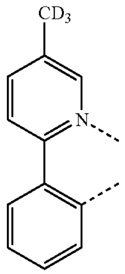
$L_{B12}$
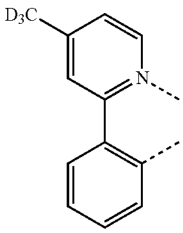
$L_{B13}$
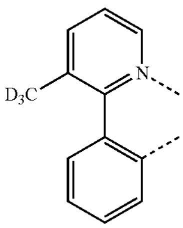

-continued
$L_{B14}$
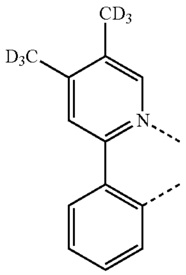
$L_{B15}$
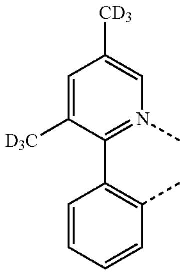
$L_{B16}$
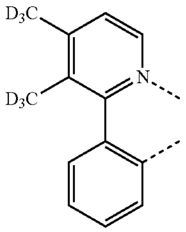
$L_{B17}$
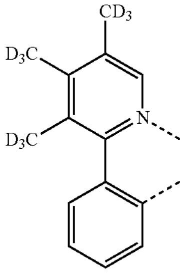
$L_{B18}$
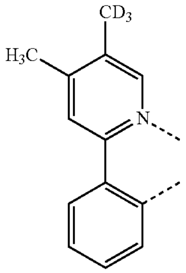
$L_{B19}$
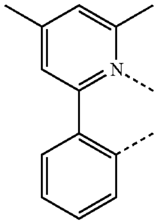
-continued
$L_{B20}$
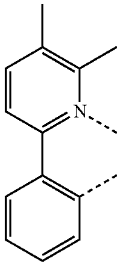
$L_{B21}$
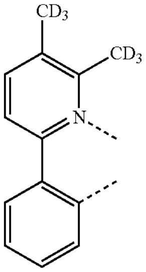
$L_{B22}$
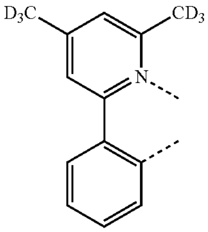
$L_{B23}$
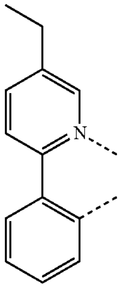
$L_{B24}$
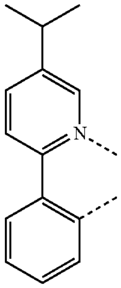
$L_{B25}$
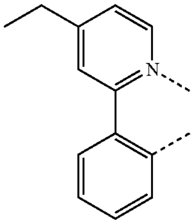

-continued
$L_{B26}$
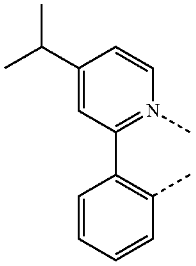
$L_{B27}$
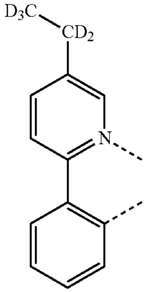
$L_{B28}$
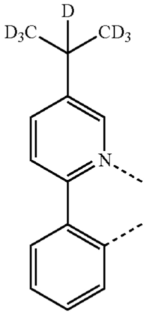
$L_{B29}$
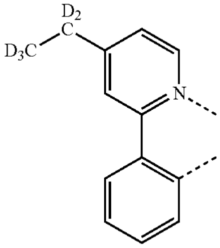
$L_{B30}$
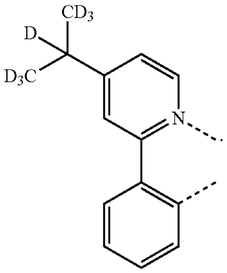
In one embodiment, the compound of Formula II is selected from the group consisting of:
Compound II-1
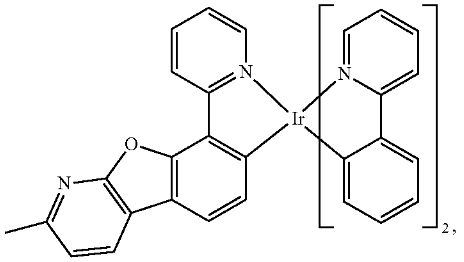
Compound II-2
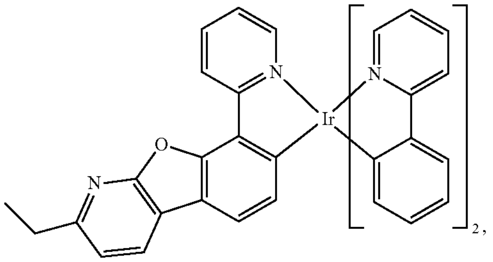
Compound II-3
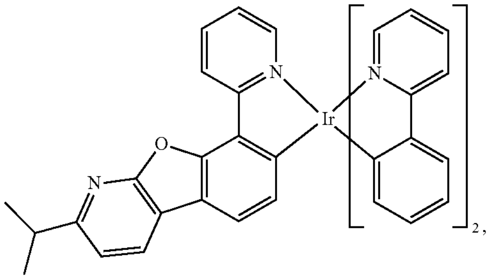
Compound II-4
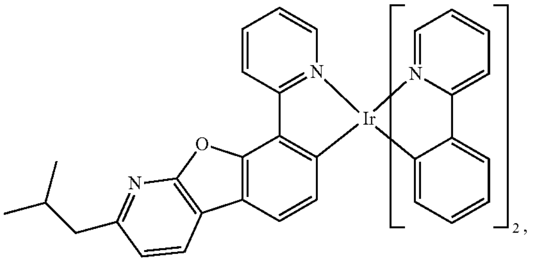
Compound II-5
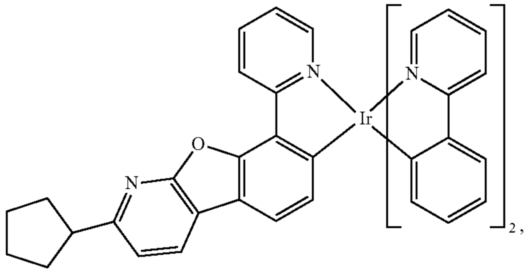

-continued
Compound II-6
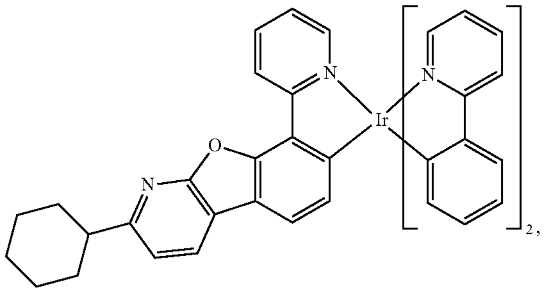
Compound II-7
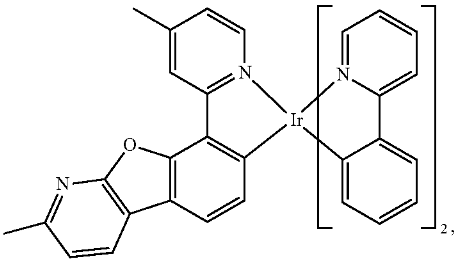
Compound II-8
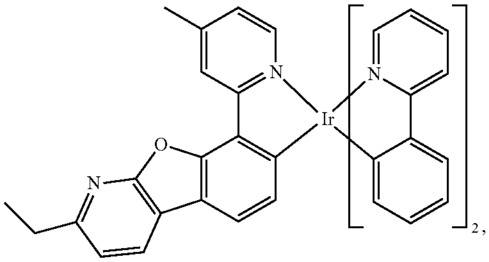
Compound II-9
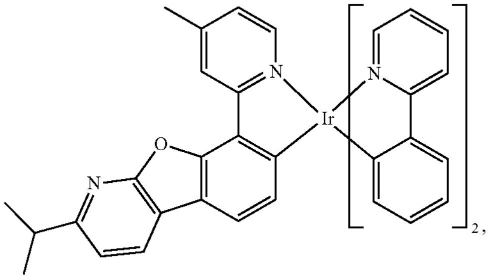
Compound II-10
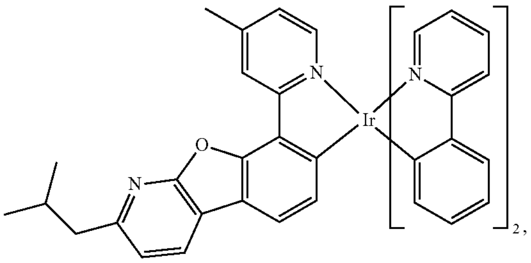
-continued
Compound II-11
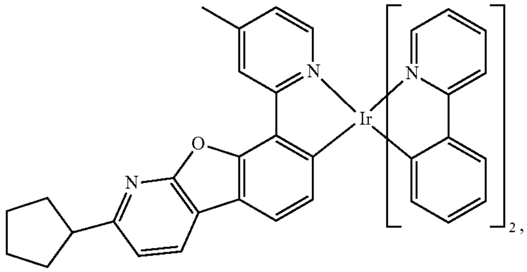
Compound II-12
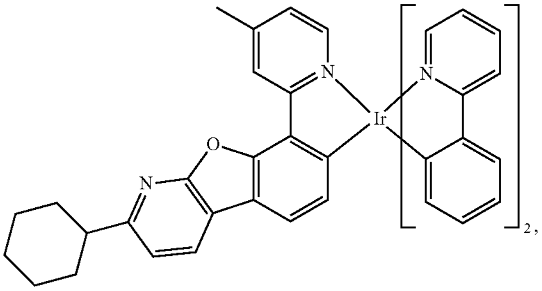
Compound II-13
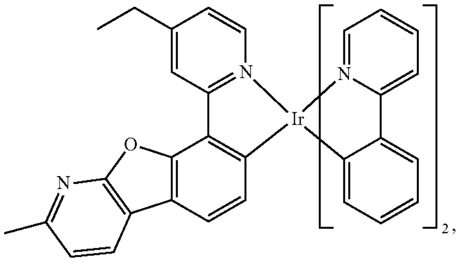
Compound II-14
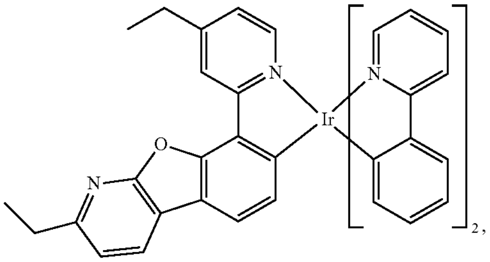
Compound II-15
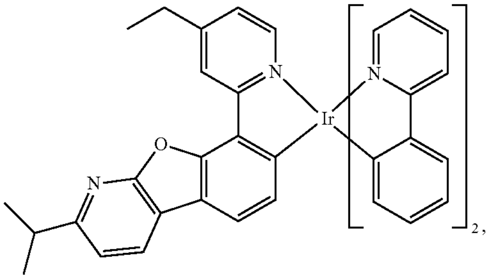

-continued
Compound II-16
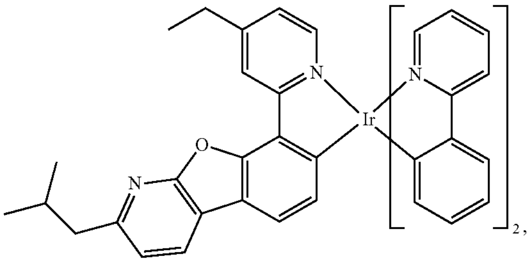
Compound II-17
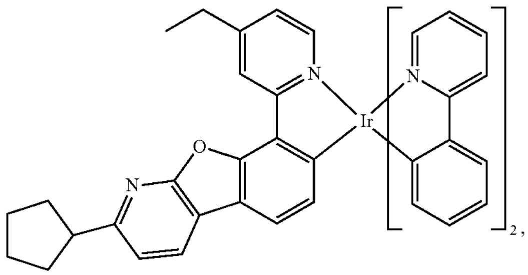
Compound II-18
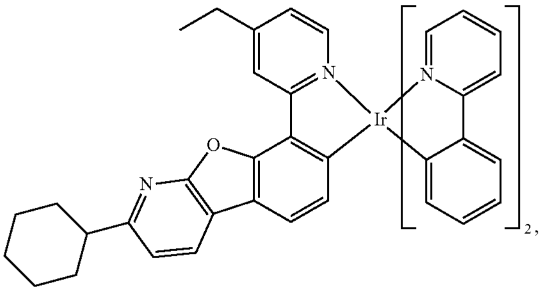
Compound II-19
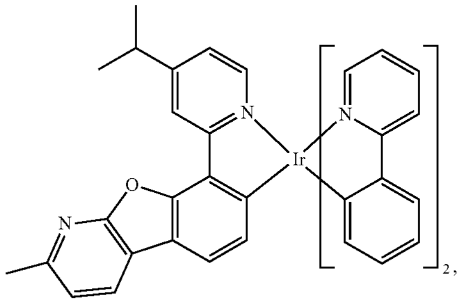
Compound II-20
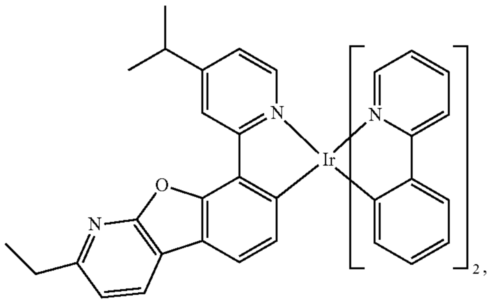
-continued
Compound II-21
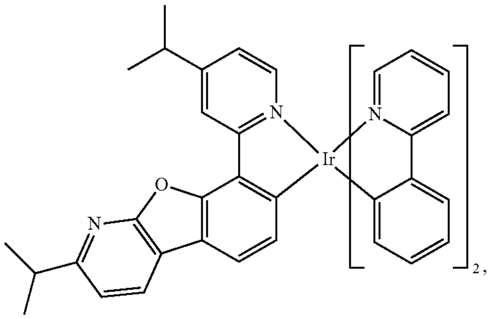
Compound II-22
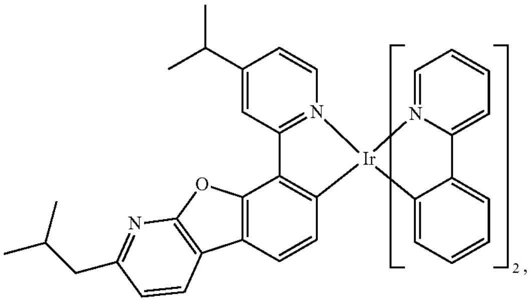
Compound II-23
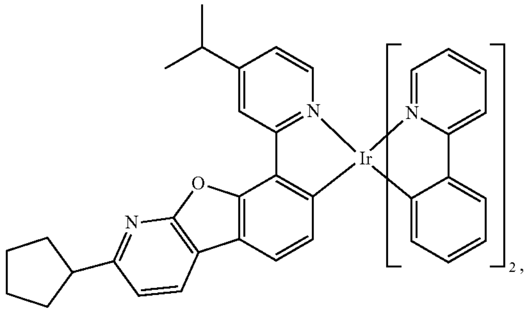
Compound II-24
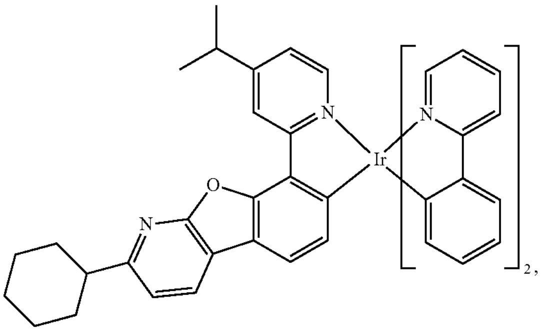

-continued
Compound II-25
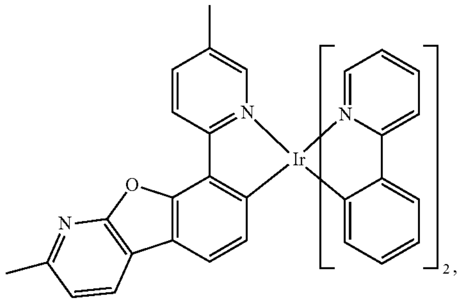
Compound II-26
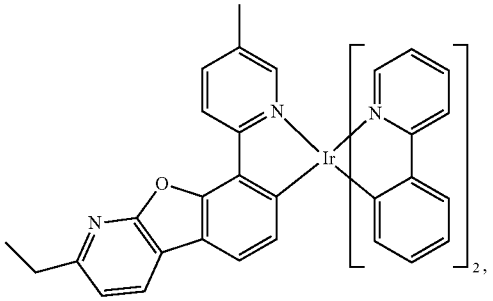
Compound II-27
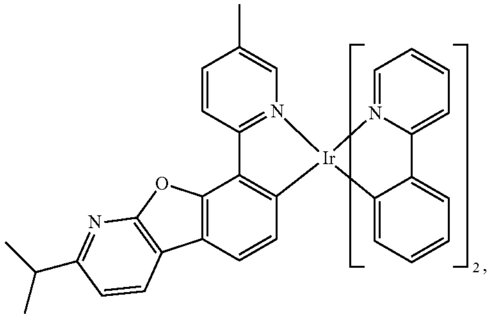
Compound II-28
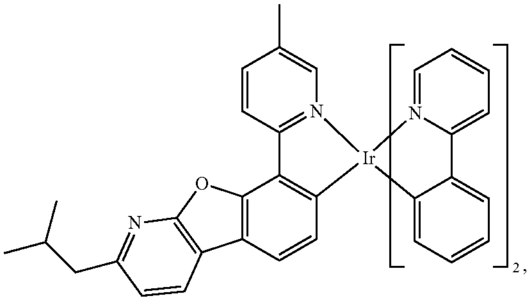
-continued
Compound II-29
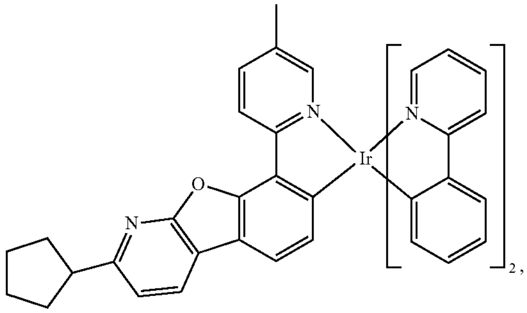
Compound II-30
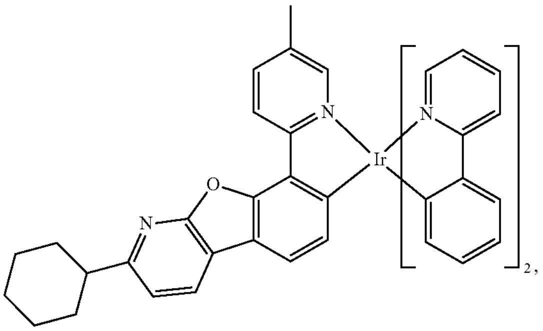
Compound II-31
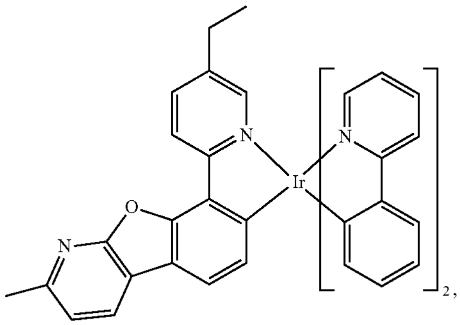
Compound II-32
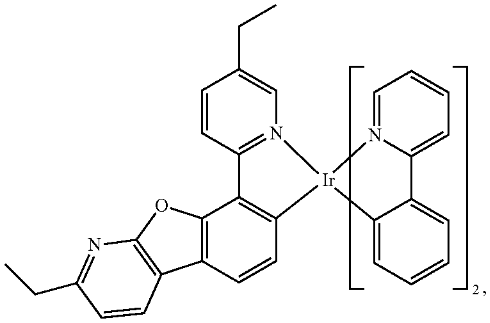

-continued
Compound II-33
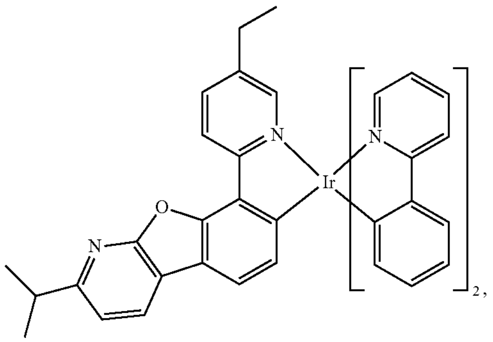
Compound II-34
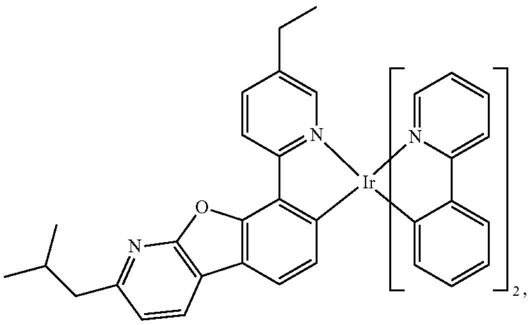
Compound II-35
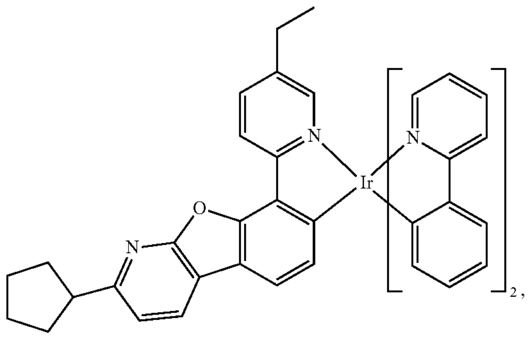
Compound II-36
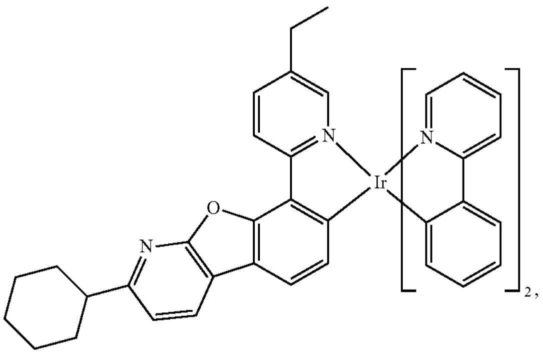
-continued
Compound II-37
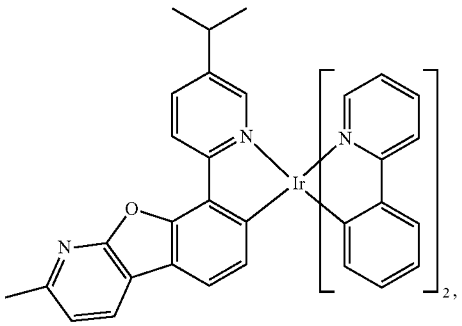
Compound II-38
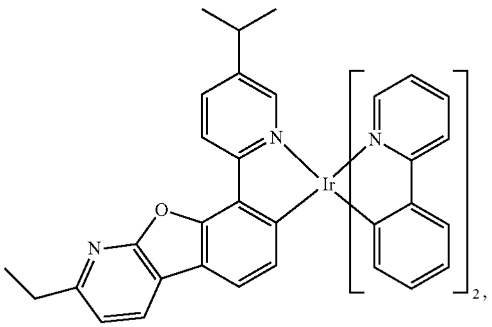
Compound II-39
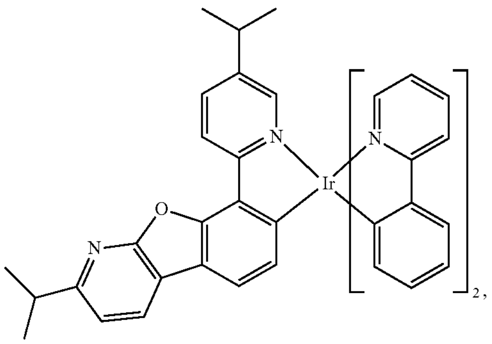
Compound II-40
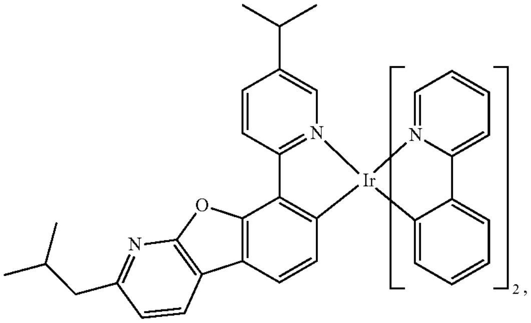

-continued
Compound II-41
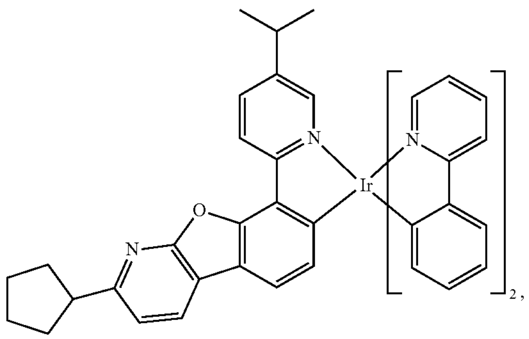
Compound II-42
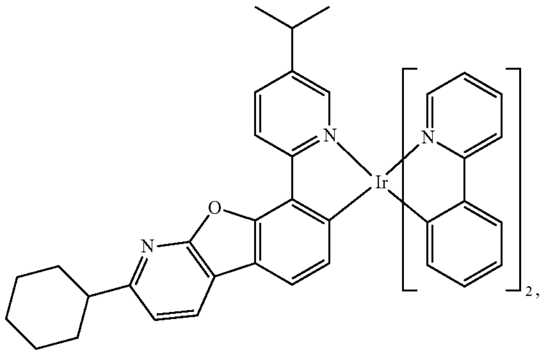
Compound II-43
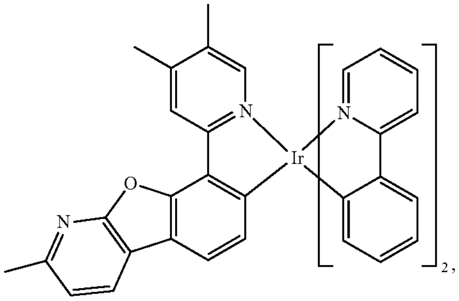
Compound II-44
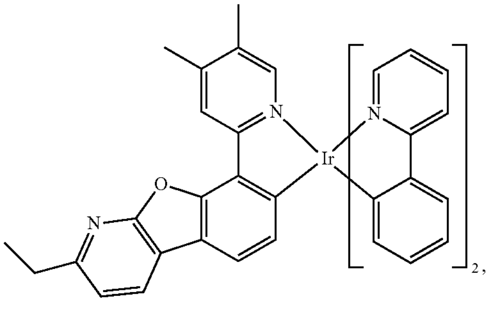
-continued
Compound II-45
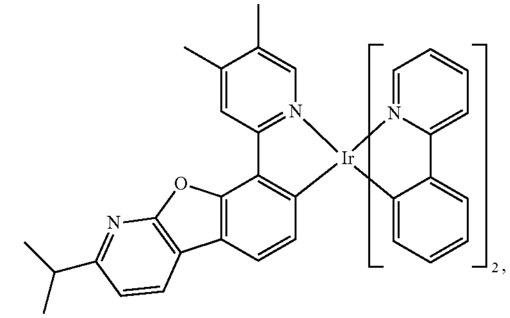
Compound II-46
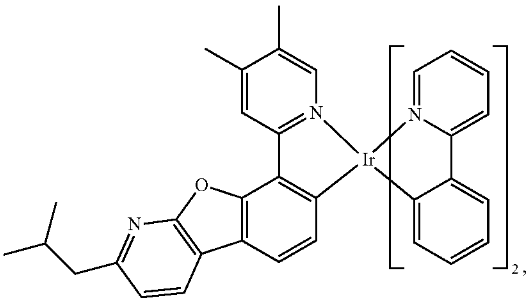
Compound II-47
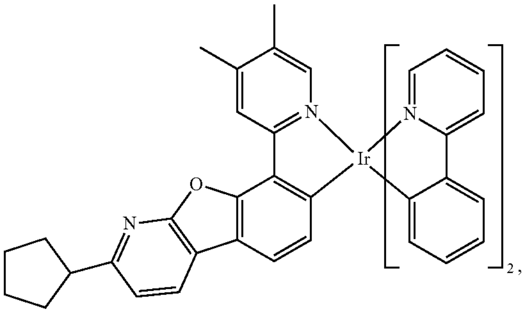
Compound II-48
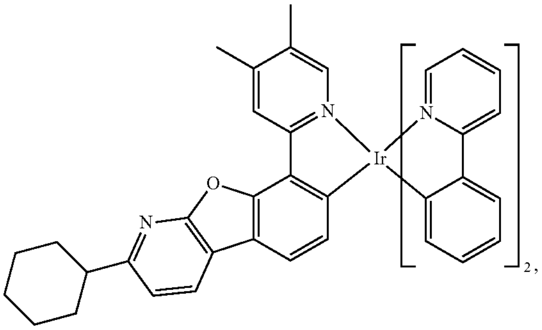
Compound II-49
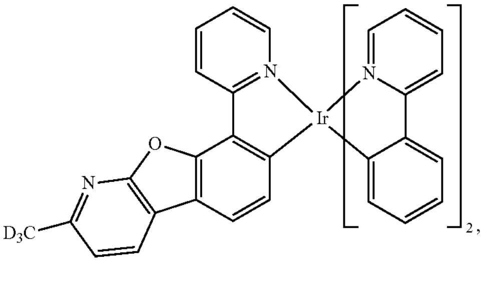

-continued
Compound II-50
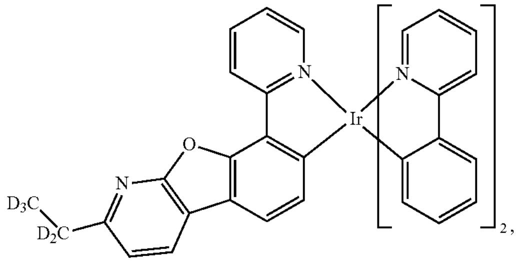
Compound II-51
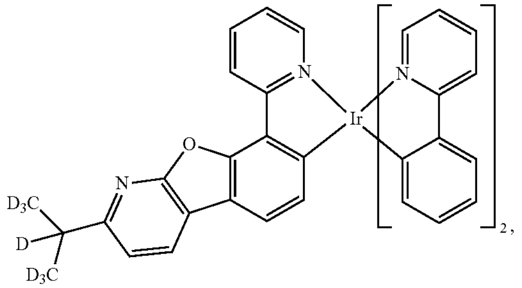
Compound II-52
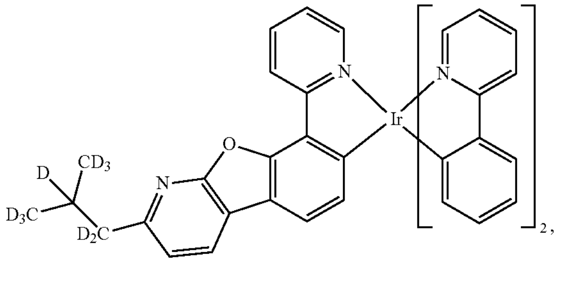
Compound II-53
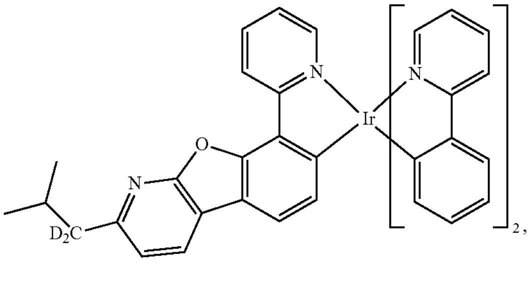
Compound II-54
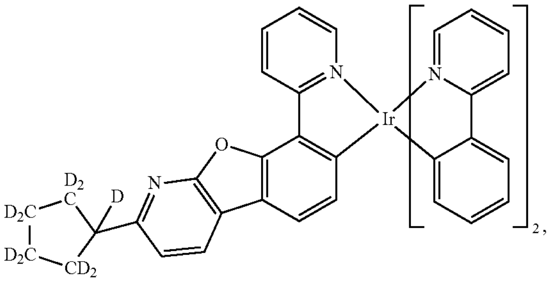
-continued
Compound II-55
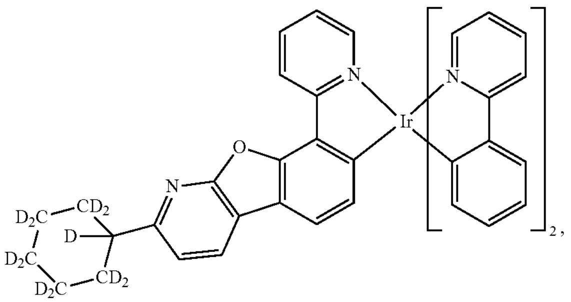
Compound II-56
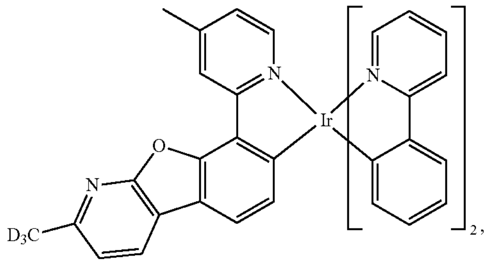
Compound II-57
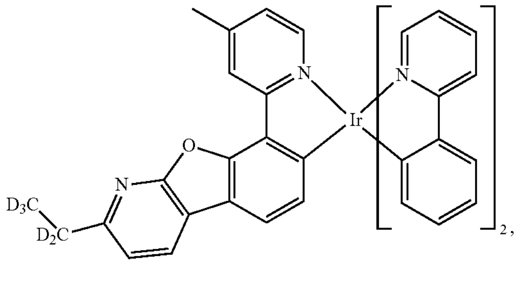
Compound II-58
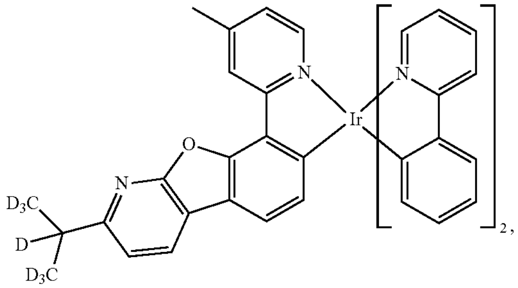
Compound II-59
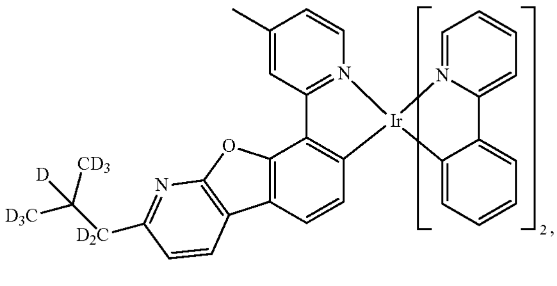

-continued
Compound II-60
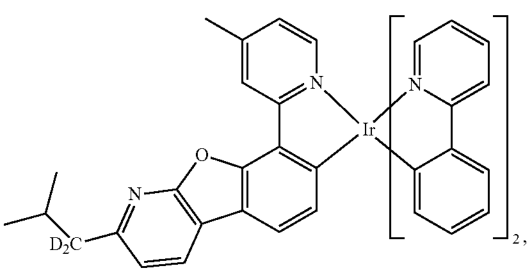
Compound II-61
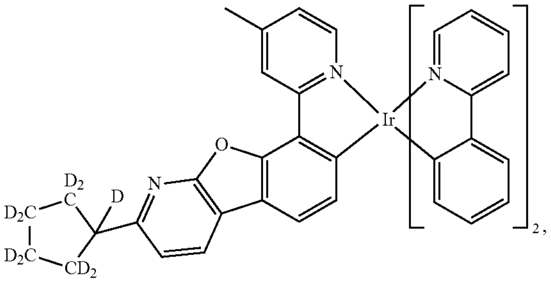
Compound II-62
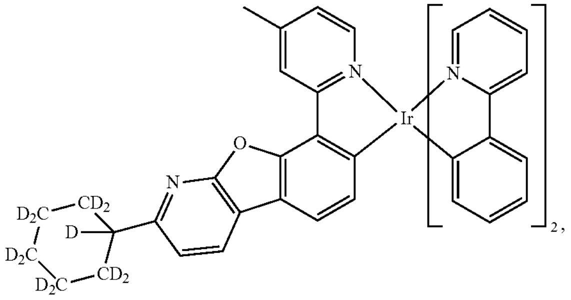
Compound II-63
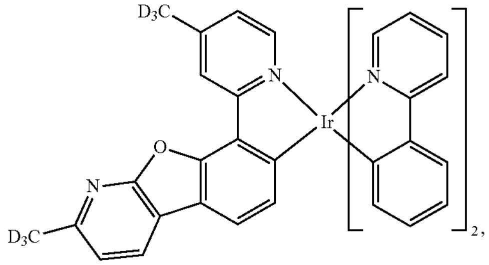
Compound II-64
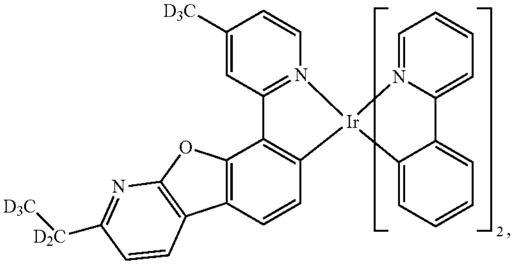
-continued
Compound II-65
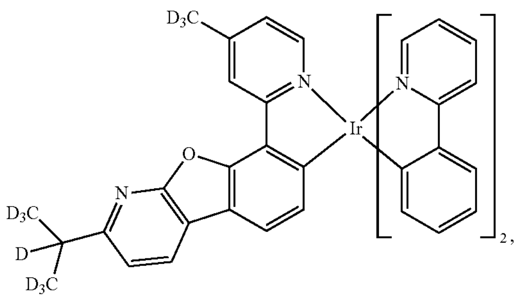
Compound II-66
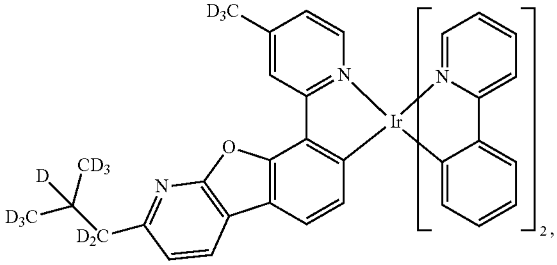
Compound II-67
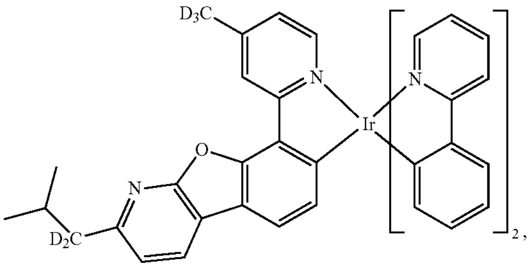
Compound II-68
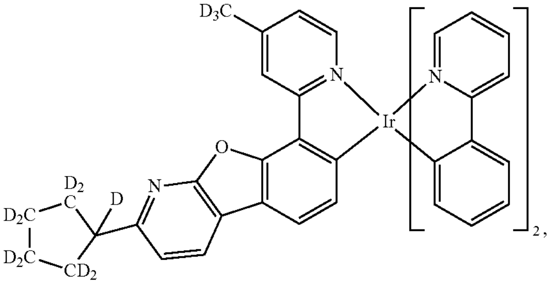
Compound II-69
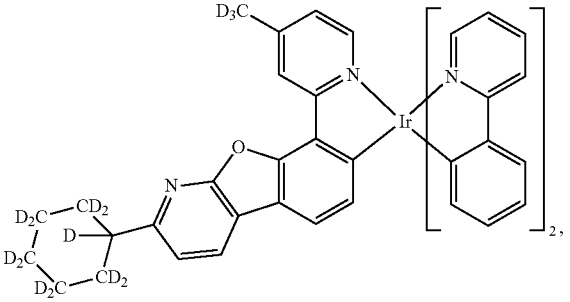

Compound II-70
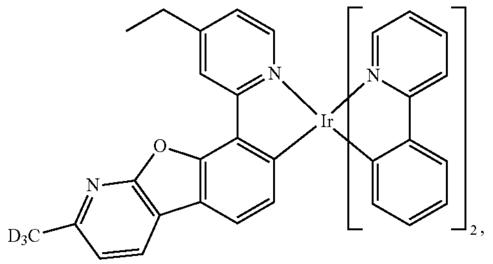
Compound II-71
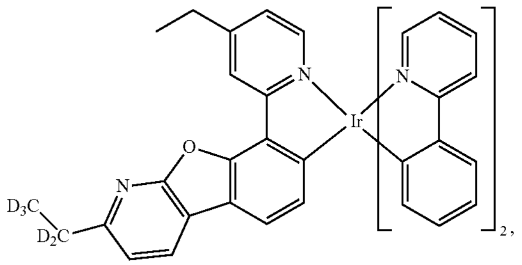
Compound II-72
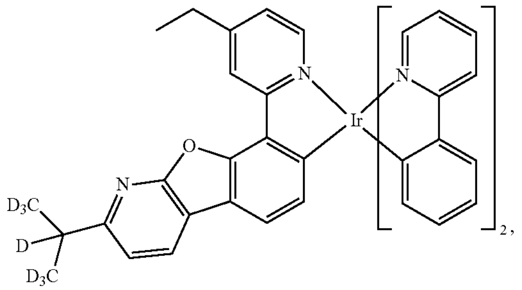
Compound II-73
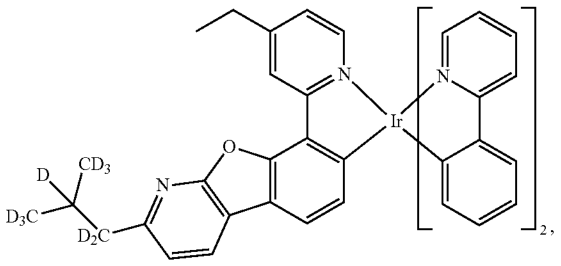
Compound II-74
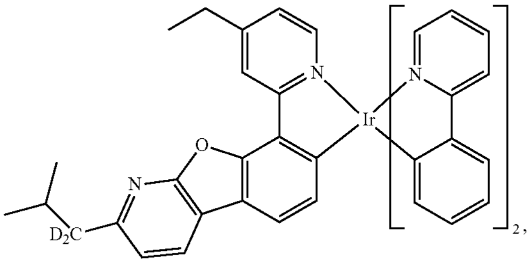
Compound II-75
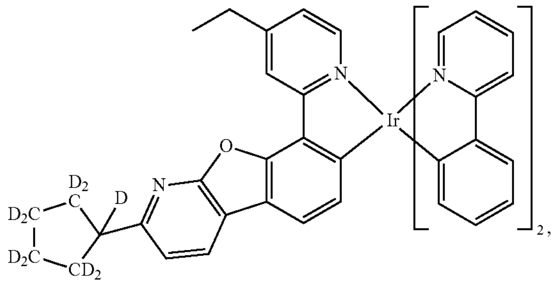
Compound II-76
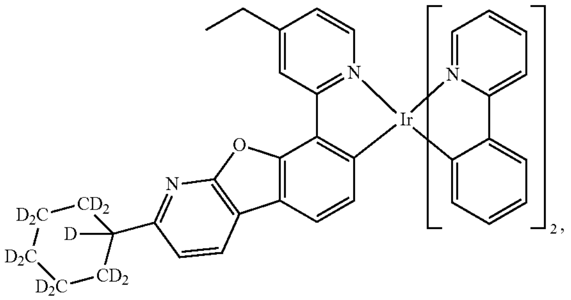
Compound II-77
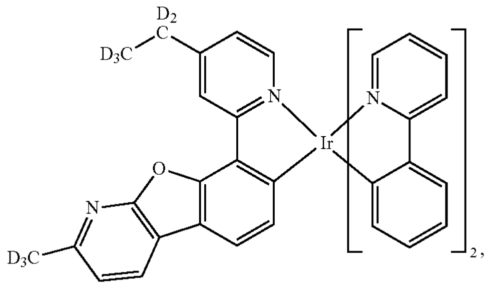
Compound II-78
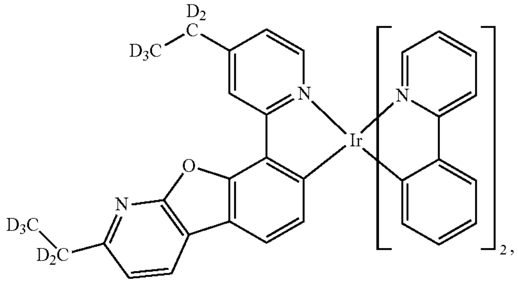
Compound II-79
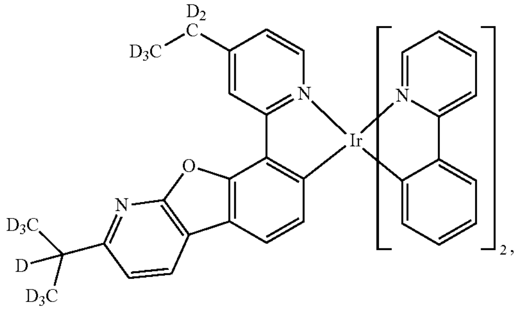

-continued
Compound II-80
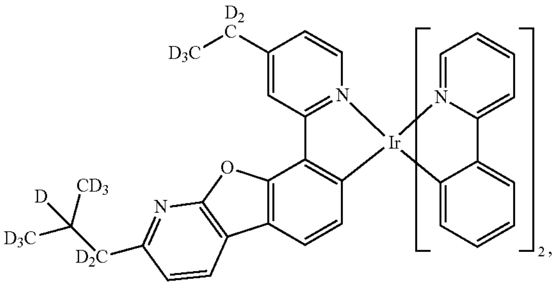
Compound II-81
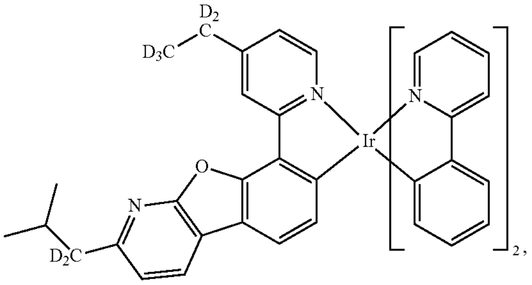
Compound II-82
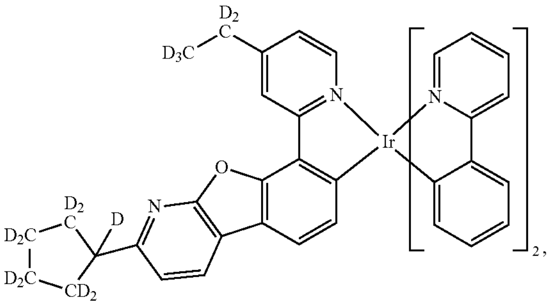
Compound II-83
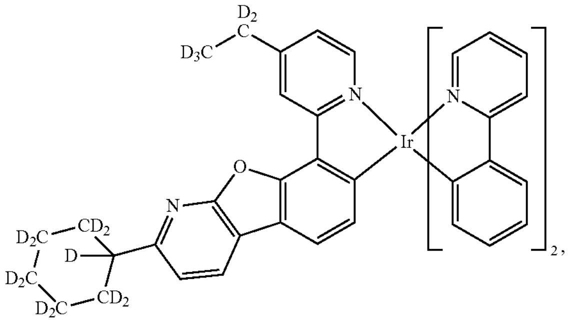
Compound II-84
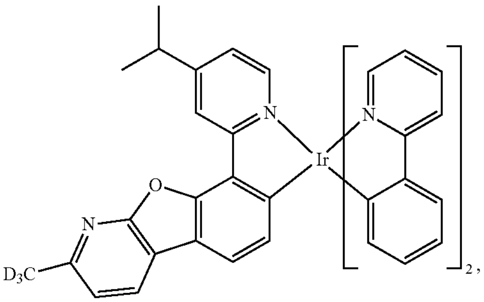
-continued
Compound II-85
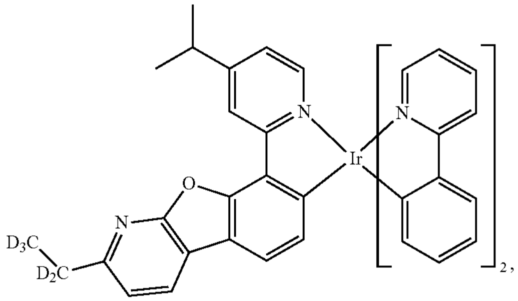
Compound II-86
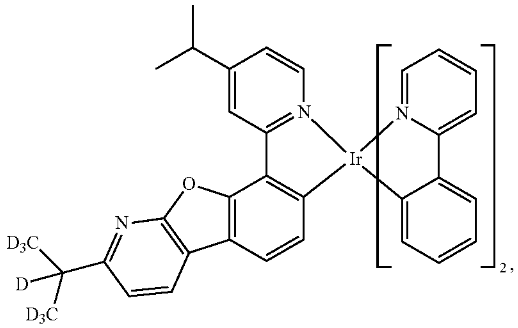
Compound II-87
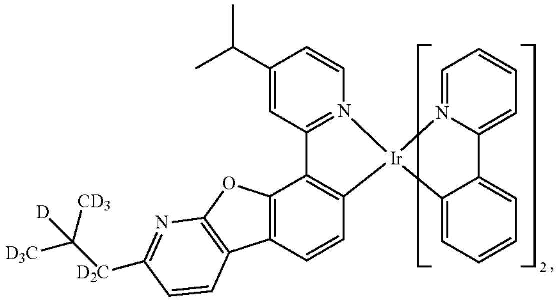
Compound II-88
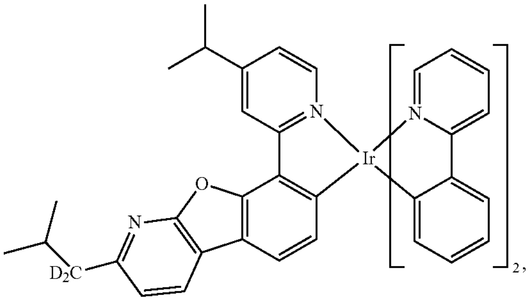

-continued
Compound II-89
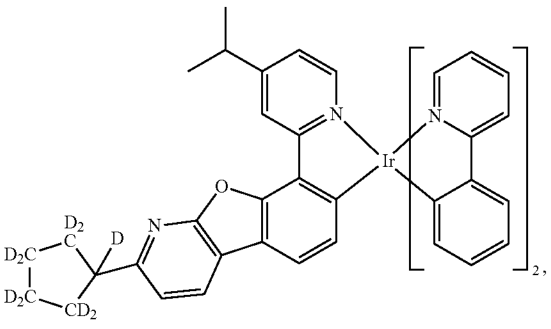
Compound II-90
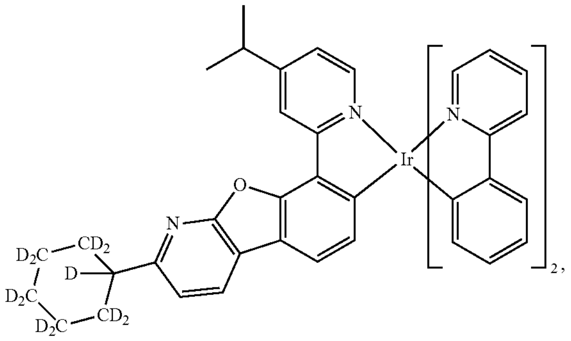
Compound II-91
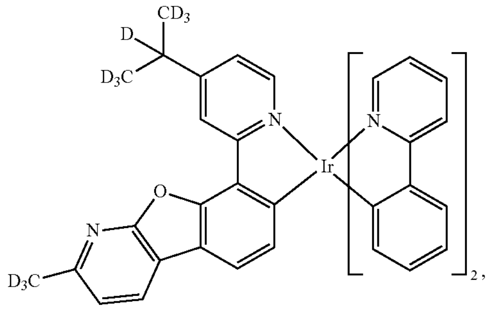
Compound II-92
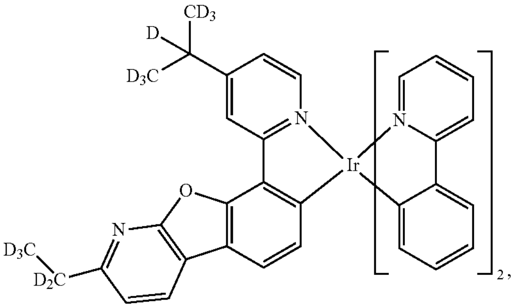
-continued
Compound II-93
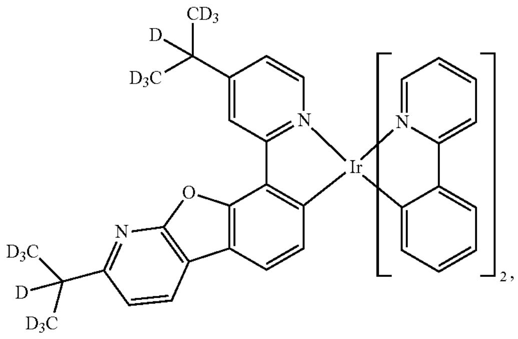
Compound II-94
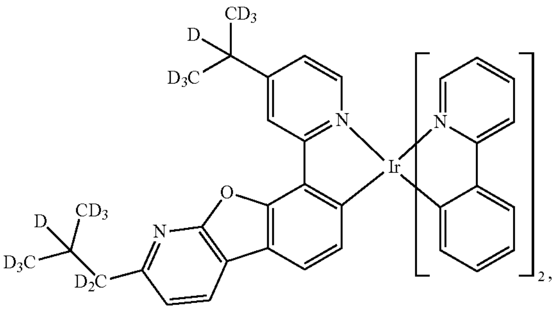
Compound II-95
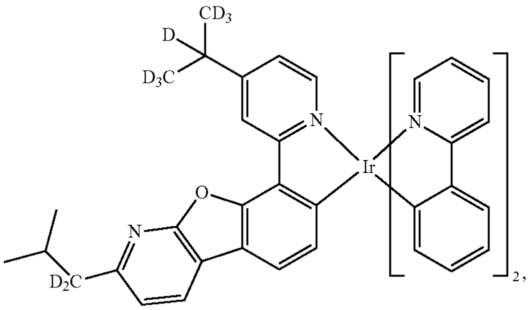
Compound II-96
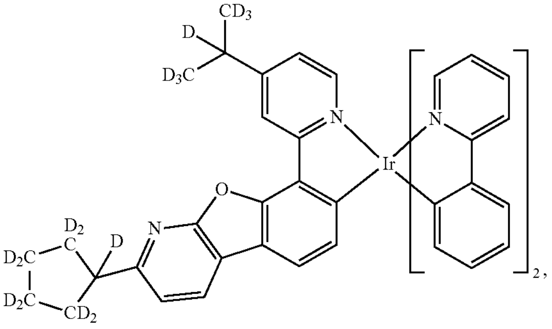

Compound II-97
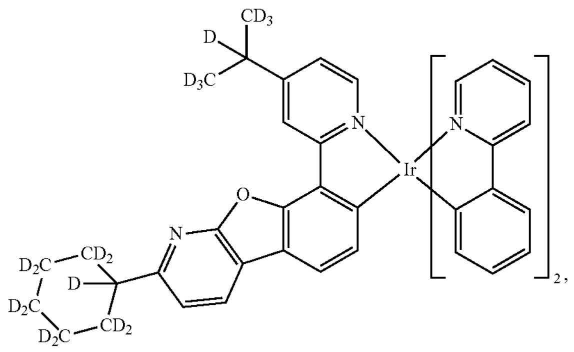
Compound II-98
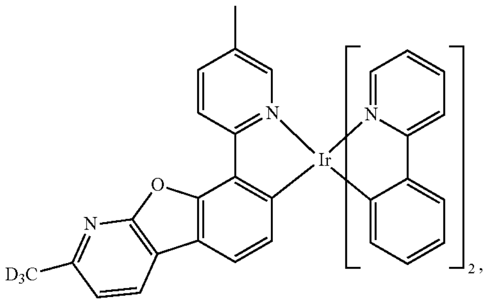
Compound II-99
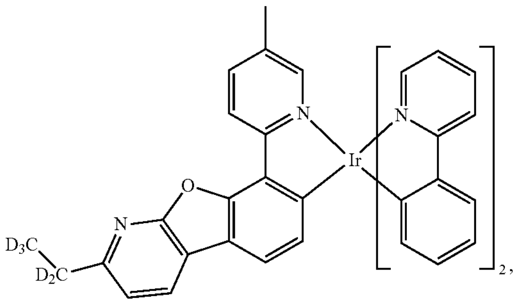
Compound II-100
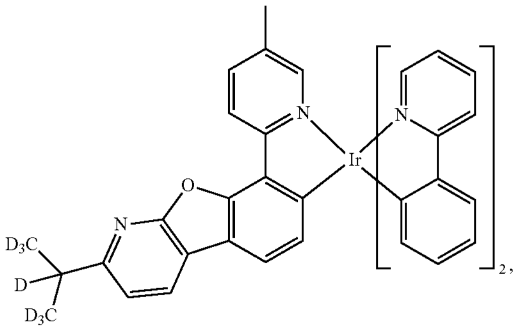
Compound II-101
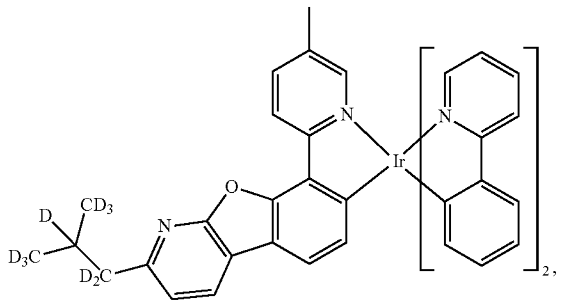
Compound II-102
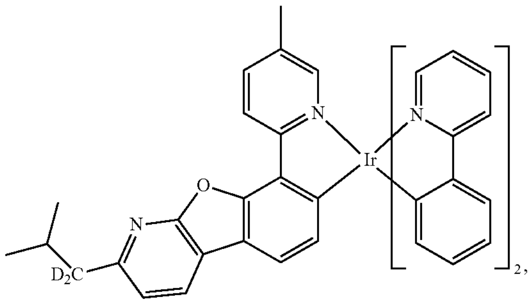
Compound II-103
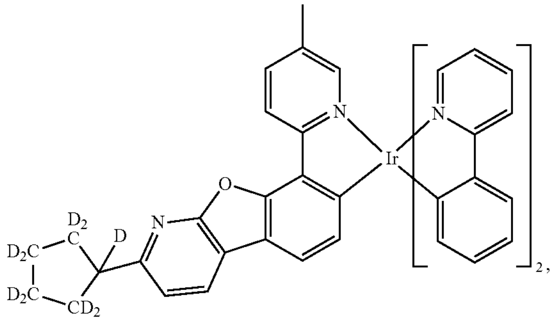
Compound II-104
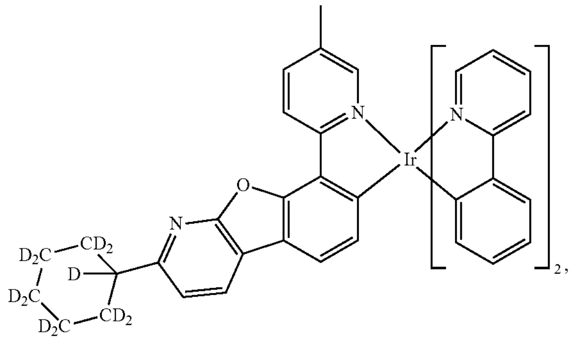

-continued
Compound II-105
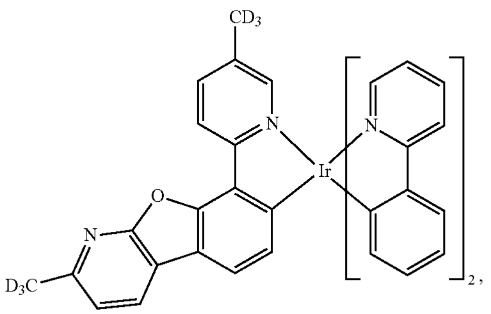
Compound II-106
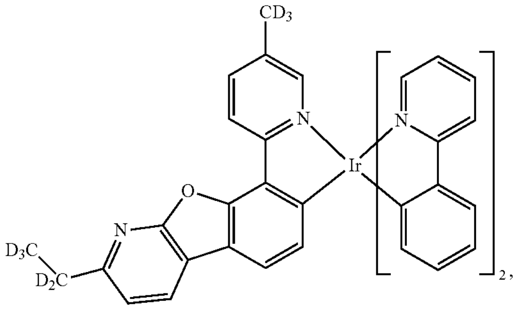
Compound II-107
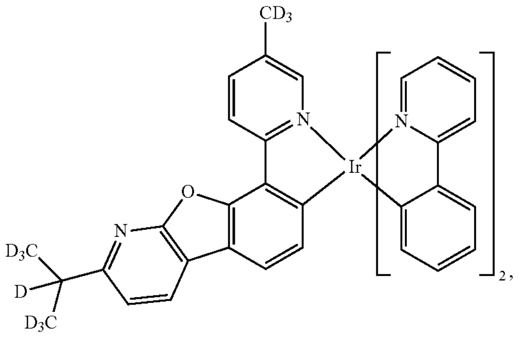
Compound II-108
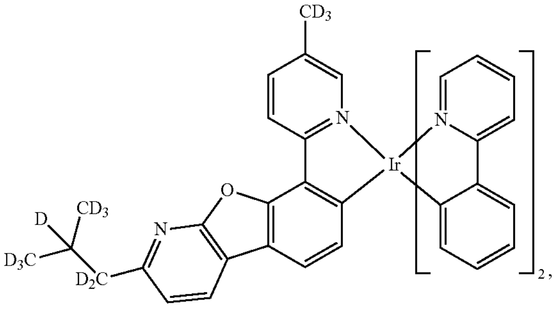
-continued
Compound II-109
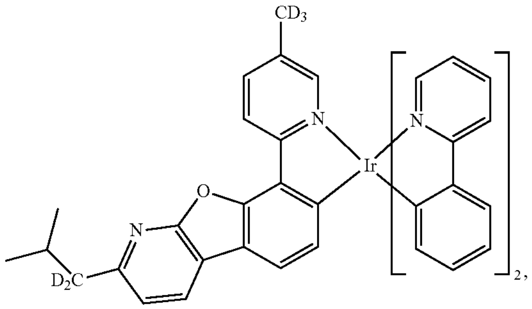
Compound II-110
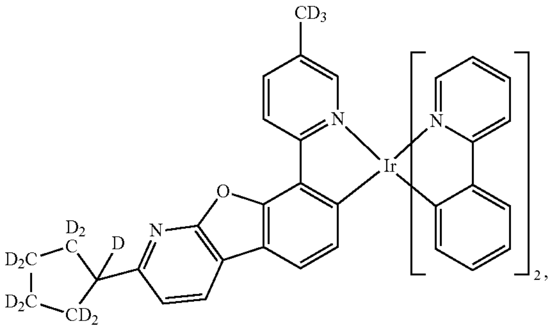
Compound II-111
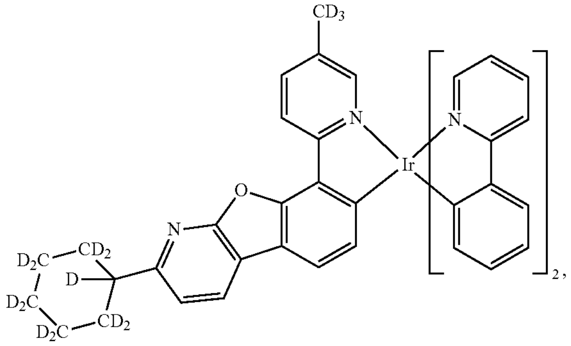
Compound II-112
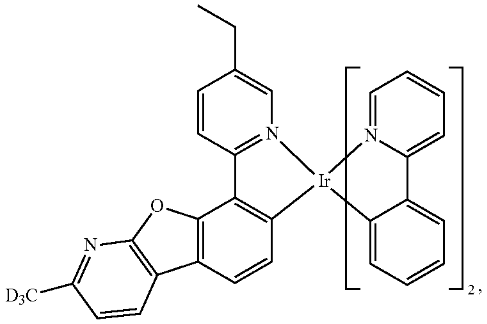

-continued
Compound II-113
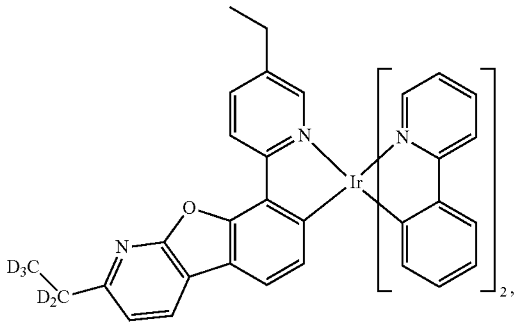
Compound II-114
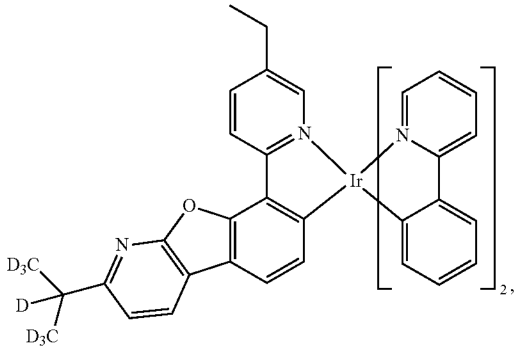
Compound II-115
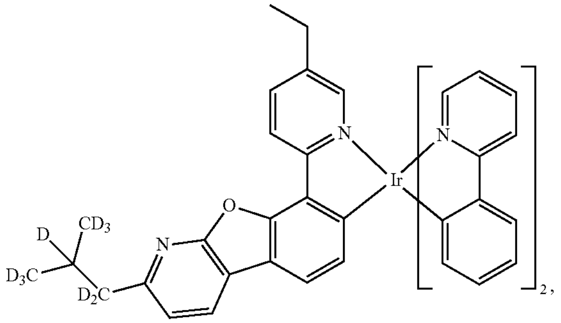
Compound II-116
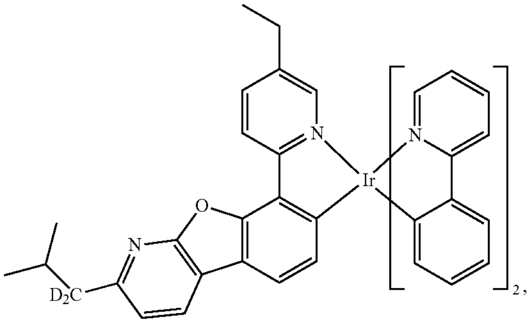
-continued
Compound II-117
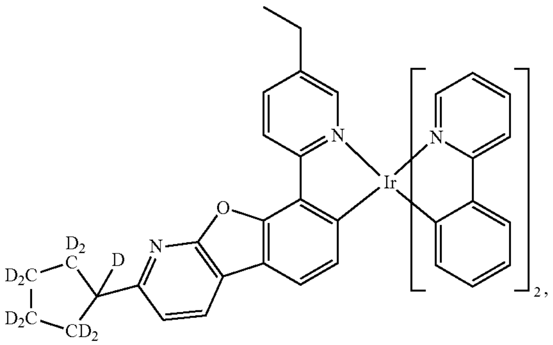
Compound II-118
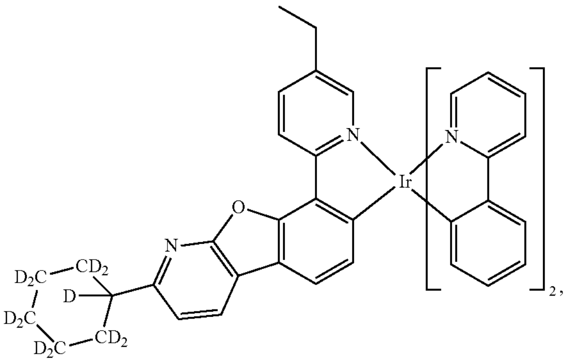
Compound II-119
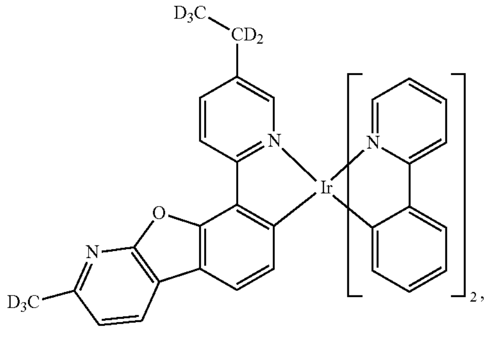
Compound II-120
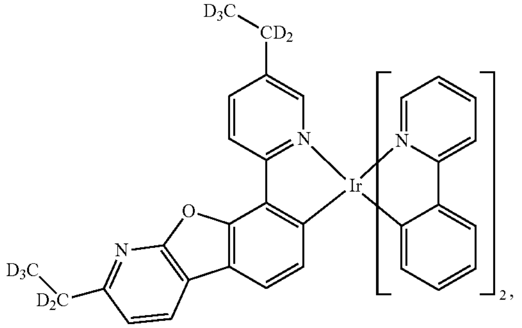

-continued
Compound II-121
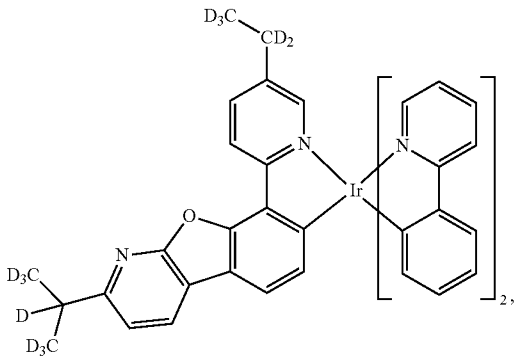
Compound II-122
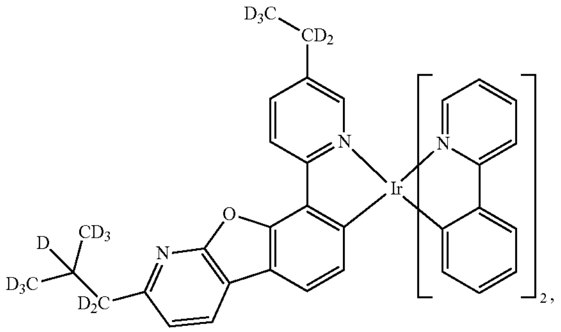
Compound II-123
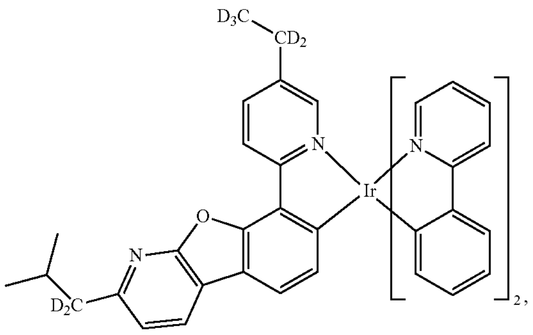
Compound II-124
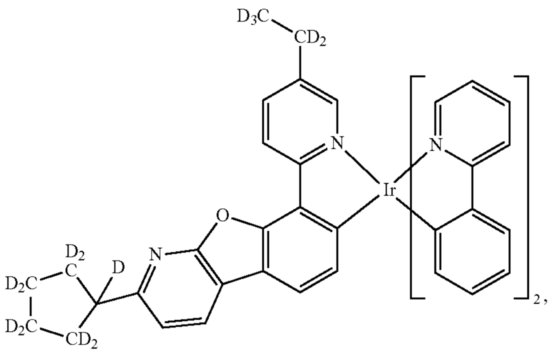
-continued
Compound II-125
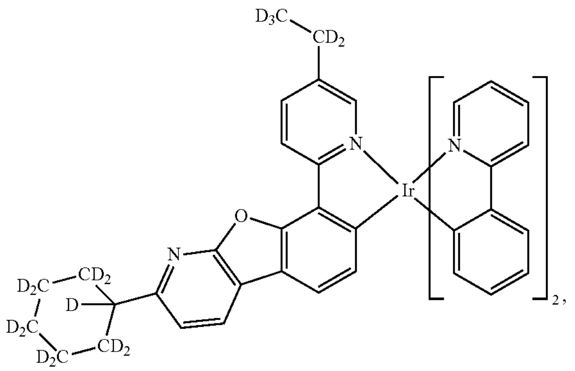
Compound II-126
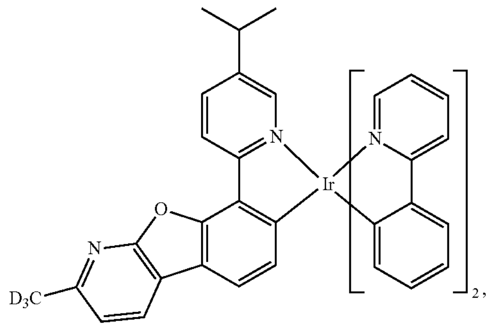
Compound II-127
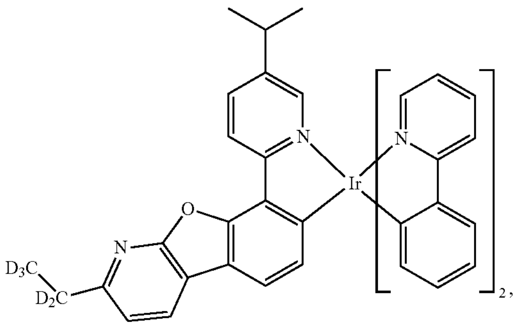
Compound II-128
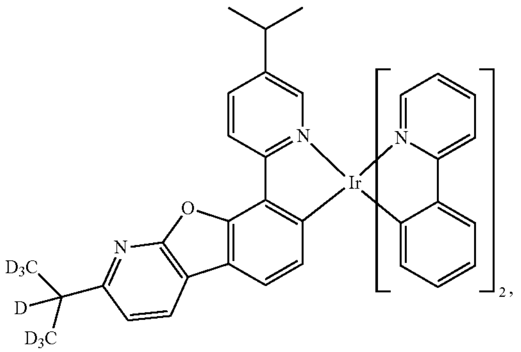

-continued
Compound II-129
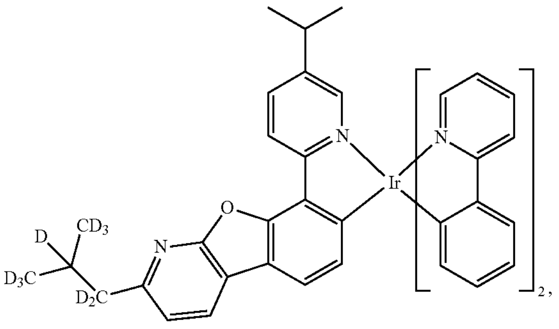
Compound II-130
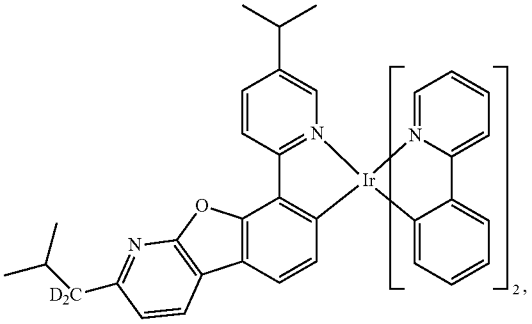
Compound II-131
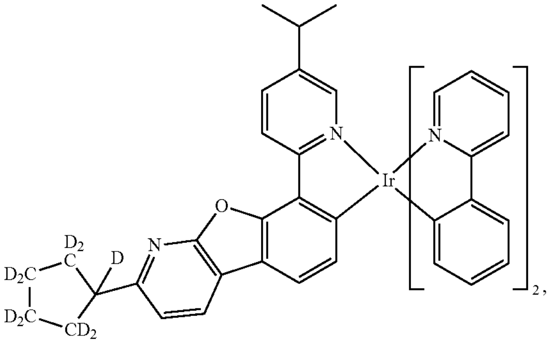
Compound II-132
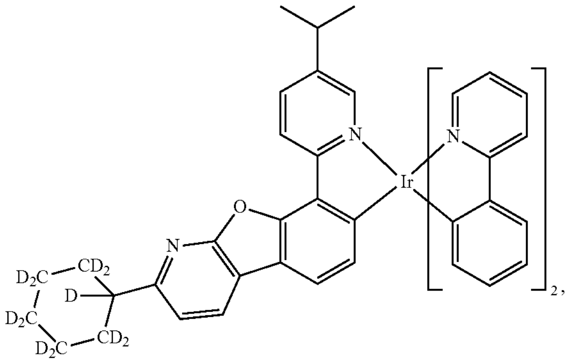
-continued
Compound II-133
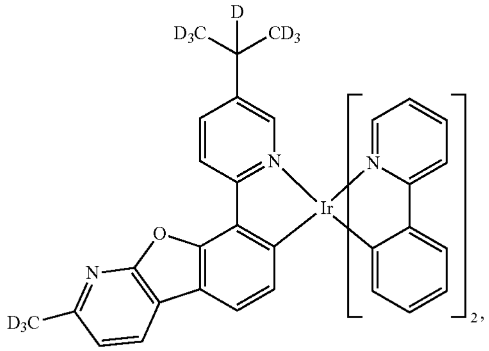
Compound II-134
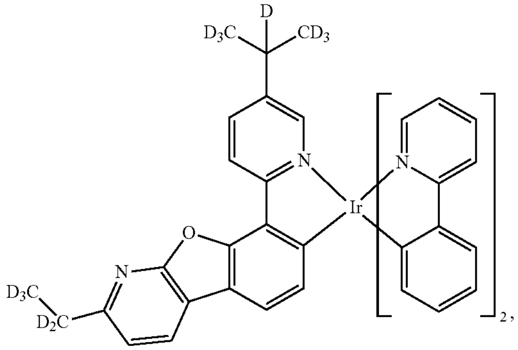
Compound II-135
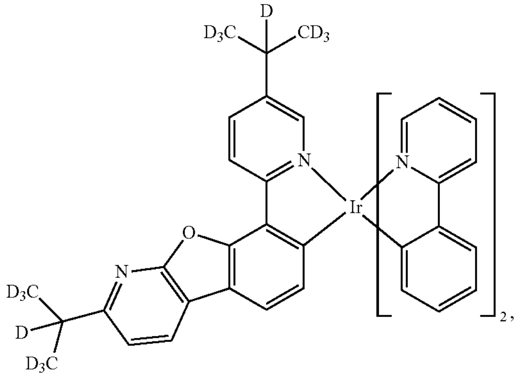
Compound II-136
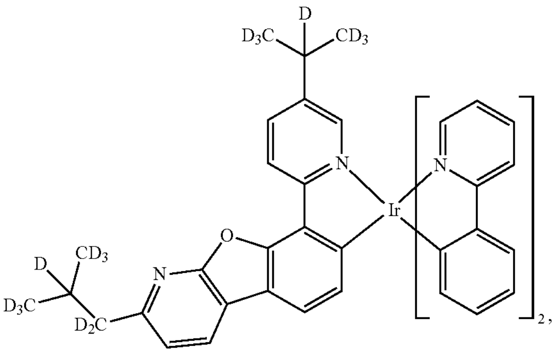

-continued
Compound II-137
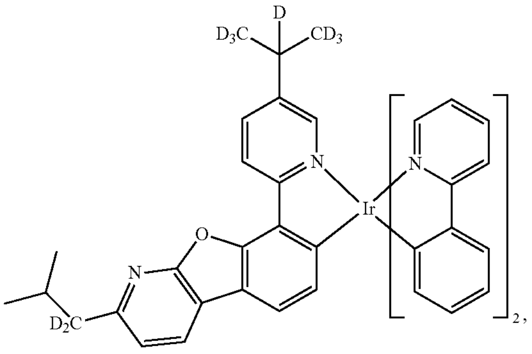
Compound II-138
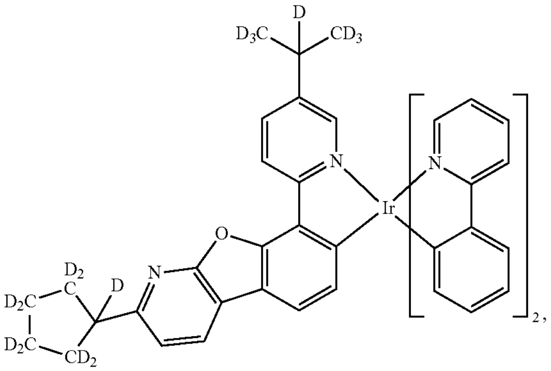
Compound II-139
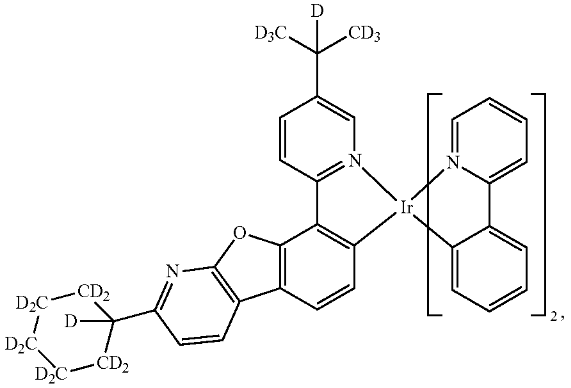
Compound II-140
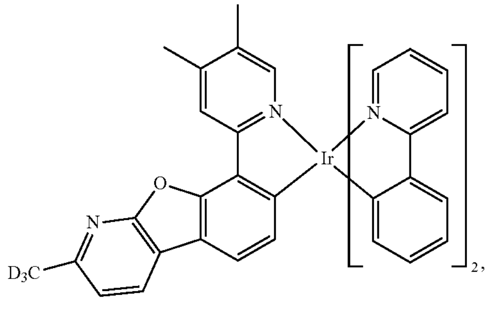
-continued
Compound II-141
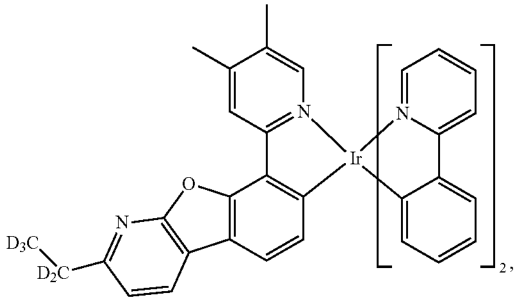
Compound II-142
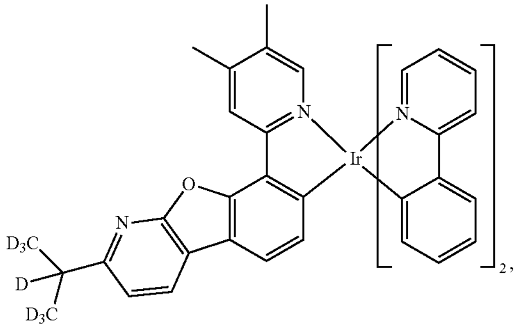
Compound II-143
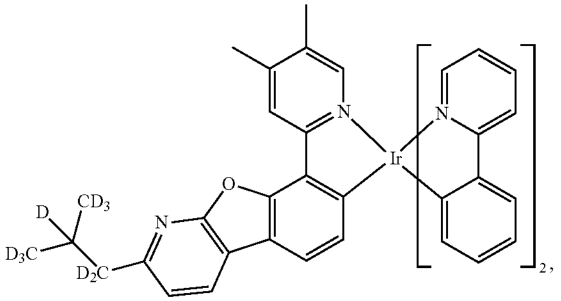
Compound II-144
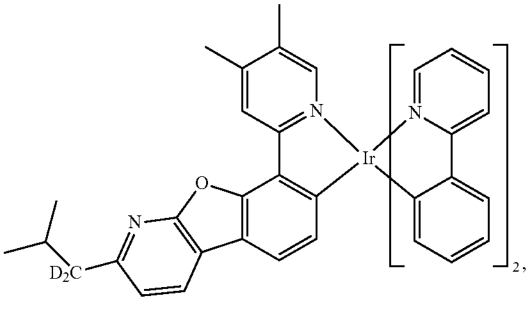

-continued
Compound II-145
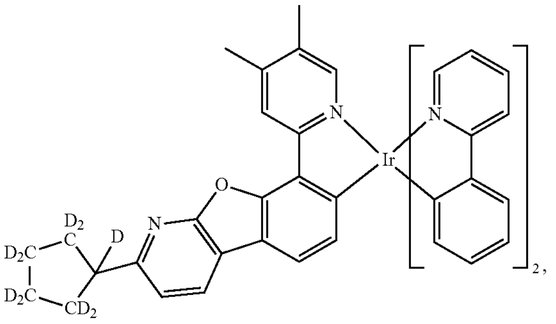
Compound II-146
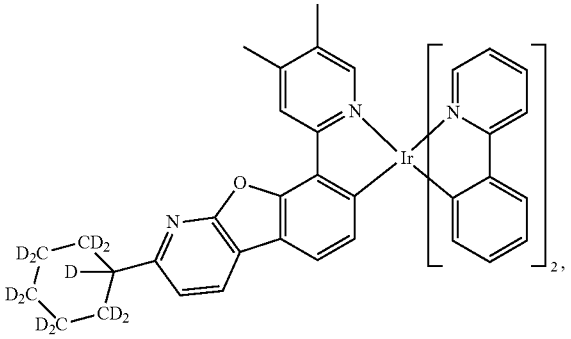
Compound II-147
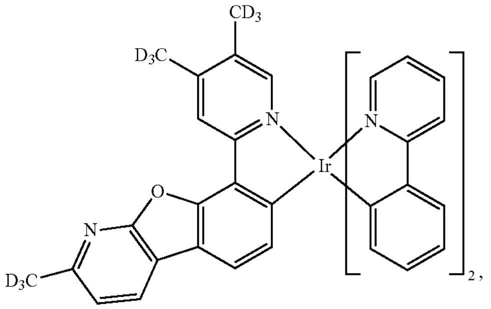
Compound II-148
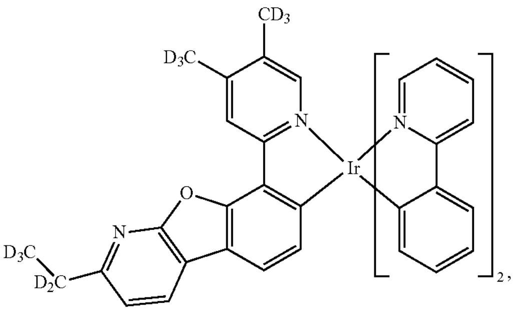
-continued
Compound II-149
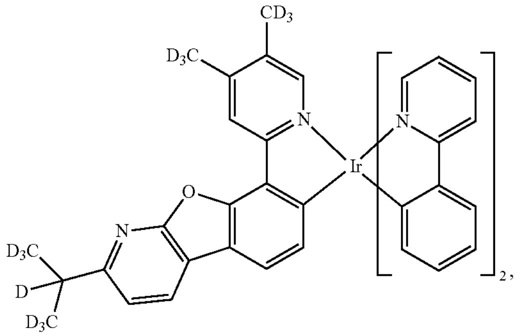
Compound II-150
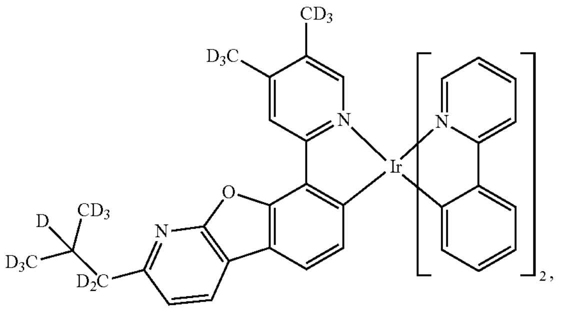
Compound II-151
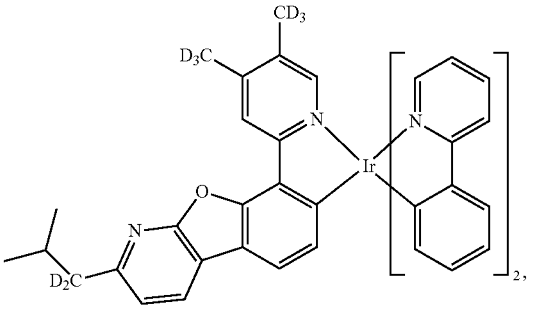
Compound II-152
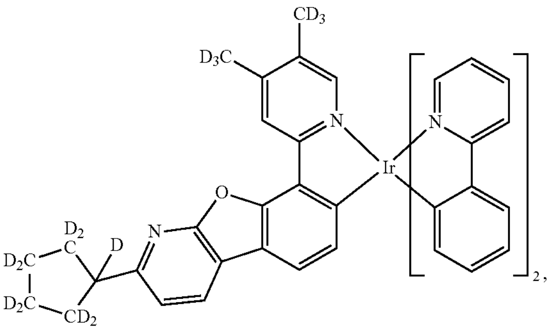

-continued
Compound II-153
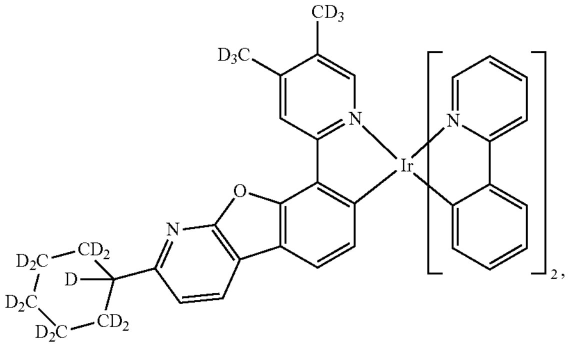
Compound II-154
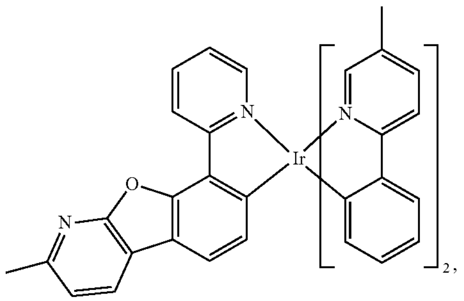
Compound II-155
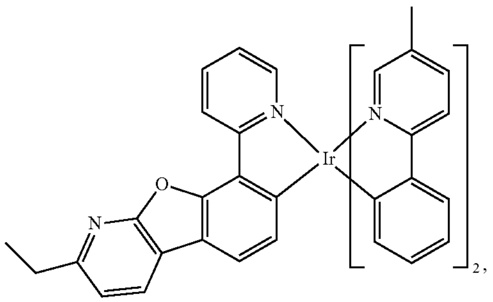
Compound II-156
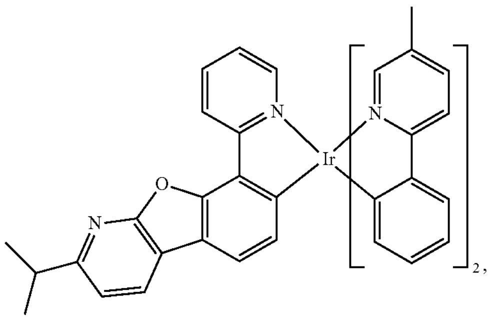
-continued
Compound II-157
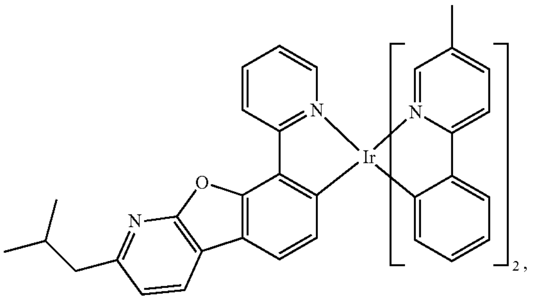
Compound II-158
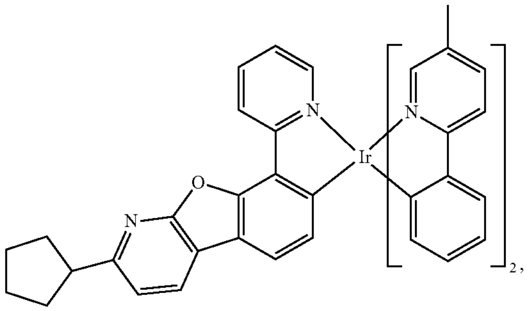
Compound II-159
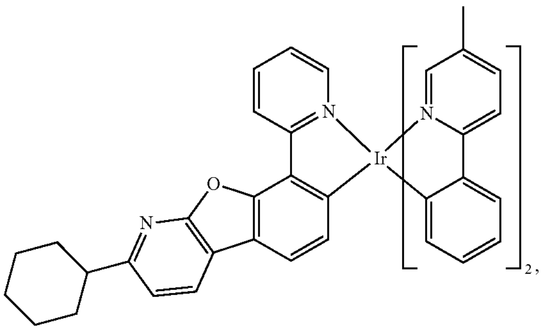
Compound II-160
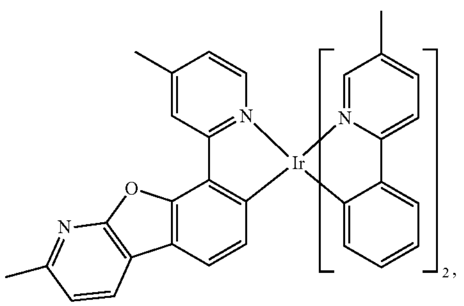

-continued
Compound II-161
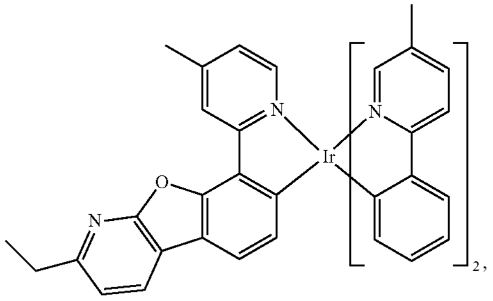
Compound II-162
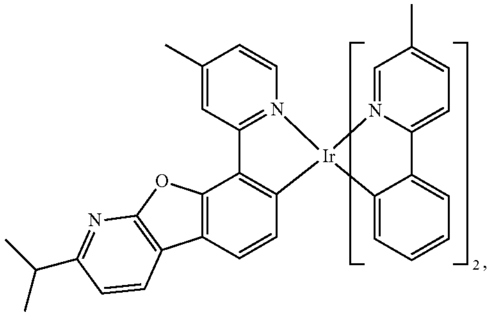
Compound II-163
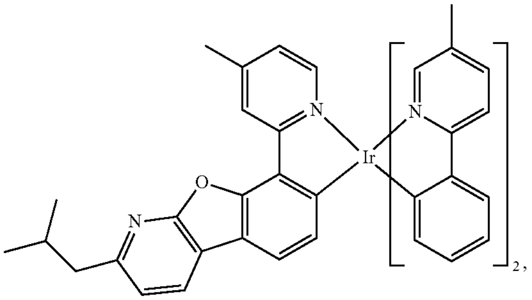
Compound II-164
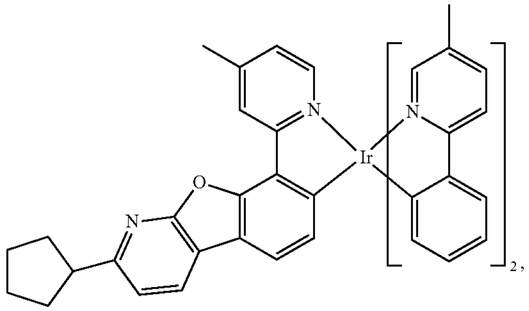
-continued
Compound II-165
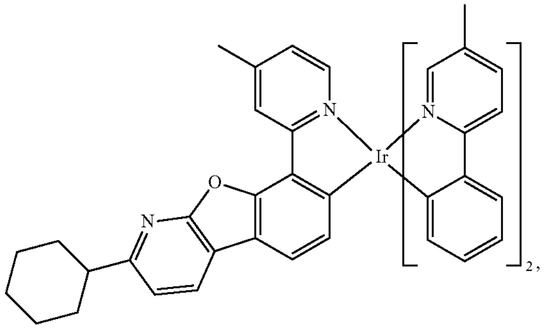
Compound II-166
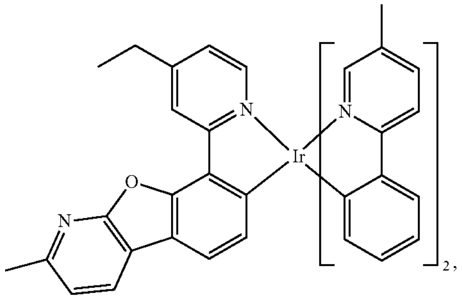
Compound II-167
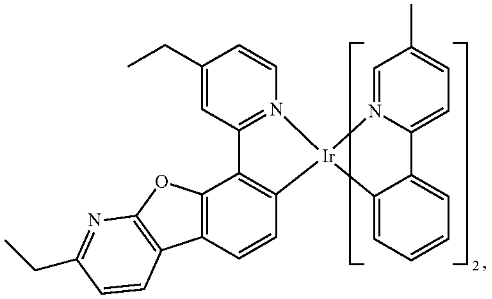
Compound II-168
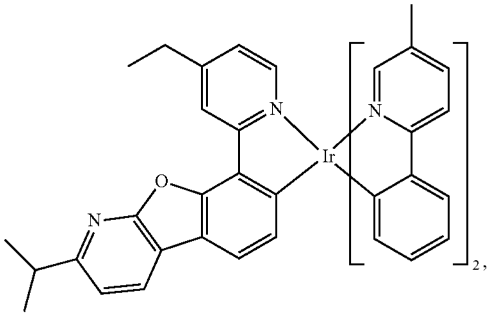

-continued
Compound II-169
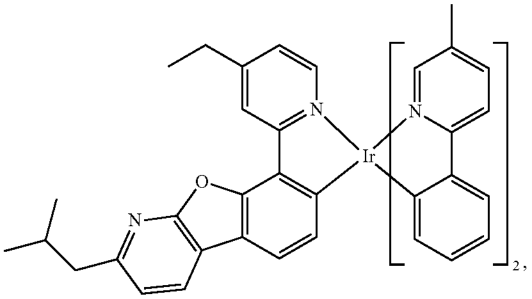
Compound II-170
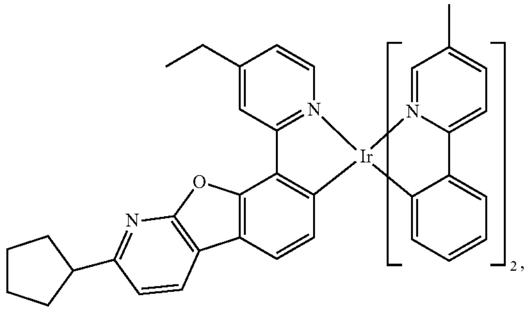
Compound II-171
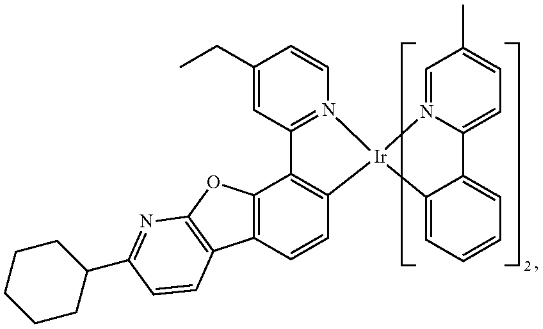
Compound II-172
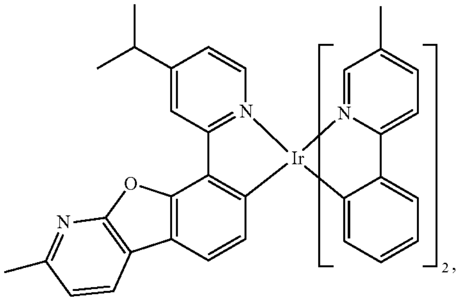
-continued
Compound II-173
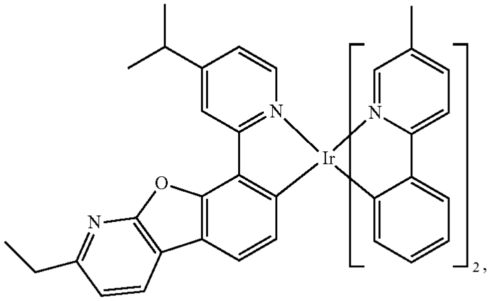
Compound II-174
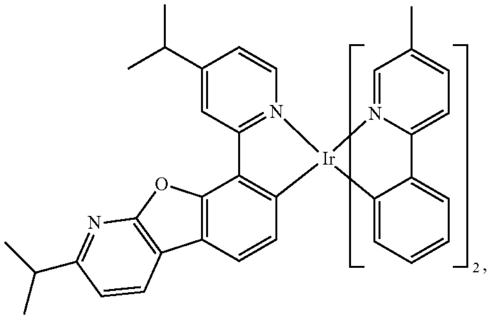
Compound II-175
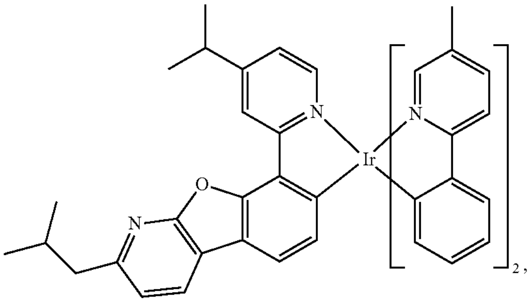
Compound II-176
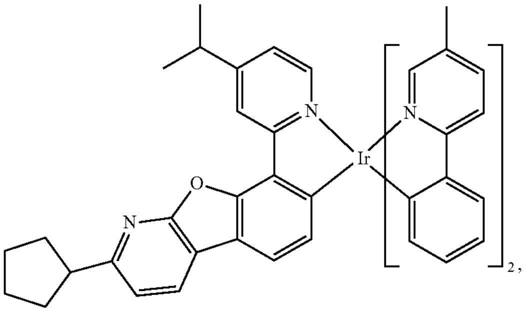

-continued
Compound II-177
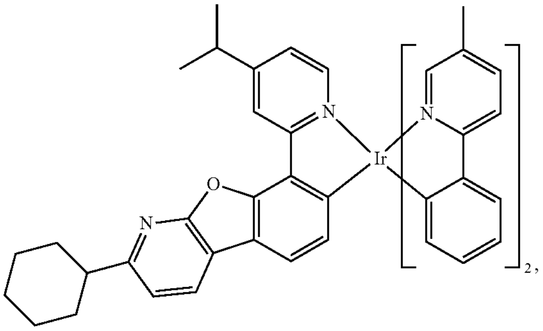
Compound II-178
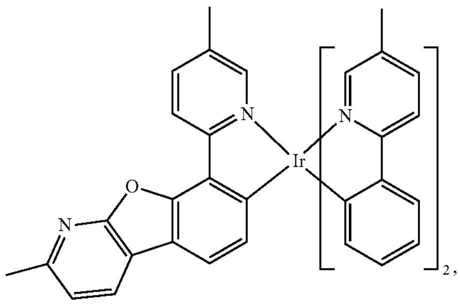
Compound II-179
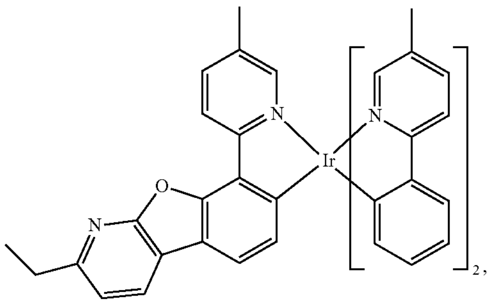
Compound II-180
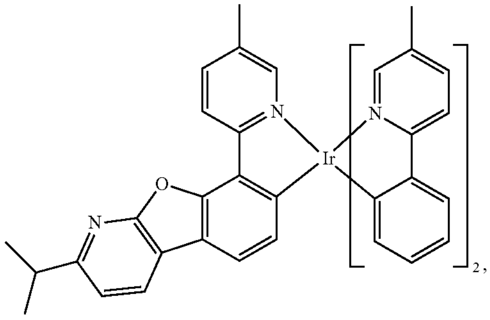
-continued
Compound II-181
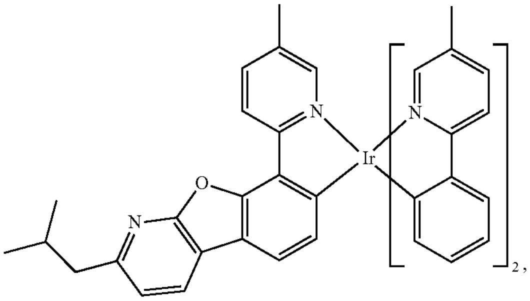
Compound II-182
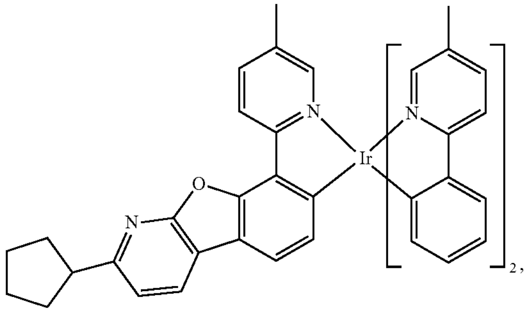
Compound II-183
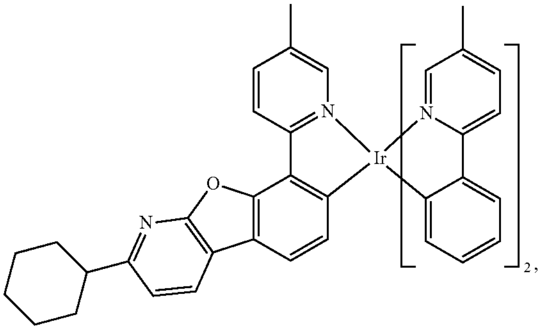
Compound II-184
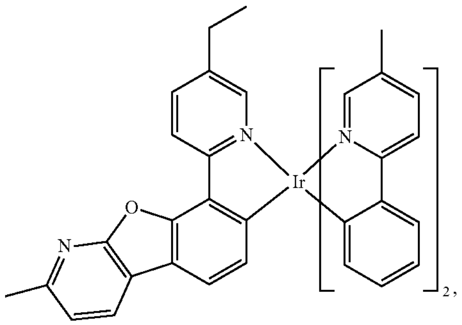

-continued
Compound II-185
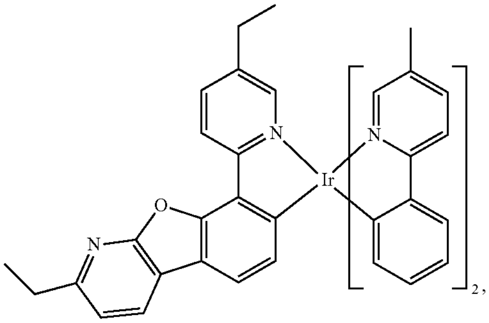
Compound II-186
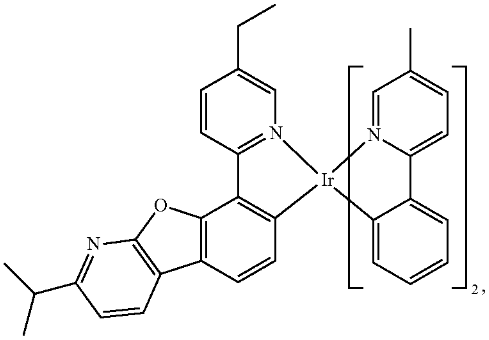
Compound II-187
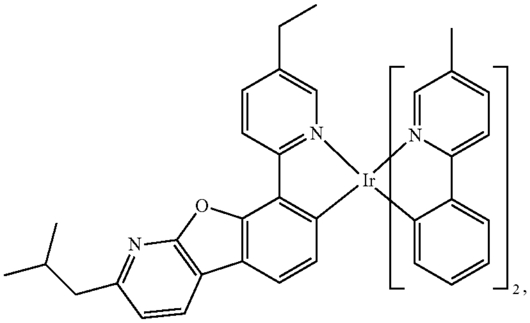
Compound II-188
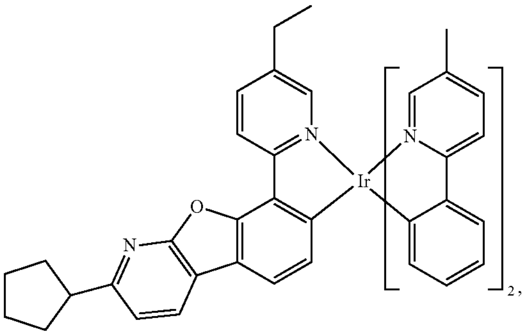
-continued
Compound II-189
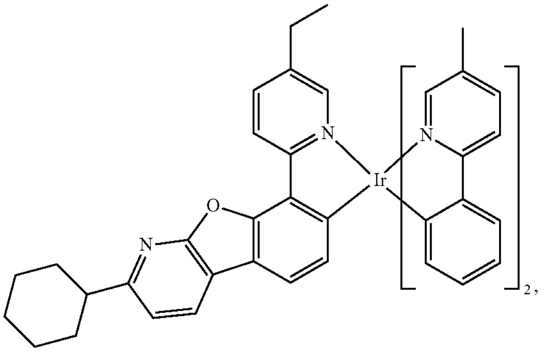
Compound II-190
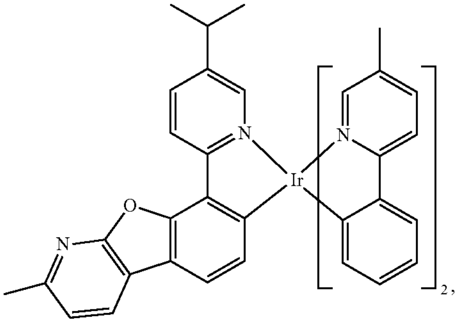
Compound II-191
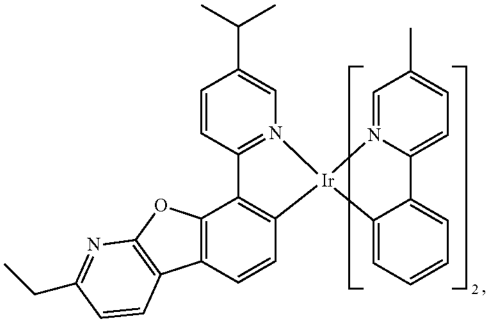
Compound II-192
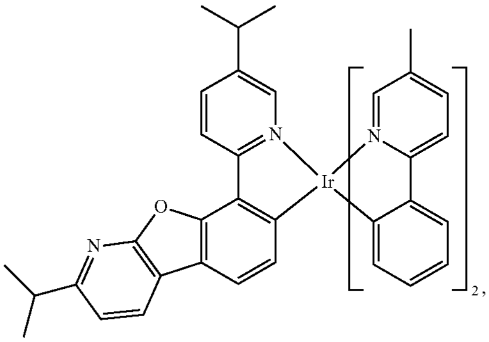

-continued
Compound II-193
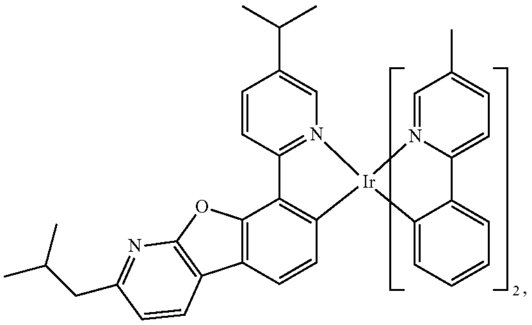
Compound II-194
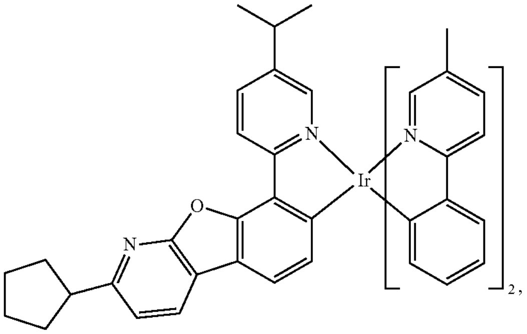
Compound II-195
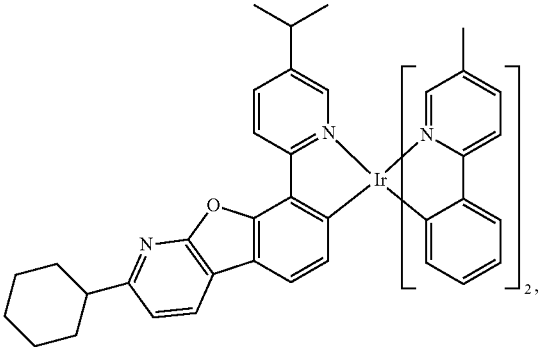
Compound II-196
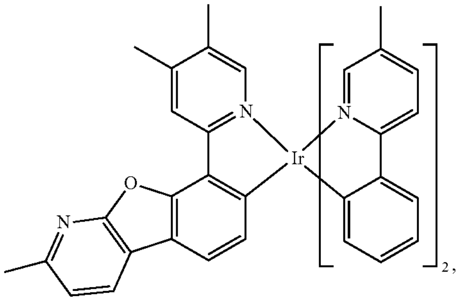
-continued
Compound II-197
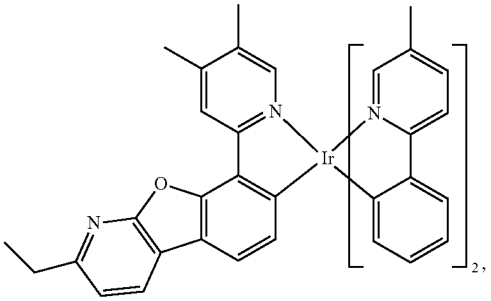
Compound II-198
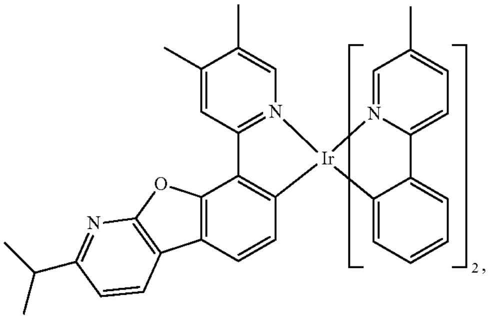
Compound II-199
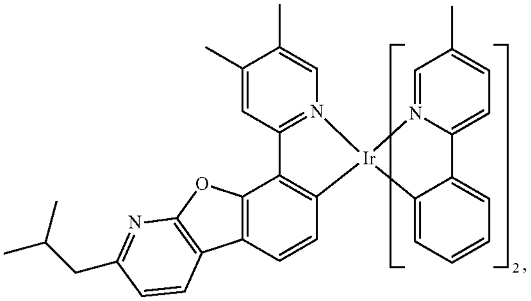
Compound II-200
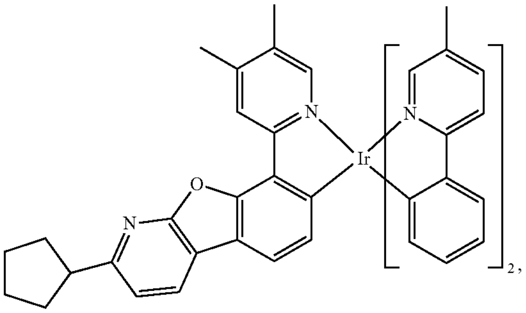

-continued
Compound II-201
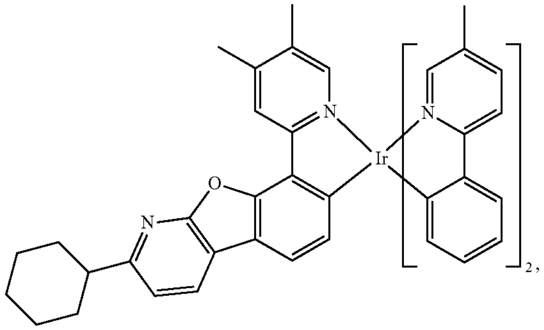
Compound II-202
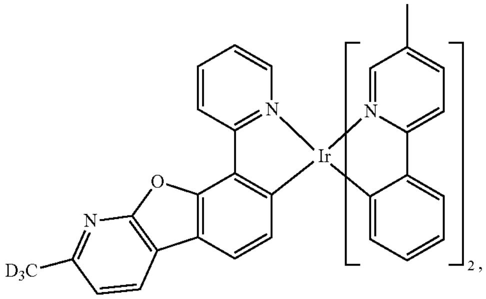
Compound II-203
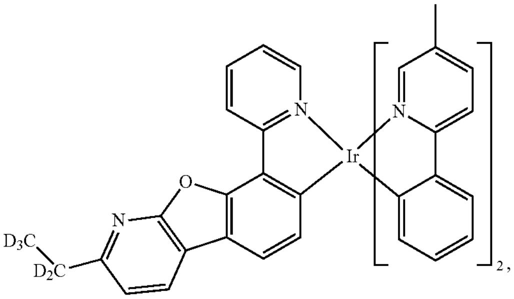
Compound II-204
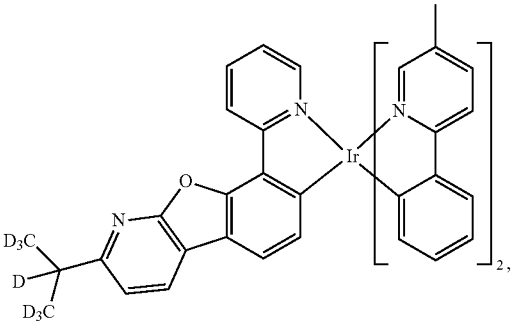
-continued
Compound II-205
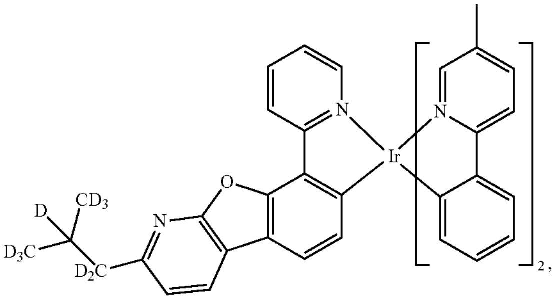
Compound II-206
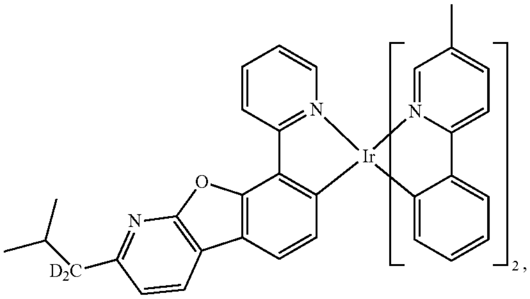
Compound II-207
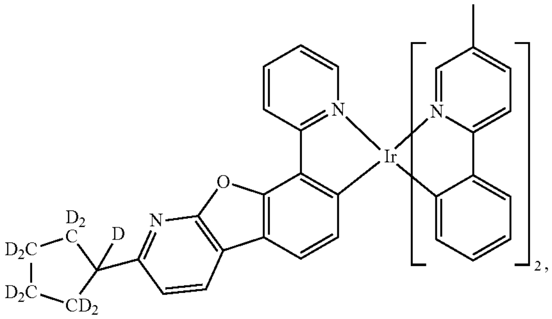
Compound II-208
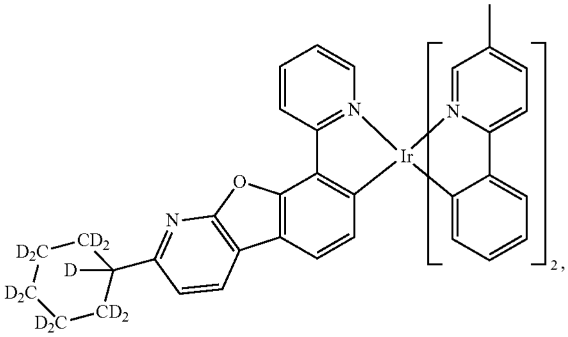

-continued
Compound II-209
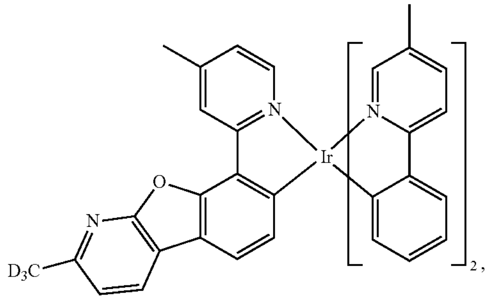
Compound II-210
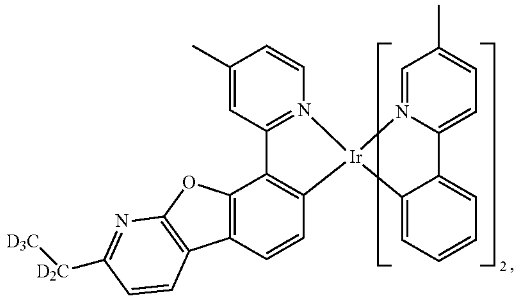
Compound II-211
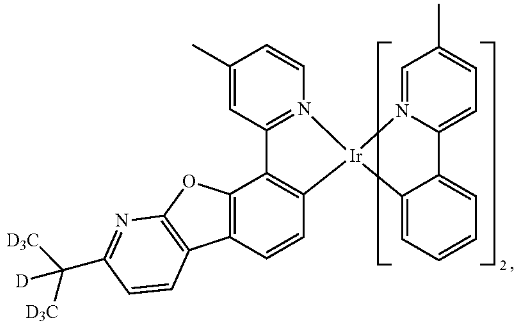
Compound II-212
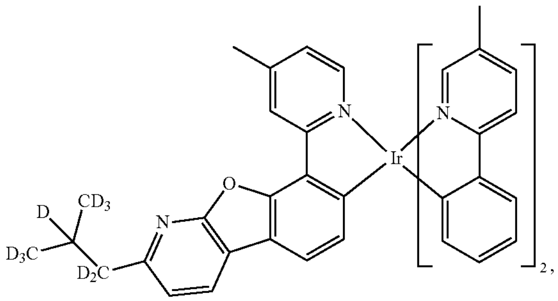
Compound II-213
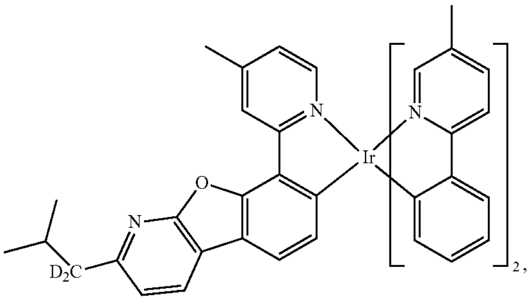
-continued
Compound II-214
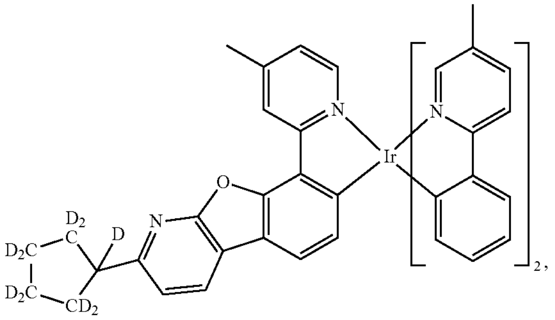
Compound II-215
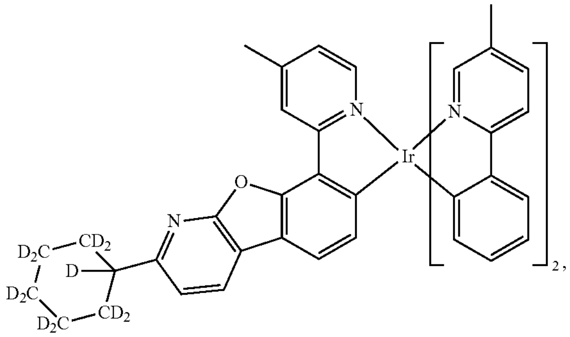
Compound II-216
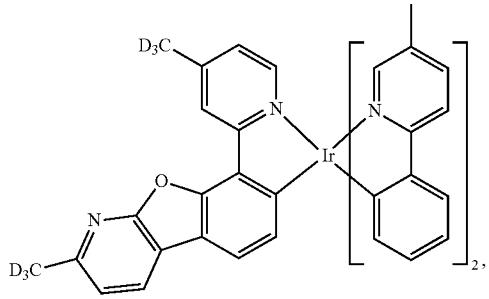
Compound II-217
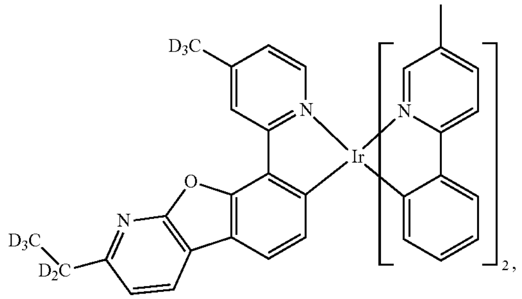

-continued
Compound II-218
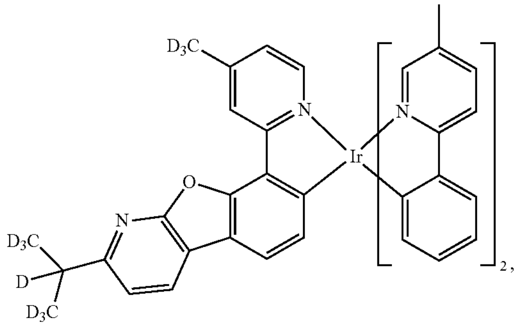
Compound II-219
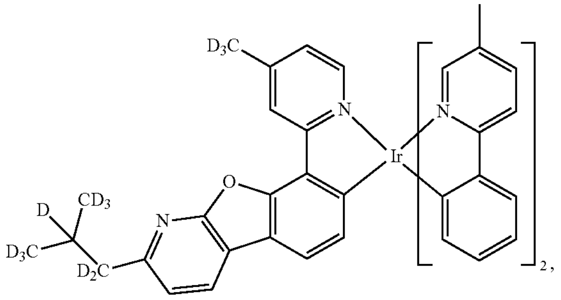
Compound II-220
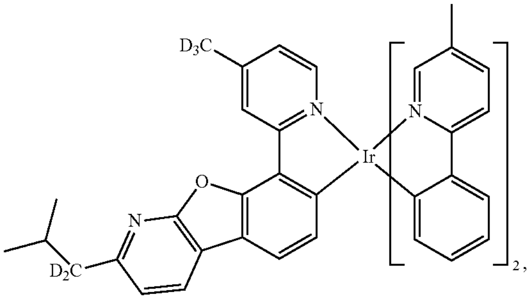
Compound II-221
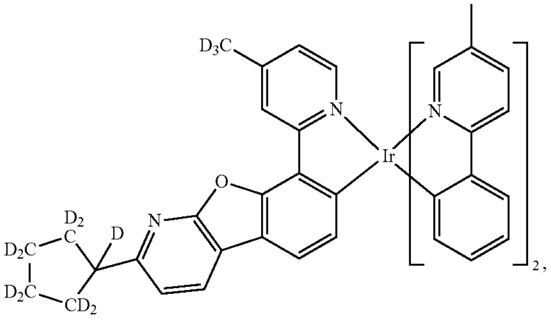
-continued
Compound II-222
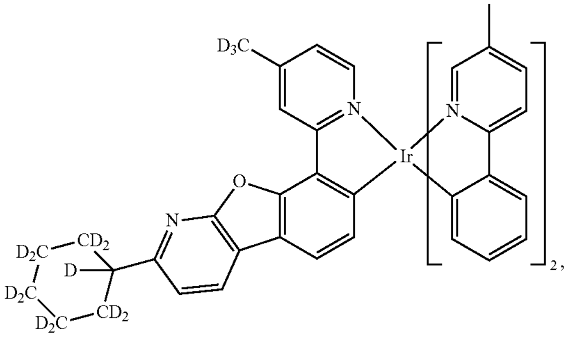
Compound II-223
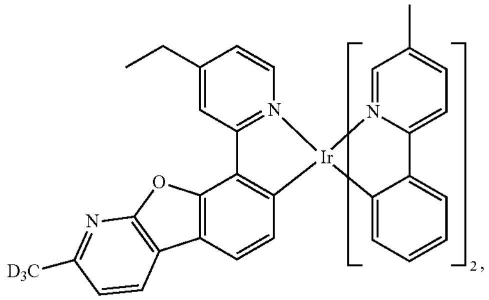
Compound II-224
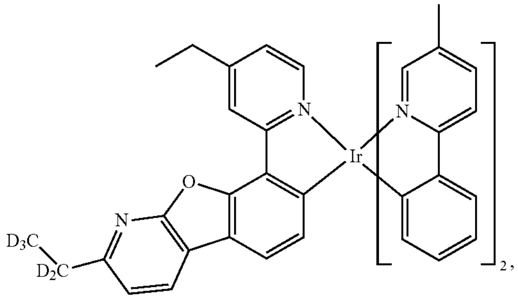
Compound II-225
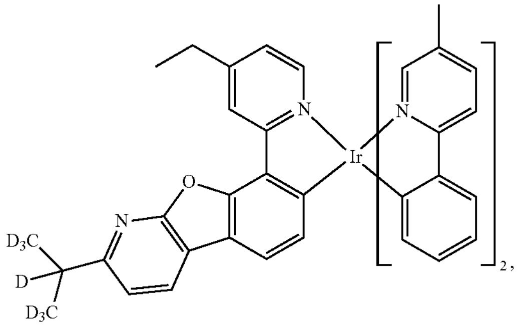

-continued
Compound II-226
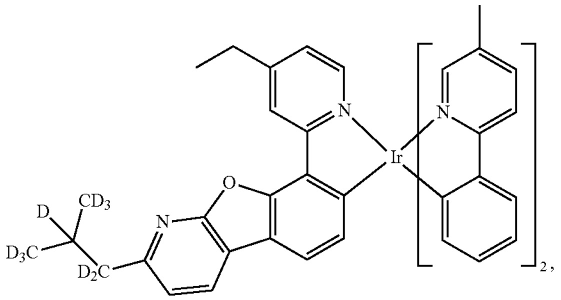
Compound II-227
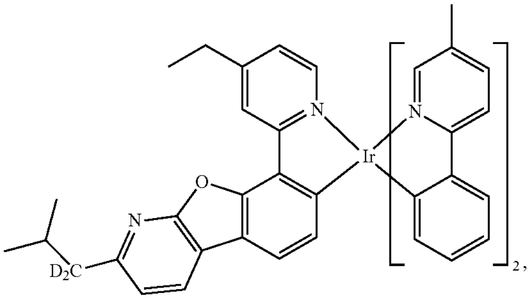
Compound II-228
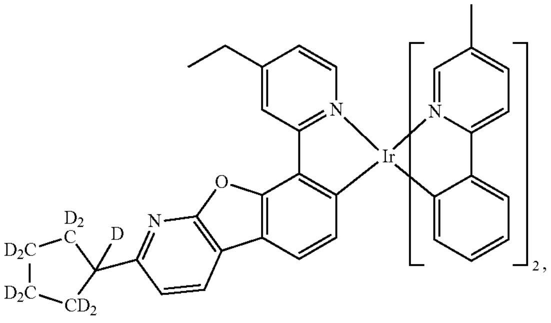
Compound II-229
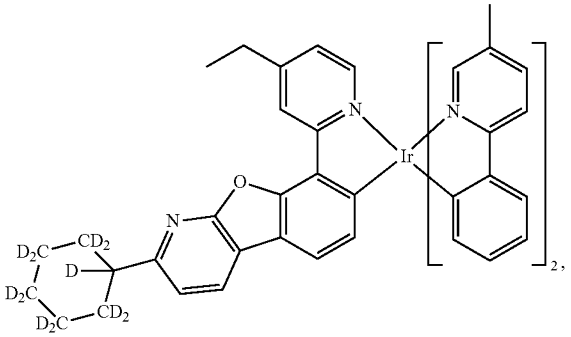
-continued
Compound II-230
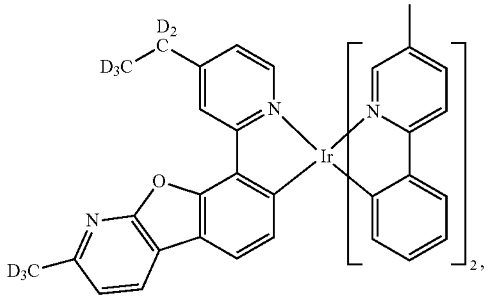
Compound II-231
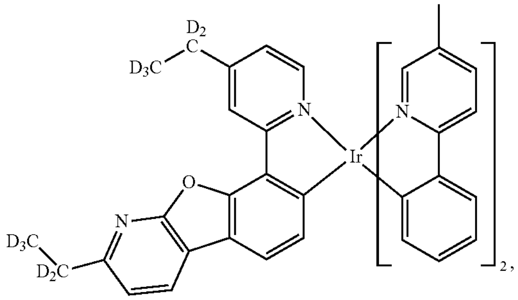
Compound II-232
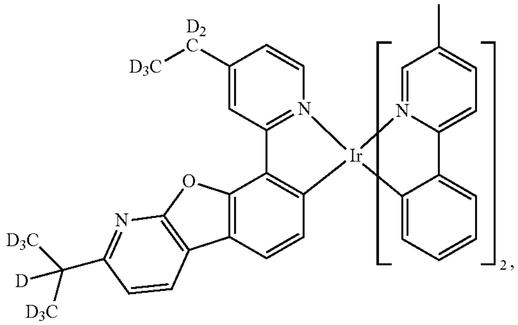
Compound II-233
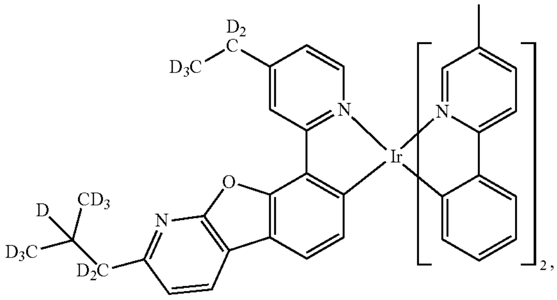
Compound II-234
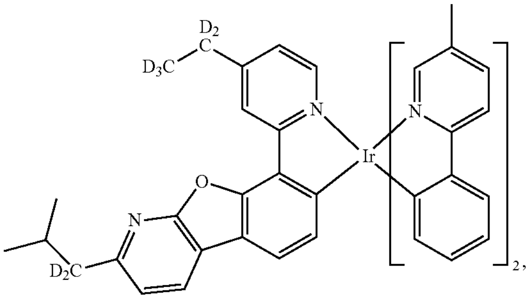

-continued
Compound II-235
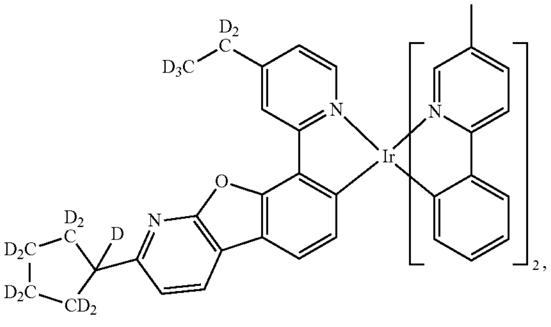
Compound II-236
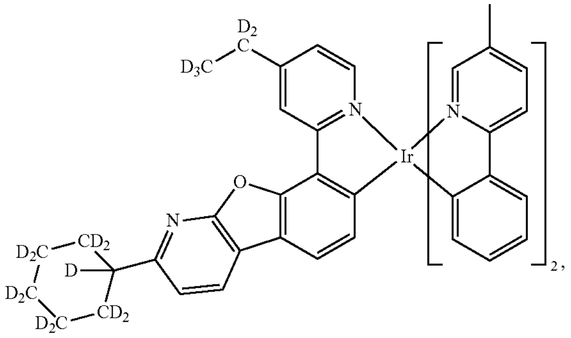
Compound II-237
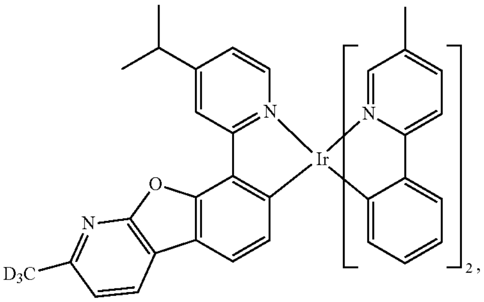
Compound II-238
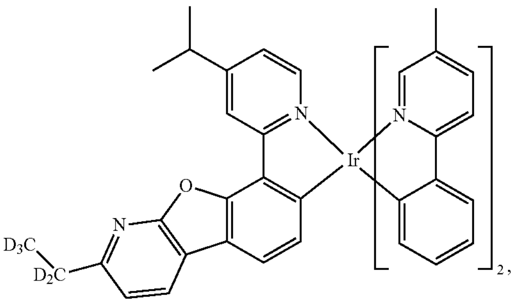
-continued
Compound II-239
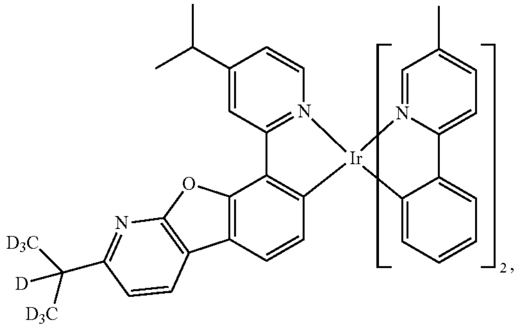
Compound II-240
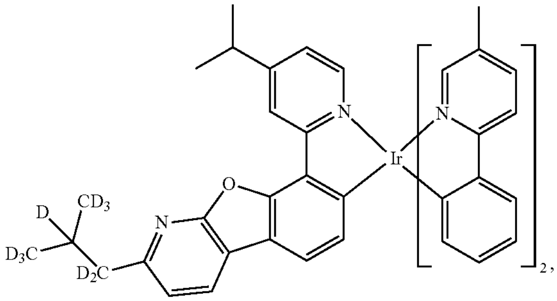
Compound II-241
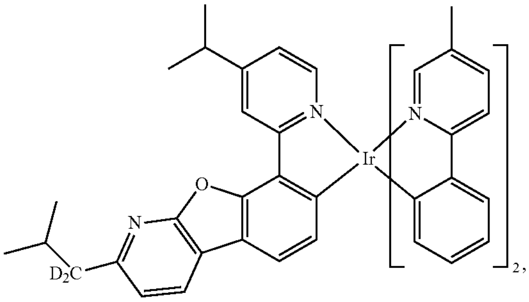
Compound II-242
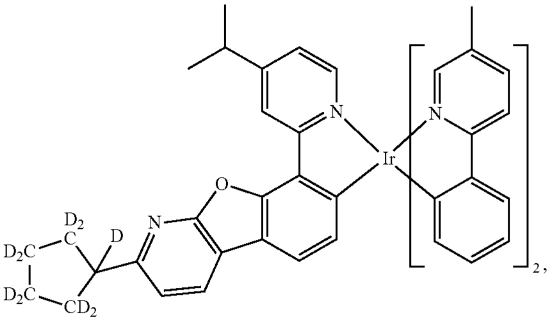

-continued
Compound II-243
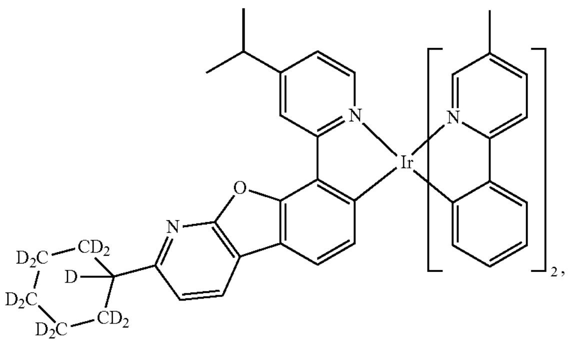
Compound II-244
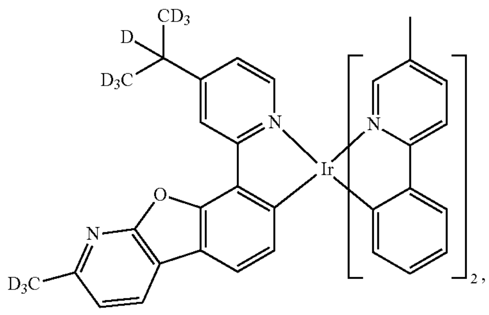
Compound II-245
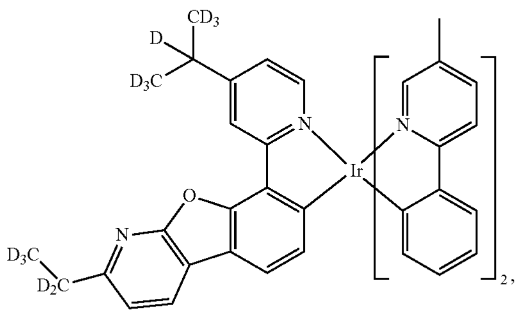
Compound II-246
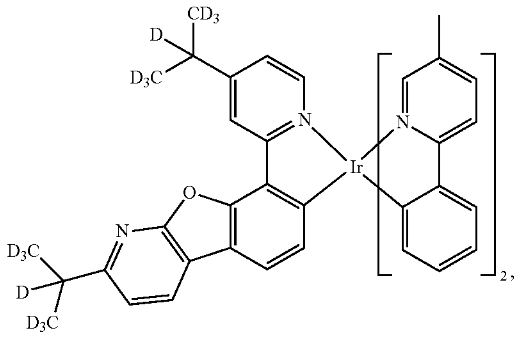
-continued
Compound II-247
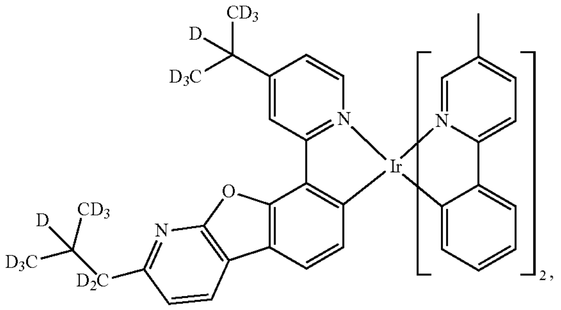
Compound II-248
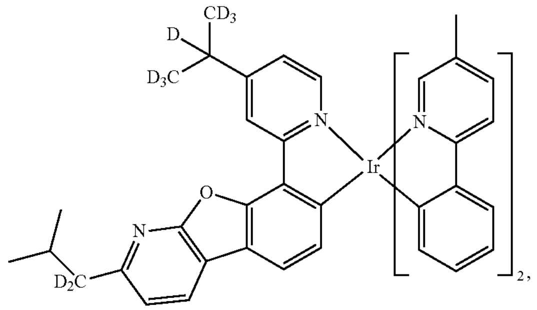
Comnpound II-249
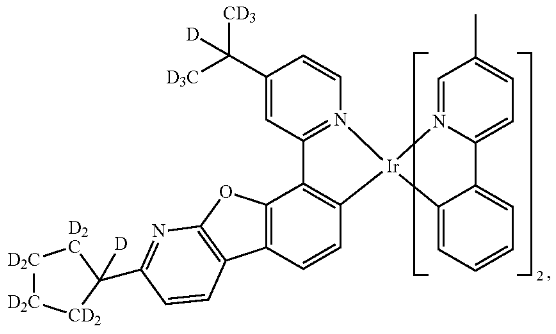
Compound II-250
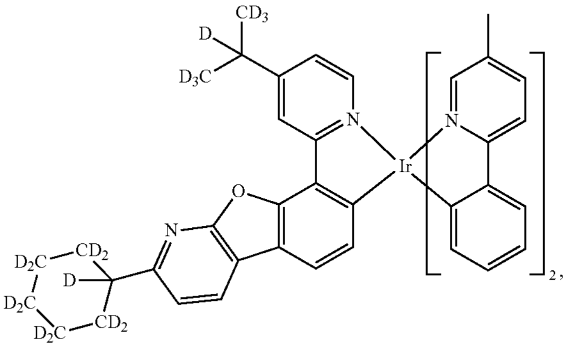

-continued
Compound II-251
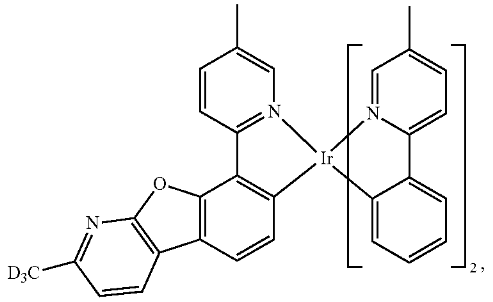
Compound II-252
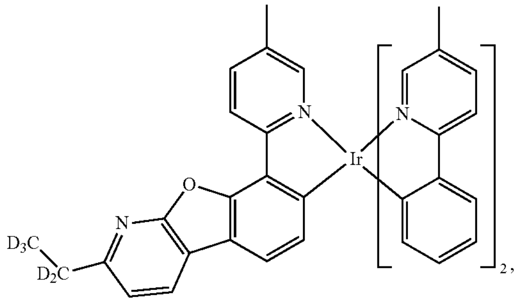
Compound II-253
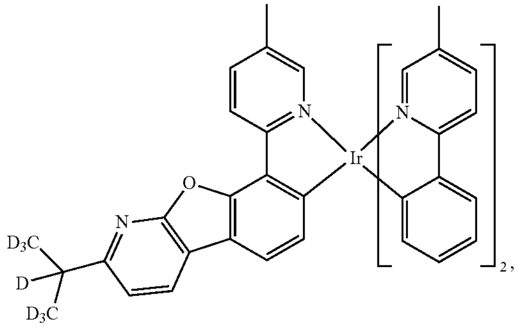
Compound II-254
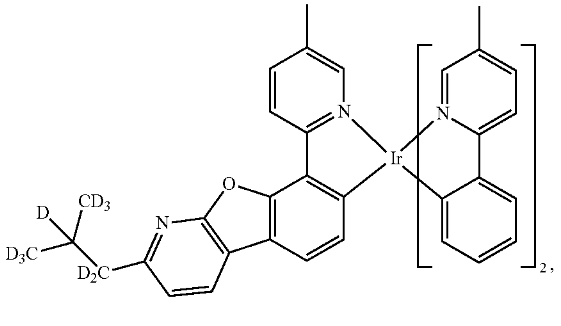
-continued
Compound II-255
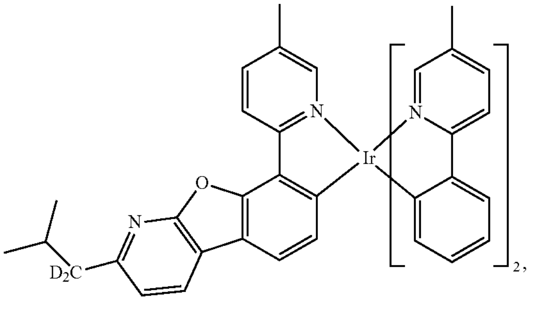
Compound II-256
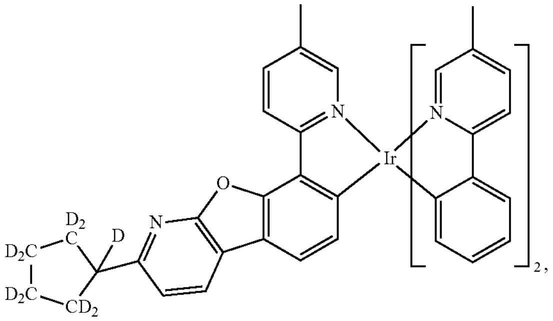
Compound II-257
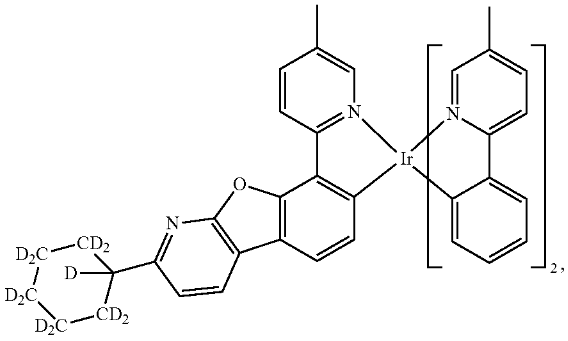
Compound II-258
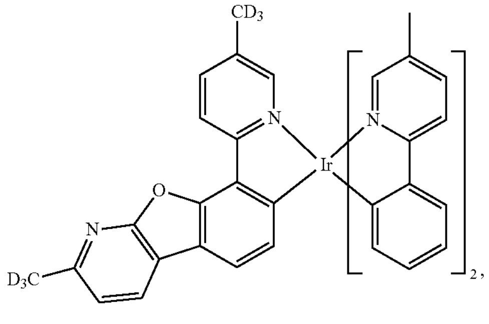

Compound II-259
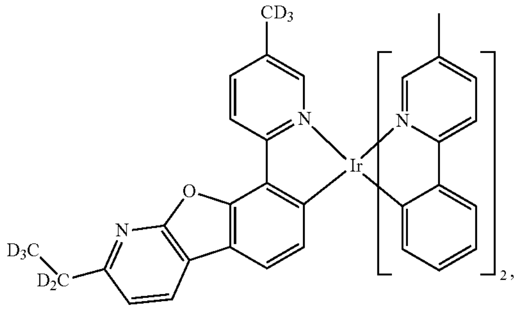
Compound II-260
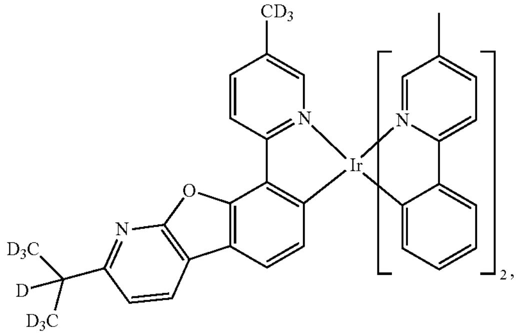
Compound II-261
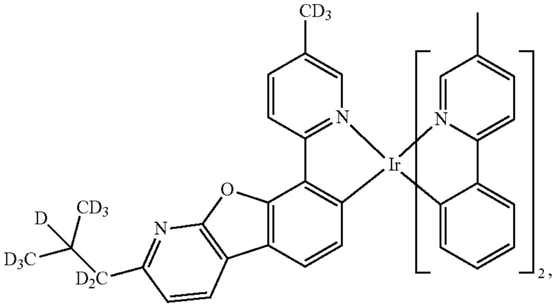
Compound II-262
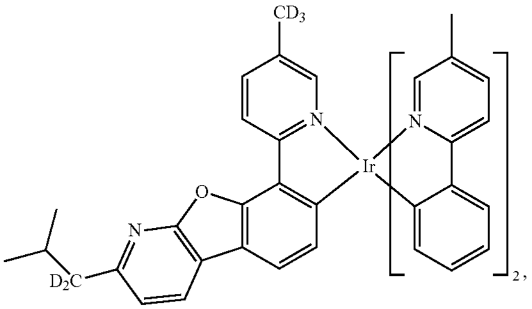
Compound II-263
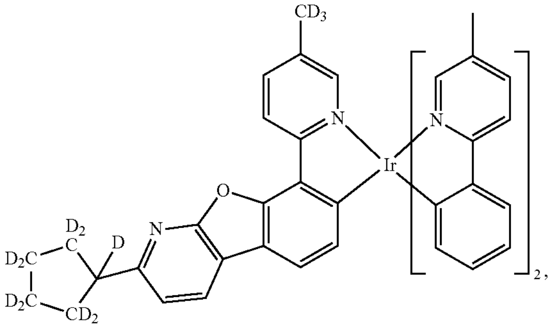
Compound II-264
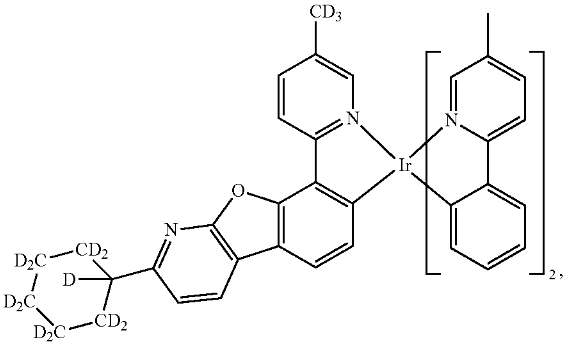
Compound II-265
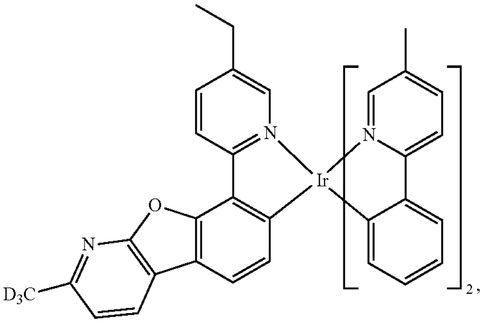
Compound II-266
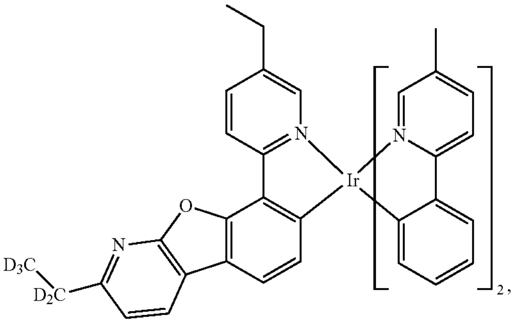

-continued
Compound II-267
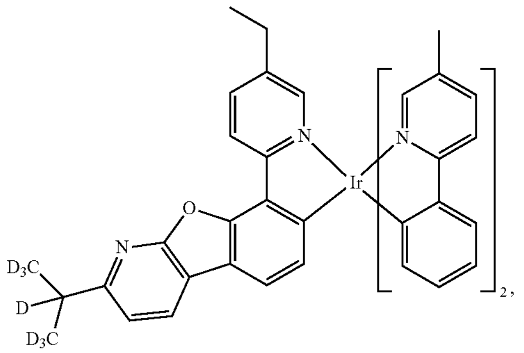
Compound II-268
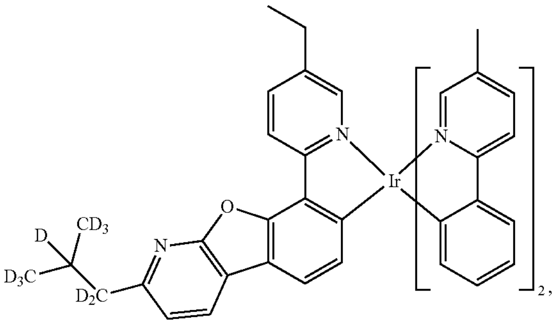
Compound II-269
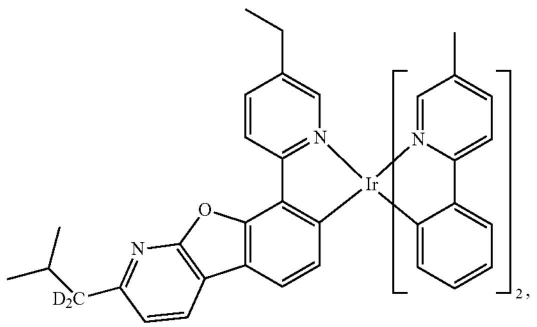
Compound II-270
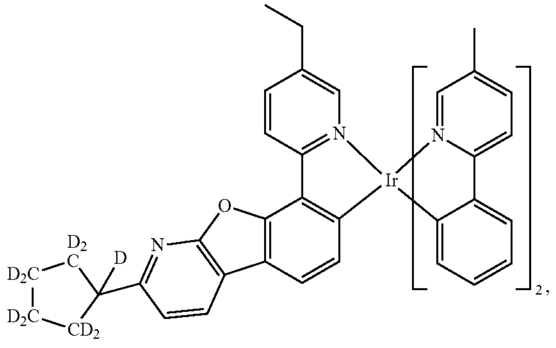
-continued
Compound II-271
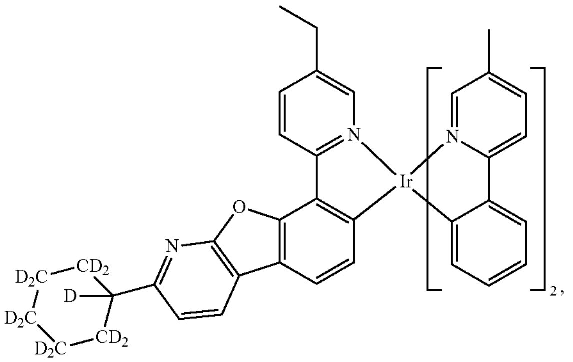
Compound II-272
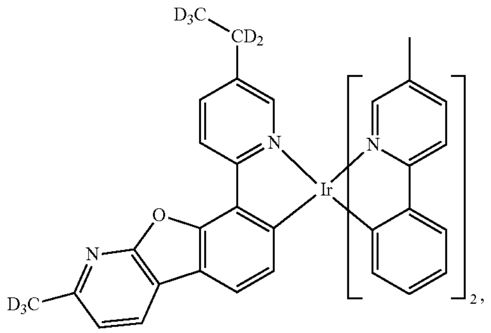
Compound II-273
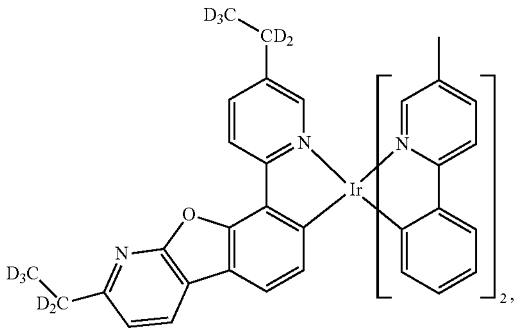
Compound II-274
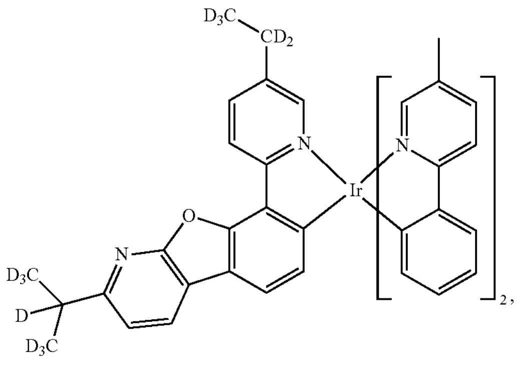

-continued
Compound II-275
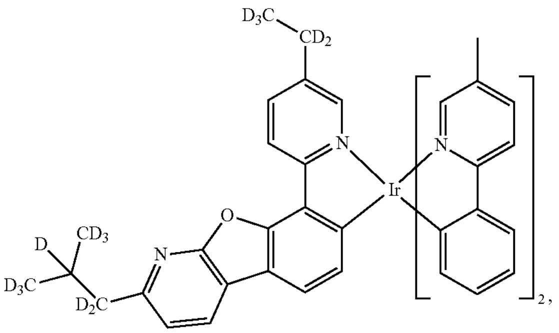
Compound II-276
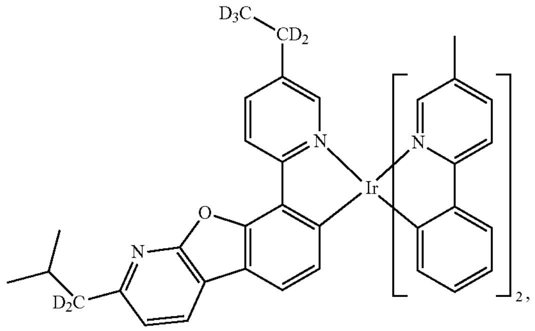
Compound II-277
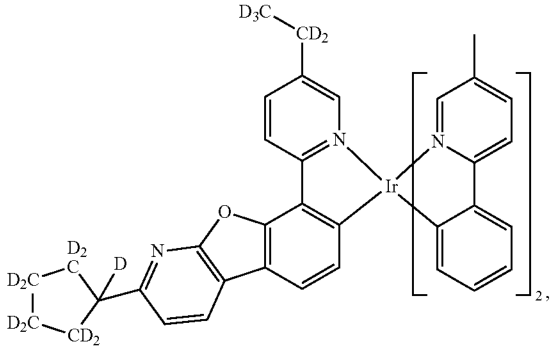
Compound II-278
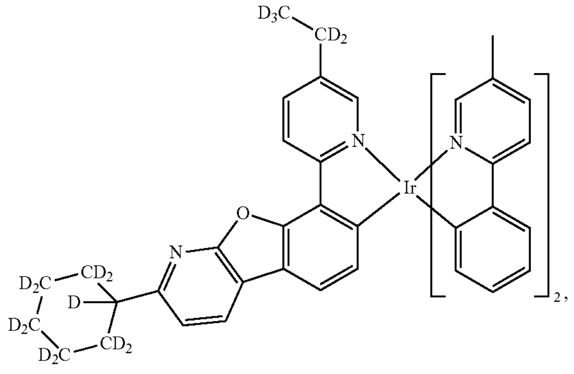
-continued
Compound II-279
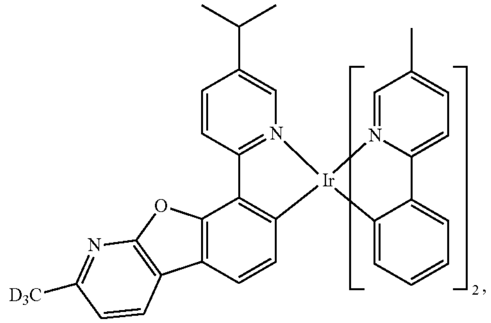
Compound II-280
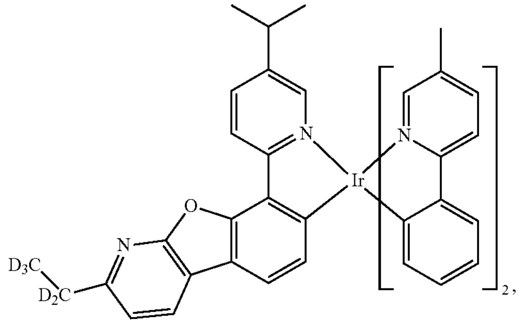
Compound II-281
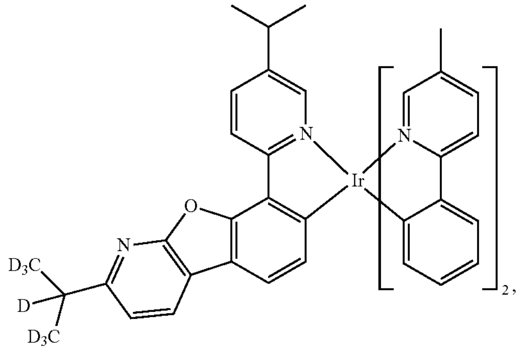
Compound II-282
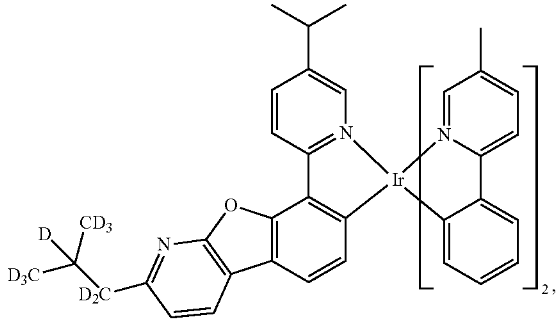

-continued
Compound II-283
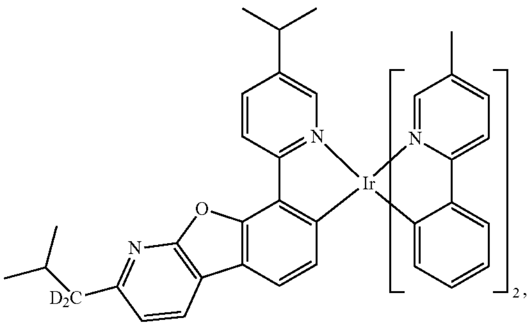
Compound II-284
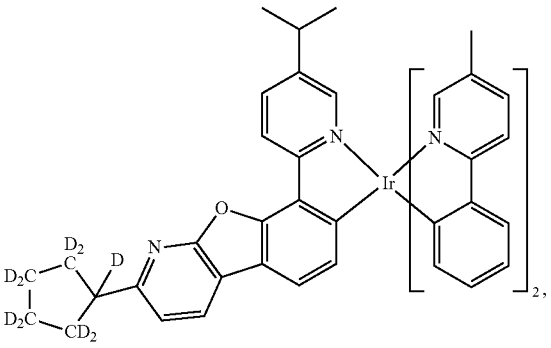
Compound II-285
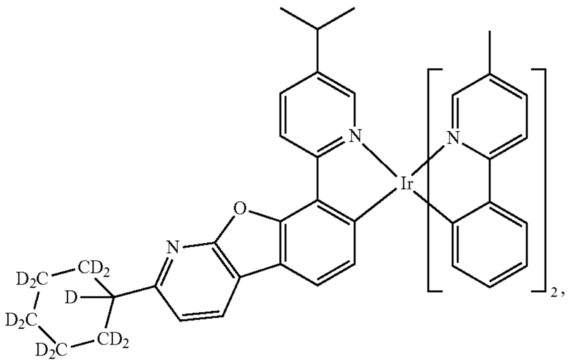
Compound II-286
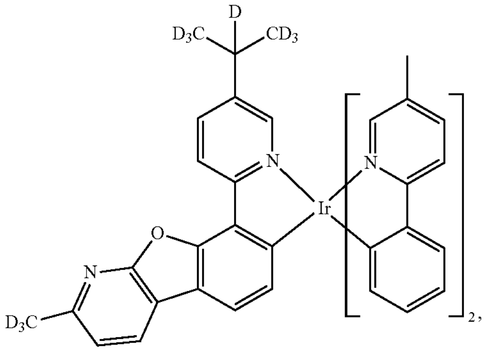
-continued
Compound II-287
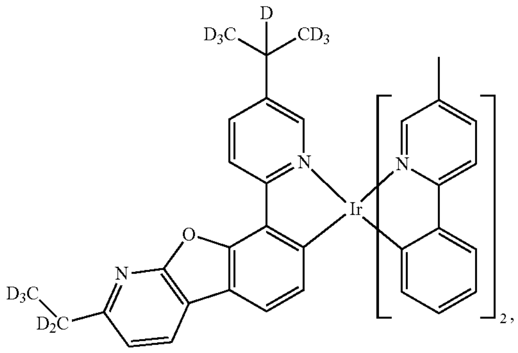
Compound II-288
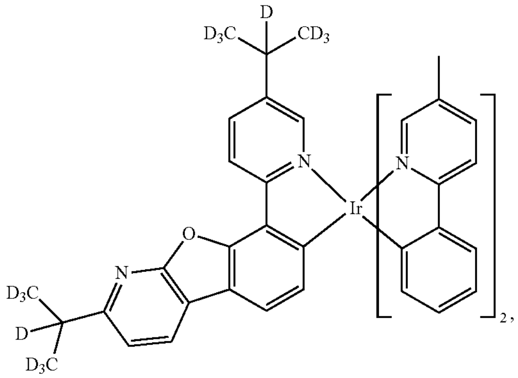
Compound II-289
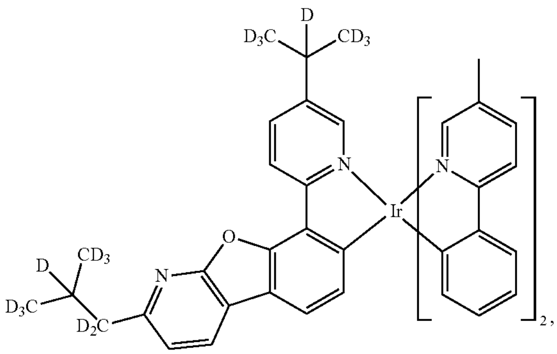
Compound II-290
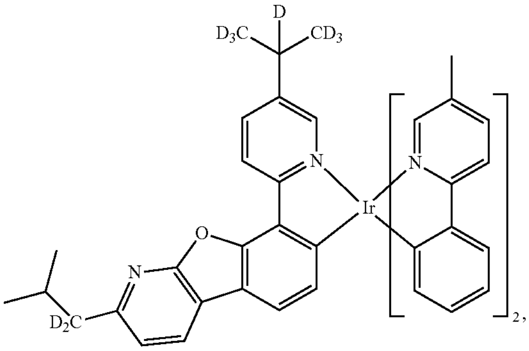

-continued
Compound II-291
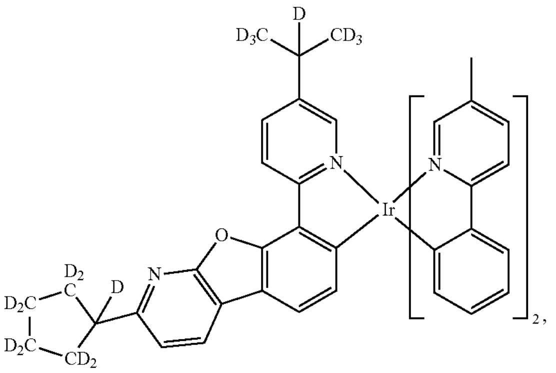
Compound II-292
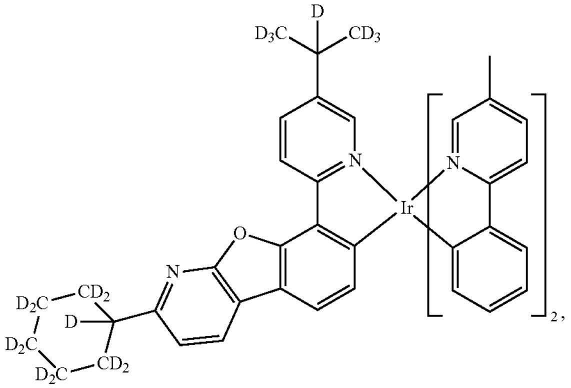
Compound II-293
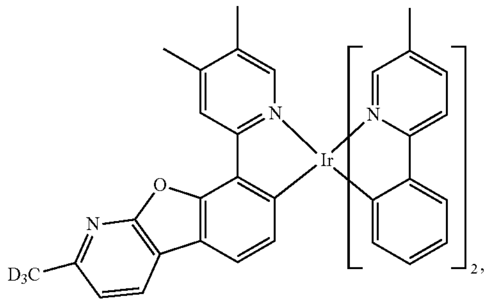
Compound II-294
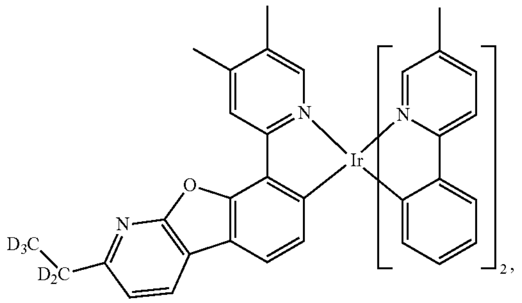
-continued
Compound II-295
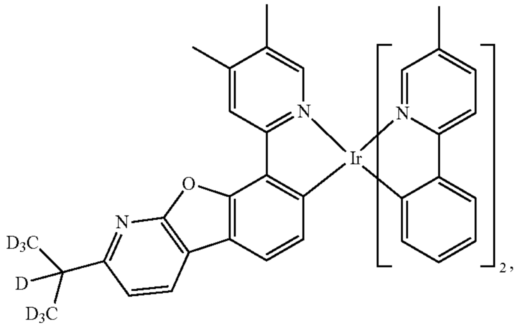
Compound II-296
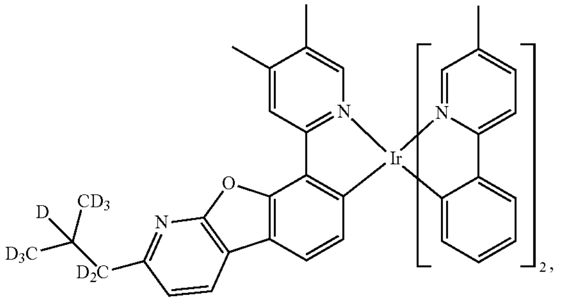
Compound II-297
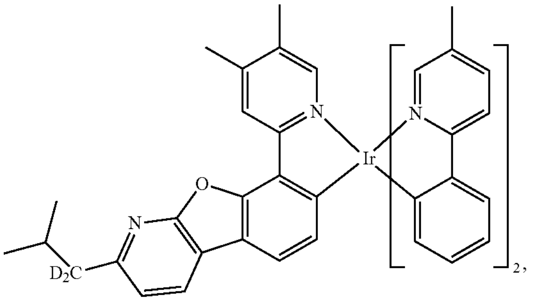
Compound II-298
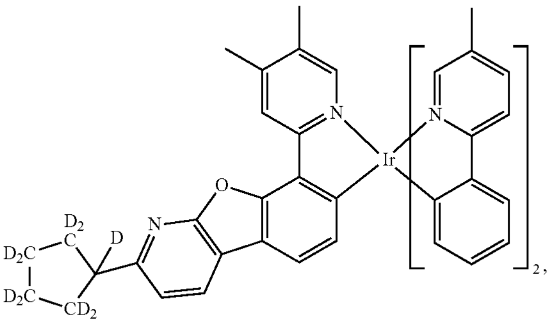

-continued
Compound II-299
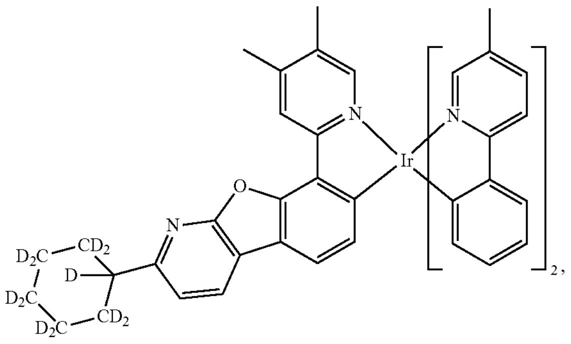
Compound II-300
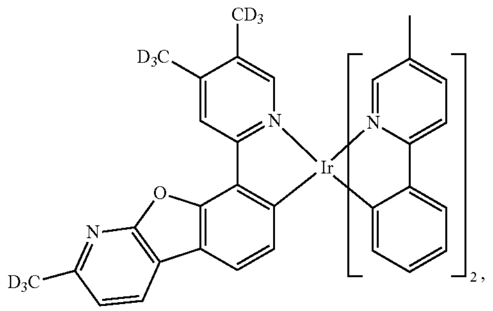
Compound II-301
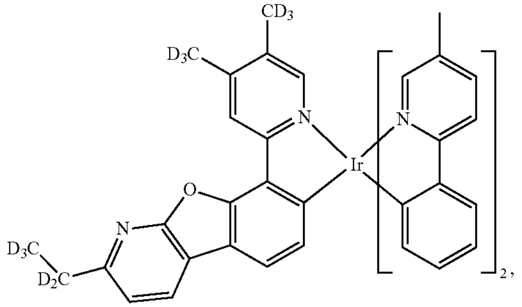
Compound II-302
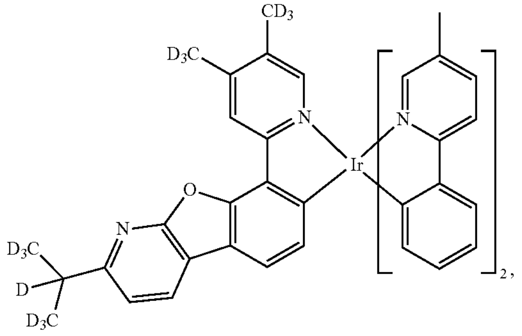
-continued
Compound II-303
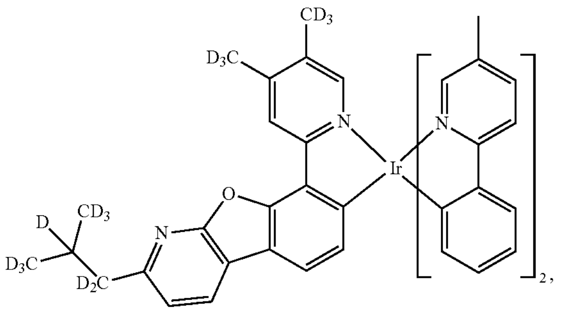
Compound II-304
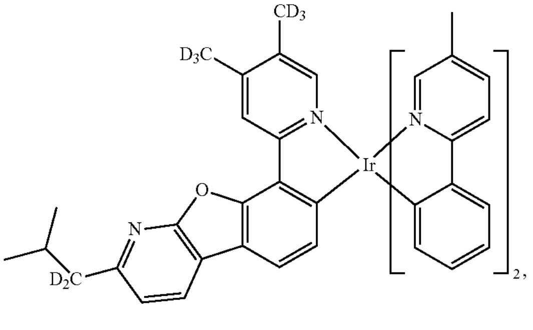
Compound II-305
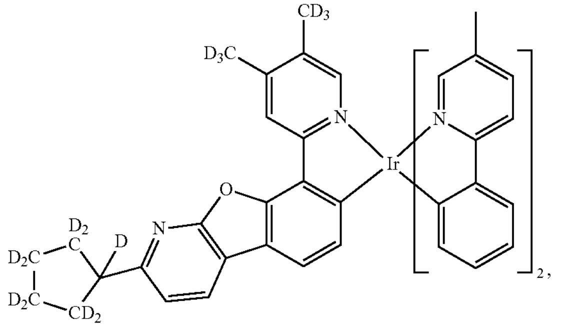
Compound II-306
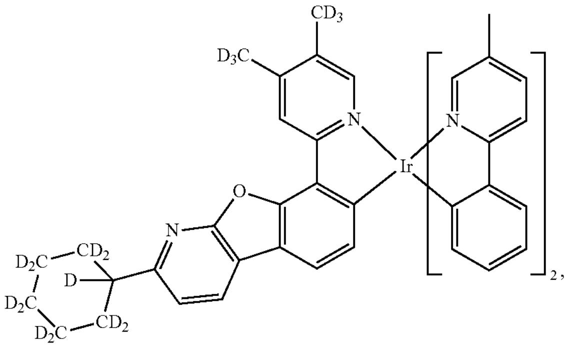

-continued
Compound II-307
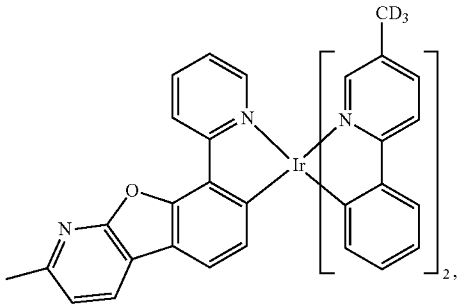
Compound II-308
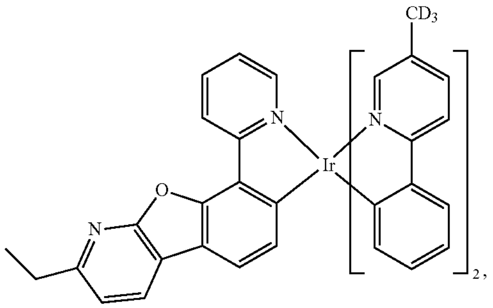
Compound II-309
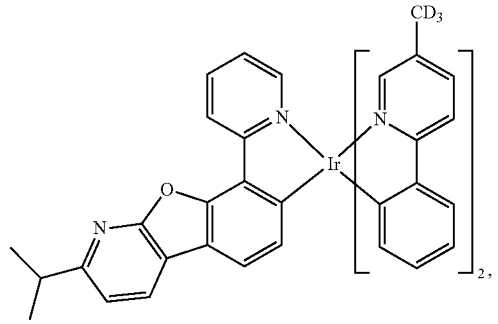
Compound II-310
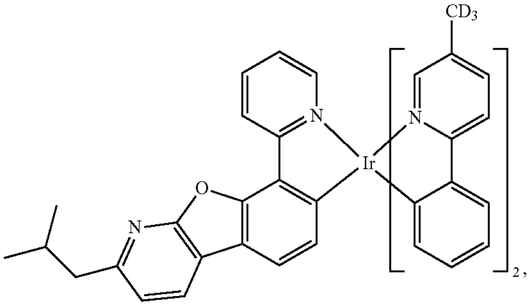
-continued
Compound II-311
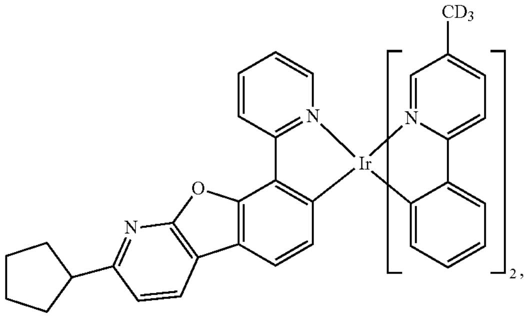
Compound II-312
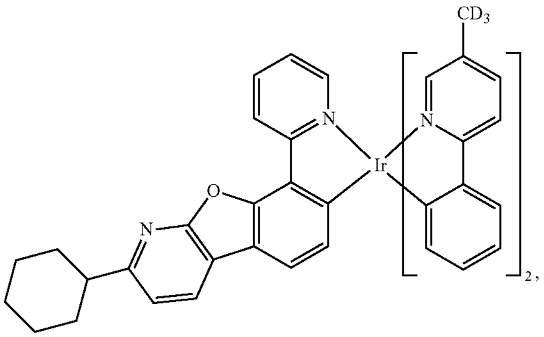
Compound II-313
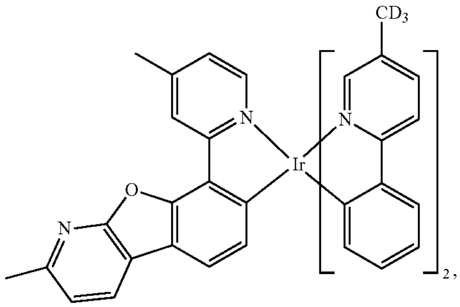
Compound II-314
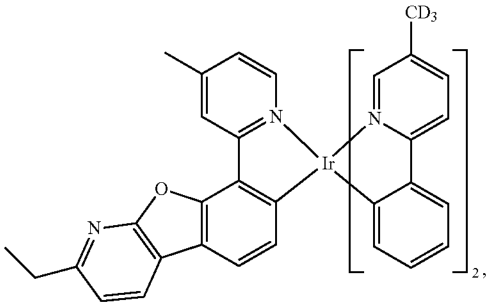

-continued
Compound II-315
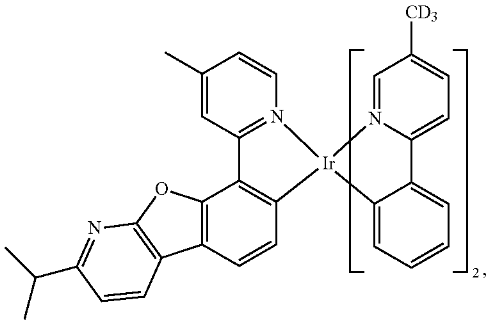
Compound II-316
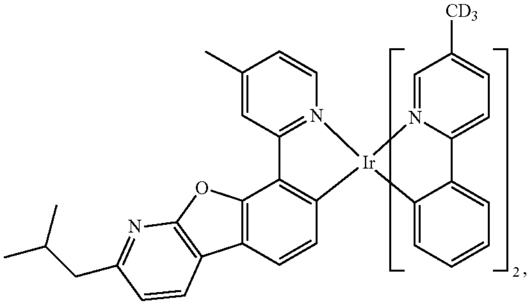
Compound II-317
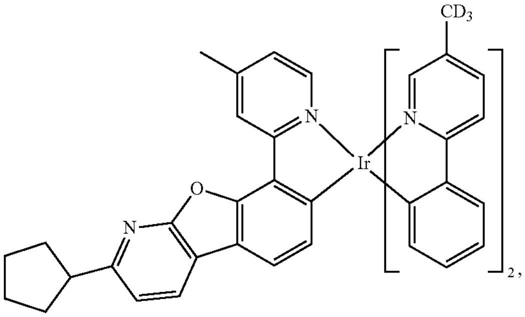
Compound II-318
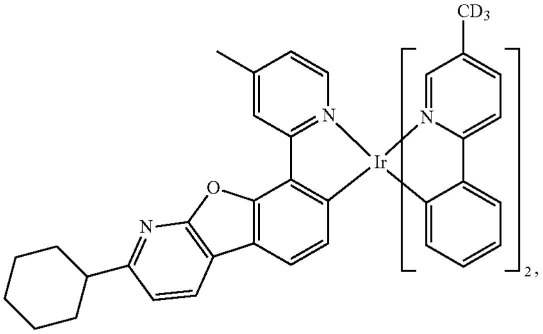
-continued
Compound II-319
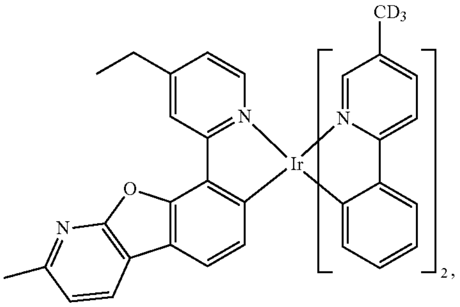
Compound II-320
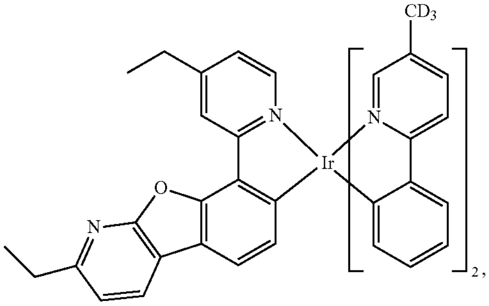
Compound II-321
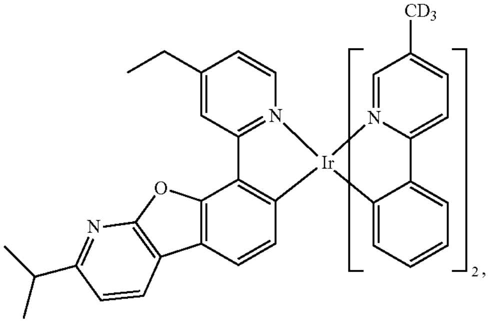
Compound II-322
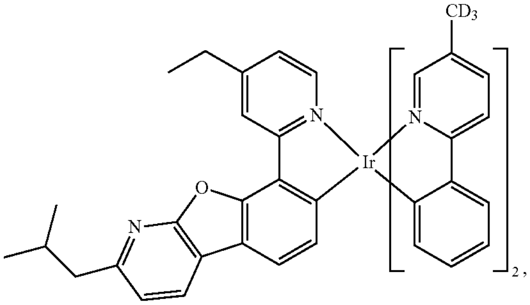

Compound II-323
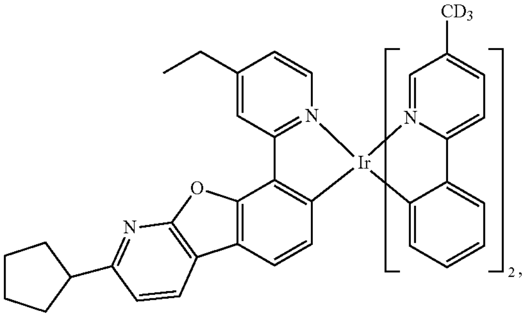
Compound II-324
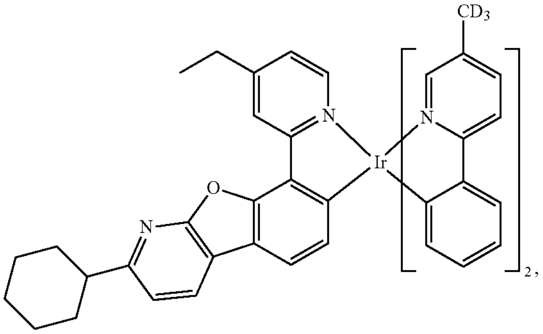
Compound II-325
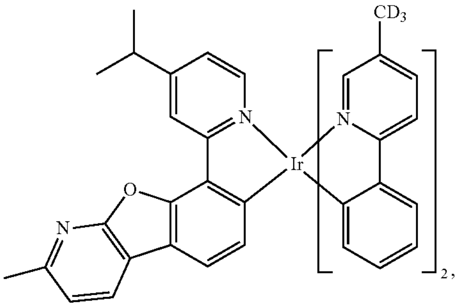
Compound II-326
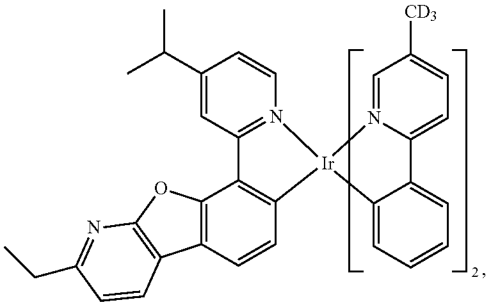
Compound II-327
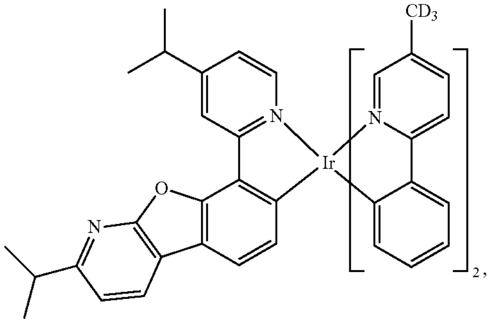
Compound II-328
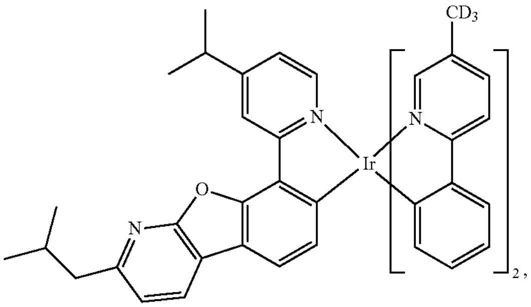
Compound II-329
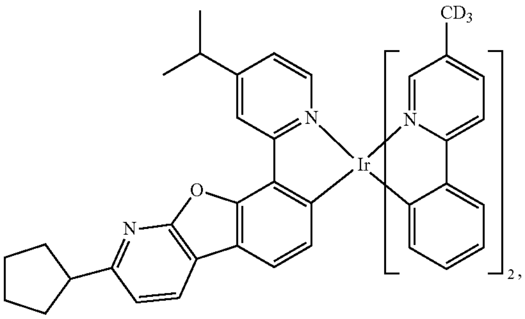
Compound II-330
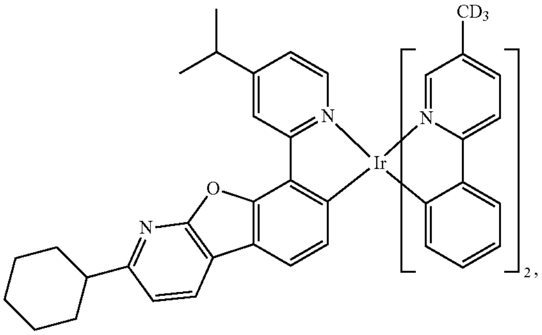

-continued
Compound II-331
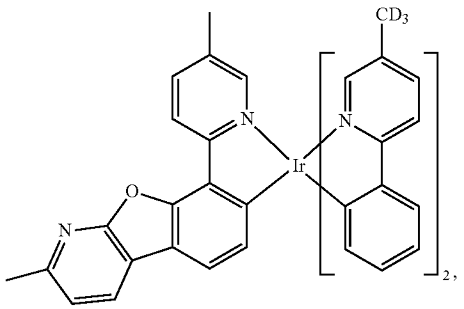
Compound II-332
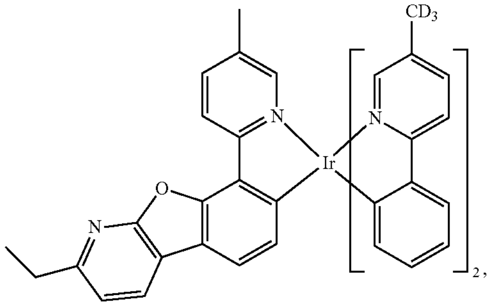
Compound II-333
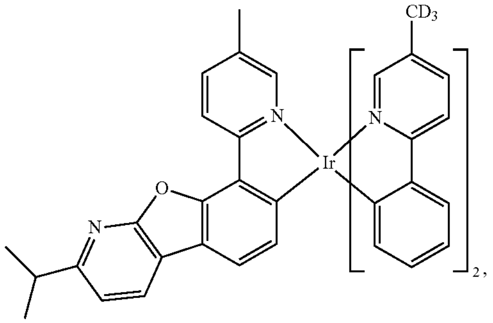
Compound II-334
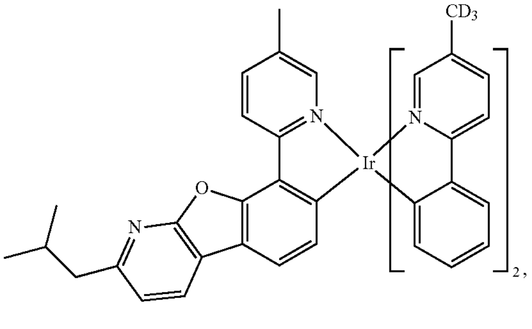
-continued
Compound II-335
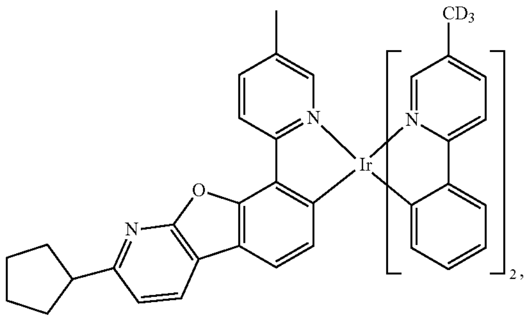
Compound II-336
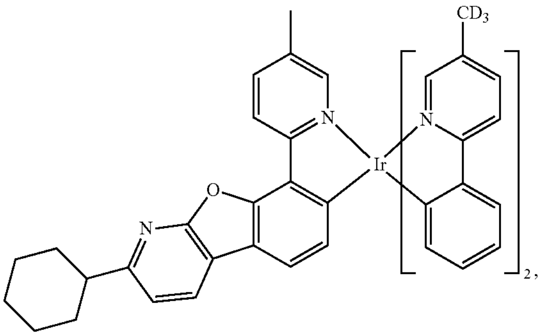
Compound II-337
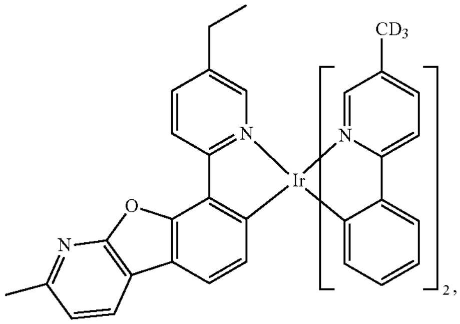
Compound II-338
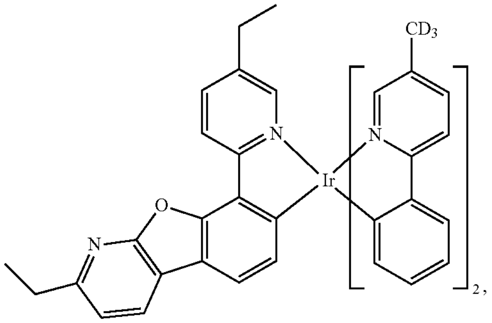

-continued
Compound II-339
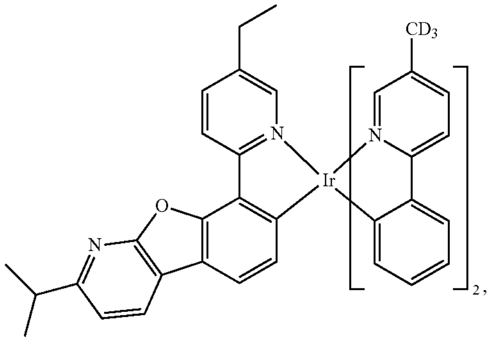
Compound II-340
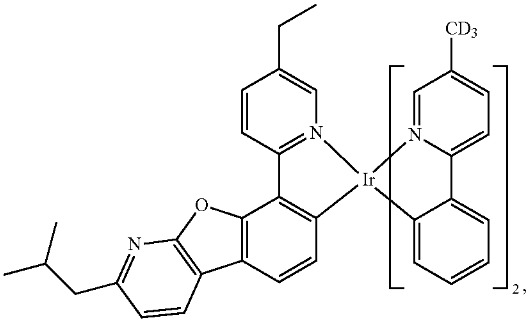
Compound II-341
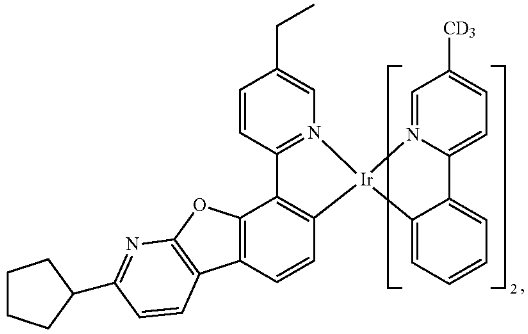
Compound II-342
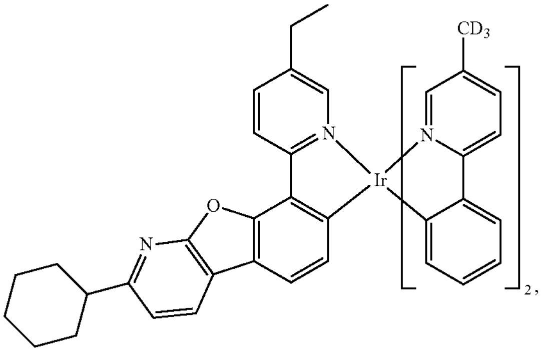
-continued
Compound II-343
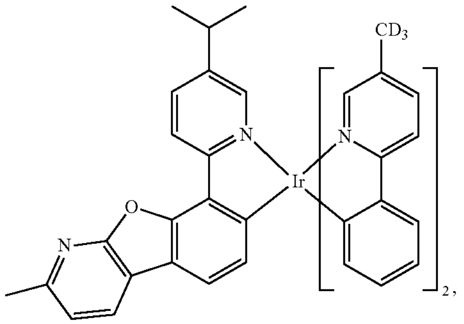
Compound II-344
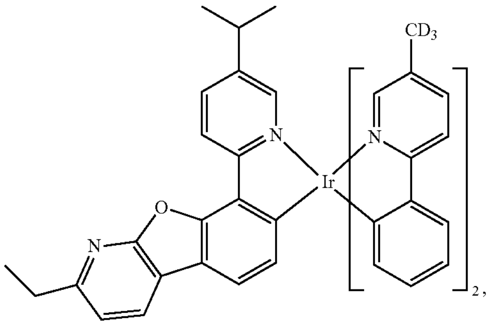
Compound II-345
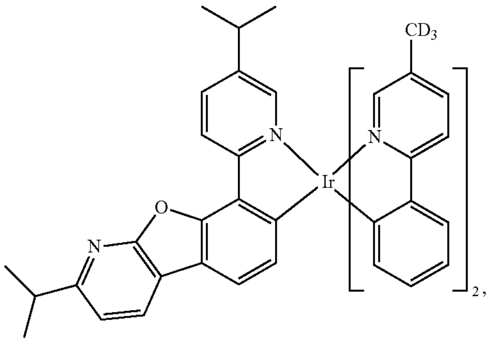
Compound II-346
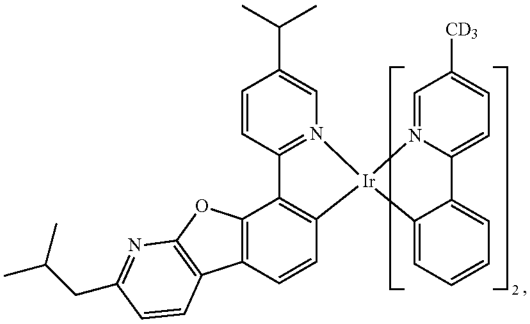

-continued
Compound II-347
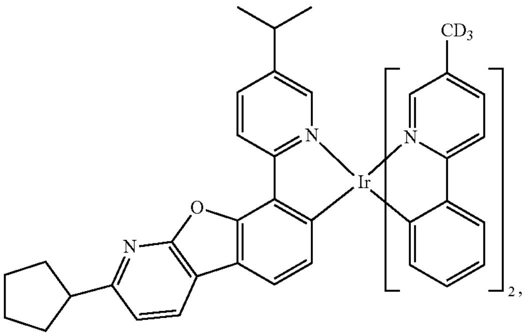
Compound II-348
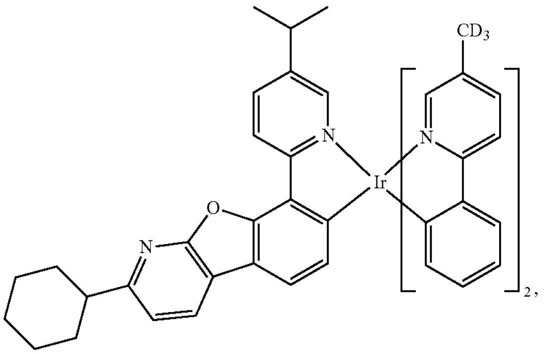
Compound II-349
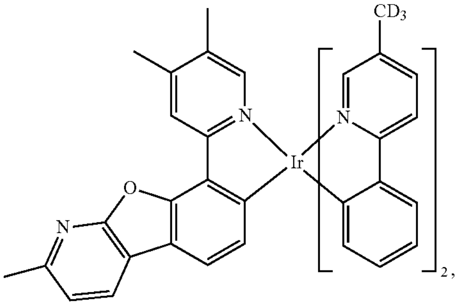
Compound II-350
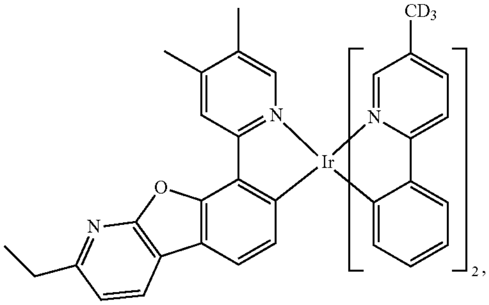
-continued
Compound II-351
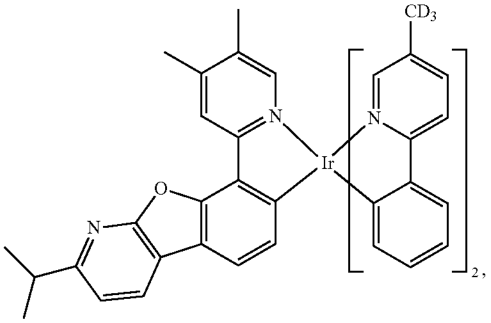
Compound II-352
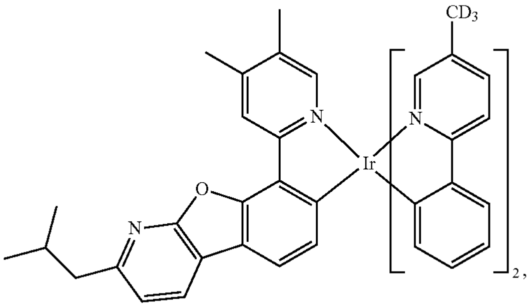
Compound II-353
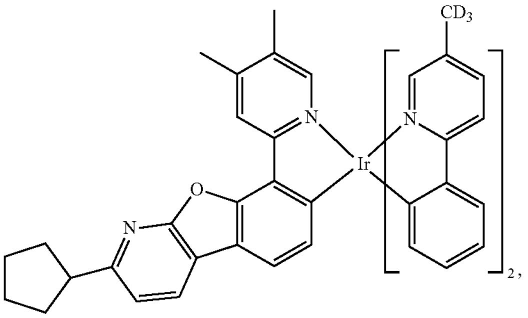
Compound II-354
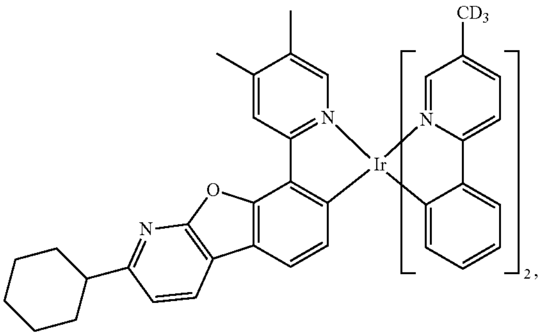

-continued
Compound II-355
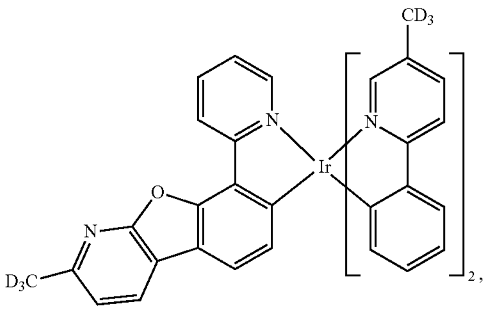
Compound II-356
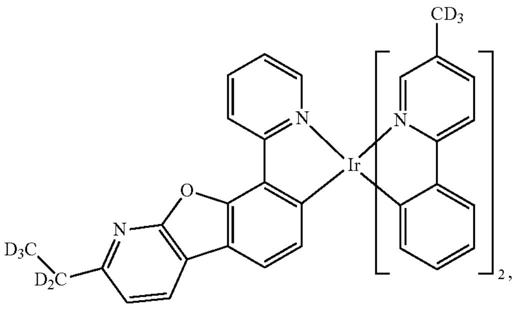
Compound II-357
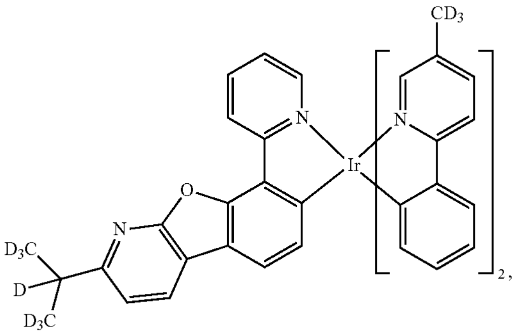
Compound II-358
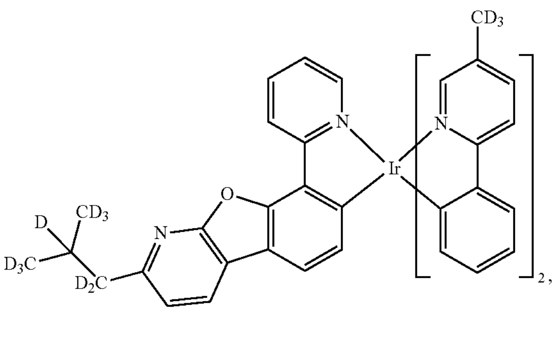
-continued
Compound II-359
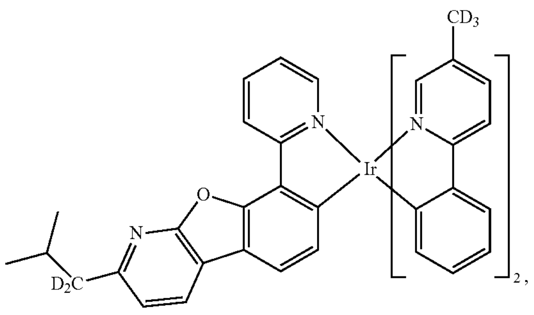
Compound II-360
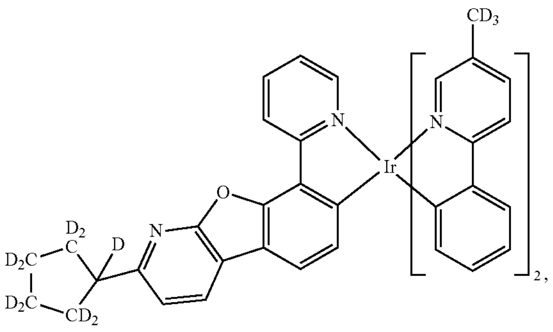
Compound II-361
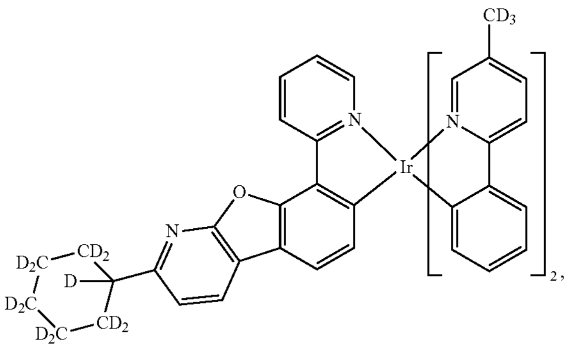
Compound II-362
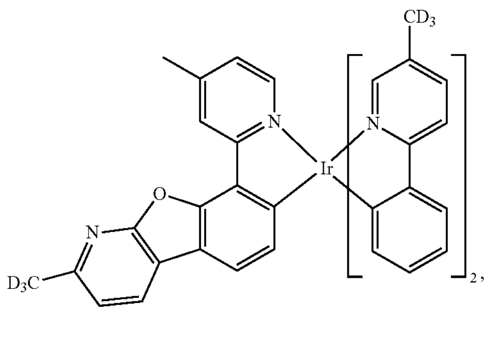

-continued
Compound II-363
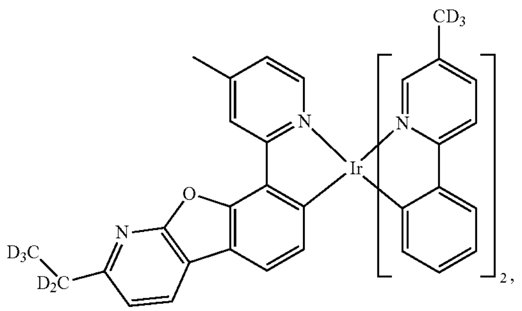
Compound II-364
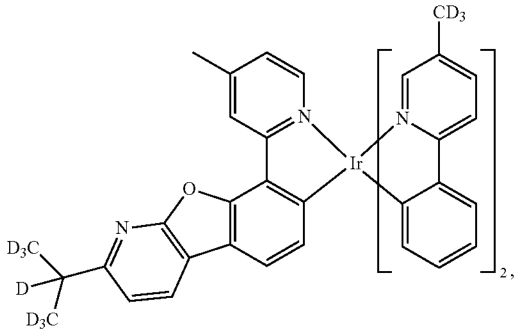
Compound II-365
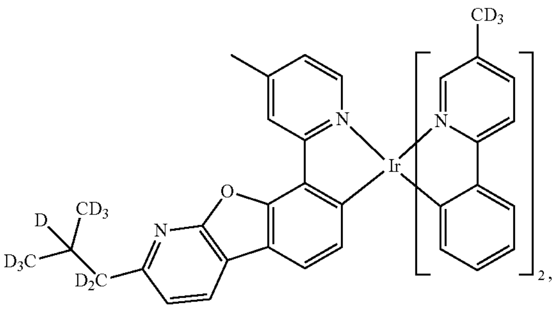
Compound II-366
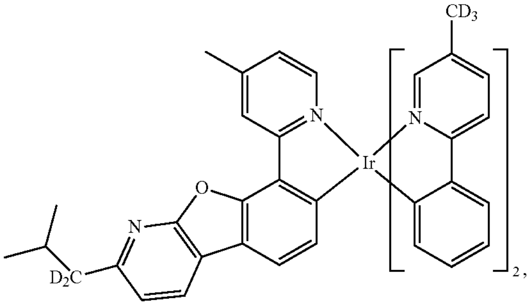
-continued
Compound II-367
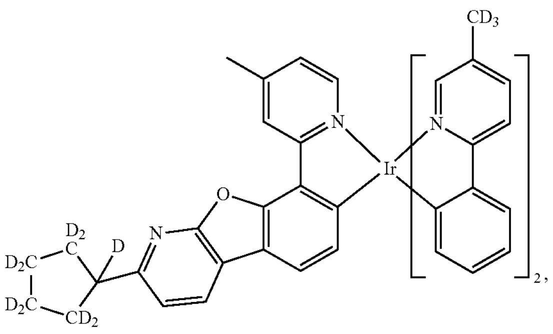
Compound II-368
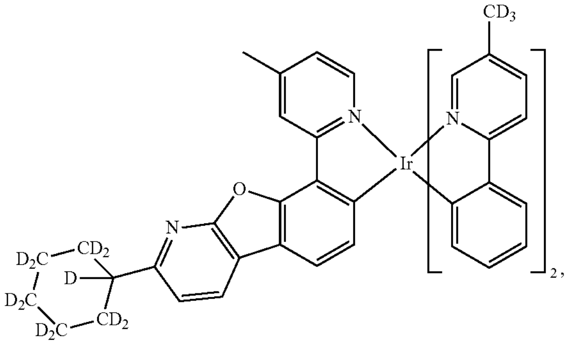
Compound II-369
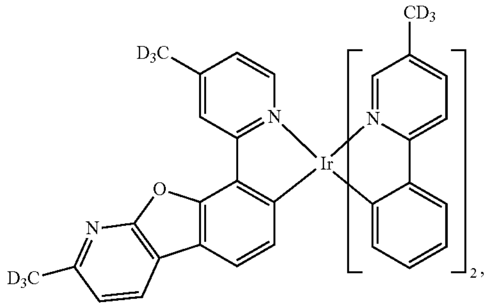
Compound II-370
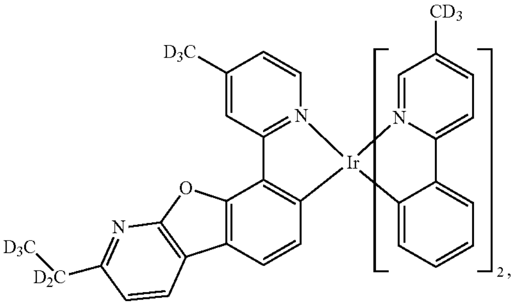

-continued
Compound II-371
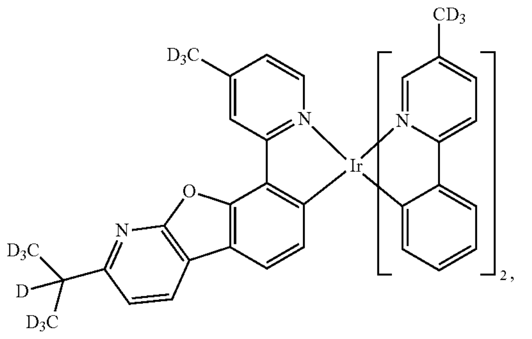
Compound II-372
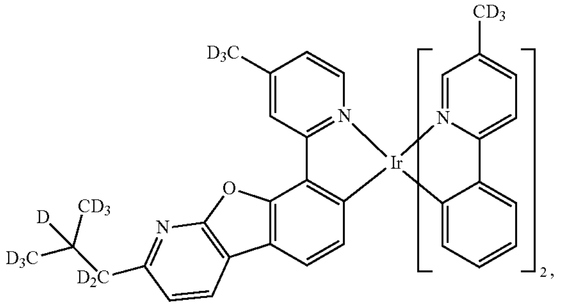
Compound II-373
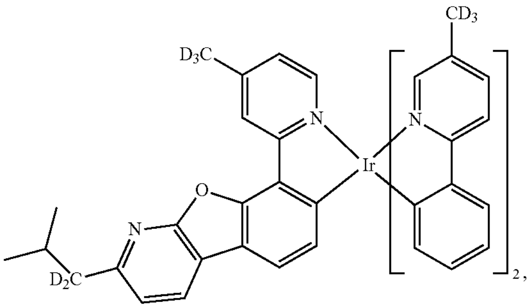
Compound II-374
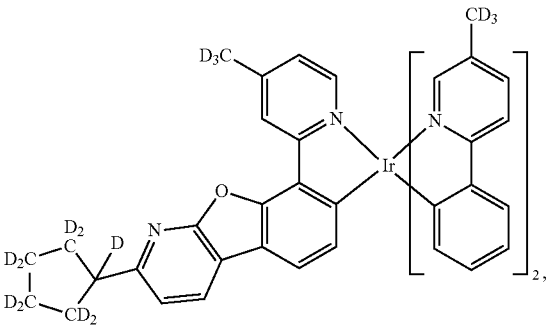
-continued
Compound II-375
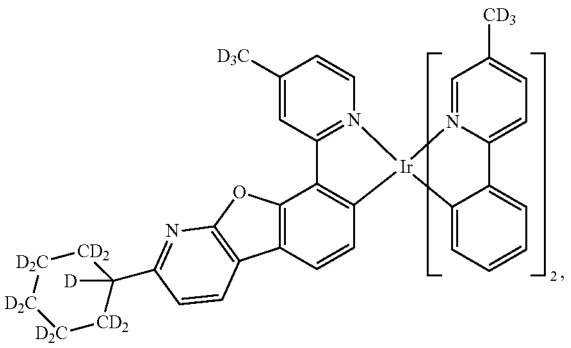
Compound II-376
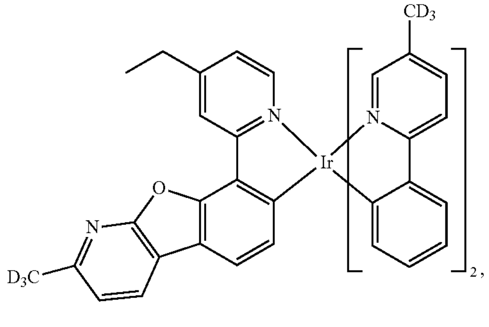
Compound II-377
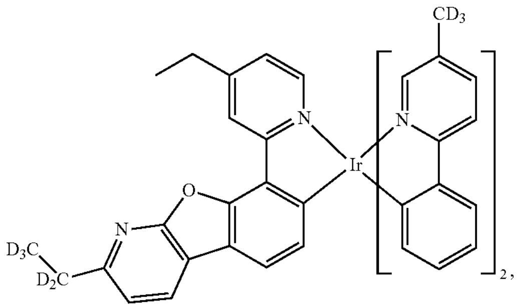
Compound II-378
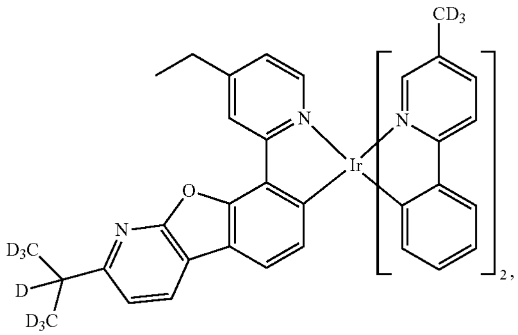

-continued
Compound II-379
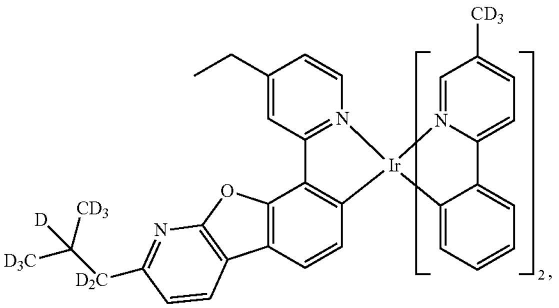
Compound II-380
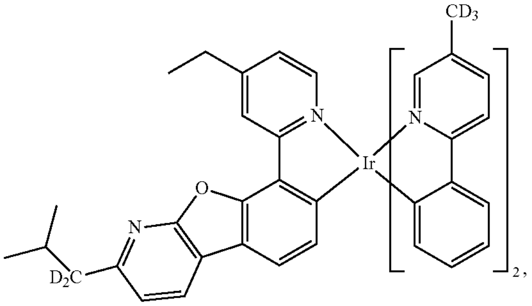
Compound II-381
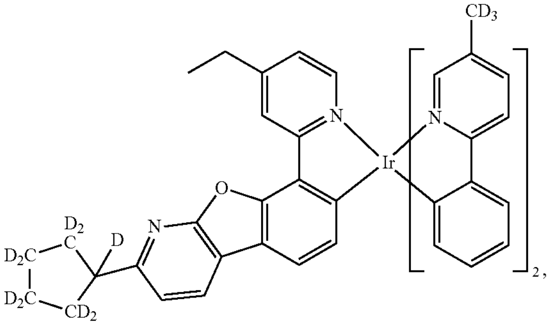
Compound II-382
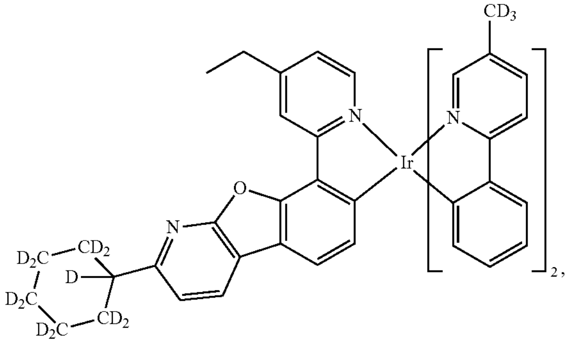
-continued
Compound II-383
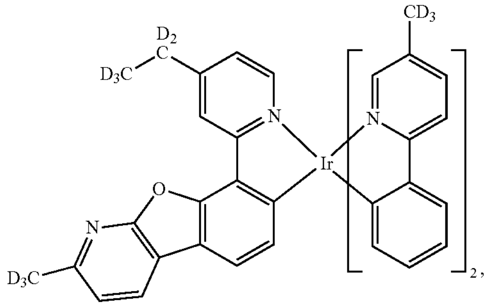
Compound II-384
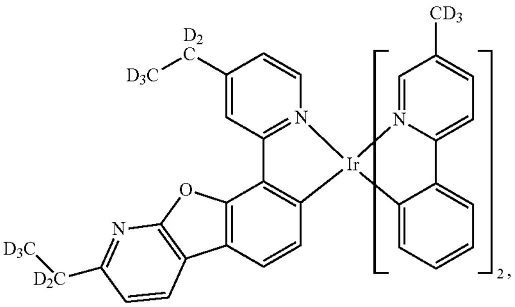
Compound II-385
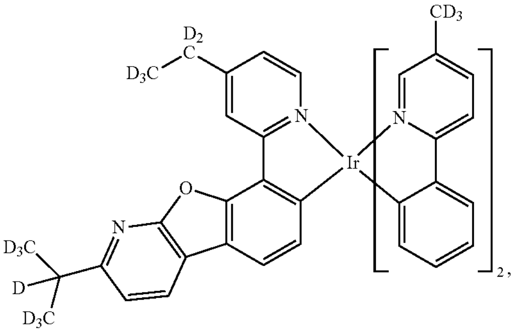
Compound II-386
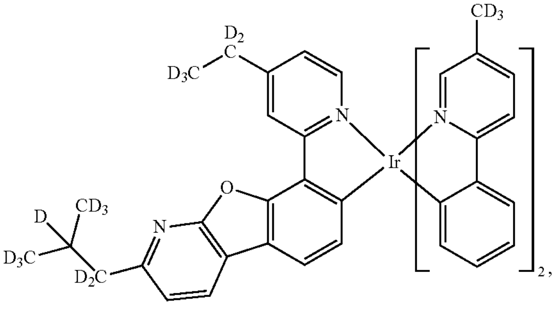

-continued
Compound II-387
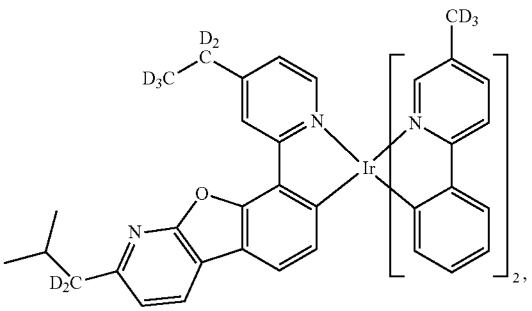
Compound II-388
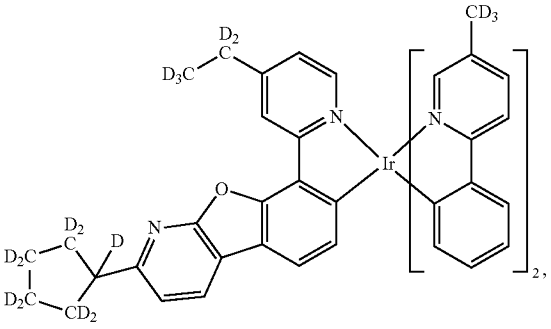
Compound II-389
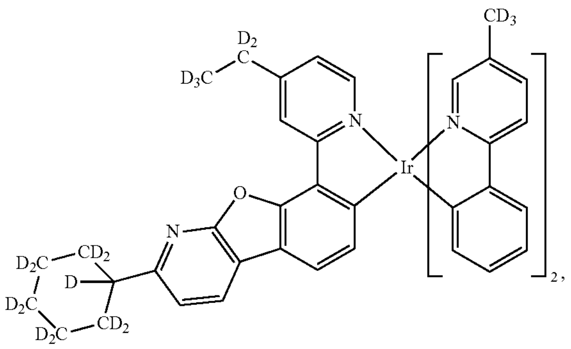
Compound II-390
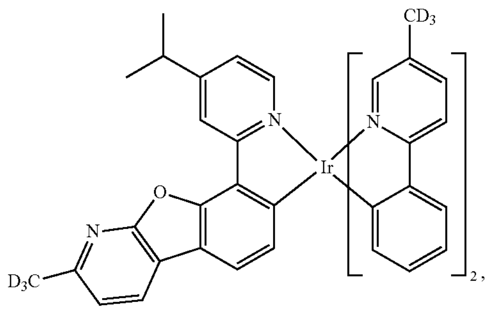
-continued
Compound II-391
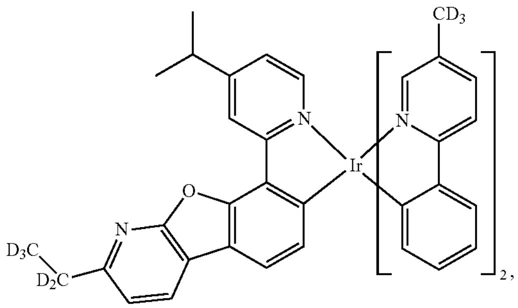
Compound II-392
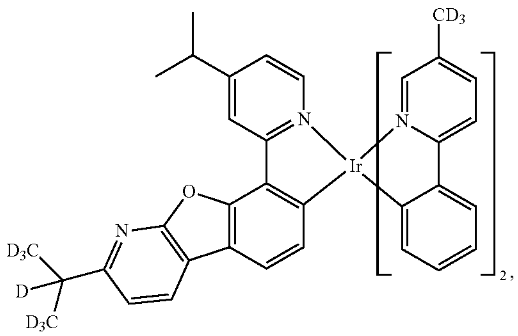
Compound II-393
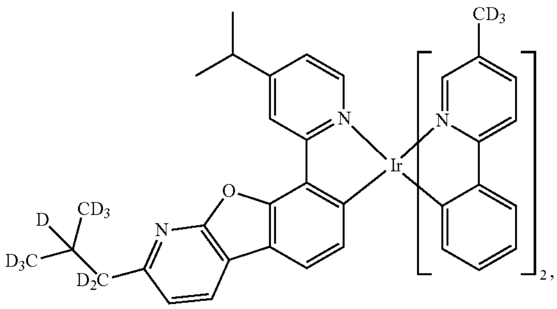
Compound II-394
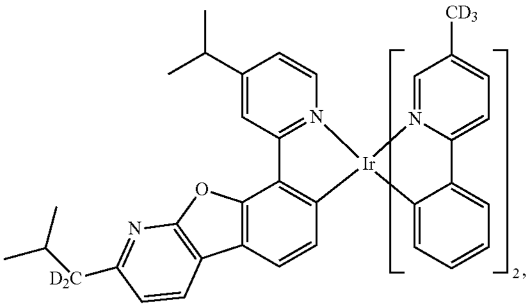

Compound II-395
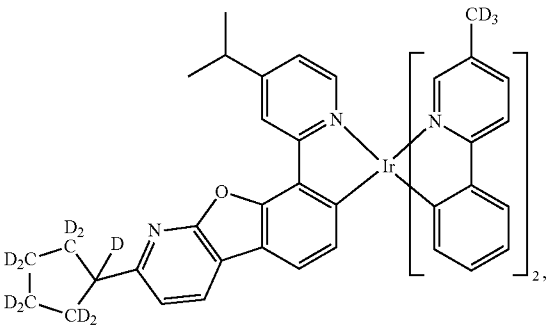
Compound II-396
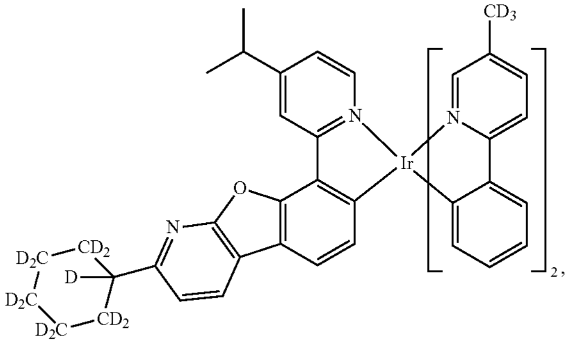
Compound II-397
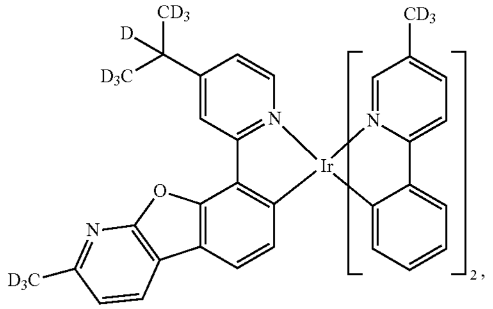
Compound II-398
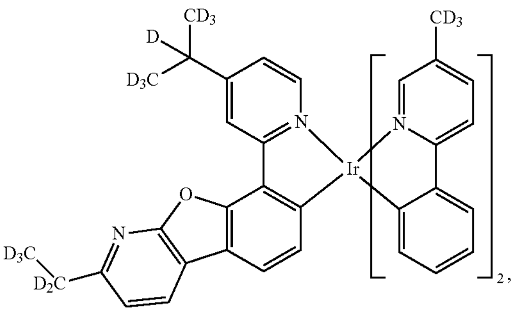
Compound II-399
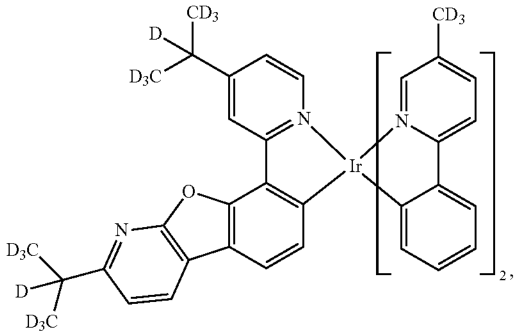
Compound II-400
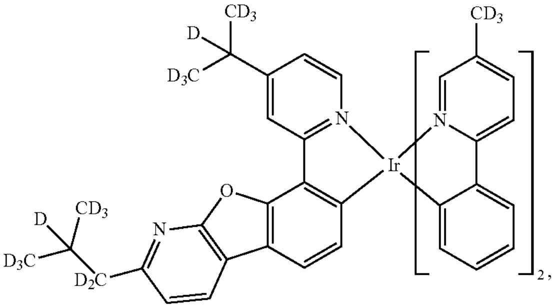
Compound II-401
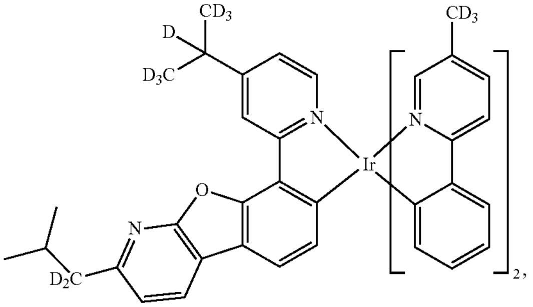
Compound II-402
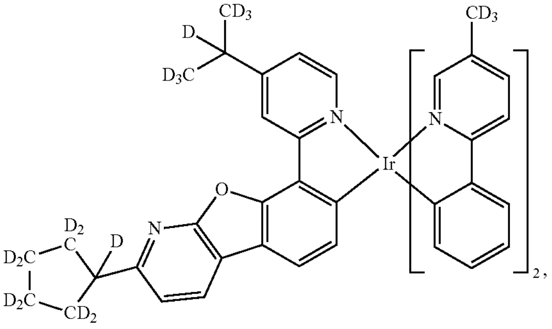

-continued
Compound II-403
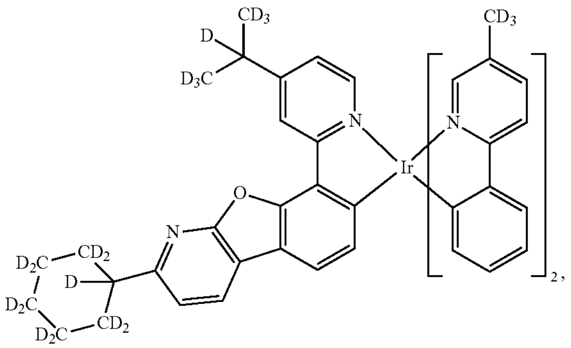
Compound II-404
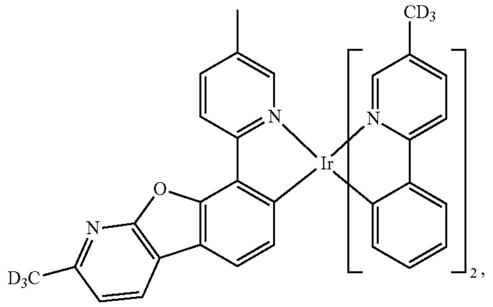
Compound II-405
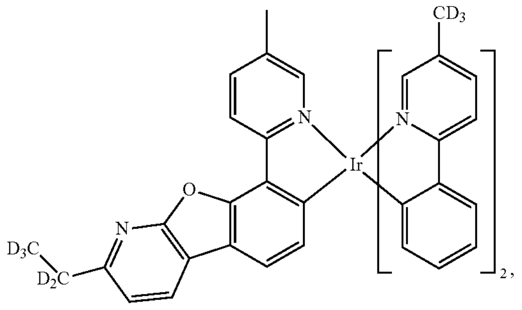
Compound II-406
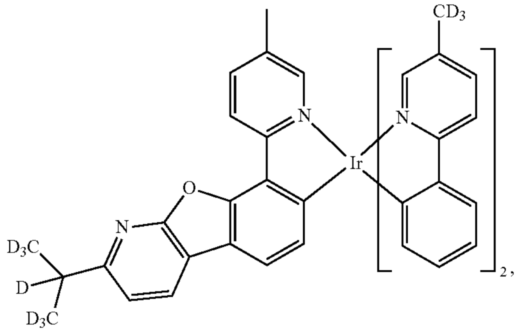
-continued
Compound II-407
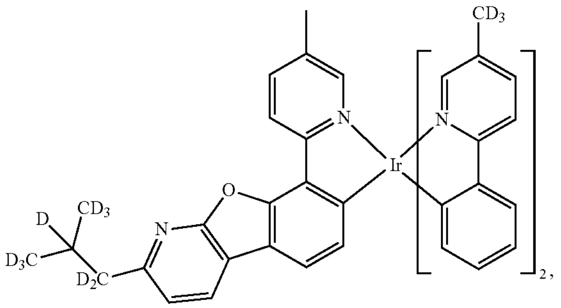
Compound II-408
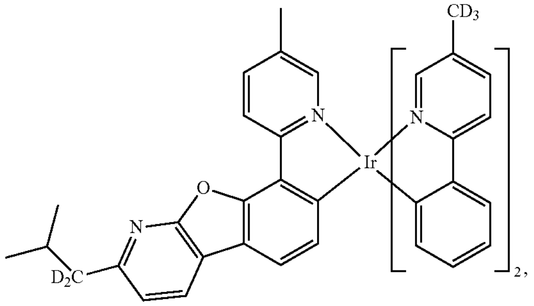
Compound II-409
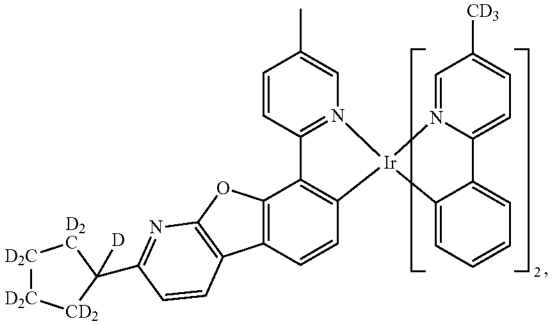
Compound II-410
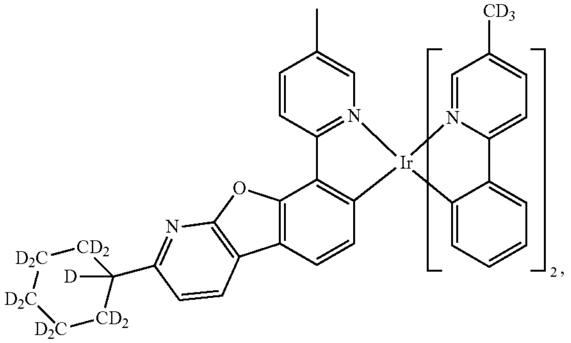

-continued
Compound II-411
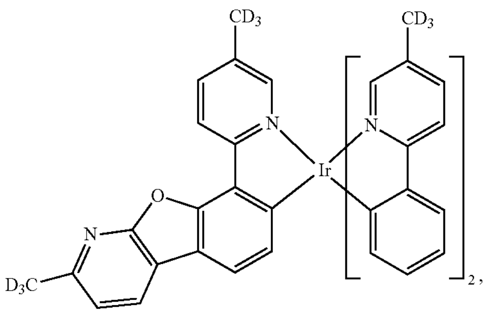
Compound II-412
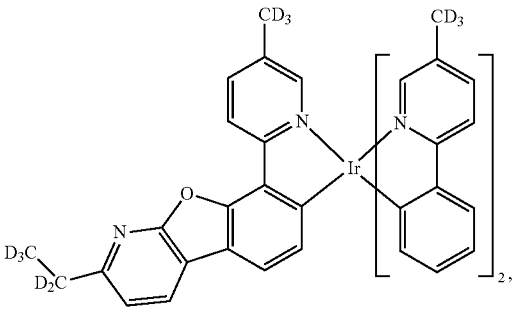
Compound II-413
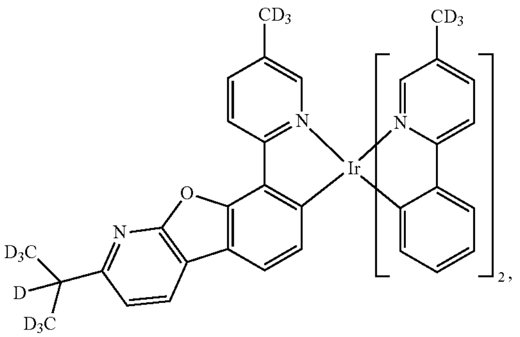
Compound II-414
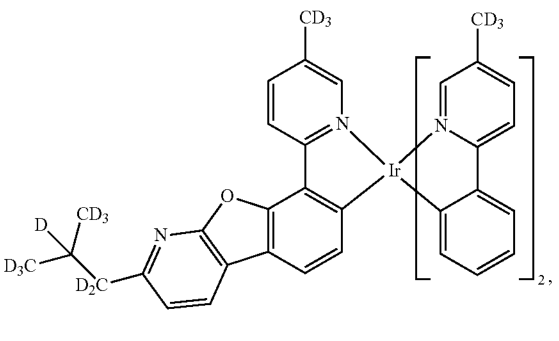
-continued
Compound II-415
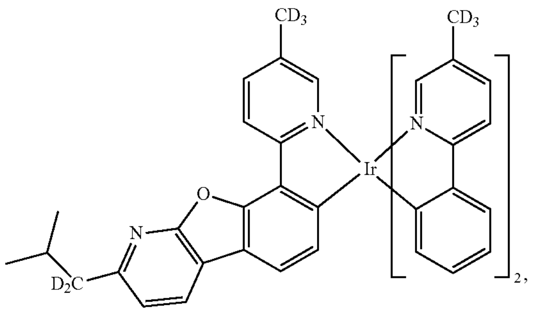
Compound II-416
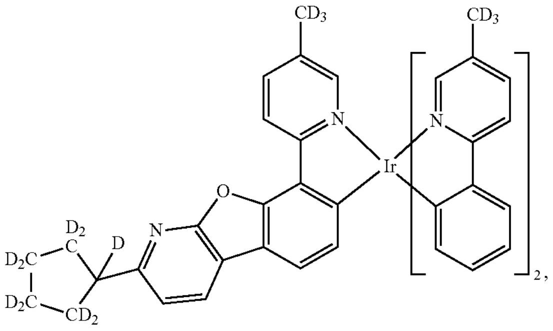
Compound II-417
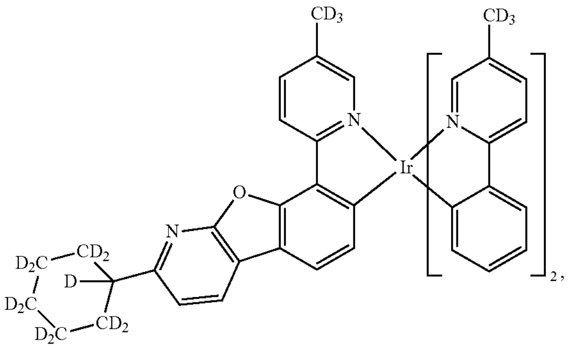
Compound II-418
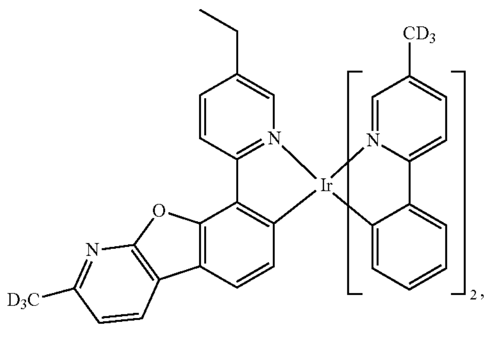

-continued
Compound II-419
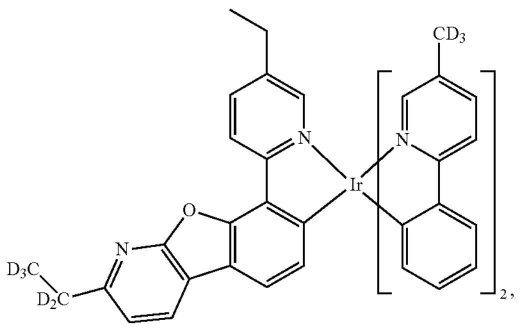
Compound II-420
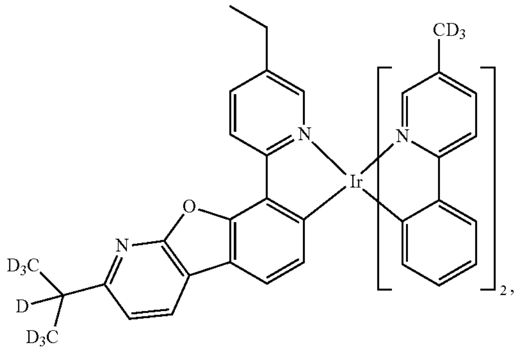
Compound II-421
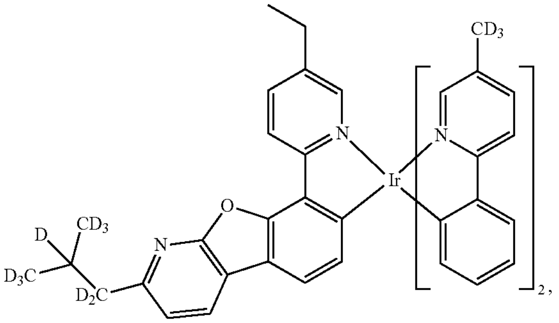
Compound II-422
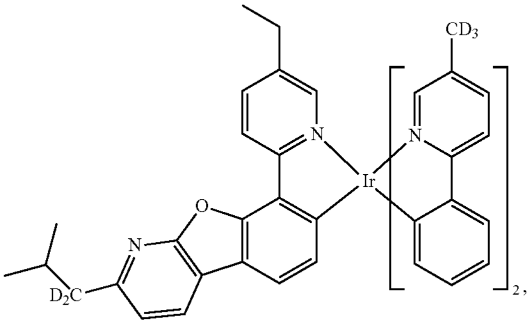
-continued
Compound II-423
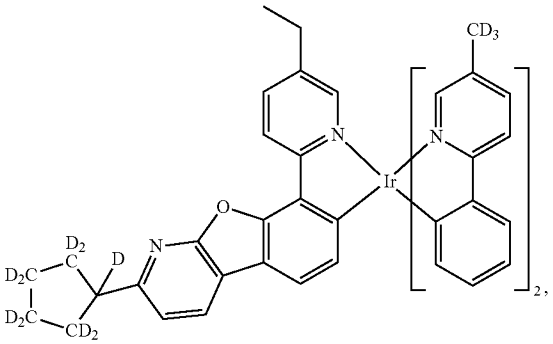
Compound II-424
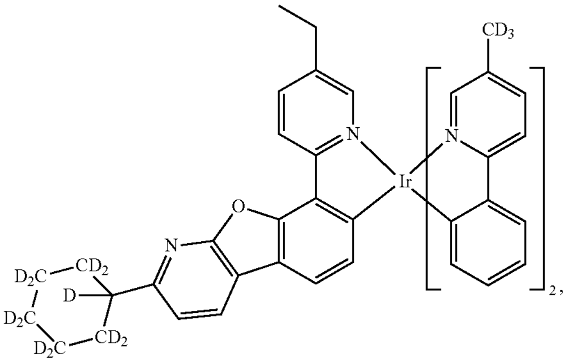
Compound II-425
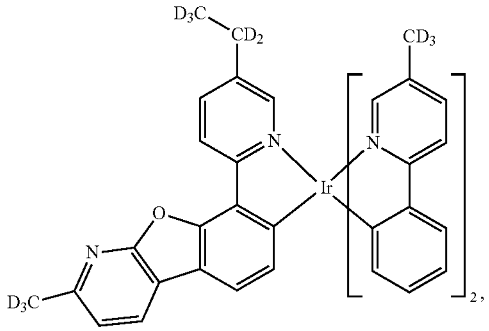
Compound II-426
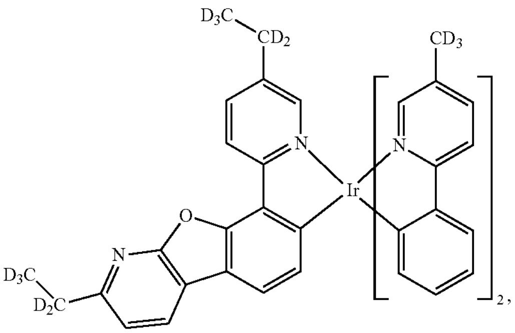

-continued
Compound II-427
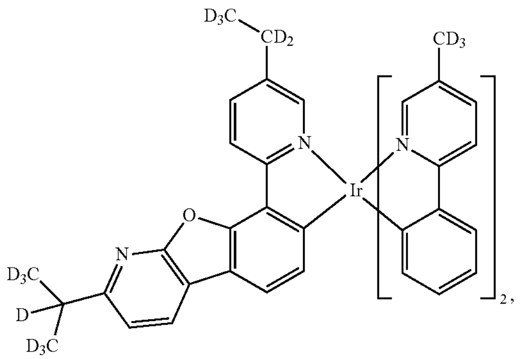
Compound II-428
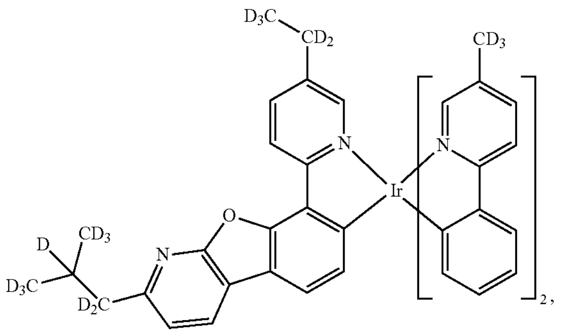
Compound II-429
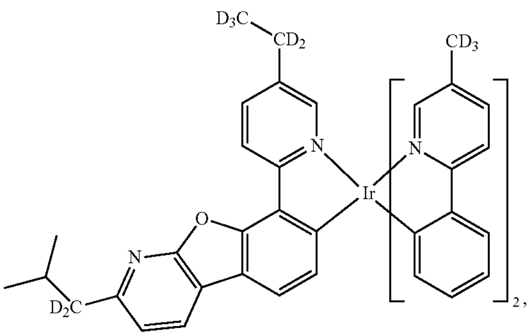
Compound II-430
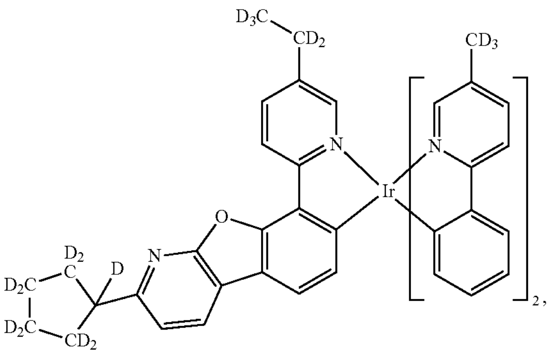
-continued
Compound II-431
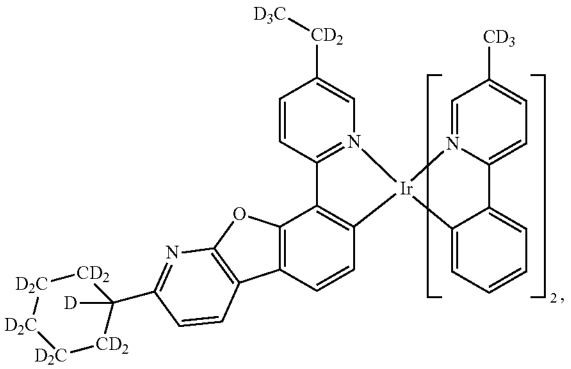
Compound II-432
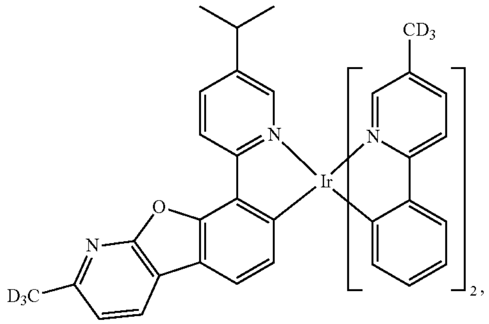
Compound II-433
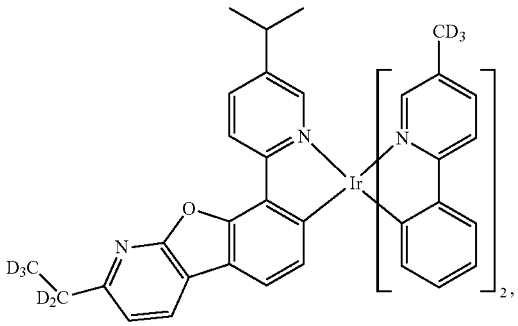
Compound II-434
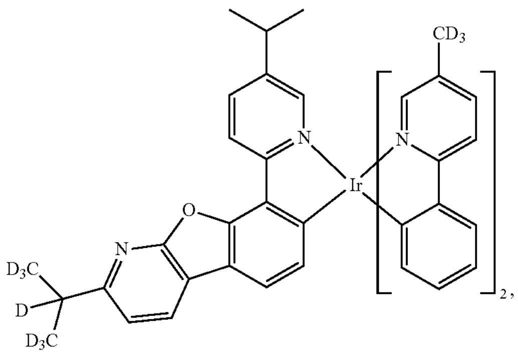

-continued
Compound II-435
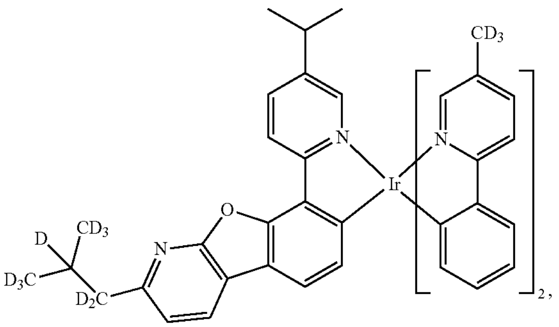
Compound II-436
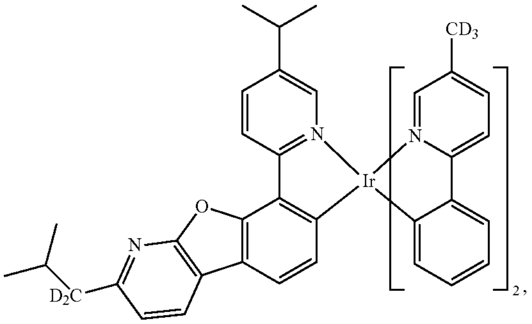
Compound II-437
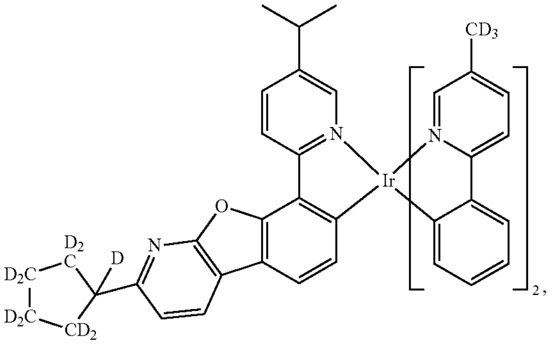
Compound II-438
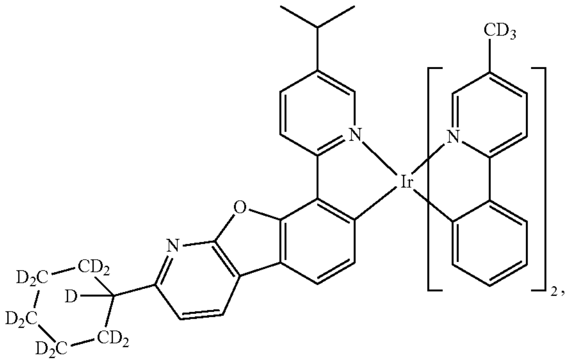
-continued
Compound II-439
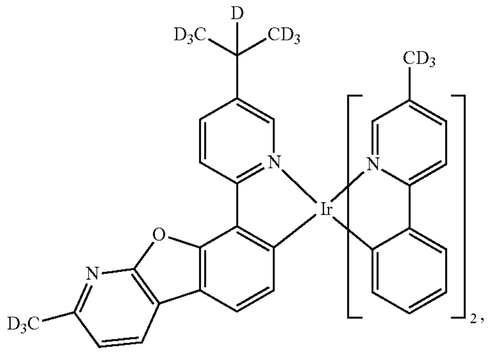
Compound II-440
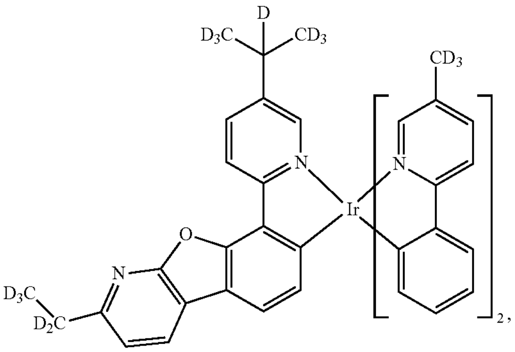
Compound II-441
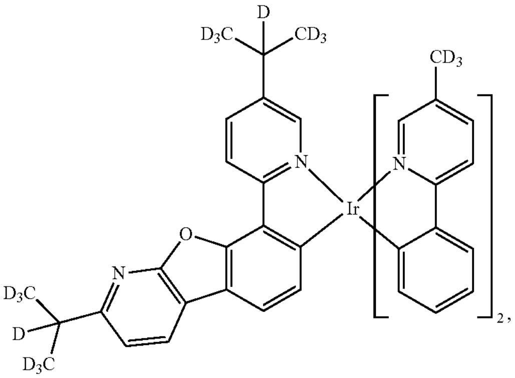
Compound II-442
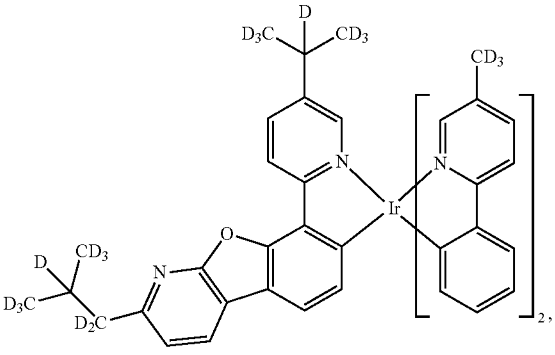

-continued
Compound II-443
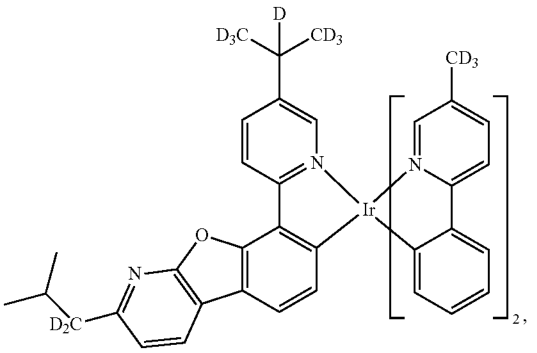
Compound II-444
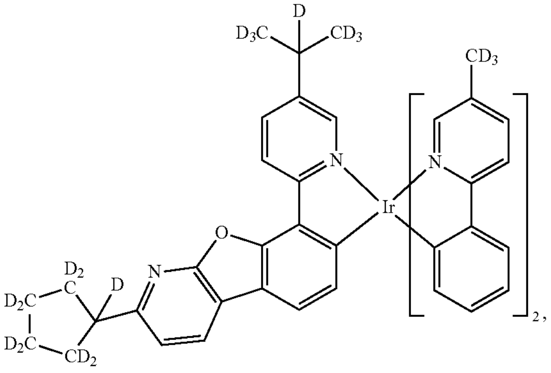
Compound II-445
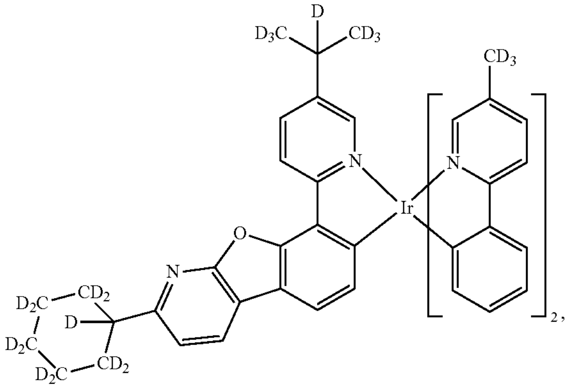
Compound II-446
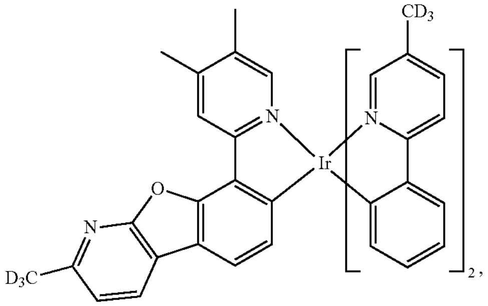
-continued
Compound II-447
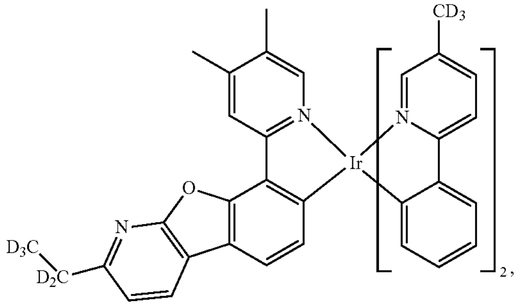
Compound II-448
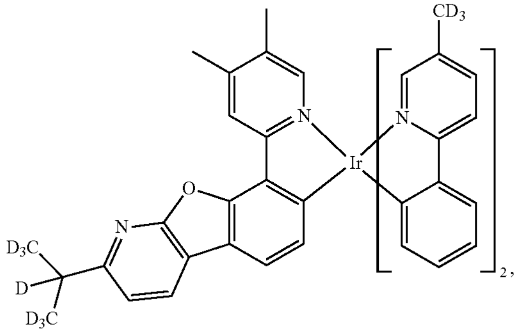
Compound II-449
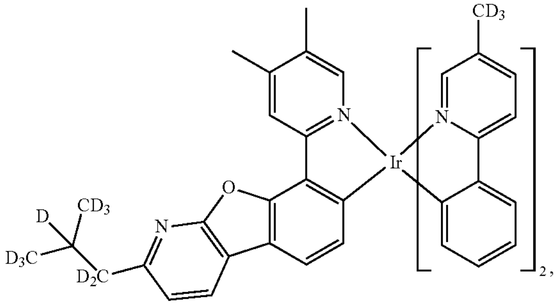
Compound II-450
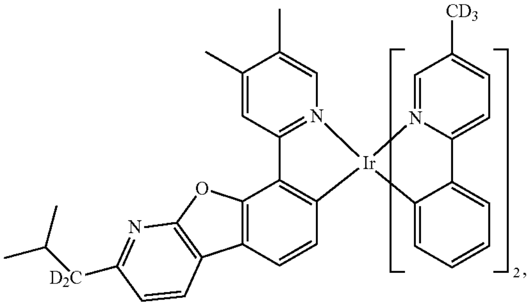

-continued
Compound II-451
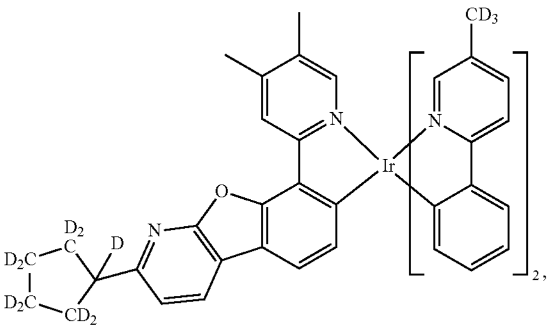
Compound II-452
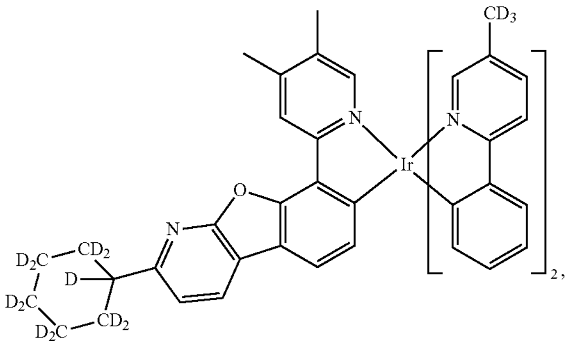
Compound II-453
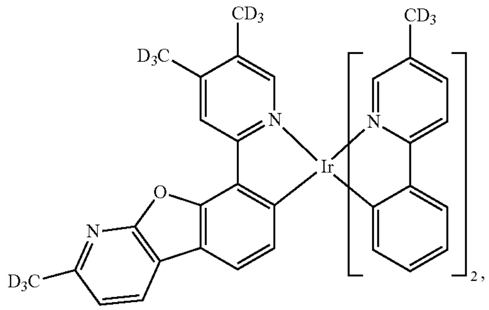
Compound II-454
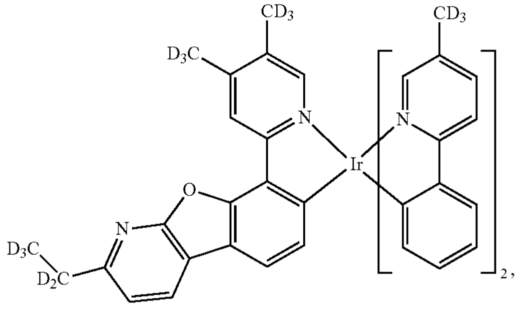
Compound II-455
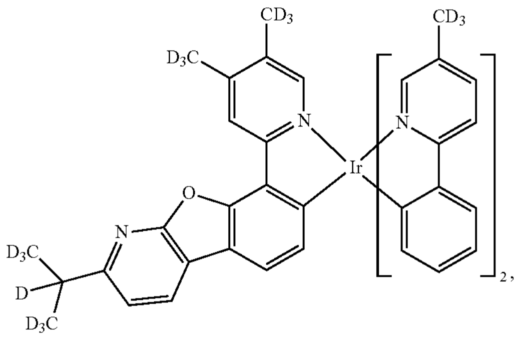
Compound II-456
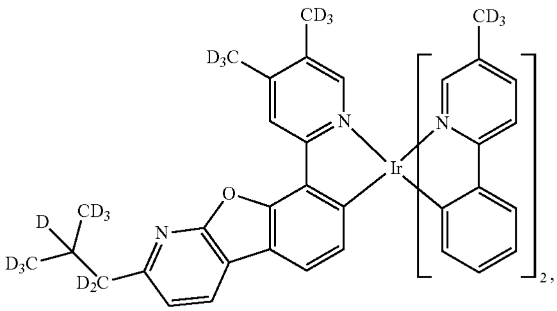
Compound II-457
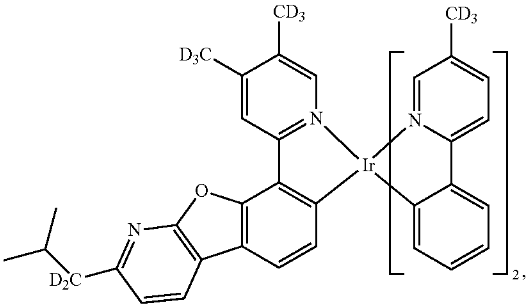
Compound II-458
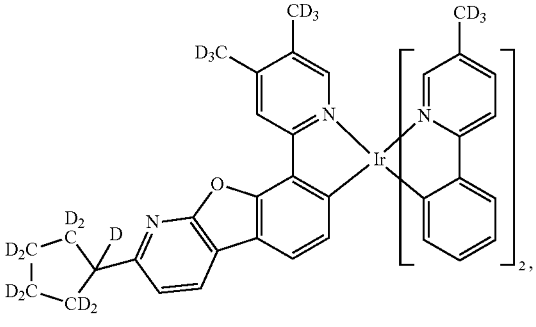
and -continued Compound II-459

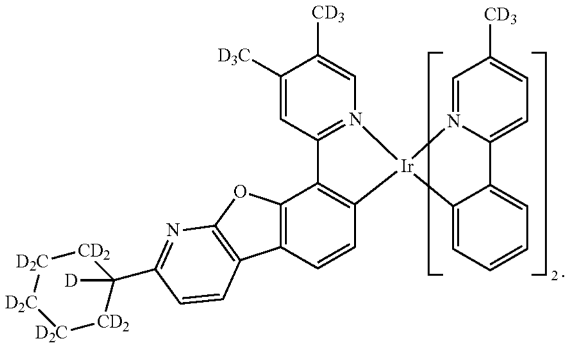

According to another aspect, the organic layer in the first device described above can comprise a compound having the formula $Ir(L_A)_n(L_B)_{3-n}$, having the structure according Formula II as defined above.

According to another aspect, a formulation comprising the compound of Formula I and/or Formula II is also within the scope of the present disclosure.

Device Examples

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound B as the hole injection layer (HIL), 300 Å of 4,4'-bis[N-(1-naphthyl)-N-phenylamino]biphenyl (α-NPD) as the hole transporting layer (HTL), 300 Å of the compound of Formula I doped in with Compound C as host, with 10-15 wt % of the iridium phosphorescent compound as the emissive layer (EML), 50 Å of Compound C as a blocking layer (BL), 450 Å of tris-8-hydroxyquinoline aluminum (Alq) as the ETL. The comparative Example with Compound A was fabricated similarly to the Device Examples except that Compound A was used as the emitter in the EML.

The device results and data comparing the compounds of Formula I to the comparative compounds are summarized in Tables 2 and 3. The device results and data comparing the compounds of Formula II to the comparative compounds are summarized in Tables 4 and 5. As used herein, NPD, Alq, and comparative Compounds A to D have the following structures:

Compound A

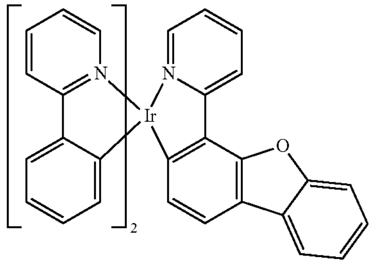

-continued

Compound B

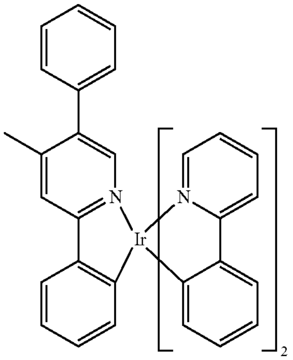

Compound C

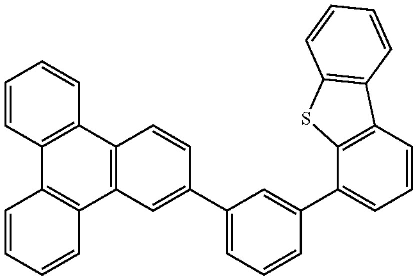

Compound D

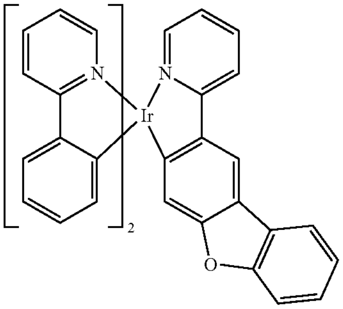

Compound 105

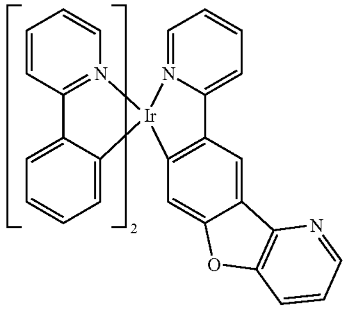

Compound E

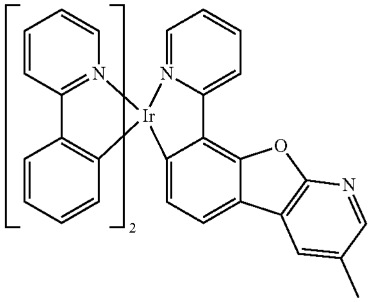

-continued

NPD

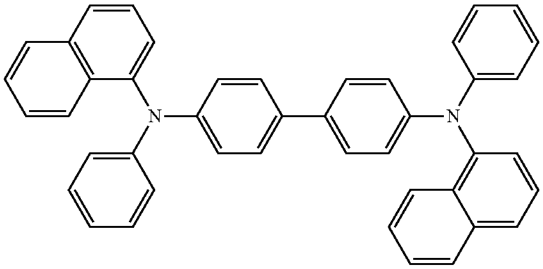

Alq

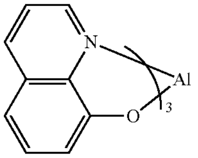

-continued

Compound F

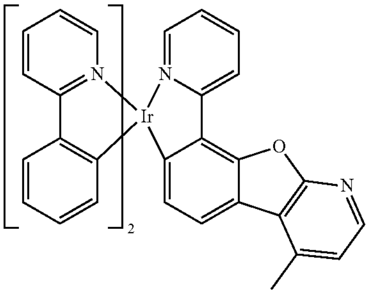

Compound 4

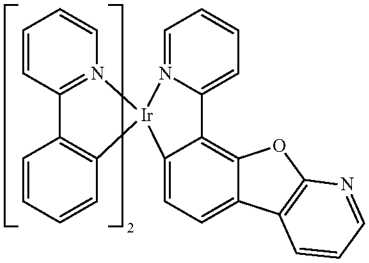

TABLE 2 device Structures of Inventive Compound and Comparative Compound

| Example | HIL (100 Å) | HTL (300 Å) | EML (300 Å, doping %) | | BL (50 Å) | ETL (450 Å) |
|---|---|---|---|---|---|---|
| Comparative Example 1 | Compound B | NPD | Compound C | Compound A 10% | Compound C | Alq |
| Inventive Example 1 | Compound B | NPD | Compound C | Compound 1 10% | Compound C | Alq |
| Comparative Example 2 | Compound B | NPD | Compound C | Compound D 10% | Compound C | Alq |
| Inventive Example 2 | Compound B | NPD | Compound C | Compound 105 10% | Compound C | Alq |
| Inventive Example 3 | Compound B | NPD | Compound C | Compound 4 10% | Compound C | Alq |

TABLE 3

VTE Device Results

| | 1931 CIE | | At 1000 nits | | | | | | At 40 mA/cm$^2$ | |
|---|---|---|---|---|---|---|---|---|---|---|
| | | | $\lambda_{max}$ | FWHM | Voltage | LE | EQE | PE | $L_0$ | $LT_{80}$ |
| Example | x | y | (nm) | (nm) | (V) | (Cd/A) | (%) | (lm/W) | (nits) | (h) |
| Comparative Example 1 | 0.350 | 0.619 | 530 | 62 | 6.2 | 64.8 | 17.2 | 33 | 18,482 | 121 |
| Inventive Example 1 | 0.340 | 0.625 | 526 | 60 | 5.9 | 61.9 | 16.5 | 32.9 | 18,466 | 184 |
| Comparative Example 2 | 0.319 | 0.618 | 520 | 74 | 6.2 | 51 | 14.4 | 25.9 | 15,504 | 65 |
| Inventive Example 2 | 0.298 | 0.621 | 514 | 72 | 6.5 | 39.9 | 11.5 | 19.9 | 12,605 | 41 |
| Inventive Example 3 | 0.343 | 0.623 | 528 | 62 | 6.8 | 47.1 | 12.5 | 21.8 | 13,471 | 370 |

Table 2 summarizes the performance of the devices. The driving voltage (V), luminous efficiency (LE), external quantum efficiency (EQE) and power efficiency (PE) are shown at 1000 nits. $LT_{80}$ was measured under a constant current density of 40 $mA/cm^2$ at the initial luminance ($L_0$).

As can be seen from the table, the EL peak of Compound 1 was at 526 nm, which is 4 nm blue shifted compared to that of Compound A. This is also consistent with the PL spectra. Both compounds showed very narrow FWHMs (full width at half maximum) at 60 and 62 nm, respectively. Both compounds showed high EQE in the same structure. The driving voltage of Compound 1 at 1000 nits is slightly lower than that of compound A, 5.9 V vs. 6.2 V. Devices incorporating compounds of Formula I, such as Compound 1, also had longer device lifetimes than devices that used Compound A (184 h vs. 121 h). Compound 4 also displayed a 2 nm blue shift relative to Compound A (528 vs. 530 nm). Additionally the $LT_{80}$ of Compound 4 is significantly longer than that of Compound A (370 vs. 121 h). Compound 105 was also blue shifted compared to Comparative Compound D (514 nm vs. 520 nm). The color of Compound 105 was also more saturated. Compounds of Formula I have unexpected and desirable properties for use as saturated green emitters in OLEDs.

Device Data for Compounds of Formula II:

The organic stack of the device examples consisted of sequentially, from the ITO surface, 100 Å of Compound B as the hole injection layer (HIL), 300 Å of 4,4'-bis[N-(1-naphthyl)-N-phenylamino]biphenyl (NPD) as the hole transporting layer (HTL), 300 Å of the invention compound doped in Compound C as host with as the emissive layer (EML), 50 Å of Compound C as blocking layer, 450 Å of tris-8-hydroxyquinoline aluminum (Alq) as the ETL. In order to show Comparative Example using a compound having Formula I, Compound 4, was fabricated similarly to the Device Examples except that the Compound 4 was used as the emitter in the EML.

The device results and data are summarized in Tables 4 and 5 below.

TABLE 4 device Structures of Inventive Compound and Comparative Compound. The thickness of each layer is provided.

| Example | HIL (100 Å) | HTL (300 Å) | EML (300 Å, doping %) | | BL (50 Å) | ETL (450 Å) |
|---|---|---|---|---|---|---|
| Comparative Example 3 | Compound B | NPD | Compound C | Compound 4 7% | Compound C | Alq |
| Inventive Example 4 | Compound B | NPD | Compound C | Compound II-1 7% | Compound C | Alq |
| Inventive Example 5 | Compound B | NPD | Compound C | Compound II-49 7% | Compound C | Alq |
| Inventive Example 6 | Compound B | NPD | Compound C | Compound II-355 7% | Compound C | Alq |
| Comparative Example 4 | Compound B | NPD | Compound C | Compound E 7% | Compound C | Alq |
| Comparative Example 5 | Compound B | NPD | Compound C | Compound F | Compound C | Alq |

TABLE 5

VTE Device Results

| | 1931 | | λ | | At 1,000 nits | | | | 40 $mA/cm^2$ | |
|---|---|---|---|---|---|---|---|---|---|---|
| | CIE | | max | FWHM | Voltage | LE | EQE | PE | Lo | $LT_{80\%}$ |
| Example | x | y | [nm] | [nm] | relative | relative | relative | relative | [nits] | relative |
| Comparative Example 3 | 0.342 | 0.623 | 526 | 60 | 1 | 1 | 1 | 1 | 16,133 | 1 |
| Inventive Example 4 | 0.362 | 0.611 | 530 | 66 | 0.98 | 1.14 | 1.13 | 1.15 | 18,749 | 1.2 |
| Inventive Example 5 | 0.352 | 0.616 | 528 | 62 | 0.97 | 1.03 | 1.03 | 1.05 | 16,537 | 1.64 |
| Inventive Example 6 | 0.365 | 0.609 | 530 | 64 | 0.95 | 1.28 | 1.28 | 1.34 | 17,522 | 1.53 |
| Comparative Example 4 | 0.351 | 0.62 | 528 | 62 | 0.97 | 0.86 | 0.85 | 0.88 | 15,467 | 0.6 |
| Comparative Example 5 | 0.344 | 0.621 | 526 | 64 | 0.98 | 0.79 | 0.78 | 0.79 | 13,896 | 1.16 |

Table 5 summarizes the performance of the devices. The driving voltage (V), luminous efficiency (LE), external quantum efficiency (EQE) and power efficiency (PE) are shown at 1000 nits, while the lifetime ($LT_{80}$%) was defined as the time required for the device to decay to 80% of its initial luminance ($L_0$) under a constant current density of 40 $mA/cm^2$. All measured values are listed as relative to the comparative example which is denoted as 1. As shown in Table 5 all three inventive compounds required slightly less driving voltage (0.98, 0.97 and 0.95) relative to the comparative compound (1.0). The inventive compounds demonstrated superior efficiency in all three categories also: the relative LE values were 1.14, 1.03 and 1.28 for the Inventive Examples 4, 5 and 6, respectively, compared to 1.0 for Comparative Example 3 and 0.86 and 0.79 for Comparative Examples 4 and 5, respectively. The relative EQE of values were 1.13, 1.03 and 1.28 for Inventive Examples 4, 5 and 6, respectively, compared to 1.0 for Comparative Example 3 and 0.85 and 0.78 for Comparative Examples 4 and 5, respectively. The relative PE values were 1.15, 1.05, 1.34 for the Inventive Examples 4, 5 and 6, respectively, compared to 1.0 for the Comparative Example 3 and 0.88 and 0.79 for Comparative Examples 4 and 5, respectively. Finally the superior device stability of the inventive compounds were shown by the relative $LT_{80}$ values of 1.20, 1.64, 1.53 for the Inventive Examples 4, 5, and 6, respectively compared to 1.0 for the Comparative Example 3 and 0.6 for Comparative Example 4.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

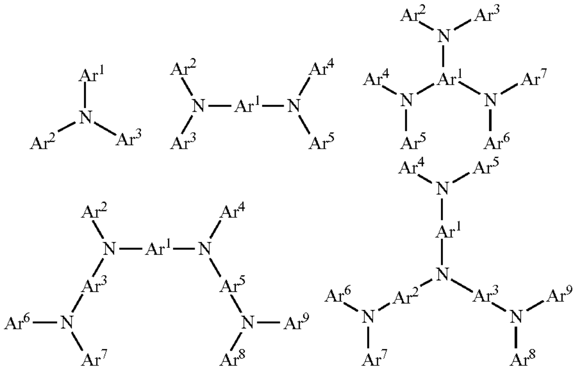

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

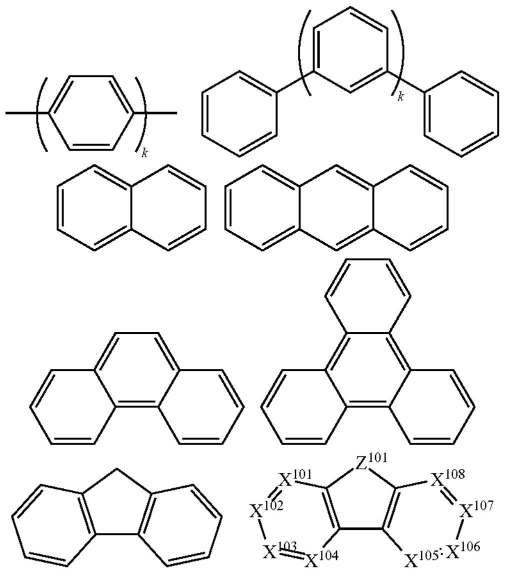

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

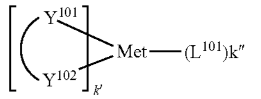

Met is a metal; ($Y^{101}$-$Y^{102}$) is a bidentate ligand, $Y^{101}$ and $Y^{102}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative.

In another aspect, ($Y^{101}$-$Y^{102}$) is a carbene ligand.

In another aspect, Met is selected from Ir, Pt, Os, and Zn.

In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

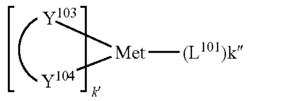

Met is a metal; ($Y^{103}$-$Y^{104}$) is a bidentate ligand, $Y^{103}$ and $Y^{104}$ are independently selected from C, N, O, P, and S; $L^{101}$ is another ligand; k' is an integer value from 1 to the maximum number of ligands that may be attached to the metal; and k'+k" is the maximum number of ligands that may be attached to the metal.

In one aspect, the metal complexes are:

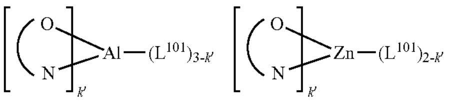

(O—N) is a bidentate ligand, having metal coordinated to atoms O and N.

In another aspect, Met is selected from Ir and Pt.

In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

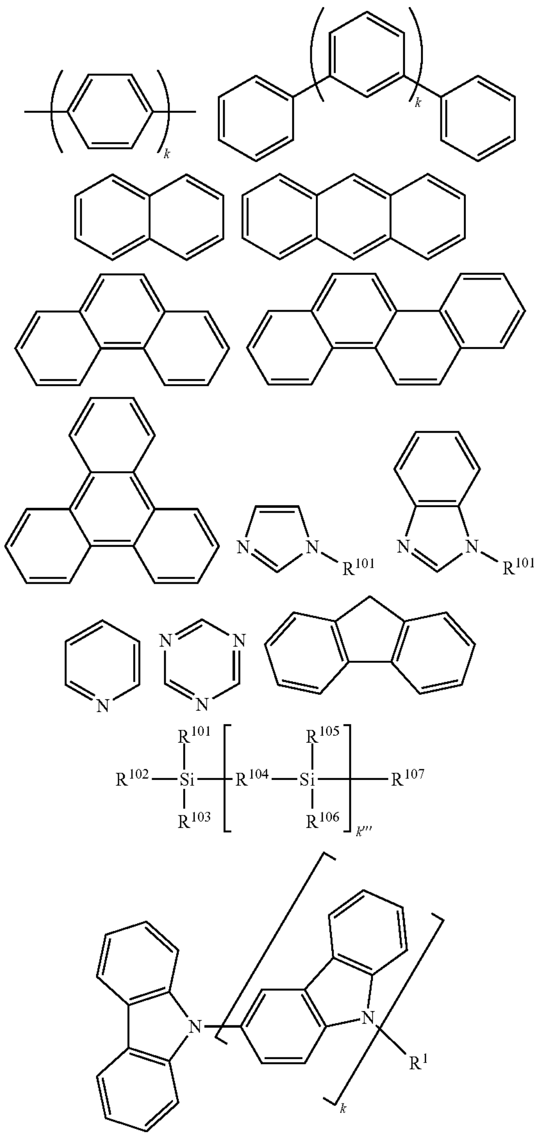

-continued

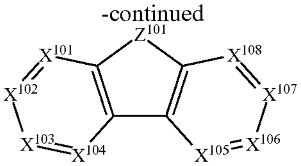

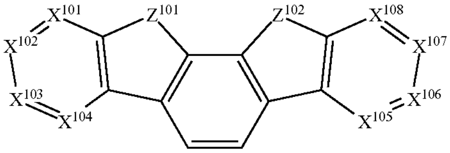

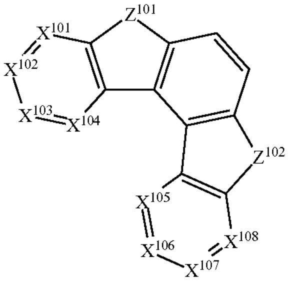

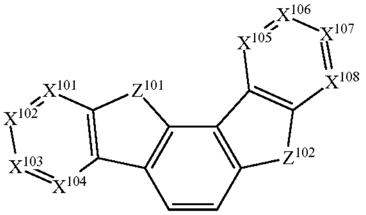

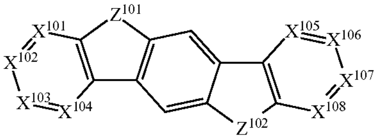

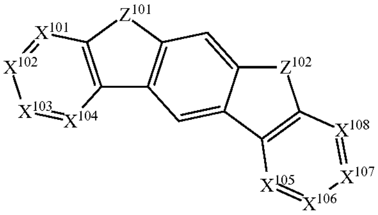

$R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.

$X^{101}$ to $X^{108}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

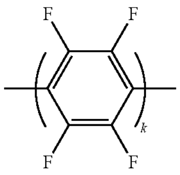

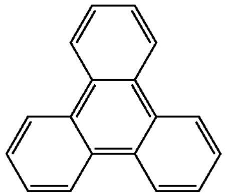

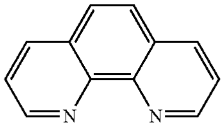

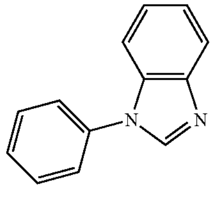

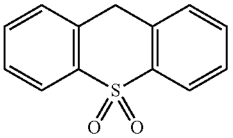

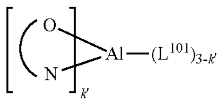

k is an integer from 1 to 20; $L^{101}$ is another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

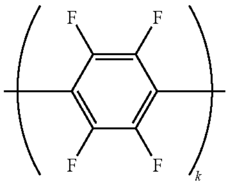

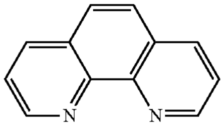

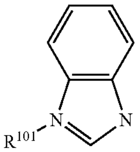

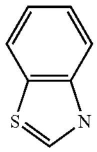

-continued

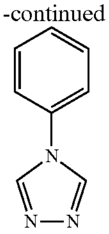

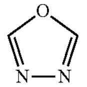

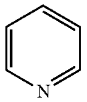

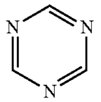

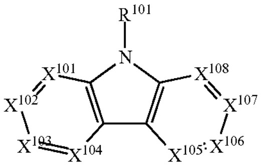

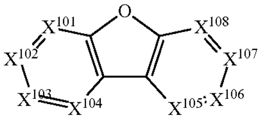

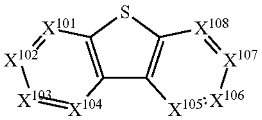

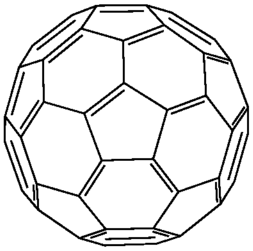

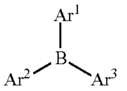

$R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 1 to 20.

$X^{101}$ to $X^{108}$ is selected from C (including CH) or N.

In another aspect, the metal complexes used in ETL contains, but not limit to the following general formula:

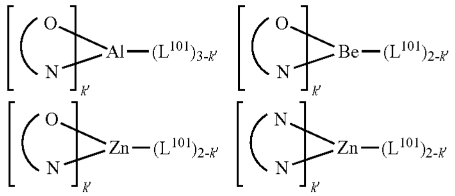

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4
| MATERIAL | EXAMPLES OF MATERIAL | PUBLICATIONS |
| --- | --- | --- |
| | Hole injection materials | |
| Phthalocyanine and porphryin compounds | 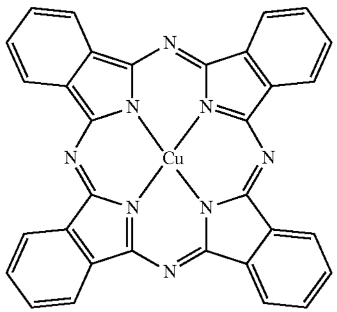 | Appl. Phys. Lett. 69, 2160 (1996) |
| Starburst triarylamines | 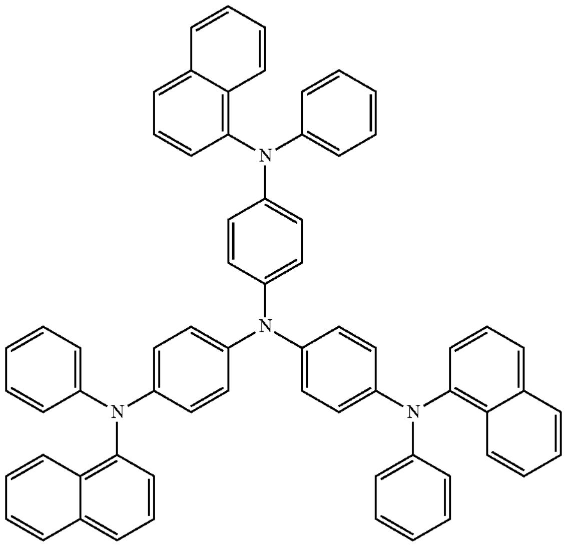 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |

TABLE 4-continued
| MATERIAL | EXAMPLES OF MATERIAL | PUBLICATIONS |
|---|---|---|
| Conducting polymers (e.g., PEDOT:PSS, polyaniline, polypthiophene) | 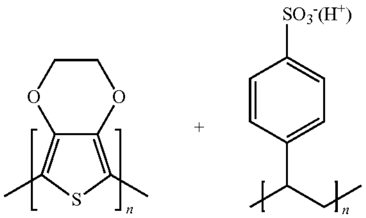 | Synth. Met. 87, 171 (1997) WO2007002683 |
| Phosphonic acid and sliane SAMs | 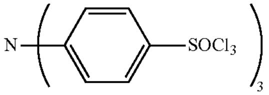 | US20030162053 |
| Triarylamine or polythiophene polymers with conductivity dopants | 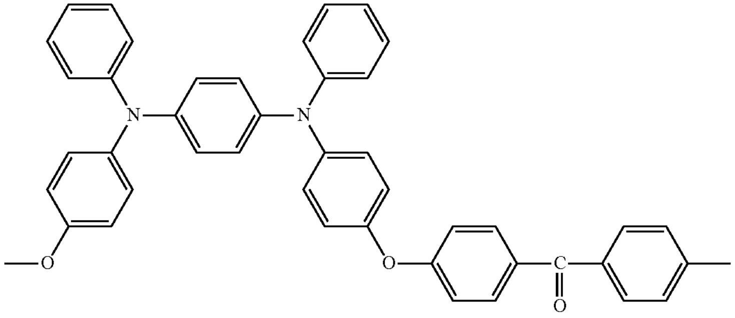 and | EP1725079A1 |

TABLE 4-continued
| MATERIAL | EXAMPLES OF MATERIAL | PUBLICATIONS |
| --- | --- | --- |
| | 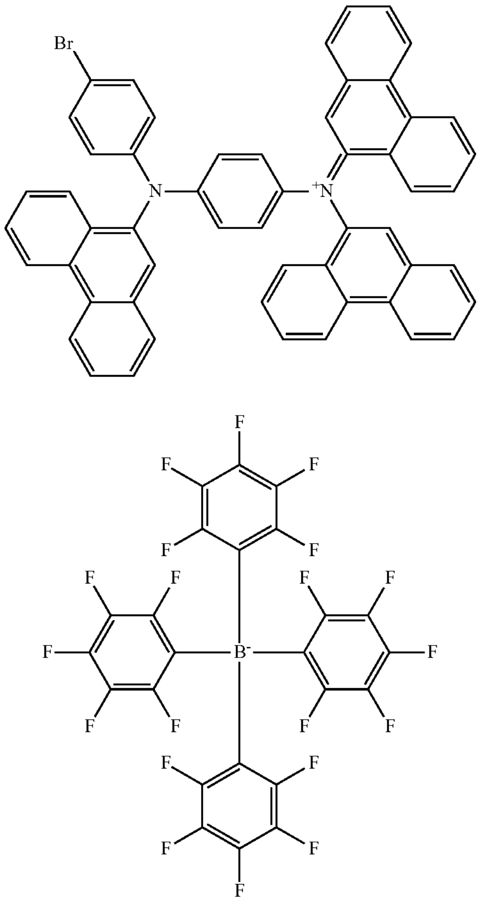 | |

TABLE 4-continued

| MATERIAL | EXAMPLES OF MATERIAL | PUBLICATIONS |
|---|---|---|
| Organic compounds with conductive inorganic compounds, such as molybdenum and tungsten oxides | 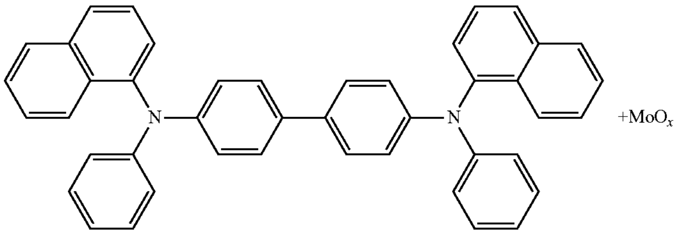 [SMILES: c1ccc(N(c2ccc(-c3ccc(N(c4ccccc4)c4cccc5ccccc45)cc3)cc2)c2cccc3ccccc23)cc1] | US20050123751<br>SID Symposium Digest, 37, 923 (2006)<br>WO2009018009 |
| n-type semiconducting organic complexes<br>Metal organometallic complexes<br>Cross-linkable compounds | | US20020158242<br>US20060240279<br>US20080220265 |
| Polythiophene based polymers and copolymers | 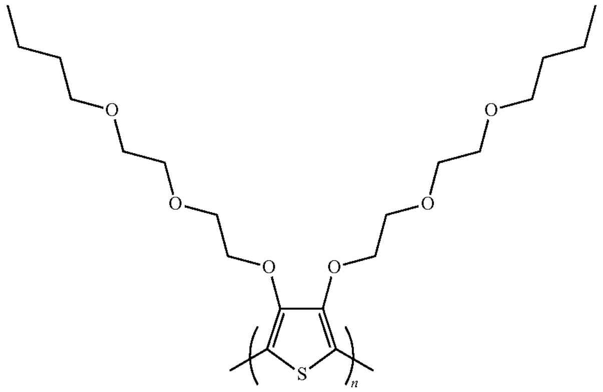 | WO 2011075644<br>EP2350216 |
| | Hole transporting materials | |
| Triarylamines (e.g., TPD, α-NPD) | 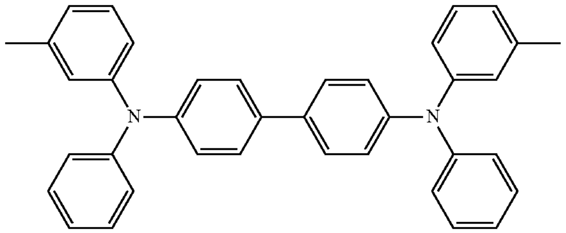 | Appl. Phys. Lett. 51, 913 (1987) |

TABLE 4-continued
| MATERIAL | EXAMPLES OF MATERIAL | PUBLICATIONS |
|---|---|---|
| | 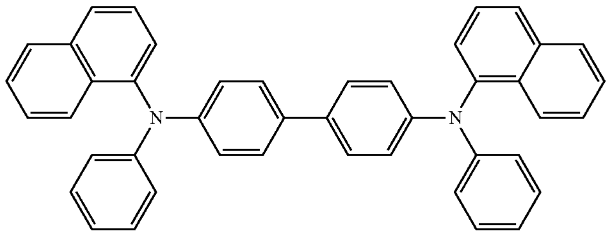 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 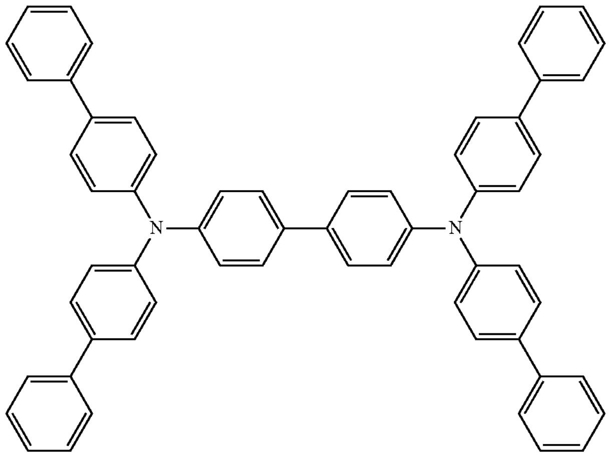 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 4-continued
| MATERIAL | EXAMPLES OF MATERIAL | PUBLICATIONS |
|---|---|---|
| | 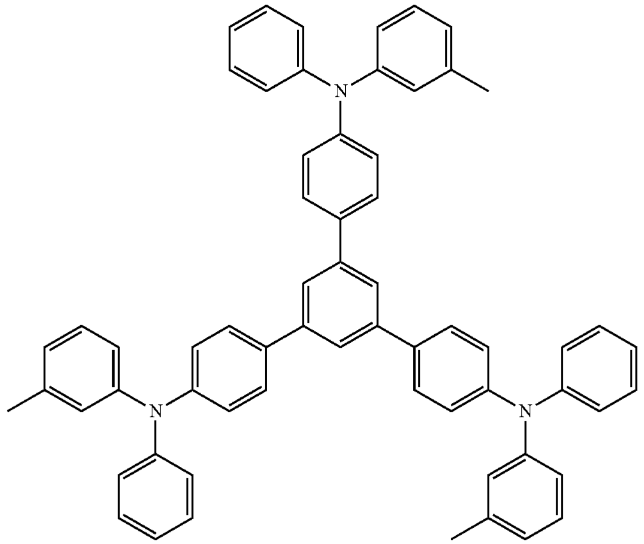 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 4-continued
| MATERIAL | EXAMPLES OF MATERIAL | PUBLICATIONS |
|---|---|---|
| | 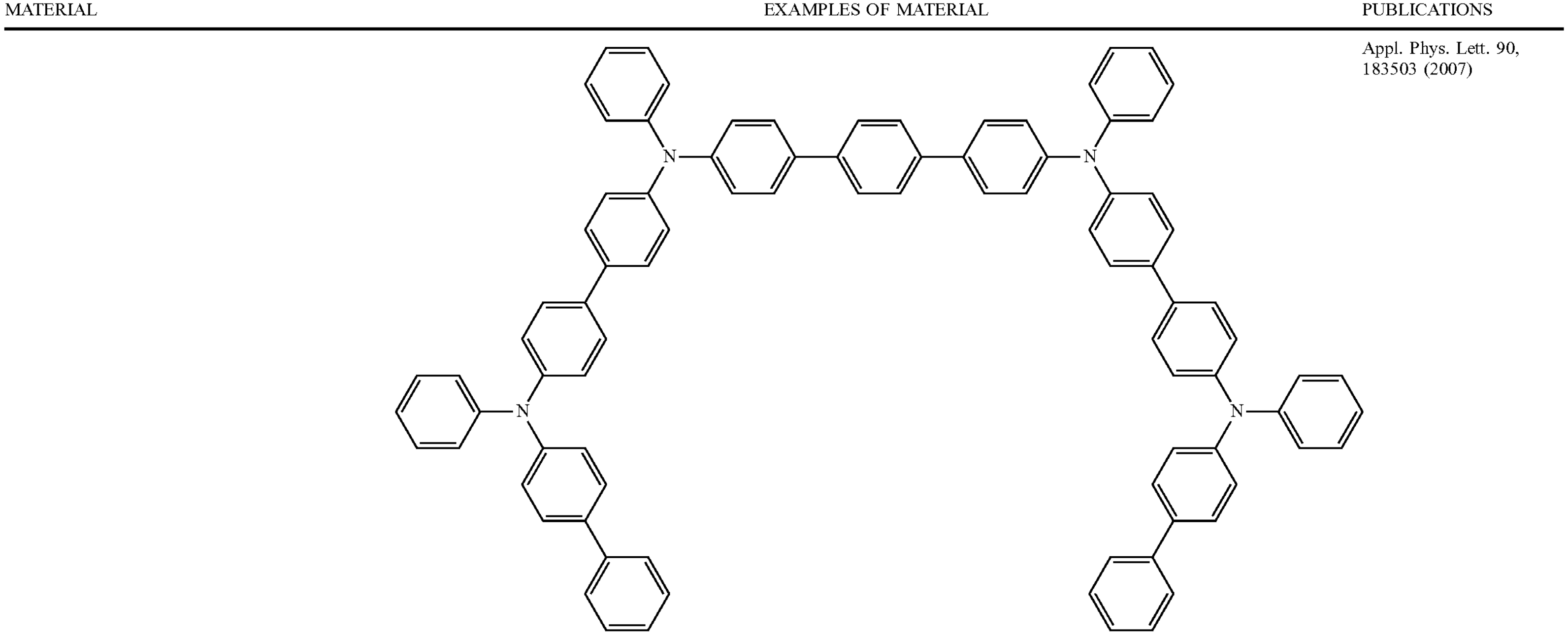 | Appl. Phys. Lett. 90, 183503 (2007) |

TABLE 4-continued
| MATERIAL | EXAMPLES OF MATERIAL | PUBLICATIONS |
|---|---|---|
| | 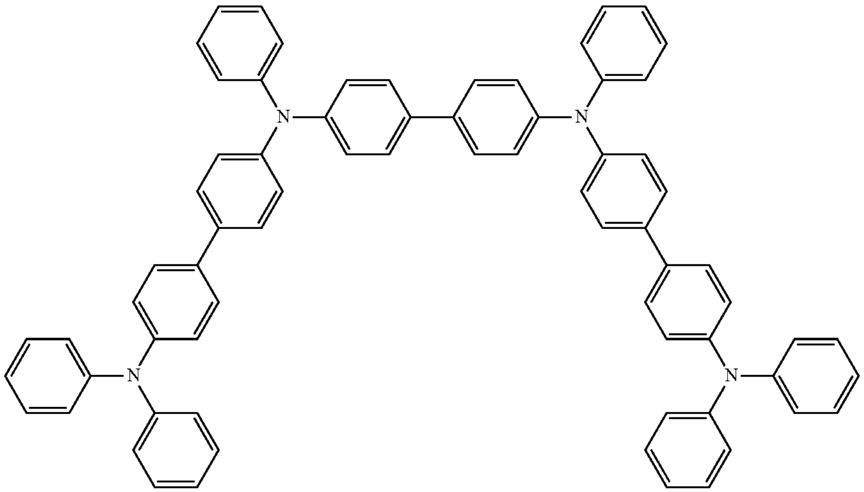 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 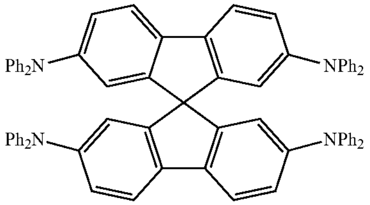 | Synth. Met. 91, 209 (1997) |

TABLE 4-continued
| MATERIAL | EXAMPLES OF MATERIAL | PUBLICATIONS |
| --- | --- | --- |
| Arylamine carbazole compounds | 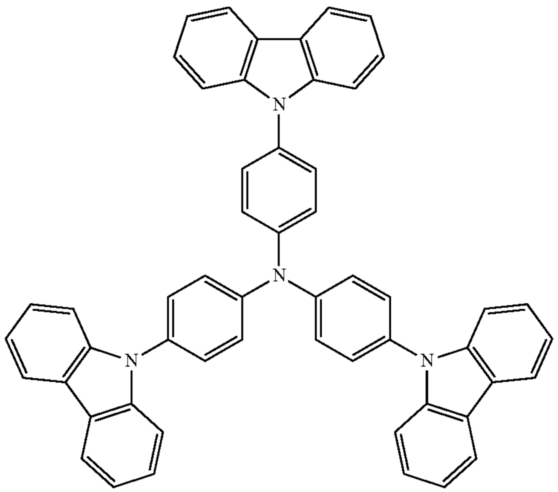 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/(di) benzofuran | 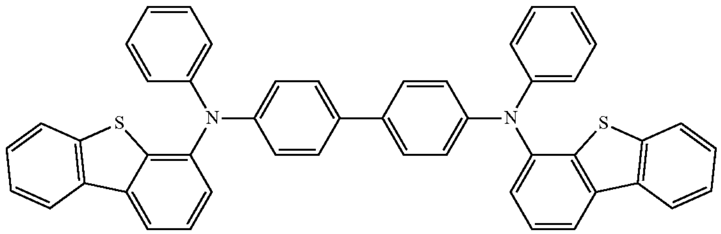 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |

TABLE 4-continued
| MATERIAL | EXAMPLES OF MATERIAL | PUBLICATIONS |
|---|---|---|
| Indolocarbazoles | 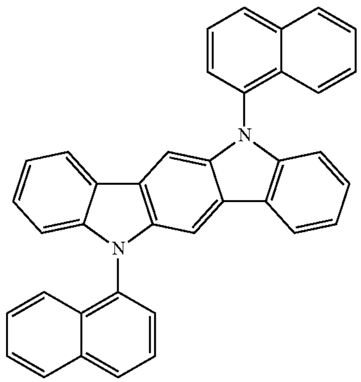 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 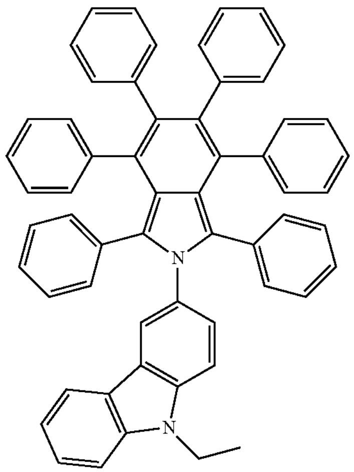 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |

TABLE 4-continued
| MATERIAL | EXAMPLES OF MATERIAL | PUBLICATIONS |
| --- | --- | --- |
| Metal carbene complexes | 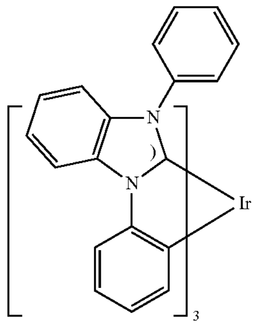 | US20080018221 |
| | Phosphorescent OLED host materials<br>Red hosts | |
| Arylcarbazoles | 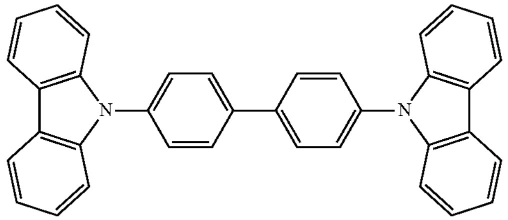 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| Metal 8-hydroxyquinolates (e.g., $Alq_3$, BAlq) | 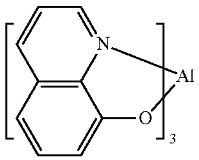 | Nature 395, 151 (1998) |
| | 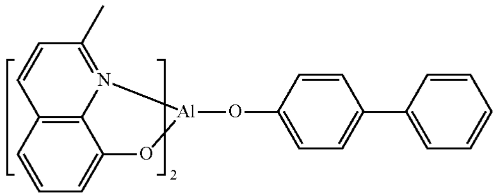 | US20060202194 |

TABLE 4-continued
| MATERIAL | EXAMPLES OF MATERIAL | PUBLICATIONS |
| --- | --- | --- |
| | 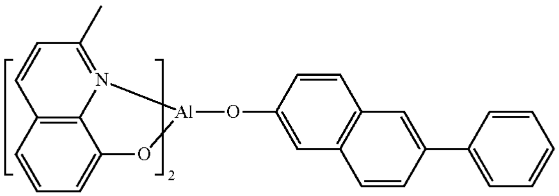 | WO2005014551 |
| | 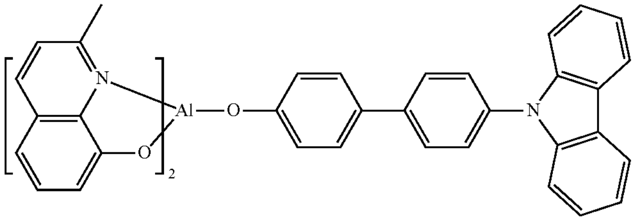 | WO2006072002 |
| Metal phenoxybenzothiazole compounds | 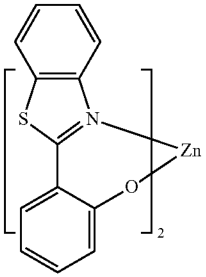 | Appl. Phys. Lett. 90, 123509 (2007) |
| Conjugated oligomers and polymers (e.g., polyfluorene) | 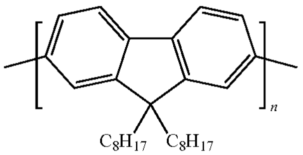 | Org. Electron. 1, 15 (2000) |

TABLE 4-continued
| MATERIAL | EXAMPLES OF MATERIAL | PUBLICATIONS |
| --- | --- | --- |
| Aromatic fused rings | 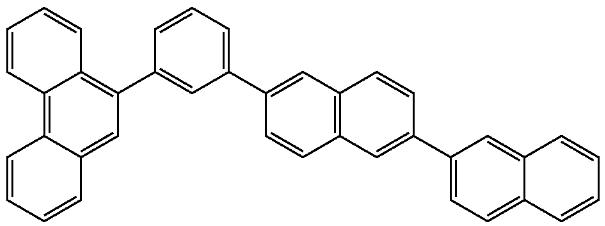 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 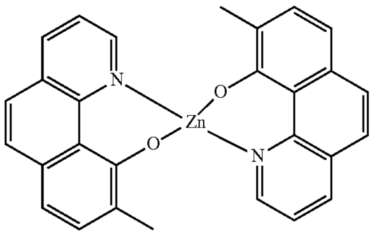 | WO201056066 |
| Chrysene based compounds | 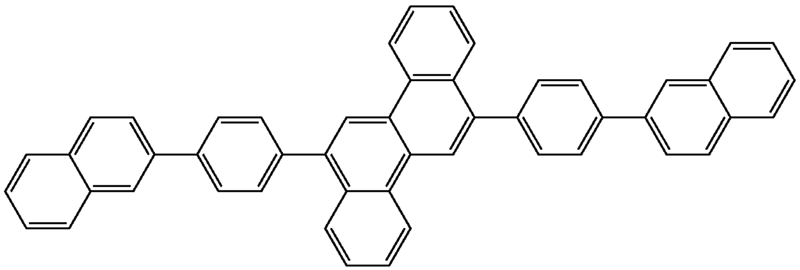 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| | Green hosts | |
| Arylcarbazoles | 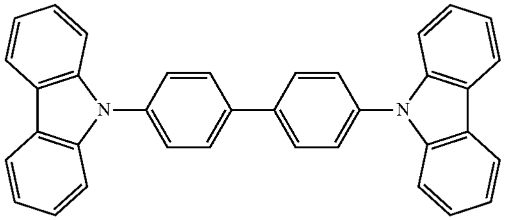 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE 4-continued
| MATERIAL | EXAMPLES OF MATERIAL | PUBLICATIONS |
|---|---|---|
| | 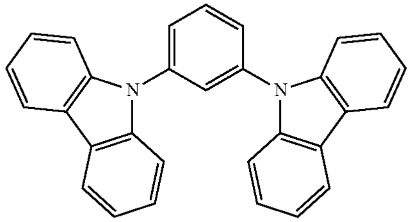 [SMILES: c1cc(-n2c3ccccc3c3ccccc32)cc(-n2c3ccccc3c3ccccc32)c1] | US20030175553 |
| | 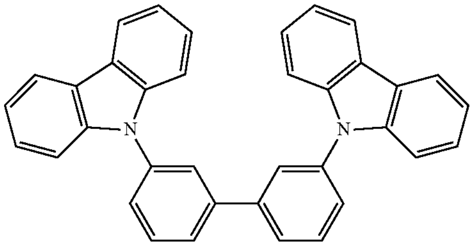 [SMILES: c1cc(-c2cccc(-n3c4ccccc4c4ccccc43)c2)cc(-n2c3ccccc3c3ccccc32)c1] | WO2001039234 |
| Aryltriphenylene compounds | 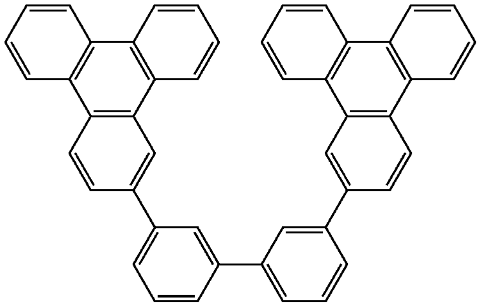 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE 4-continued
| MATERIAL | EXAMPLES OF MATERIAL | PUBLICATIONS |
|---|---|---|
| | 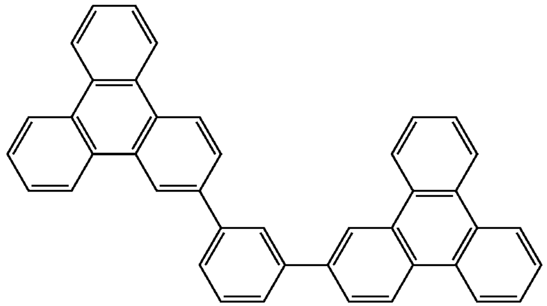 [SMILES: c1cc(-c2ccc3c4ccccc4c4ccccc4c3c2)cc(-c2ccc3c4ccccc4c4ccccc4c3c2)c1] | US20060280965 |
| | 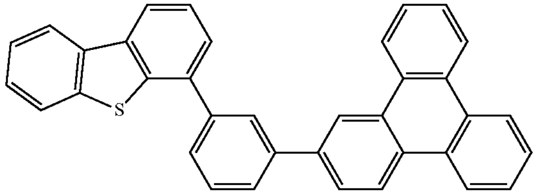 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 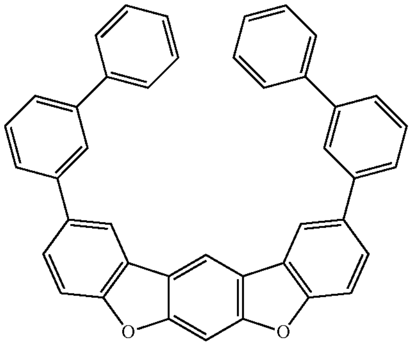 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |

TABLE 4-continued
| MATERIAL | EXAMPLES OF MATERIAL | PUBLICATIONS |
| --- | --- | --- |
| Donor acceptor type molecules | 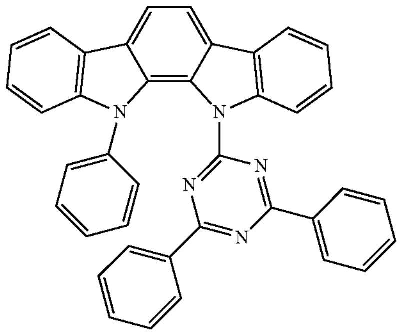 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 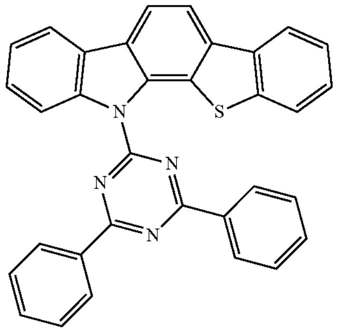 [SMILES: c1ccc(-c2nc(-c3ccccc3)nc(-n3c4ccccc4c4ccc5c6ccccc6sc5c43)n2)cc1] | WO2010107244 |

TABLE 4-continued
| MATERIAL | EXAMPLES OF MATERIAL | PUBLICATIONS |
| --- | --- | --- |
| Aza-carbazole/DBT/DBF | 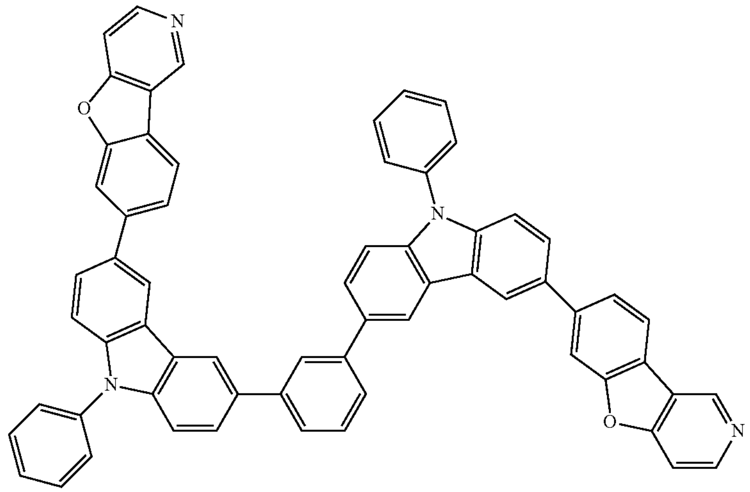 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 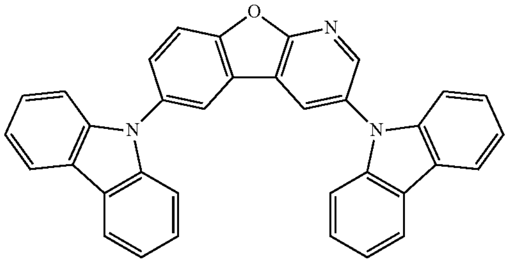 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 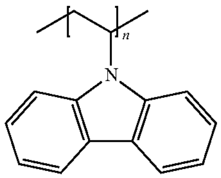 | Appl. Phys. Lett. 77, 2280 (2000) |

TABLE 4-continued
| MATERIAL | EXAMPLES OF MATERIAL | PUBLICATIONS |
| --- | --- | --- |
| Spirofluorene compounds | 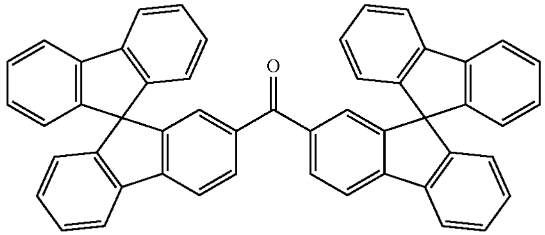 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxybenzooxazole compounds | 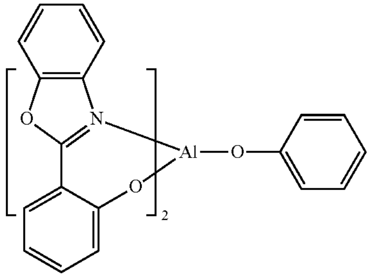 | WO2005089025 |
| | 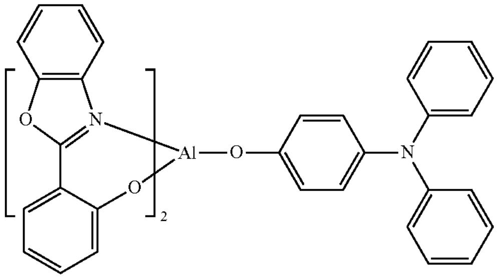 | WO2006132173 |

TABLE 4-continued
| MATERIAL | EXAMPLES OF MATERIAL | PUBLICATIONS |
| --- | --- | --- |
| | 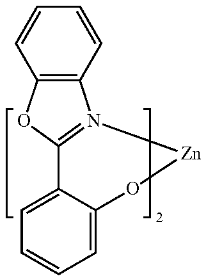 | JP200516610 |
| Spirofluorene-carbazole compounds | 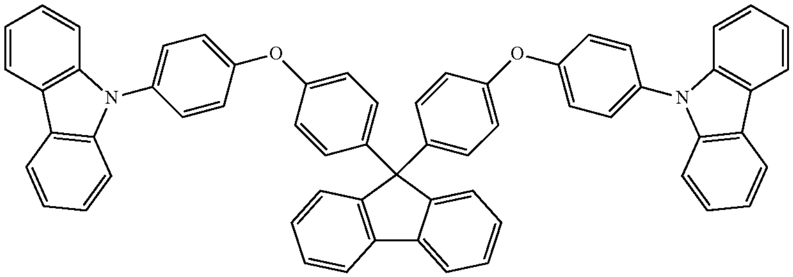 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 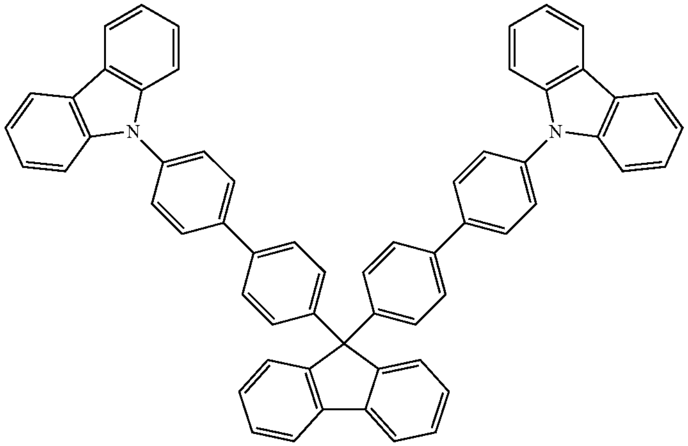 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 4-continued
| MATERIAL | EXAMPLES OF MATERIAL | PUBLICATIONS |
|---|---|---|
| Indolocabazoles | 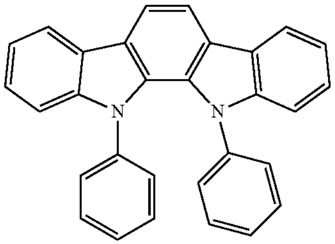 [SMILES: c1ccc(-n2c3ccccc3c3ccc4c5ccccc5n(-c5ccccc5)c4c32)cc1] | WO2007063796 |
| | 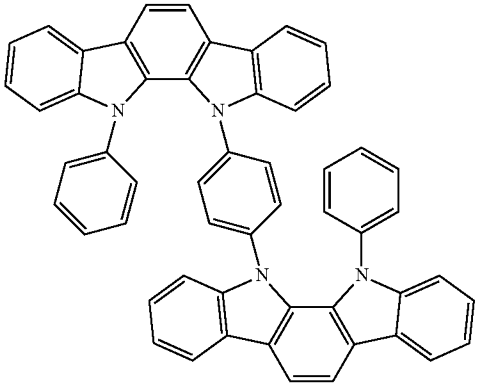 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 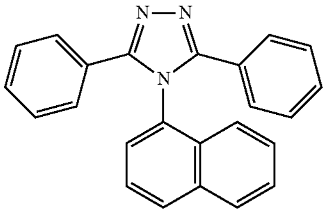 [SMILES: c1ccc(-c2nnc(-c3ccccc3)n2-c2cccc3ccccc23)cc1] | J. Appl. Phys. 90, 5048 (2001) |

TABLE 4-continued
| MATERIAL | EXAMPLES OF MATERIAL | PUBLICATIONS |
|---|---|---|
| | 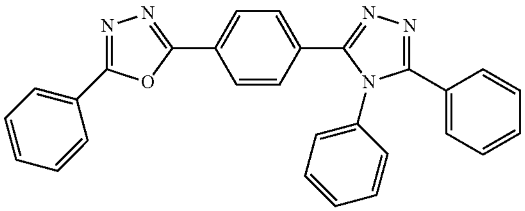 [SMILES: c1ccc(-c2nnc(-c3ccc(-c4nnc(-c5ccccc5)n4-c4ccccc4)cc3)o2)cc1] | WO2004107822 |
| Tetraphenylene complexes | 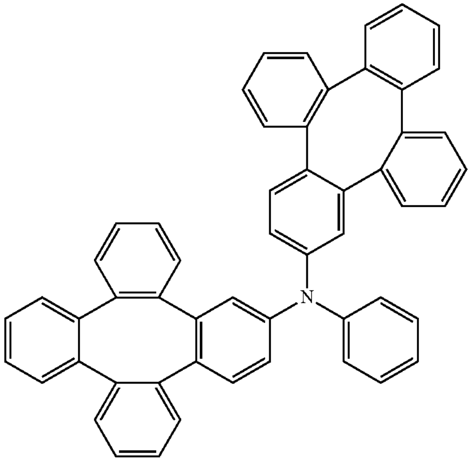 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 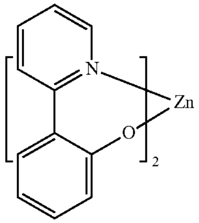 | WO2005030900 |

TABLE 4-continued
| MATERIAL | EXAMPLES OF MATERIAL | PUBLICATIONS |
|---|---|---|
| Metal coordination complexes (e.g., Zn, Al with N^N ligands) | 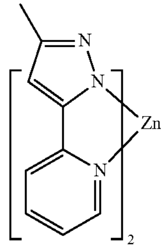 | US20040137268, US20040137267 |
| | Blue hosts | |
| Arylcarbazoles | 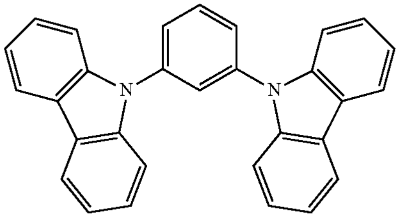 [SMILES: c1cc(-n2c3ccccc3c3ccccc32)cc(-n2c3ccccc3c3ccccc32)c1] | Appl. Phys. Lett, 82, 2422 (2003) |
| | 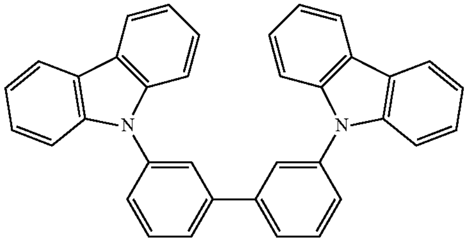 [SMILES: c1cc(-c2cccc(-n3c4ccccc4c4ccccc43)c2)cc(-n2c3ccccc3c3ccccc32)c1] | US20070190359 |
| Dibenzothiophene/Dibenzofuran-carbazole compounds | 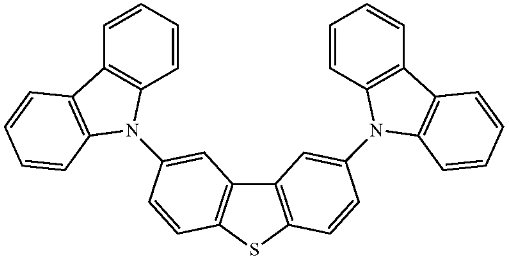 [SMILES: c1ccc2c(c1)c1ccccc1n2-c1ccc2sc3ccc(-n4c5ccccc5c5ccccc54)cc3c2c1] | WO2006114966, US20090167162 |

TABLE 4-continued
| MATERIAL | EXAMPLES OF MATERIAL | PUBLICATIONS |
| --- | --- | --- |
| | 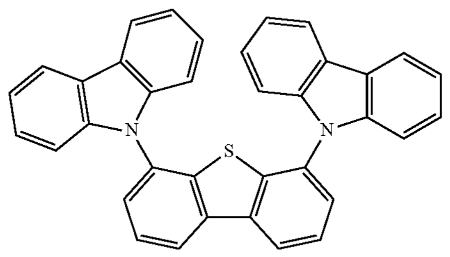 [SMILES: c1cc(-n2c3ccccc3c3ccccc32)c2sc3c(-n4c5ccccc5c5ccccc54)cccc3c2c1] | US20090167162 |
| | 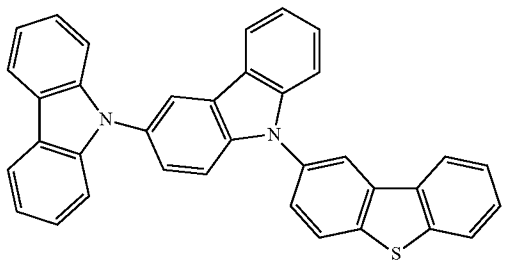 [SMILES: c1ccc2c(c1)sc1ccc(-n3c4ccccc4c4cc(-n5c6ccccc6c6ccccc65)ccc43)cc12] | WO2009086028 |
| | 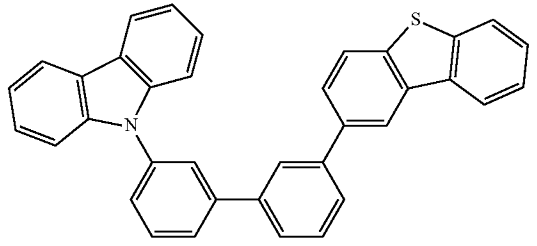 [SMILES: c1cc(-c2cccc(-n3c4ccccc4c4ccccc43)c2)cc(-c2ccc3sc4ccccc4c3c2)c1] | US20090030202, US20090017330 |

TABLE 4-continued
| MATERIAL | EXAMPLES OF MATERIAL | PUBLICATIONS |
|---|---|---|
| | 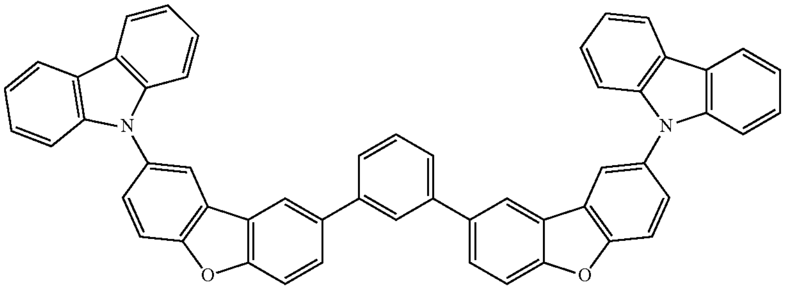 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 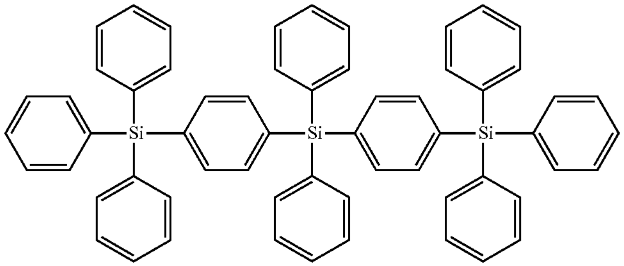 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 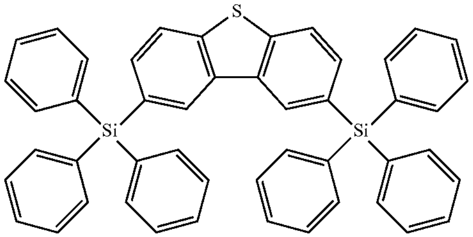 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 4-continued
| MATERIAL | EXAMPLES OF MATERIAL | PUBLICATIONS |
|---|---|---|
| Silicon/Germanium aryl compounds | 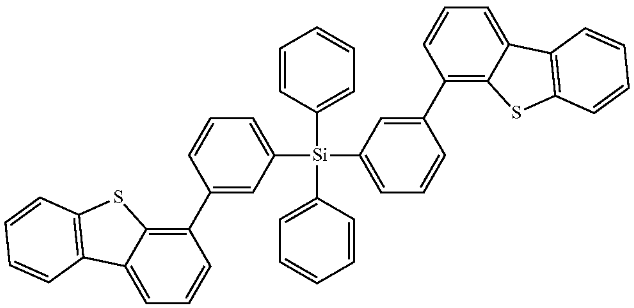 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 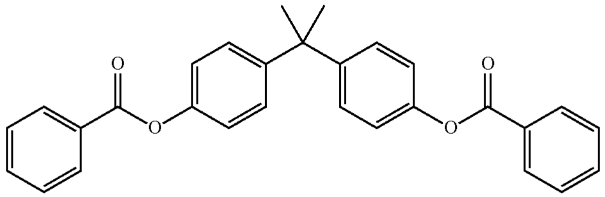 [SMILES: CC(C)(c1ccc(OC(=O)c2ccccc2)cc1)c1ccc(OC(=O)c2ccccc2)cc1] | WO2006100298 |
| Carbazole linked by non-conjugated groups | 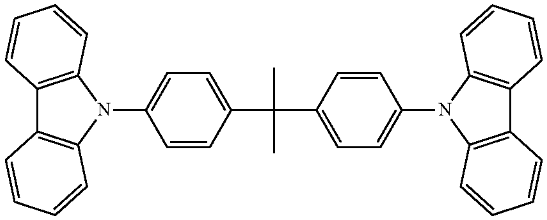 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 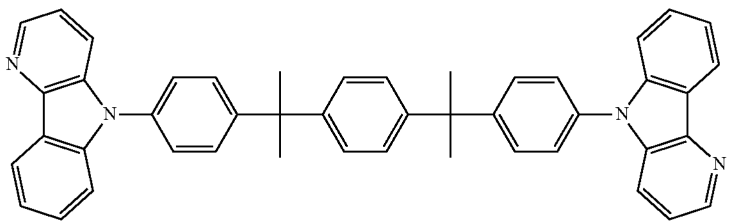 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |

TABLE 4-continued
| MATERIAL | EXAMPLES OF MATERIAL | PUBLICATIONS |
|---|---|---|
| High triplet metal organometallic complex | 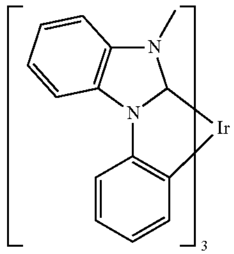 | U.S. Pat. No. 7,154,114 |
| | Phosphorescent dopants<br>Red dopants | |
| Heavy metal porphyrins (e.g., PtOEP) | 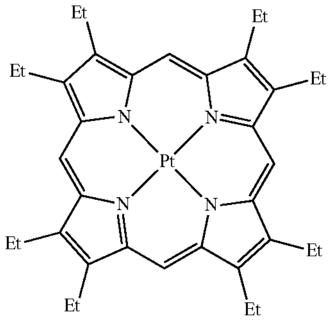 | Nature 395, 151 (1998) |
| Iridium(III) organometallic complexes | 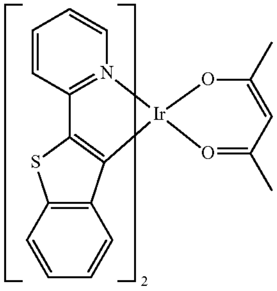 | Appl. Phys. Lett. 78, 1622 (2001) |

TABLE 4-continued
| MATERIAL | EXAMPLES OF MATERIAL | PUBLICATIONS |
|---|---|---|
| | 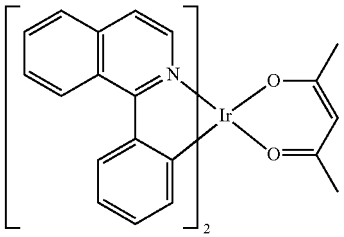 | US2006835469 |
| | 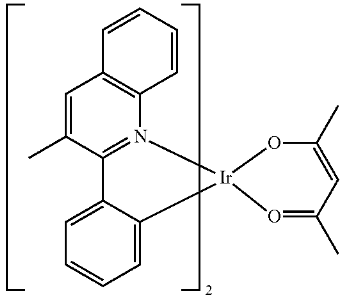 | US2006835469 |
| | 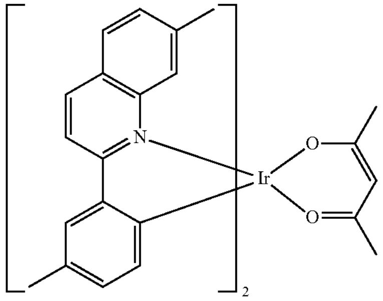 | US20060202194 |

TABLE 4-continued
| MATERIAL | EXAMPLES OF MATERIAL | PUBLICATIONS |
|---|---|---|
| | 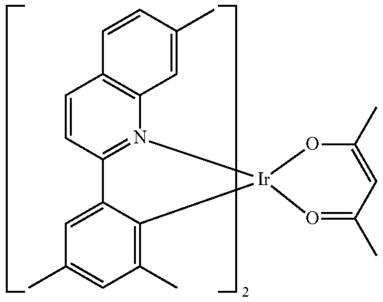 | US20060202194 |
| | 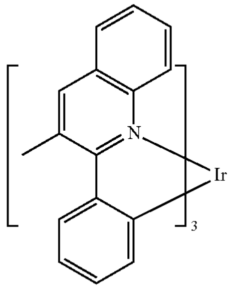 | US20070087321 |
| | 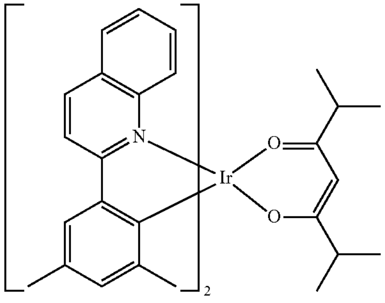 | US20080261076<br>US20100090591 |

TABLE 4-continued
| MATERIAL | EXAMPLES OF MATERIAL | PUBLICATIONS |
|---|---|---|
| | 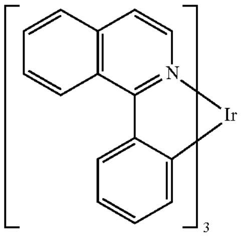 | US20070087321 |
| | 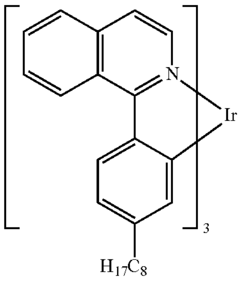 | Adv. Mater. 19, 739 (2007) |
| | 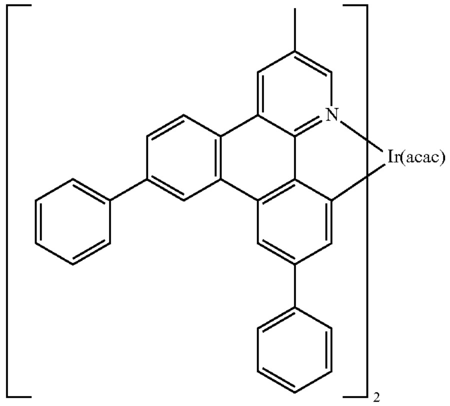 | WO2009100991 |

TABLE 4-continued
| MATERIAL | EXAMPLES OF MATERIAL | PUBLICATIONS |
| --- | --- | --- |
| | 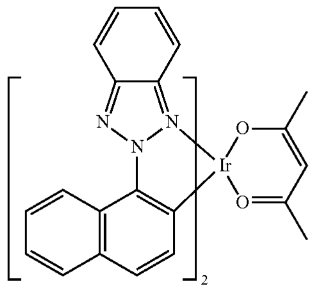 | WO2008101842 |
| | 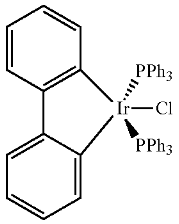 | U.S. Pat. No. 7,232,618 |
| Platinum(II) Organometallic complexes | 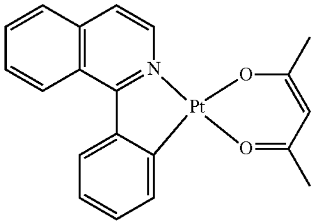 | WO2003040257 |

TABLE 4-continued
| MATERIAL | EXAMPLES OF MATERIAL | PUBLICATIONS |
|---|---|---|
| | 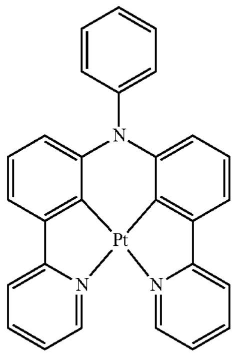 | US20070103060 |
| Osminum(III) complexes | 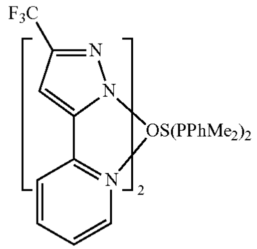 | Chem. Mater. 17, 3532 (2005) |
| Ruthenium(II) complexes | 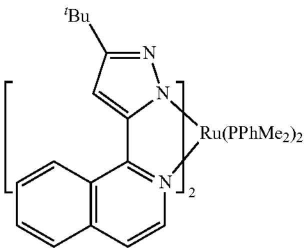 | Adv. Mater. 17, 1059 (2005) |
| Rhenium (I), (II), and (III) complexes | | US20050244673 |

TABLE 4-continued
| MATERIAL | EXAMPLES OF MATERIAL | PUBLICATIONS |
|---|---|---|
| | Green dopants | |
| Iridium(III) organometallic complexes | 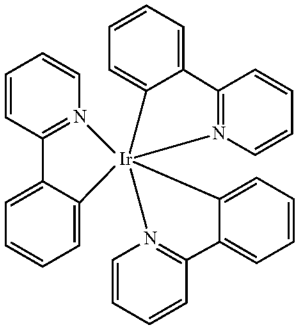 and its derivatives | Inorg. Chem. 40, 1704 (2001) |
| | 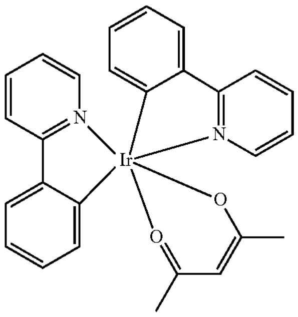 | US20020034656 |

TABLE 4-continued
| MATERIAL | EXAMPLES OF MATERIAL | PUBLICATIONS |
| --- | --- | --- |
| | 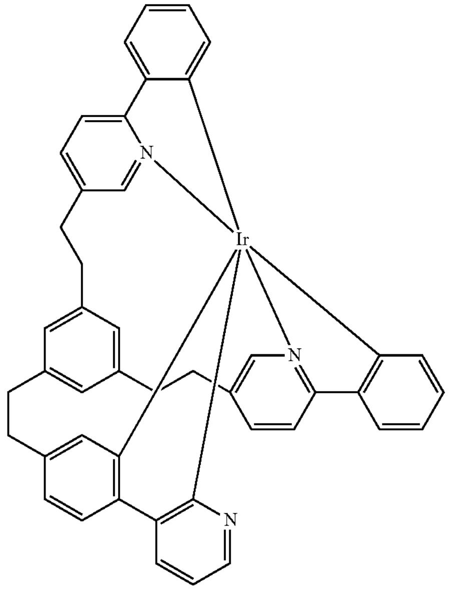 | U.S. Pat. No. 7,332,232 |
| | 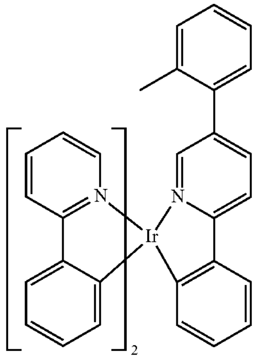 | US20090108737<br>WO2010028151 |

TABLE 4-continued
| MATERIAL | EXAMPLES OF MATERIAL | PUBLICATIONS |
|---|---|---|
| | 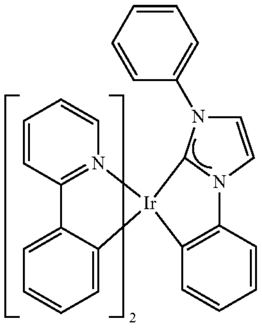 | EP1841834B |
| | 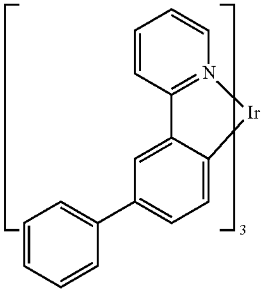 | US20060127696 |
| | 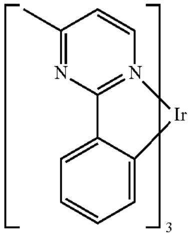 | US20090039776 |

TABLE 4-continued
| MATERIAL | EXAMPLES OF MATERIAL | PUBLICATIONS |
|---|---|---|
| | 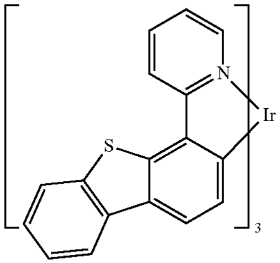 | U.S. Pat. No. 6,921,915 |
| | 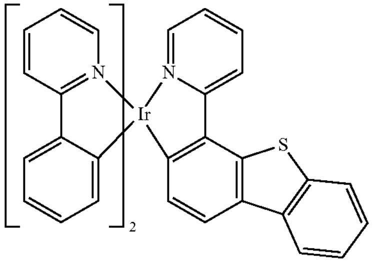 | US20100244004 |
| | 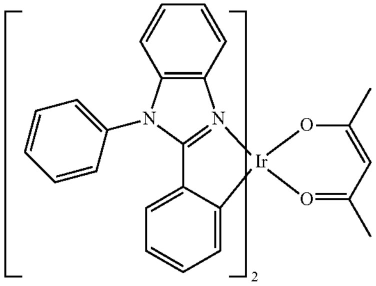 | U.S. Pat. No. 6,687,266 |

TABLE 4-continued
| MATERIAL | EXAMPLES OF MATERIAL | PUBLICATIONS |
|---|---|---|
| | 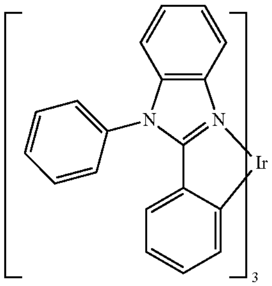 | Chem. Mater. 16, 2480 (2004) |
| | 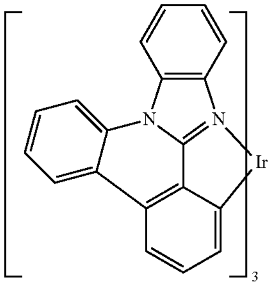 | US20070190359 |
| | 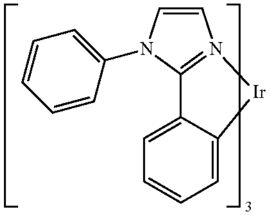 | US 20060008670<br>JP2007123392 |

TABLE 4-continued
| MATERIAL | EXAMPLES OF MATERIAL | PUBLICATIONS |
|---|---|---|
| | 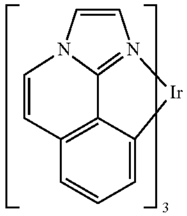 | WO2010086089, WO2011044988 |
| | 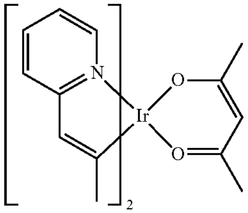 | Adv. Mater. 16, 2003 (2004) |
| | 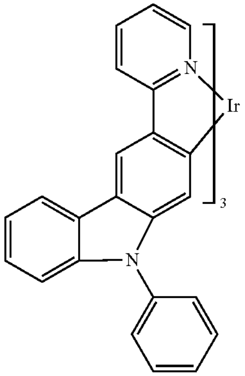 | Angew. Chem. Int. Ed. 2006, 45, 7800 |

TABLE 4-continued
| MATERIAL | EXAMPLES OF MATERIAL | PUBLICATIONS |
|---|---|---|
| | 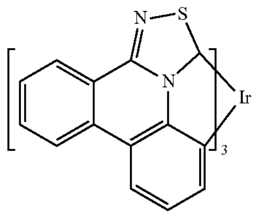 | WO2009050290 |
| | 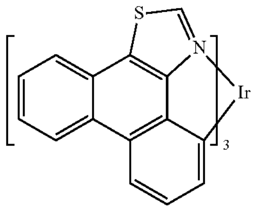 | US20090165846 |
| | 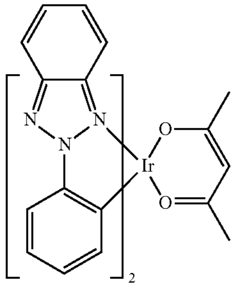 | US20080015355 |
| | 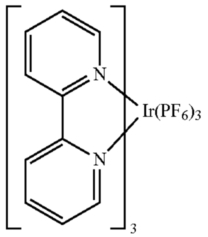 | US20010015432 |

TABLE 4-continued
| MATERIAL | EXAMPLES OF MATERIAL | PUBLICATIONS |
|---|---|---|
| | 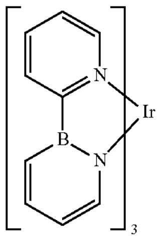 | US20100295032 |
| Monomer for polymeric metal organometallic compounds | 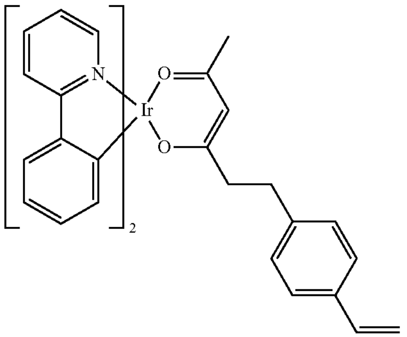 | U.S. Pat. No. 7,250,226, U.S. Pat. No. 7,396,598 |
| Pt(II) organometallic complexes, including polydentated ligands | 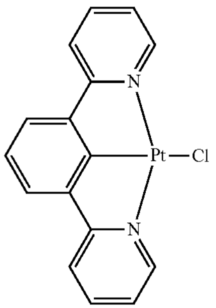 | Appl. Phys. Lett. 86, 153505 (2005) |

TABLE 4-continued
| MATERIAL | EXAMPLES OF MATERIAL | PUBLICATIONS |
| --- | --- | --- |
| | 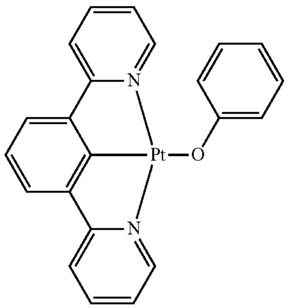 | Appl. Phys. Lett. 86, 153505 (2005) |
| | 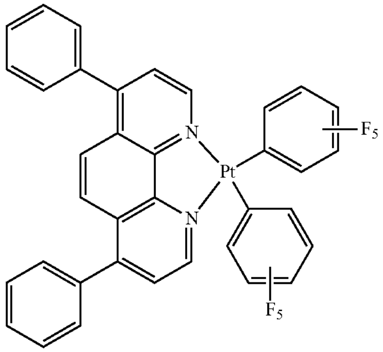 | Chem. Lett. 34, 592 (2005) |
| | 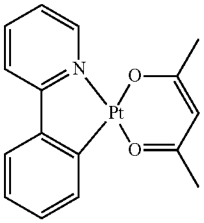 | WO2002015645 |

TABLE 4-continued
| MATERIAL | EXAMPLES OF MATERIAL | PUBLICATIONS |
|---|---|---|
| | 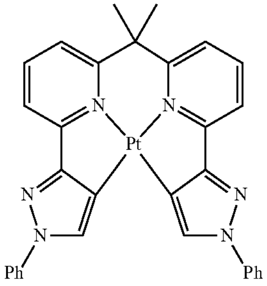 | US20060263635 |
| | 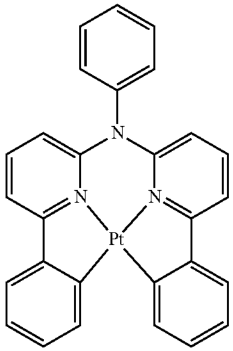 | US20060182992<br>US20070103060 |

TABLE 4-continued
| MATERIAL | EXAMPLES OF MATERIAL | PUBLICATIONS |
| --- | --- | --- |
| Cu complexes | 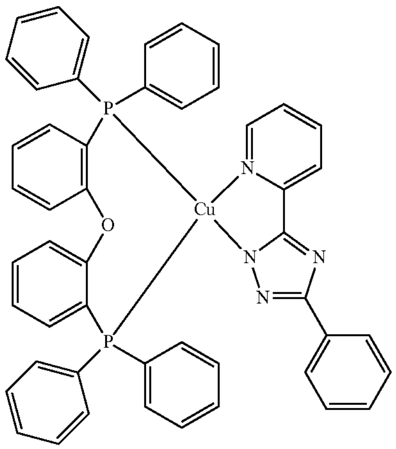 | WO2009000673 |
| | 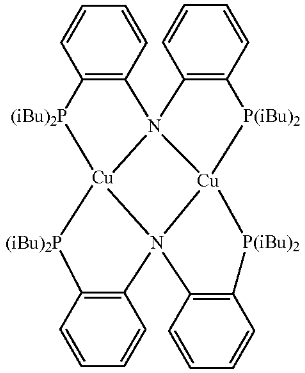 | US20070111026 |

TABLE 4-continued
| MATERIAL | EXAMPLES OF MATERIAL | PUBLICATIONS |
|---|---|---|
| Gold complexes | 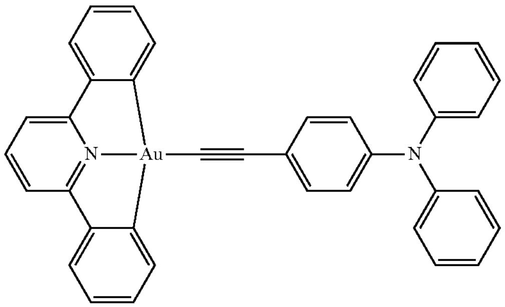 | Chem. Commun. 2906 (2005) |
| Rhenium(III) complexes | 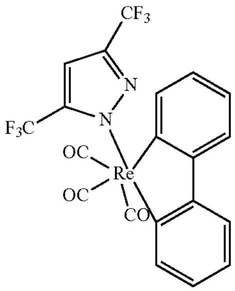 | Inorg. Chem. 42, 1248 (2003) |
| Osmium(II) complexes | | U.S. Pat. No. 7,279,704 |
| Deuterated organometallic complexes | | US20030138657 |
| Organometallic complexes with two or more metal centers | | US20030152802 |

TABLE 4-continued
| MATERIAL | EXAMPLES OF MATERIAL | PUBLICATIONS |
|---|---|---|
| | 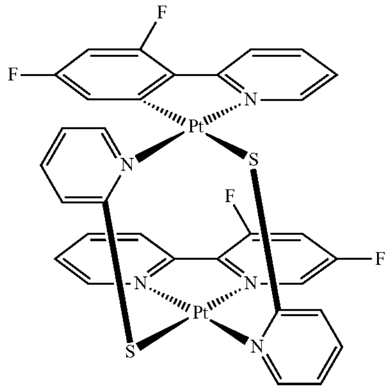 | U.S. Pat. No. 7,090,928 |
| Blue dopants | | |
| Iridium(III) organometallic complexes | 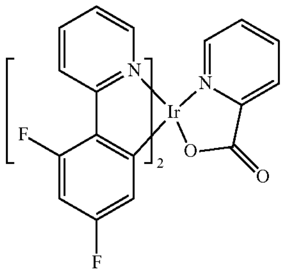 | WO2002002714 |
| | 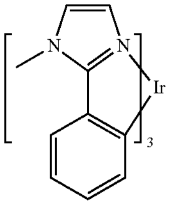 | WO2006009024 |

TABLE 4-continued
| MATERIAL | EXAMPLES OF MATERIAL | PUBLICATIONS |
|---|---|---|
| | 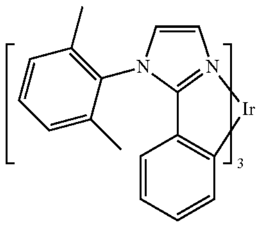 | US20060251923<br>US20110057559<br>US2011024333 |
| | 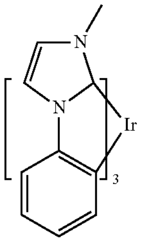 | U.S. Pat. No. 7,393,599,<br>WO2006056418,<br>US20050260441,<br>WO2005019373 |
| | 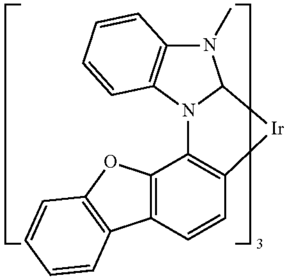 | U.S. Pat. No. 7,534,505 |

TABLE 4-continued
| MATERIAL | EXAMPLES OF MATERIAL | PUBLICATIONS |
|---|---|---|
| | 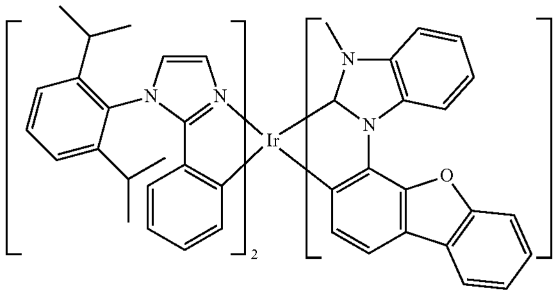 | WO2011051404 |
| | 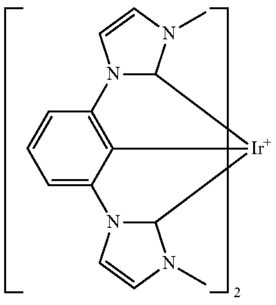 | U.S. Pat. No. 7,445,855 |
| | 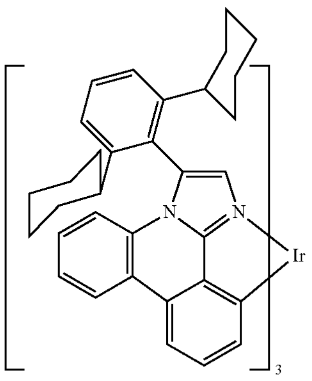 | US20070190359, US20080297033 US20100148663 |

TABLE 4-continued
| MATERIAL | EXAMPLES OF MATERIAL | PUBLICATIONS |
|---|---|---|
| | 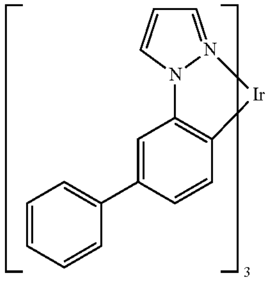 | U.S. Pat. No. 7,338,722 |
| | 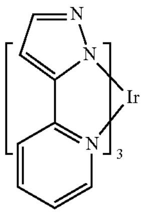 | US20020134984 |
| | 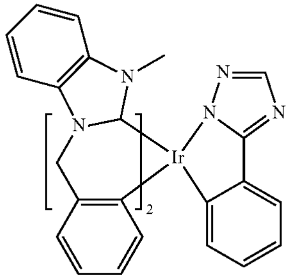 | Angew. Chem. Int. Ed. 47, 1 (2008) |
| | 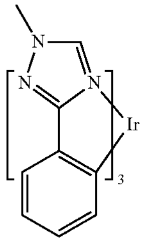 | Chem. Mater. 18, 5119 (2006) |

TABLE 4-continued
| MATERIAL | EXAMPLES OF MATERIAL | PUBLICATIONS |
|---|---|---|
| | 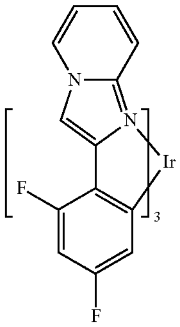 | Inorg. Chem. 46, 4308 (2007) |
| | 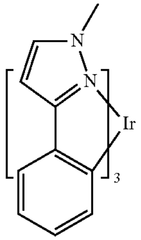 | WO2005123873 |
| | 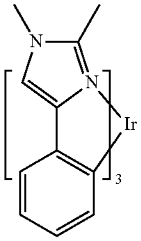 | WO2005123873 |

TABLE 4-continued
| MATERIAL | EXAMPLES OF MATERIAL | PUBLICATIONS |
|---|---|---|
| | 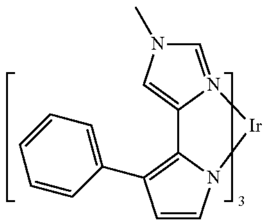 | WO2007004380 |
| | 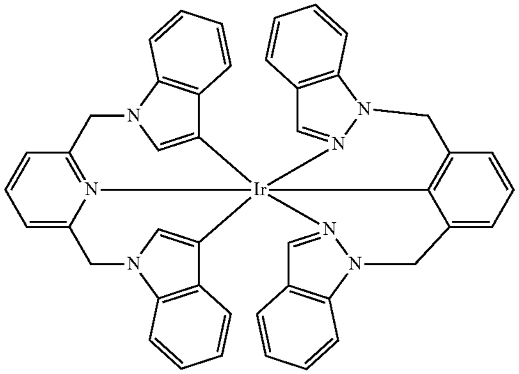 | WO2006082742 |
| Osmium(II) complexes | 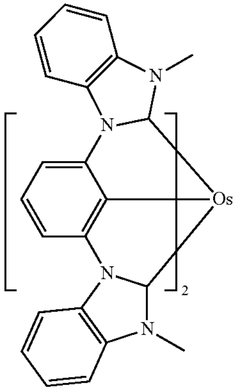 | U.S. Pat. No. 7,279,704 |

TABLE 4-continued
| MATERIAL | EXAMPLES OF MATERIAL | PUBLICATIONS |
| --- | --- | --- |
| | 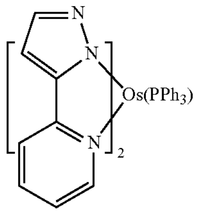 | Organometallics 23, 3745 (2004) |
| Gold complexes | 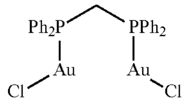 | Appl. Phys. Lett. 74, 1361 (1999) |
| Platinum(II) complexes | 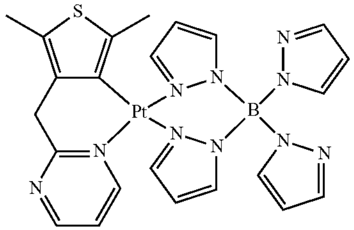 | WO2006098120, WO2006103874 |
| Pt tetradentate complexes with at least one metal-carbene bond | 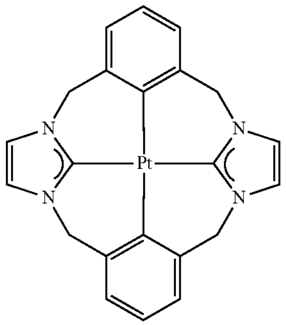 | U.S. Pat. No. 7,655,323 |

TABLE 4-continued
| MATERIAL | EXAMPLES OF MATERIAL | PUBLICATIONS |
| --- | --- | --- |
| Exciton/hole blocking layer materials | | |
| Bathocuprne compounds (e.g., BCP, BPhen) | 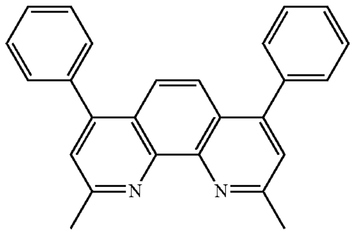 [SMILES: Cc1cc(-c2ccccc2)c2ccc3c(-c4ccccc4)cc(C)nc3c2n1] | Appl. Phys. Lett. 75, 4 (1999) |
| | 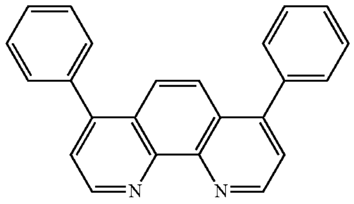 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 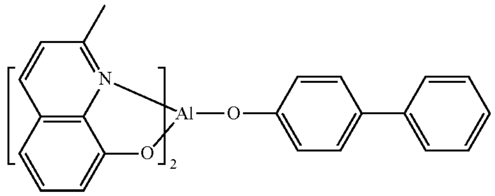 | Appl. Phys. Lett. 81, 162 (2002) |

TABLE 4-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 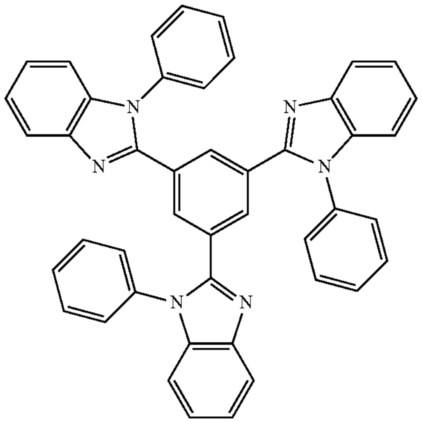 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 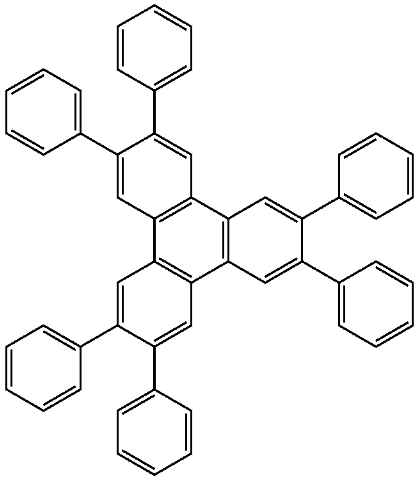 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 4-continued
| MATERIAL | EXAMPLES OF MATERIAL | PUBLICATIONS |
|---|---|---|
| Fluorinated aromatic compounds | 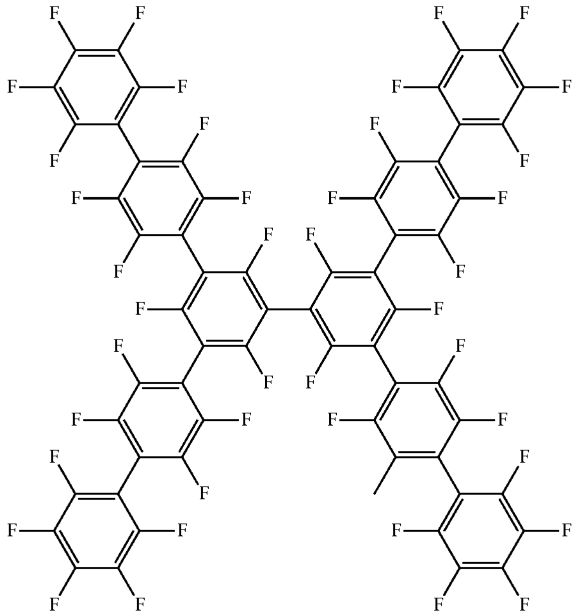 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 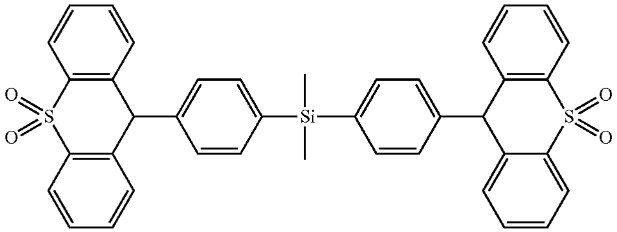 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |

TABLE 4-continued
| MATERIAL | EXAMPLES OF MATERIAL | PUBLICATIONS |
| --- | --- | --- |
| Silylated five-membered nitrogen, oxygen, sulfur or phosphorus dibenzoheterocycles | 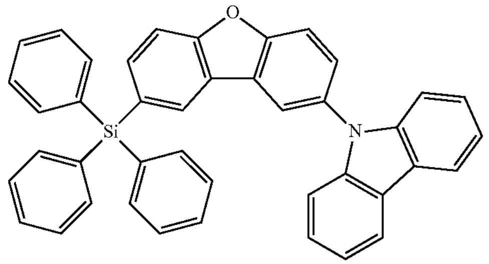 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 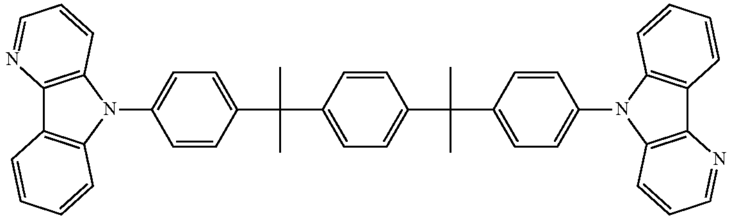 [SMILES: CC(C)(c1ccc(-n2c3ccccc3c3ncccc32)cc1)c1ccc(C(C)(C)c2ccc(-n3c4ccccc4c4ncccc43)cc2)cc1] | US2006121308 |
| Electron transporting materials | | |
| Anthracene-benzoimidazole compounds | 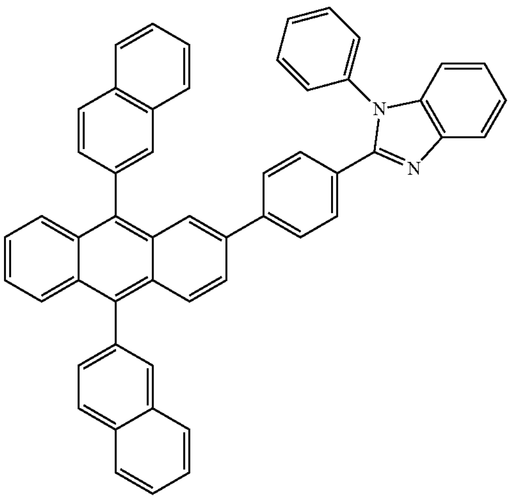 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 4-continued
| MATERIAL | EXAMPLES OF MATERIAL | PUBLICATIONS |
| --- | --- | --- |
| Aza triphenylene derivatives | 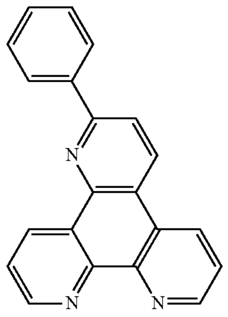 [SMILES: c1ccc(-c2ccc3c4cccnc4c4ncccc4c3n2)cc1] | US20090179554<br>US20090115316 |
| Anthracene-benzothiazole compounds | 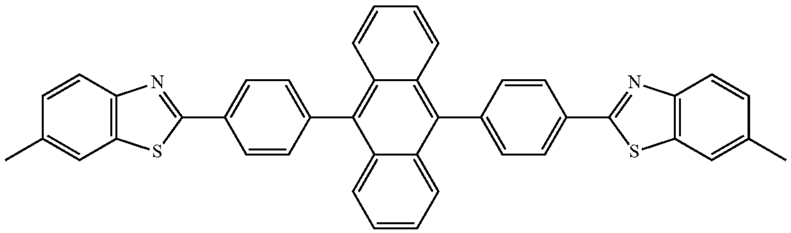 | Appl. Phys. Lett. 89, 063504 (2006) |
| Metal 8-hydroxyquinolates (e.g., $Alq_3$, $Zrq_4$) | 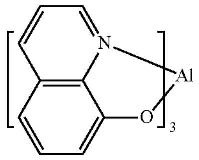 | Appl. Phys. Lett. 51, 913 (1987)<br>U.S. Pat. No. 7,230,107 |
| Metal hydroxybenoquinolates | 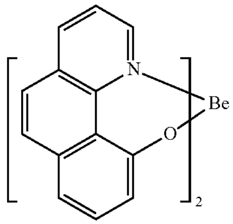 | Chem. Lett. 5, 905 (1993) |

TABLE 4-continued
| MATERIAL | EXAMPLES OF MATERIAL | PUBLICATIONS |
| --- | --- | --- |
| Bathocuprine compounds such as BCP, BPhen, etc | 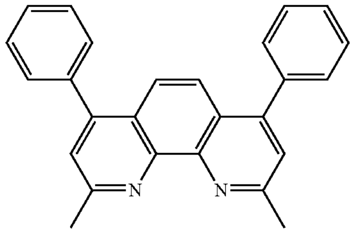 [SMILES: Cc1cc(-c2ccccc2)c2ccc3c(-c4ccccc4)cc(C)nc3c2n1] | Appl. Phys. Lett. 91, 263503 (2007) |
| | 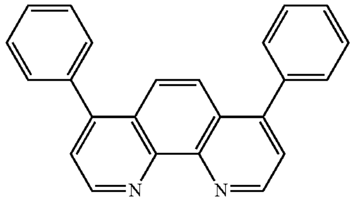 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 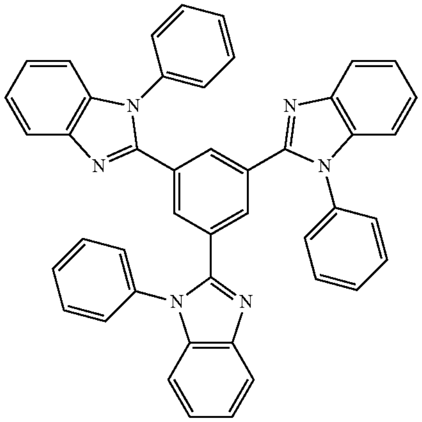 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |

TABLE 4-continued
| MATERIAL | EXAMPLES OF MATERIAL | PUBLICATIONS |
|---|---|---|
| | 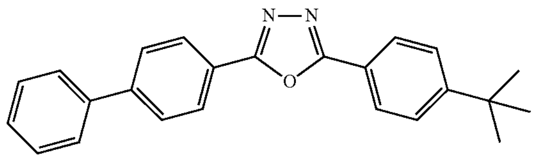 [SMILES: CC(C)(C)c1ccc(-c2nnc(-c3ccc(-c4ccccc4)cc3)o2)cc1] | Appl. Phys. Lett. 55, 1489 (1989) |
| | 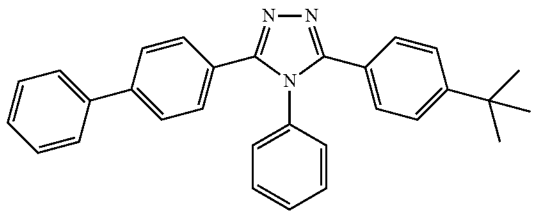 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 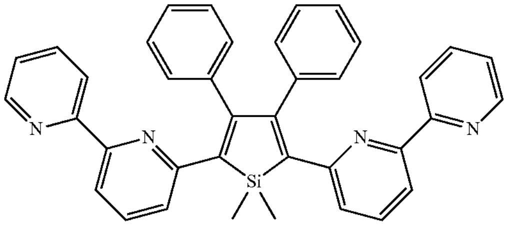 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 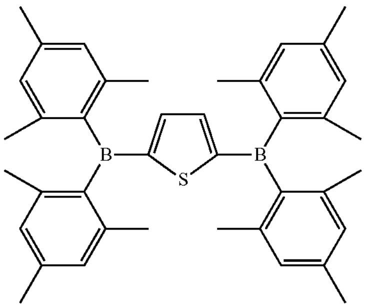 | J. Am. Chem. Soc. 120, 9714 (1998) |

TABLE 4-continued
| MATERIAL | EXAMPLES OF MATERIAL | PUBLICATIONS |
|---|---|---|
| Fluorinated aromatic compounds | 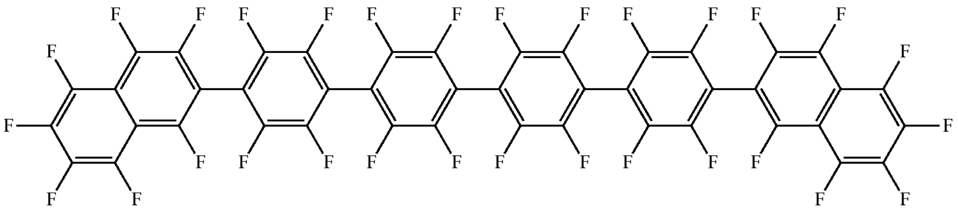 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 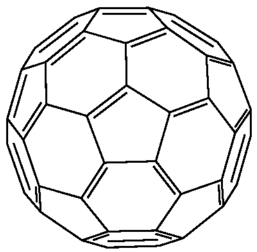 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 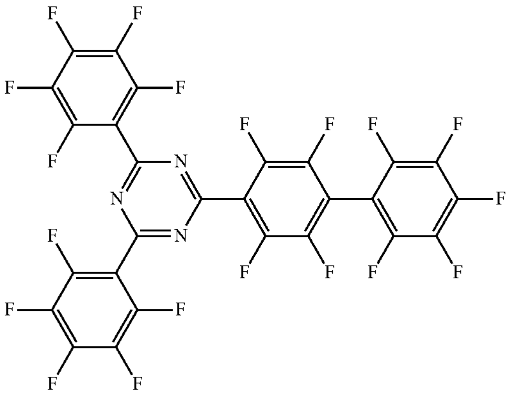 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 4-continued
| MATERIAL | EXAMPLES OF MATERIAL | PUBLICATIONS |
|---|---|---|
| Zn (N^N) complexes) | 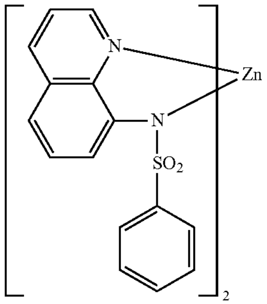 | U.S. Pat. No. 6,528,187 |

EXPERIMENTAL

Chemical abbreviations used throughout the text are as follows: DME is dimethoxyethane, THF is tetrahydrofuran, DCM is dichloromethane, DMSO is dimethyl sulfoxide, dba is dibenzylidineacetone.

Synthesis of Compound 1

Preparation of 2-(3-bromopyridin-2-yl)-6-chlorophenol

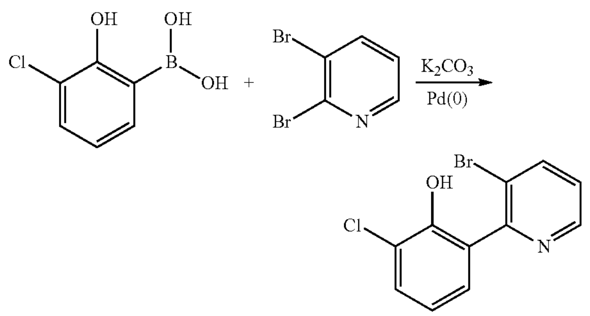

(3-Chloro-2-hydroxyphenyl)boronic acid (5.0 g, 29.0 mmol) and 2,3-dibromopyridine (6.87 g, 29.0 mmol) were added to a 500 mL 2-necked flask. The reaction mixture was diluted with DME (120 mL) and water (90 mL) with the potassium carbonate (8.02 grams, 58.0 mmol) dissolved in it. This mixture was degassed for 10 minutes before addition of $Pd(PPh_3)_4$ (1.00 grams, 3 mol %). The reaction mixture was then stirred at gentle reflux for 5 hours. The reaction mixture was then diluted with ethyl acetate and brine. The organic layer was washed with brine and dried over sodium sulfate. The product was purified using silica gel column chromatography using a mobile phase gradient of 5-10% ethyl acetate in hexane to obtain 2.8 grams (34%) of a white solid.

Preparation of 6-chlorobenzofuro[3,2-b]pyridine

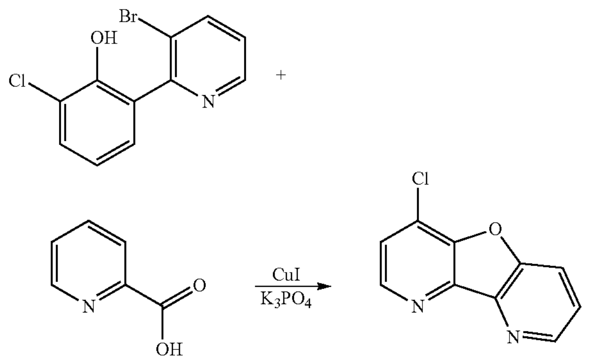

Into a 500 mL round-bottomed flask was placed 2-(3-bromopyridin-2-yl)-6-chlorophenol (4.5 g, 15.82 mmol), copper(I) iodide (0.602 g, 3.16 mmol), picolinic acid (0.779 g, 6.33 mmol) and potassium phosphate (6.71 g, 31.6 mmol) and DMSO (150 mL). This mixture was stirred in an oil bath at 125° C. for 5 hours. The heat was removed and the mixture was diluted with ethyl acetate and filtered through Celite®. The filtrate was washed with brine twice then with water. The organic layer was adsorbed onto Celite® and chromatographed eluting with 40-100% dichloromethane in hexane to obtain 2.45 grams (76%) of the desired product as a white solid.

Preparation of 6-(pyridin-2-yl)benzofuro[3,2-b]pyridine

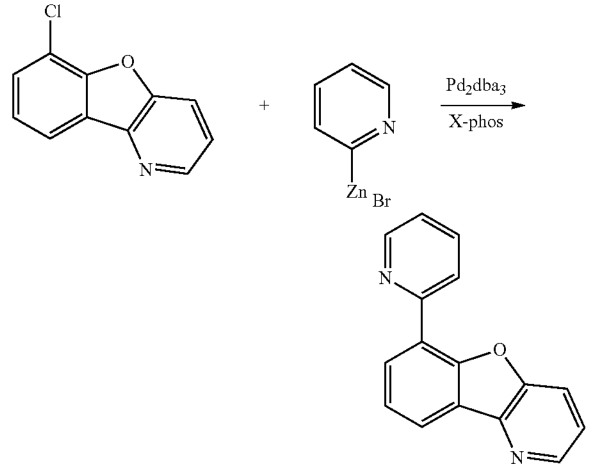

2-Dicyclohexylphosphino-2',4',6'-triisopropylbiphenyl (1.12 g, 2.36 mmol), 6-chlorobenzofuro[3,2-b]pyridine (3.0 g, 14.73 mmol), and $Pd_2$ $dba_3$ (0.54 g, 0.59 mmol) were added to a 250 mL 3-necked flask. The atmosphere in the flask was evacuated and backfilled with nitrogen. THF (15 mL) was added by syringe to the reaction flask. Pyridin-2-yl zinc(II) bromide (44.2 mL, 22.10 mmol) was then added and the flask was stirred in an oil bath at 75° C. After 2 hours, the reaction mixture was cooled and diluted with aqueous sodium bicarbonate and ethyl acetate. The aqueous layer was extracted with ethyl acetate and the combined organic layers were dried with sodium sulfate. The crude product was purified using silica gel column chromatography eluted with 0-5% methanol in DCM to give 3.2 g (88%) of desired product. This product was further purified by column chromatography over silica gel using DCM followed by up to 40% ethyl acetate/DCM mixture as eluent to obtain 2.8 g (77%) 6-(pyridin-2-yl)benzofuro[3,2-b]pyridine as a white solid.

Preparation of Compound 1

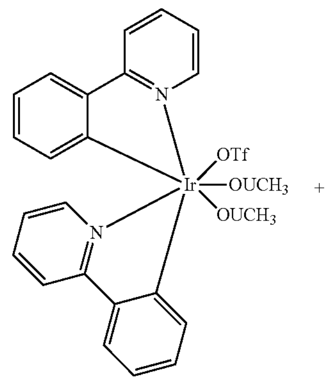

-continued

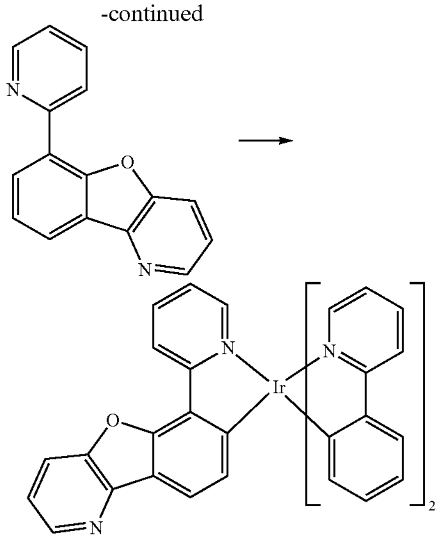

6-(Pyridin-2-yl)benzofuro[3,2-b]pyridine (2.71 g, 11.00 mmol) and iridium complex (1.964 g, 2.75 mmol) were added to ethanol (90 mL) and degassed for 15 minutes with nitrogen. The reaction mixture was heated to reflux until the iridium triflate intermediate disappeared. The reaction mixture was cooled to room temperature and filtered through a Celite® plug and washed with ethanol and hexanes. The yellow color precipitate was dissolved in DCM. Solvents were removed under reduced pressure from the DCM solution to give 1.65 g of crude material which was purified by silica gel column chromatography using 1:1 DCM/hexanes (v/v) followed by 95:5 DCM/methanol (v/v) as eluent. The isolated material was further purified by reversed phase column chromatography over C18 stationary phase using 95:5% acetonitrile/water as eluent to give 0.7 g (34%) of Compound 1.

Synthesis of Compound 4

Preparation of 3-(2,3-dimethoxyphenyl)pyridin-2-amine

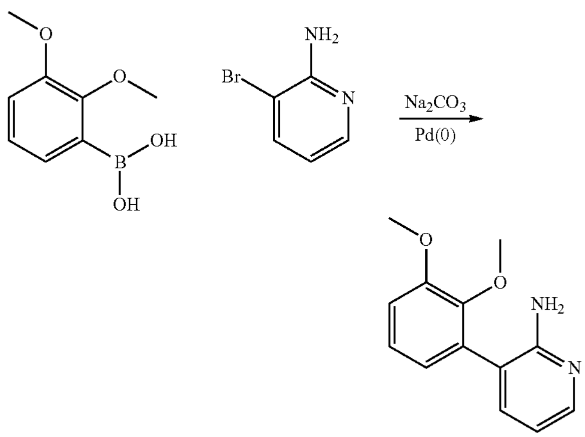

3-Bromopyridin-2-amine (23.77 g, 137 mmol), (2,3-dimethoxyphenyl)boronic acid (25 g, 137 mmol), and $Pd(Ph_3P)_4$ (4.76 g, 4.12 mmol) were added to a 2 L 2-necked flask. The reaction mixture was diluted with THF (600 mL). A solution of water (300 mL) with sodium carbonate (14.56 g, 137 mmol) dissolved in it was then added. This mixture was degassed and stirred at reflux for 20 hours. The mixture was then diluted with ethyl acetate and brine. The organic layer was washed with water and dried over sodium sulfate. The product was chromatographed on a silica gel column eluted with 0-50% ethyl acetate in DCM to obtain 28.9 g (91%) of the desired material.

Preparation of 8-methoxybenzofuro[2,3-b]pyridine

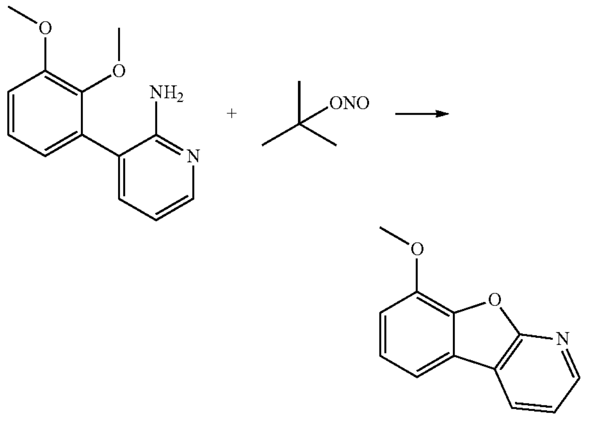

3-(2,3-Dimethoxyphenyl)pyridin-2-amine (14 g, 60.8 mmol) was added to a 500 mL round bottom flask. Acetic acid (220 mL) and THF (74 mL) were added. This mixture was stirred in a salt water ice bath. t-Butyl nitrite (14.5 mL, 109 mmol) was added drop-wise. The reaction mixture was stirred in the bath for 3 hours and then was allowed to warm ambient temperature with stirring. This mixture was evaporated in vacuo and partitioned between ethyl acetate and aqueous sodium bicarbonate. The product was chromatographed on silica gel. Elution with 25% ethyl acetate in hexane gave 6.61 g (54.6%) of 8-methoxybenzofuro[2,3-b]pyridine as a white solid.

Preparation of benzofuro[2,3-b]pyridin-8-ol

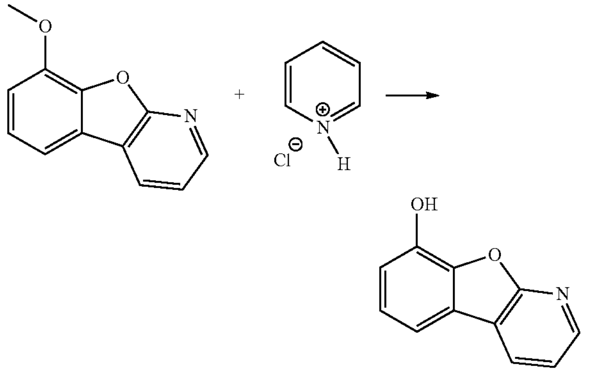

8-Methoxybenzofuro[2,3-b]pyridine (6.6 g, 33.1 mmol) was added along with pyridine HCl (25 g) to a 250 mL round bottom flask. This mixture was stirred in an oil bath at 200°

C. for 10 hours. Aqueous sodium bicarbonate and DCM were added to the mixture. The organic layer was dried and evaporated to a brown solid to obtain 5.07 g (83%) of the desired product.

Preparation of benzofuro[2,3-b]pyridin-8-yl trifluoromethanesulfonate

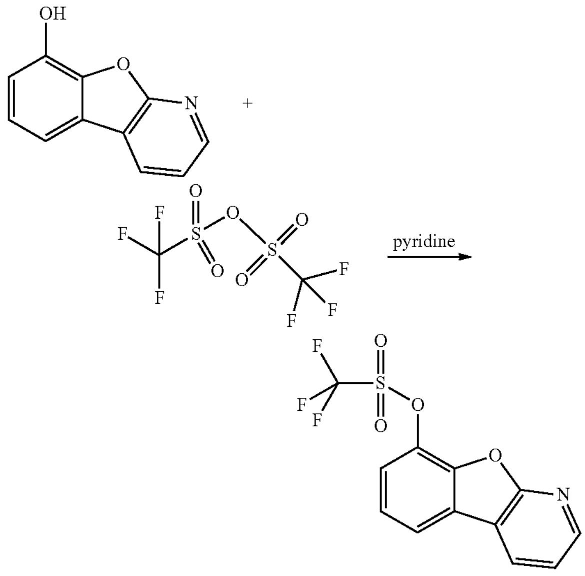

Benzofuro[2,3-b]pyridin-8-ol (5.5 g, 29.7 mmol) was added to a 500 mL round bottom flask and DCM (250 mL) was added. Pyridine (6.01 mL, 74.3 mmol) was added and the flask was placed in an ice bath. Triflic anhydride (7.5 mL, 44.6 mmol) was dissolved in DCM (30 mL) and added drop-wise over 10 min. The bath was removed and the reaction was allowed to warm to ambient temperature and stirred overnight. The solution was washed with saturated sodium bicarbonate solution then water. The product was chromatographed on a silica gel column, which was eluted with DCM to obtain 8.1 g (86%) of the desired product as a white solid was obtained.

Preparation of 8-(pyridin-2-yl)benzofuro[2,3-b]pyridine

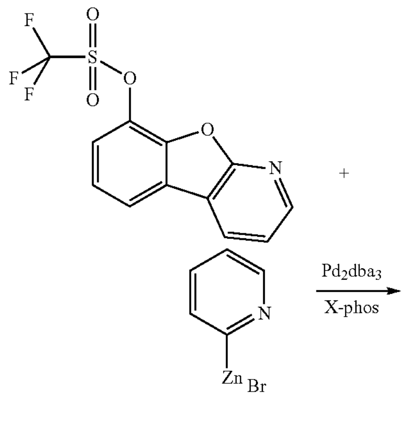

-continued

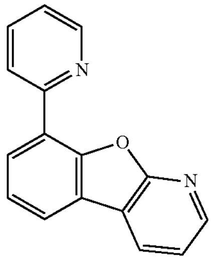

Benzofuro[2,3-b]pyridin-8-yl trifluoromethanesulfonate (4 g, 12.61 mmol), X-Phos (0.481 g, 1.009 mmol) and $Pd_2dba_3$ (0.231 g, 0.252 mmol) were added to a 250 mL 3-necked flask. The atmosphere in the flask was evacuated and backfilled with nitrogen. THF (40 mL) and pyridin-2-yl zinc(II) bromide (37.8 mL, 18.91 mmol) were added. This mixture was stirred in an oil bath at 70° C. for 4 hours. The mixture was filtered through Celite®, and the filter cake was washed with ethyl acetate. The crude material was adsorbed on to Celite® and chromatographed on a silica gel column eluted with 25-50% ethyl acetate in hexane to obtain 2.7 g (87%) of the desired product as a white solid.

Preparation of Compound 4

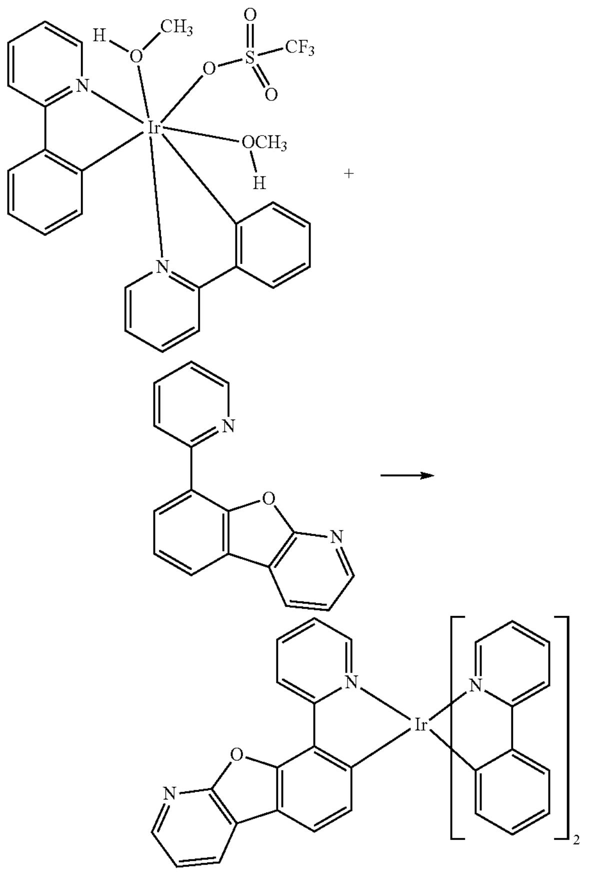

8-(Pyridin-2-yl)benzofuro[2,3-b]pyridine (3.8 g, 15.4 mmol) and iridium complex (3.67 g, 5.10 mmol) were combined in a 500 mL round bottom flask. 2-Ethoxyethanol (125 mL) and dimethylformamide (125 mL) were each added and the mixture was stirred in an oil bath at 135° C. for 18 hours. The mixture was concentrated first on a rotary evaporator then on a Kugelrohr apparatus. The residue was purified on a silica gel column eluted with 0-3% ethyl acetate in dichloromethane to afford 2.48 g (65%) of the desired product as yellow solid.

Synthesis of Compound 105

Preparation of 2-(5-chloro-2-methoxyphenyl)pyridin-3-amine

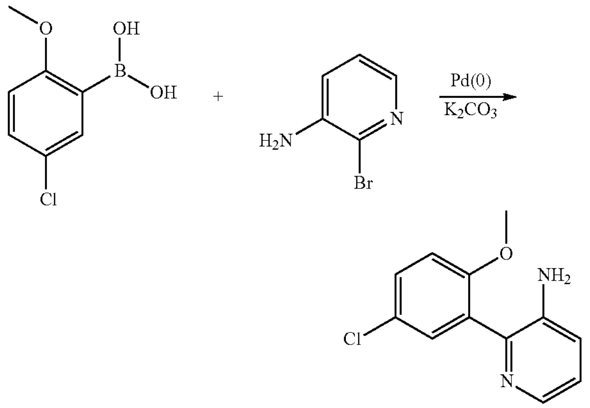

(5-Chloro-2-methoxyphenyl)boronic acid (12 g, 64.4 mmol), 2-bromopyridin-3-amine (11.14 g, 64.4 mmol) potassium carbonate (17.79 g, 129 mmol) and $Pd(Ph_3P)_4$ (3.72 g, 3.22 mmol) were added to a 1 L 3-necked flask. The reaction mixture was diluted with DME (300 mL) and water (150 mL). This mixture was stirred at reflux for 3 hours. The mixture was filtered through Celite® and the filter cake was washed with ethyl acetate. Water was added and the layers were separated. The organic layer was chromatographed on a silica gel column which was eluted with 0-10% ethyl acetate in DCM to give 10.9 g (72%) of the desired compound.

Preparation of 8-chlorobenzofuro[3,2-b]pyridine

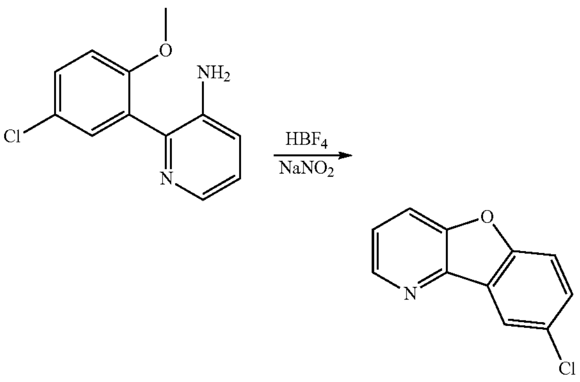

In a 1 L round-bottomed flask was placed 2-(5-chloro-2-methoxyphenyl)pyridin-3-amine (10.9 g, 46.4 mmol) and THF (85 mL). Tetrafluoroboric acid (85 mL, 678 mmol) was added along with water (50 mL). The flask was placed in an ethylene glycol-dry ice bath. Sodium nitrite (6.73 g, 98 mmol) was dissolved water (30 mL) and added drop-wise to the flask. The solution turned from yellow to orange with evolution of gas. This reaction mixture was stirred in the bath for 4 hours, and allowed to warm to ambient temperature. Aqueous saturated sodium bicarbonate (500 mL) was added. The product was extracted with DCM and chromatographed on a 200 gram silica gel column eluted with 20-40% ethyl acetate in hexane to obtain 3.26 g (34.5%) of the desired product as a white solid.

Preparation of 8-(pyridin-2-yl)benzofuro[3,2-b]pyridine

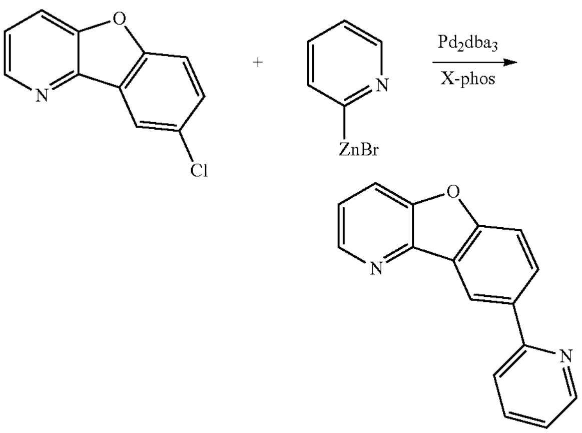

8-Chlorobenzofuro[3,2-b]pyridine (3.2 g, 15.72 mmol) and $Pd_2$ $dba_3$ (0.288 g, 0.314 mmol) and X-Phos (0.599 g, 1.257 mmol) were added to a 250 mL 3-necked flask. The atmosphere in the flask was evacuated and backfilled with nitrogen. THF (40 mL) was added. Next, pyridin-2-yl zinc (II) bromide (47.1 mL, 23.57 mmol) was added. This mixture was stirred in an oil bath at 70° C. for 4 hours. The mixture was then diluted with aqueous sodium bicarbonate and ethyl acetate. This mixture was filtered through Celite®, and the organic and aqueous layers were separated. The aqueous layer was extracted once more with ethyl acetate. The combined organic layers were chromatographed on a 150 gram silica gel column eluted first with 20% ethyl acetate in hexane then 10% ethyl acetate in DCM and finally 2.5% methanol in DCM. The eluent triturated in hexane and filtered giving 3.2 g (83%) of the desired product as a beige powder.

Preparation of Compound 105

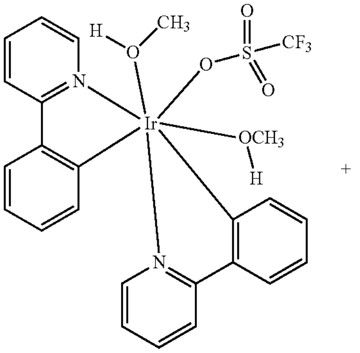

-continued

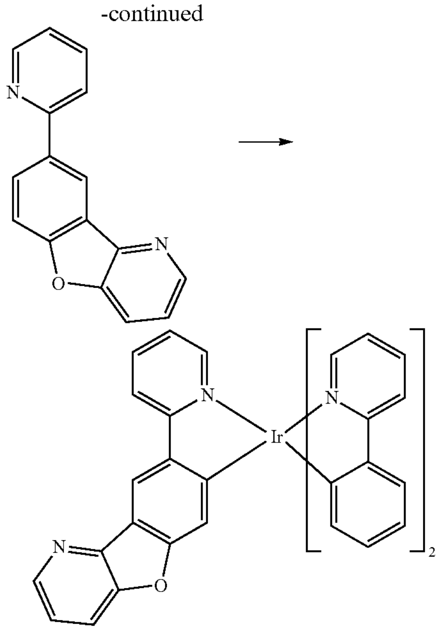

Iridium complex (2.99 g, 4.20 mmol) and 8-(pyridin-2-yl)benzofuro[3,2-b]pyridine (3.1 g, 12.59 mmol) were each added to a 250 mL round bottom flask. 2-Ethoxyethanol (50 mL) and dimethylformamide (50 mL) were added and this was stirred in an oil bath at 150° C. for 18 hours. The flask was placed on a Kugelrohr apparatus and the solvents were removed. The crude material was chromatographed on a silica gel column eluted with 0-10% ethyl acetate in DCM to obtain 2.07 g (66%) of the desired compound.

Synthesis of Compound II-1

Preparation of 3-(2,3-dimethoxyphenyl)-6-methylpyridin-2-amine

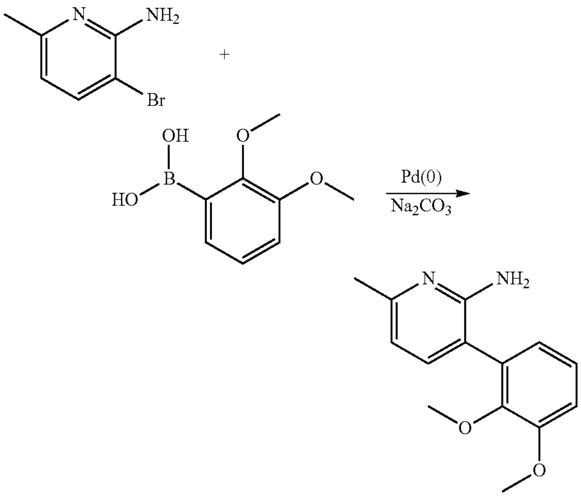

A solution of 3-bromo-6-methylpyridin-2-amine (12.33 g, 65.9 mmol) and (2,3-dimethoxyphenyl)boronic acid (12.0 g, 65.9 mmol), $Pd(PPh_3)_4$ (2.286 g, 1.978 mmol) and sodium carbonate (6.99 g, 65.9 mmol) in DME (250 ml) and water (125 ml) was stirred at reflux for 5 h. The crude mix was filtered through celite and the solid was washed with ethyl acetate. The filtrate was washed with brine and the solvent was evaporated. The crude product was purified by column chromatography on silica gel with 0-5% methanol in DCM as eluent to obtain 14.5 grams (90%) of the desired product as a cream colored solid.

Preparation of 8-methoxy-2-methylbenzofuro[2,3-b]pyridine

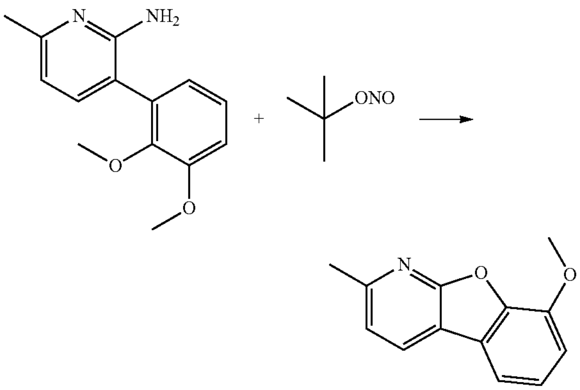

Into a solution of 3-(2,3-dimethoxyphenyl)-6-methylpyridin-2-amine (14.5 g, 59.4 mmol) in acetic acid (200 ml) and THF (67 ml) was added dropwise tert-butylnitrite (14.1 ml, 106.9 mmol) at 0° C. After stirring at this temperature for 2 h, the reaction mixture was allowed to warm to room temperature. Upon evaporation off the solvent, the residue was partitioned between ethyl acetate and water. The organic phase was isolated, washed with aqueous sodium bicarbonate and brine, dried over sodium sulfate. Upon evaporation off the solvent, the residue was purified by column chromatography on silica gel with 25% ethyl acetate in hexane to obtain 7.65 g (60.4%) of desired product as a pale yellow solid.

Preparation of 2-methylbenzofuro[2,3-b]pyridin-8-ol

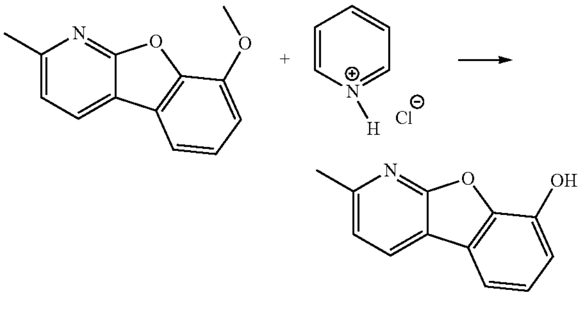

A mixture of 8-methoxy-2-methylbenzofuro[2,3-b]pyridine (7.6 g, 35.6 mmol) and pyridine hydrochloride (25 g, 216 mmol) was heated at 200° C. for 15 h. After cooling to room temperature, the solid was sonicated with aqueous sodium bicarbonate solution. The solid was isolated by filtration to yield 6.72 g (95%) of desired product as a brown powder.

Preparation of 2-methylbenzofuro[2,3-b]pyridin-8-yltrifluoromethanesulfonate

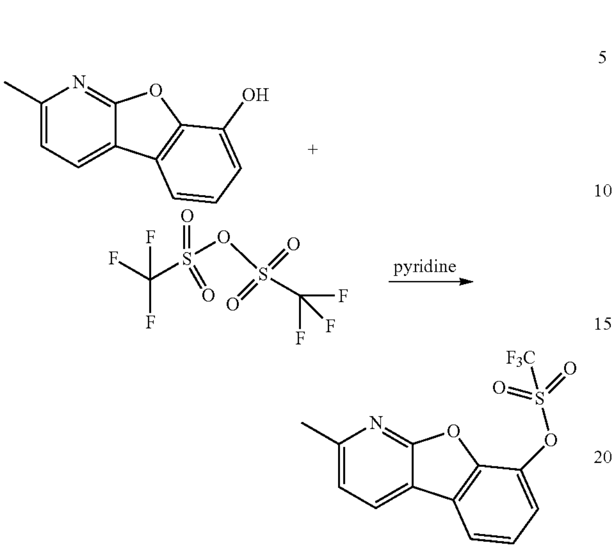

Into a suspension of 2-methylbenzofuro[2,3-b]pyridin-8-ol (6.7 g, 33.6 mmol) in dichloromethane (300 ml) was added dropwise a solution of trifluoromethanesulfonic anhydride (8.47 ml, 50.5 mmol) in dichloromethane (30 ml) at 0° C. After stirring overnight, the reaction was quenched with saturated sodium bicarbonate. The organic phase was isolated, washed with brine and dried over sodium sulfate. Upon evaporation off the solvent, the crude product was purified by column chromatography on silica gel with dichloromethane as eluent to obtain 8.95 g (80%) of desired product as a pale yellow solid.

Preparation of 2-methyl-8-(pyridin-2-yl)benzofuro[2,3-b]pyridine

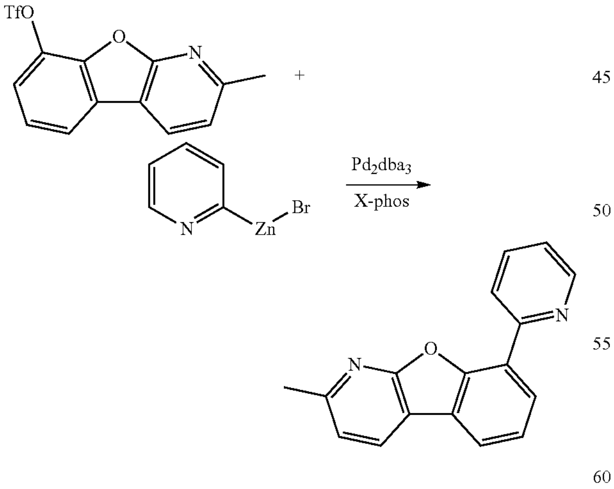

Into a solution of 2-methylbenzofuro[2,3-b]pyridin-8-yl trifluoromethanesulfonate (4 g, 12.07 mmol), $Pd_2$ $dba_3$ (0.221 g, 0.241 mmol) and 2-dicyclohexylphosphino-2',4',6'-triisopropylbiphenyl (0.230 g, 0.483 mmol) in THF (80 ml) was added a solution of pyridin-2-ylzinc(II) bromide (36.2 ml, 0.5 M, 18.11 mmol) in THF at 60° C. It was stirred at 65° C. for 12 h and quenched with saturated ammonium chloride solution. The organic phase was isolated, diluted with ethyl acetate, washed with brine, and dried over magnesium sulfate. Upon evaporation off the solvent, the residue was purified by column chromatography on silica gel with 5-20% ethyl acetate in dichlomethane as eluent to yield 2.05 g (65%) of desired product as a white solid.

Preparation of Compound II-1

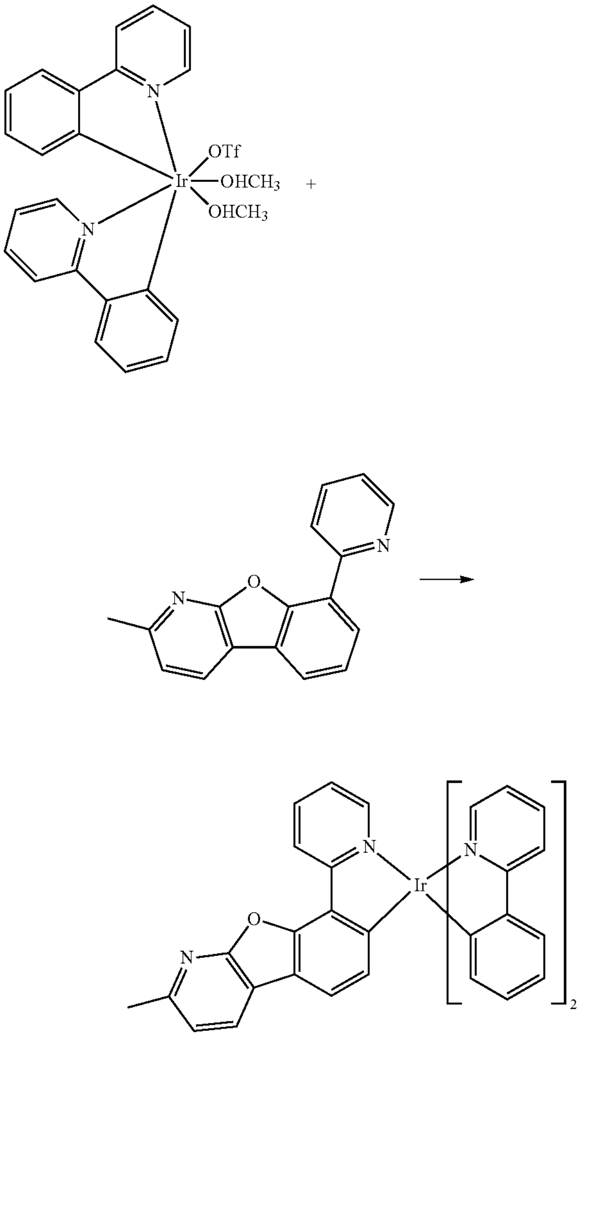

Iridium complex (1.828 g, 2.56 mmol) and 2-methyl-8-(pyridine-2-yl)benzofuro[2,3-b]pyridine (2 g, 7.68 mmol) were added to 85 mL ethanol and the reaction mixture was heated to reflux for 20 h. The reaction mixture was cooled, filtered through a Celite® pad and the filtrate was discarded. Collected precipitate was washed with ethanol, dried and purified by column chromatography on silica gel with dichloromethane as eluent to yield 0.9 g (46%) of Compound II-1 as a yellow solid.

Synthesis of Compound II-49

Preparation of 2-$d_3$-methyl-8-(pyridin-2-yl)benzofuro[2,3-b]pyridine

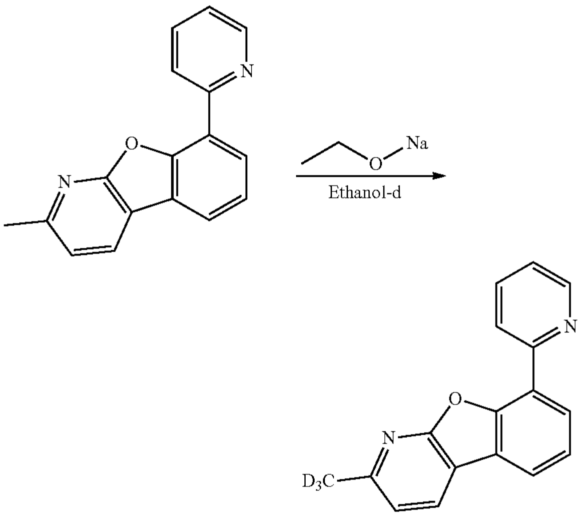

A solution of 2-methyl-8-(pyridin-2-yl)benzofuro[2,3-b]pyridine (6.3 g, 24.20 mmol) and sodium ethoxide (3.29 grams, 48.4 mmol) in ethanol-D (100 ml) was refluxed for 72 h. The solvent was evaporated and the residue was partitioned between ethyl acetate and water. The organic phase was isolated, dried over sodium sulfate and evaporated. Upon evaporation of the solvent, the residue was purified by column chromatography on silica gel with 0-15% ethyl acetate in dichloromethane to yield 5.1 g (80%) of desired compound as a white solid.

Preparation of Compound II-49

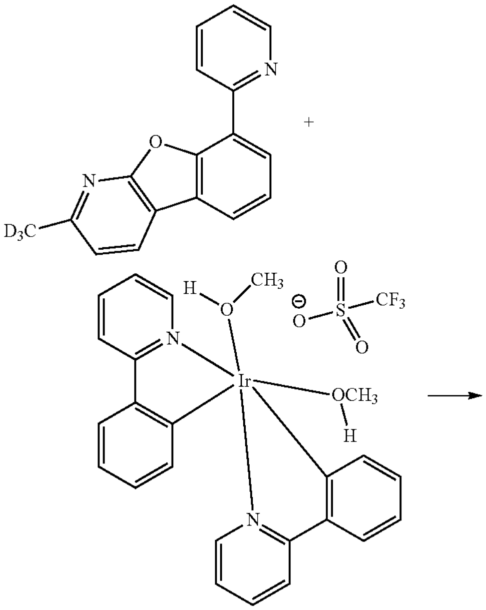

-continued

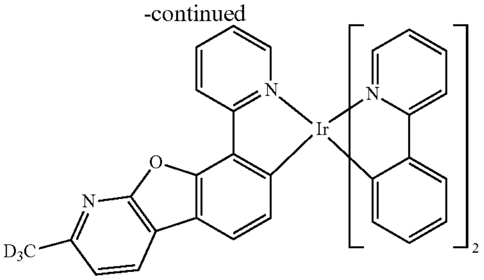

A solution of 2-$d_3$-methyl-8-(pyridin-2-yl)benzofuro[2,3-b]pyridine (3.8 grams, 14.4 mmol) and iridium complex (3.43 grams, 4.81 mmol) in DMF (100 ml) and 2-ethoxyethanol (100 ml) were heated at 130° C. for 18 h. Upon evaporation off the solvent, the crude product was purified by column chromatography on silica gel with 65-100% dichloromethane in hexane to yield 2.77 g (75%) of Compound II-49 as a yellow solid.

Preparation of Compound II-355

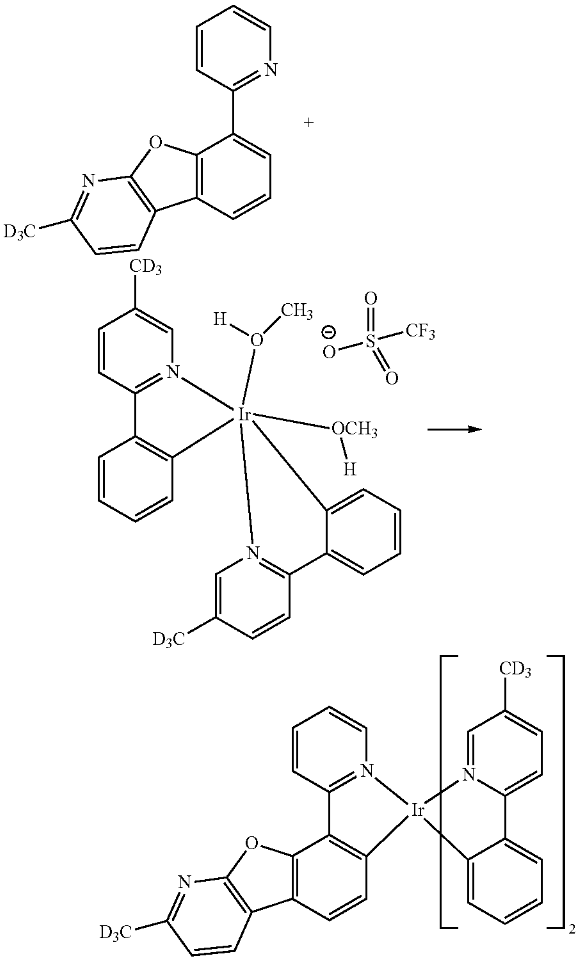

A solution of 2-$d_3$-methyl-8-(pyridin-2-yl)benzofuro[2,3-b]pyridine (4.45 g, 16.90 mmol) and iridium complex (4.21 g, 5.63 mmol) in DMF (100 ml) and 2-ethoxyethanol (100 ml) was heated at 130° C. under nitrogen for 18 h. Upon evaporation off the solvent, the crude product was purified by column chromatography on silica gel with 70-100% dichloromethane in hexane to yield 3.30 g (74%) of Compound II-355 as a yellow solid.

Synthesis of Compound II-7

Preparation of 2-methyl-8-(4-methylpyridin-2-yl)benzofuro[2,3-b]pyridine

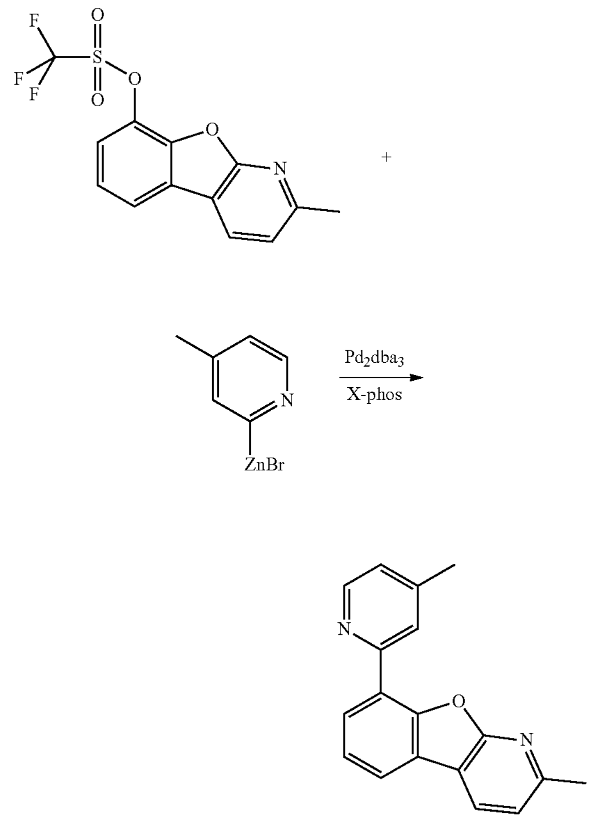

Into a solution of 2-methylbenzofuro[2,3-b]pyridin-8-yl-trifluoromethanesulfonate (4.45 g, 13.43 mmol), dicyclohexyl(2',4',6'-triisopropyl-[1',1'-biphenyl]-2-yl)phosphine (0.512 g, 1.075 mmol) and $Pd_2$ $dba_3$ (0.246 g, 0.269 mmol) in THF 50 ml was added a solution of 4-methyl-2-pyridylzinc bromide solution (50 ml, 0.5 M, 25 mmol). The reaction mixture was heated at 60-65° C. under nitrogen for 12 h and quenched with saturated sodium bicarbonate solution. The suspension was filtered through a short plug of Celite®. The filtrate was washed with brine and dried over magnesium sulfate. Upon evaporation off the solvent, the residue was purified by column chromatography on silica gel with 25-50% ethyl acetate in dichlomethane as eluent to yield 3.02 g (82%) of desired product as a white solid.

Preparation of Compound II-7

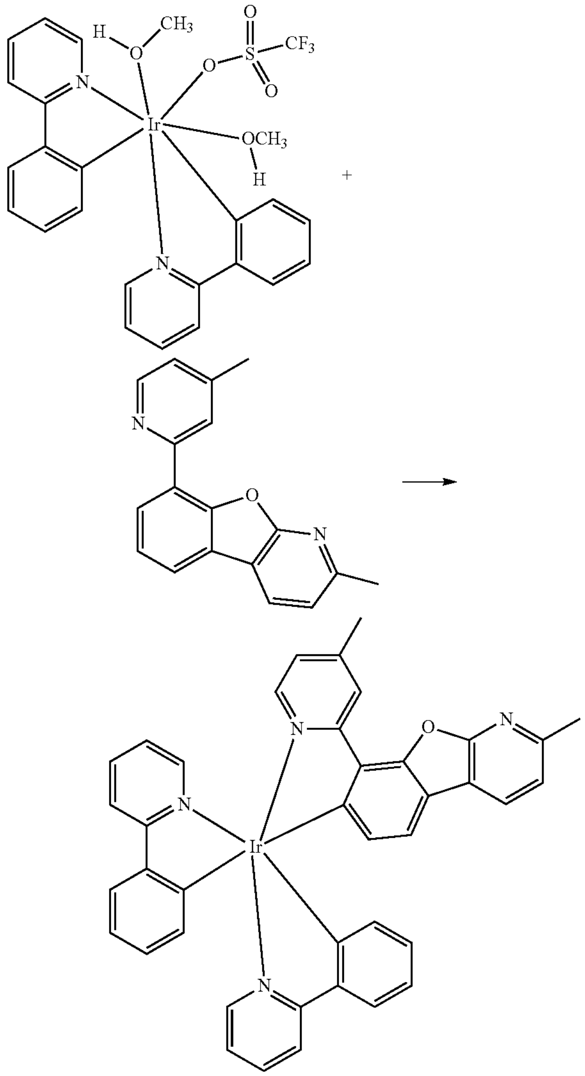

A solution of iridium complex (2.60 g, 3.65 mmol) and 2-methyl-8-(4-methylpyridin-2-yl)benzofuro[2,3-b]pyridine (3.0 g, 10.94 mmol) in ethanol (120 ml) was refluxed for 24 h. After cooling to room temperature, the solic was collected by filtration and purified by column chromatography on silica gel with 65-100% DCM in hexane to yield 1.5 g (53%) of Compound 7 as a yellow solid.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having a structure $Ir(L_A)_n(L_B)_{3-n}$ according to Formula II

Formula II

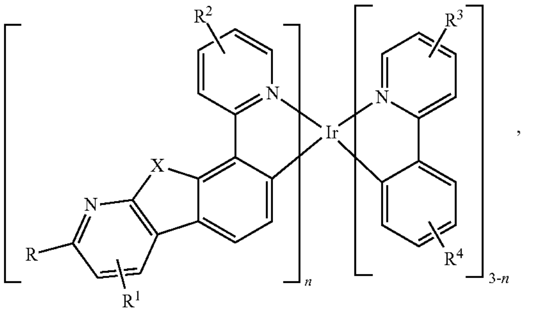

wherein R is selected from the group consisting of alkyl, cycloalkyl, and combinations thereof, any of which may be partially or fully deuterated;

wherein $R^1$ represent mono-, di-substitution, or no substitution;

wherein $R^2$, $R^3$, and $R^4$ independently represent mono-, di-, tri-, tetra-substitution, or no substitution;

wherein any adjacent substitutions in $R^1$, $R^2$, $R^3$, and $R^4$ are optionally linked together to form a ring;

wherein $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein X is O, S, or Se; and wherein n is an integer from 1 to 3.

2. The compound of claim 1, wherein n is 1.

3. The compound of claim 1, wherein X is O.

4. The compound of claim 1, wherein R is alkyl.

5. The compound of claim 1, wherein R is cycloalkyl.

6. The compound of claim 1, wherein R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof.

7. The compound of claim 1, wherein $R^1$, $R^2$, $R^3$, and $R^4$ are independently selected from the group consisting of hydrogen, deuterium, alkyl, and combinations thereof.

8. The compound of claim 1, wherein $R^2$ is alkyl, or partially or fully deuterated alkyl.

9. The compound of claim 1, wherein $R^3$ is alkyl, or partially or fully deuterated alkyl.

10. The compound of claim 1, wherein $R^1$, $R^2$, $R^3$, and $R^4$ are H.

11. The compound of claim 10, wherein R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof.

12. The compound of claim 10, wherein R is selected from the group consisting of methyl, ethyl, propyl, 1-methylethyl, butyl, 1-methylpropyl, 2-methylpropyl, and partially or fully deuterated variants thereof.

13. The compound of claim 1, wherein $R^1$, $R^2$, $R^3$, and $R^4$ are independently selected from the group consisting of hydrogen, deuterium, alkyl, and combinations thereof.

14. The compound of claim 13, wherein R is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, partially or fully deuterated variants thereof, and combinations thereof.

15. The compound of claim 1, wherein $L_A$ is selected from the group consisting of:

$L_{A120}$

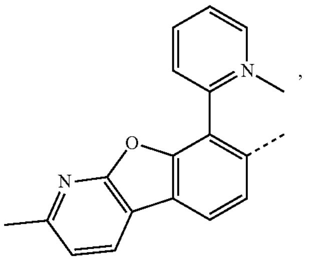

$L_{A121}$

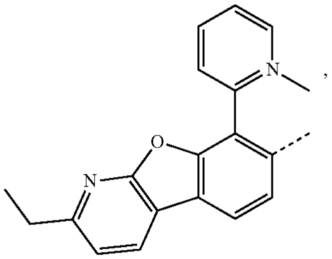

$L_{A122}$

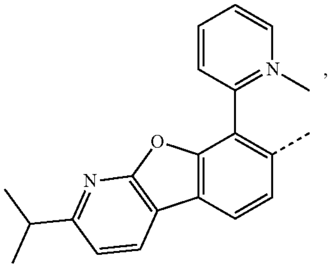

$L_{A123}$

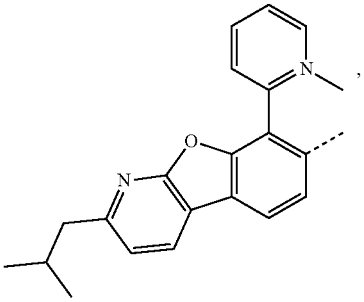

-continued
$L_{A124}$
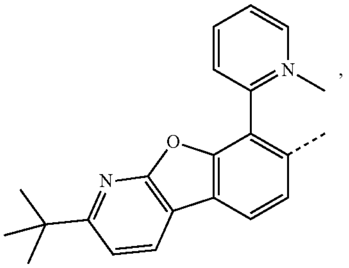
$L_{A125}$
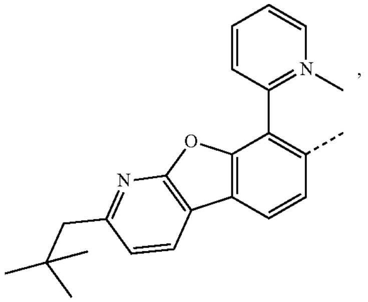
$L_{A126}$
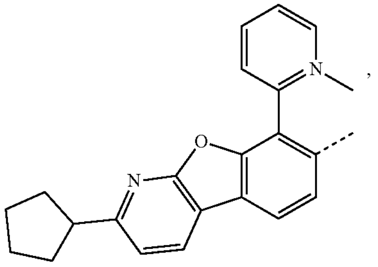
$L_{A127}$
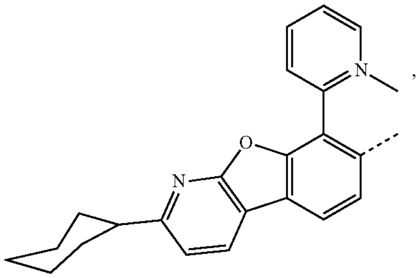
$L_{A128}$
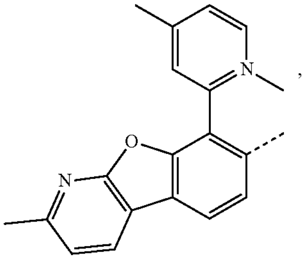
-continued
$L_{A129}$
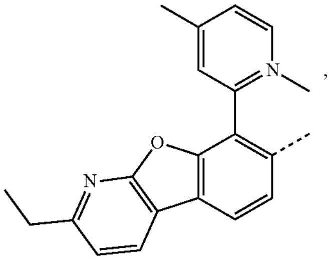
$L_{A130}$
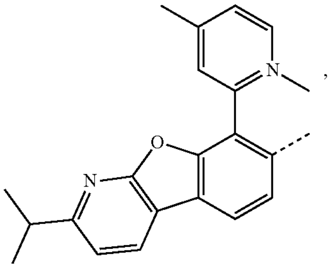
$L_{A131}$
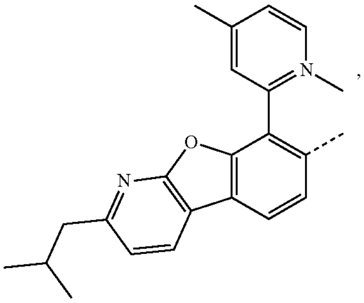
$L_{A132}$
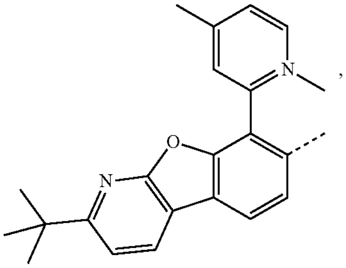
$L_{A133}$
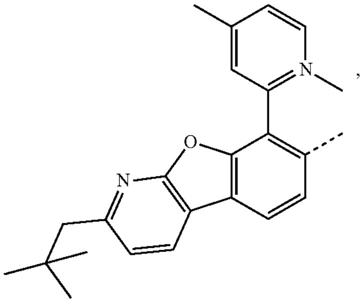

-continued
LA134
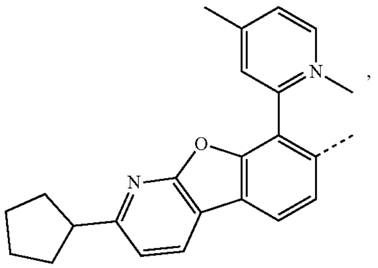
LA135
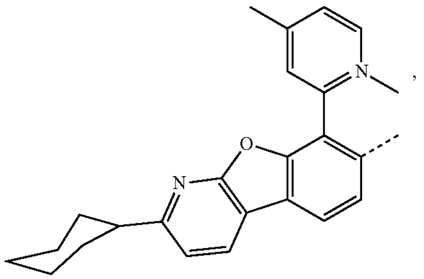
LA136
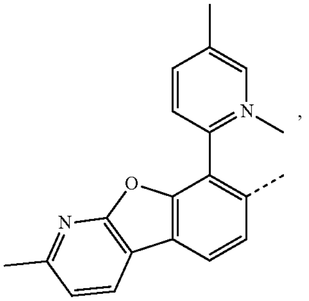
LA137
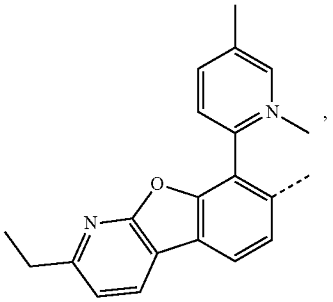
LA138
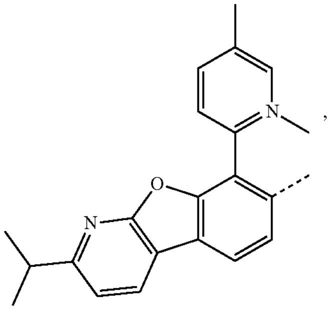
-continued
LA139
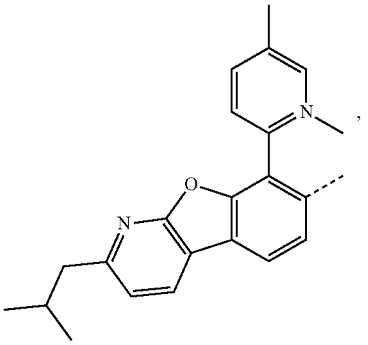
LA140
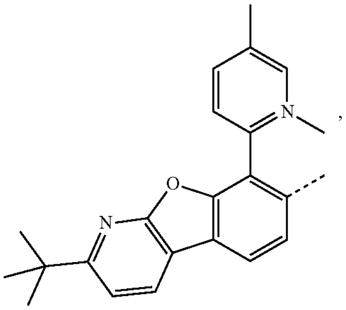
LA141
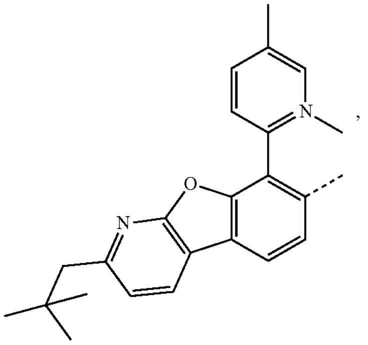
LA142
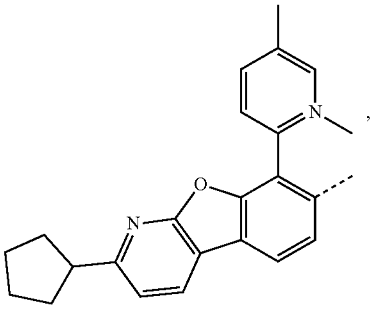

-continued
$L_{A143}$
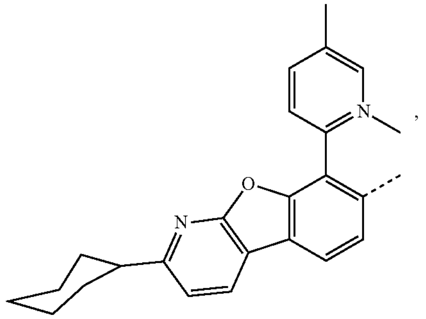
$L_{A144}$
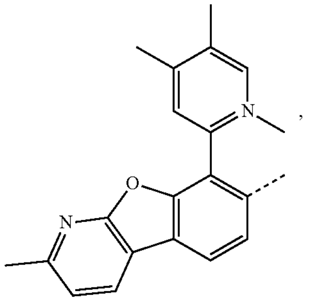
$L_{A145}$
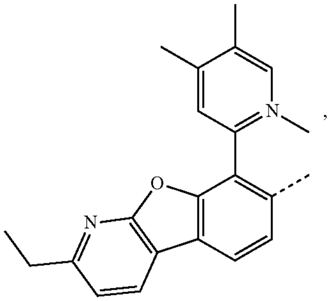
$L_{A146}$
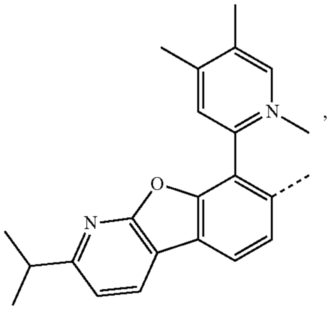
$L_{A147}$
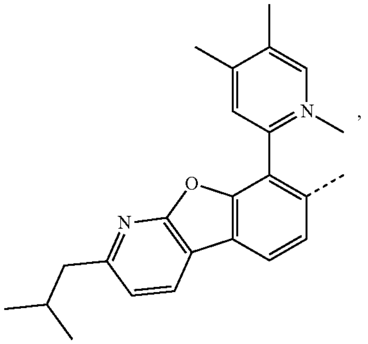
-continued
$L_{A148}$
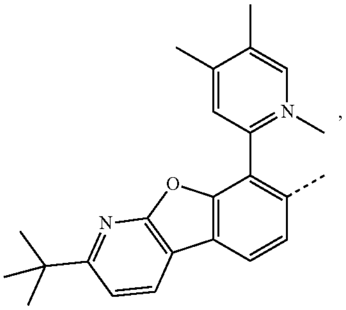
$L_{A149}$
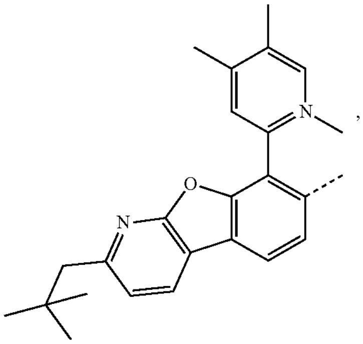
$L_{A150}$
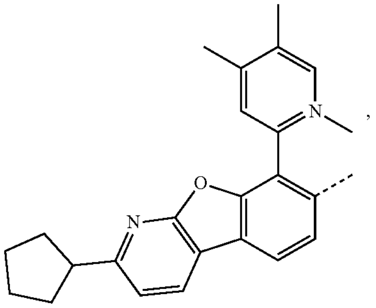
$L_{A151}$
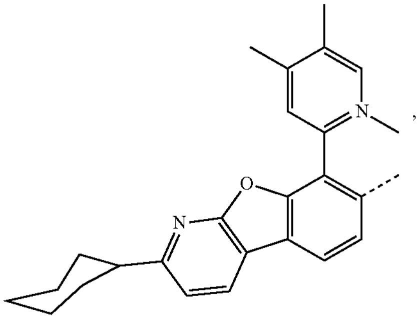
$L_{A152}$
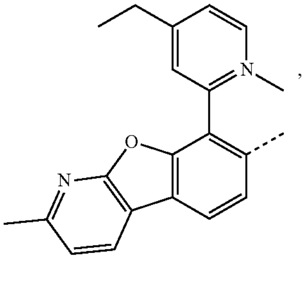

-continued
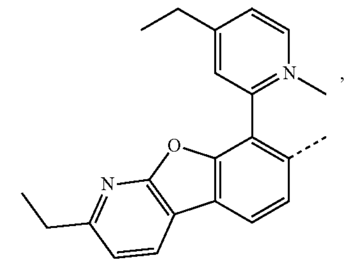
$L_{A153}$
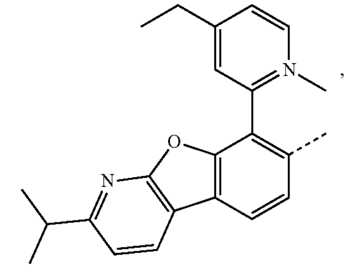
$L_{A154}$
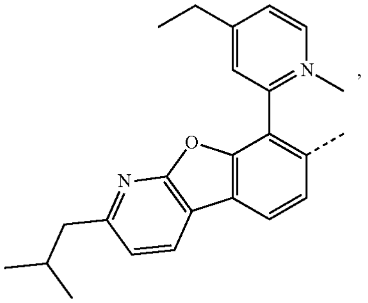
$L_{A155}$
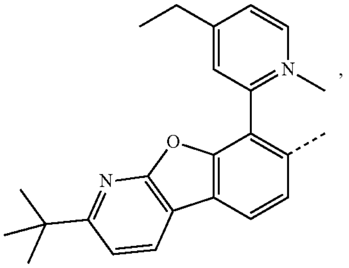
$L_{A156}$
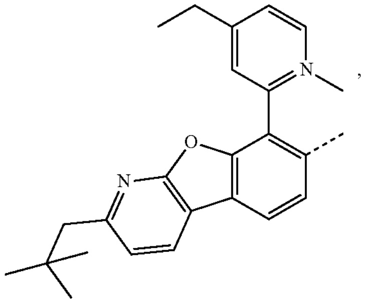
$L_{A157}$
-continued
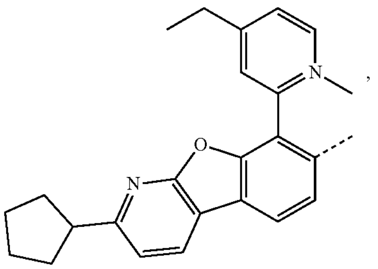
$L_{A158}$
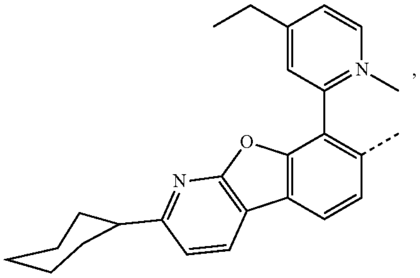
$L_{A159}$
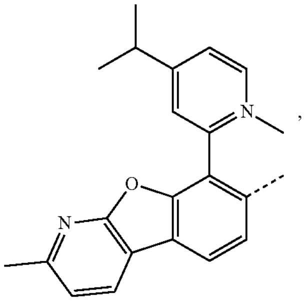
$L_{A160}$
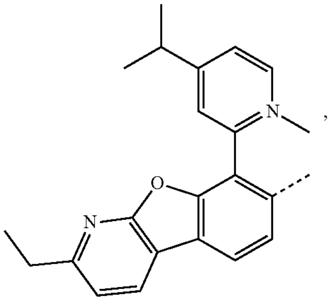
$L_{A161}$
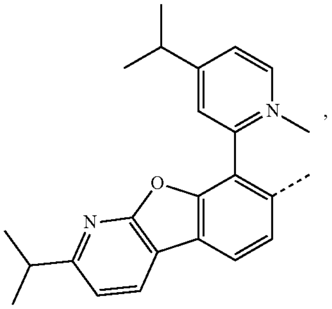
$L_{A162}$

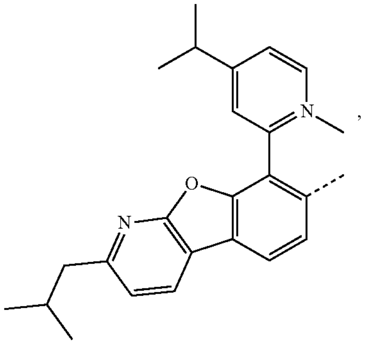
$L_{A163}$
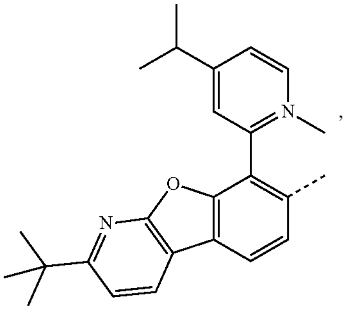
$L_{A164}$
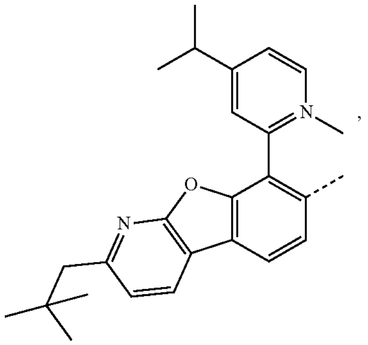
$L_{A165}$
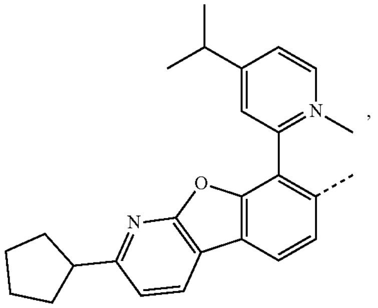
$L_{A166}$
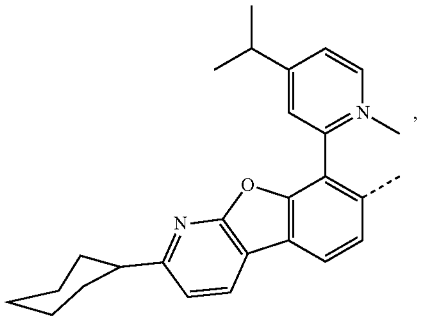
$L_{A167}$
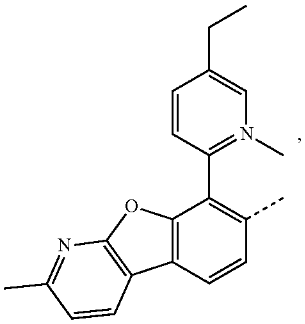
$L_{A168}$
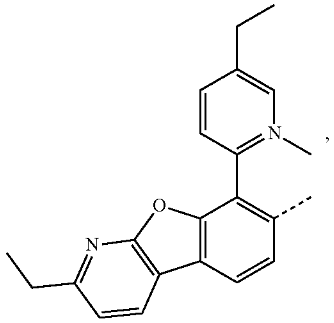
$L_{A169}$
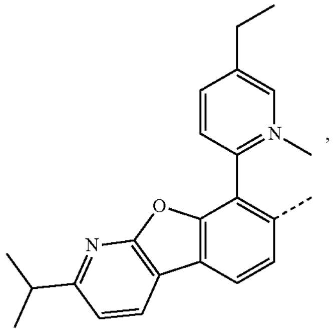
$L_{A170}$ -continued
$L_{A171}$
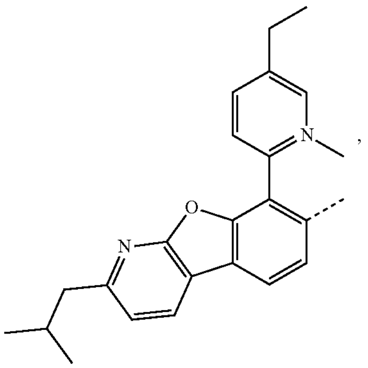
$L_{A172}$
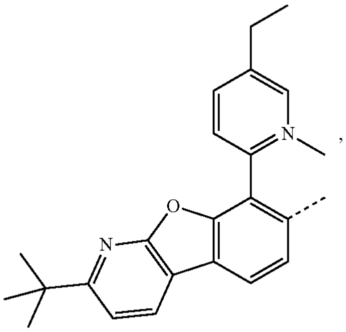
$L_{A173}$
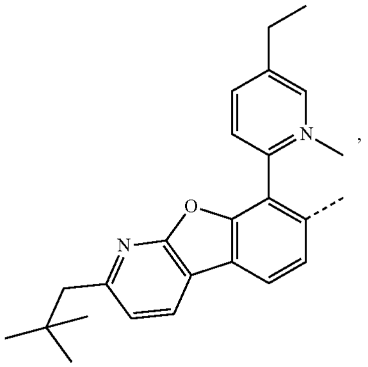
$L_{A174}$
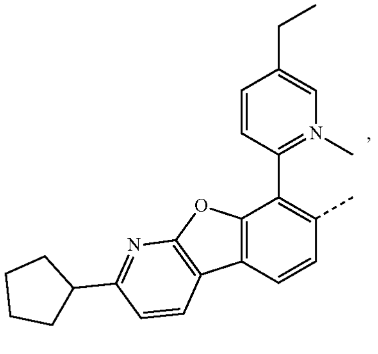
-continued
$L_{A175}$
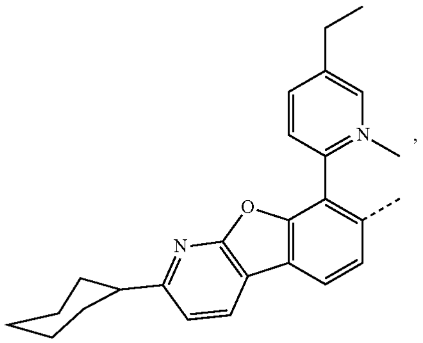
$L_{A176}$
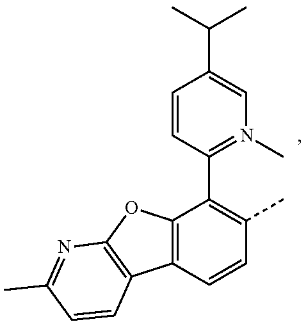
$L_{A177}$
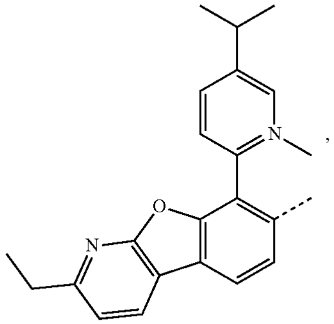
$L_{A178}$
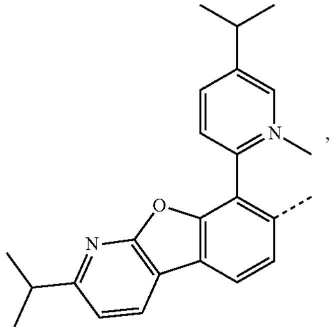

-continued
L_A179
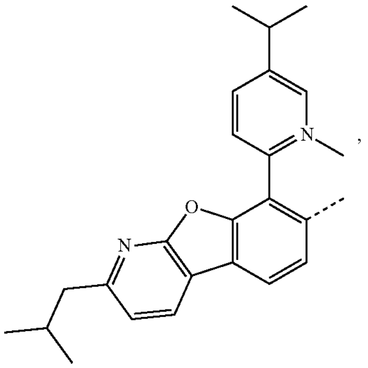
L_A180
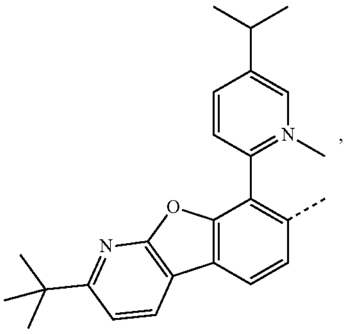
L_A181
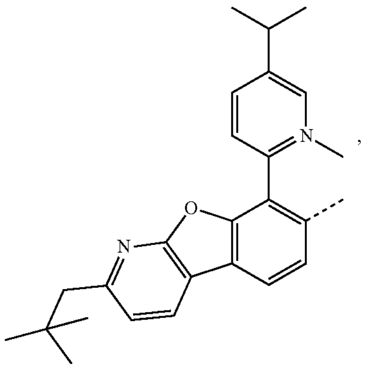
L_A182
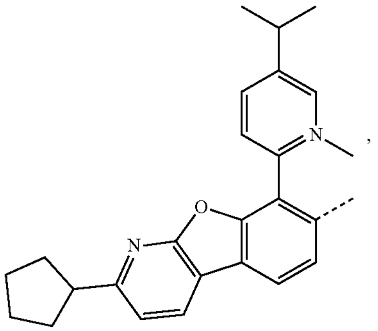
-continued
L_A183
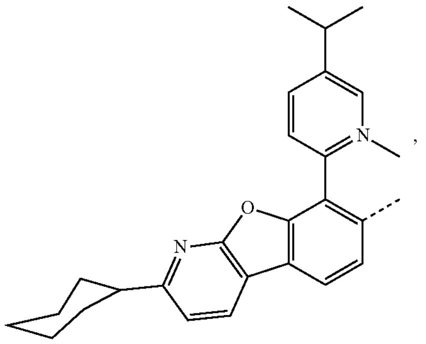
L_A184
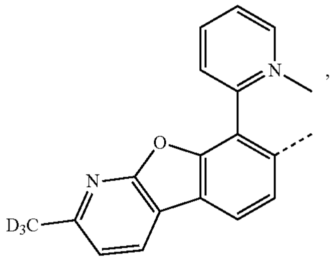
L_A185
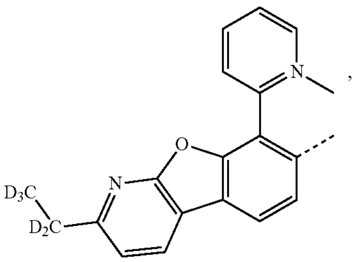
L_A186
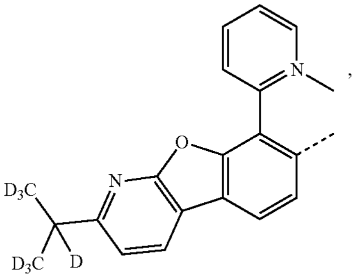
L_A187
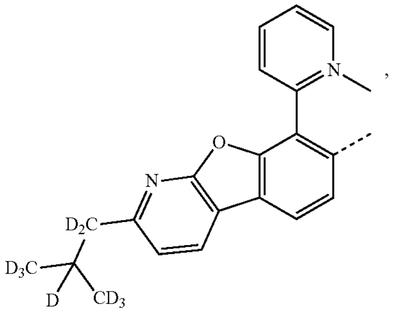

-continued
$L_{A188}$
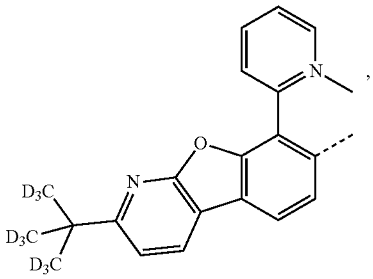
$L_{A189}$
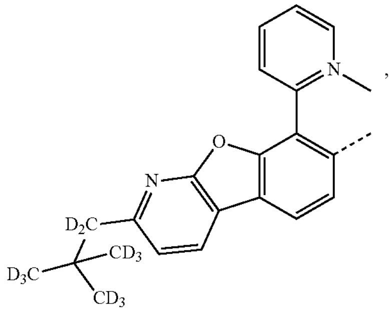
$L_{A190}$
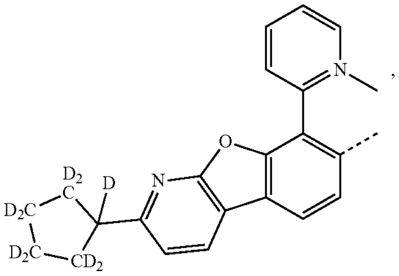
$L_{A191}$
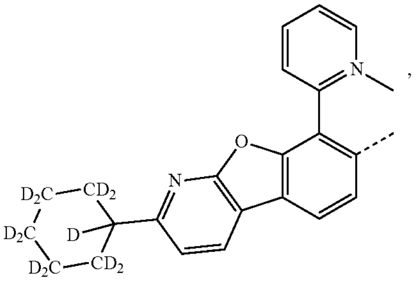
$L_{A192}$
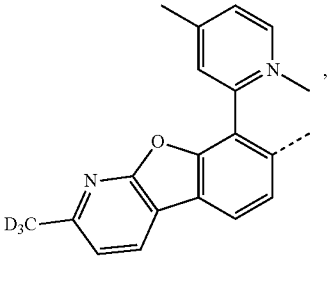
-continued
$L_{A193}$
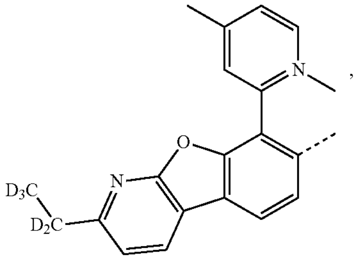
$L_{A194}$
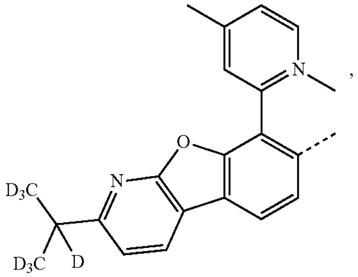
$L_{A195}$
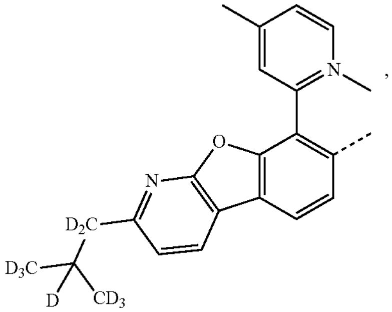
$L_{A196}$
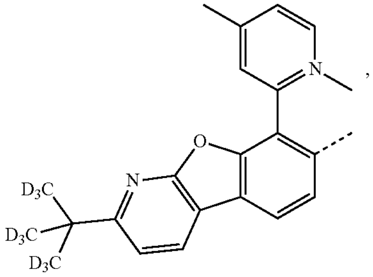
$L_{A197}$
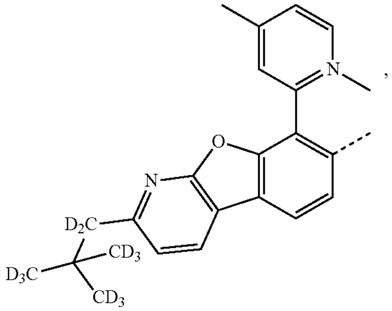

-continued
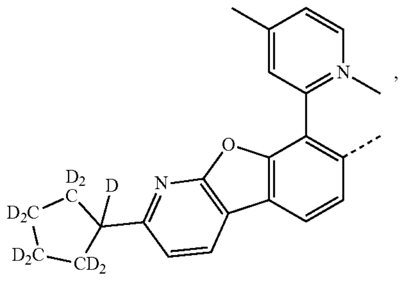
$L_{A198}$
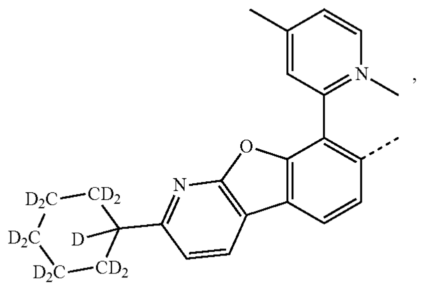
$L_{A199}$
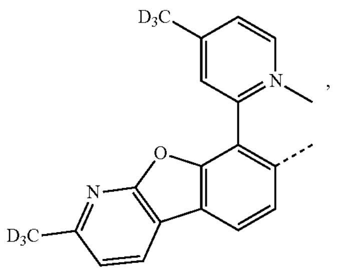
$L_{A200}$
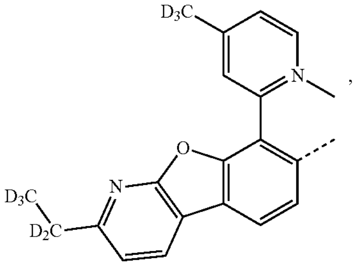
$L_{A201}$
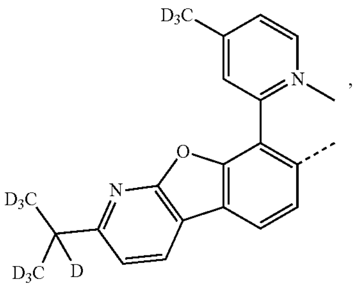
$L_{A202}$
-continued
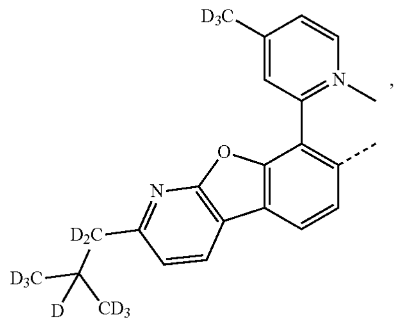
$L_{A203}$
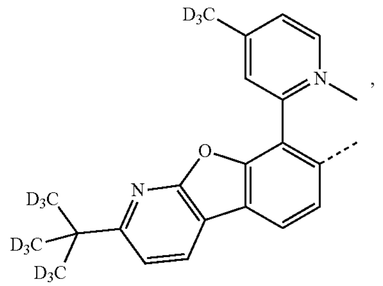
$L_{A204}$
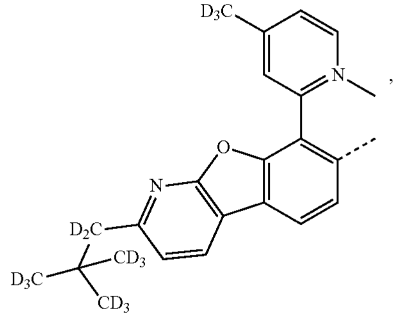
$L_{A205}$
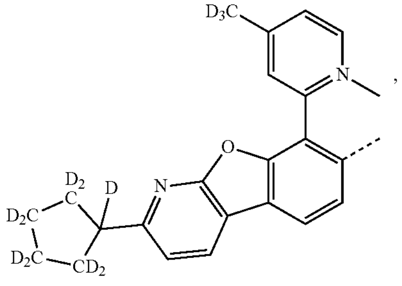
$L_{A206}$
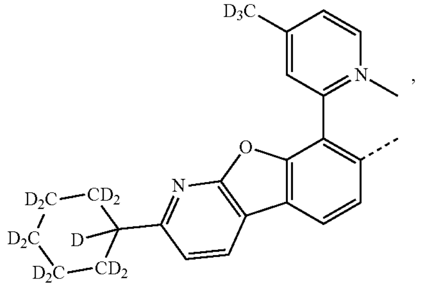
$L_{A207}$ -continued
$L_{A208}$
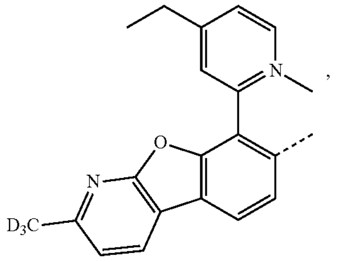
$L_{A209}$
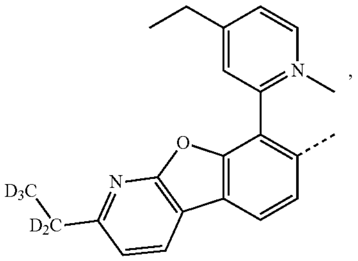
$L_{A210}$
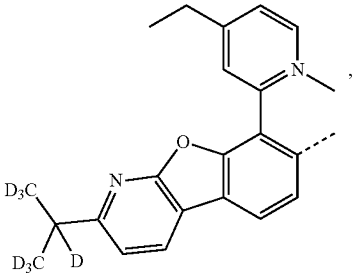
$L_{A211}$
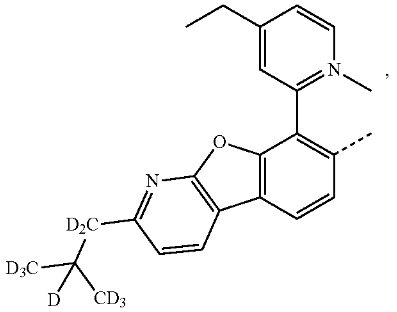
$L_{A212}$
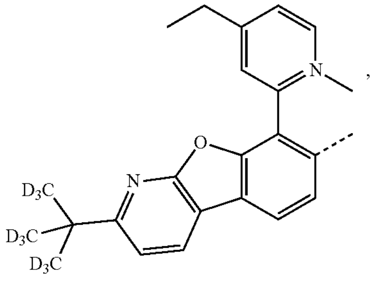
-continued
$L_{A213}$
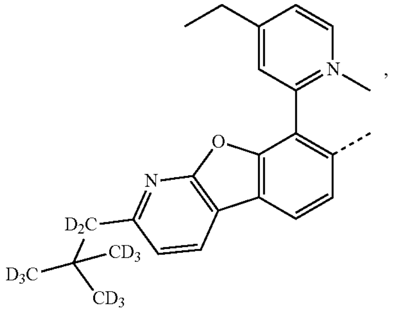
$L_{A214}$
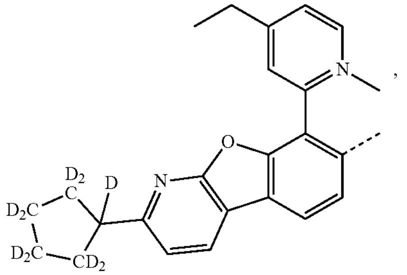
$L_{A215}$
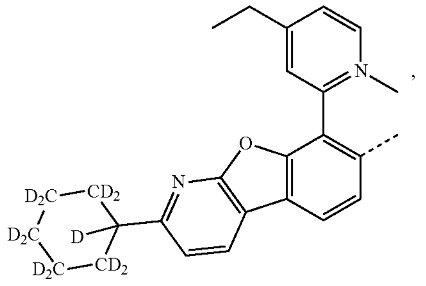
$L_{A216}$
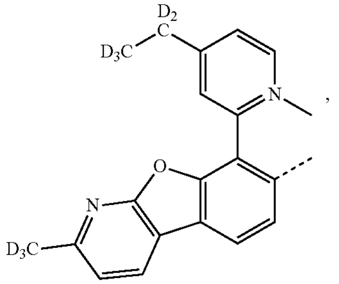
$L_{A217}$
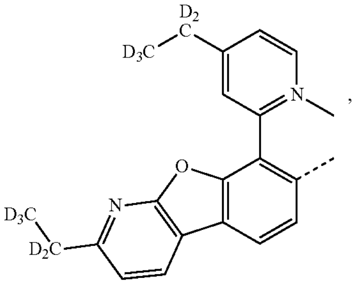

-continued
$L_{A218}$
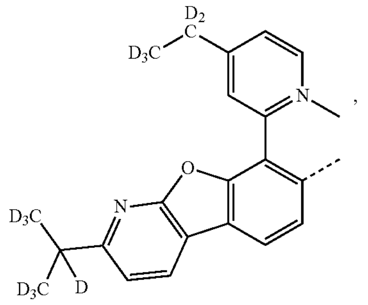
$L_{A219}$
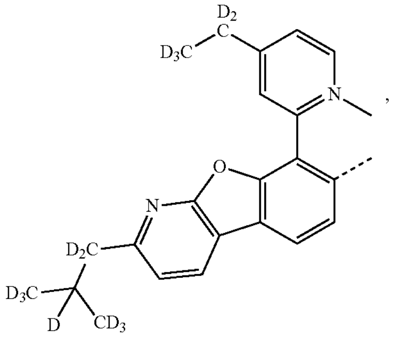
$L_{A220}$
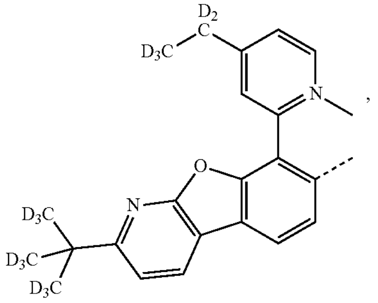
$L_{A221}$
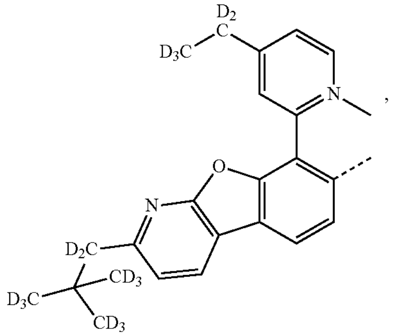
$L_{A222}$
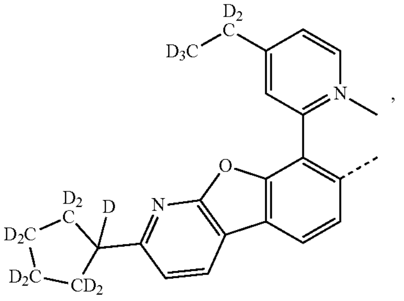
-continued
$L_{A223}$
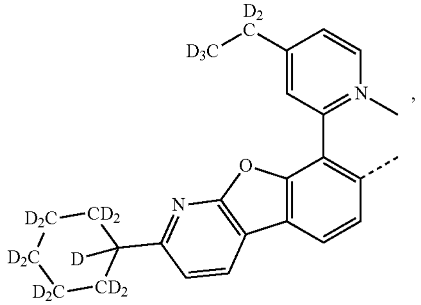
$L_{A224}$
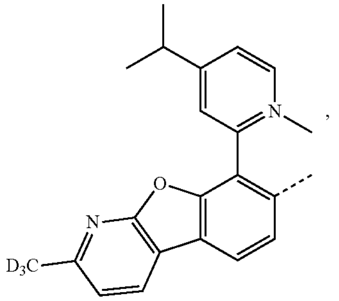
$L_{A225}$
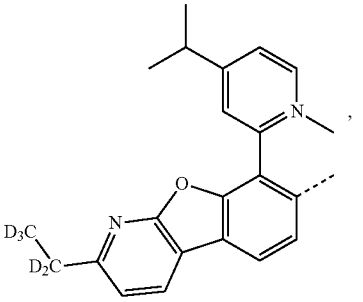
$L_{A226}$
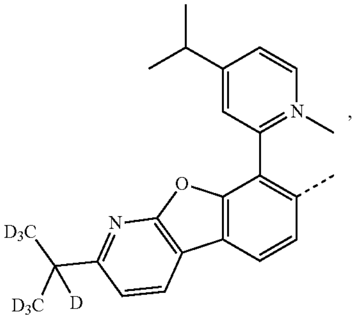
$L_{A227}$
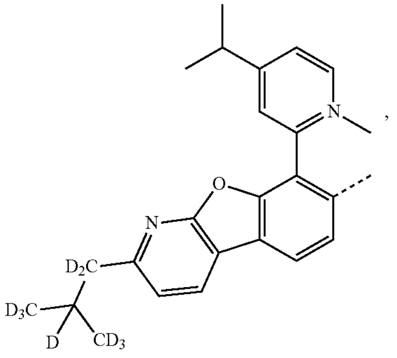

-continued
L_{A228}
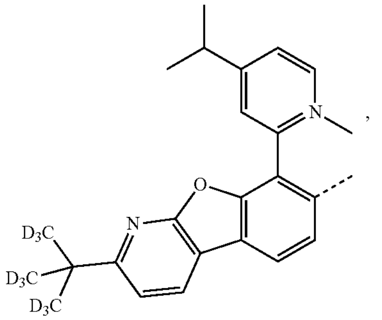
L_{A229}
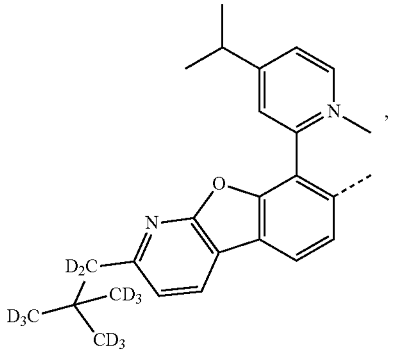
L_{A230}
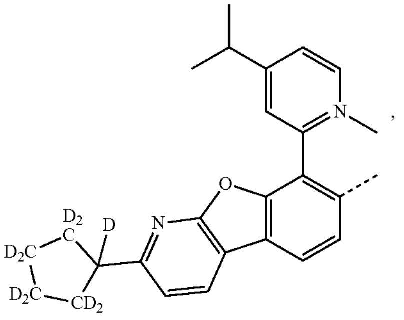
L_{A231}
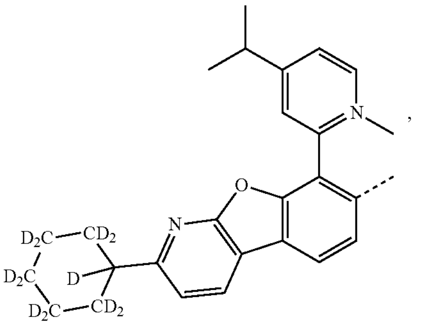
-continued
L_{A232}
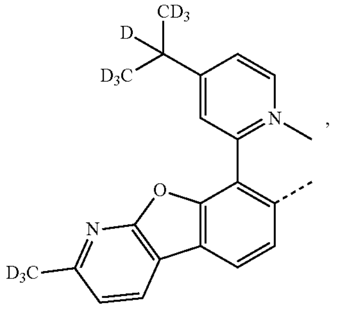
L_{A233}
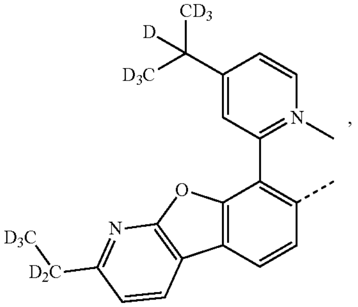
L_{A234}
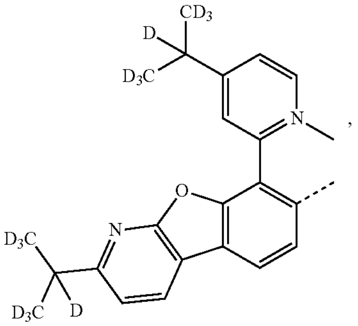
L_{A235}
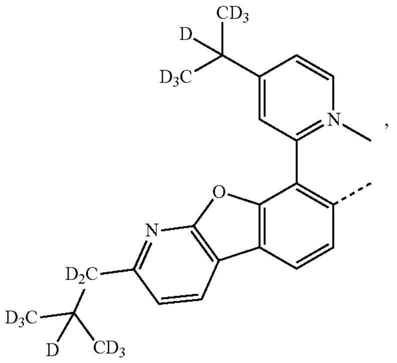

-continued
$L_{A236}$
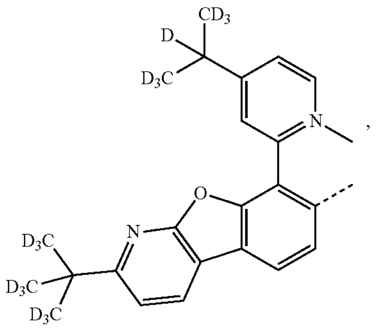
$L_{A237}$
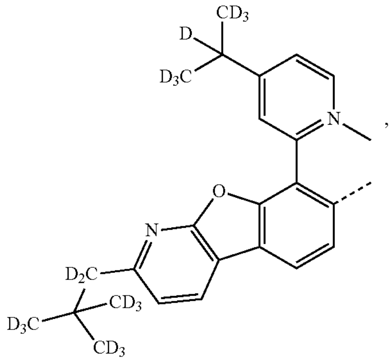
$L_{A238}$
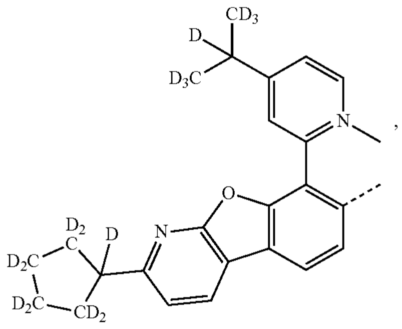
$L_{A239}$
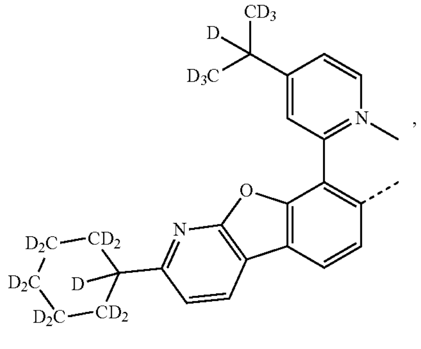
-continued
$L_{A240}$
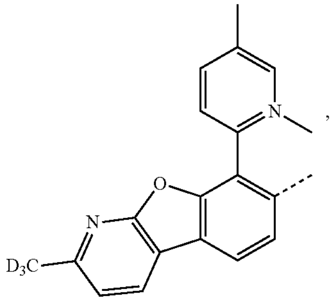
$L_{A241}$
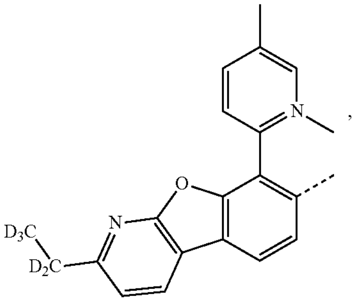
$L_{A242}$
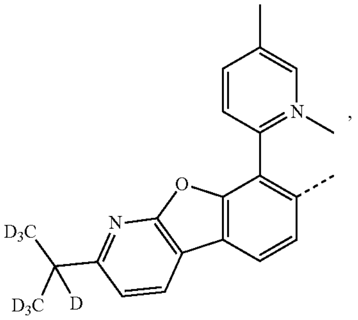
$L_{A243}$
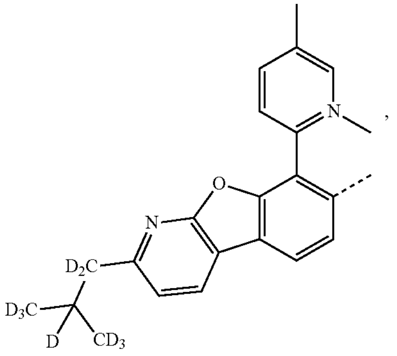
$L_{A244}$
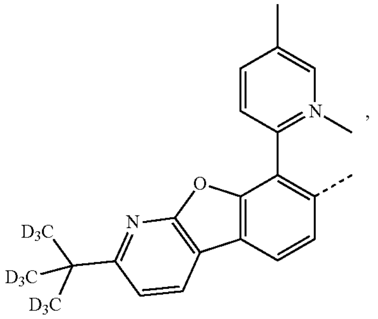

-continued
$L_{A245}$
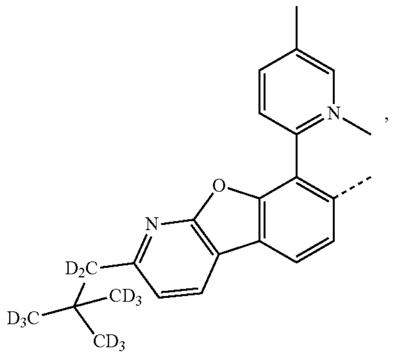
$L_{A246}$
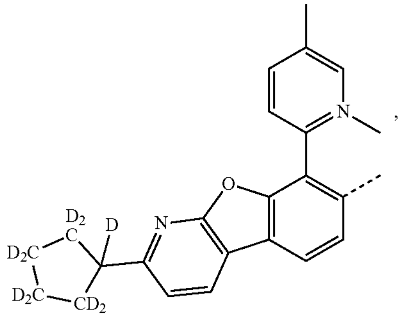
$L_{A247}$
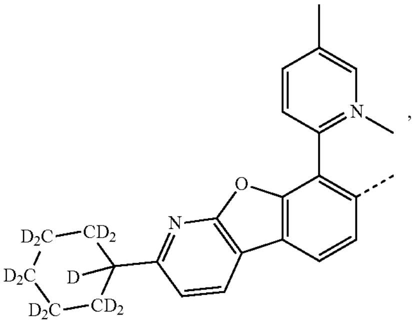
$L_{A248}$
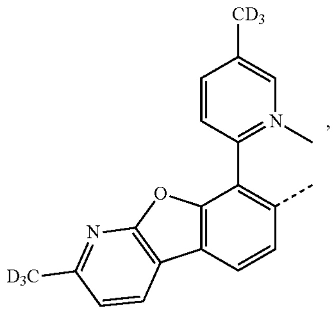
-continued
$L_{A249}$
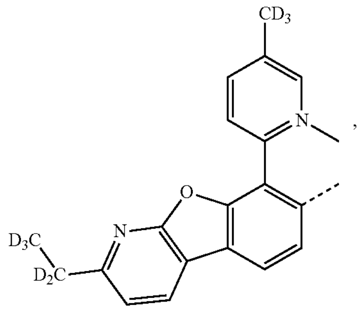
$L_{A250}$
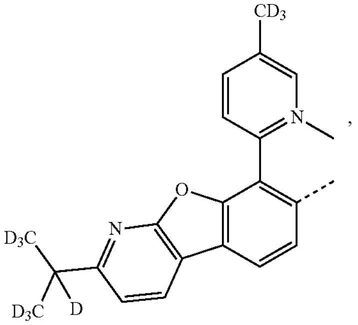
$L_{A251}$
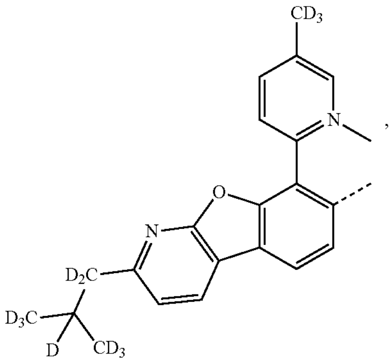
$L_{A252}$
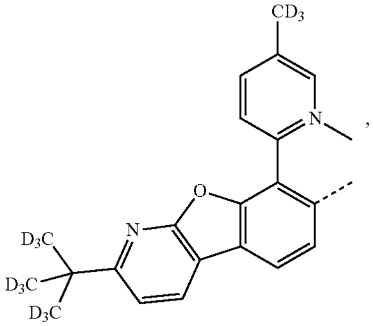

-continued
L<sub>A253</sub>
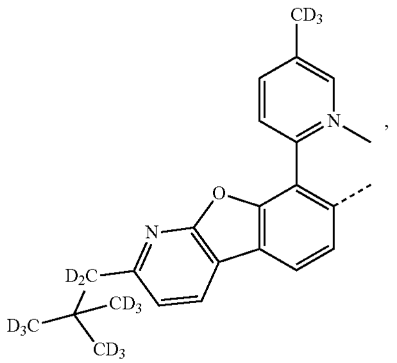
L$_{A254}$
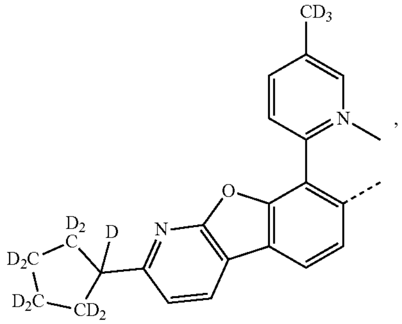
L$_{A255}$
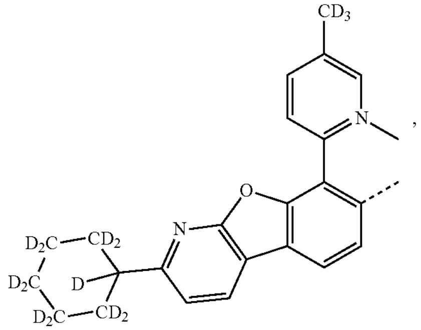
L$_{A256}$
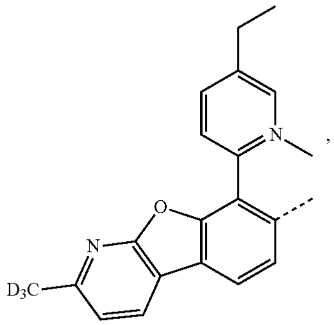
-continued
L$_{A257}$
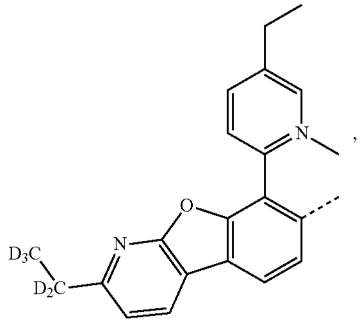
L$_{A258}$
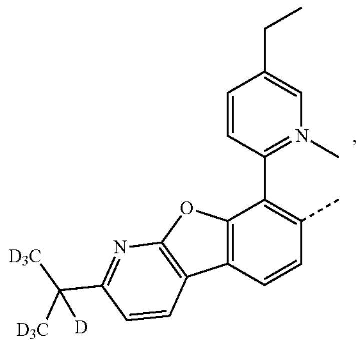
L$_{A259}$
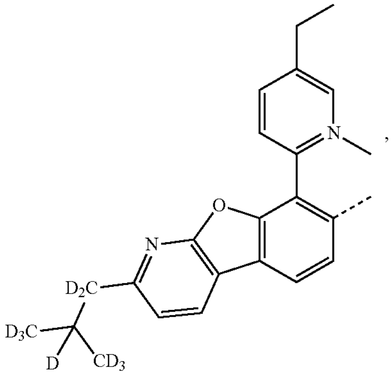
L$_{A260}$
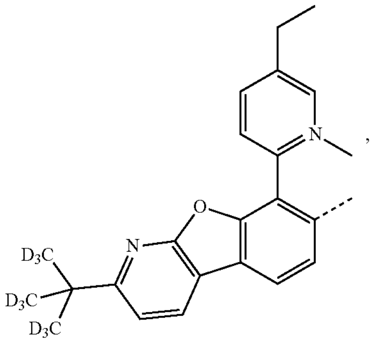

-continued
$L_{A261}$
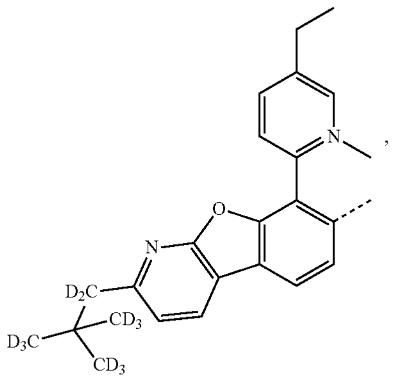
$L_{A262}$
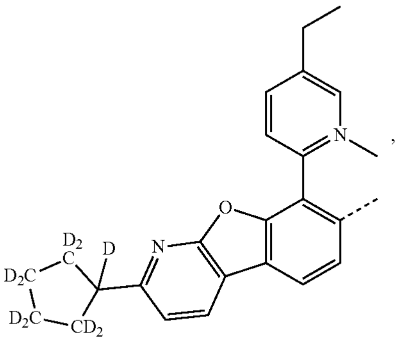
$L_{A263}$
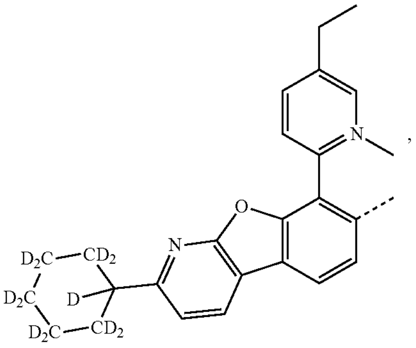
$L_{A264}$
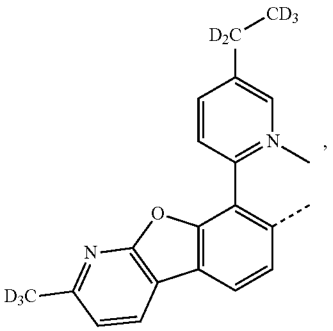
-continued
$L_{A265}$
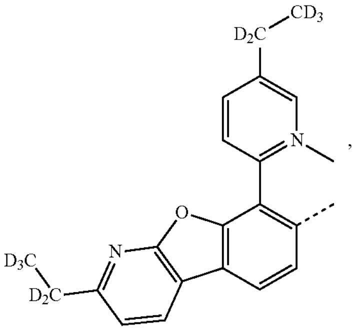
$L_{A266}$
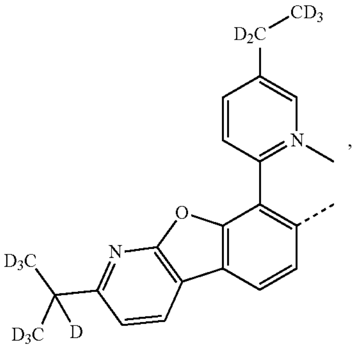
$L_{A267}$
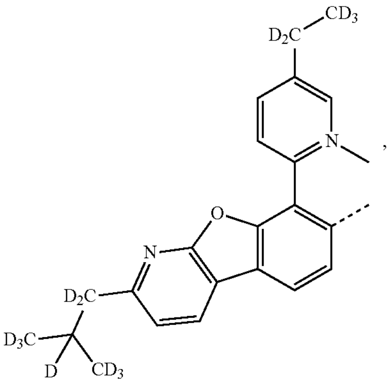
$L_{A268}$
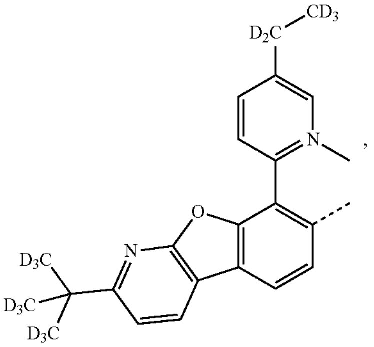

-continued
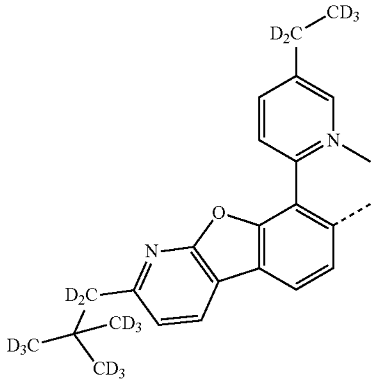
$L_{A269}$
,
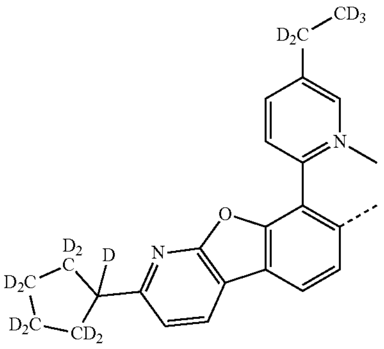
$L_{A270}$
,
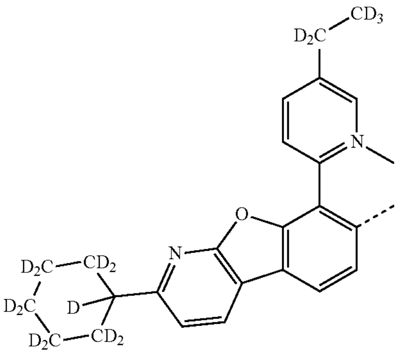
$L_{A271}$
,
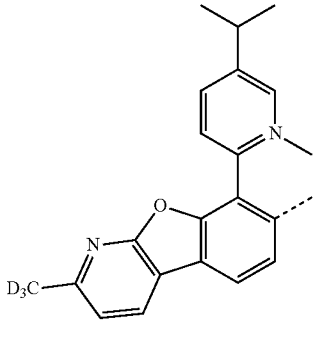
$L_{A272}$
,
-continued
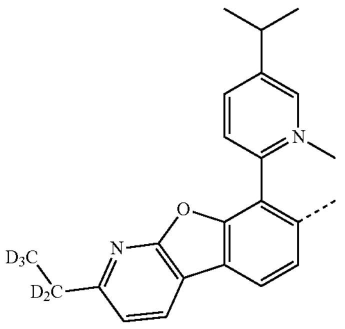
$L_{A273}$
,
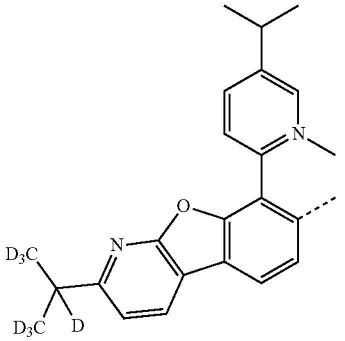
$L_{A274}$
,
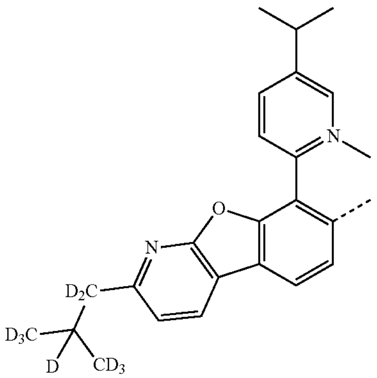
$L_{A275}$
,
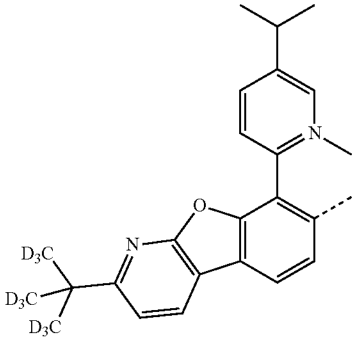
$L_{A276}$
, -continued
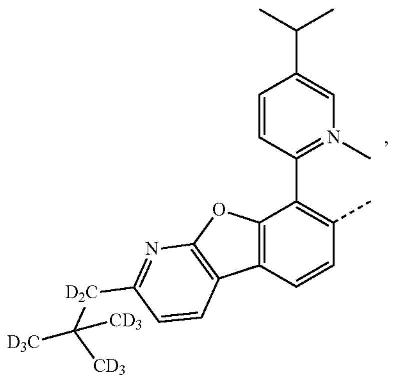
$L_{A277}$
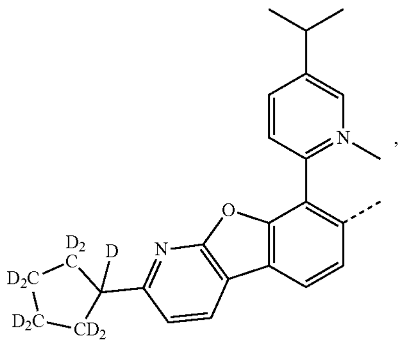
$L_{A278}$
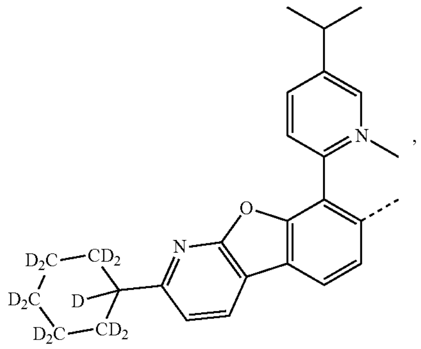
$L_{A279}$
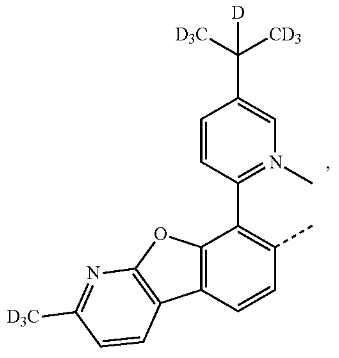
$L_{A280}$
-continued
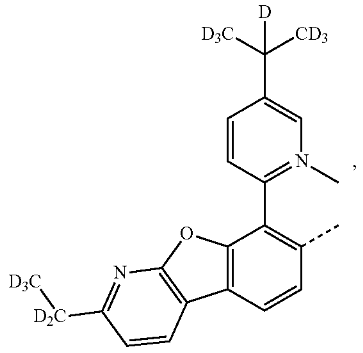
$L_{A281}$
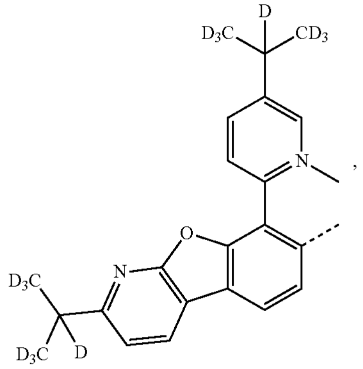
$L_{A282}$
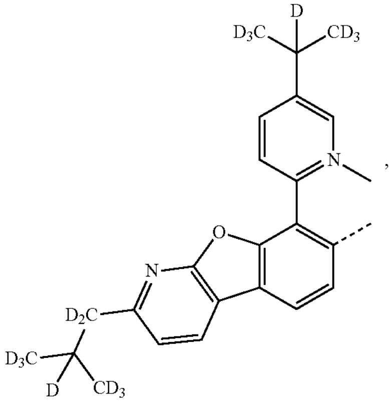
$L_{A283}$
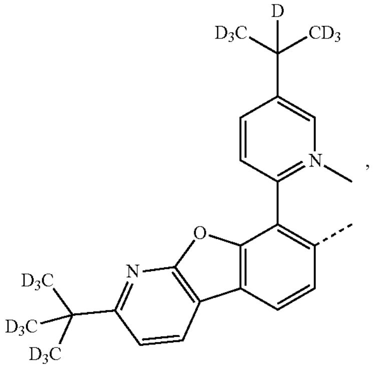
$L_{A284}$ $L_{A285}$
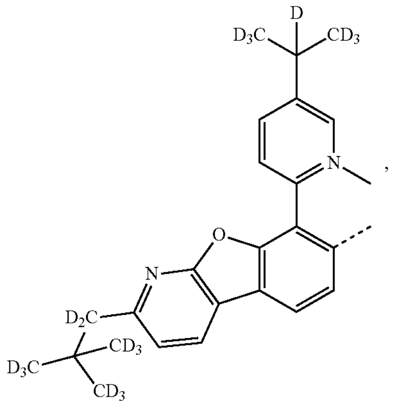
$L_{A286}$
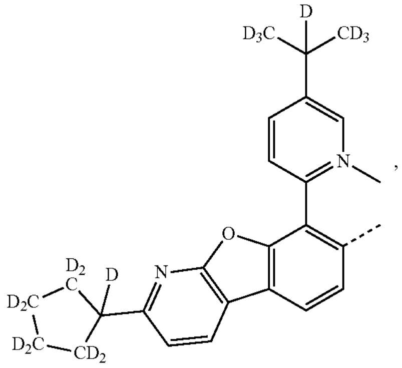
$L_{A287}$
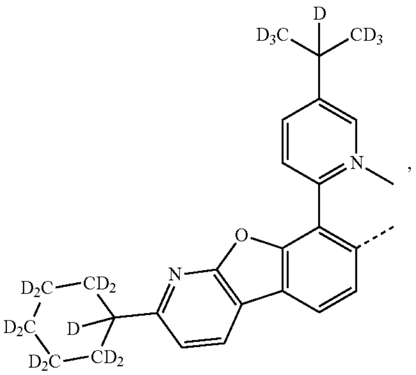
$L_{A288}$
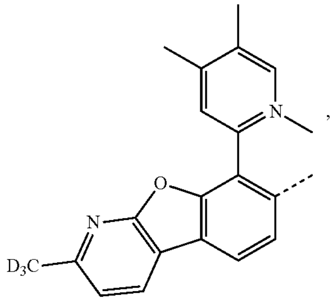
$L_{A289}$
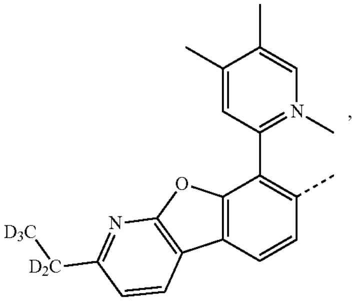
$L_{A290}$
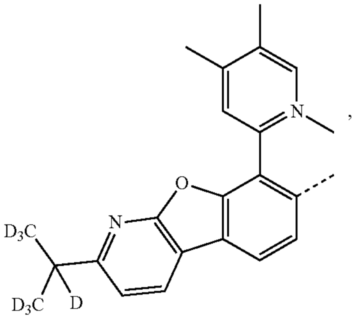
$L_{A291}$
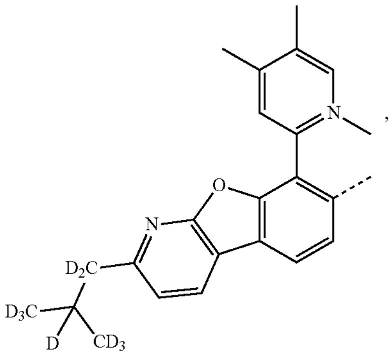
$L_{A292}$
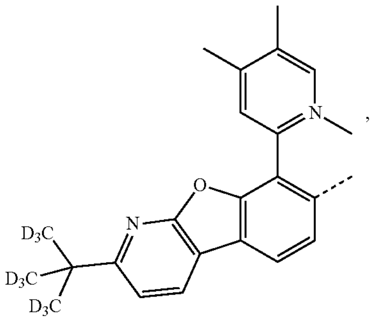

-continued
$L_{A293}$
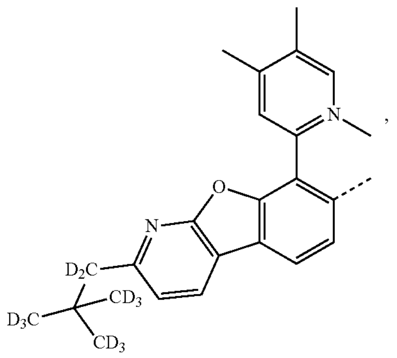
$L_{A294}$
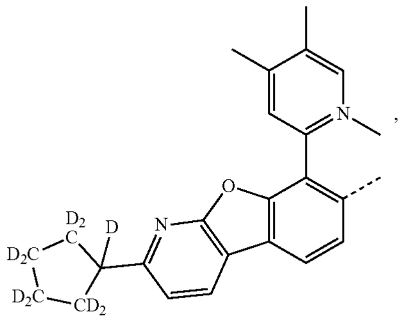
$L_{A295}$
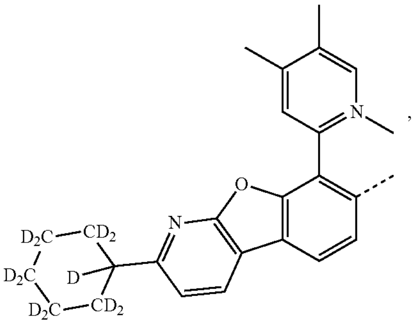
$L_{A296}$
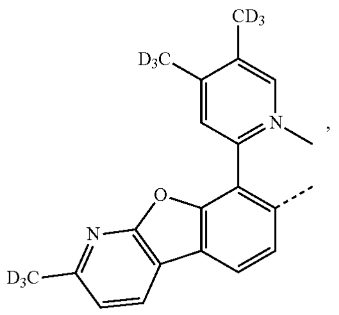
-continued
$L_{A297}$
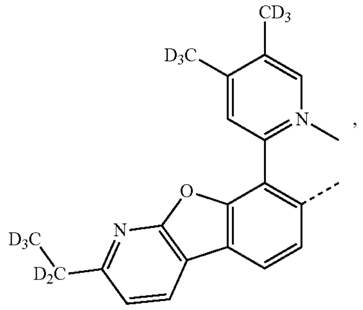
$L_{A298}$
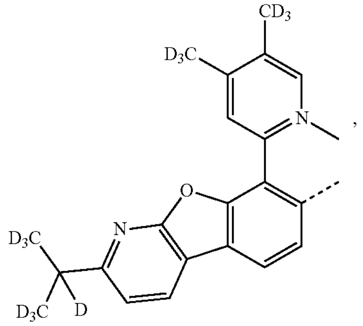
$L_{A299}$
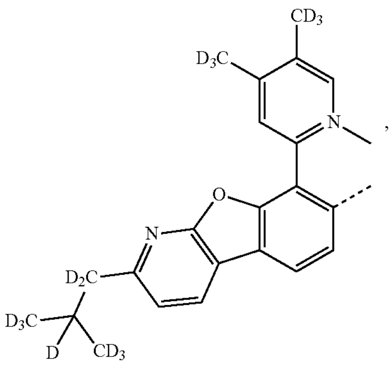
$L_{A300}$
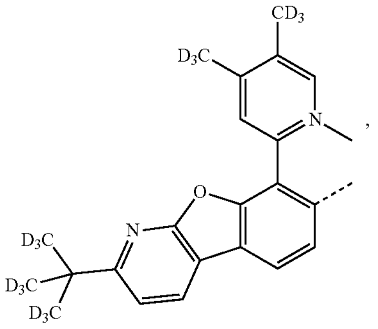

-continued
$L_{A301}$
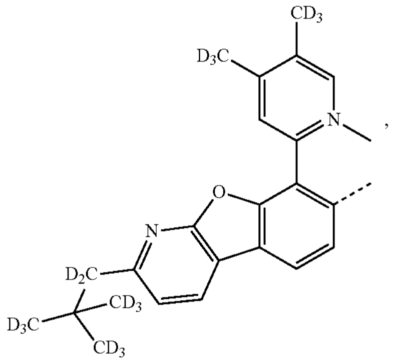
$L_{A302}$
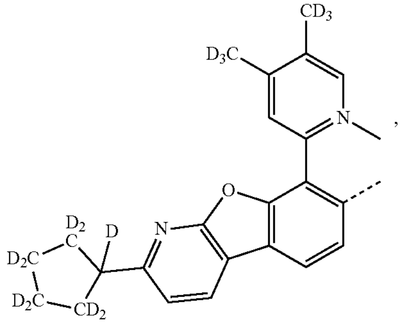
$L_{A303}$
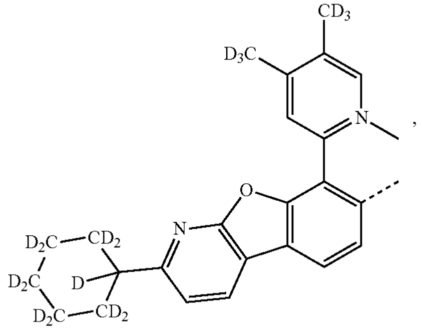
$L_{A304}$
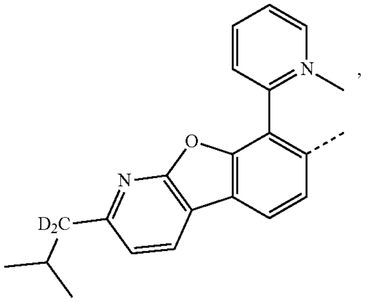
-continued
$L_{A305}$
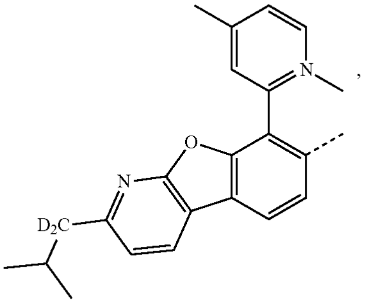
$L_{A306}$
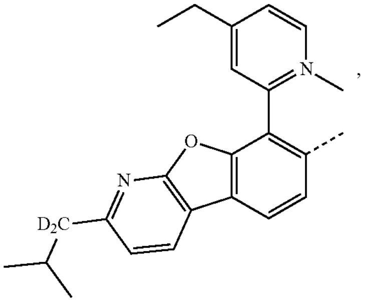
$L_{A307}$
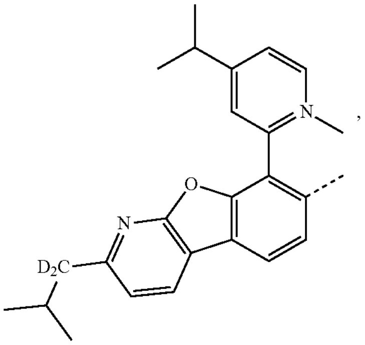
$L_{A308}$
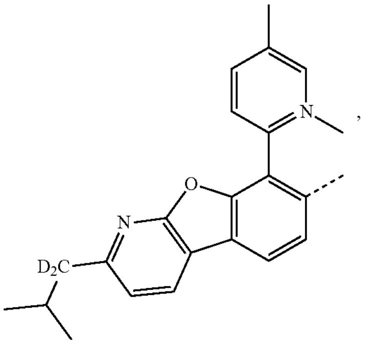

-continued
L_A309
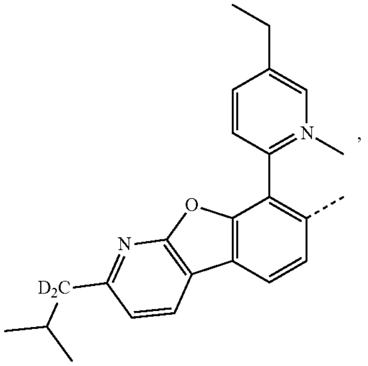
L_A310
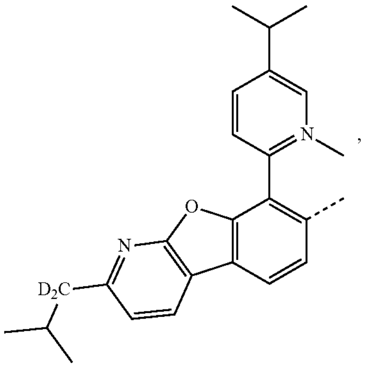
L_A311
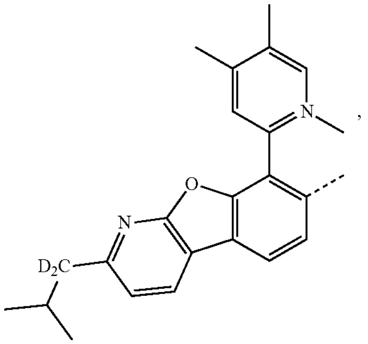
L_A312
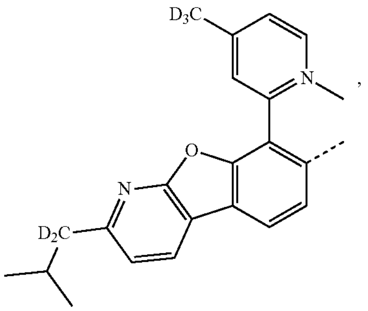
L_A313
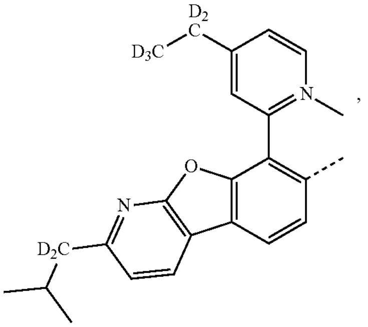
L_A314
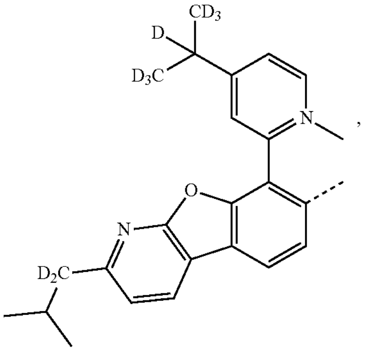
L_A315
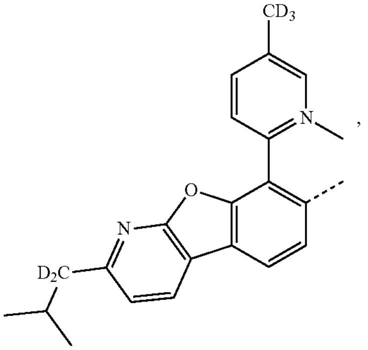
L_A316
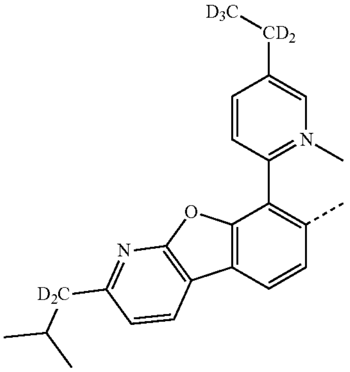
, and -continued
$L_{A317}$
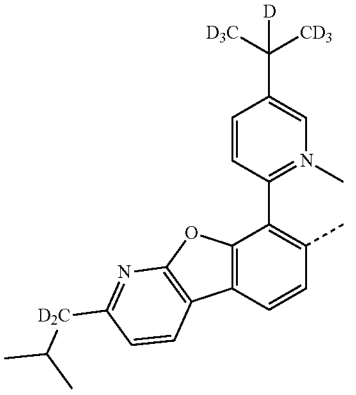
16. The compound of claim 15, wherein $R^3$ and $R^4$ are independently selected from the group consisting of hydrogen, deuterium, alkyl, and combinations thereof.
17. The compound of claim 15, wherein $R^3$ and $R^4$ are H.
18. The compound of claim 1, wherein $L_B$ is selected from the group consisting of:
$L_{B1}$
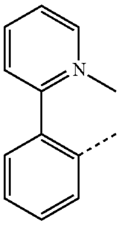
$L_{B2}$
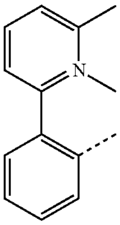
$L_{B3}$
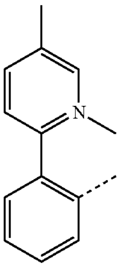
$L_{B4}$
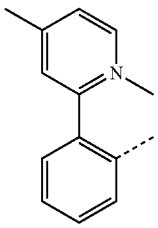
-continued
$L_{B5}$
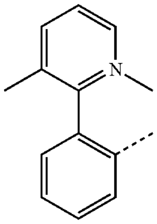
$L_{B6}$
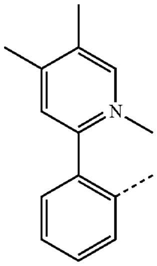
$L_{B7}$
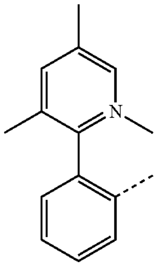
$L_{B8}$
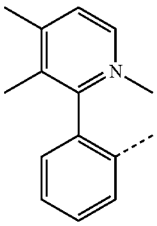
$L_{B9}$
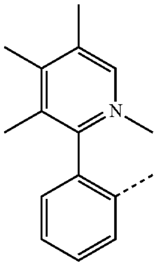
$L_{B10}$
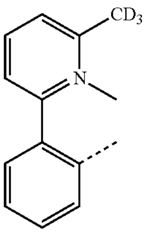

-continued
LB11
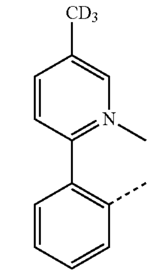
LB12
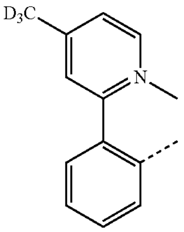
LB13
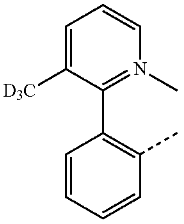
LB14
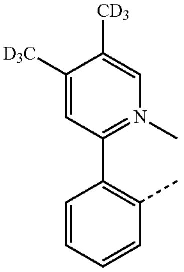
LB15
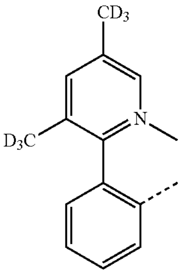
LB16
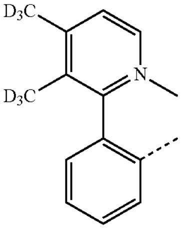
-continued
LB17
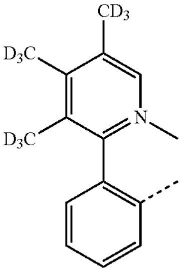
LB18
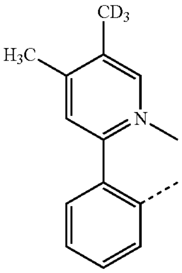
LB19
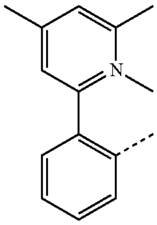
LB20
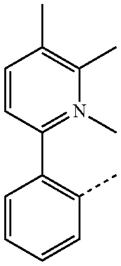
LB21
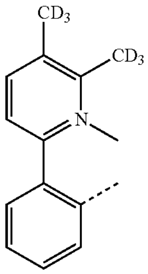
LB22
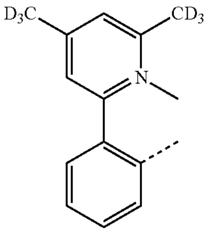

$L_{B23}$
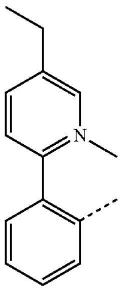
$L_{B24}$
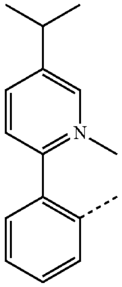
$L_{B25}$
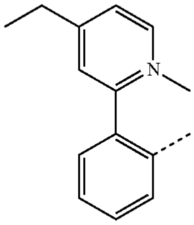
$L_{B26}$
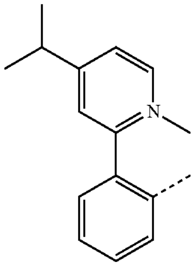
$L_{B27}$
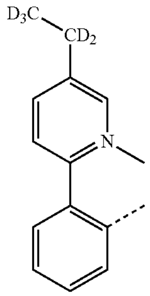
$L_{B28}$
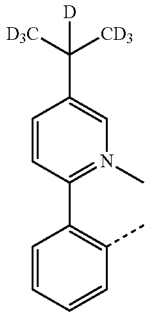
$L_{B29}$
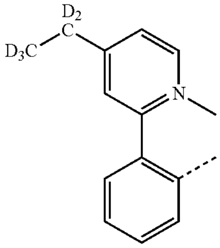
, and
$L_{B30}$
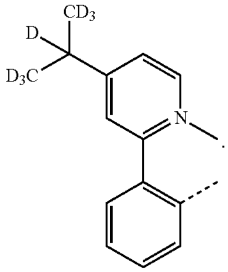
.
19. The compound of claim 1, wherein the compound is selected from the group consisting of:
Compound II-1
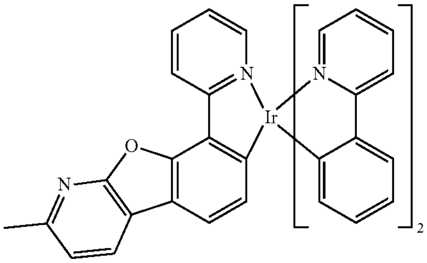
,
Compound II-2
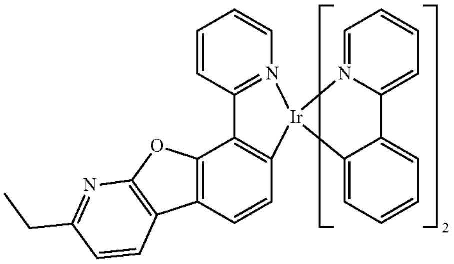
, Compound II-3
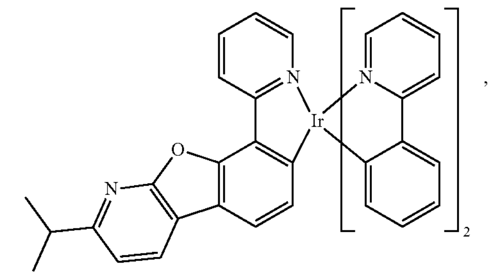
Compound II-4
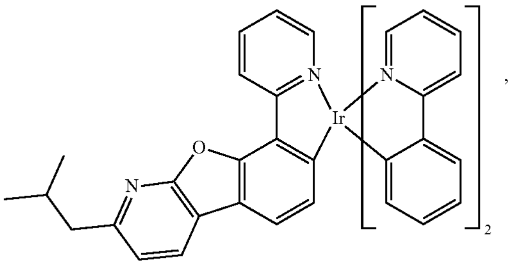
Compound II-5
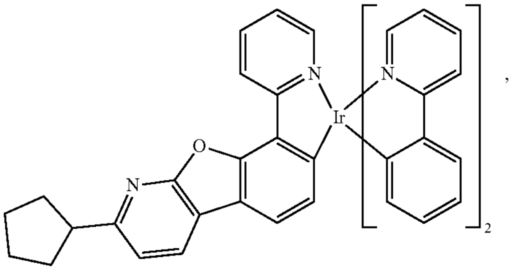
Compound II-6
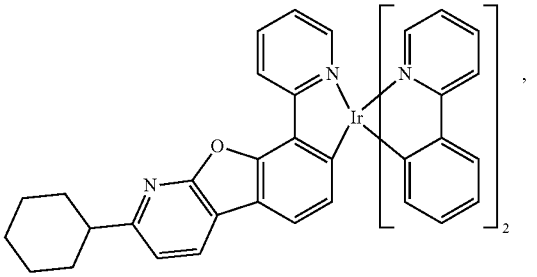
Compound II-7
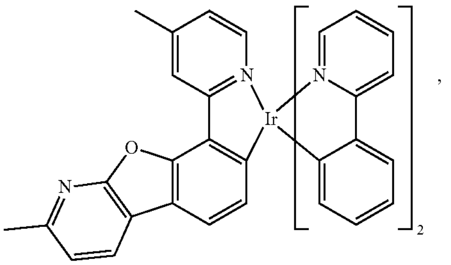
Compound II-8
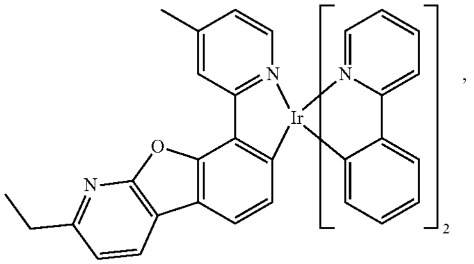
Compound II-9
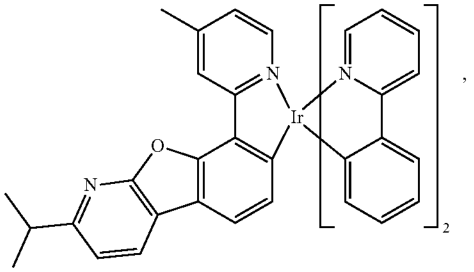
Compound II-10
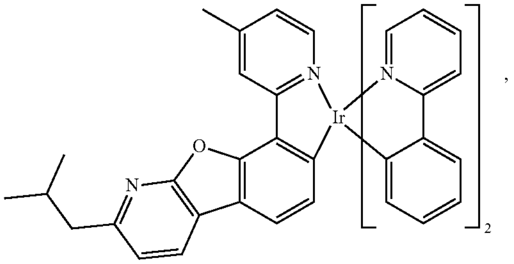
Compound II-11
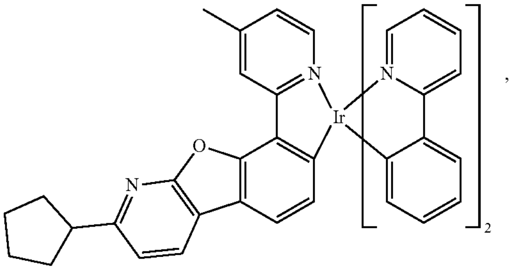
Compound II-12
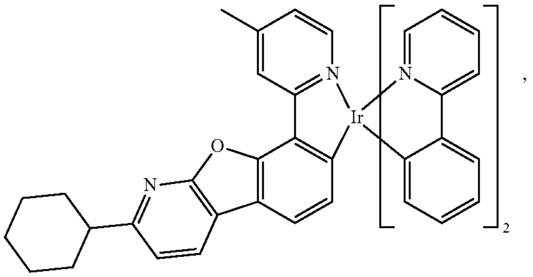

-continued
Compound II-13
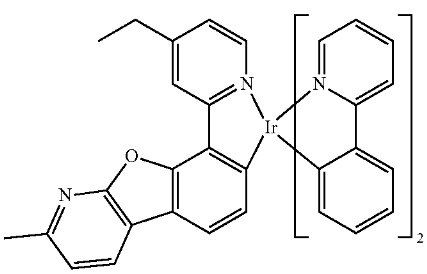
,
Compound II-14
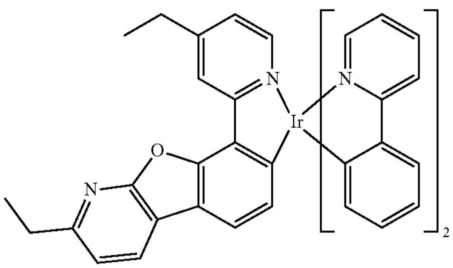
,
Compound II-15
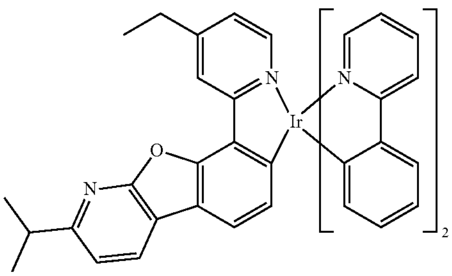
,
Compound II-16
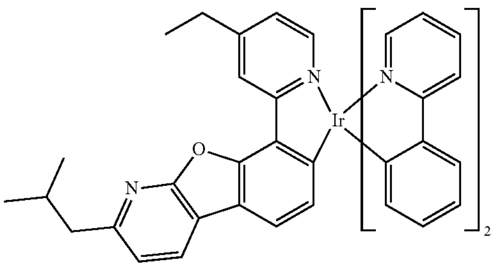
,
Compound II-17
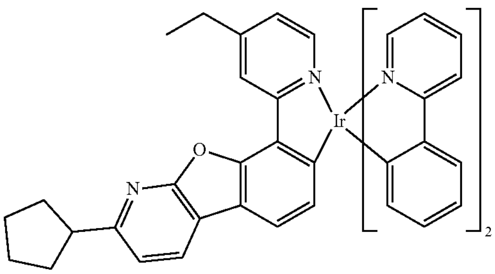
,
-continued
Compound II-18
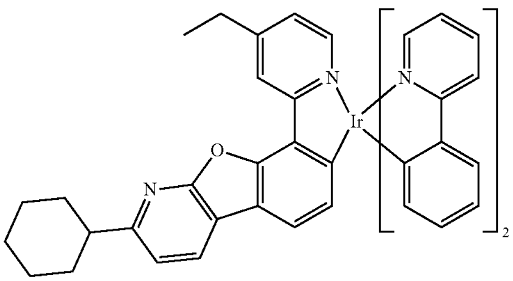
,
Compound II-19
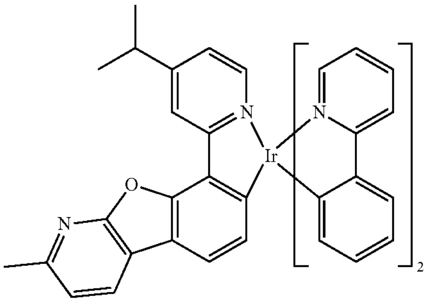
,
Compound II-20
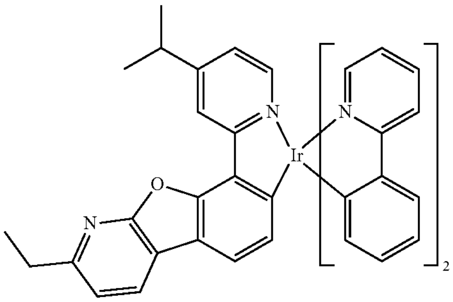
,
Compound II-21
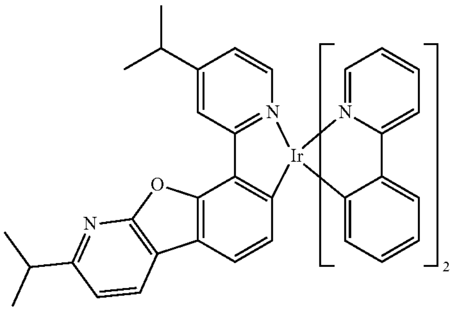
,
Compound II-22
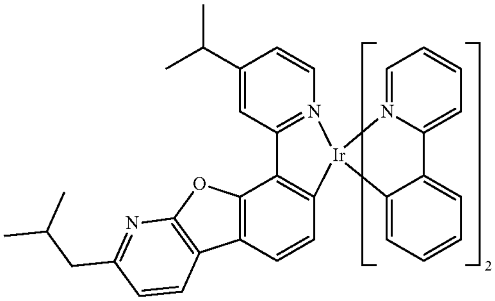
, -continued
Compound II-23
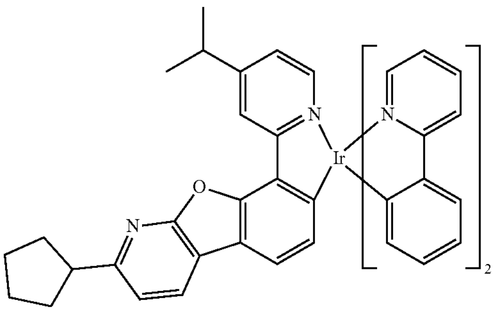
,
Compound II-24
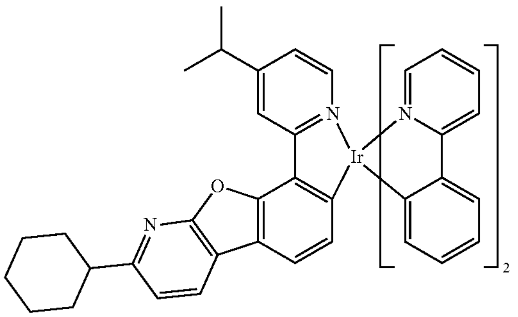
,
Compound II-25
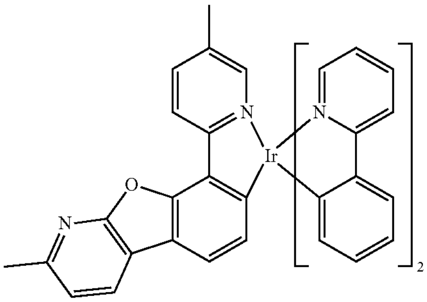
,
Compound II-26
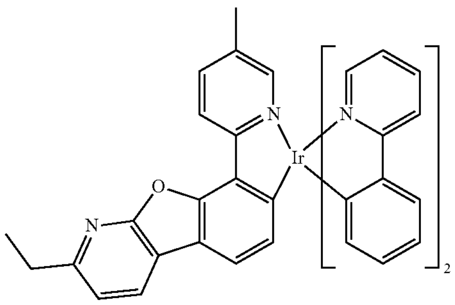
,
-continued
Compound II-27
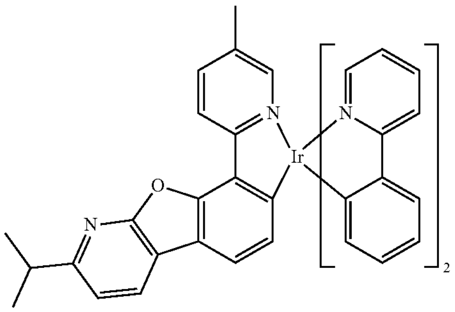
,
Compound II-28
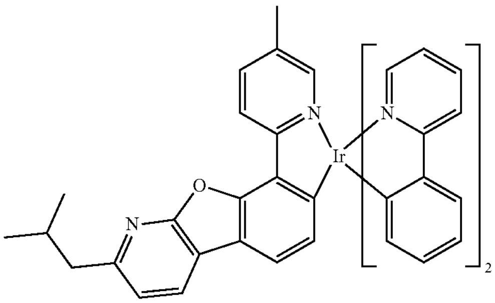
,
Compound II-29
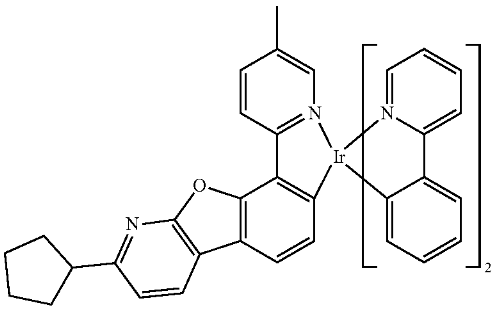
,
Compound II-30
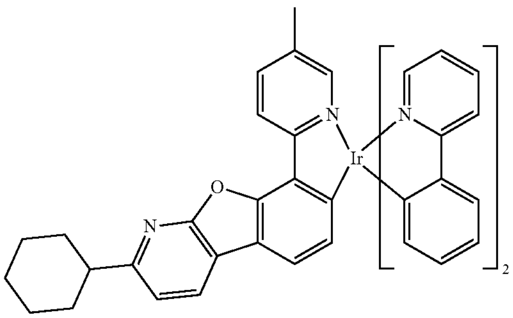
, -continued
Compound II-31
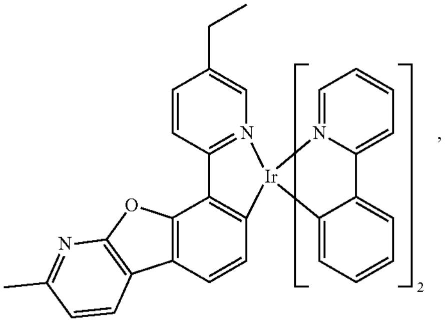
,
Compound II-32
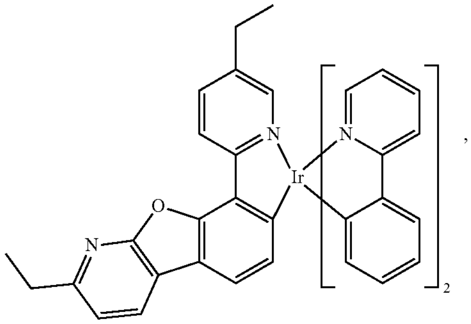
,
Compound II-33
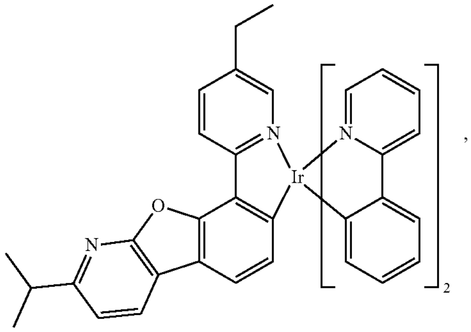
,
Compound II-34
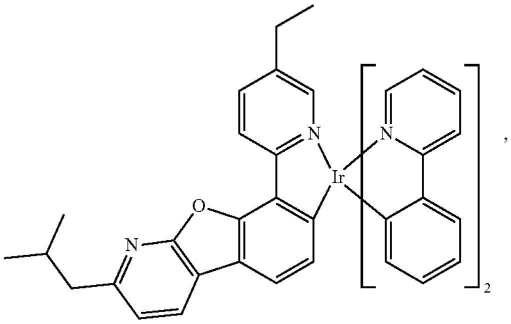
,
-continued
Compound II-35
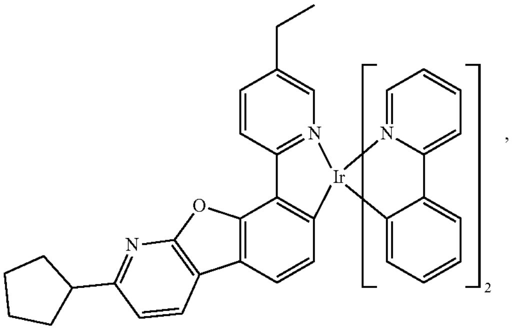
,
Compound II-36
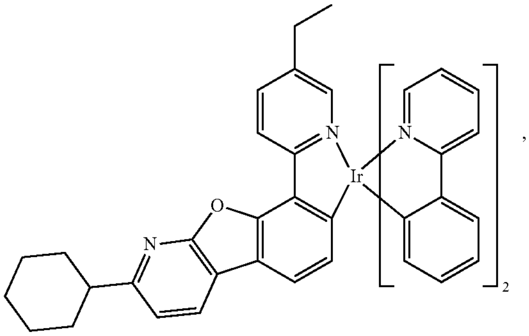
,
Compound II-37
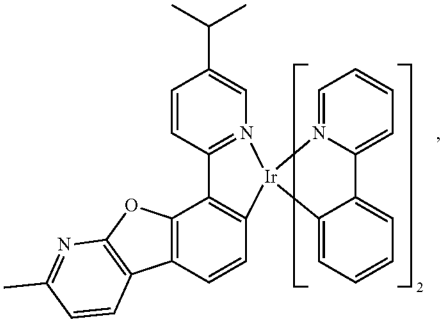
,
Compound II-38
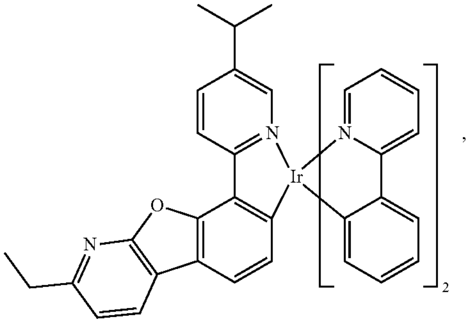
, -continued
Compound II-39
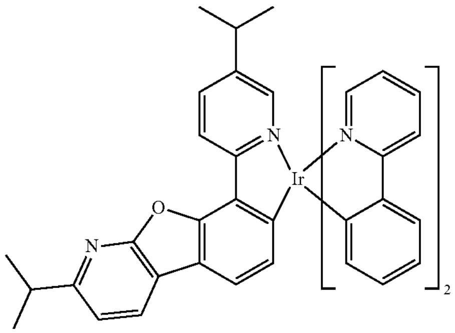
,
Compound II-40
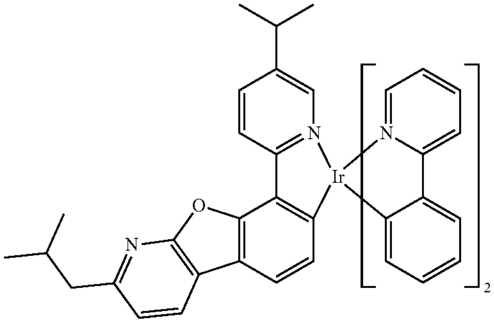
,
Compound II-41
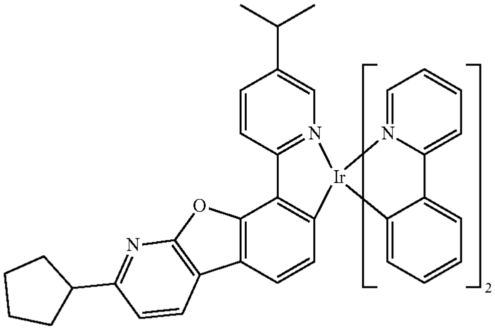
,
Compound II-42
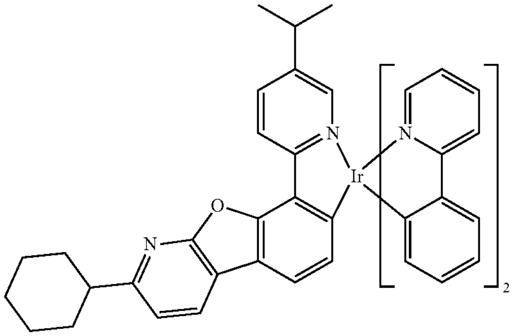
,
-continued
Compound II-43
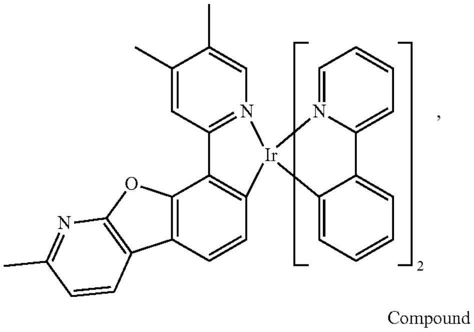
,
Compound II-44
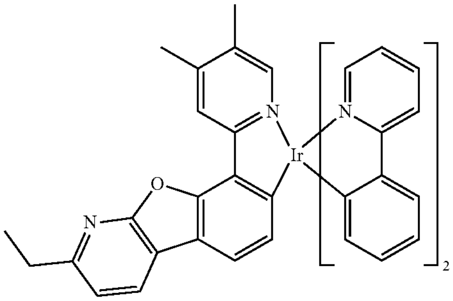
,
Compound II-45
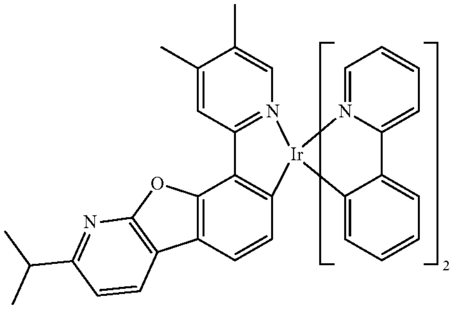
,
Compound II-46
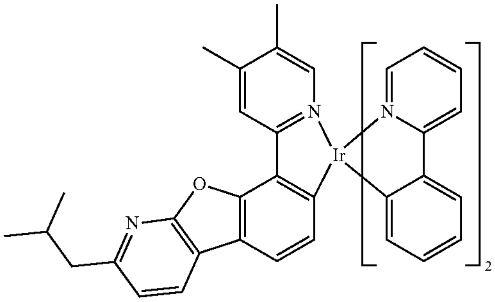
,
Compound II-47
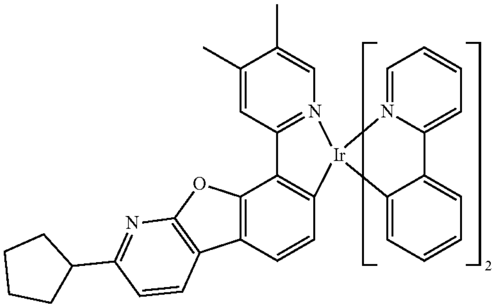
, -continued
Compound II-48
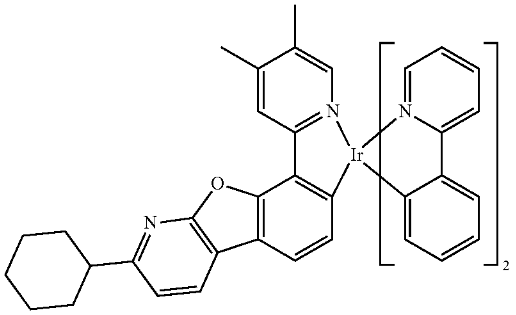
,
Compound II-49
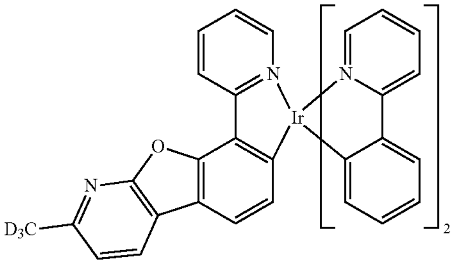
,
Compound II-50
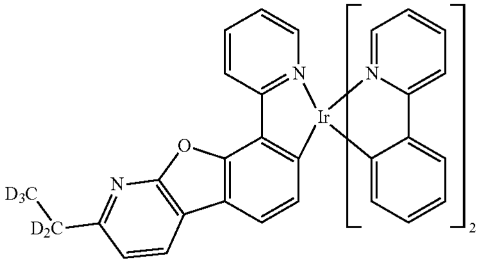
,
Compound II-51
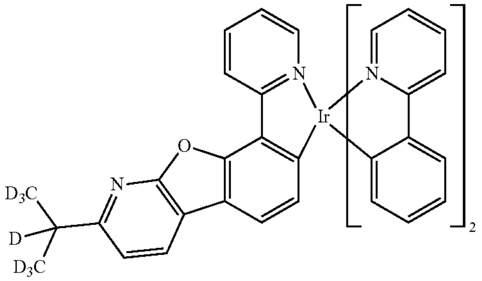
,
Compound II-52
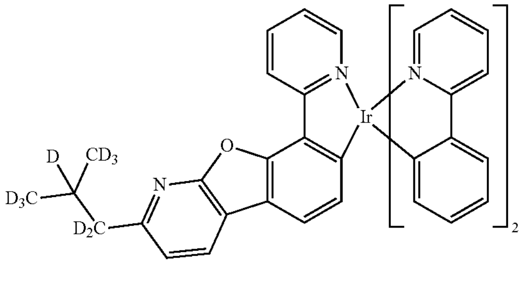
,
-continued
Compound II-53
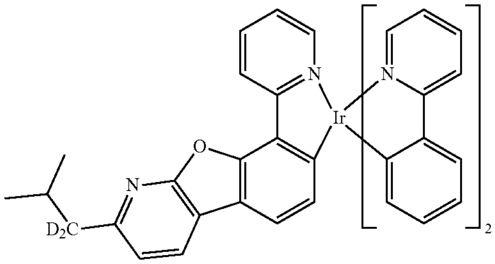
,
Compound II-54
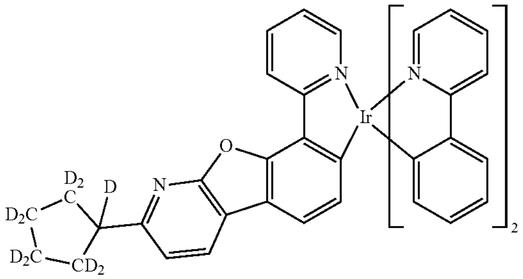
,
Compound II-55
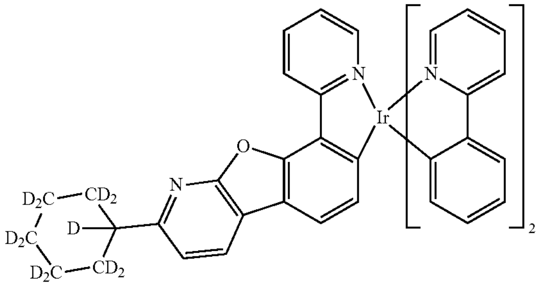
,
Compound II-56
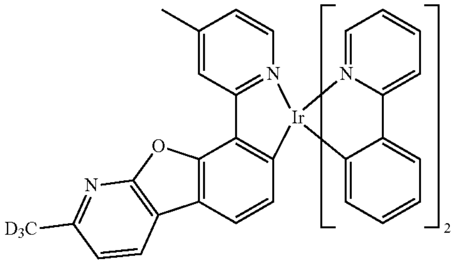
,
Compound II-57
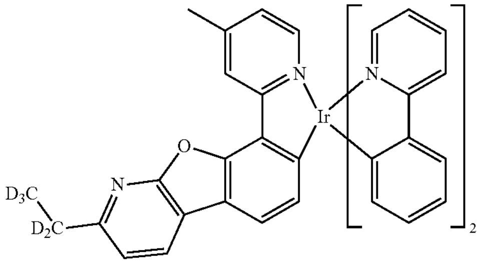
, -continued
Compound II-58
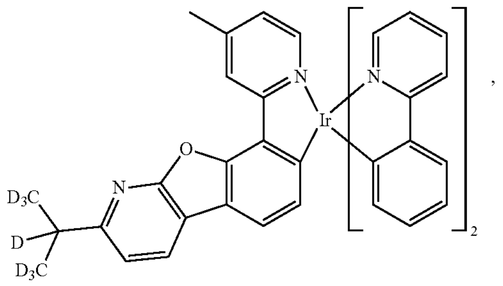
Compound II-59
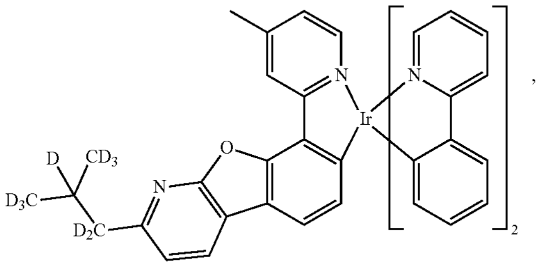
Compound II-60
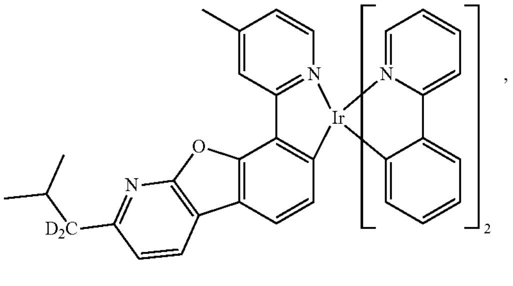
Compound II-61
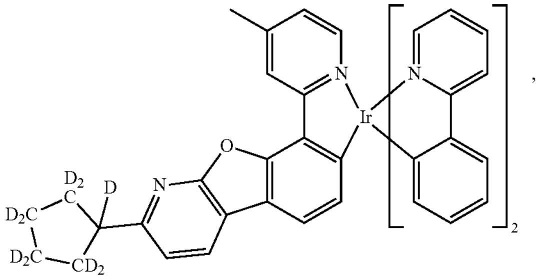
Compound II-62
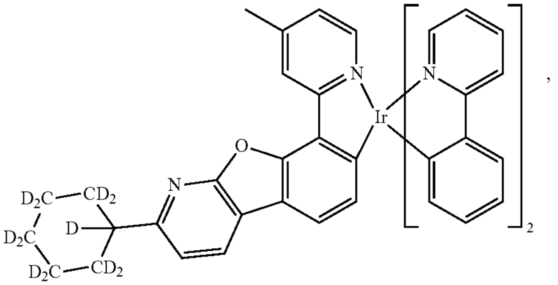
-continued
Compound II-63
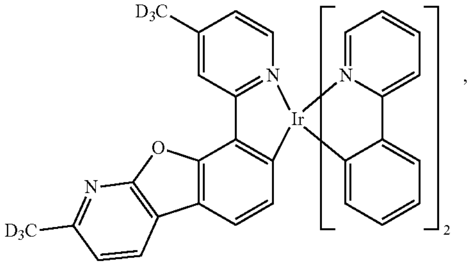
Compound II-64
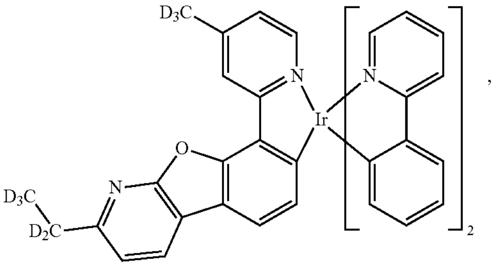
Compound II-65
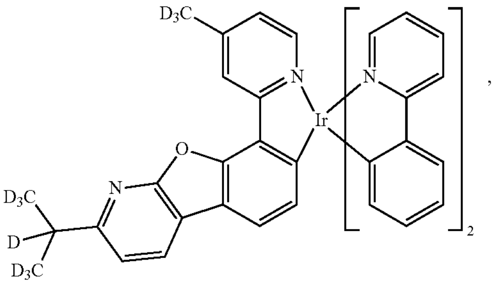
Compound II-66
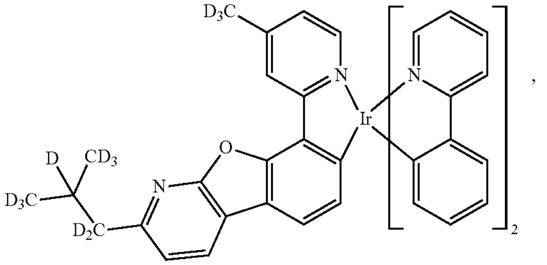
Compound II-67
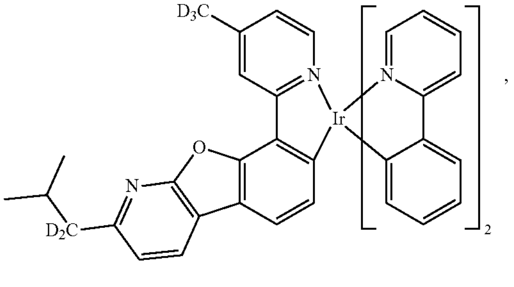

-continued
Compound II-68
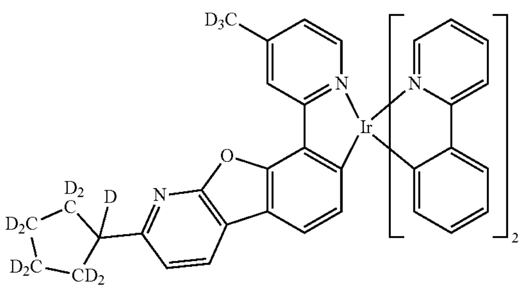
,
Compound II-69
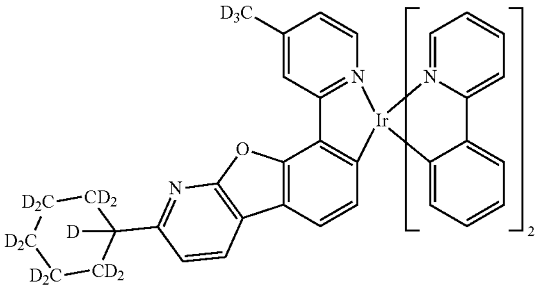
,
Compound II-70
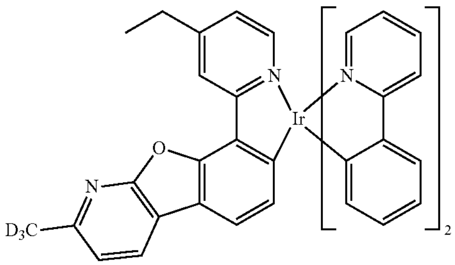
,
Compound II-71
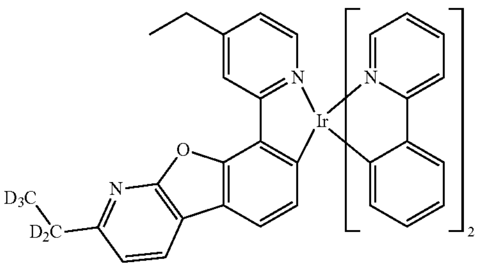
,
Compound II-72
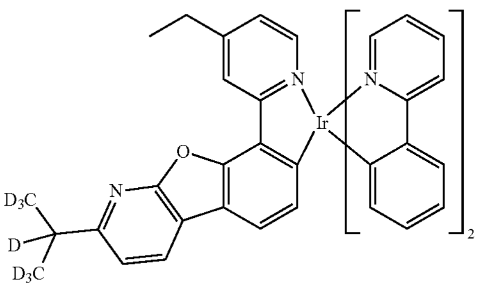
,
-continued
Compound II-73
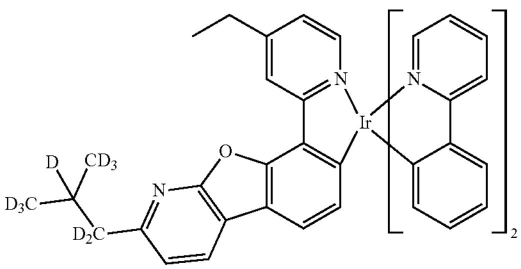
,
Compound II-74
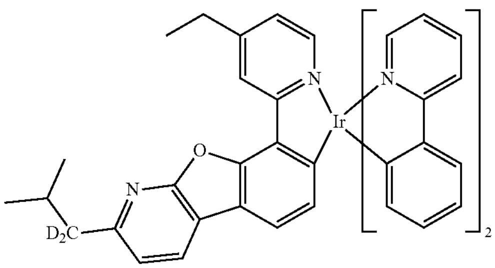
,
Compound II-75
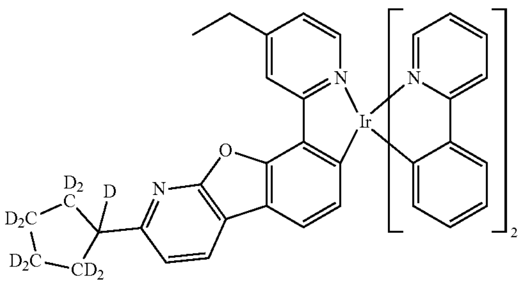
,
Compound II-76
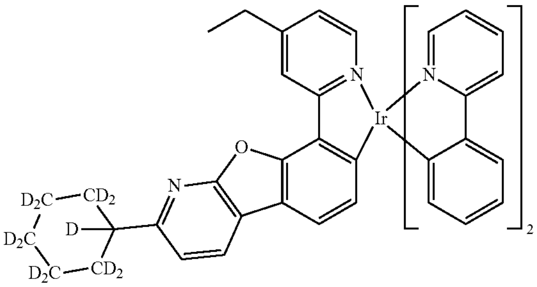
,
Compound II-77
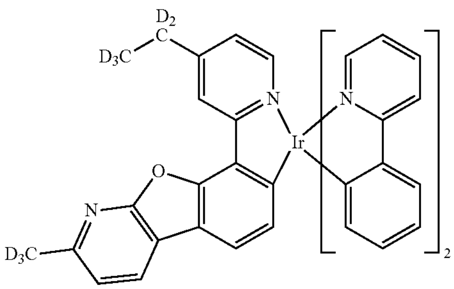
, -continued
Compound II-78
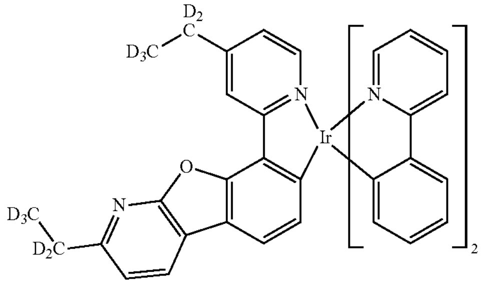
,
Compound II-79
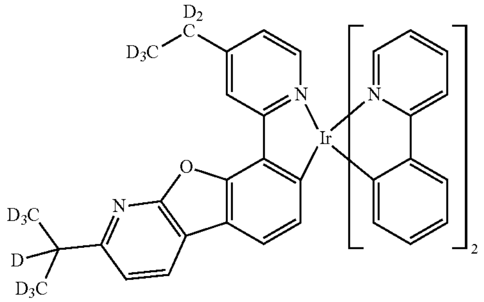
,
Compound II-80
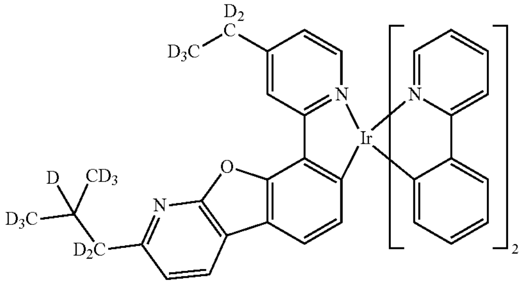
,
Compound II-81
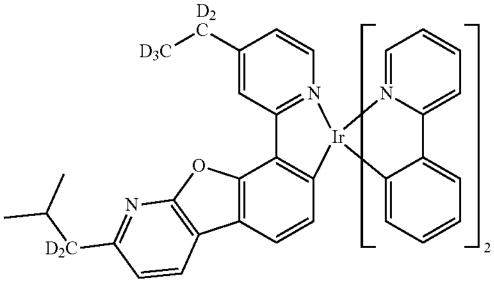
,
Compound II-82
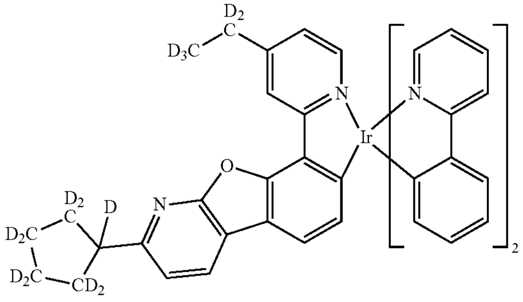
,
-continued
Compound II-83
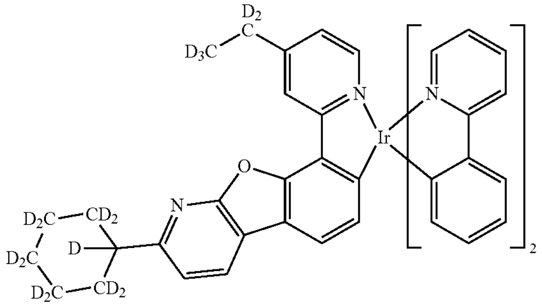
,
Compound II-84
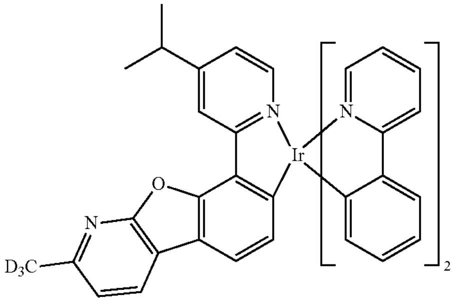
,
Compound II-85
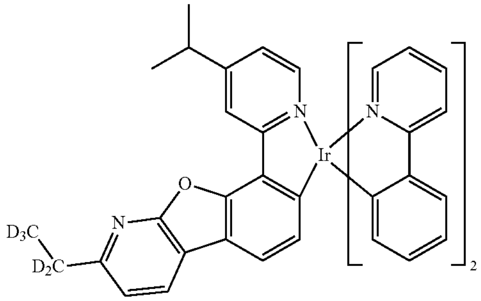
,
Compound II-86
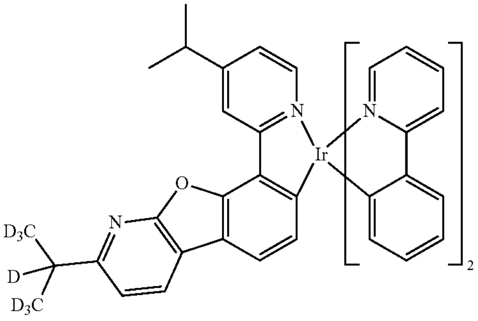
, -continued
Compound II-87
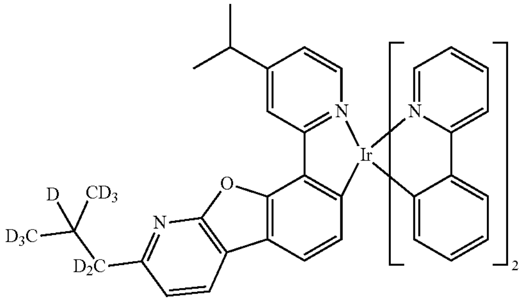
,
Compound II-88
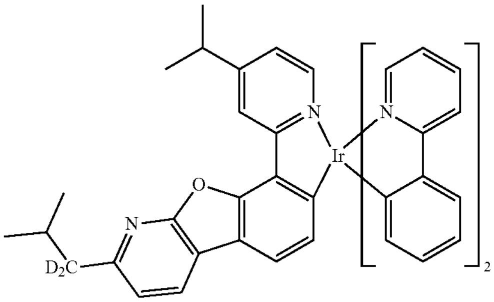
,
Compound II-89
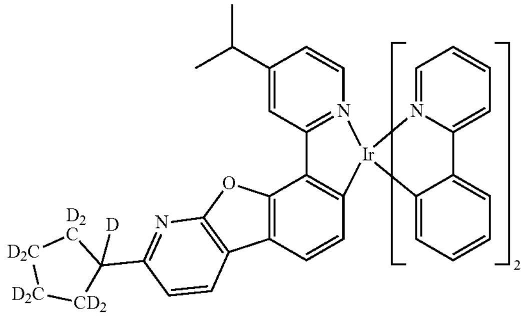
,
Compound II-90
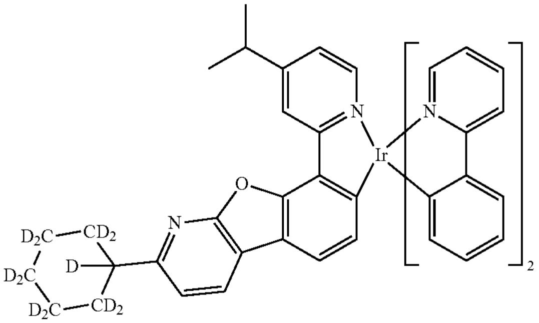
,
-continued
Compound II-91
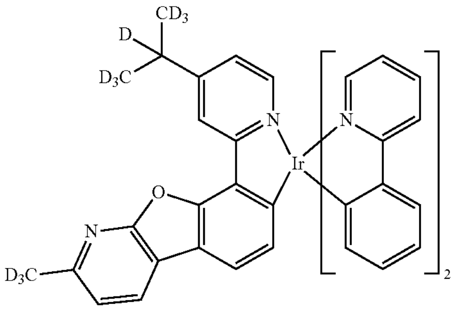
,
Compound II-92
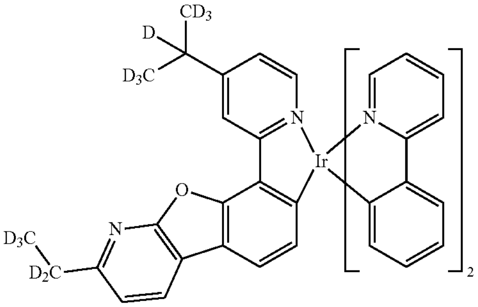
,
Compound II-93
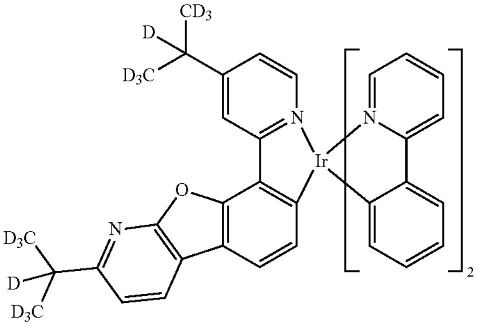
,
Compound II-94
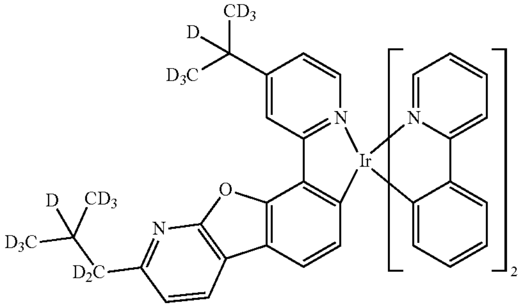
, -continued
Compound II-95
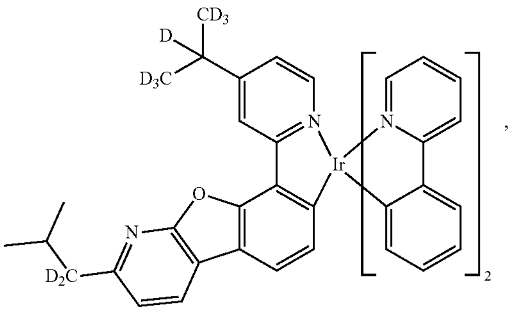
Compound II-96
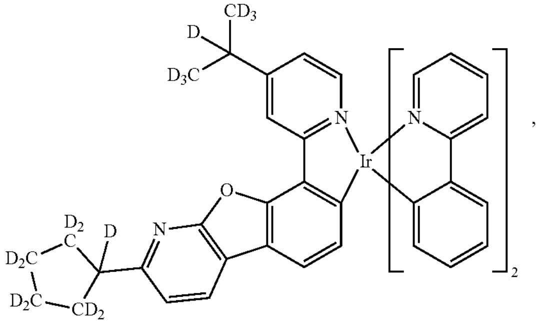
Compound II-97
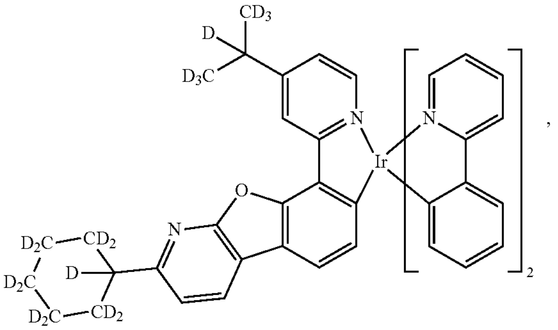
Compound II-98
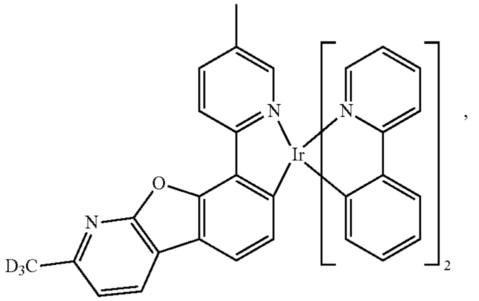
-continued
Compound II-99
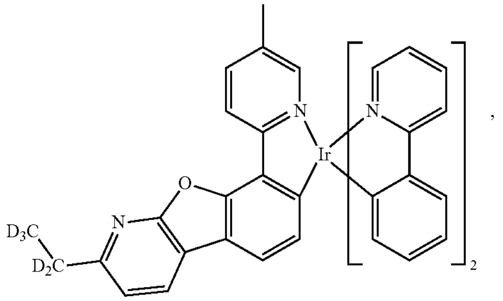
Compound II-100
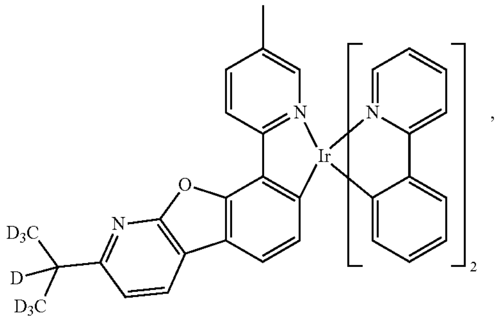
Compound II-101
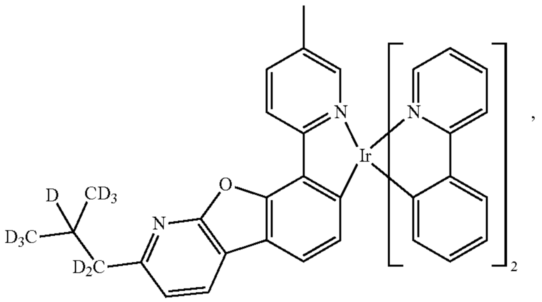
Compound II-102
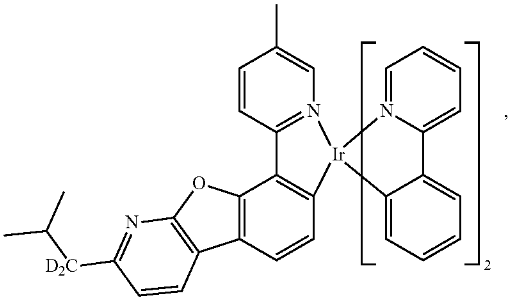

-continued
Compound II-103
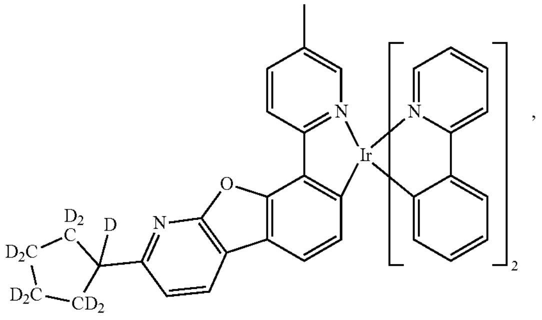
Compound II-104
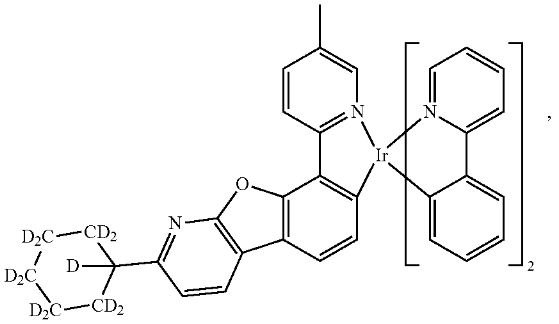
Compound II-105
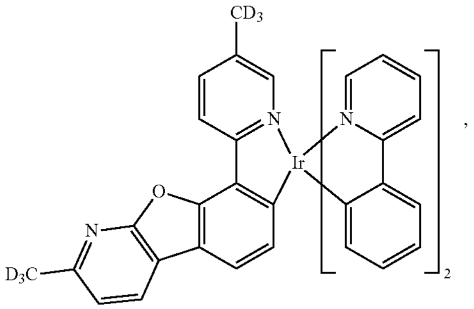
Compound II-106
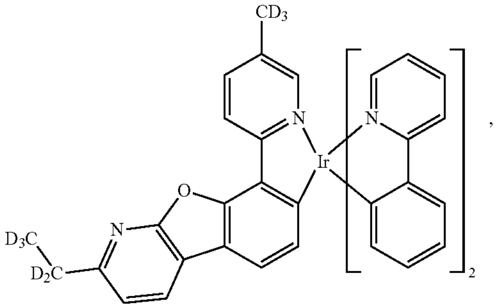
-continued
Compound II-107
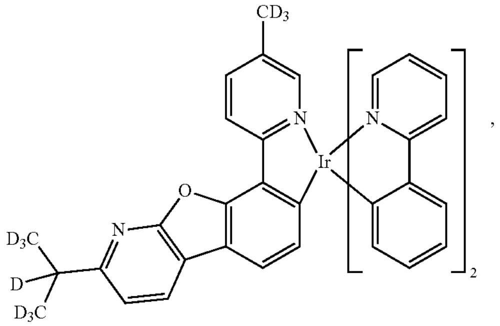
Compound II-108
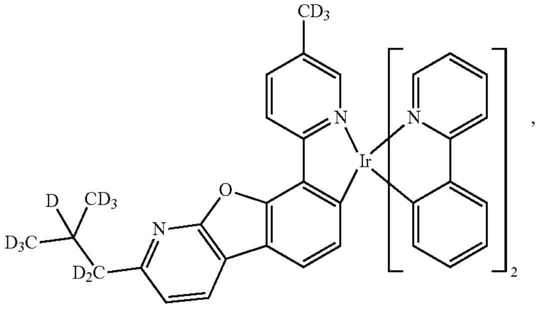
Compound II-109
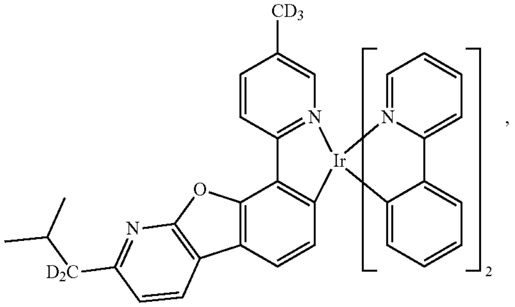
Compound II-110
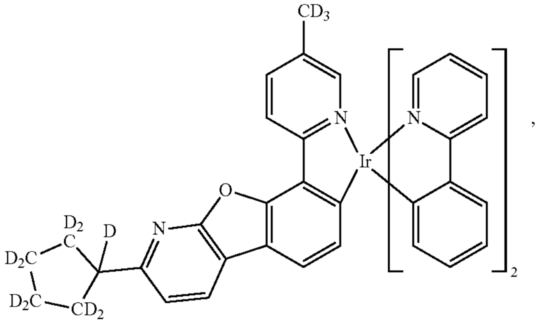

-continued
Compound II-111
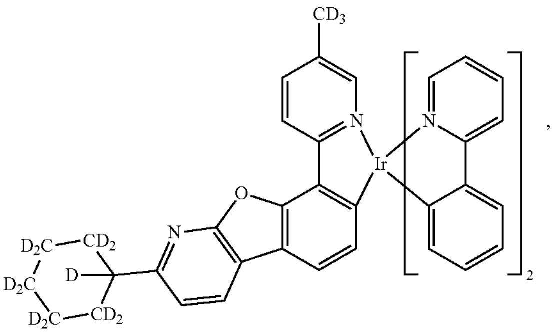
Compound II-112
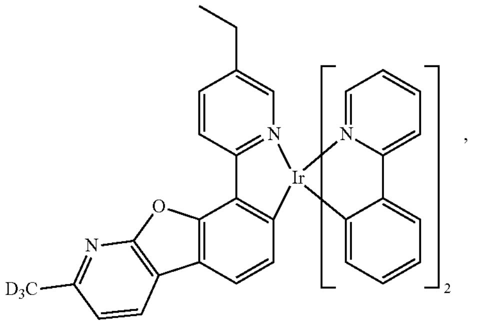
Compound II-113
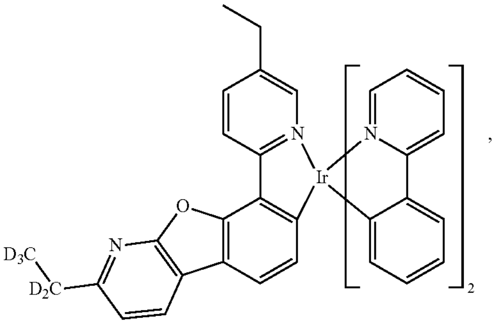
Compound II-114
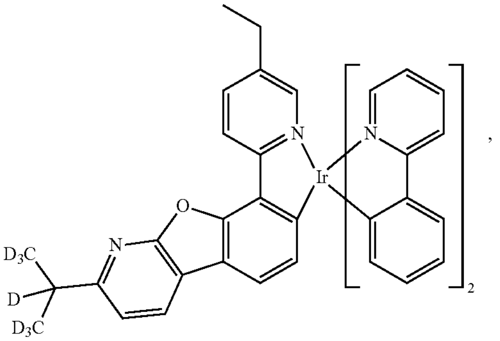
-continued
Compound II-115
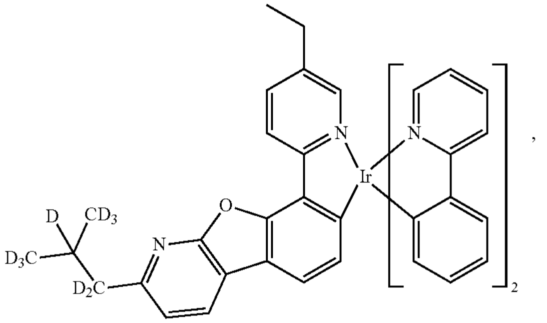
Compound II-116
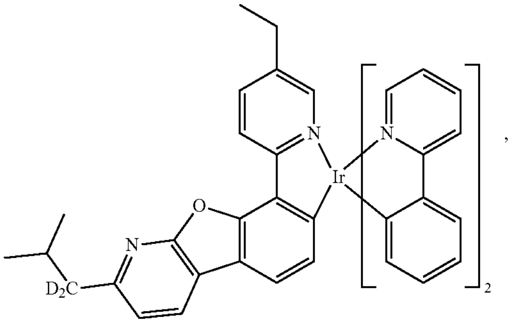
Compound II-117
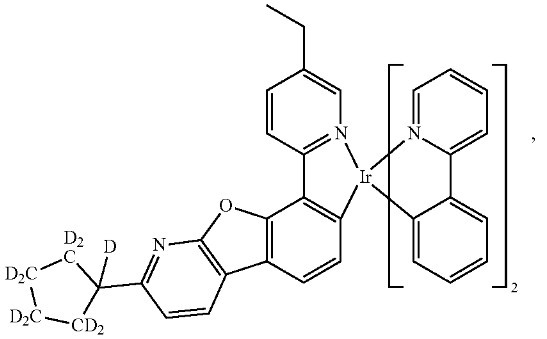
Compound II-118
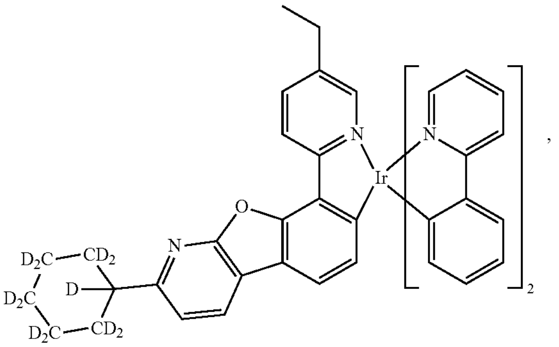

-continued
Compound II-119
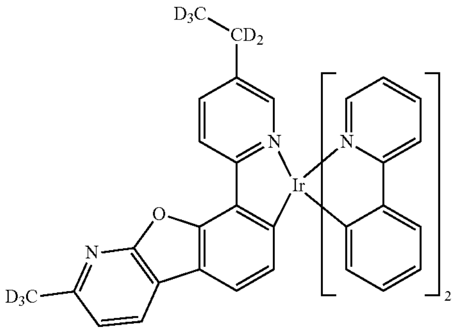
,
Compound II-120
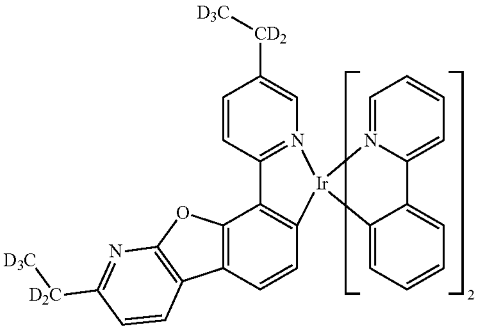
,
Compound II-121
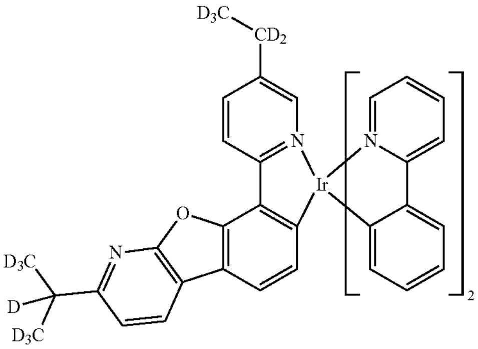
,
Compound II-122
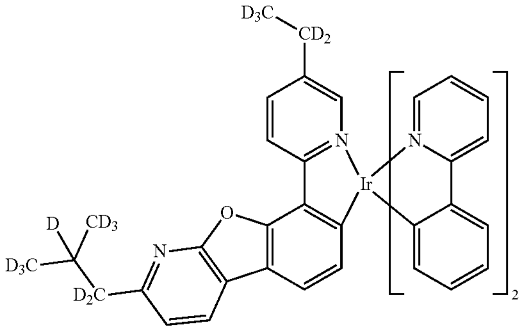
,
-continued
Compound II-123
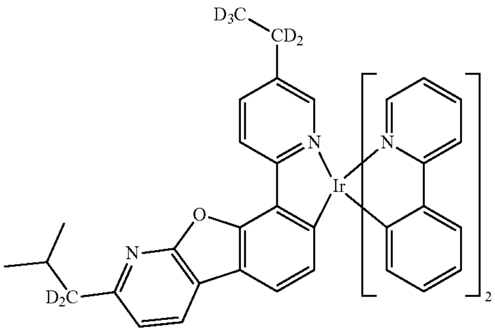
,
Compound II-124
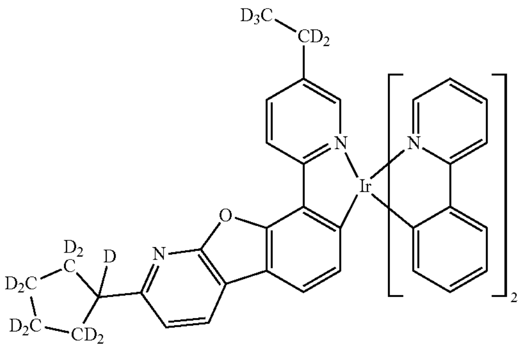
,
Compound II-125
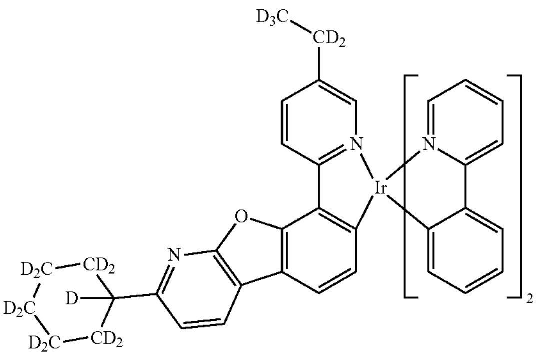
,
Compound II-126
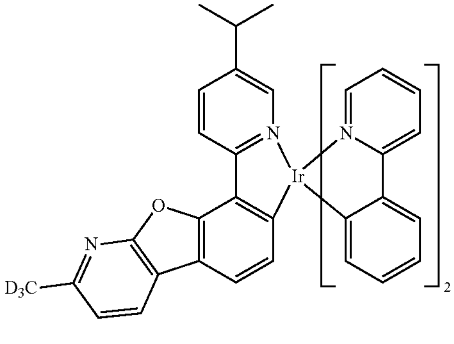
, -continued
Compound II-127
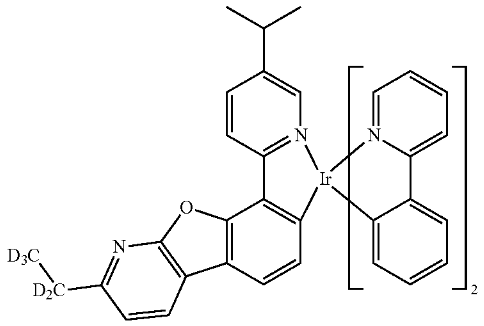
,
Compound II-128
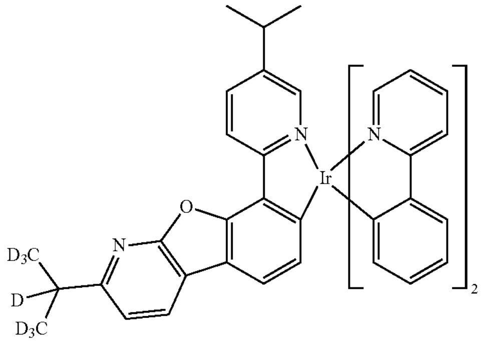
,
Compound II-129
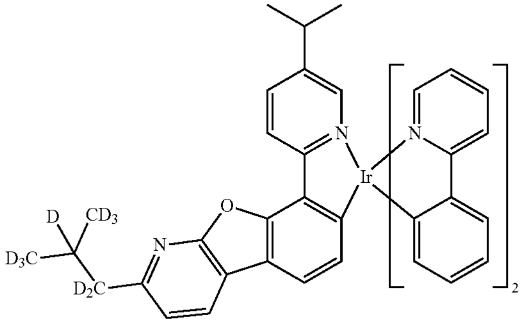
,
Compound II-130
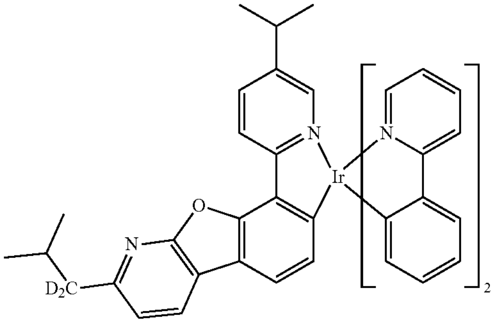
,
-continued
Compound II-131
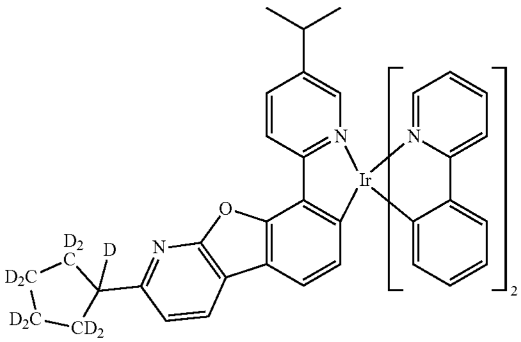
,
Compound II-132
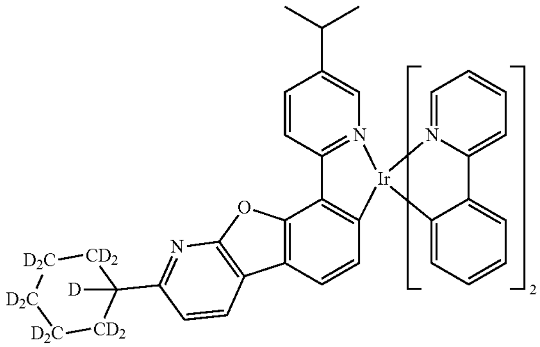
,
Compound II-133
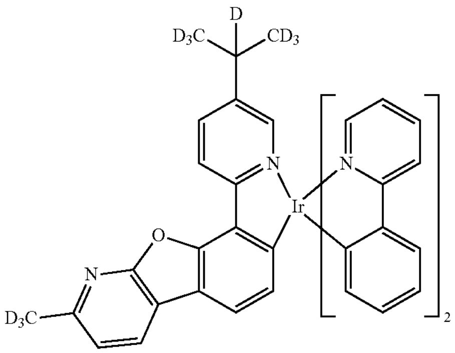
,
Compound II-134
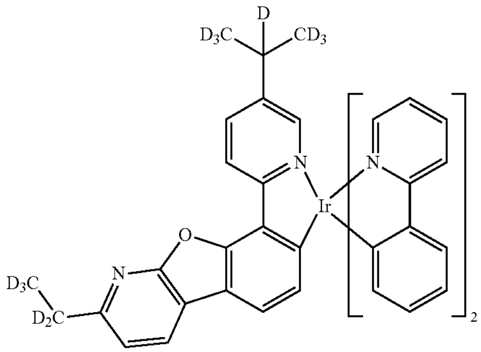
, -continued
Compound II-135
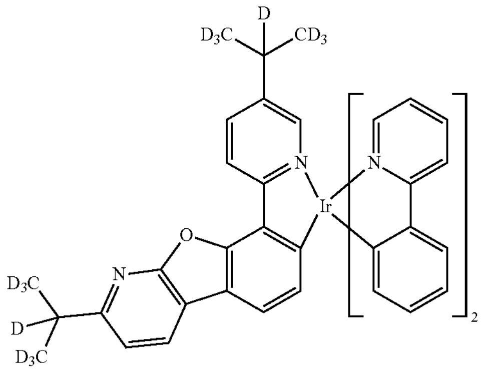
,
Compound II-136
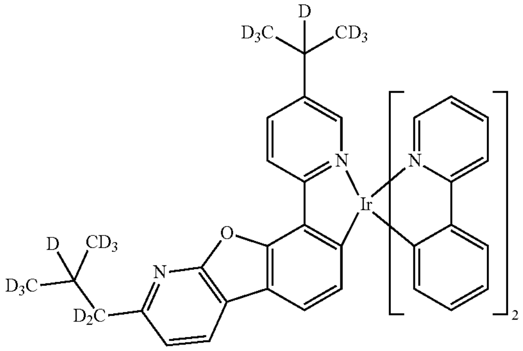
,
Compound II-137
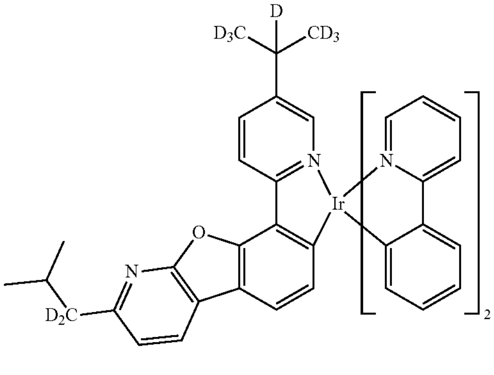
,
Compound II-138
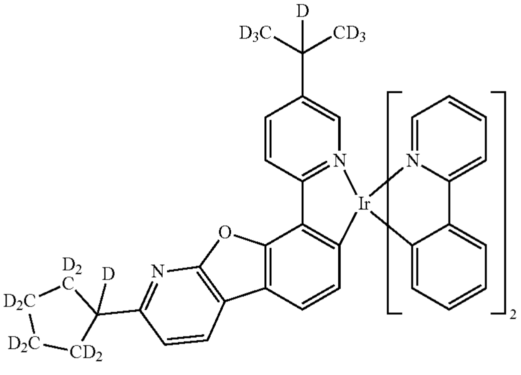
,
-continued
Compound II-139
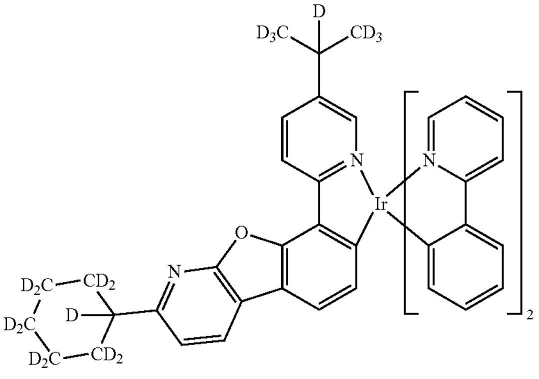
,
Compound II-140
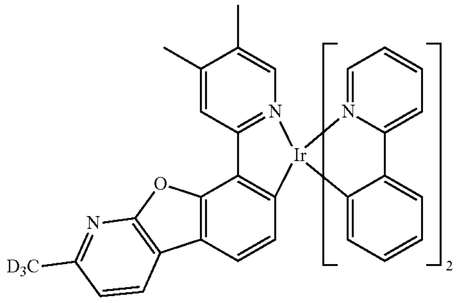
,
Compound II-141
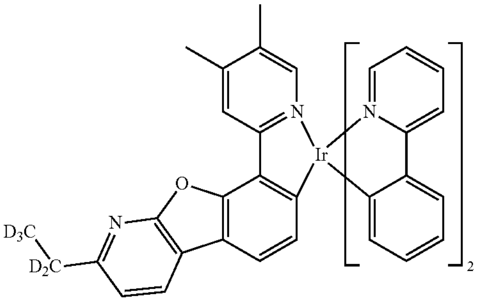
,
Compound II-142
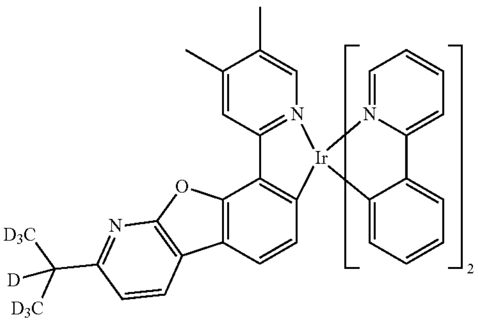
, -continued
Compound II-143
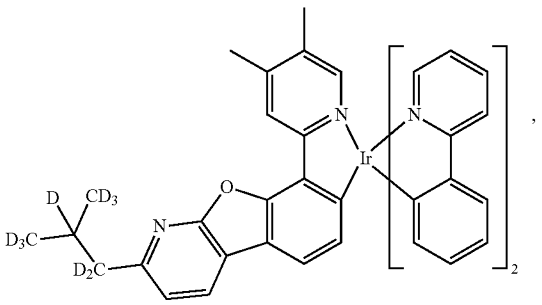
Compound II-144
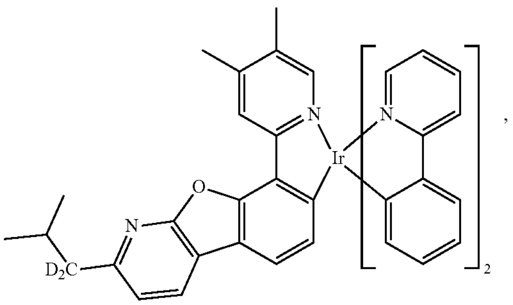
Compound II-145
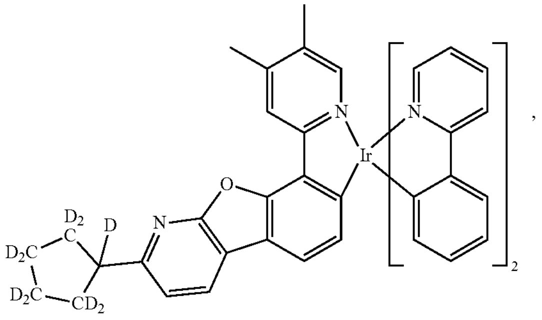
Compound II-146
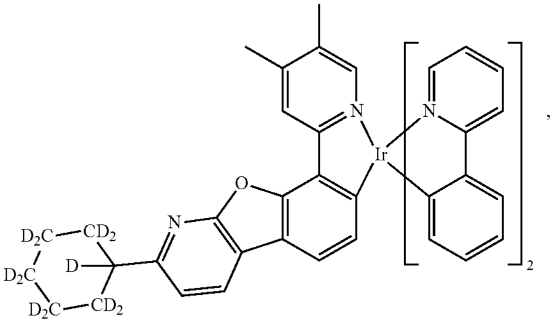
-continued
Compound II-147
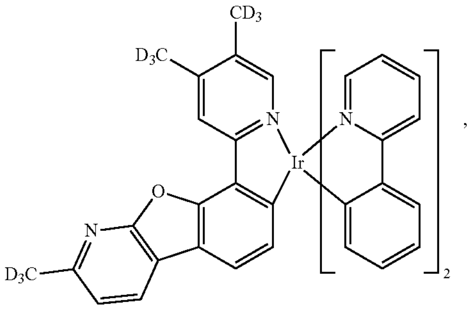
Compound II-148
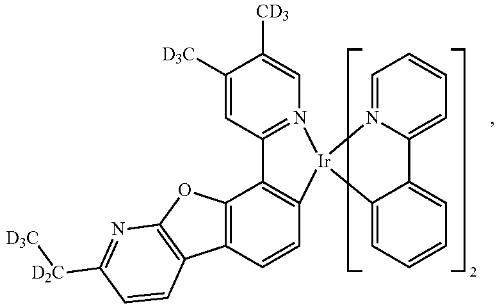
Compound II-149
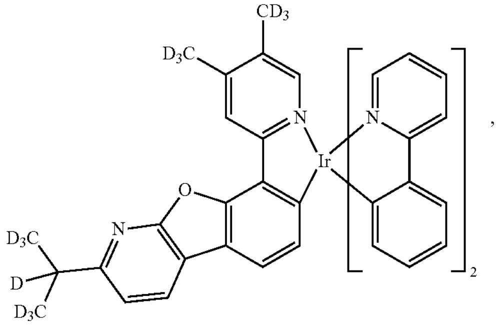
Compound II-150
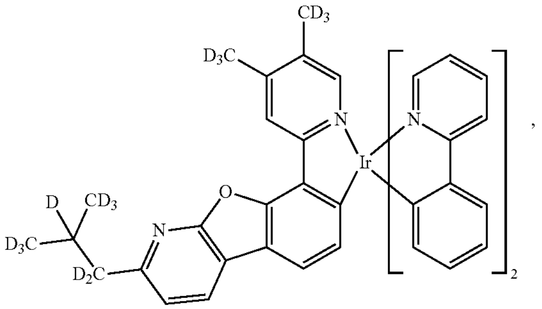

-continued
Compound II-151
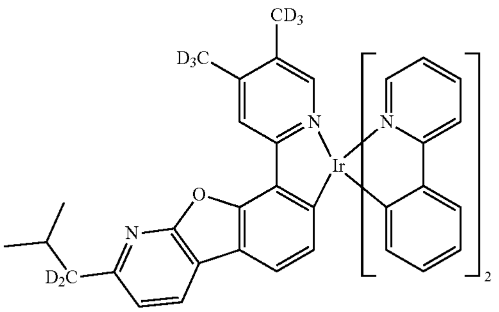
,
Compound II-152
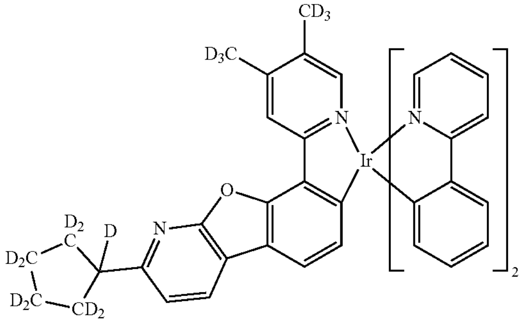
,
Compound II-153
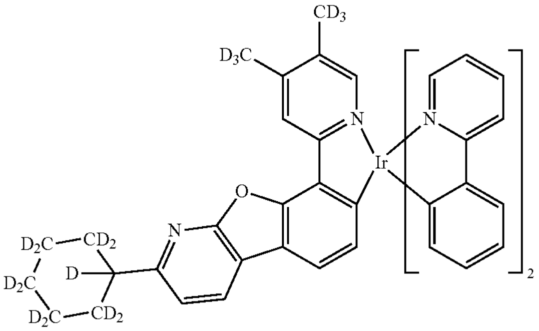
,
Compound II-154
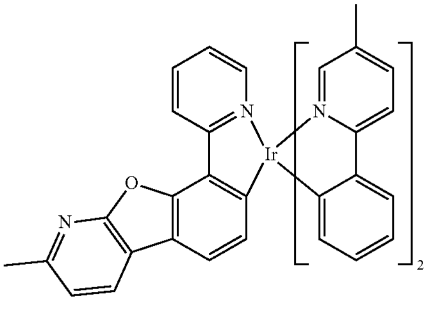
,
-continued
Compound II-155
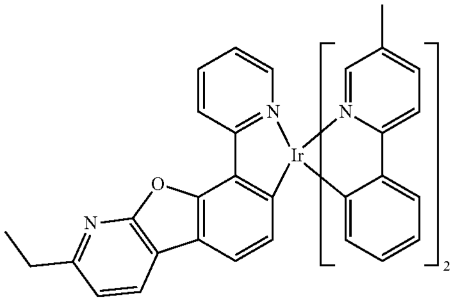
,
Compound II-156
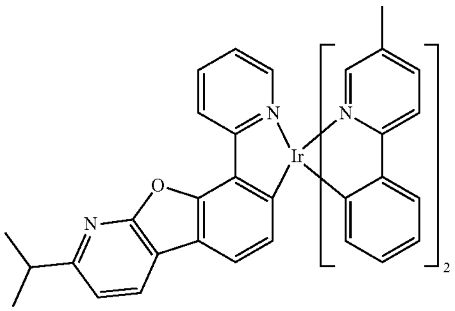
,
Compound II-157
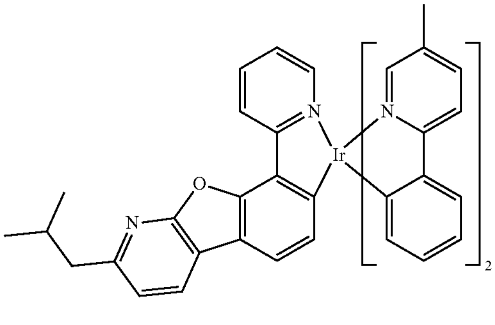
,
Compound II-158
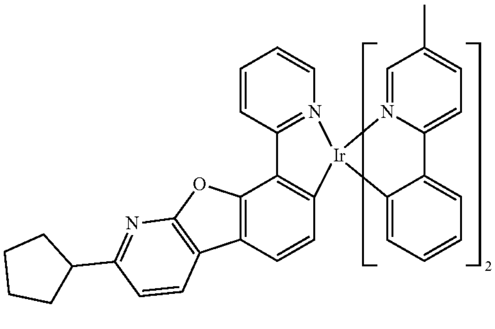
, -continued
Compound II-159
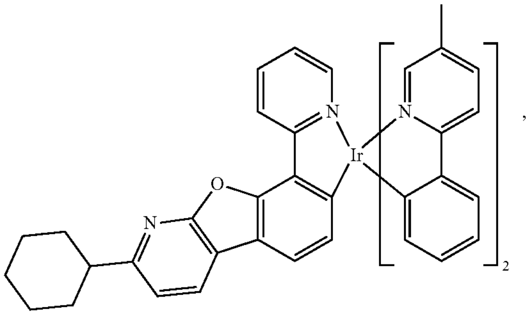
Compound II-160
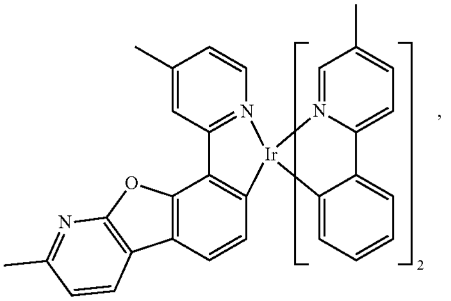
Compound II-161
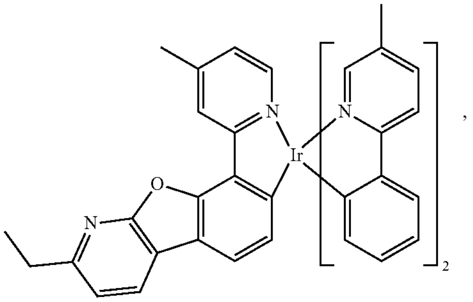
Compound II-162
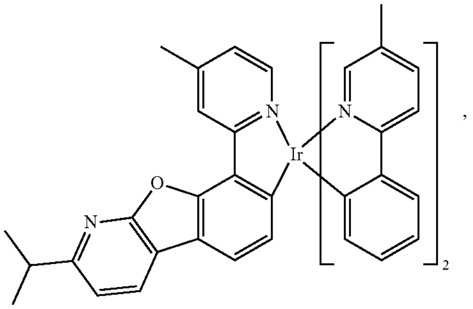
Compound II-163
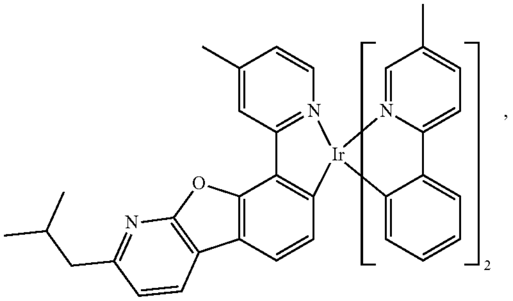
-continued
Compound II-164
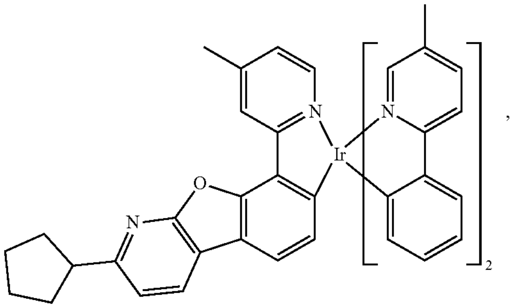
Compound II-165
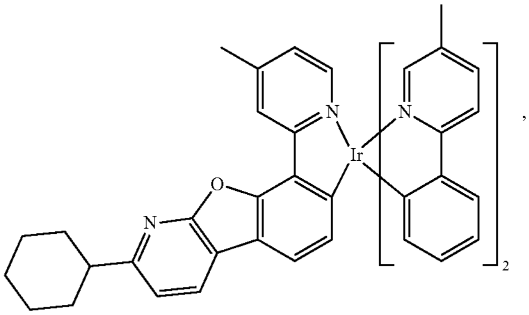
Compound II-166
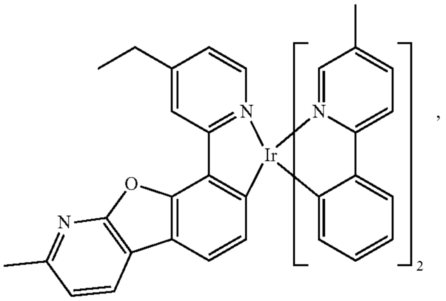
Compound II-167
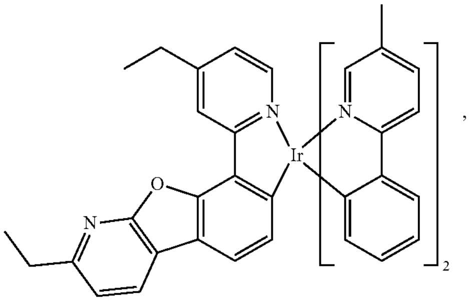

-continued
Compound II-168
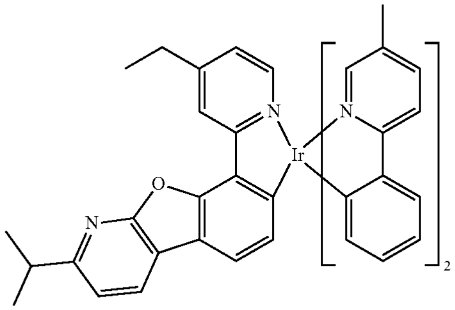
,
Compound II-169
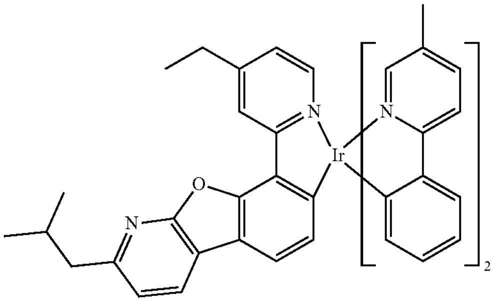
,
Compund II-170
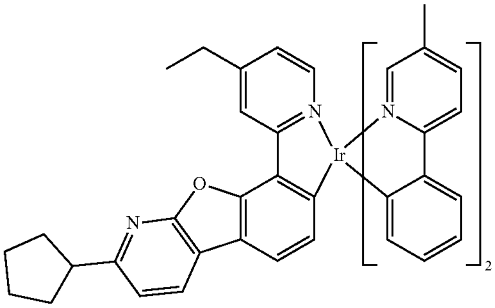
,
Compound II-171
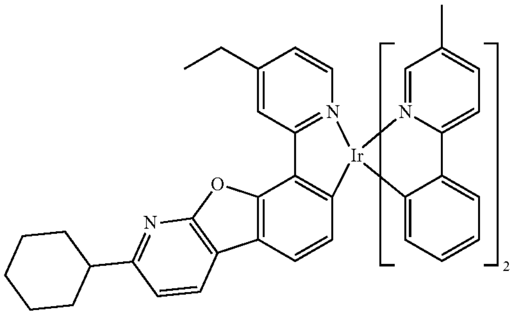
,
-continued
Compound II-172
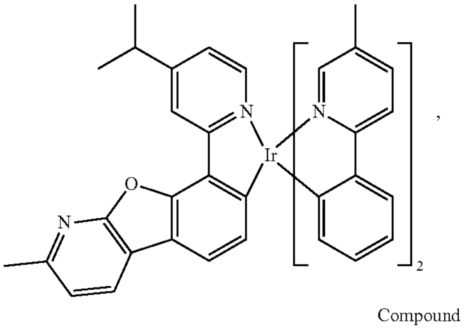
,
Compound II-173
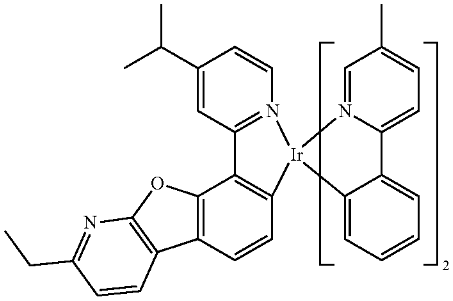
,
Compound II-174
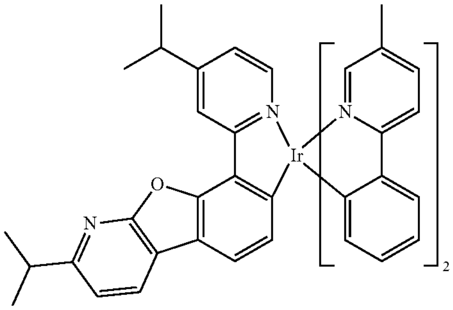
,
Compound II-175
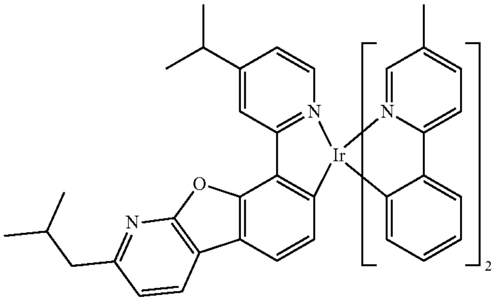
,
Compound II-176
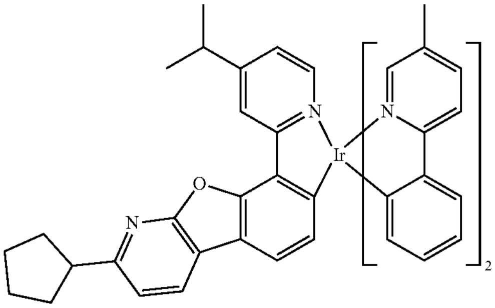
, -continued
Compound II-177
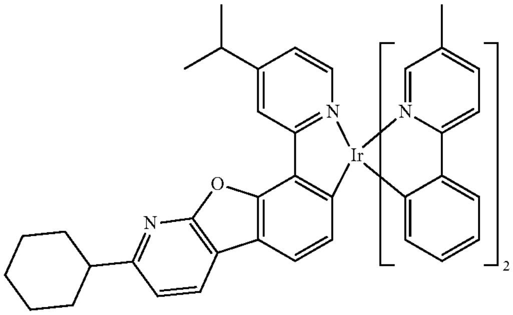
,
Compound II-178
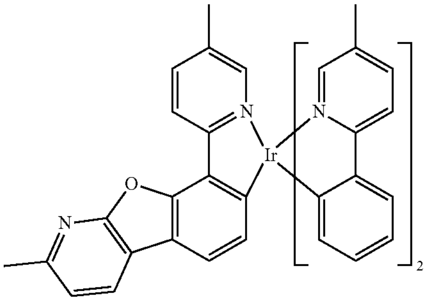
,
Compound II-179
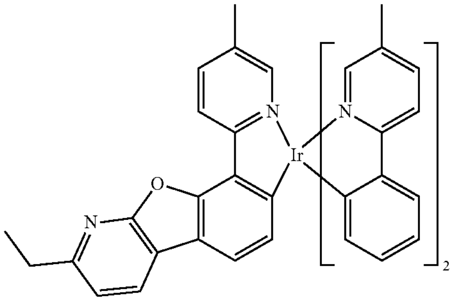
,
Compound II-180
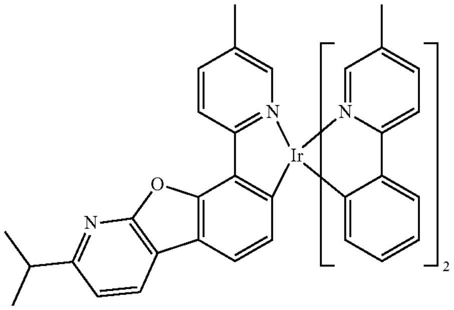
,
Compound II-181
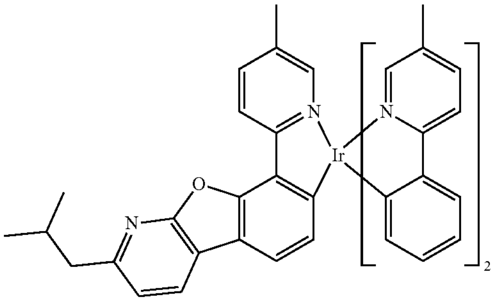
,
-continued
Compound II-182
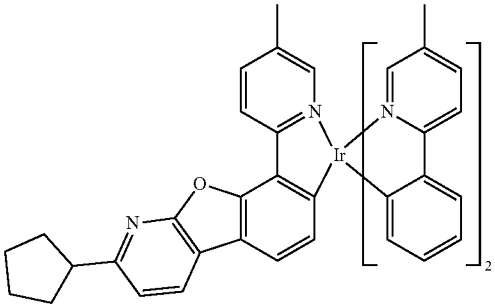
,
Compound II-183
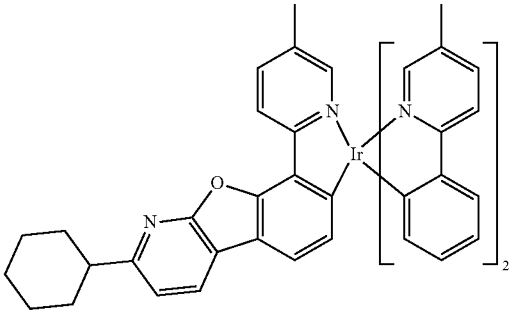
,
Compound II-184
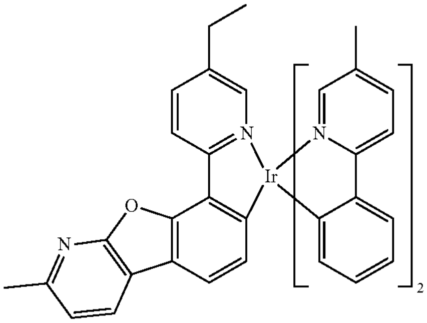
,
Compound II-185
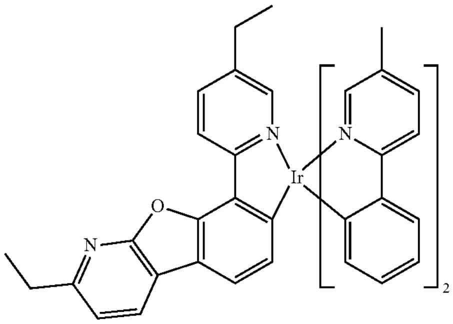
, -continued
Compound II-186
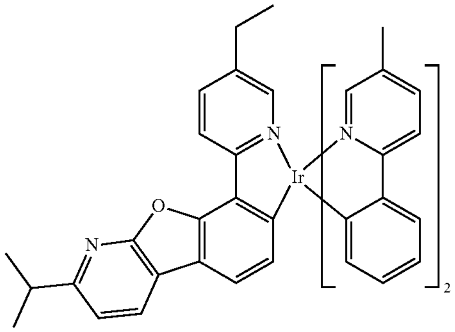
,
Compound II-187
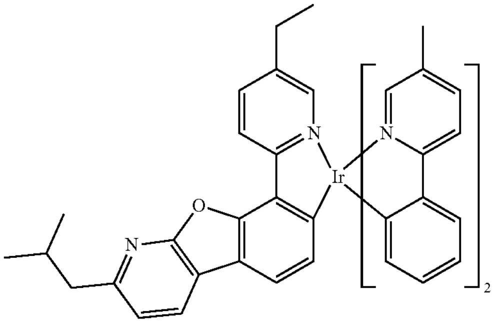
,
Compound II-188
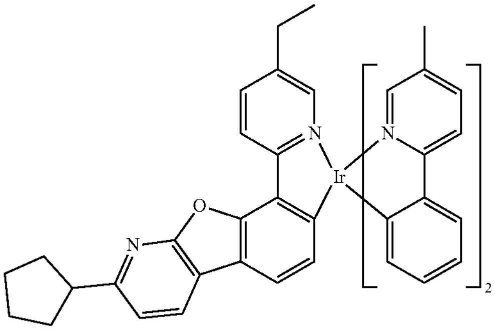
,
Compound II-189
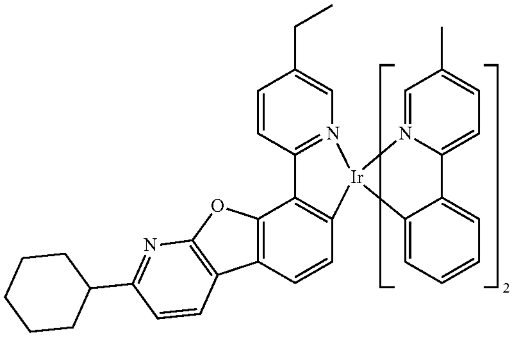
,
-continued
Compound II-190
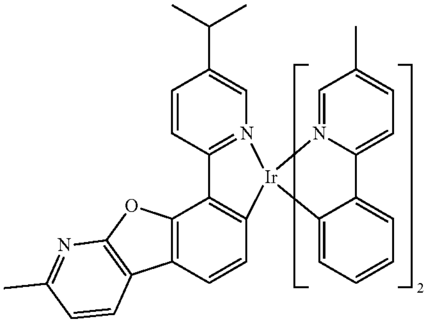
,
Compound II-191
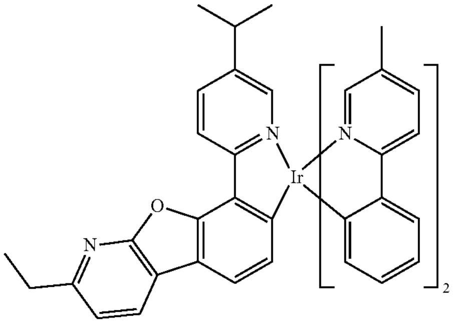
,
Compound II-192
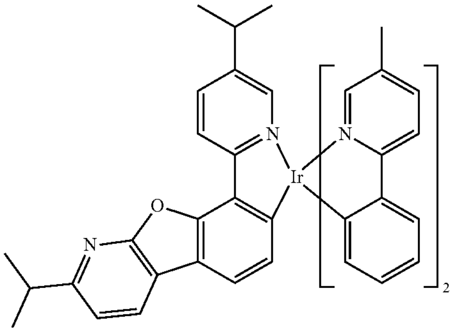
,
Compound II-193
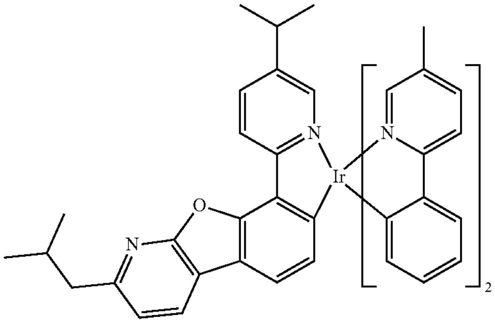
, -continued
Compound II-194
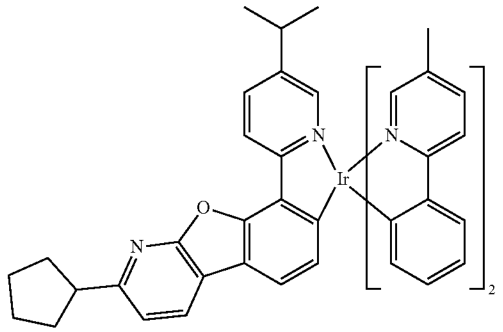
,
Compound II-195
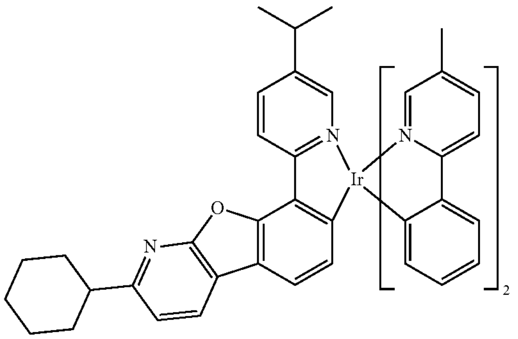
,
Compound II-196
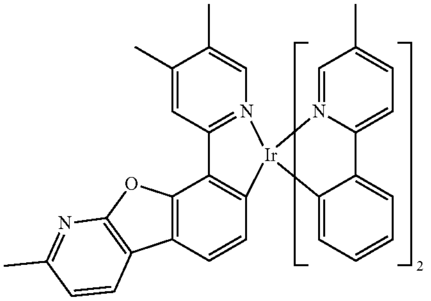
,
Compound II-197
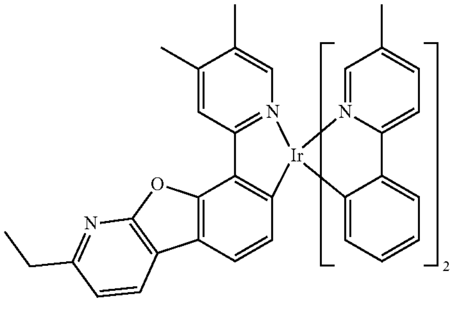
,
-continued
Compound II-198
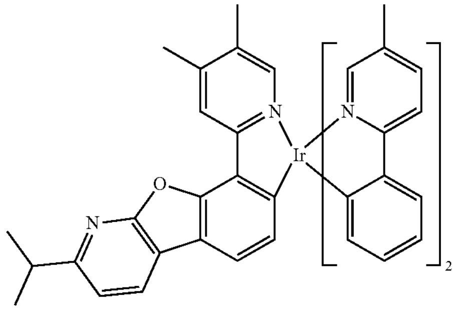
,
Compound II-199
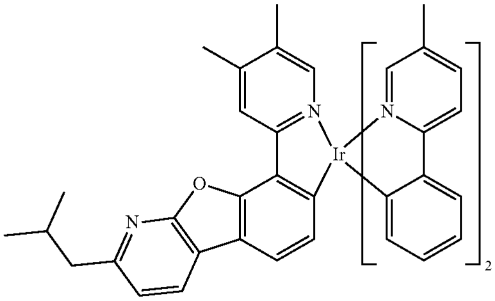
,
Compound II-200
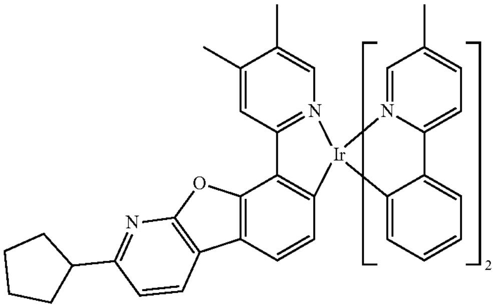
,
Compound II-201
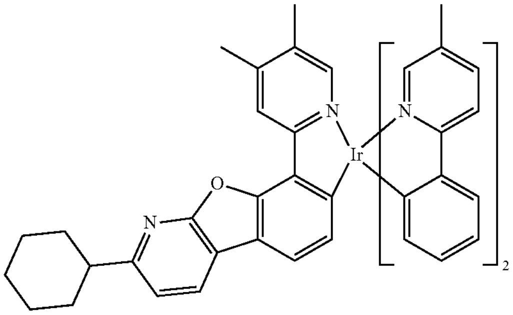
, -continued
Compound II-202
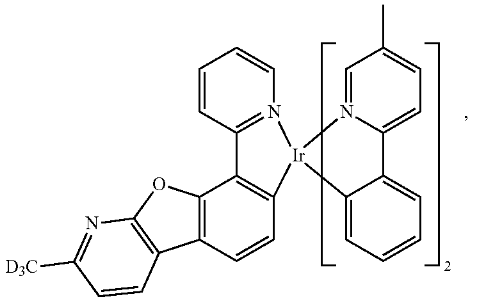
Compound II-203
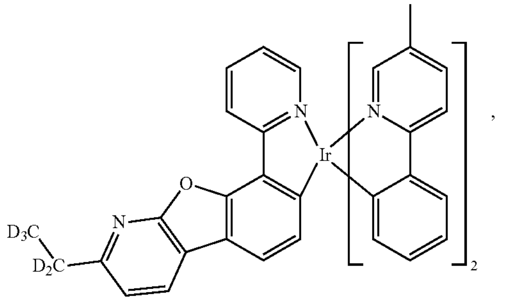
Compound II-204
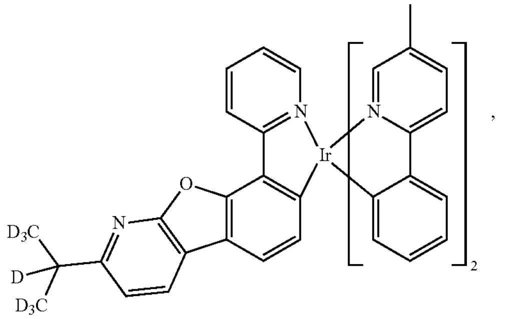
Compound II-205
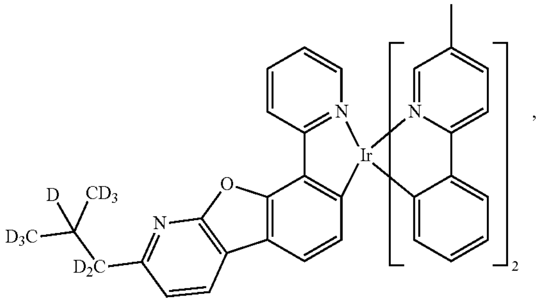
Compound II-206
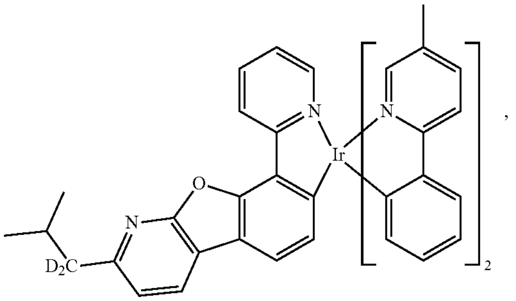
-continued
Compound II-207
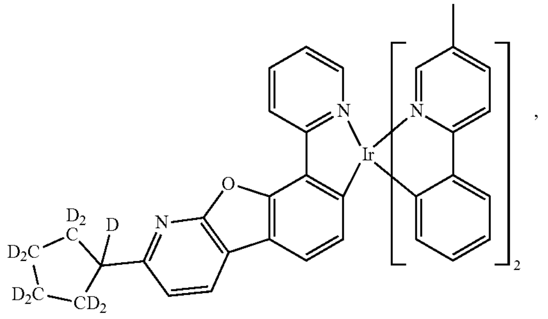
Compound II-208
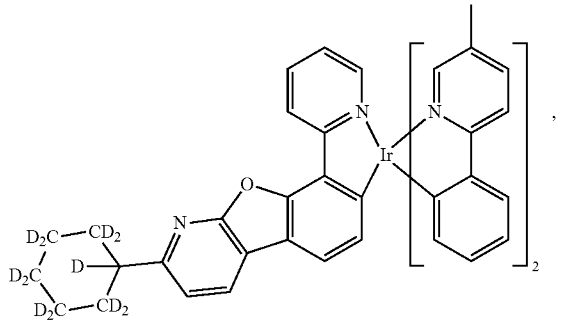
Compound II-209
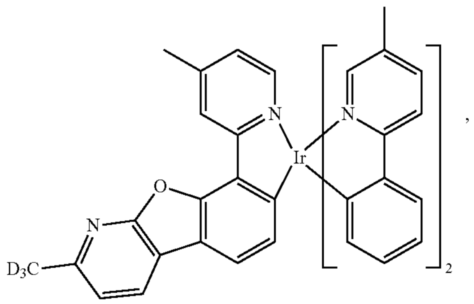
Compound II-210
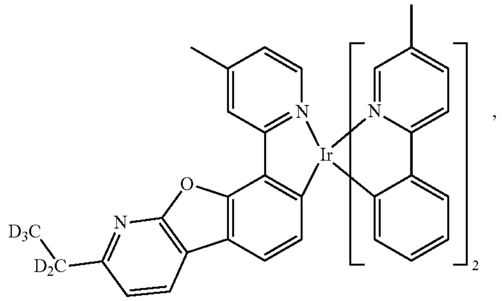

-continued
Compound II-211
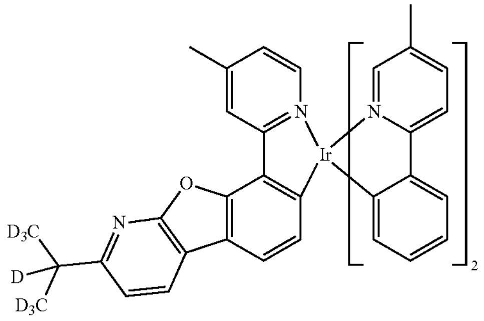
,
Compound II-212
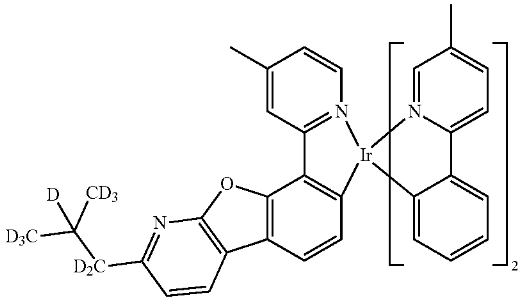
,
Compound II-213
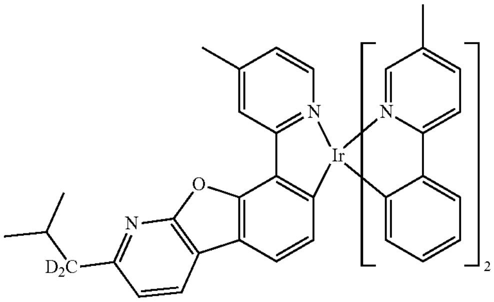
,
Compound II-214
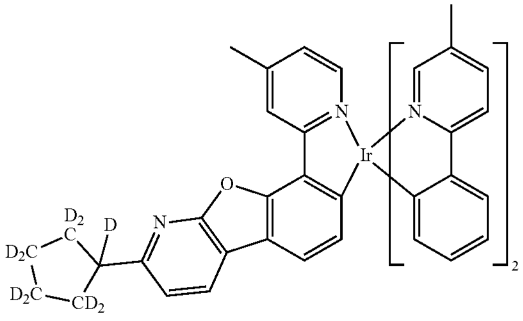
,
-continued
Compound II-215
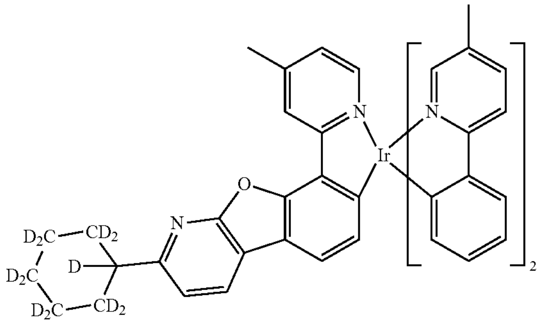
,
Compound II-216
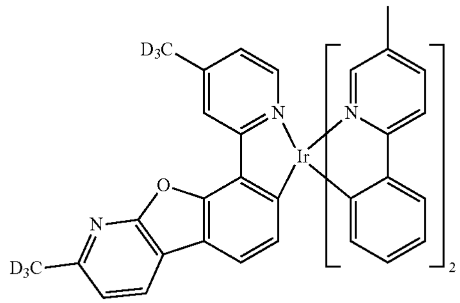
,
Compound II-217
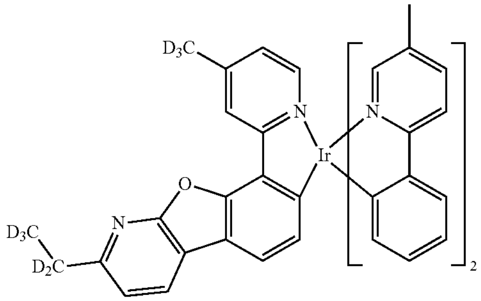
,
Compound II-218
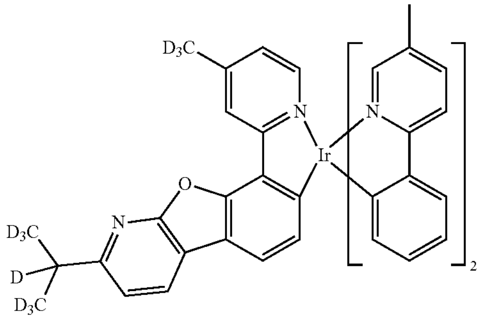
, Compound II-219
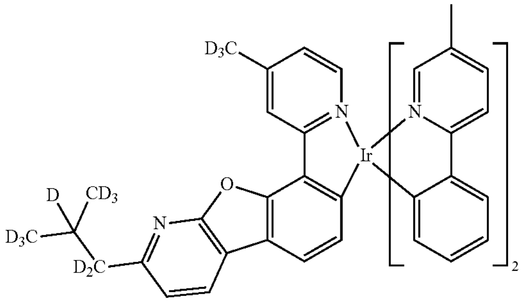
,
Compound II-220
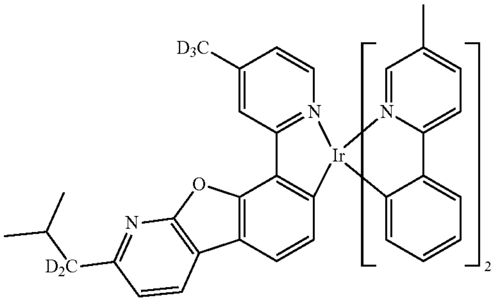
,
Compound II-221
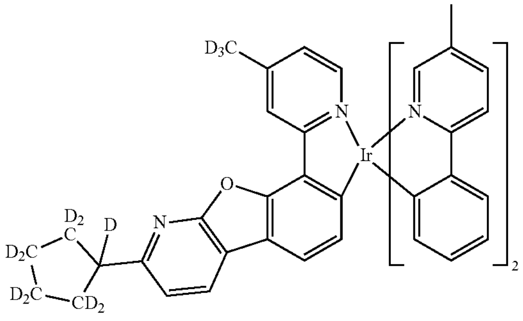
,
Compound II-222
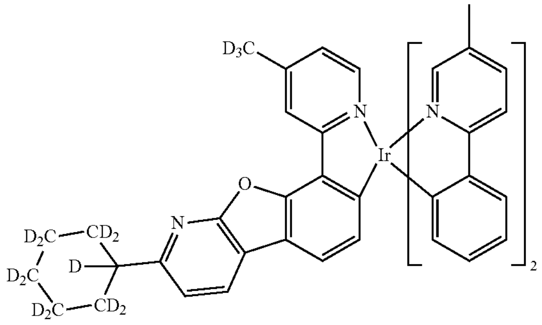
,
Compound II-223
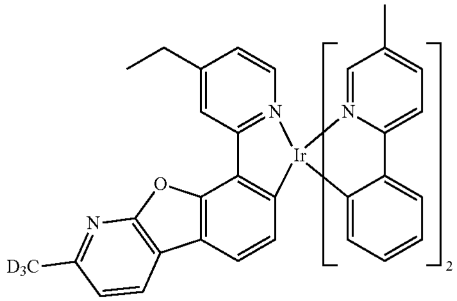
,
Compound II-224
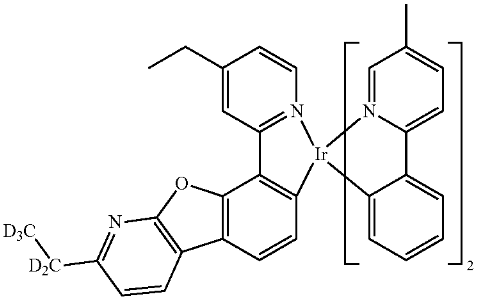
,
Compound II-225
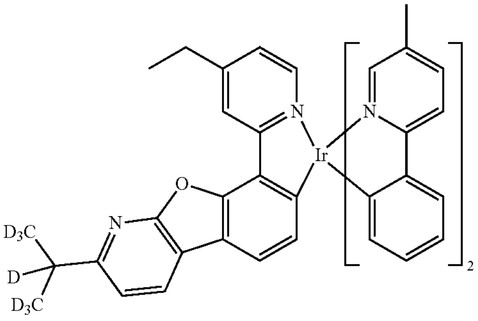
,
Compound II-226
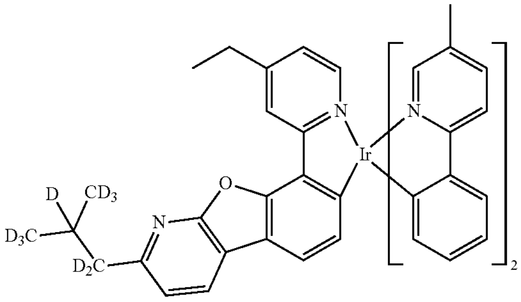
,
Compound II-227
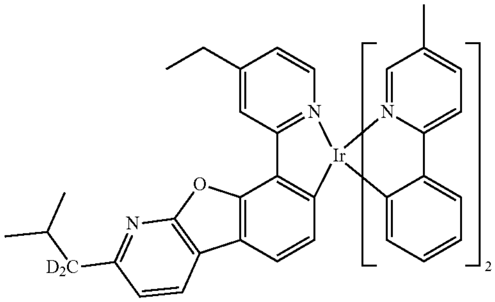
, -continued
Compound II-228
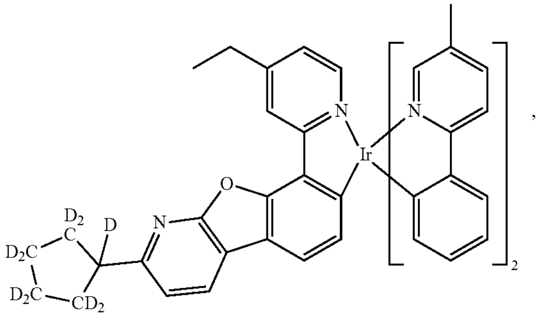
Compound II-229
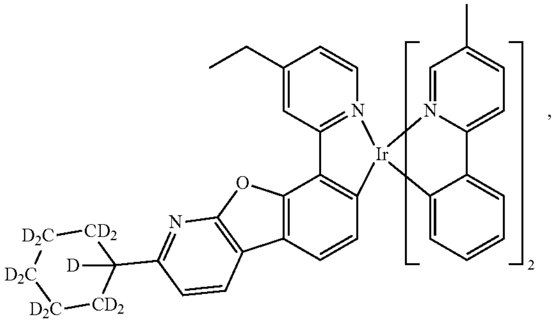
Compound II-230
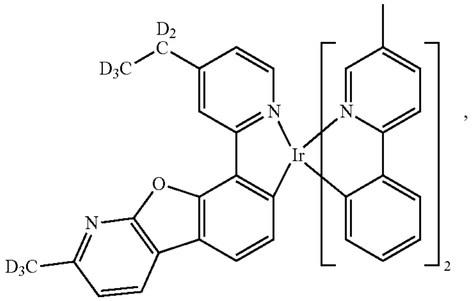
Compound II-231
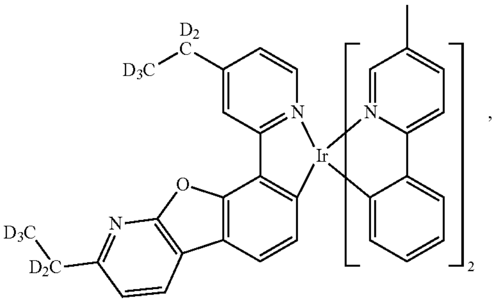
-continued
Compound II-232
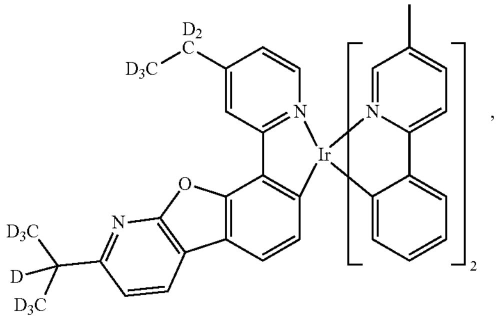
Compound II-233
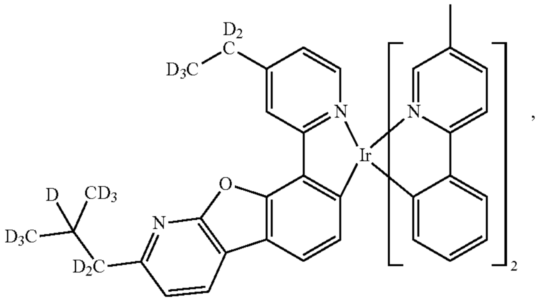
Compound II-234
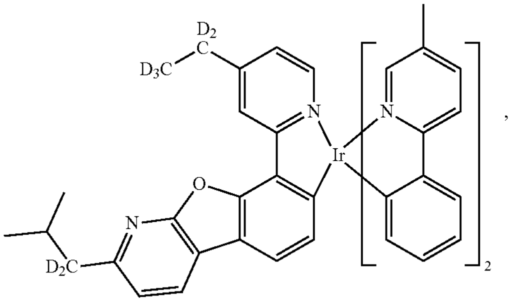
Compound II-235
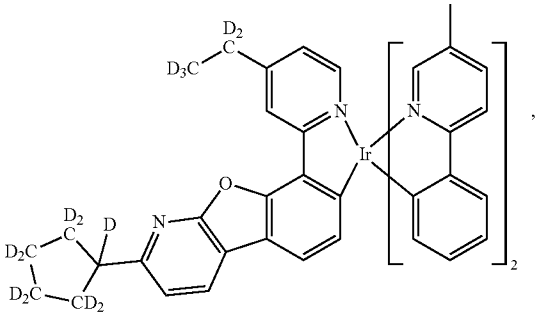

-continued
Compound II-236
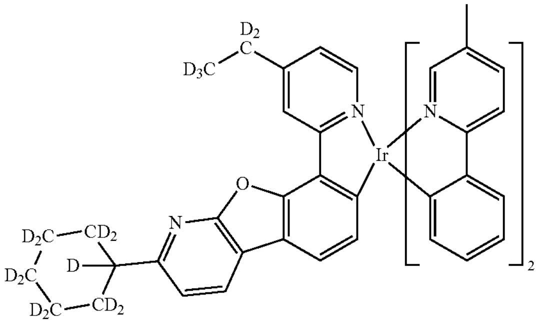
,
Compound II-237
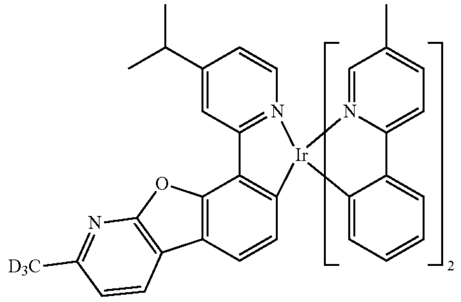
,
Compound II-238
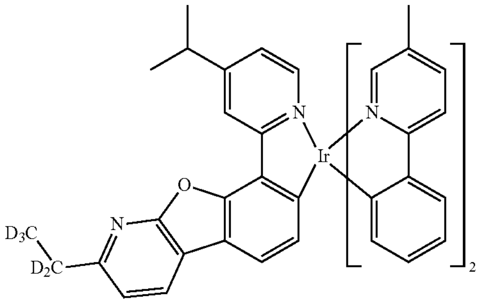
,
Compound II-239
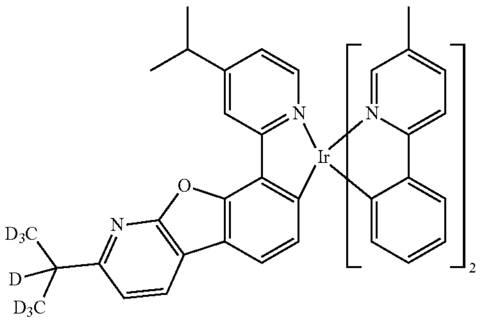
,
-continued
Compound II-240
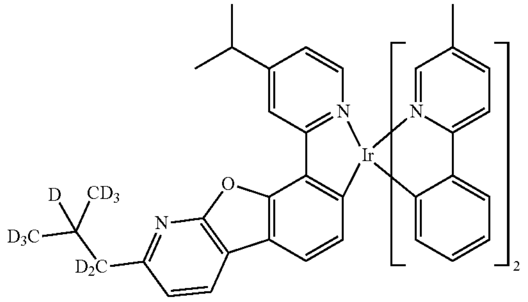
,
Compound II-241
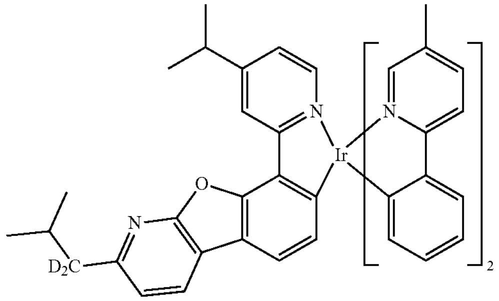
,
Compound II-242
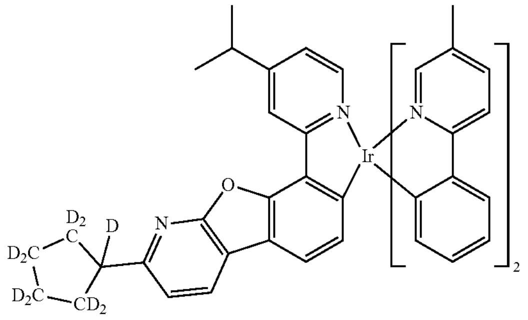
,
Compound II-243
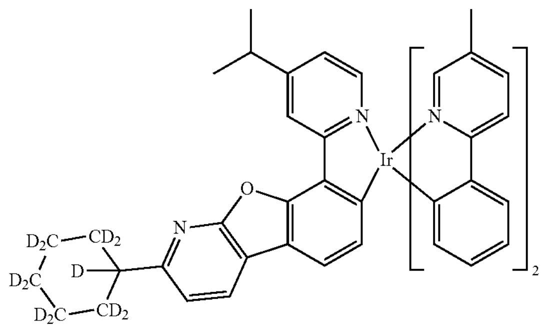
, -continued
Compound II-244
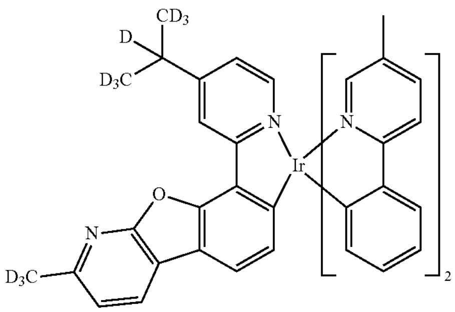
,
Compound II-245
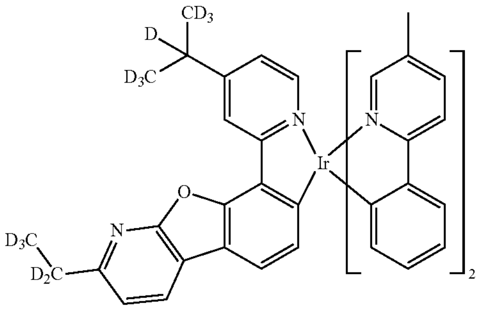
,
Compound II-246
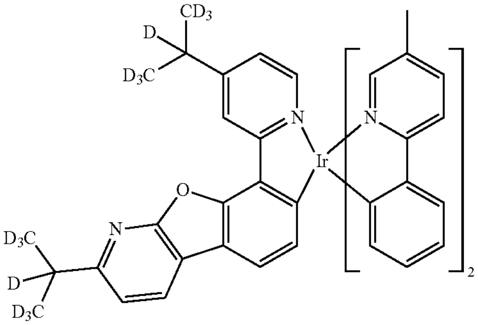
,
Compound II-247
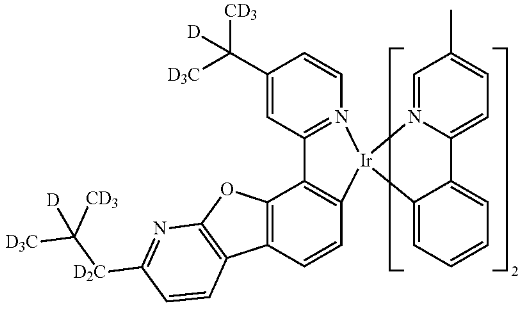
,
-continued
Compound II-248
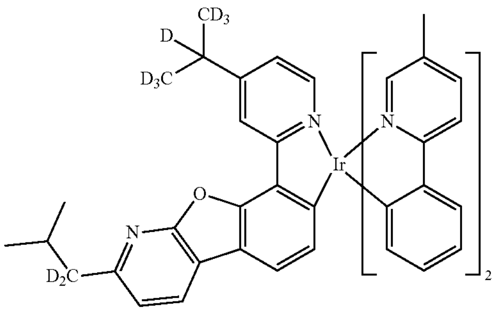
,
Compound II-249
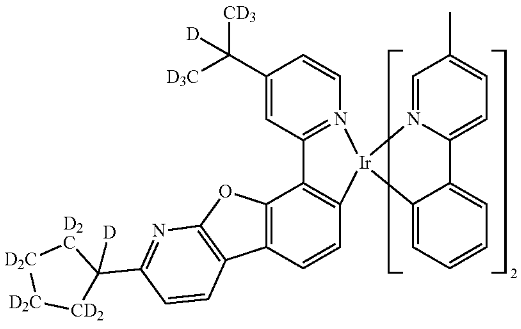
,
Compound II-250
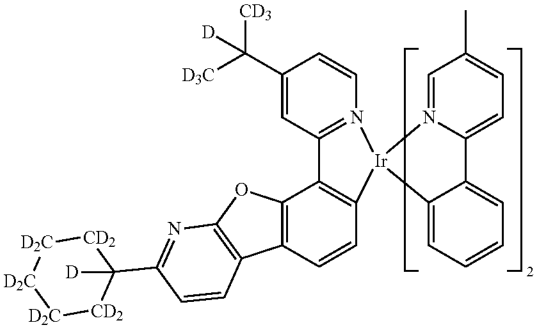
,
Compound II-251
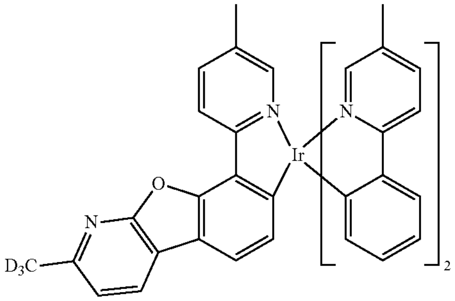
, -continued
Compound II-252
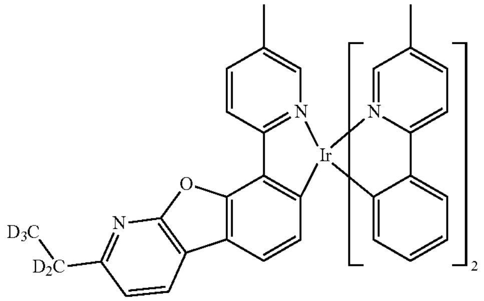
,
Compound II-253
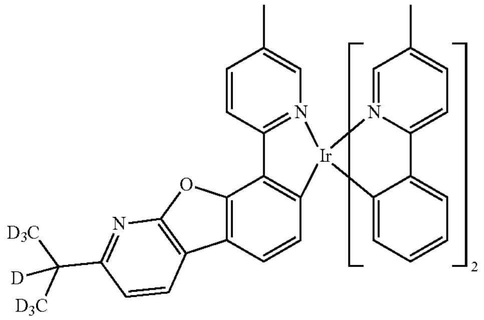
,
Compound II-254
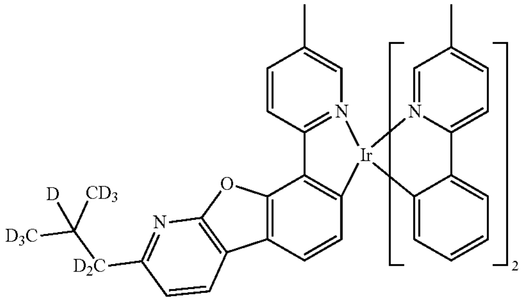
,
Compound II-255
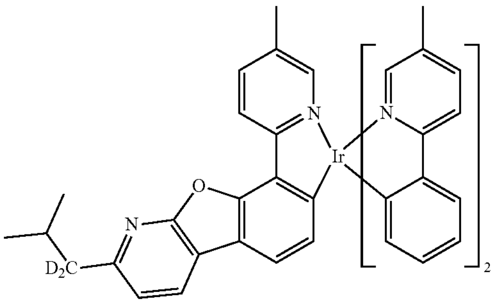
,
-continued
Compound II-256
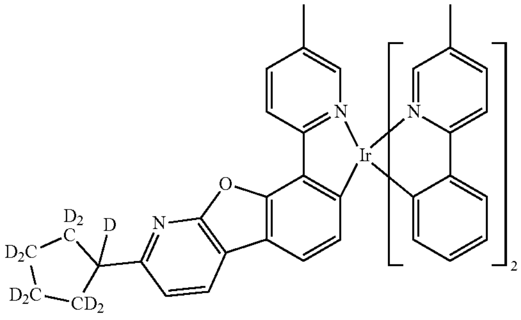
,
Compound II-257
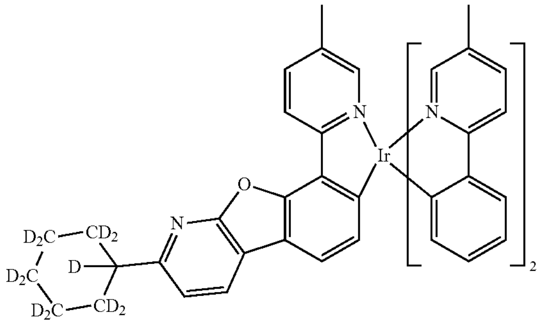
,
Compound II-258
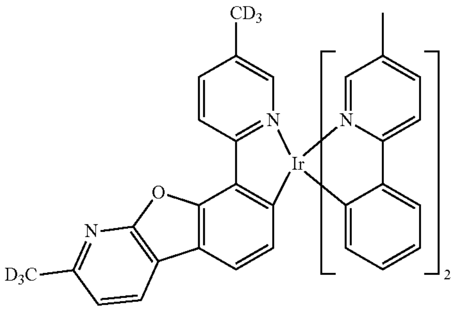
,
Compound II-259
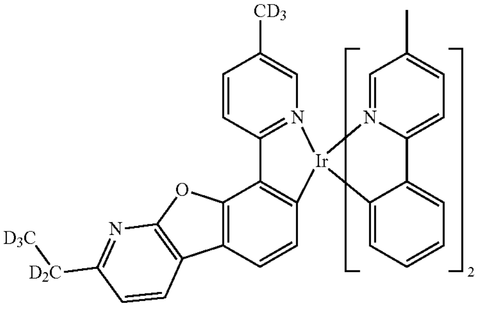
, -continued
Compound II-260
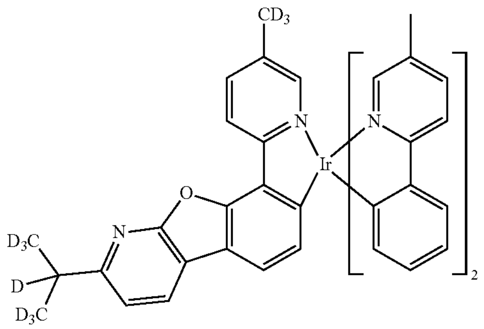
,
Compound II-261
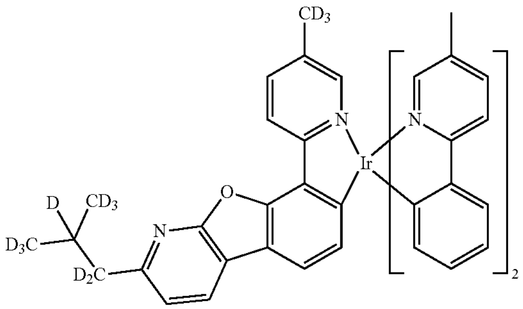
,
Compound II-262
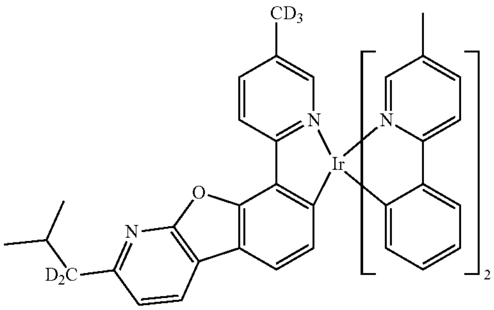
,
Compound II-263
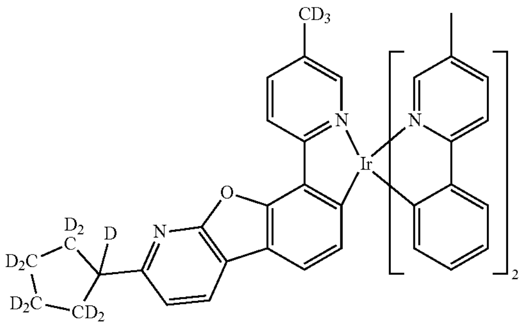
,
-continued
Compound II-264
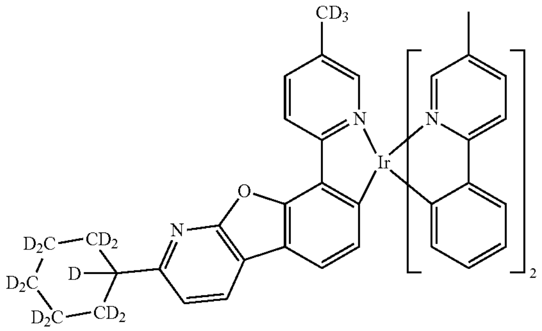
,
Compound II-265
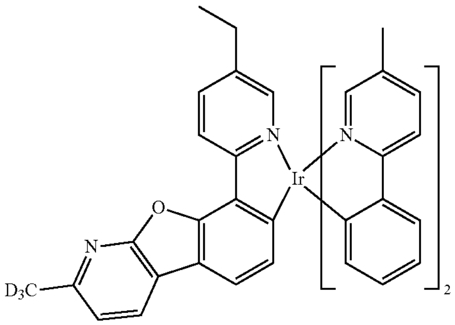
,
Compound II-266
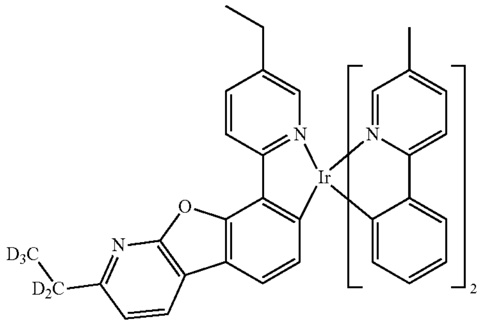
,
Compound II-267
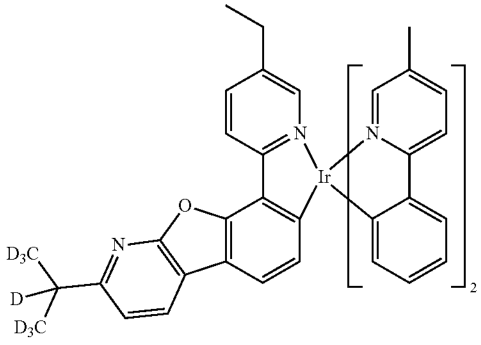
, -continued
Compound II-268
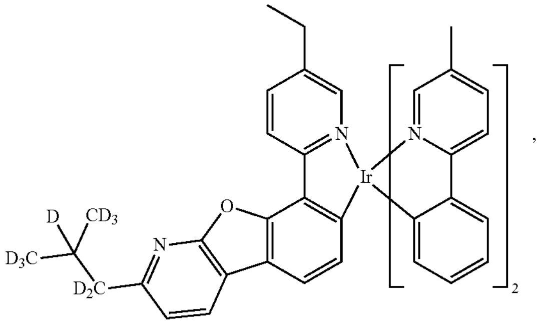
Compound II-269
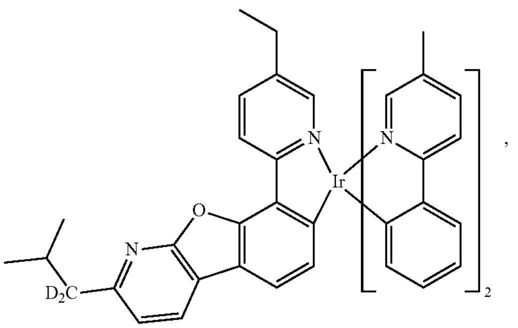
Compound II-270
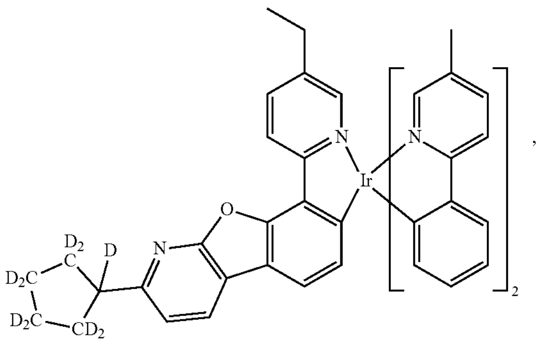
Compound II-271
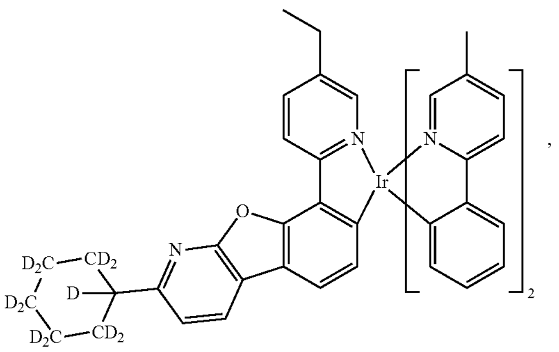
-continued
Compound II-272
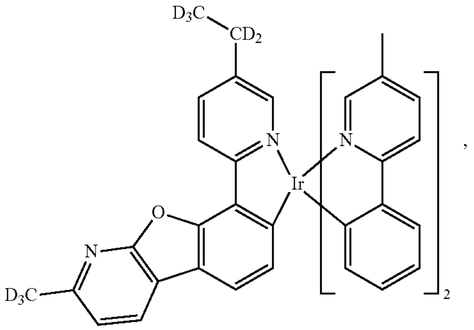
Compound II-273
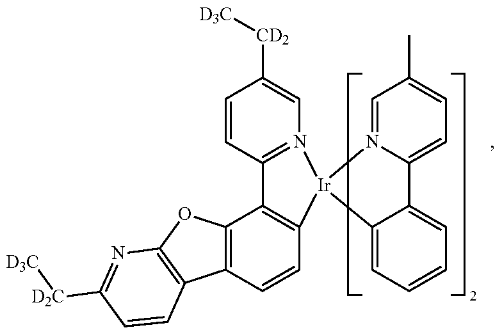
Compound II-274
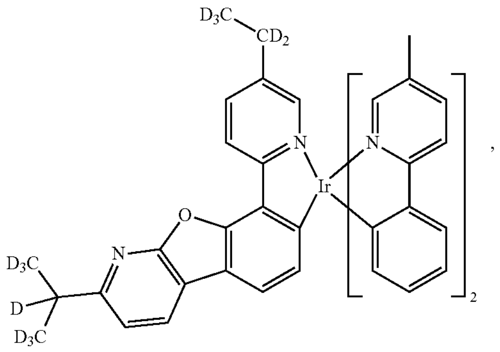
Compound II-275
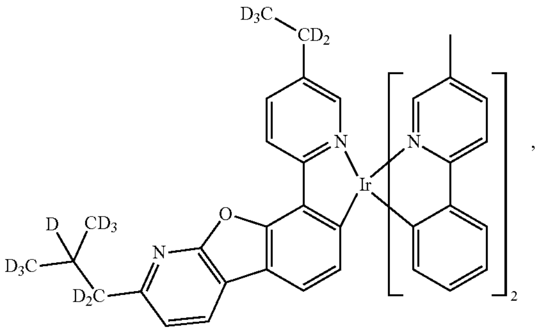

-continued
Compound II-276
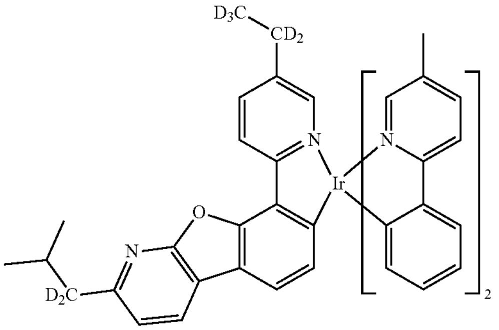
,
Compound II-277
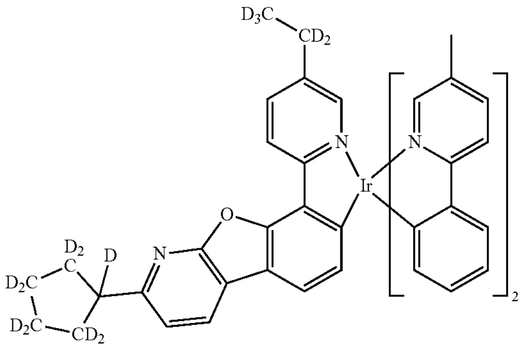
,
Compound II-278
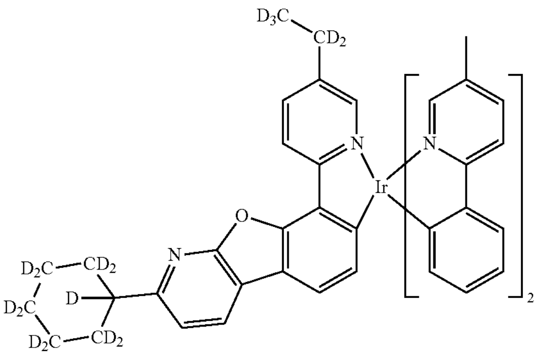
,
Compound II-279
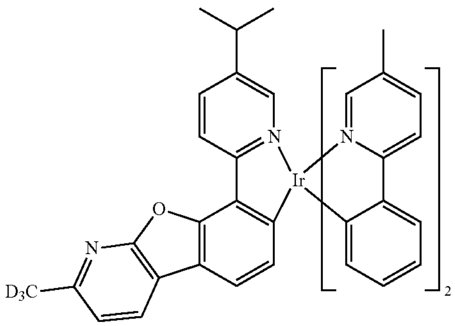
,
-continued
Compound II-280
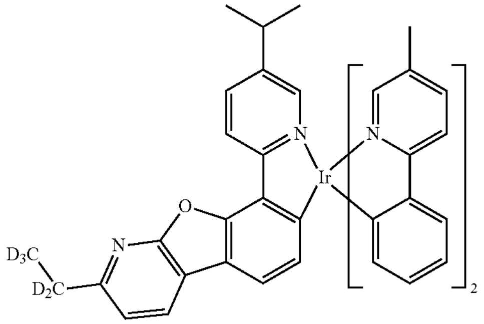
,
Compound II-281
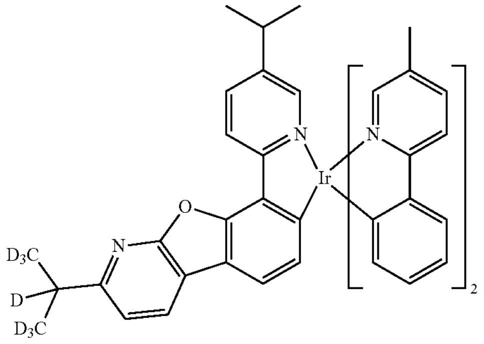
,
Compound II-282
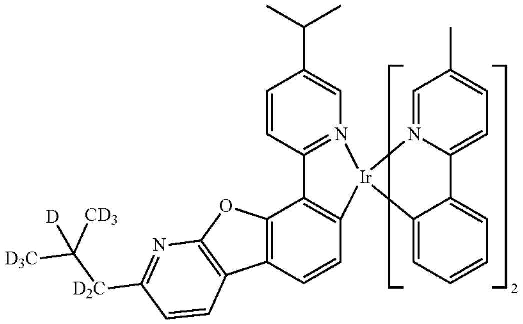
,
Compound II-283
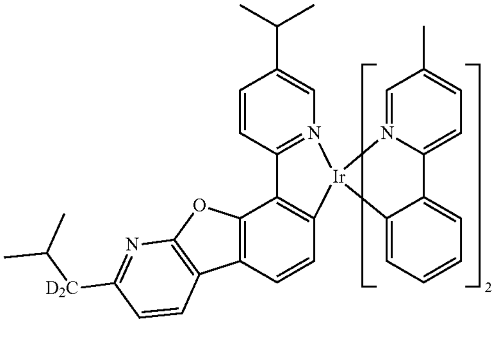
, -continued
Compound II-284
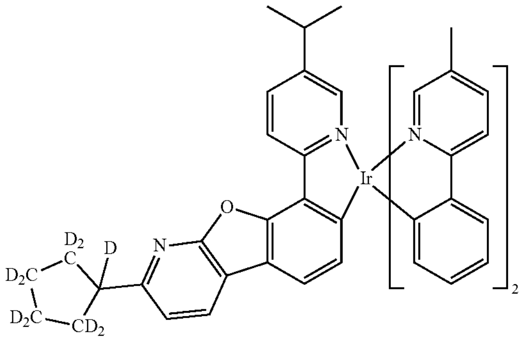
,
Compound II-285
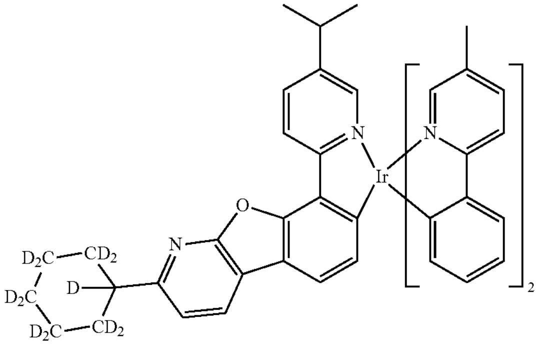
,
Compound II-286
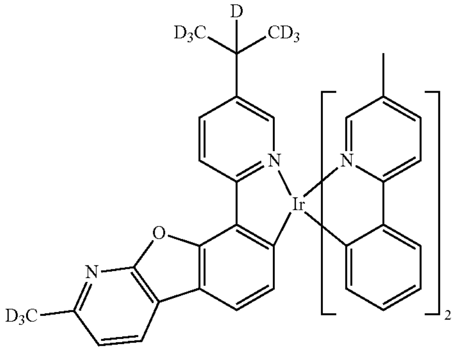
,
Compound II-287
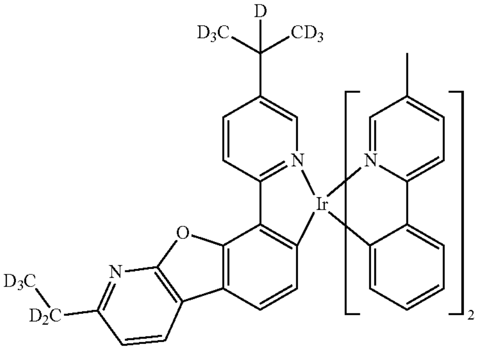
,
-continued
Compound II-288
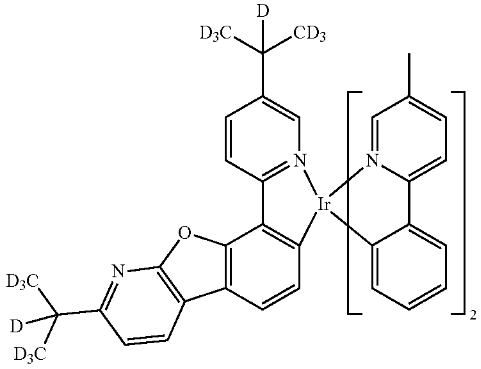
,
Compound II-289
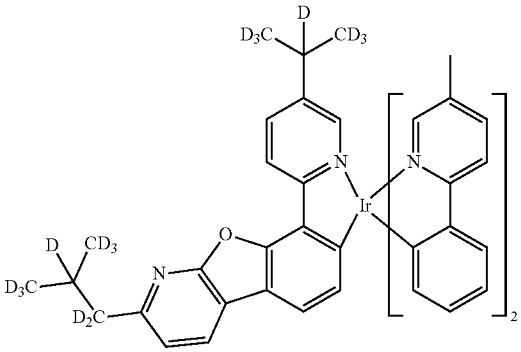
,
Compound II-290
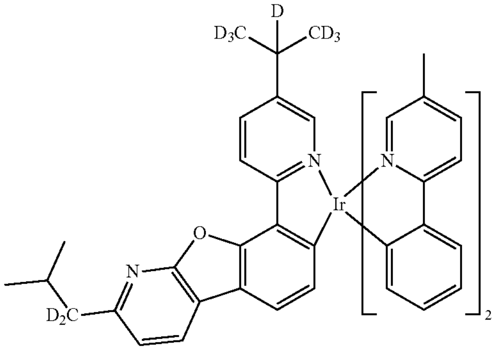
,
Compound II-291
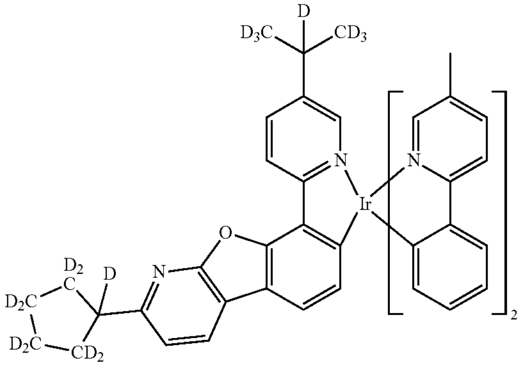
, -continued
Compound II-292
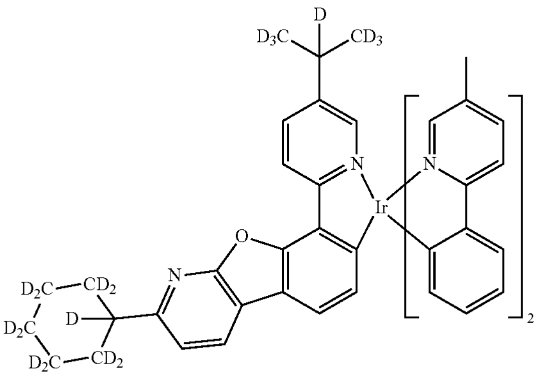
,
Compound II-293
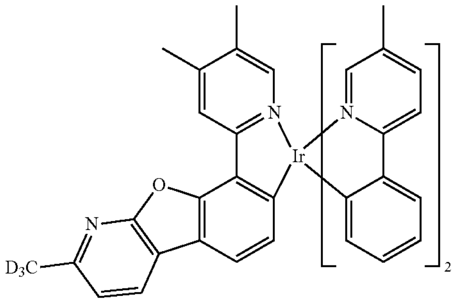
,
Compound II-294
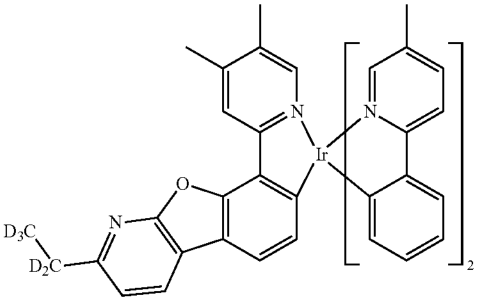
,
Compound II-295
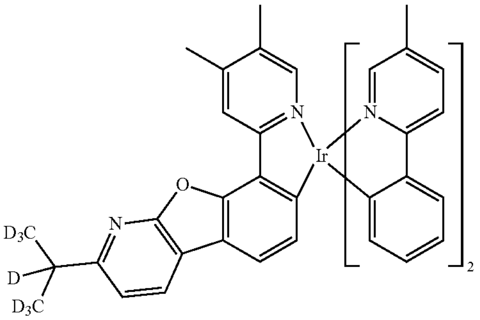
,
-continued
Compound II-296
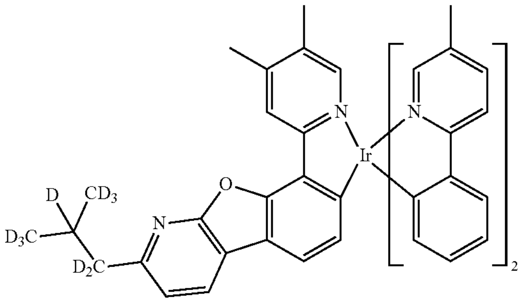
,
Compound II-297
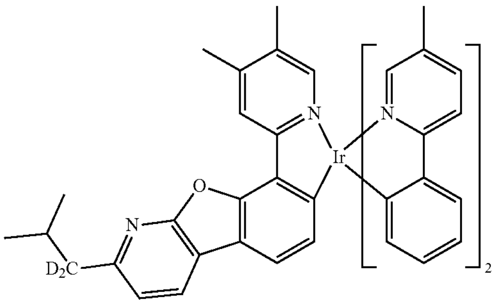
,
Compound II-298
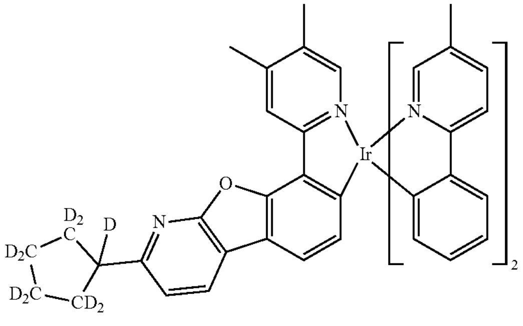
,
Compound II-299
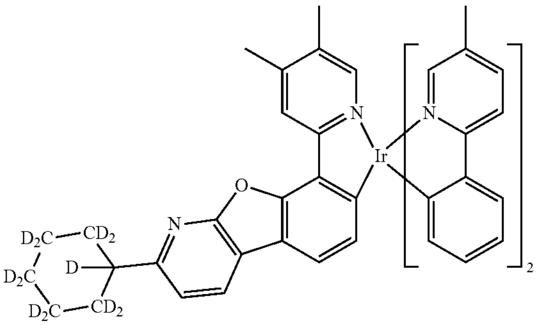
, -continued
Compound II-300
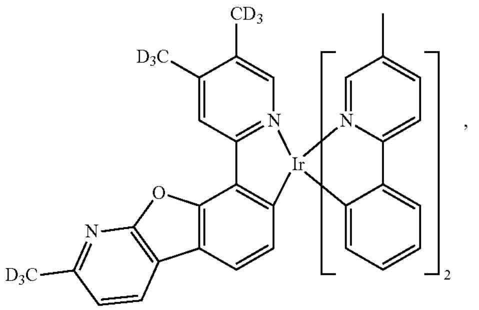
Compound II-301
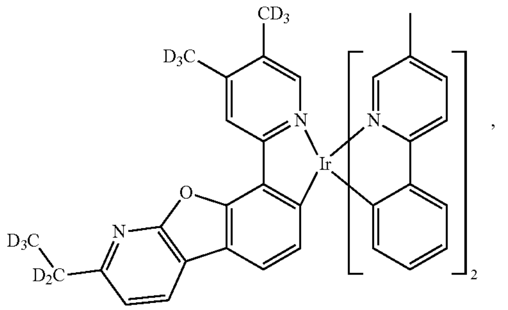
Compound II-302
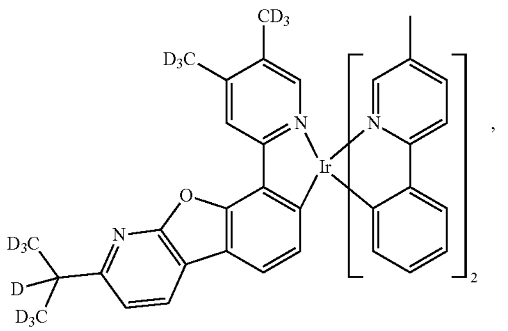
Compound II-303
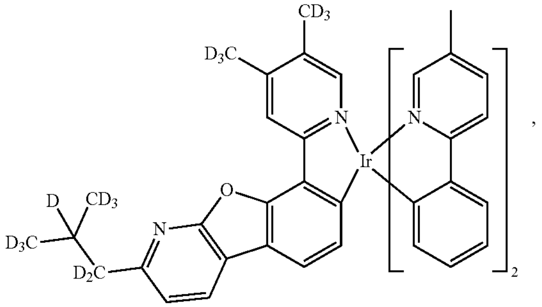
-continued
Compound II-304
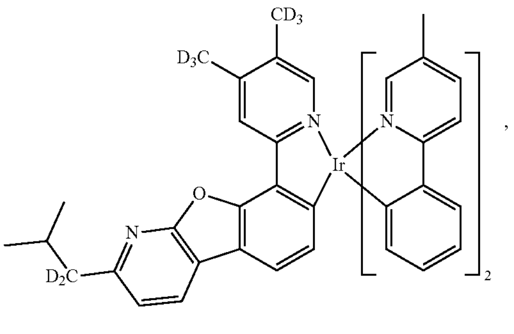
Compound II-305
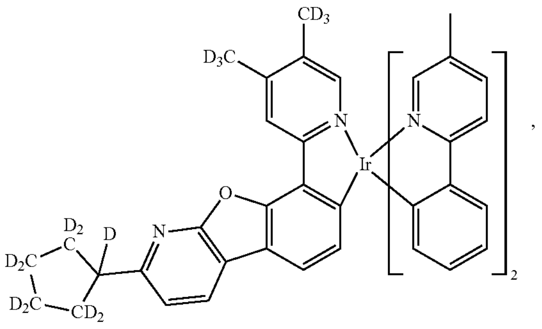
Compound II-306
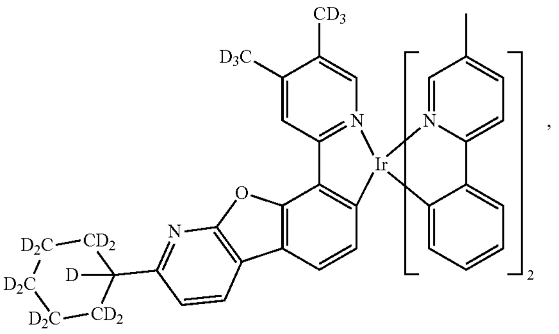
Compound II-307
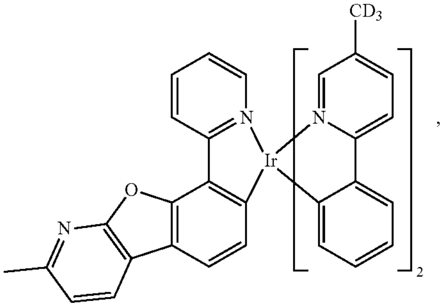

-continued
Compound II-308
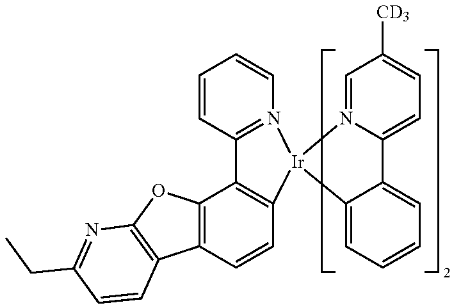
,
Compound II-309
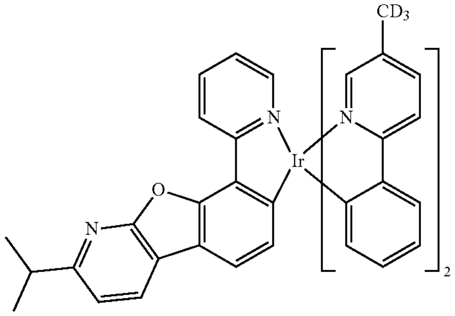
,
Compound II-310
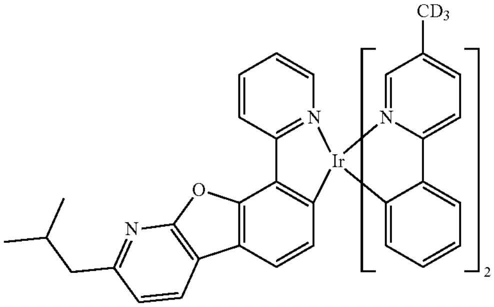
,
Compound II-311
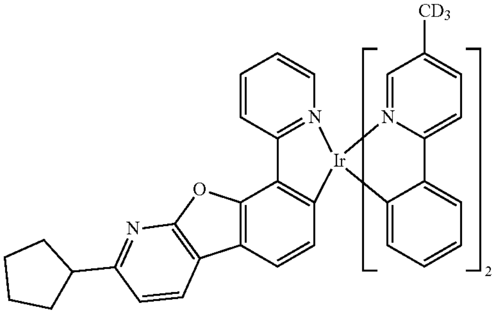
,
-continued
Compound II-312
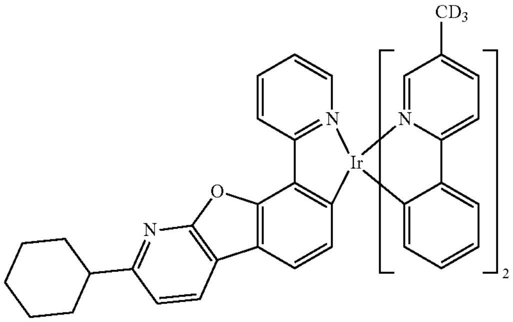
,
Compound II-313
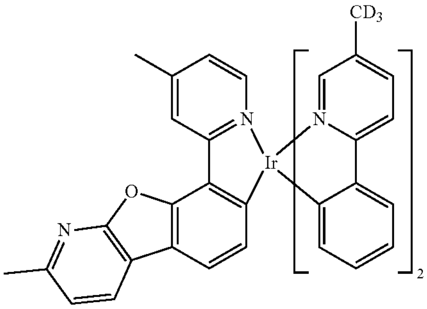
,
Compound II-314
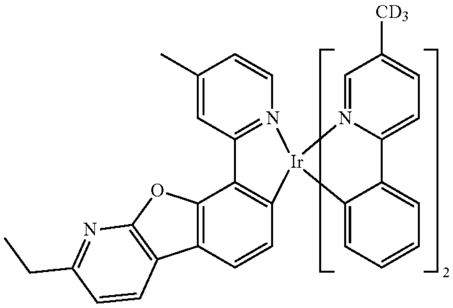
,
Compound II-315
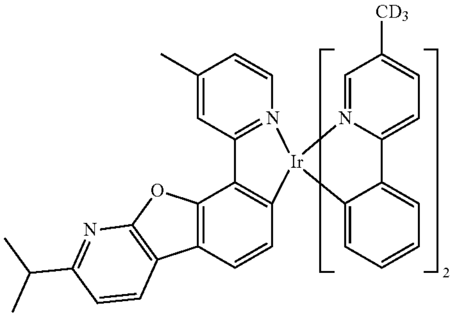
, -continued
Compound II-316
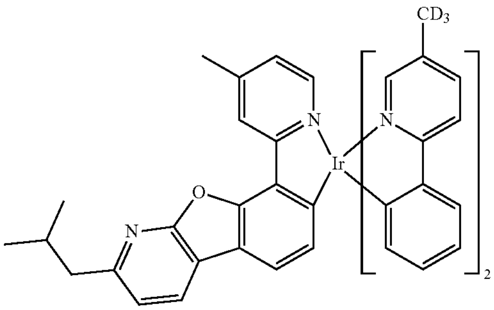
,
Compound II-317
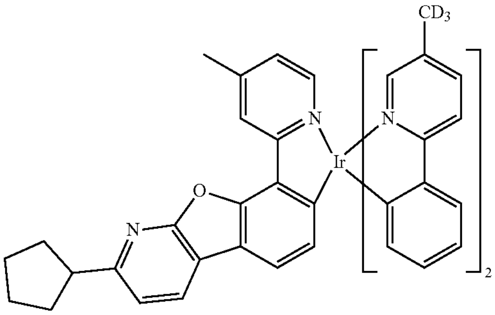
,
Compound II-318
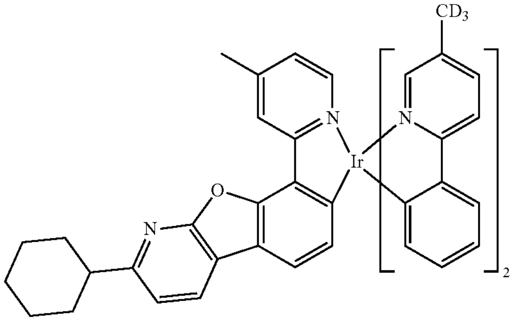
,
Compound II-319
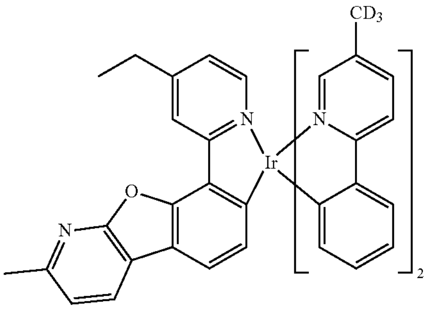
,
-continued
Compound II-320
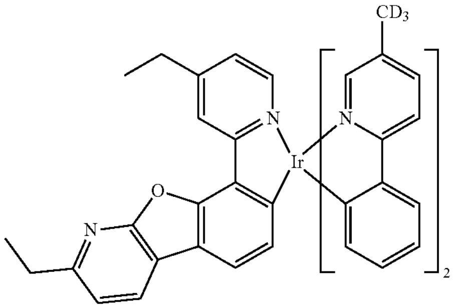
,
Compound II-321
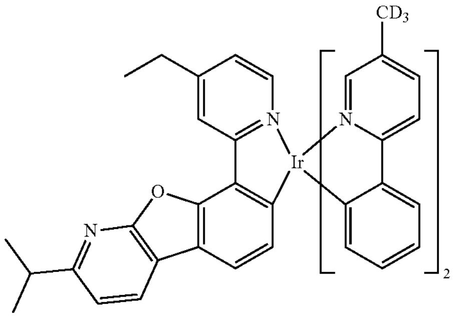
,
Compound II-322
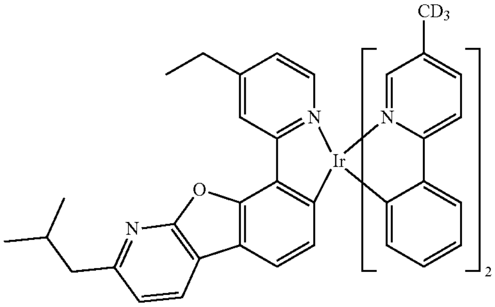
,
Compound II-323
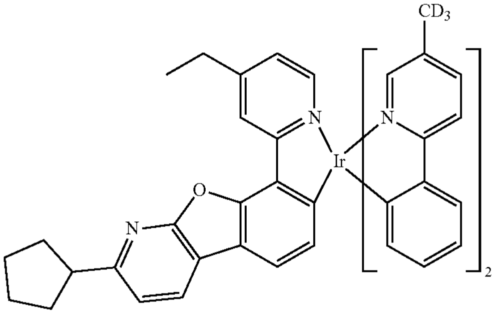
, -continued
Compound II-324
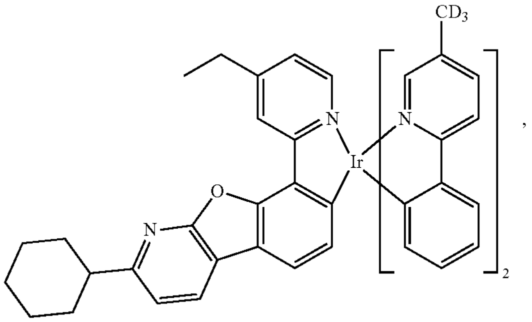
Compound II-325
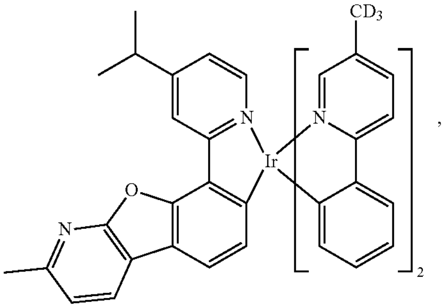
Compound II-326
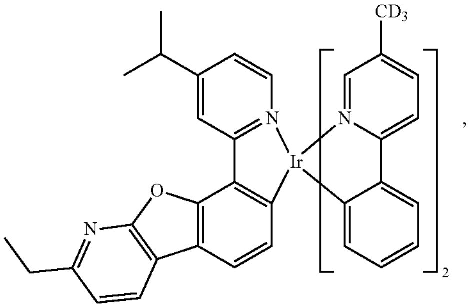
Compound II-327
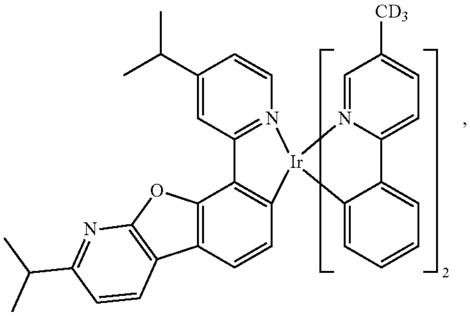
-continued
Compound II-328
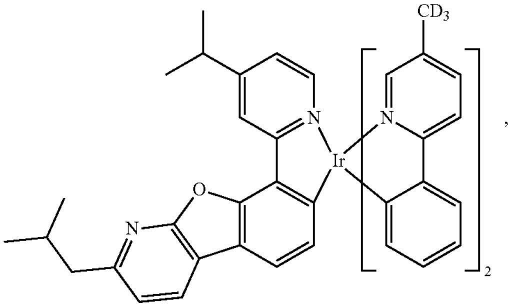
Compound II-329
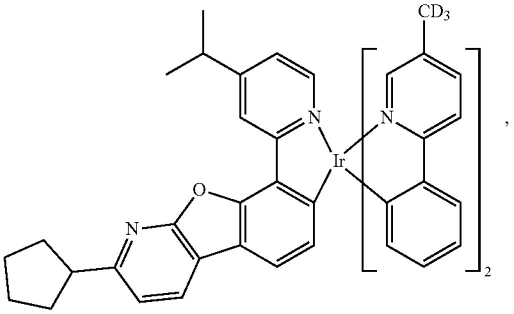
Compound II-330
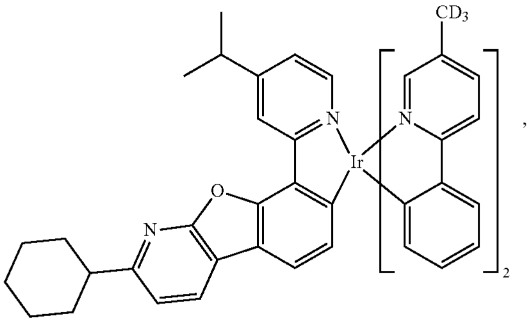
Compound II-331
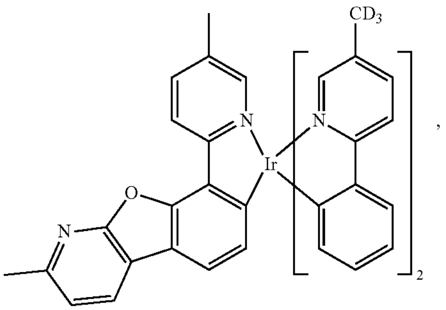

Compound II-332
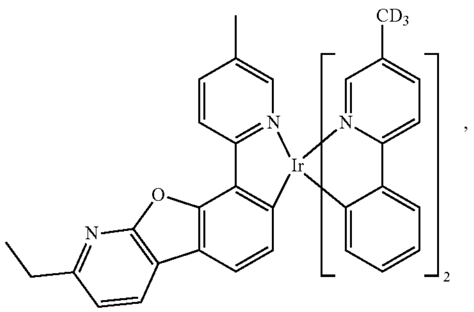
Compound II-333
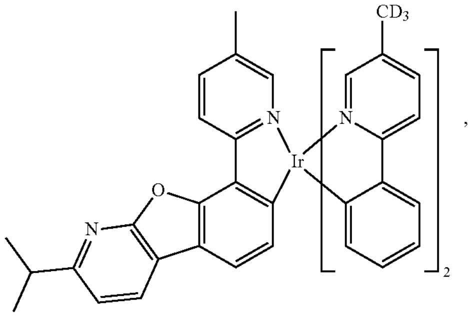
Compound II-334
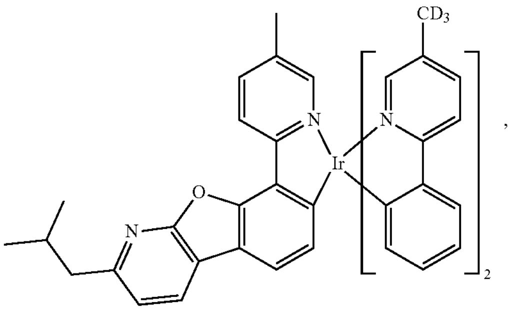
Compound II-335
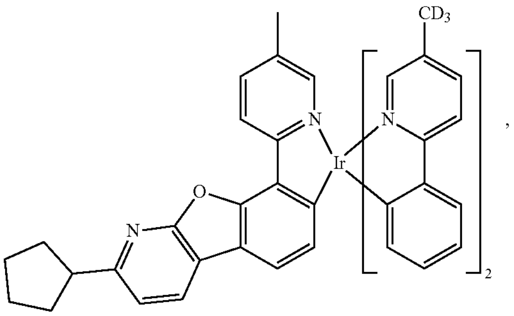
Compound II-336
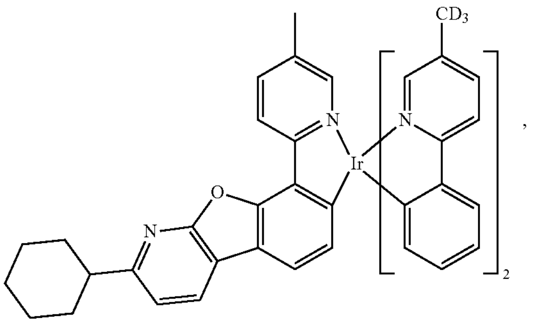
Compound II-337
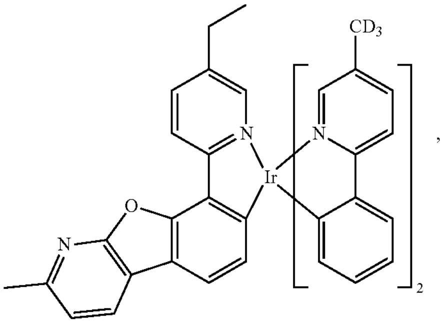
Compound II-338
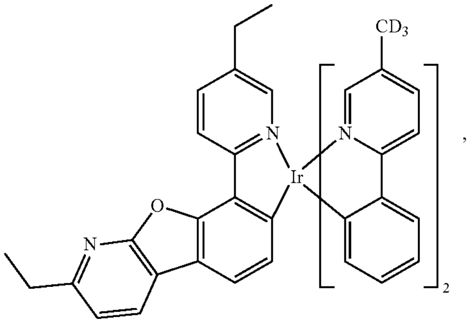
Compound II-339
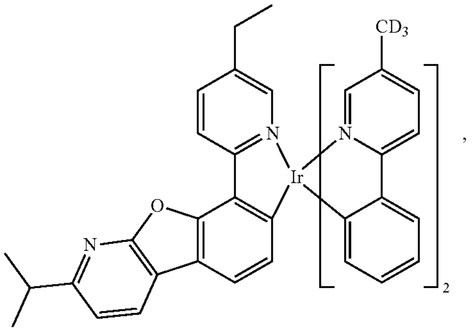

-continued
Compound II-340
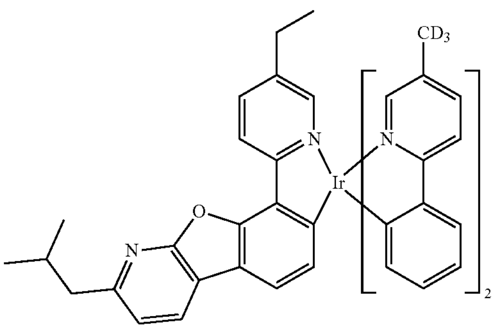
,
Compound II-341
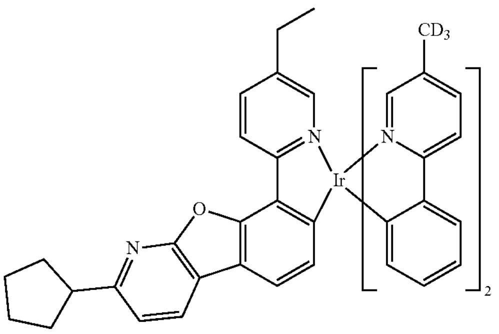
,
Compound II-342
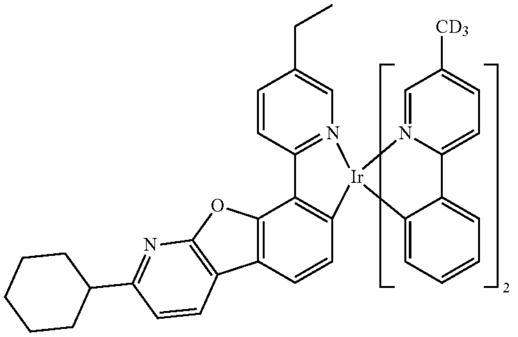
,
Compound II-343
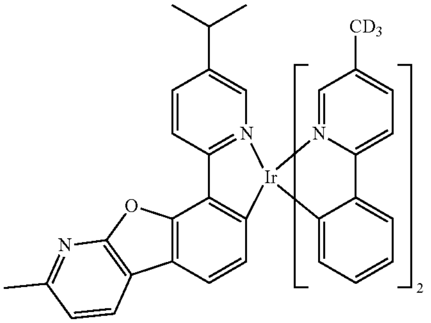
,
-continued
Compound II-344
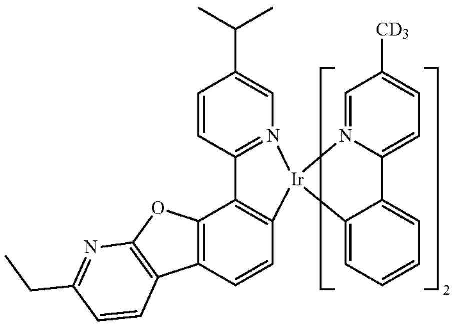
,
Compound II-345
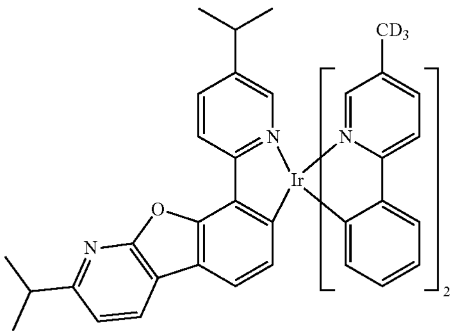
,
Compound II-346
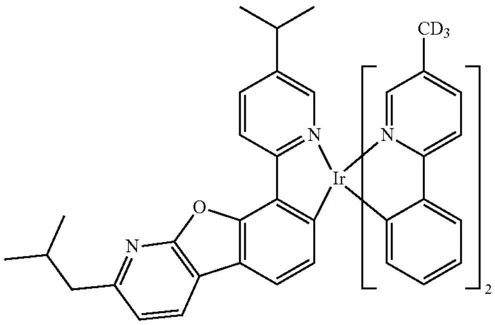
,
Compound II-347
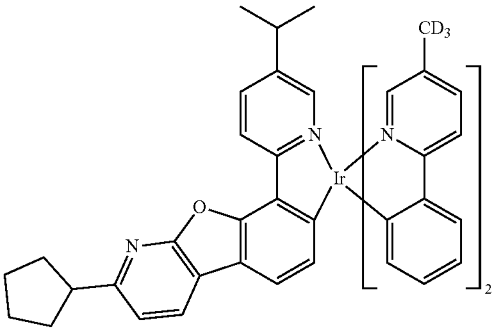
, -continued
Compound II-348
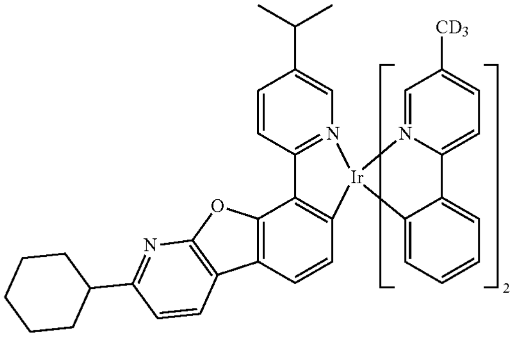
,
Compound II-349
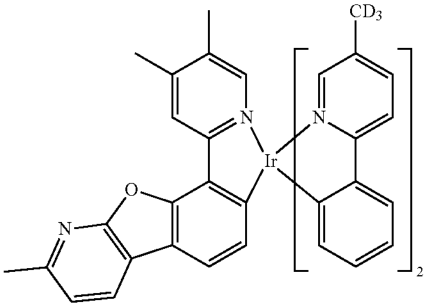
,
Compound II-350
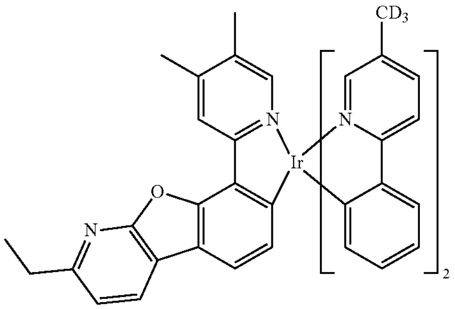
,
Compound II-351
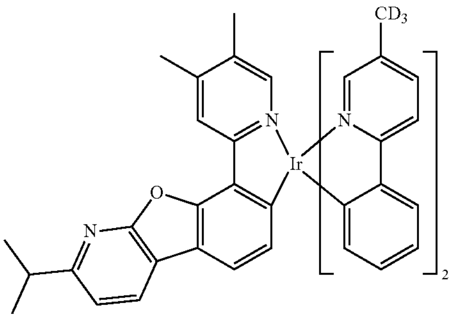
,
-continued
Compound II-352
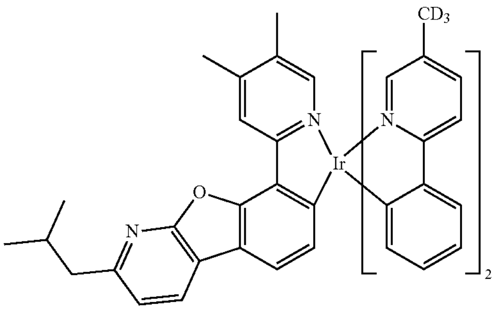
,
Compound II-353
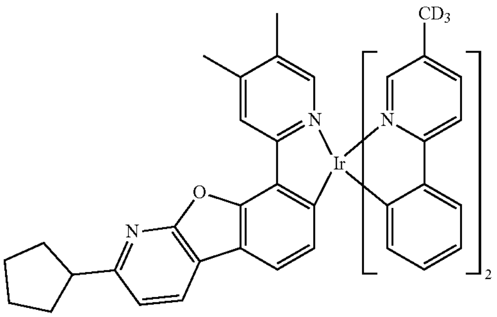
,
Compound II-354
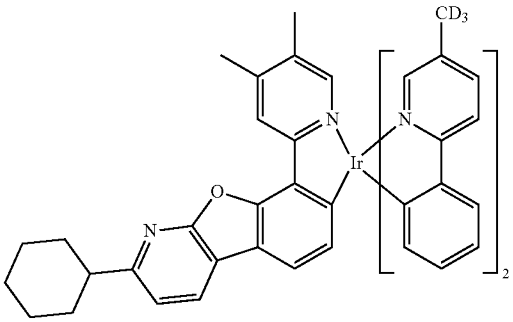
,
Compound II-355
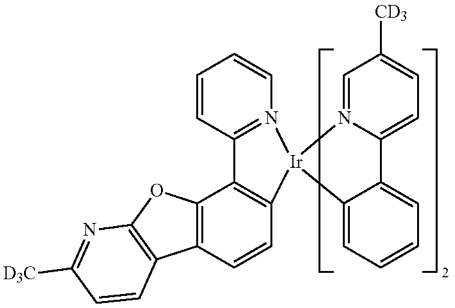
, -continued
Compound II-356
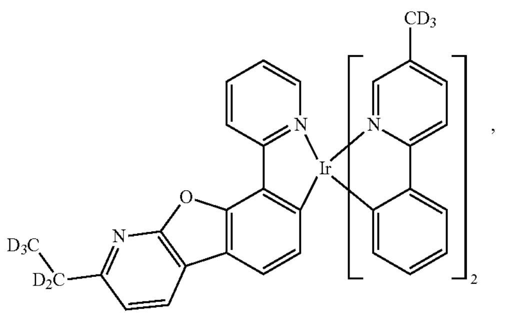
Compound II-357
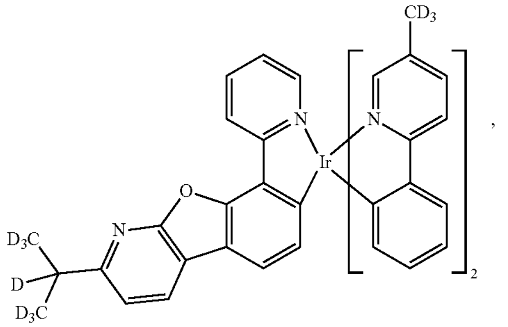
Compound II-358
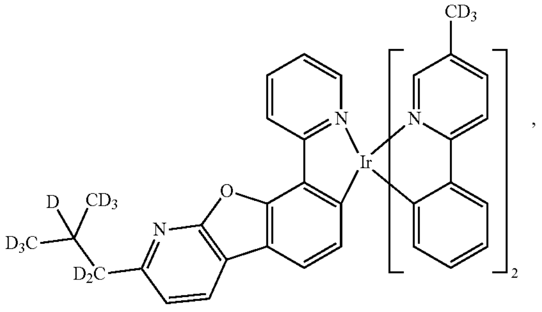
Compound II-359
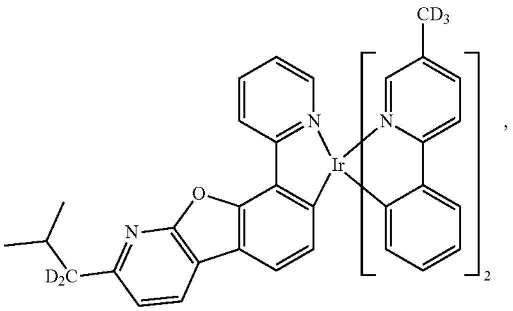
-continued
Compound II-360
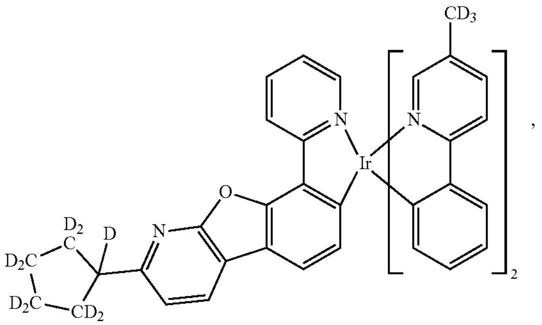
Compound II-361
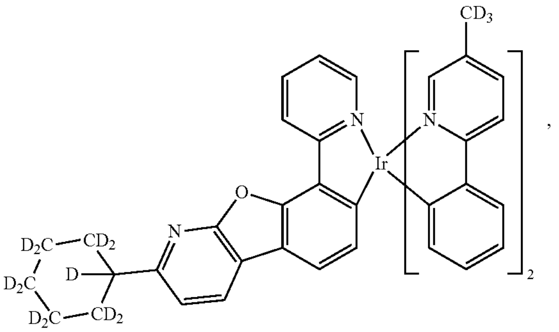
Compound II-362
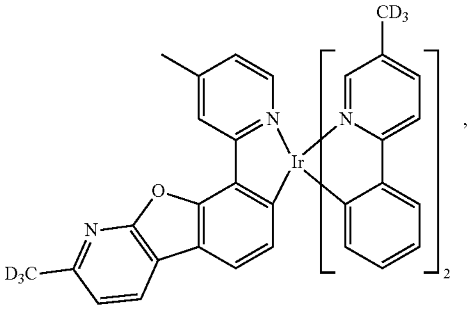
Compound II-363
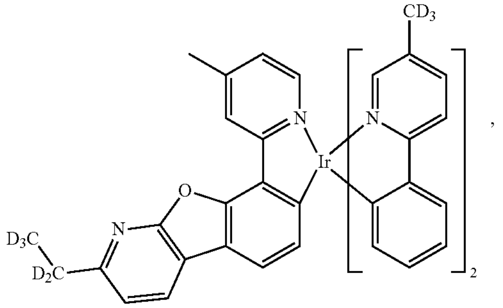

-continued
Compound II-364
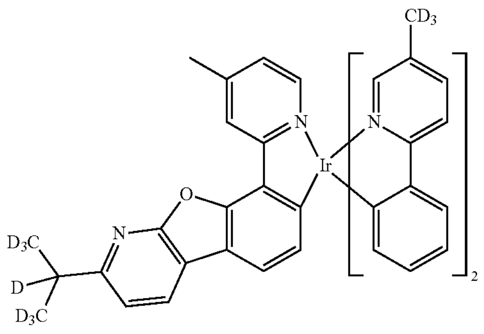
,
Compound II-365
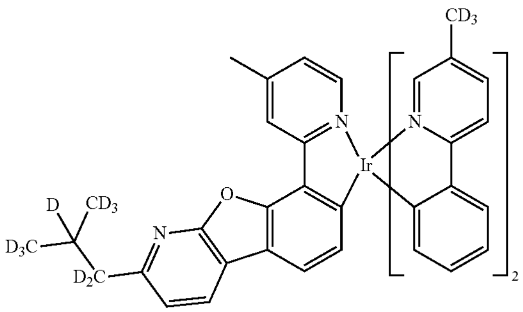
,
Compound II-366
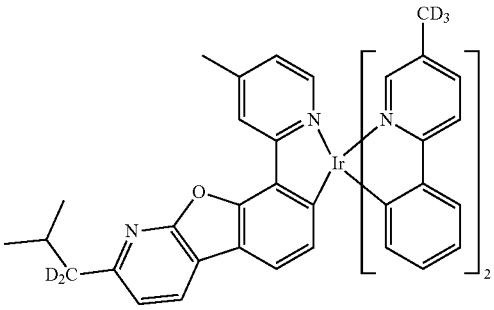
,
Compound II-367
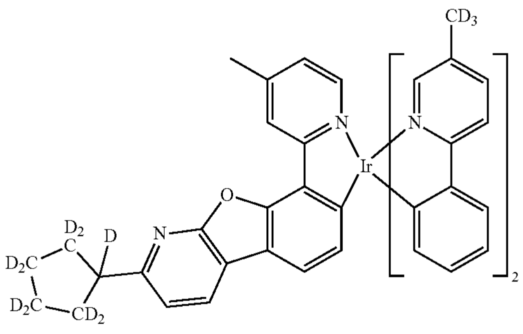
,
-continued
Compound II-368
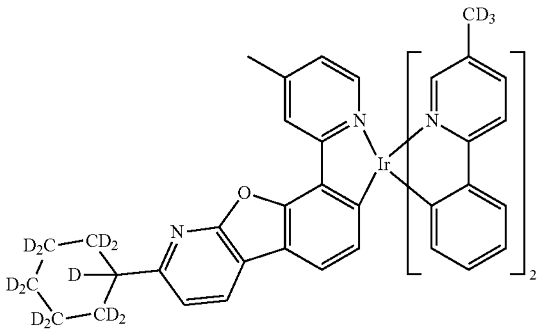
,
Compound II-369
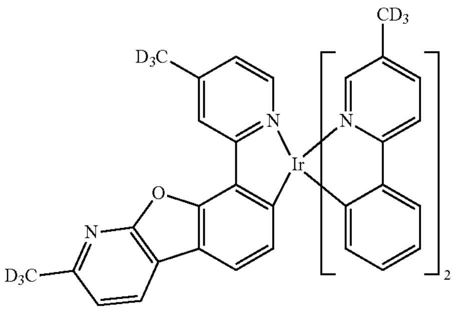
,
Compound II-370
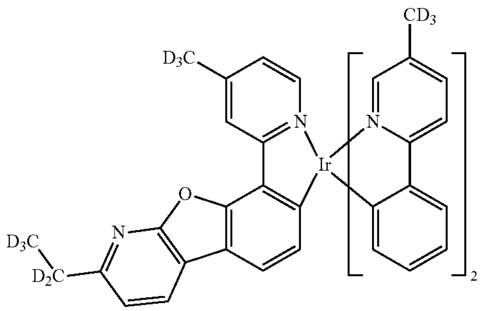
,
Compound II-371
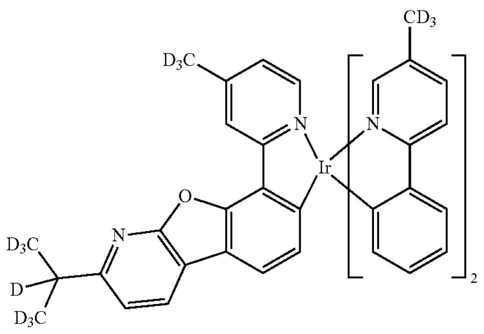
, -continued
Compound II-372
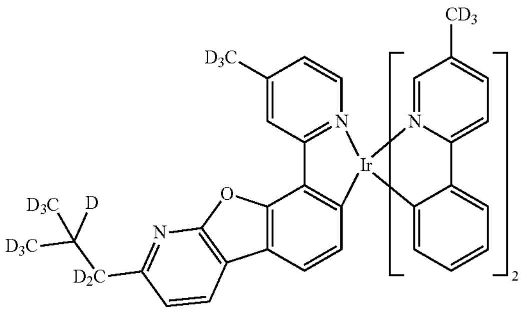
,
Compound II-373
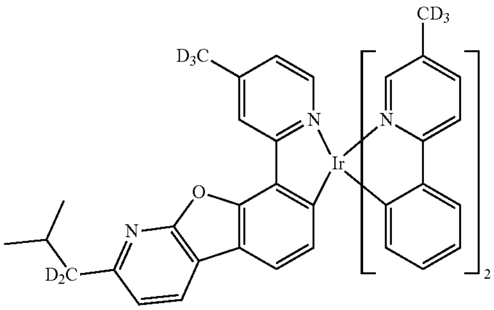
,
Compound II-374
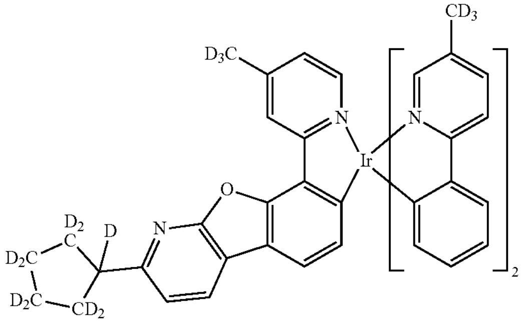
,
Compound II-375
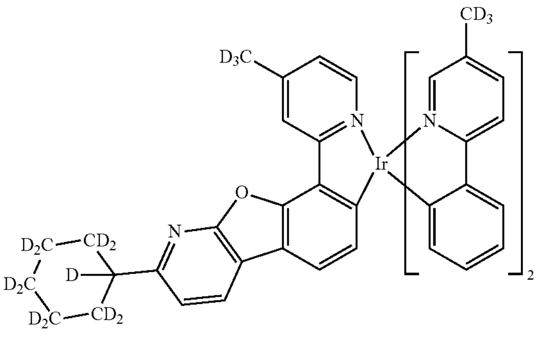
,
-continued
Compound II-376
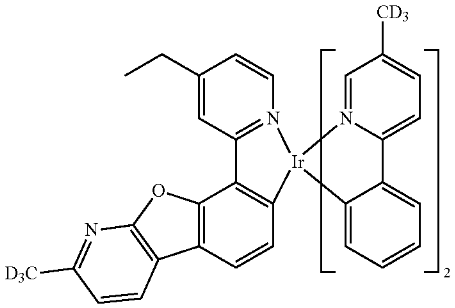
,
Compound II-377
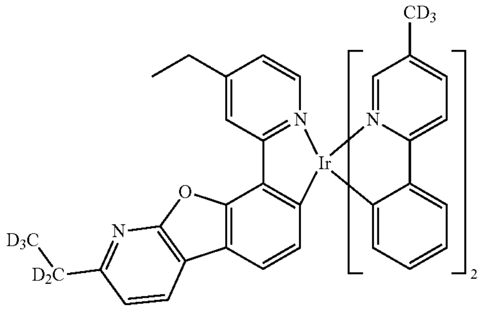
,
Compound II-378
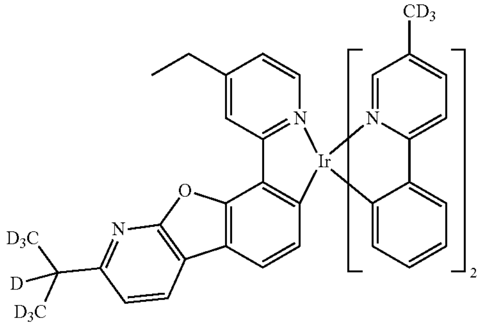
,
Compound II-379
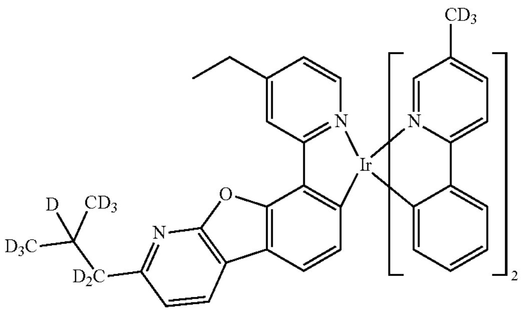
, -continued
Compound II-380
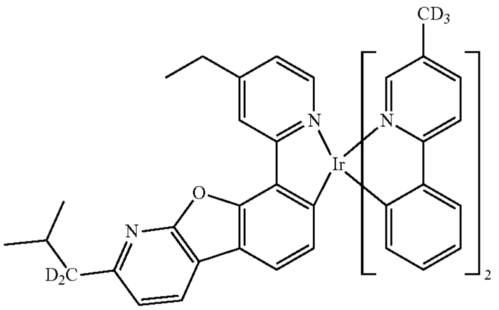
,
Compound II-381
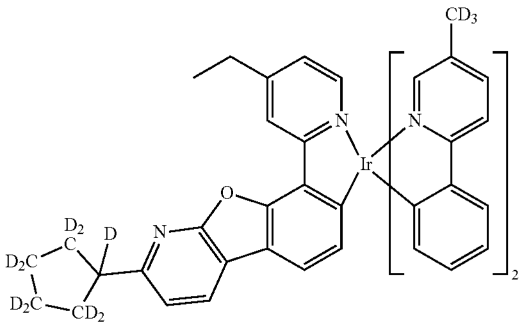
,
Compound II-382
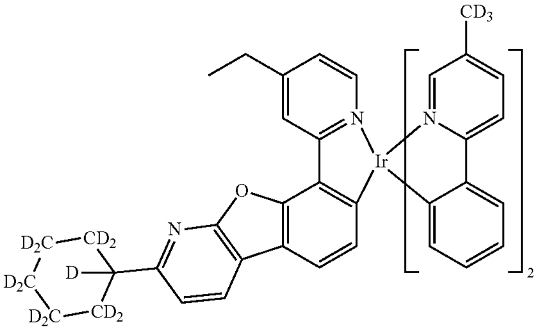
,
Compound II-383
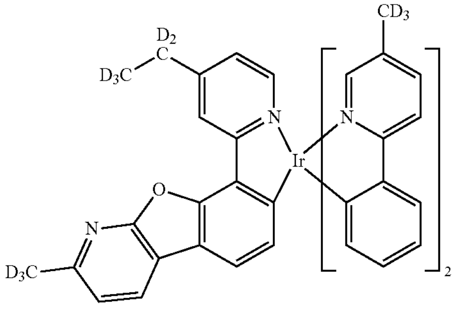
,
-continued
Compound II-384
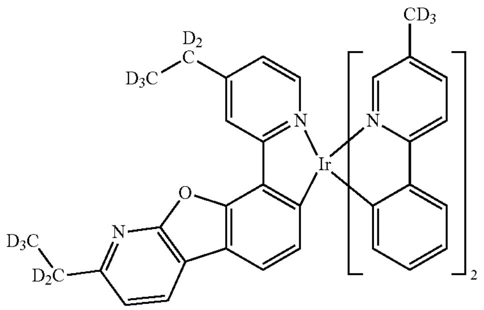
,
Compound II-385
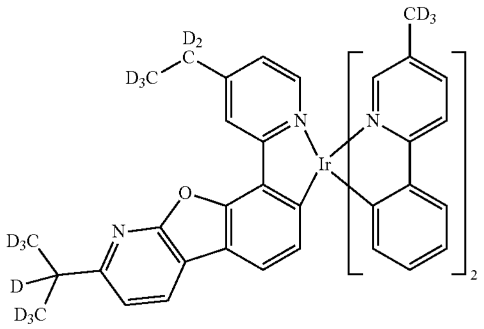
,
Compound II-386
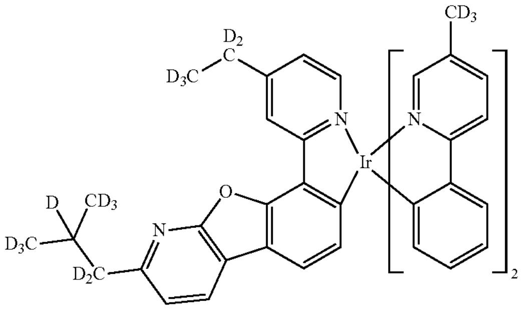
,
Compound II-387
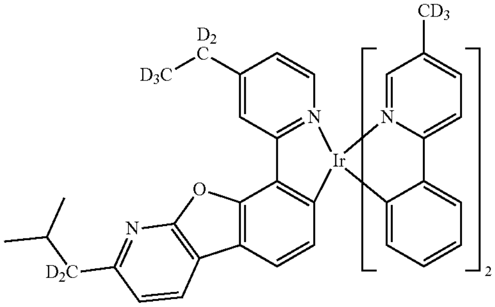
, -continued
Compound II-388
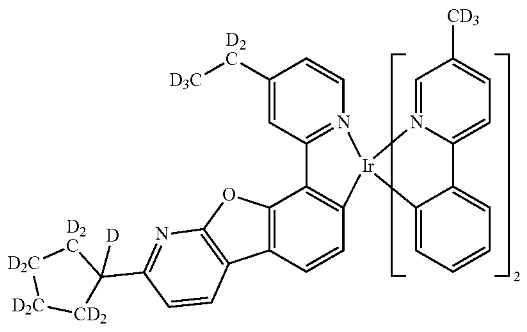
,
Compound II-389
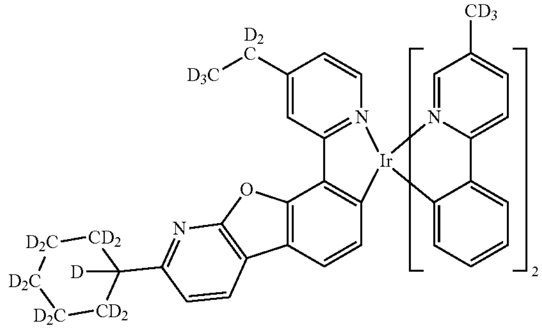
,
Compound II-390
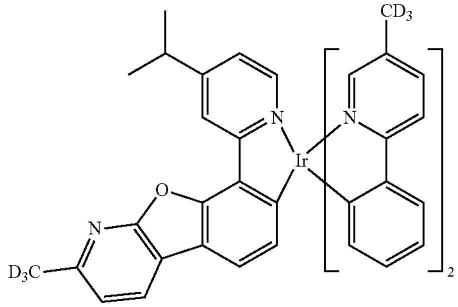
,
Compound II-391
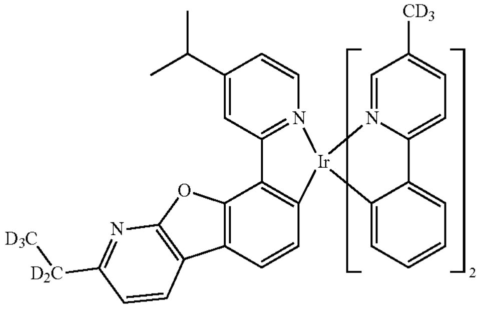
,
-continued
Compound II-392
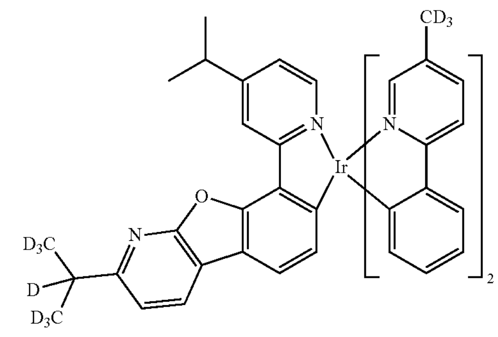
,
Compound II-393
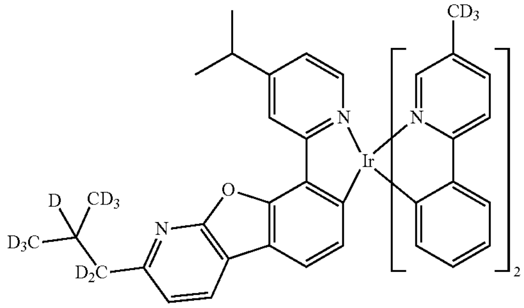
,
Compound II-394
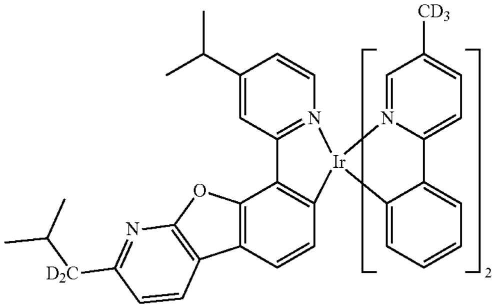
,
Compound II-395
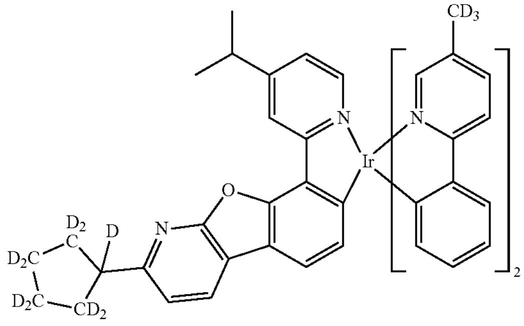
, -continued
Compound II-396
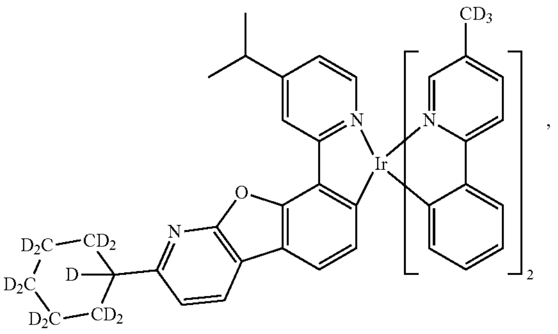
Compound II-397
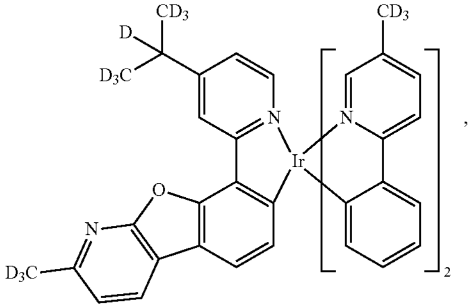
Compound II-398
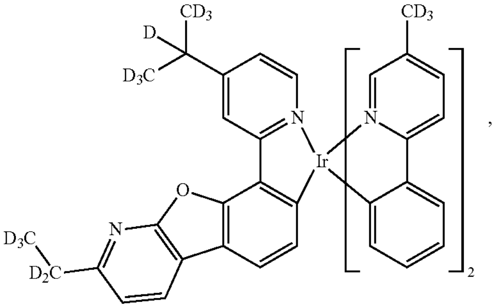
Compound II-399
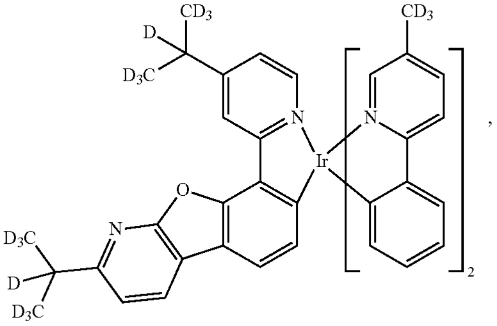
-continued
Compound II-400
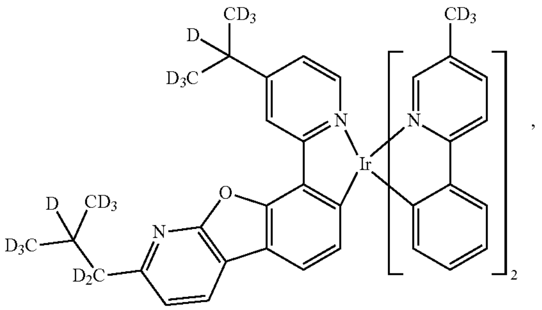
Compound II-401
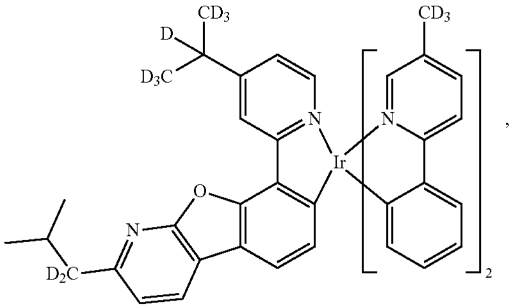
Compound II-402
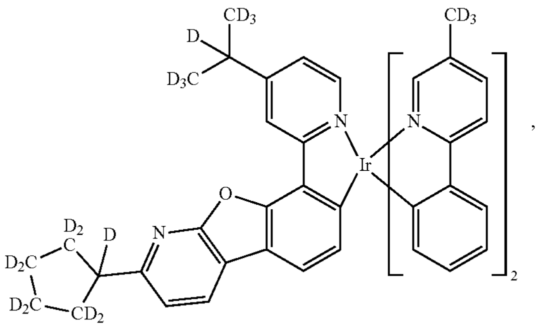
Compound II-403
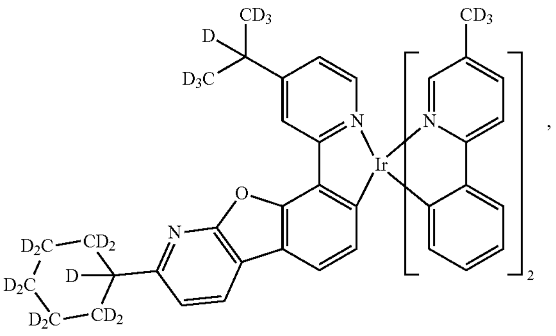

-continued
Compound II-404
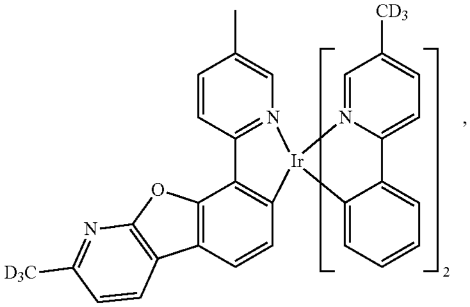
Compound II-405
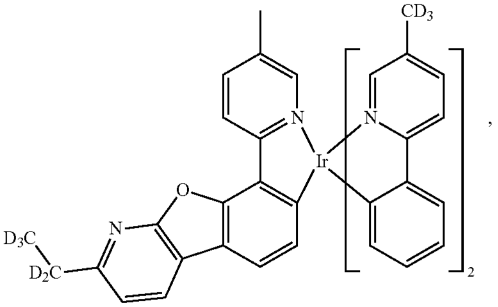
Compound II-406
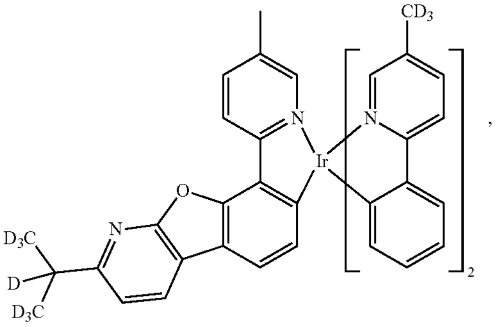
Compound II-407
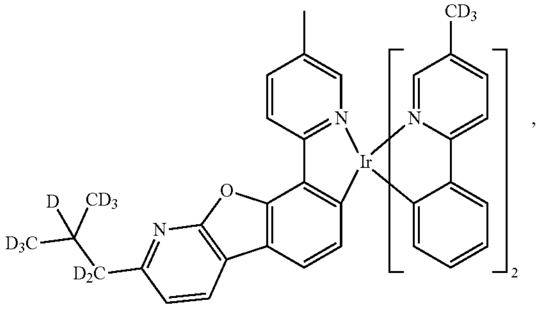
-continued
Compound II-408
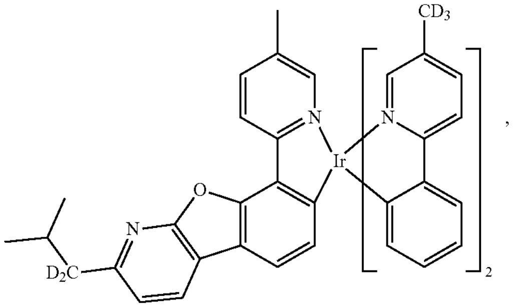
Compound II-409
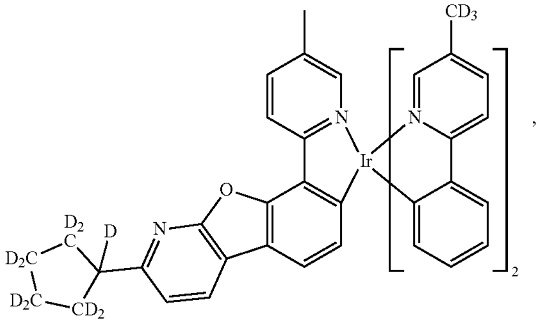
Compound II-410
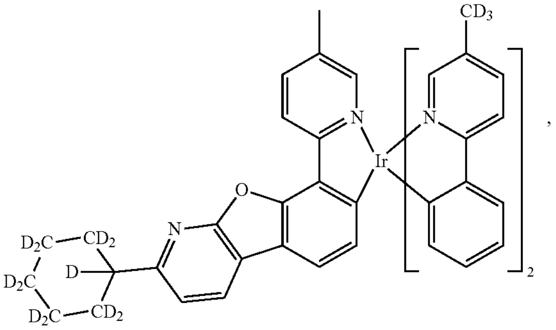
Compound II-411
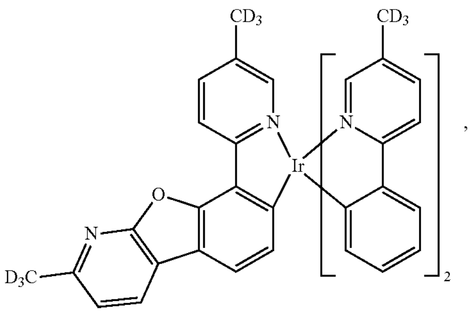

-continued
Compound II-412
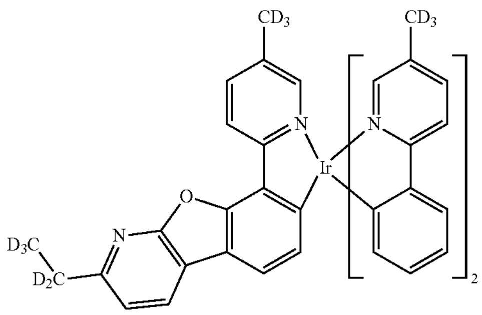
,
Compound II-413
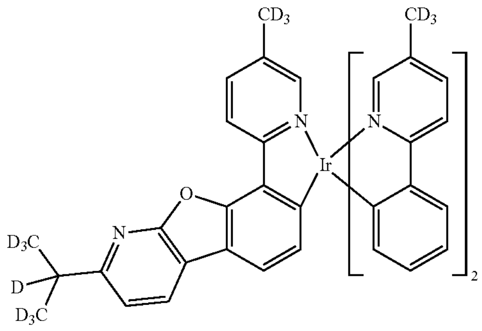
,
Compound II-414
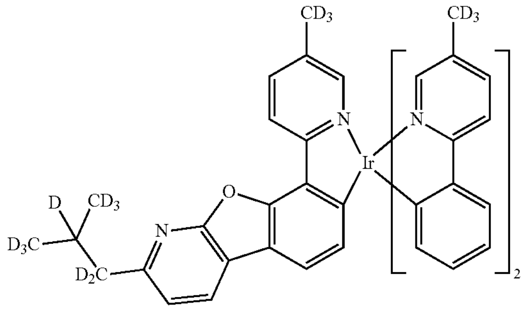
,
Compound II-415
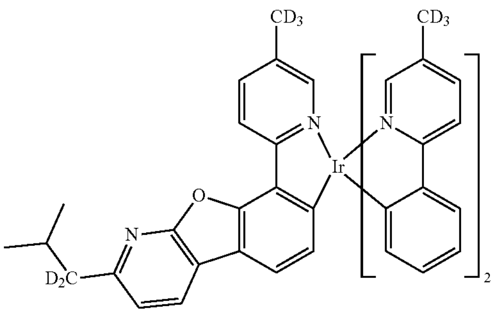
,
-continued
Compound II-416
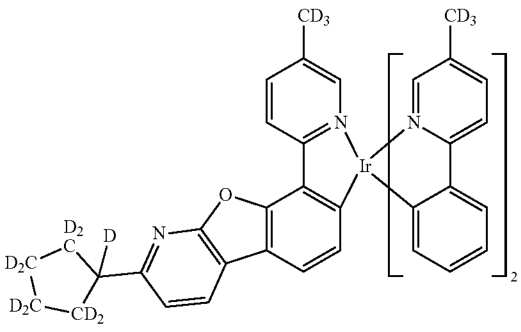
,
Compound II-417
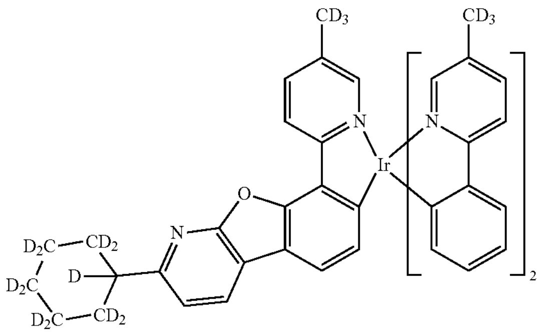
,
Compound II-418
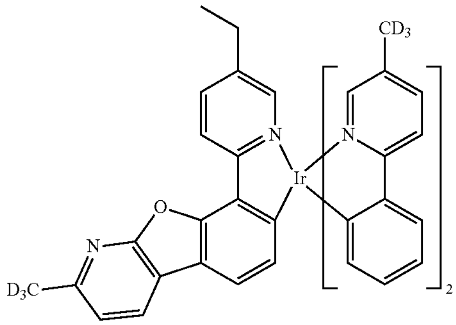
,
Compound II-419
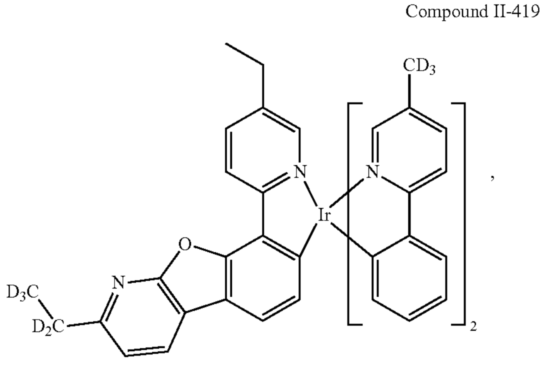
, -continued
Compound II-420
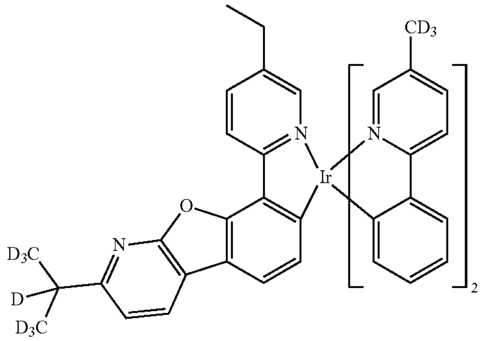
,
Compound II-421
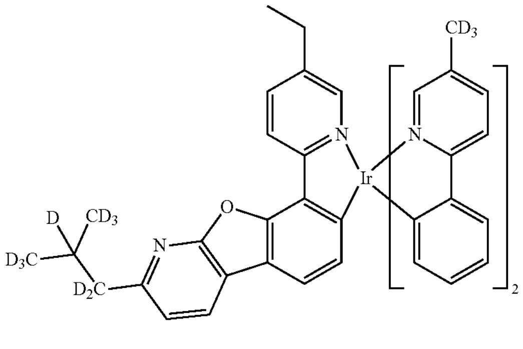
,
Compound II-422
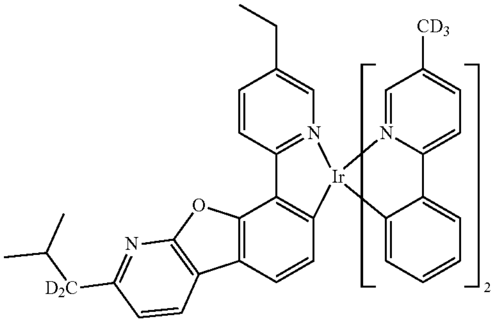
,
Compound II-423
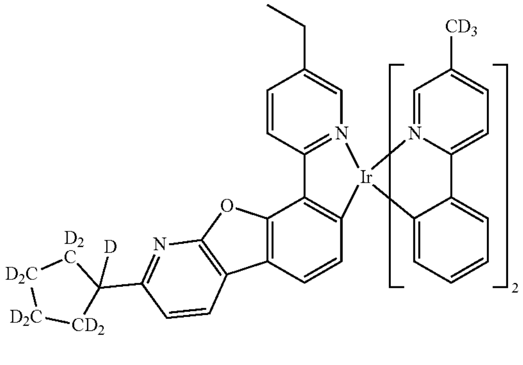
,
-continued
Compound II-424
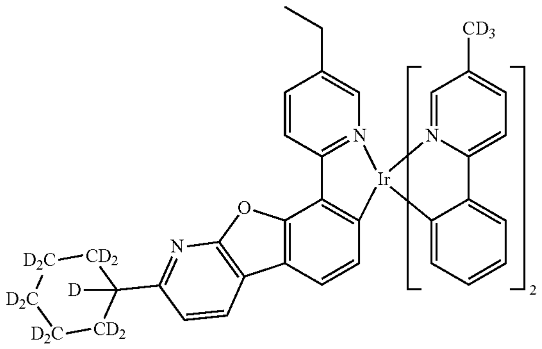
,
Compound II-425
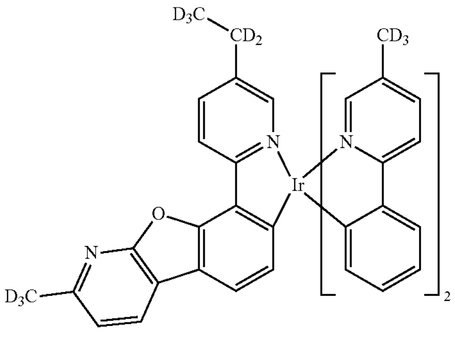
,
Compound II-426
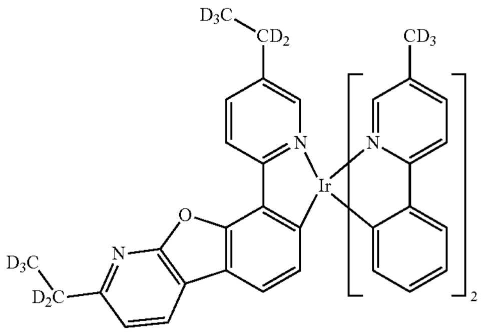
,
Compound II-427
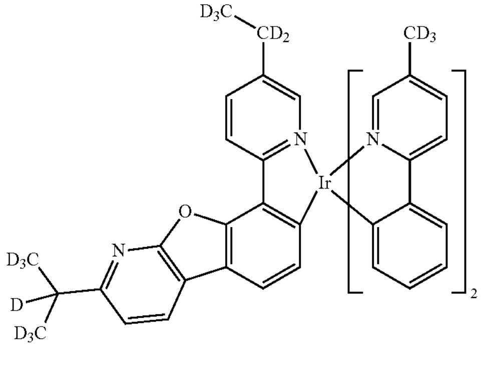
, Compound II-428
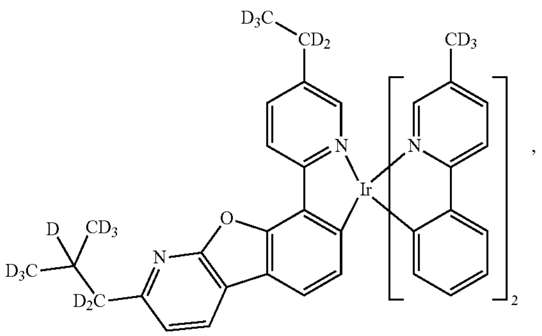
Compound II-429
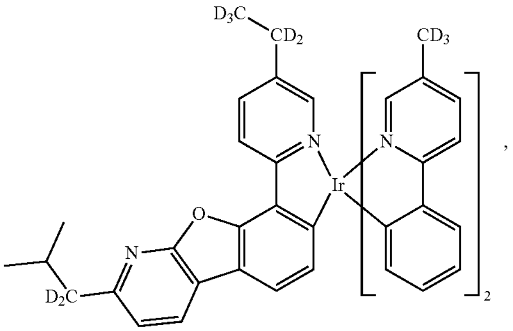
Compound II-430
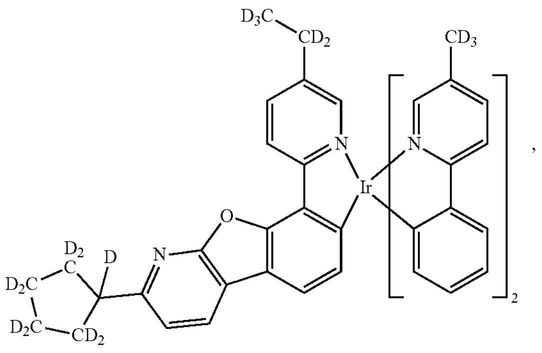
Compound II-431
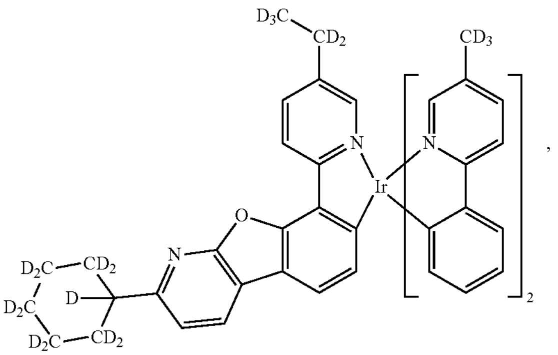
Compound II-432
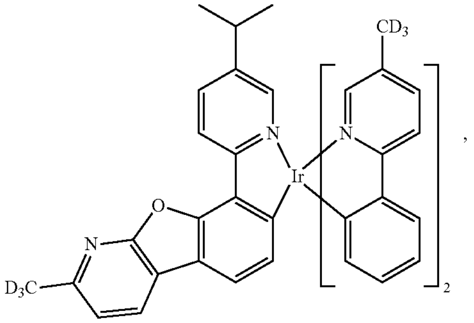
Compound II-433
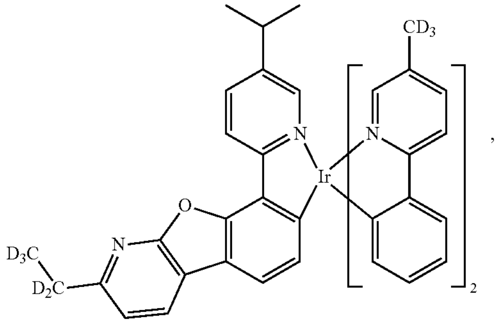
Compound II-434
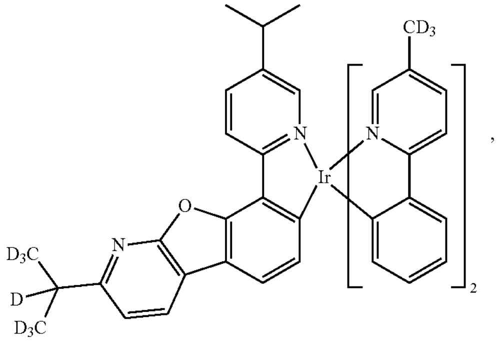
Compound II-435
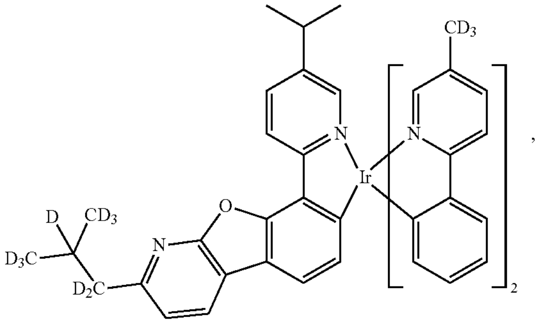

-continued
Compound II-436
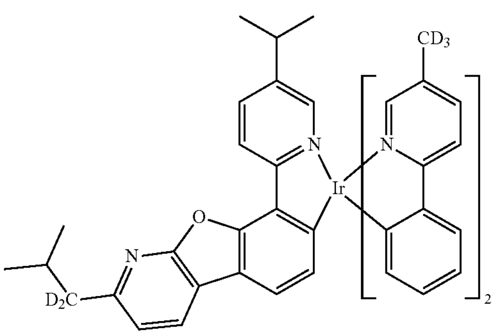
,
Compound II-437
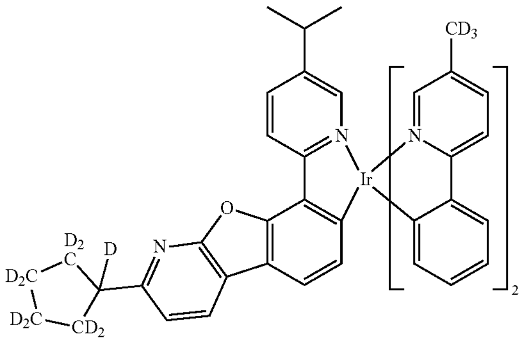
,
Compound II-438
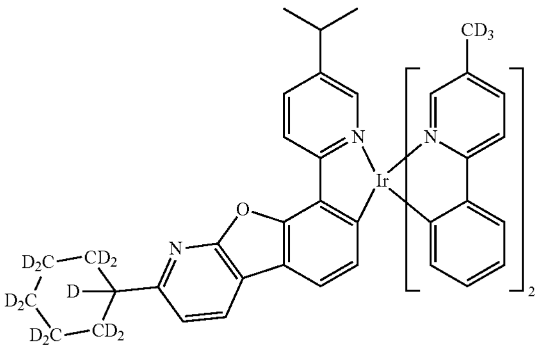
,
Compound II-439
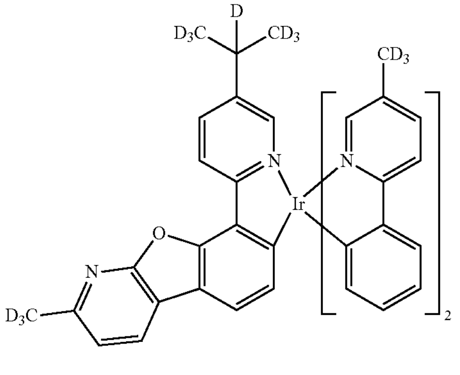
,
-continued
Compound II-440
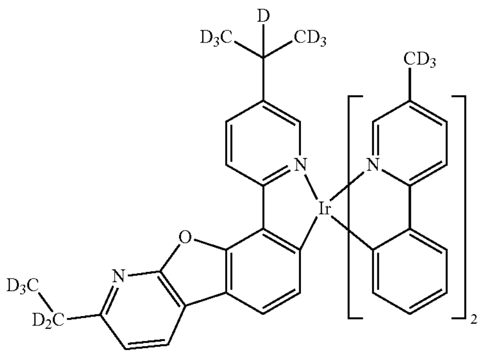
,
Compound II-441
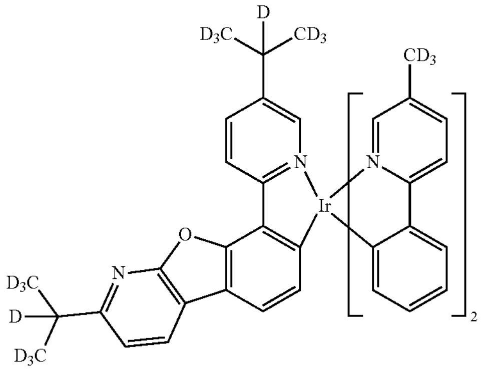
,
Compound II-442
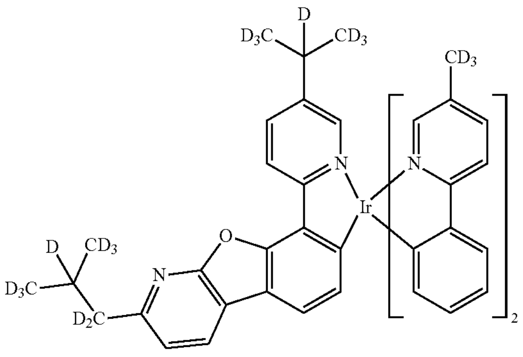
,
Compound II-443
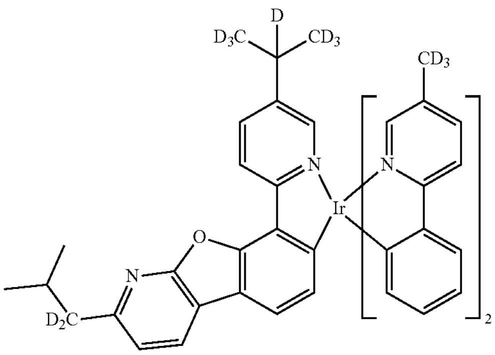
, -continued
Compound II-444
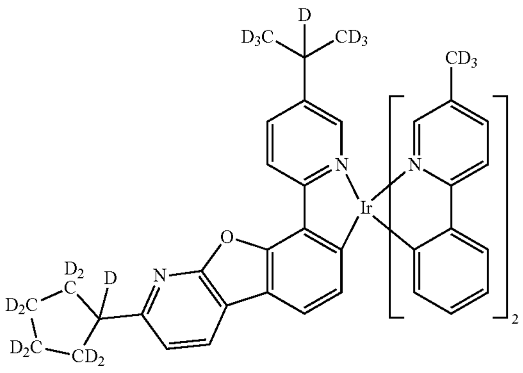
,
Compound II-445
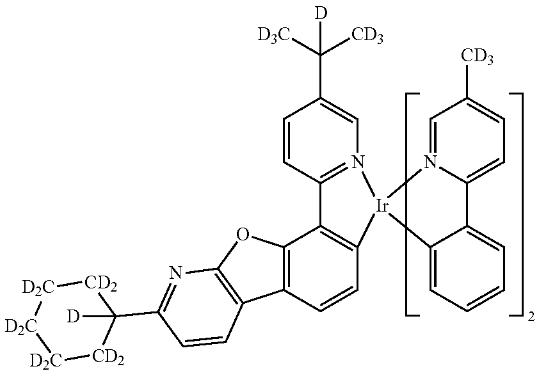
,
Compound II-446
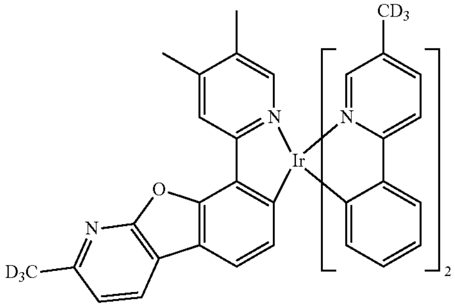
,
Compound II-447
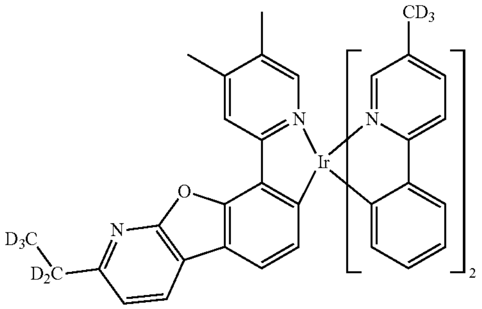
,
-continued
Compound II-448
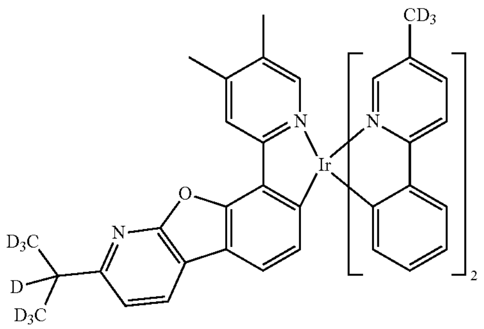
,
Compound II-449
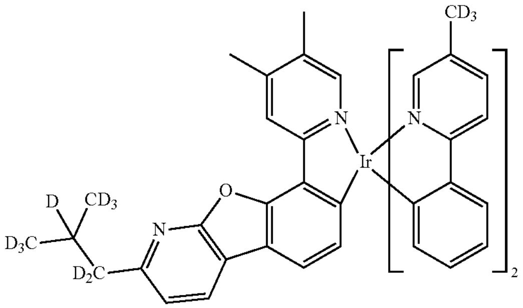
,
Compound II-450
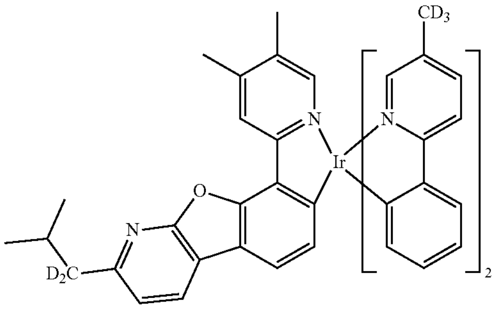
,
Compound II-451
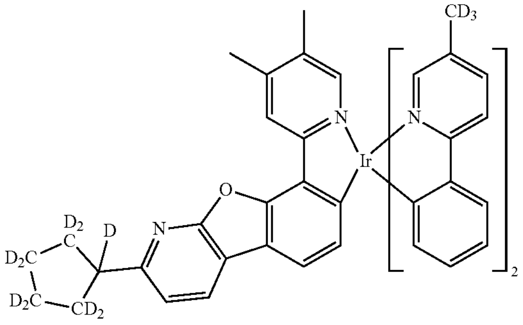
, -continued
Compound II-452
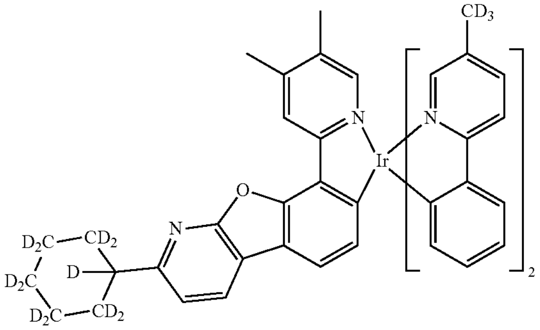
,
Compound II-453
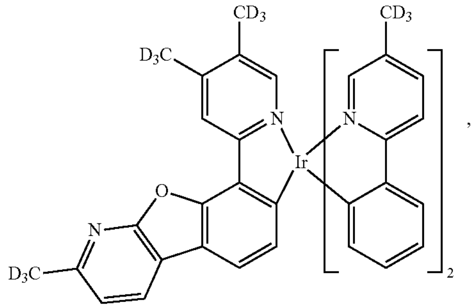
,
Compound II-454
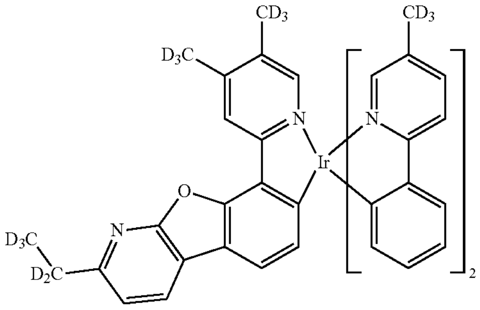
,
Compound II-455
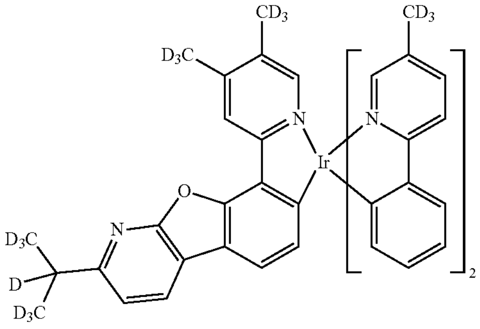
,
-continued
Compound II-456
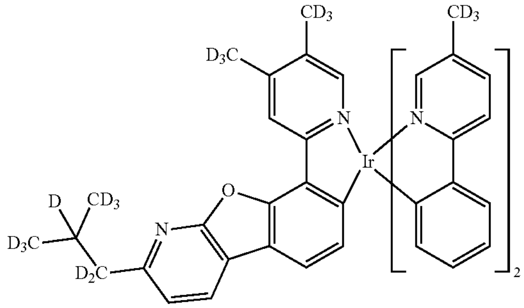
,
Compound II-457
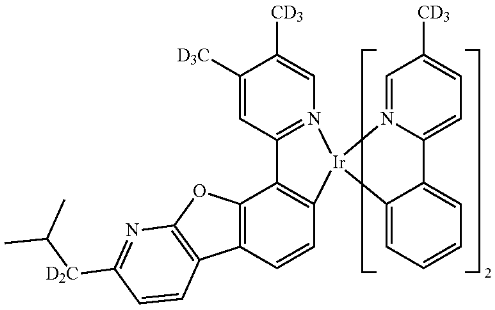
,
Compound II-458
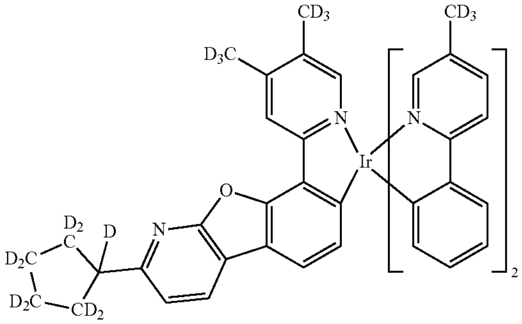
, and
Compound II-459
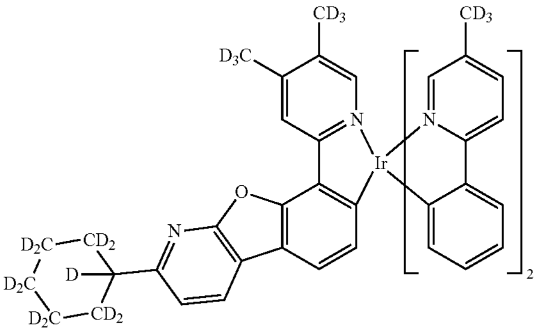
.
20. A first device comprising a first organic light emitting device, comprising:
an anode;
a cathode; and
an organic layer, disposed between the anode and the cathode, comprising a compound having the formula $Ir(L_A)_n(L_B)_{3-n}$, having the structure:

Formula II

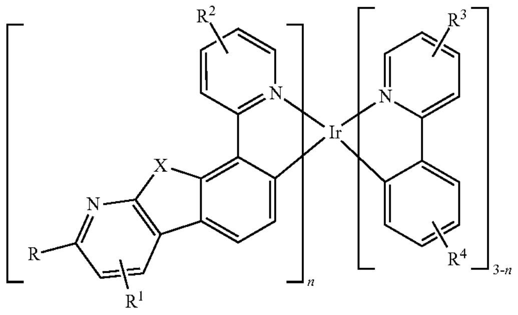

;

wherein X is O, S, or Se;

wherein R is selected from the group consisting of alkyl, cycloalkyl, and combinations thereof, any of which may be partially or fully deuterated;

wherein $R^1$ represent mono-, di-substitution, or no substitution;

wherein $R^2$, $R^3$, and $R^4$ independently represent mono-, di-, tri-, tetra-substitution, or no substitution;

wherein any adjacent substitutions in $R^1$, $R^2$, $R^3$, and $R^4$ are optionally linked together to form a ring;

wherein $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is an integer from 1 to 3.

21. The first device of claim 20, wherein the first device is a consumer product.

22. The first device of claim 20, wherein the first device is an organic light-emitting device.

23. The first device of claim 20, wherein the first device comprises a lighting panel.

24. The first device of claim 20, wherein the organic layer is an emissive layer and the compound is an emissive dopant.

25. The first device of claim 20, wherein the organic layer is an emissive layer and the compound is a non-emissive dopant.

26. The first device of claim 20, wherein the organic layer further comprises a host.

27. The first device of claim 26, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}CHC_nH_{2n+1}$, $Ar_1$, $Ar_1$-$Ar_2$, and $C_nH_{2n}{-}Ar_1$;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

28. The first device of claim 26, wherein the host comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

29. The first device of claim 26, wherein the host is selected from the group consisting of:

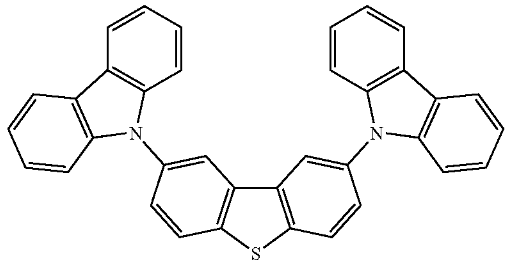

,

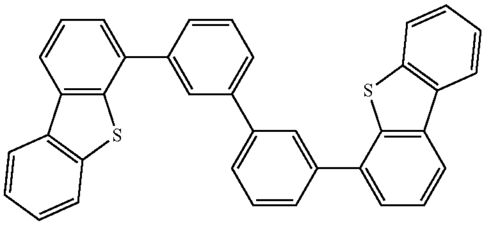

,

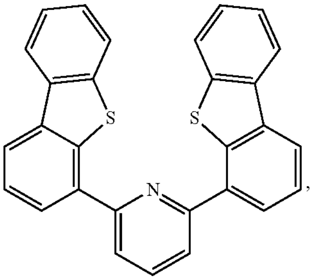

,

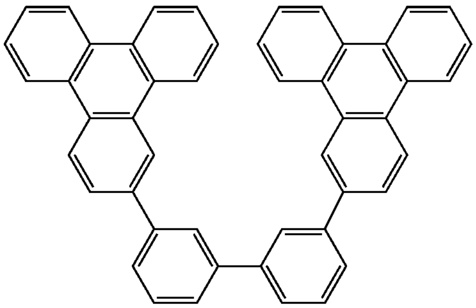

,

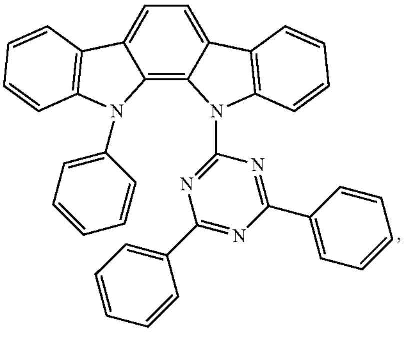

,

-continued

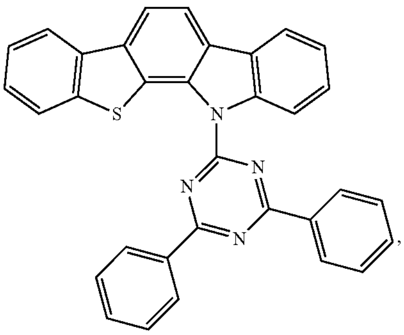

,

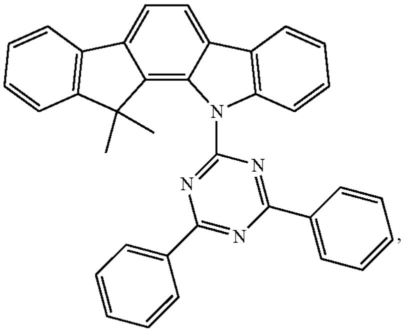

,

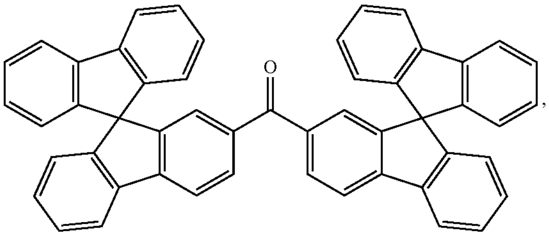

,

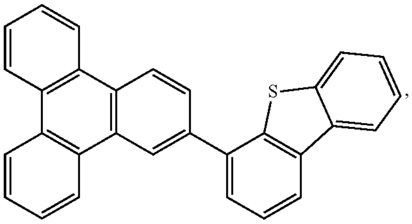

,

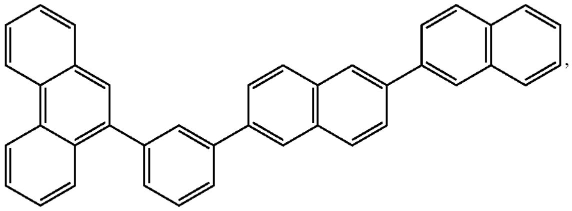

,

-continued

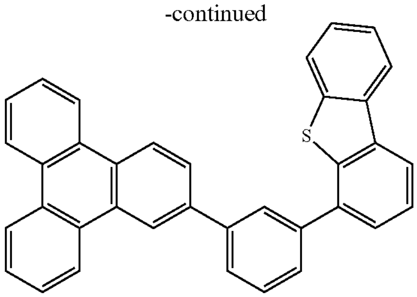

, and combinations thereof.

30. The first device of claim 26, wherein the host comprises a metal complex.

31. A formulation comprising a compound having the formula $Ir(L_A)_n(L_B)_{3-n}$, having the structure:

Formula II

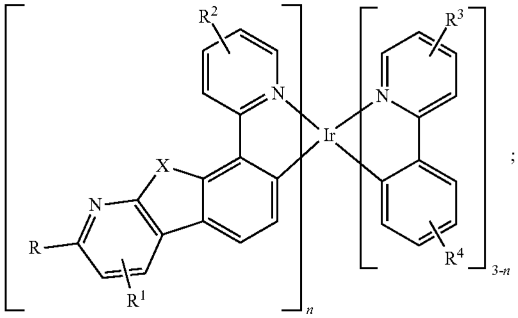

;

wherein X is O, S, or Se;

wherein R is selected from the group consisting of alkyl, cycloalkyl, and combinations thereof, any of which may be partially or fully deuterated;

wherein $R^1$ represents mono-, di-substitution or no substitution;

wherein $R^2$, $R^3$, and $R^4$ independently represent mono-, di-, tri-, tetra-substitution, or no substitution;

wherein any adjacent substitutions in $R^1$, $R^2$, $R^3$, and $R^4$ are optionally linked together to form a ring;

wherein $R^1$, $R^2$, $R^3$, and $R^4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein n is an integer from 1 to 3.

* * * * *

UNITED STATES PATENT AND TRADEMARK OFFICE

CERTIFICATE OF CORRECTION

PATENT NO. : 9,685,617 B2
APPLICATION NO. : 13/928456
DATED : June 20, 2017
INVENTOR(S) : Scott Beers et al.

It is certified that error appears in the above-identified patent and that said Letters Patent is hereby corrected as shown below:

In the Claims

Column 390, Lines 19-29, please delete $L_{A120}$

" 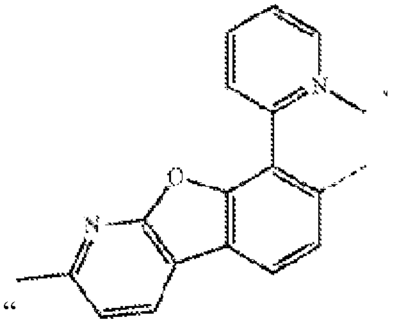 " and insert -- 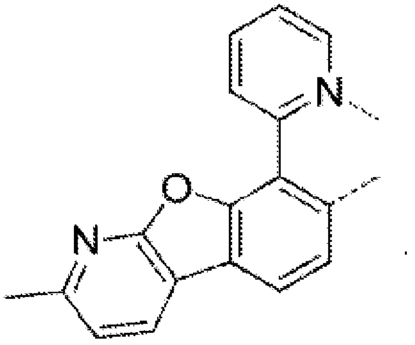 $L_{A120}$ --

Column 390, Lines 30-40, please delete $L_{A121}$

" 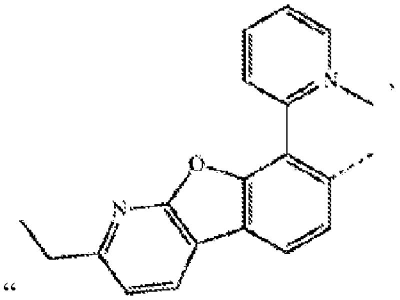 " and insert -- 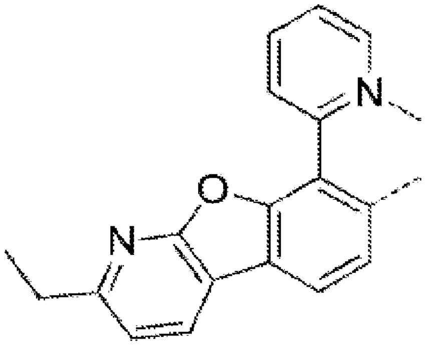 $L_{A121}$ --

Signed and Sealed this
Fifth Day of December, 2017

Joseph Matal

*Performing the Functions and Duties of the*
*Under Secretary of Commerce for Intellectual Property and*
*Director of the United States Patent and Trademark Office*

Column 390, Lines 41-53, please delete
$L_{A122}$
“ 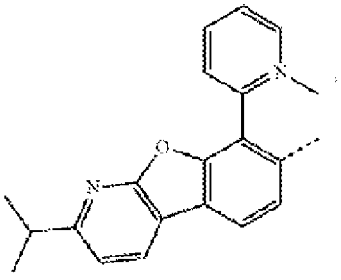 ” and insert -- 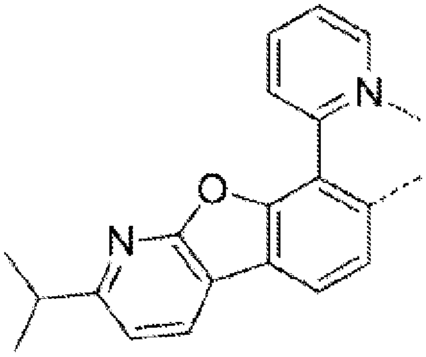
$L_{A122}$ --
Column 390, Lines 54-66, please delete
$L_{A123}$
“ 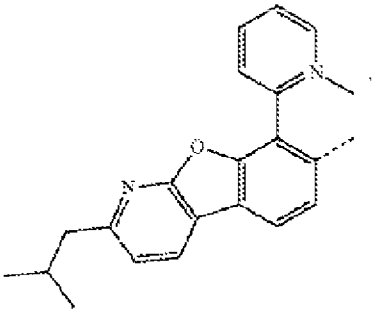 ” and insert -- 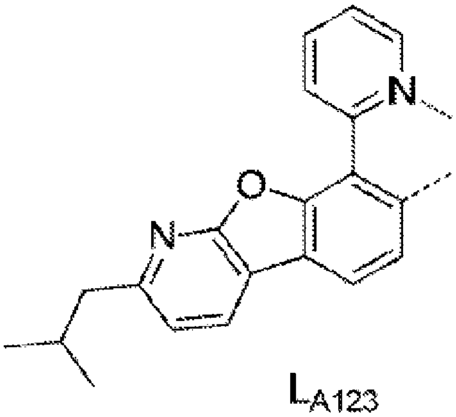
$L_{A123}$ --
Column 391, Lines 1-12, please delete
$L_{A124}$
“ 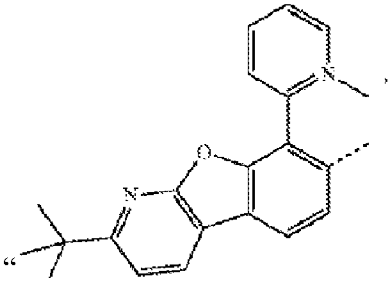 ” and insert -- 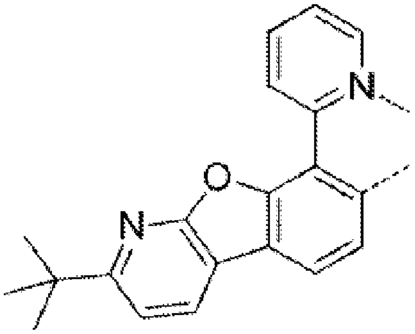
$L_{A124}$ --

Column 391, Lines 13-27, please delete
"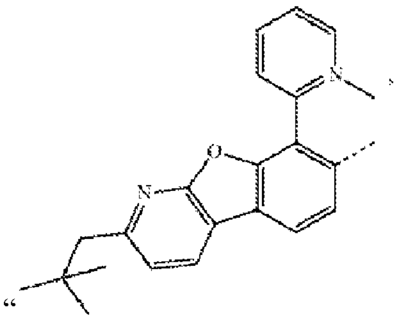 $L_{A125}$" and insert -- 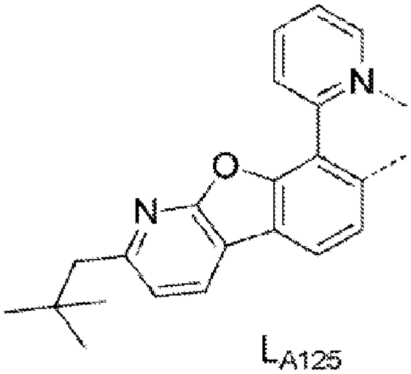 $L_{A125}$ --
Column 391, Lines 28-42, please delete
"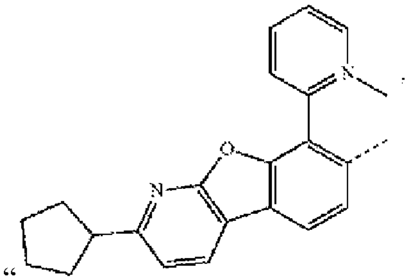 $L_{A126}$" and insert -- 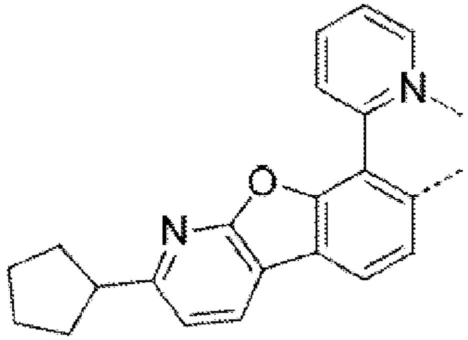 $L_{A126}$ --
Column 391, Lines 43-53, please delete
"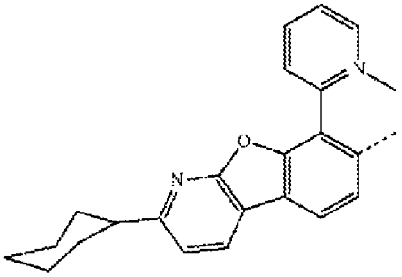 $L_{A127}$" and insert -- 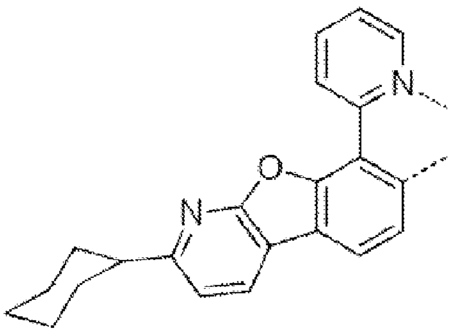 $L_{A127}$ --

Column 391, Lines 54-65, please delete
“ 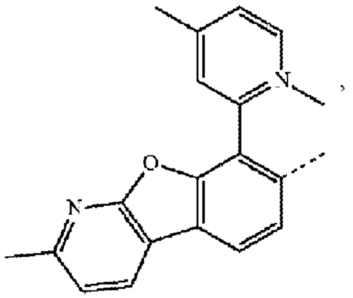 $L_{A128}$ ” and insert -- 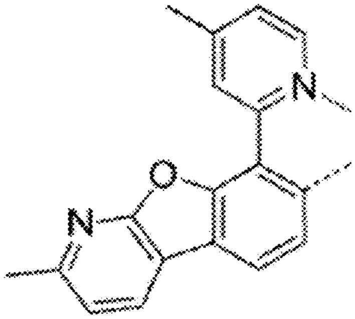 $L_{A128}$ --
Column 392, Lines 1-13, please delete
“ 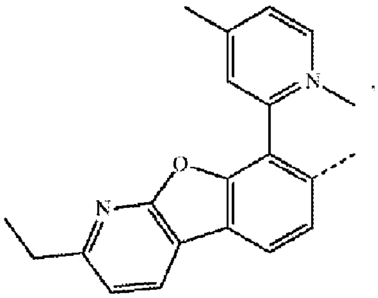 $L_{A129}$ ” and insert -- 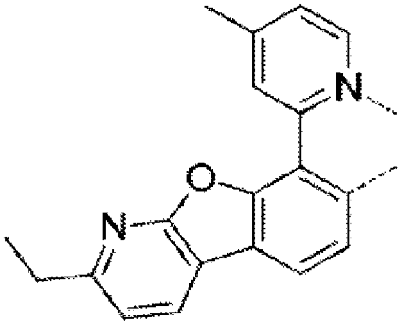 $L_{A129}$ --
Column 392, Lines 14-24, please delete
“ 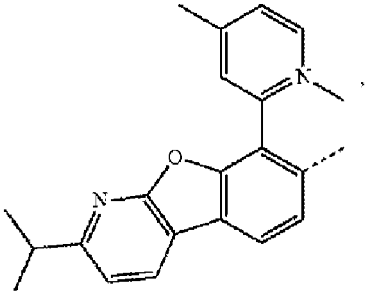 $L_{A130}$ ” and insert -- 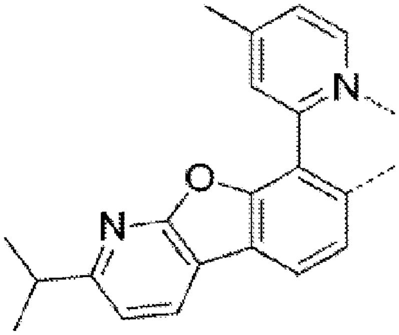 $L_{A130}$ --

Column 392, Lines 25-40, please delete
" 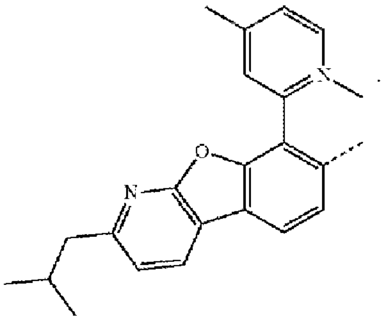 $L_{A131}$ " and insert -- 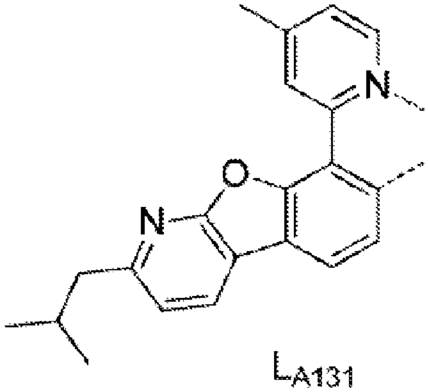 $L_{A131}$ --
Column 392, Lines 41-53, please delete
" 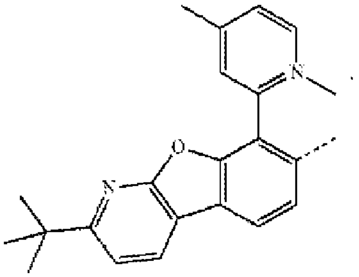 $L_{A132}$ " and insert -- 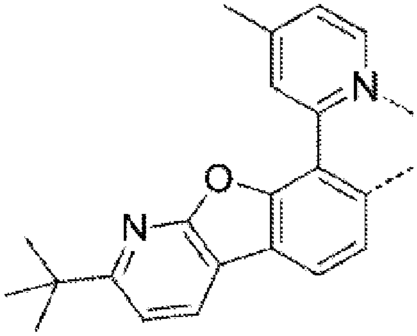 $L_{A132}$ --
Column 392, Lines 54-65, please delete
" 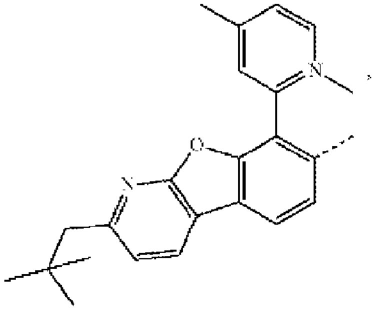 $L_{A133}$ " and insert -- 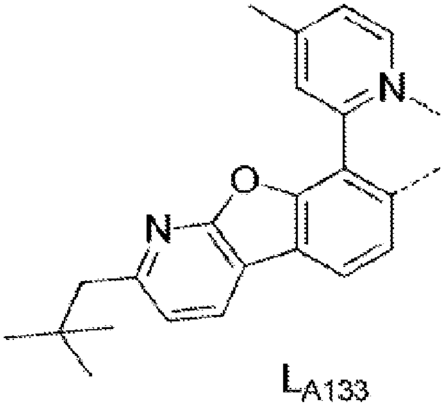 $L_{A133}$ --

Column 393, Lines 1-12, please delete
“ 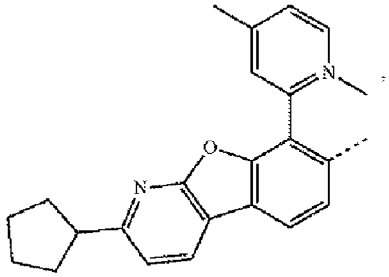 $L_{A134}$ ” and insert -- 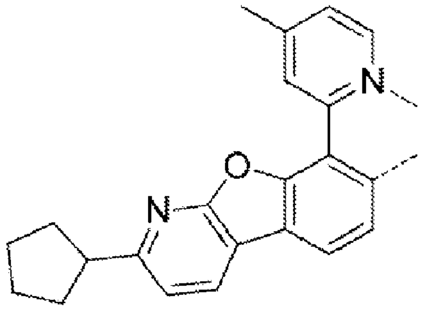 $L_{A134}$ --
Column 393, Lines 13-24, please delete
“ 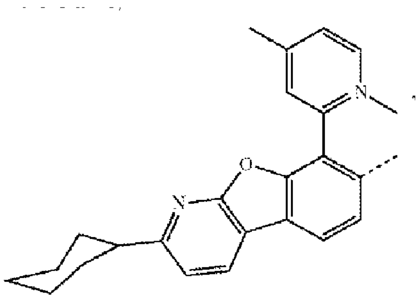 $L_{A135}$ ” and insert -- 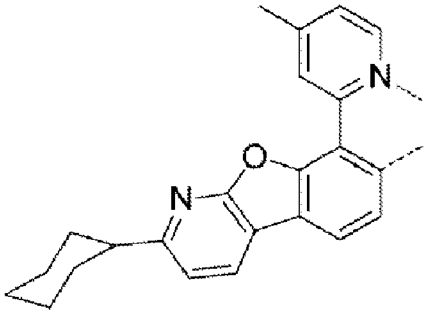 $L_{A135}$ --
Column 393, Lines 25-38, please delete
“ 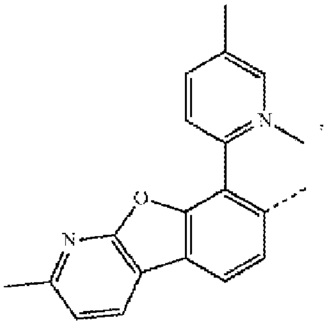 $L_{A136}$ ” and insert -- 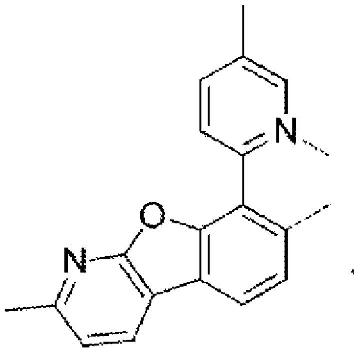 $L_{A136}$ --

Column 393, Lines 39-53, please delete
“ 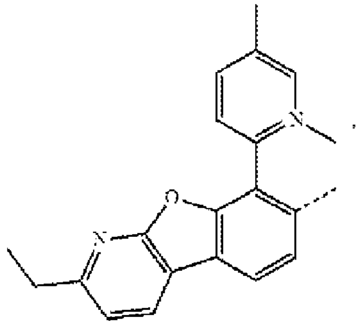 $L_{A137}$ ” and insert -- 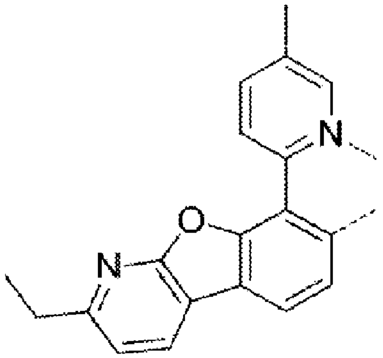
$L_{A137}$ , --
Column 393, Lines 54-66, please delete
“ 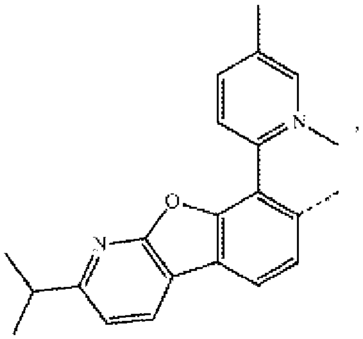 $L_{A138}$ ” and insert -- 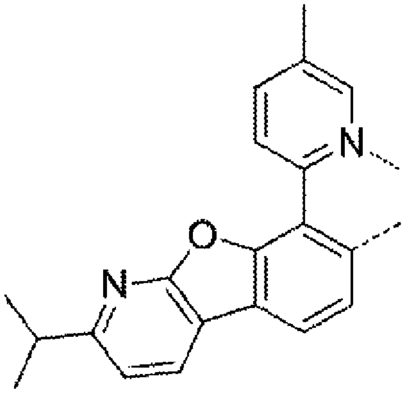
$L_{A138}$ --
Column 394, Lines 1-19, please delete
“ 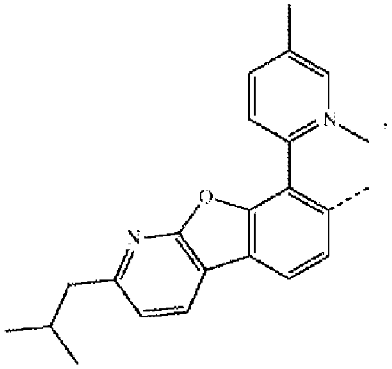 $L_{A139}$ ” and insert -- 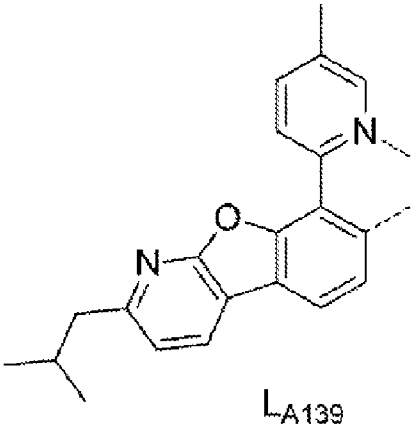
$L_{A139}$ --

Column 394, Lines 20-34, please delete
“ 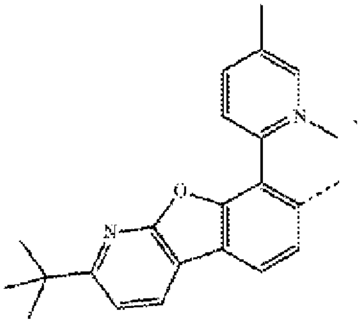 $L_{A140}$ ” and insert -- 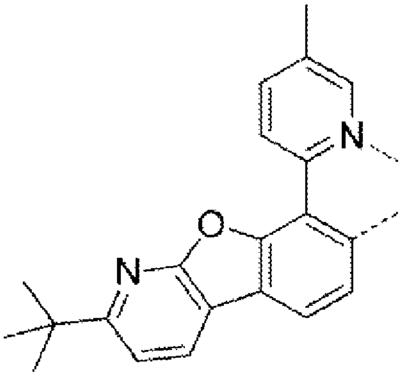 $L_{A140}$ ” --
Column 394, Lines 35-51, please delete
“ 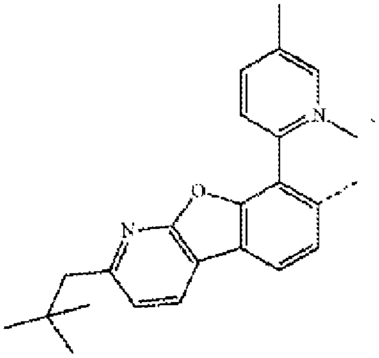 $L_{A141}$ ” and insert -- 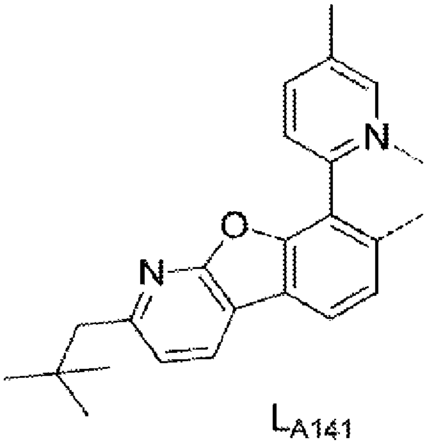 $L_{A141}$ ” --
Column 394, Lines 52-66, please delete
“ 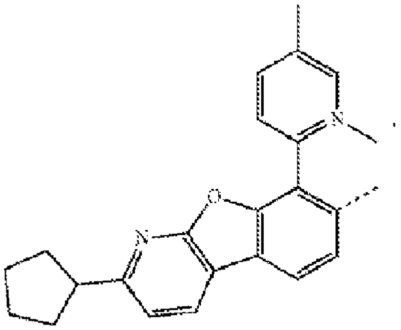 $L_{A142}$ ” and insert -- 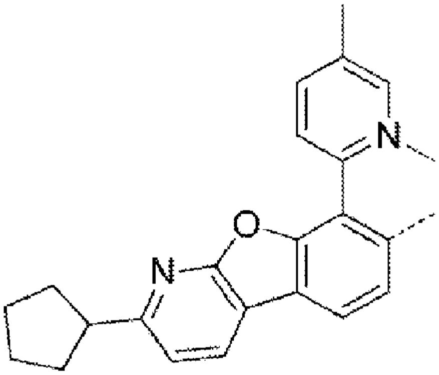 $L_{A142}$ --

Column 395, Lines 1-14, please delete
$L_{A143}$
“ 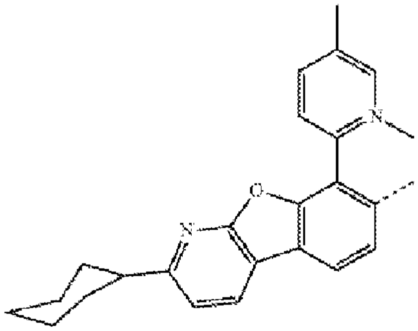 ” and insert -- 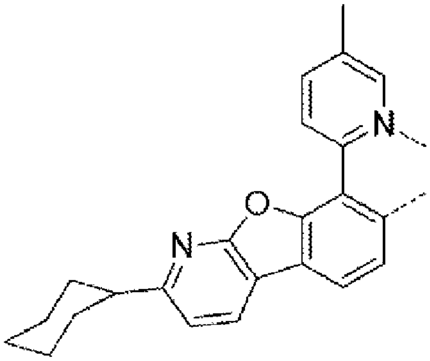 $L_{A143}$ --
Column 395, Lines 15-27, please delete
$L_{A144}$
“ 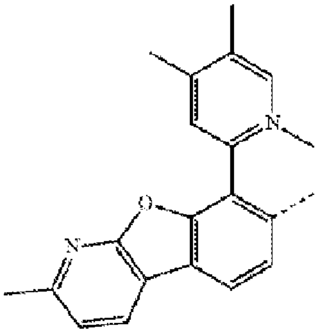 ” and insert -- 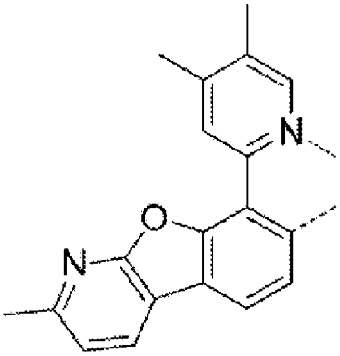 $L_{A144}$ --
Column 395, Lines 28-39, please delete
$L_{A145}$
“ 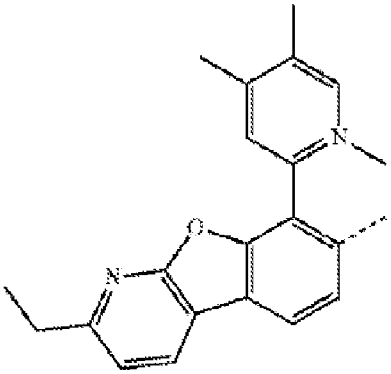 ” and insert -- 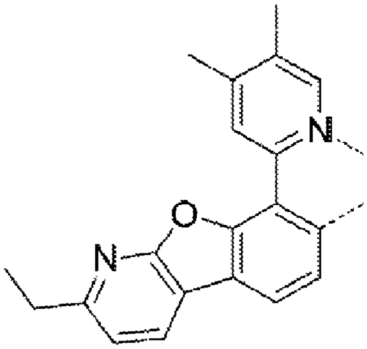 $L_{A145}$ --

Column 395, Lines 40-52, please delete
“ 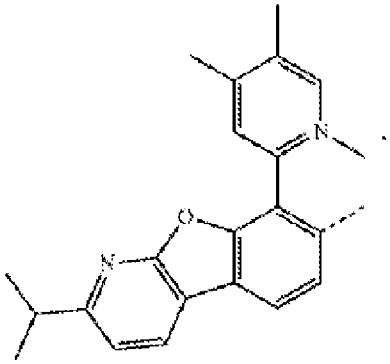 $L_{A146}$ ” and insert -- 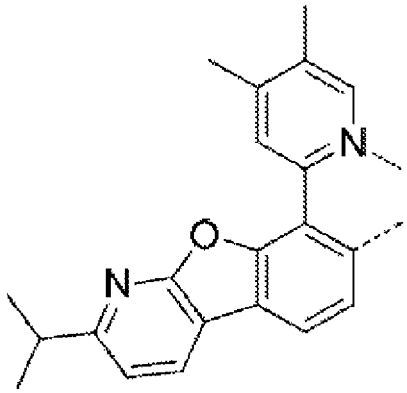 $L_{A146}$ --
Column 395, Lines 53-66, please delete
“ 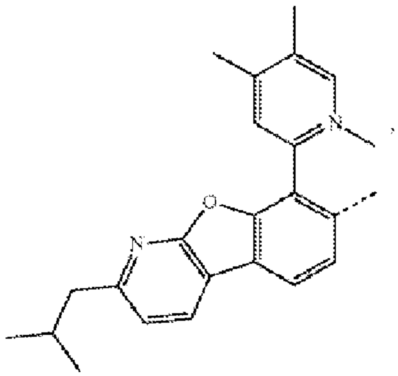 $L_{A147}$ ” and insert -- 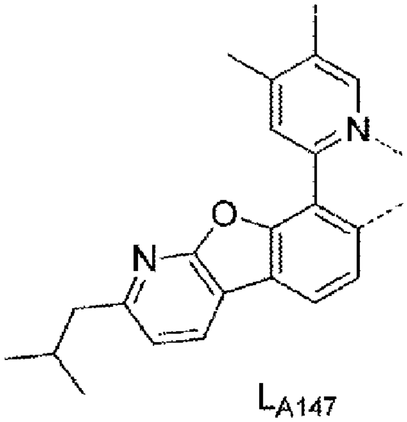 $L_{A147}$ --
Column 396, Lines 1-14, please delete
“ 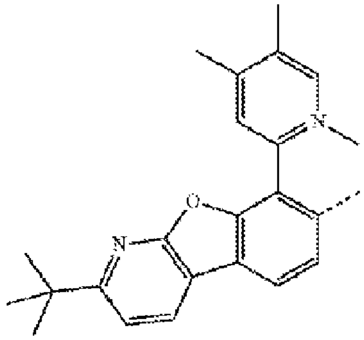 $L_{A148}$ ” and insert -- 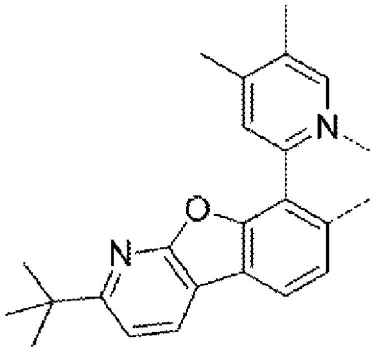 $L_{A148}$ --

Column 396, Lines 15-29, please delete
$L_{A149}$
" 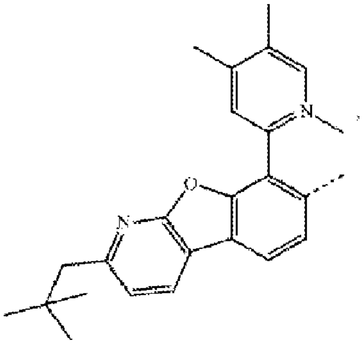 " and insert -- 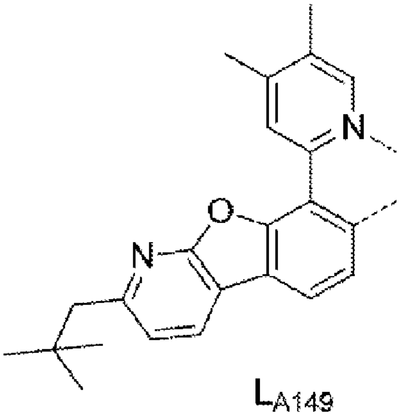
$L_{A149}$ , --
Column 396, Lines 30-42, please delete
$L_{A150}$
" 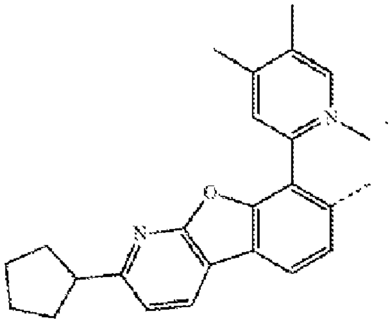 " and insert -- 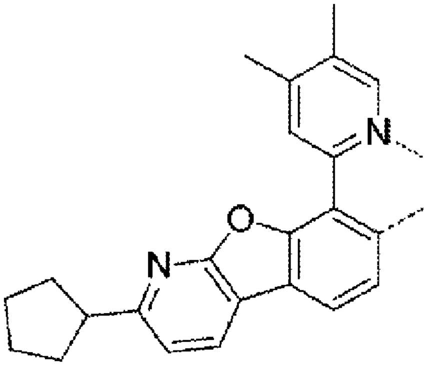
$L_{A150}$ --
Column 396, Lines 43-54, please delete
$L_{A151}$
" 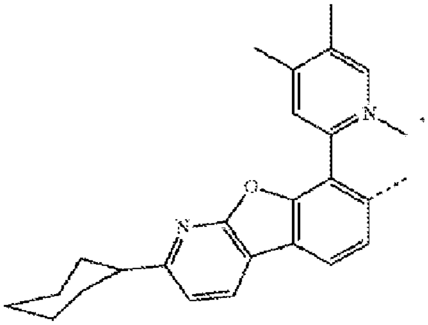 " and insert -- 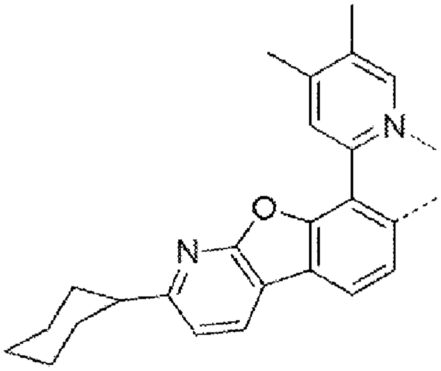
$L_{A151}$ --

Column 396, Lines 55-66, please delete
" 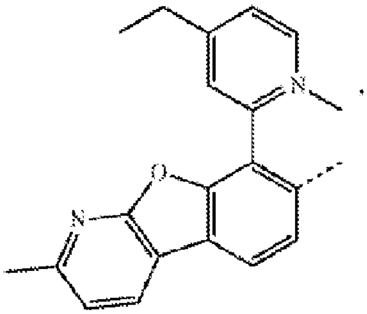 $L_{A152}$ " and insert -- 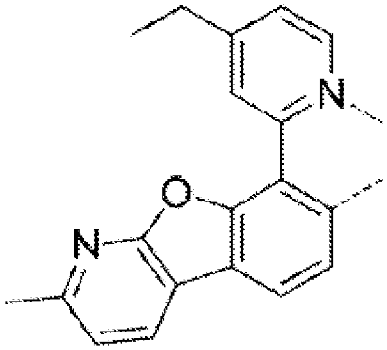 $L_{A152}$ --
Column 397, Lines 1-12, please delete
" 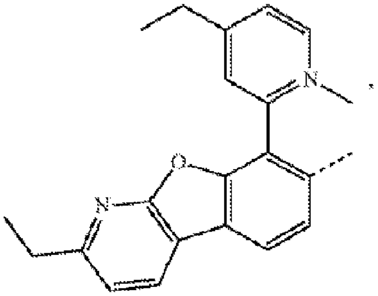 $L_{A153}$ " and insert -- 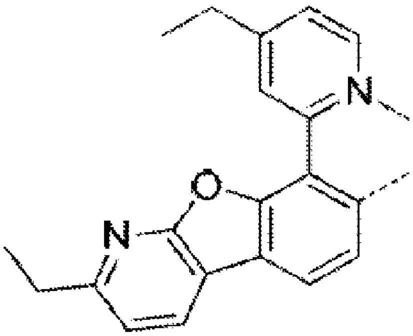 $L_{A153}$ --
Column 397, Lines 13-24, please delete
" 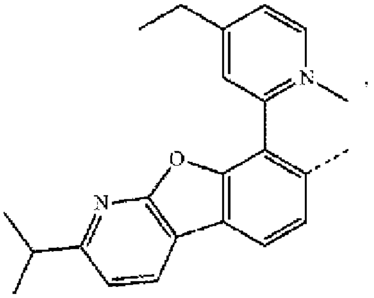 $L_{A154}$ " and insert -- 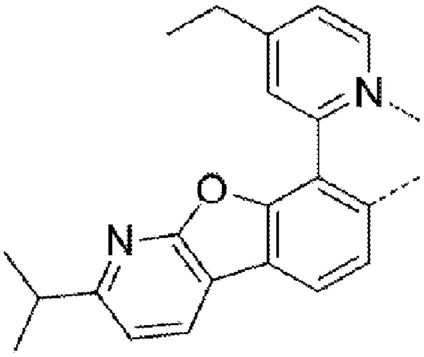 $L_{A154}$ --

Column 397, Lines 25-39, please delete
" 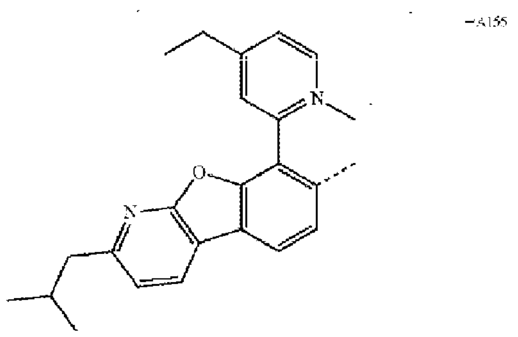 " and insert -- 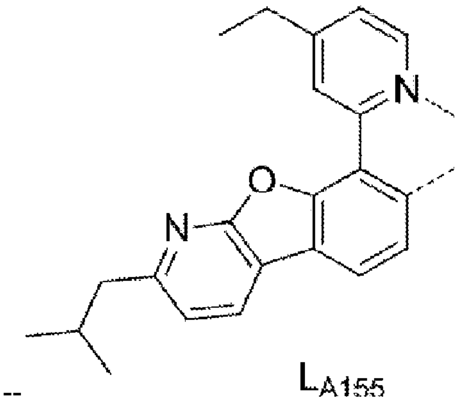 $L_{A155}$ --
Column 397, Lines 40-50, please delete
" 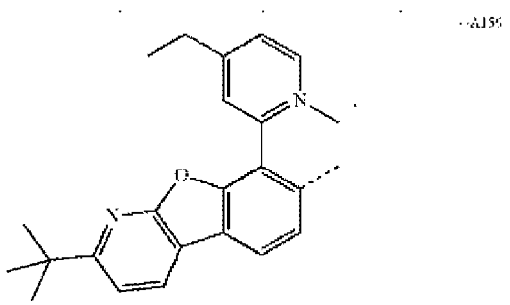 " and insert -- 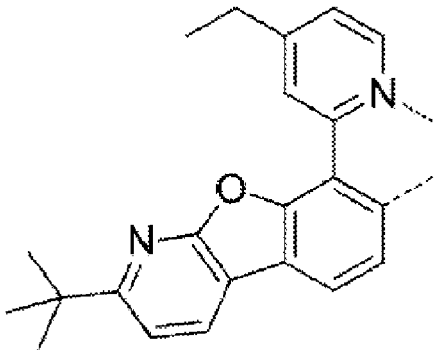 $L_{A156}$ --
Column 397, Lines 51-64, please delete
" 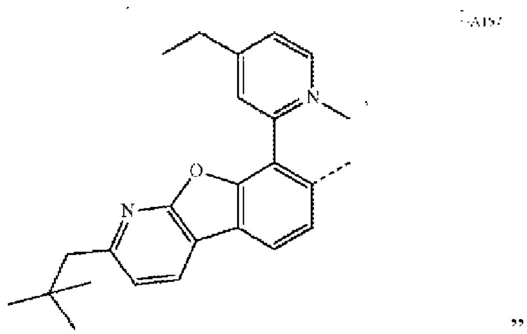 " and insert -- 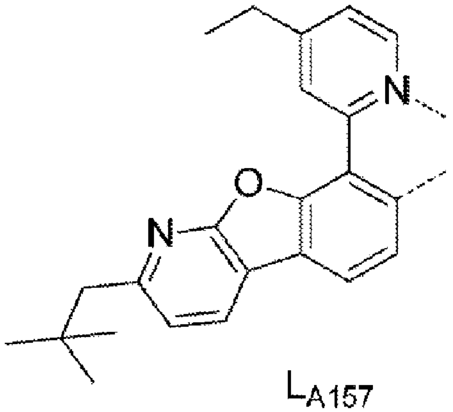 $L_{A157}$ . --

Column 398, Lines 1-12, please delete
"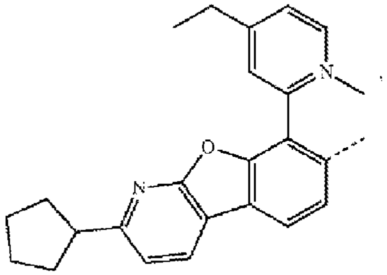
$L_{A158}$
" and insert --
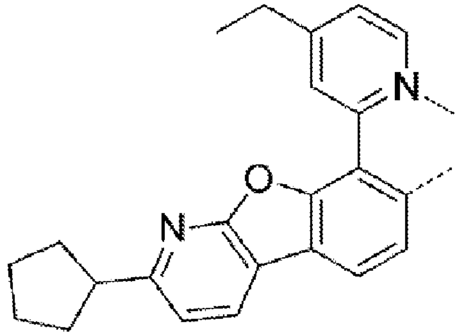
$L_{A158}$ --
Column 398, Lines 13-24, please delete
"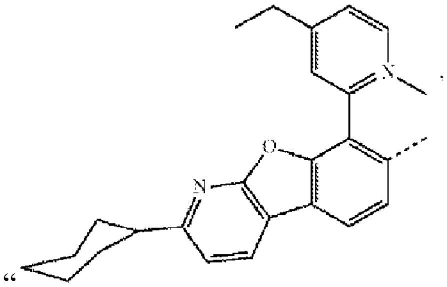
$L_{A159}$
" and insert --
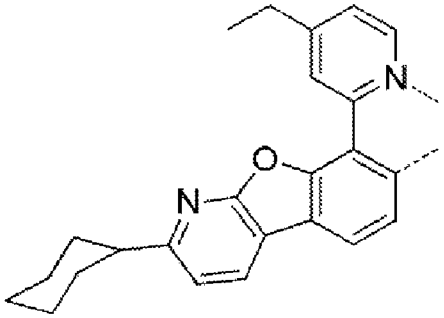
$L_{A159}$ --
Column 398, Lines 25-39, please delete
"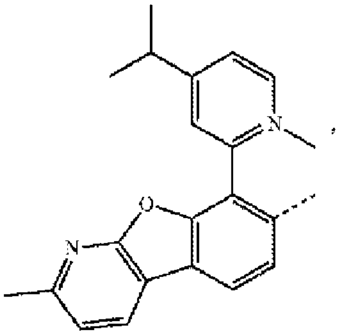
$L_{A160}$
" and insert --
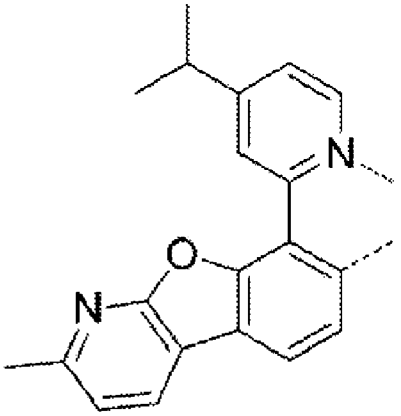
$L_{A160}$ --

Column 398, Lines 40-54, please delete
$L_{A161}$
“ 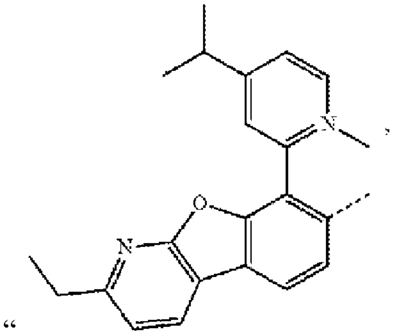 ” and insert -- 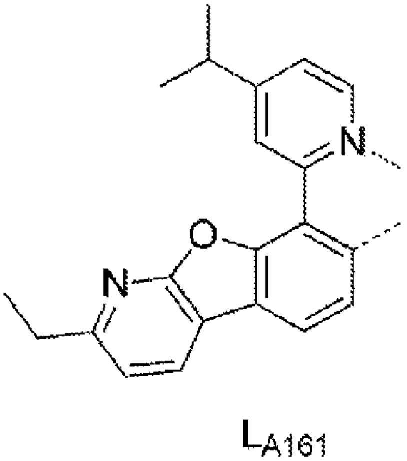 $L_{A161}$ , --
Column 398, Lines 55-66, please delete
$L_{A162}$
“ 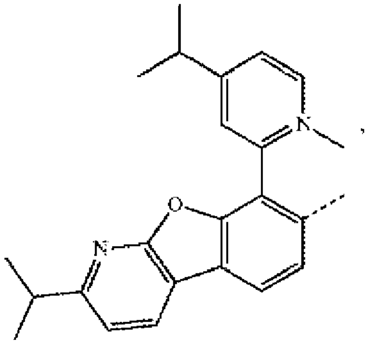 ” and insert -- 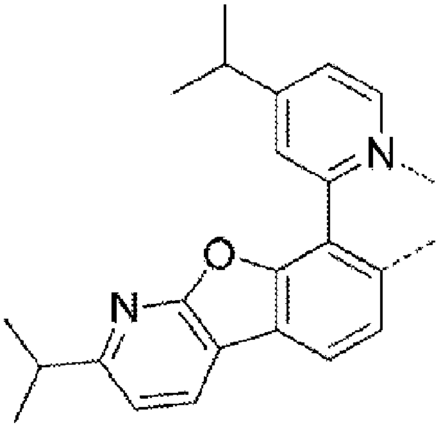 $L_{A162}$ --
Column 399, Lines 1-18, please delete
$L_{A163}$
“ 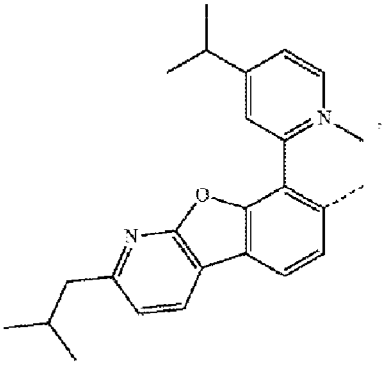 ” and insert -- 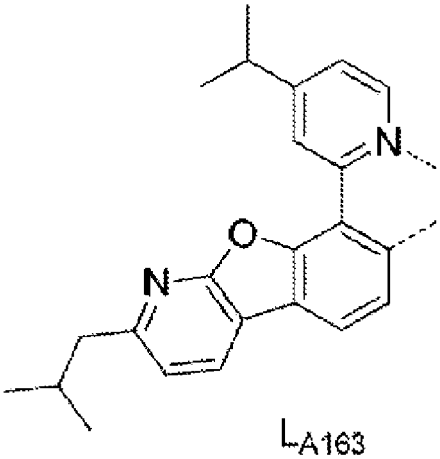 $L_{A163}$ --

Column 399, Lines 19-37, please delete
" 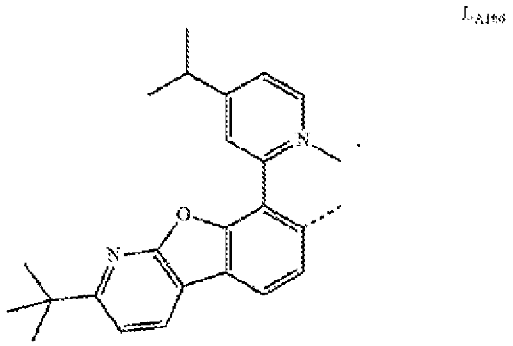 " and insert -- 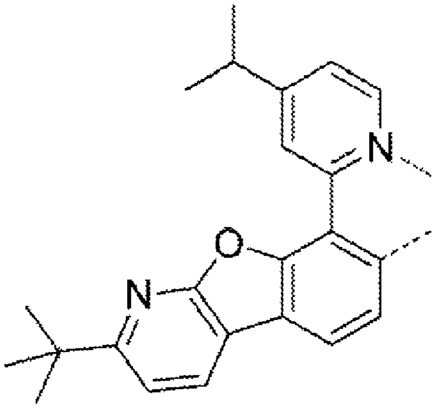 $L_{A164}$ --
Column 399, Lines 38-53, please delete
" 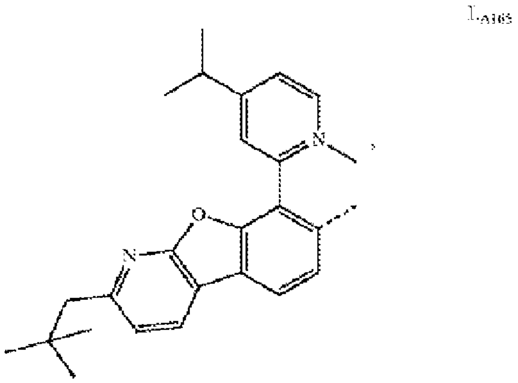 " and insert -- 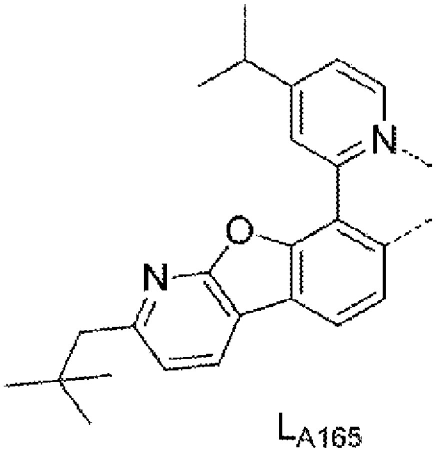 $L_{A165}$ --
Column 399, Lines 54-66, please delete
" 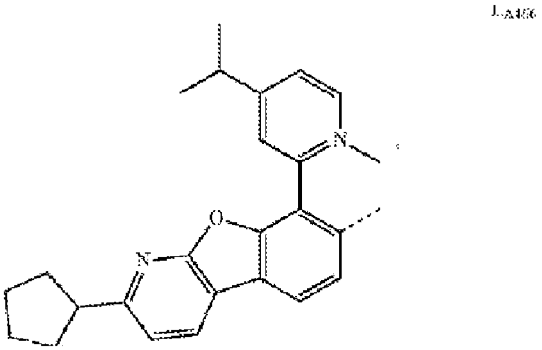 " and insert -- 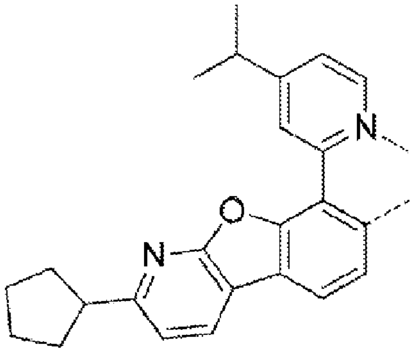 $L_{A166}$ --

Column 400, Lines 1-15, please delete
$L_{A167}$
" 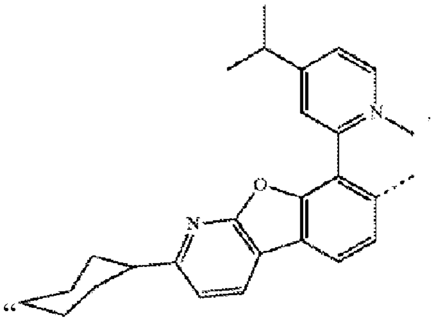 " and insert -- 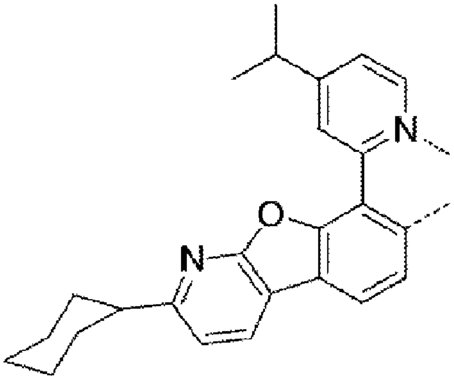 $L_{A167}$ --
Column 400, Lines 16-35, please delete
$L_{A168}$
" 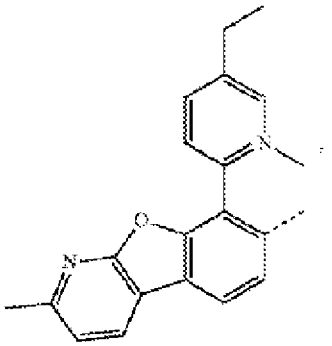 " and insert -- 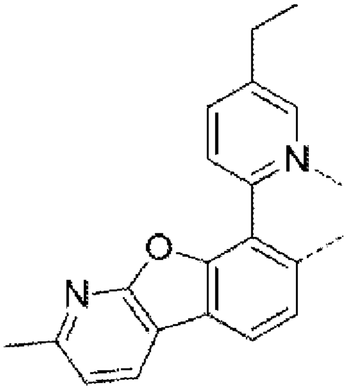 $L_{A168}$ --
Column 400, Lines 36-52, please delete
$L_{A169}$
" 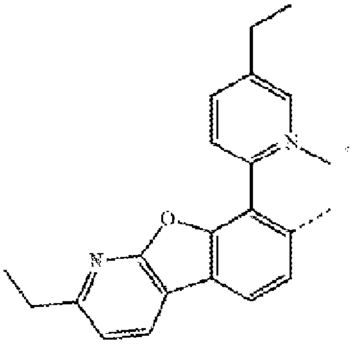 " and insert -- 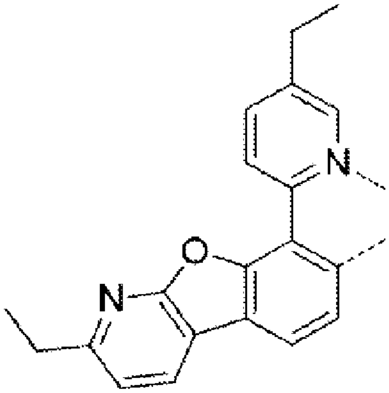 $L_{A169}$ --
Column 400, Lines 53-66, please delete “ 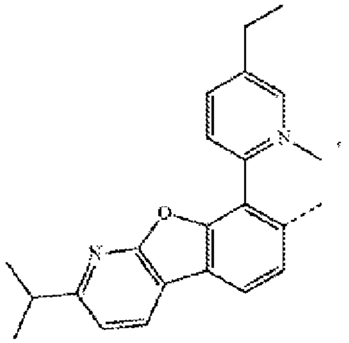 $L_{A170}$ ” and insert -- 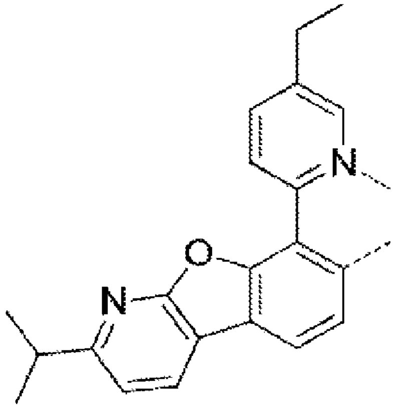 $L_{A170}$ --
Column 401, Lines 1-17, please delete
“ 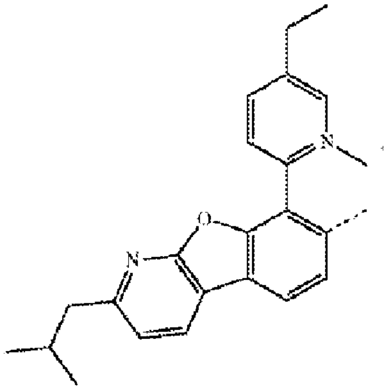 $L_{A171}$ ” and insert -- 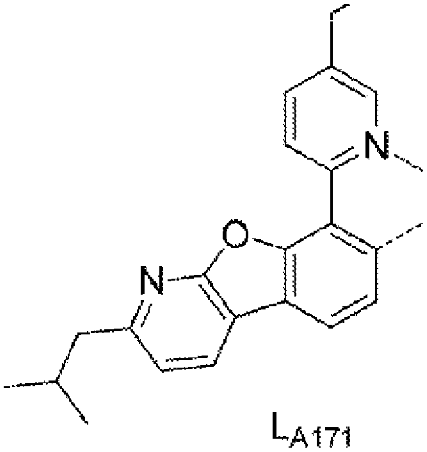 $L_{A171}$ --
Column 401, Lines 18-33, please delete
“ 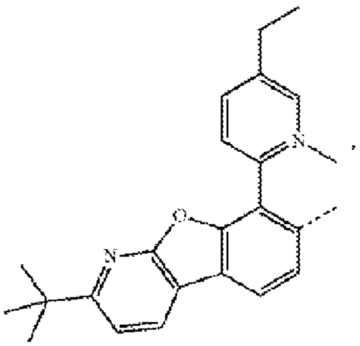 $L_{A172}$ ” and insert -- 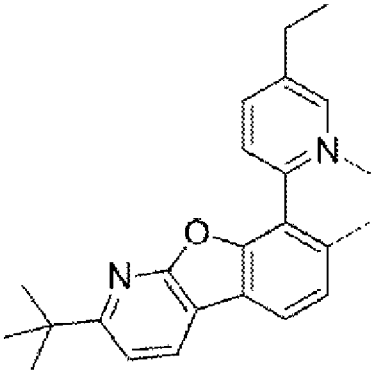 $L_{A172}$ --
Column 401, Lines 34-51, please delete LA173
“ 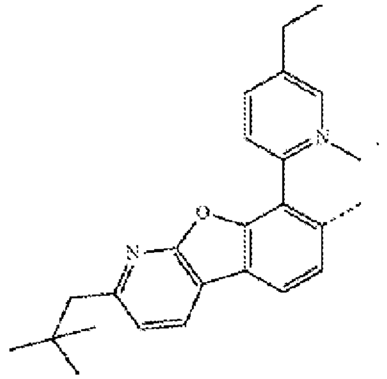 ” and insert -- 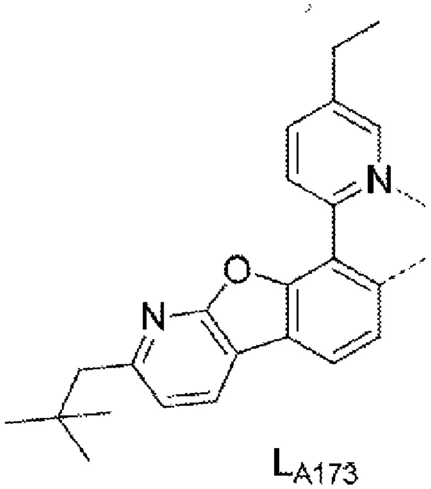 $L_{A173}$ --
Column 401, Lines 52-66, please delete
LA174
“ 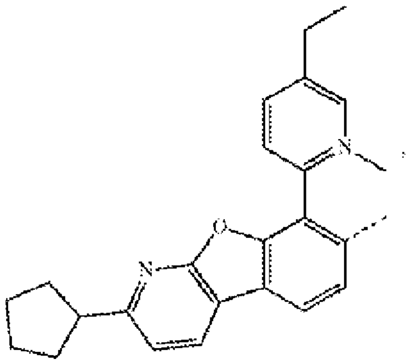 ” and insert -- 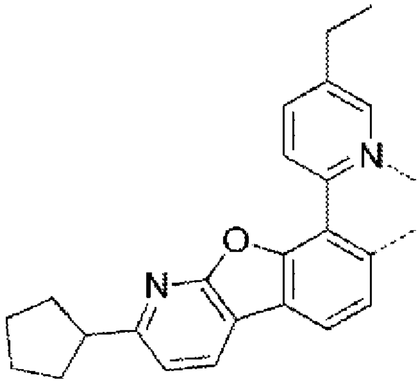 $L_{A174}$ --
Column 402, Lines 1-18, please delete
LA175
“ 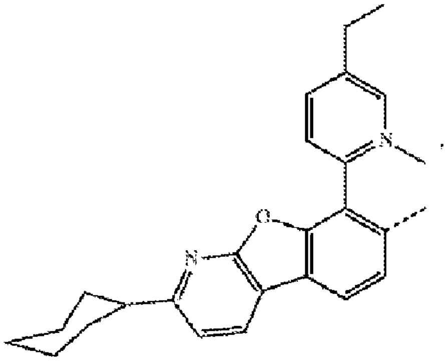 ” and insert -- 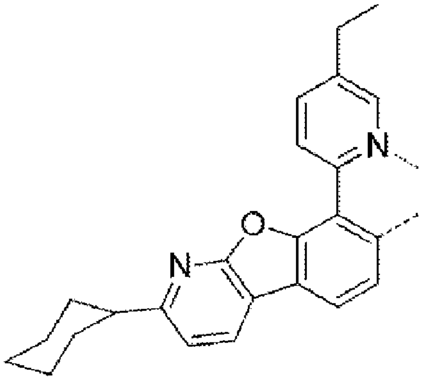 $L_{A175}$ --
Column 402, Lines 19-35, please delete “ 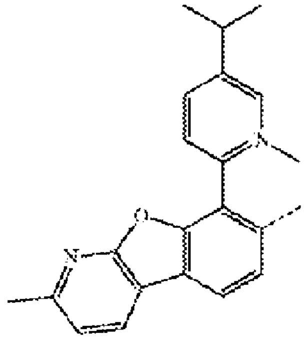 $L_{A176}$ ” and insert -- 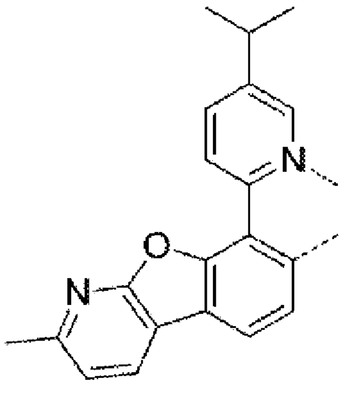 $L_{A176}$ --
Column 402, Lines 36-53, please delete
“ 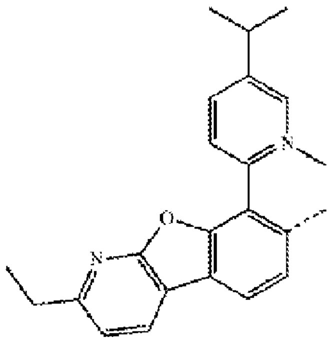 $L_{A177}$ ” and insert -- 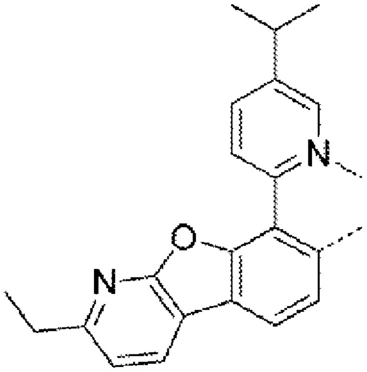 $L_{A177}$ --
Column 402, Lines 54-66, please delete
“ 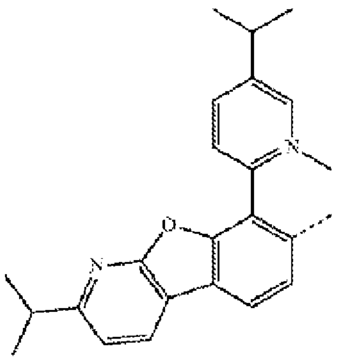 $L_{A178}$ ” and insert -- 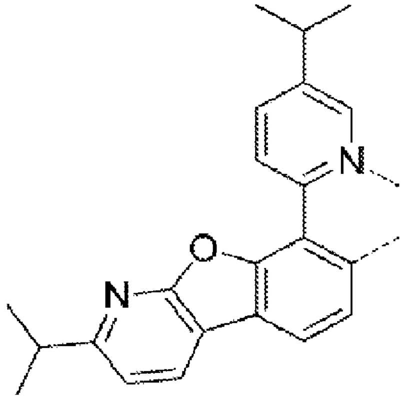 $L_{A178}$ --
Column 403, Lines 1-19, please delete “ 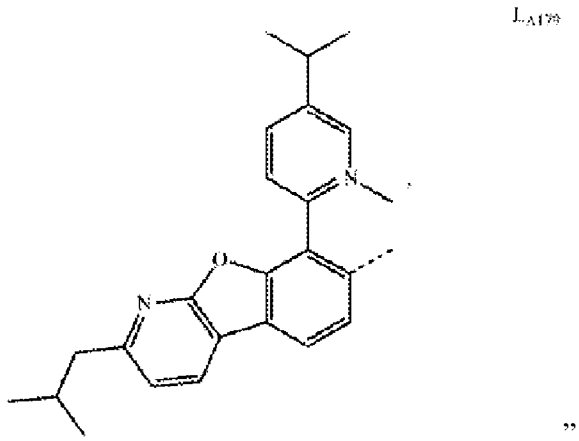 ” and insert -- 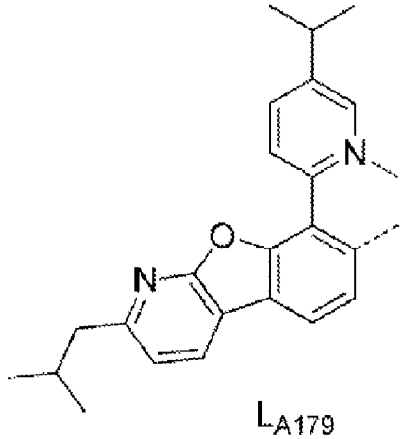 $L_{A179}$ --
Column 403, Lines 20-35, please delete
“ 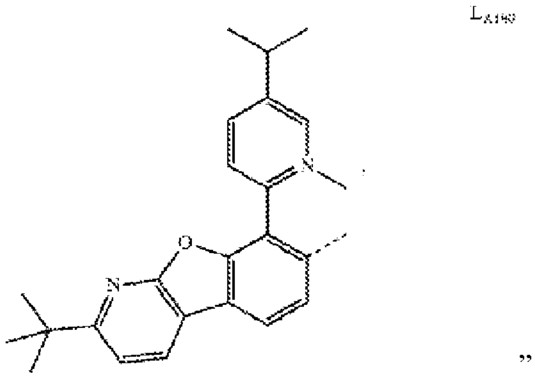 ” and insert -- 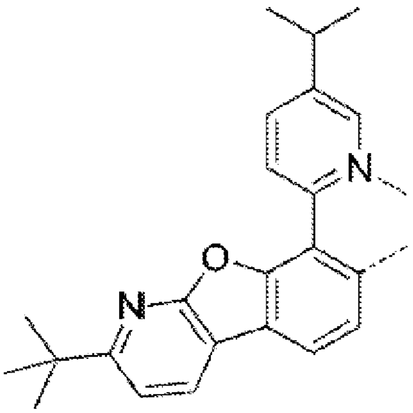 $L_{A180}$ --
Column 403, Lines 36-52, please delete
“ 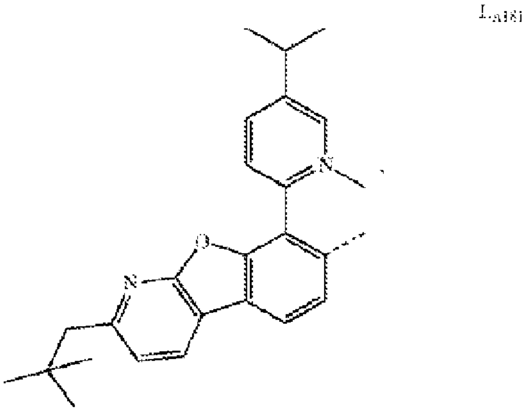 ” and insert -- 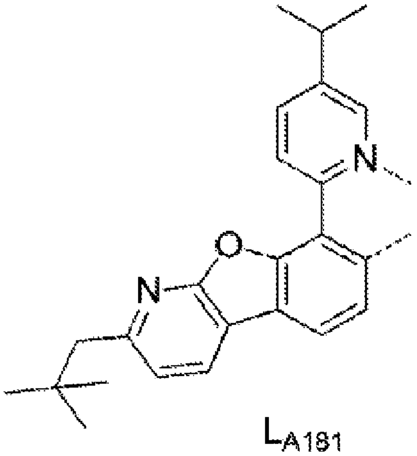 $L_{A181}$ --
Column 403, Lines 53-66, please delete “ 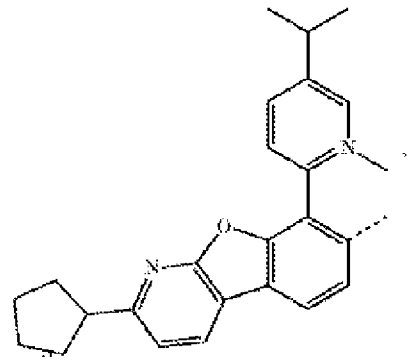 $L_{A182}$ ” and insert -- 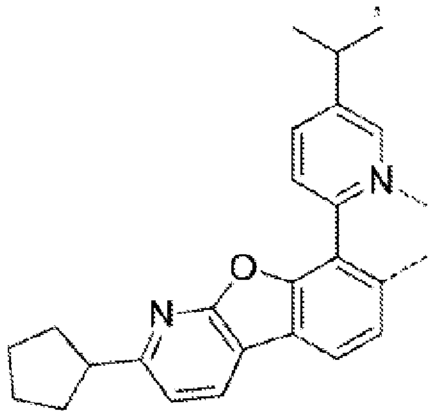 $L_{A182}$ --
Column 404, Lines 1-15, please delete
“ 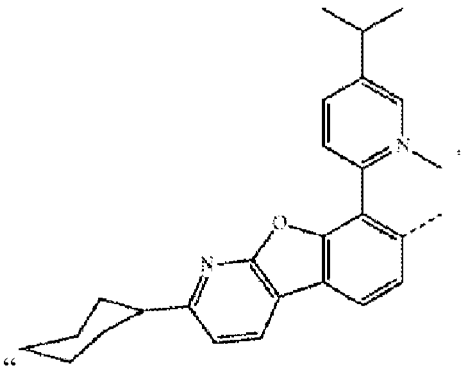 $L_{A183}$ ” and insert -- 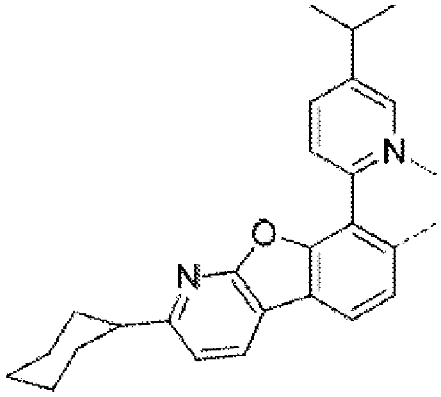 $L_{A183}$ --
Column 404, Lines 16-27, please delete
“ 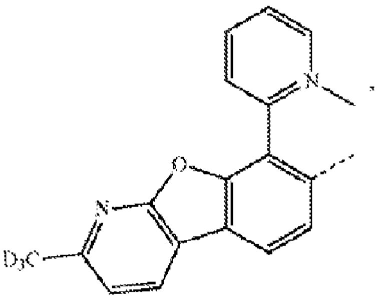 $L_{A184}$ ” and insert -- 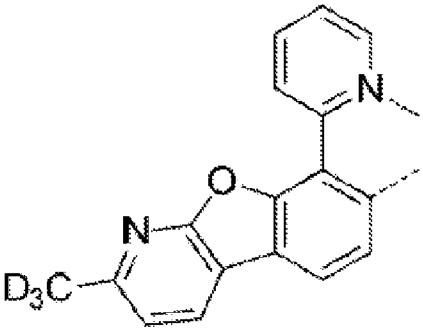 $L_{A184}$ --
Column 404, Lines 28-38, please delete “ 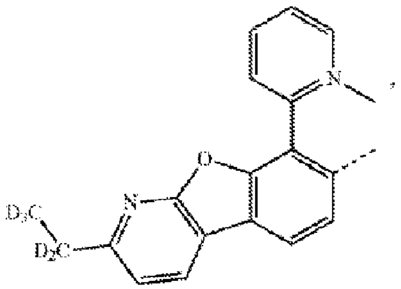 $L_{A185}$ ” and insert -- 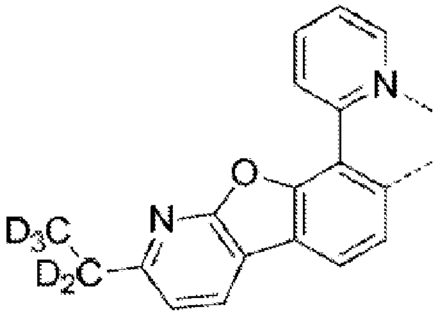 $L_{A185}$ --
Column 404, Lines 39-52, please delete
“ 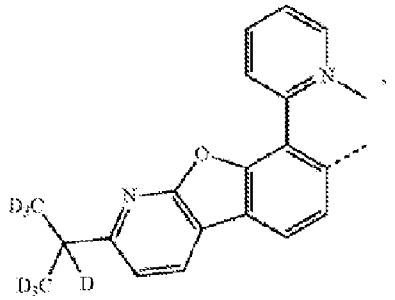 $L_{A186}$ ” and insert -- 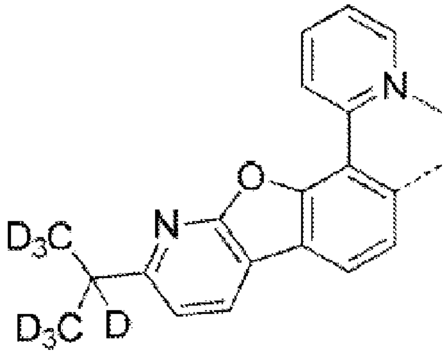 $L_{A186}$ --
Column 404, Lines 53-66, please delete
“ 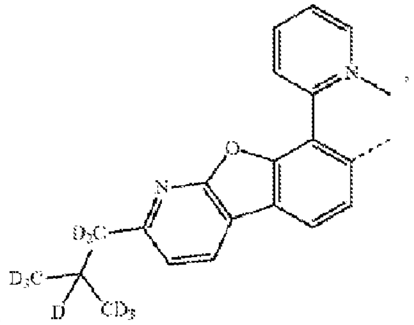 $L_{A187}$ ” and insert -- 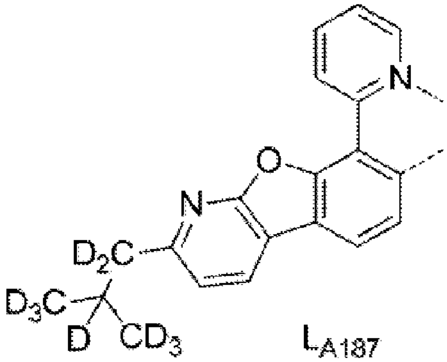 $L_{A187}$ --
Column 405, Lines 1-13, please delete “ 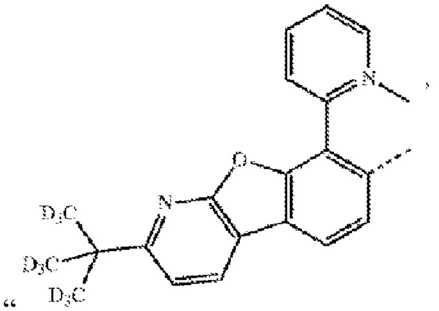 $L_{A188}$ ” and insert -- 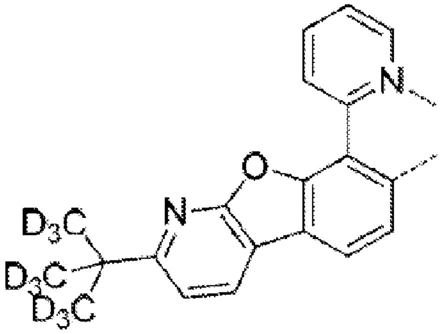 $L_{A188}$ --
Column 405, Lines 14-26, please delete
“ 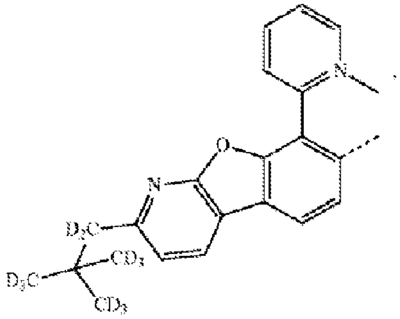 $L_{A189}$ ” and insert -- 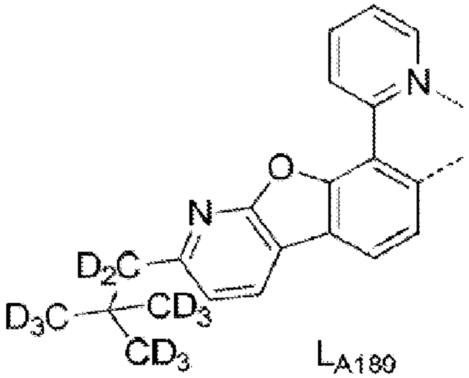 $L_{A189}$ --
Column 405, Lines 27-40, please delete
“ 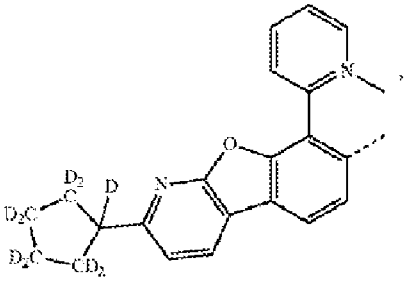 $L_{A190}$ ” and insert -- 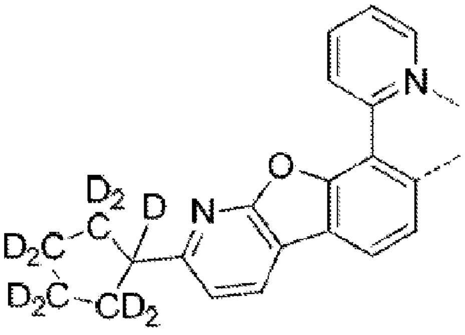 $L_{A190}$ --
Column 405, Lines 41-54, please delete “ 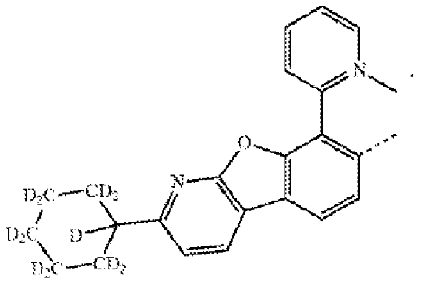 $L_{A191}$ ” and insert -- 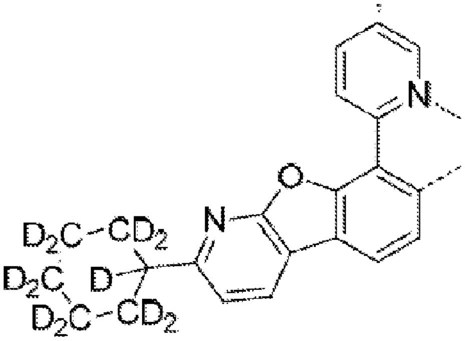 $L_{A191}$ --
Column 405, Lines 55-66, please delete
“ 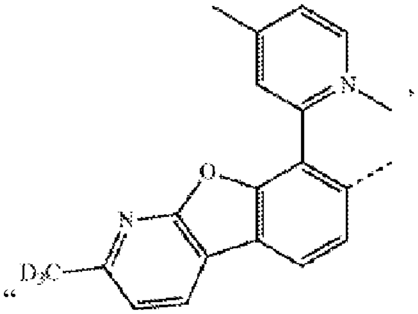 $L_{A192}$ ” and insert -- 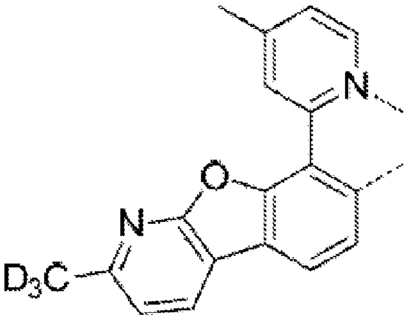 $L_{A192}$ --
Column 406, Lines 1-12, please delete
“ 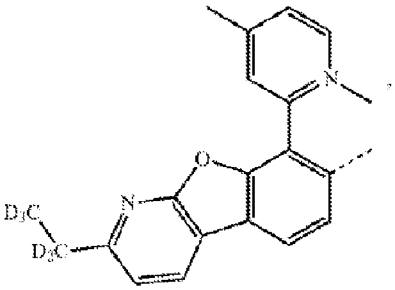 $L_{A193}$ ” and insert -- 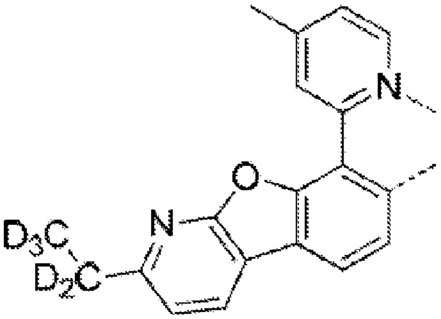 $L_{A193}$ --
Column 406, Lines 13-24, please delete “ 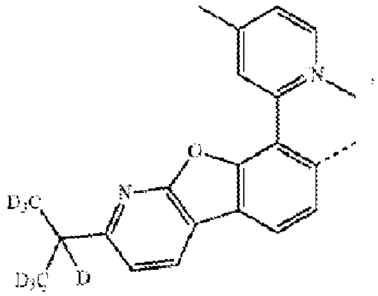 $L_{A194}$ ” and insert -- 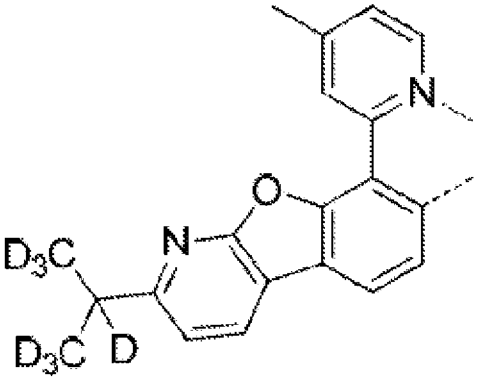 $L_{A194}$ --
Column 406, Lines 25-39, please delete
“ 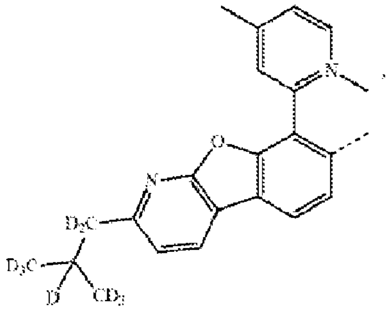 $L_{A195}$ ” and insert -- 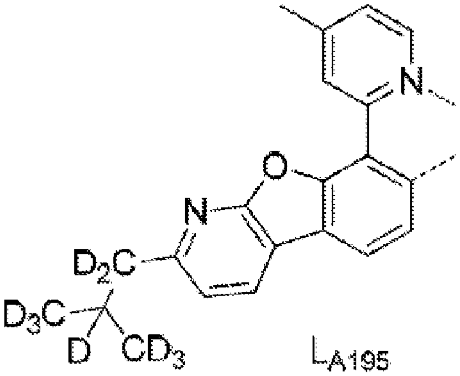 $L_{A195}$ --
Column 406, Lines 40-54, please delete
“ 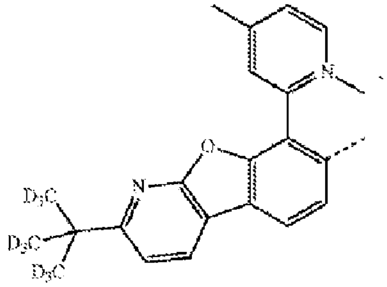 $L_{A196}$ ” and insert -- 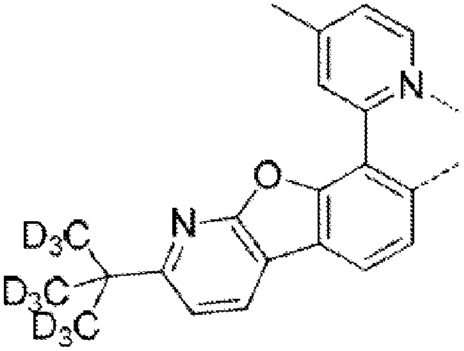 $L_{A196}$ --
Column 406, Lines 55-66, please delete “ 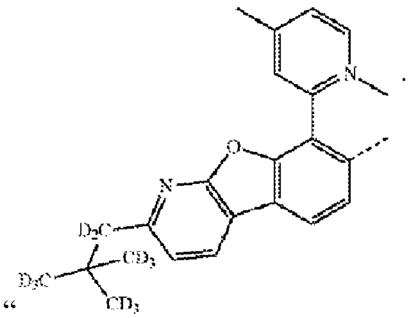 $L_{A197}$ ” and insert -- 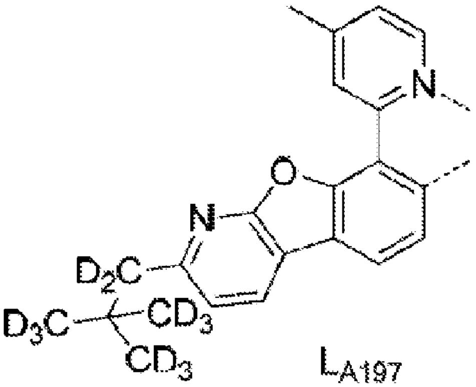 $L_{A197}$ --
Column 407, Lines 1-13, please delete
“ 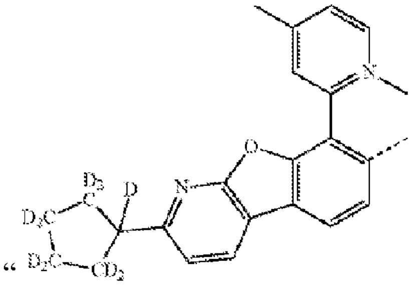 $L_{A198}$ ” and insert -- 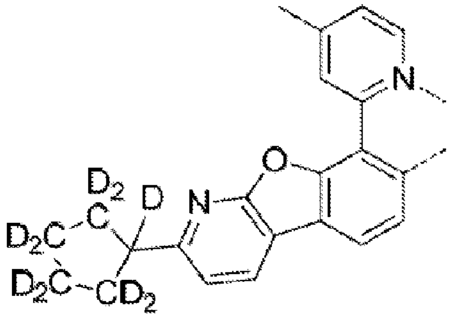 $L_{A198}$ --
Column 407, Lines 14-27, please delete
“ 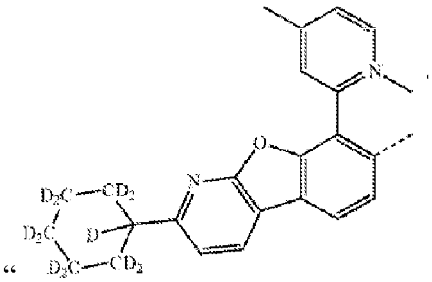 $L_{A199}$ ” and insert -- 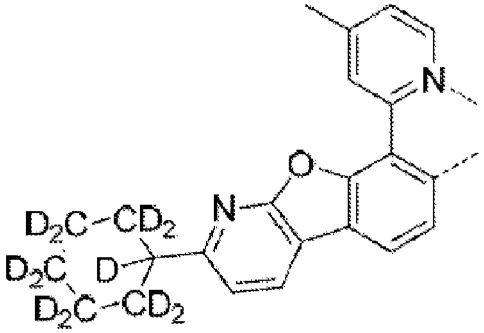 $L_{A199}$ --
Column 407, Lines 28-41, please delete “ 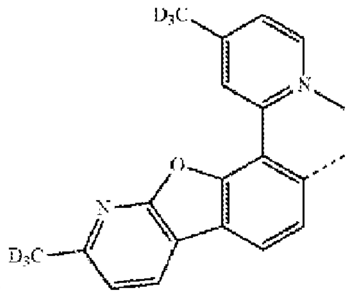 $L_{A200}$ ” and insert-- 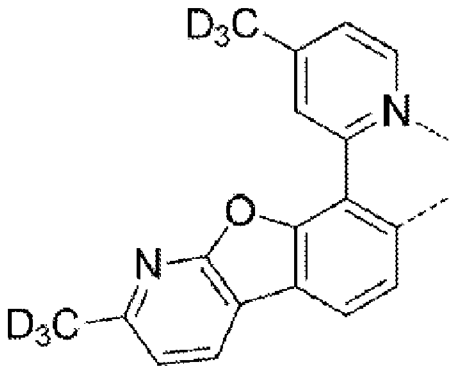 $L_{A200}$ --
Column 407, Lines 42-54, please delete
“ 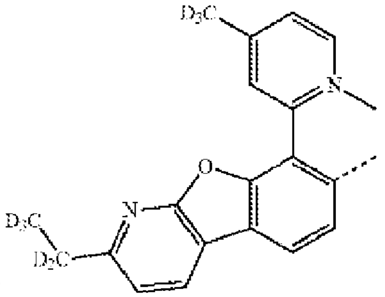 $L_{A201}$ ” and insert -- 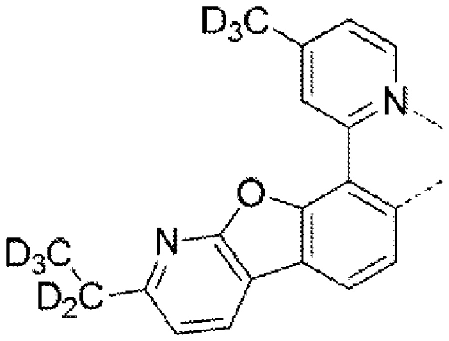 $L_{A201}$ --
Column 407, Lines 55-66, please delete
“ 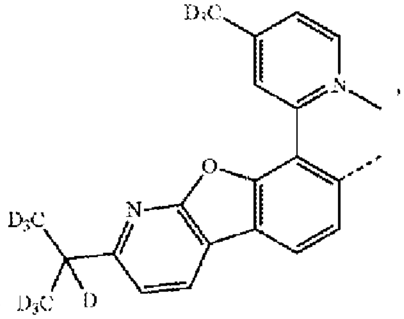 $L_{A202}$ ” and insert -- 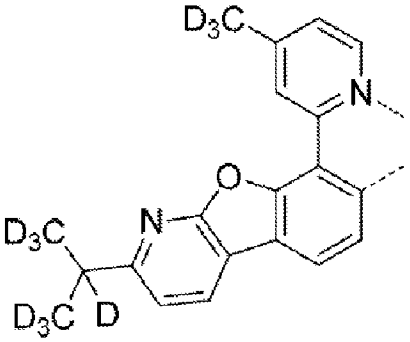 $L_{A202}$ --
Column 408, Lines 1-14, please delete “ 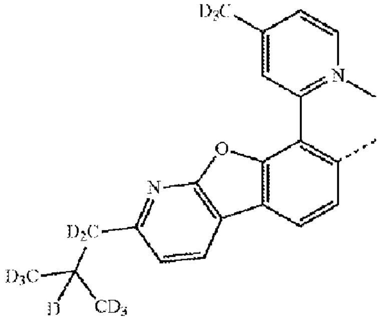 $L_{A203}$ ” and insert -- 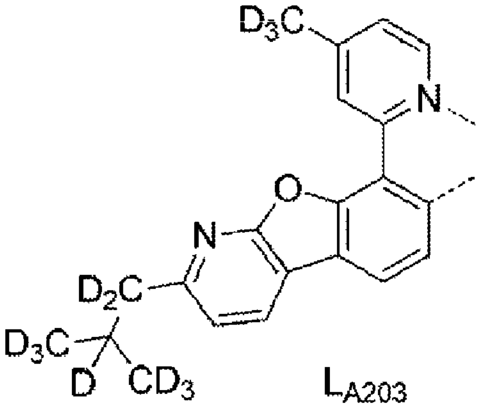 $L_{A203}$ --
Column 408, Lines 15-27, please delete
“ 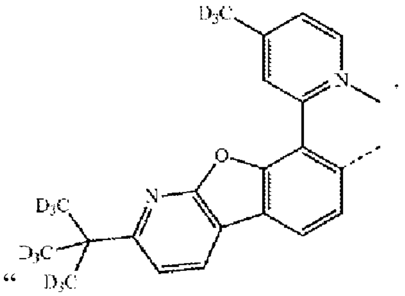 $L_{A204}$ ” and insert -- 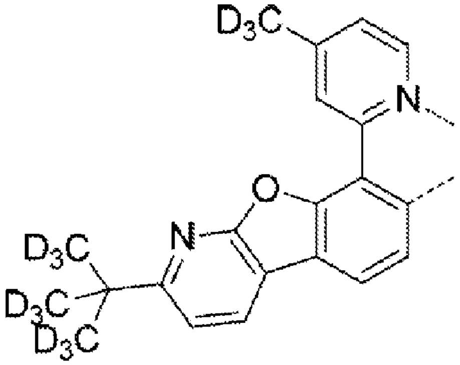 $L_{A204}$ --
Column 408, Lines 28-39, please delete
“ 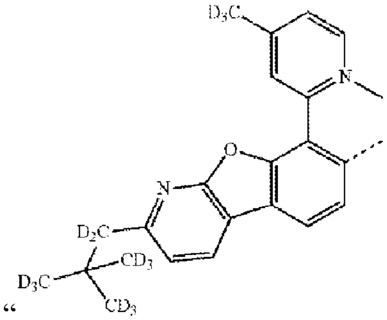 $L_{A205}$ ” and insert -- 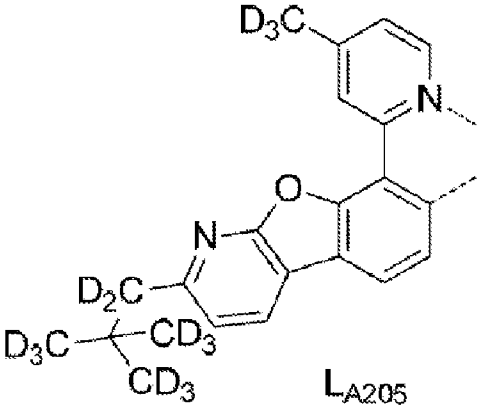 $L_{A205}$ --
Column 408, Lines 40-54, please delete “ 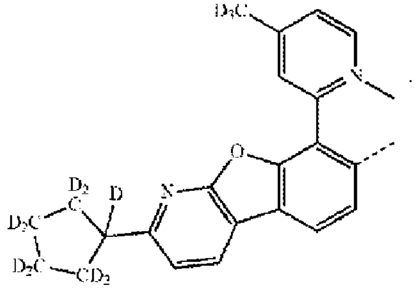 $L_{A206}$ ” and insert -- 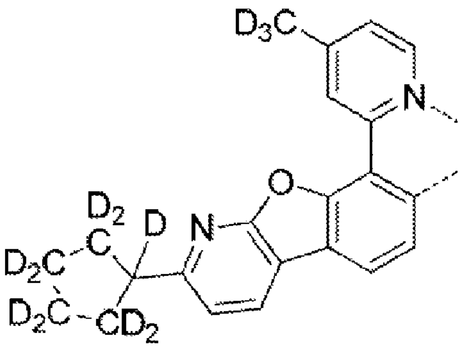 $L_{A206}$ --
Column 408, Lines 55-66, please delete
“ 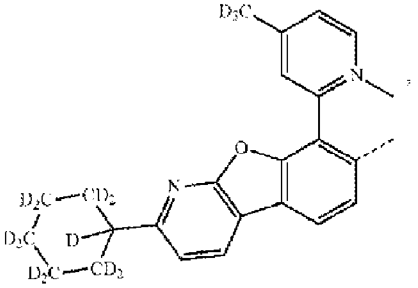 $L_{A207}$ ” and insert -- 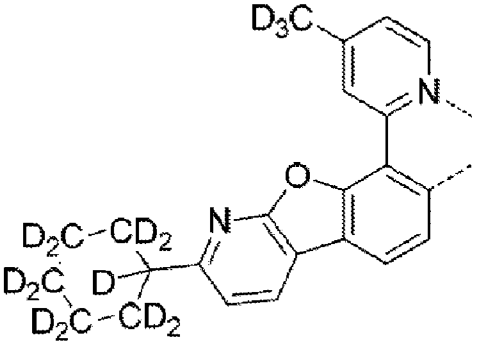 $L_{A207}$ --
Column 409, Lines 1-12, please delete
“ 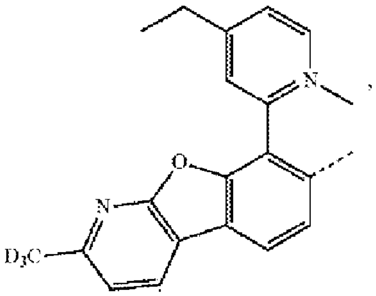 $L_{A208}$ ” and insert -- 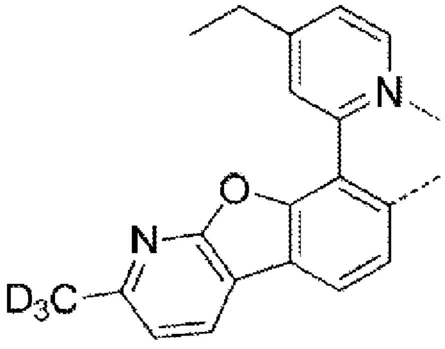 $L_{A208}$ --
Column 409, Lines 13-25, please delete L$_{A209}$
“ 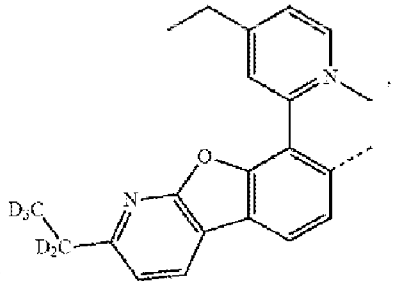 ” and insert -- 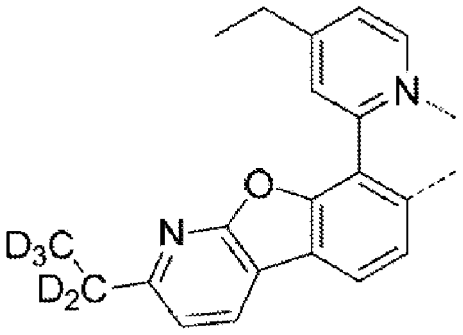 L$_{A209}$ --
Column 409, Lines 26-39, please delete
L$_{A210}$
“ 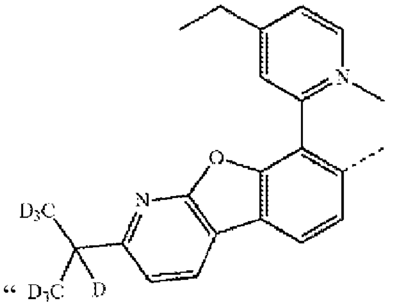 ” and insert -- 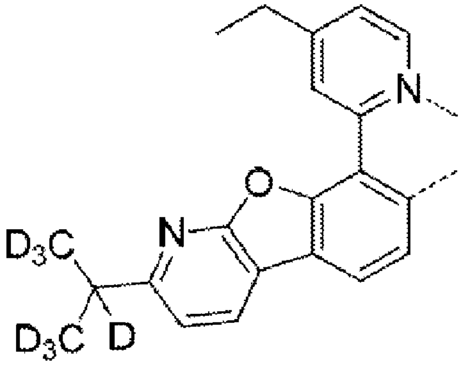 L$_{A210}$ --
Column 409, Lines 40-54, please delete
L$_{A211}$
“ 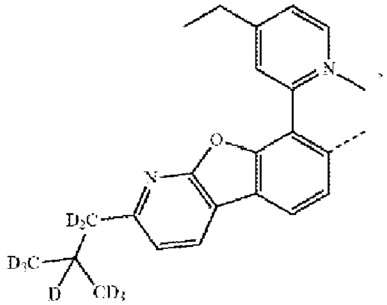 ” and insert -- 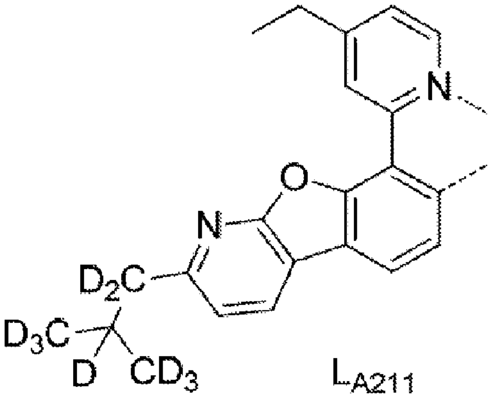 L$_{A211}$ --
Column 409, Lines 55-66, please delete “ 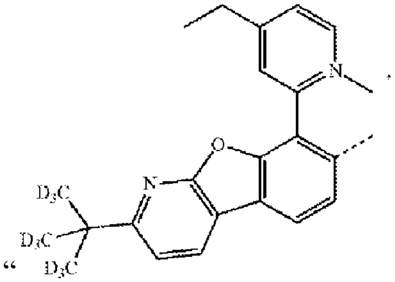 $L_{A212}$ ” and insert -- 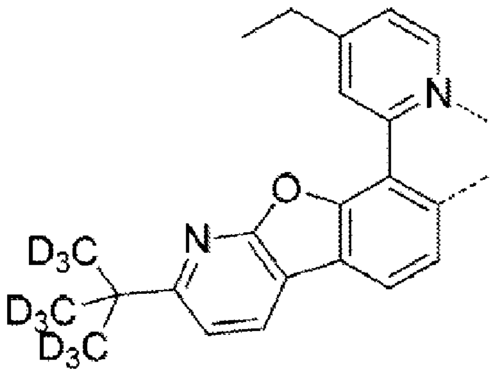 $L_{A212}$ --
Column 410, Lines 1-14, please delete
“ 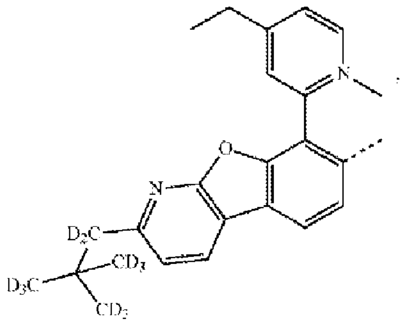 $L_{A213}$ ” and insert -- 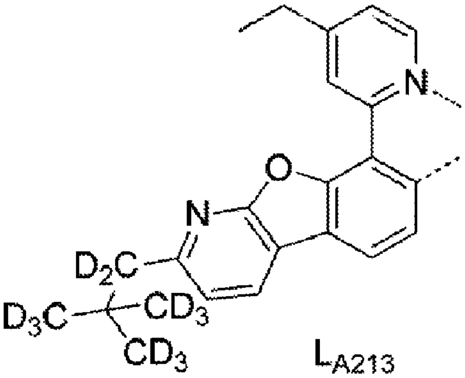 $L_{A213}$ --
Column 410, Lines 15-26, please delete
“ 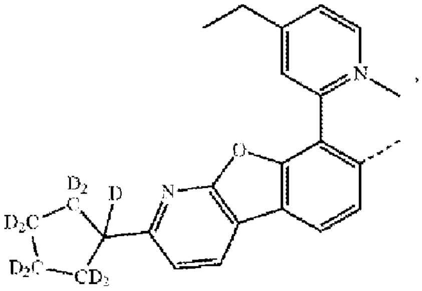 $L_{A214}$ ” and insert -- 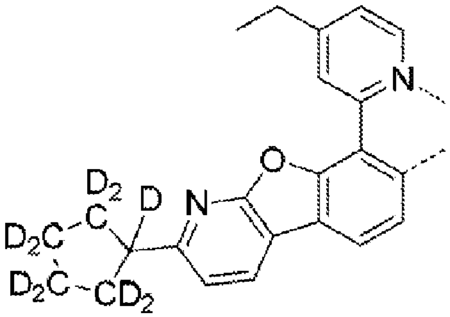 $L_{A214}$ --

Column 410, Lines 27-39, please delete
"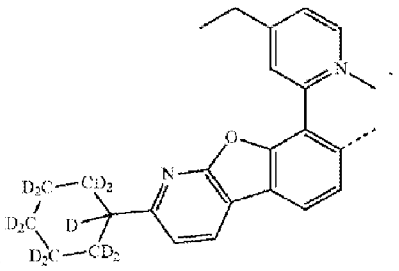 $L_{A215}$ " and insert -- 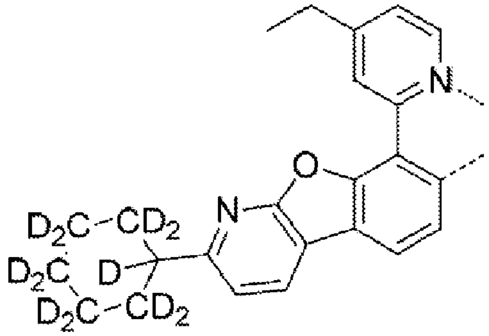
$L_{A215}$ --
Column 410, Lines 40-54, please delete
"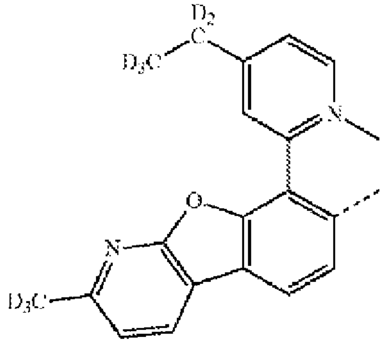 $L_{A216}$ " and insert -- 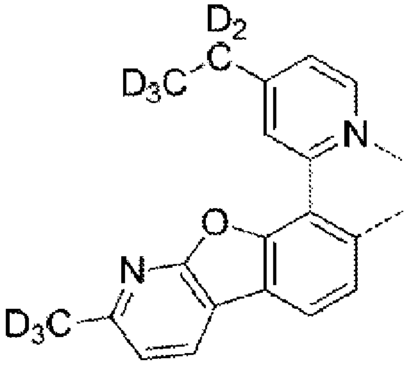
$L_{A216}$ --
Column 410, Lines 55-66, please delete
"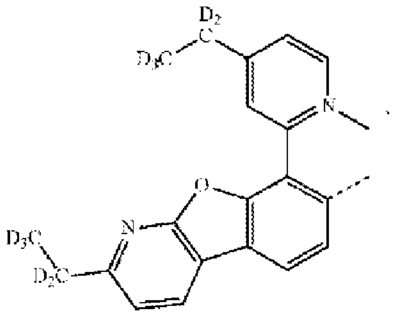 $L_{A217}$ " and insert -- 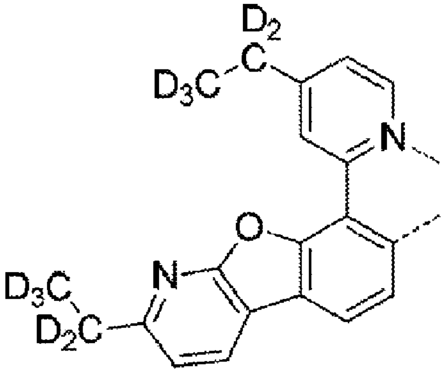
$L_{A217}$ --

Column 411, Lines 1-14, please delete
“ 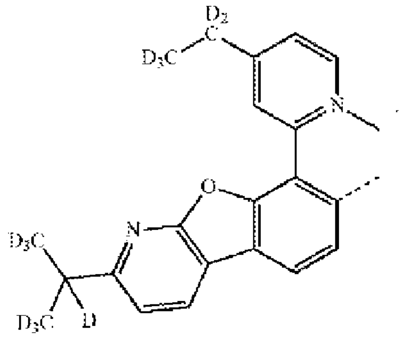 $L_{A218}$ ” and insert -- 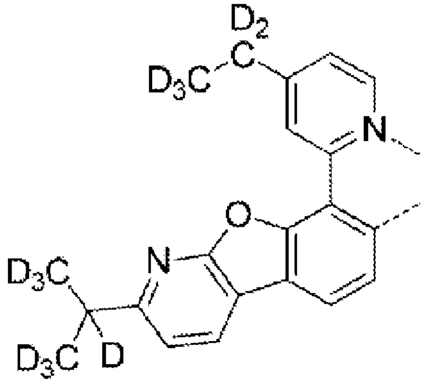 $L_{A218}$ --
Column 411, Lines 15-27, please delete
“ 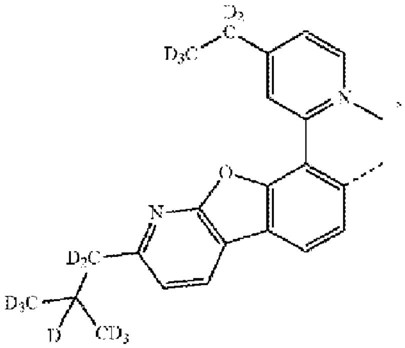 $L_{A219}$ ” and insert -- 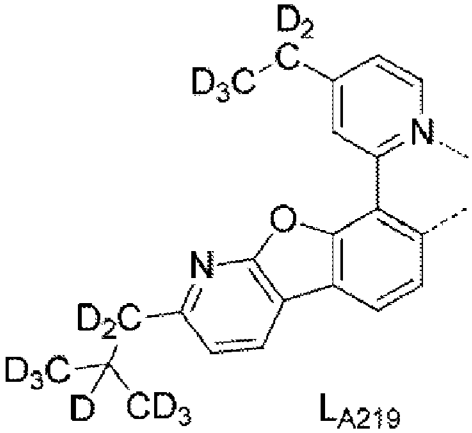 $L_{A219}$ --
Column 411, Lines 28-40, please delete
“ 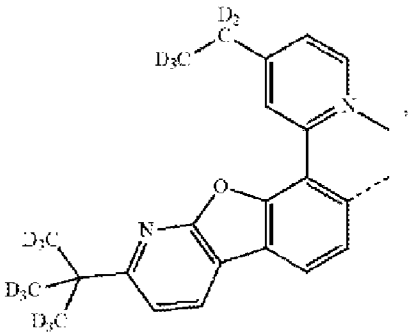 $L_{A220}$ ” and insert -- 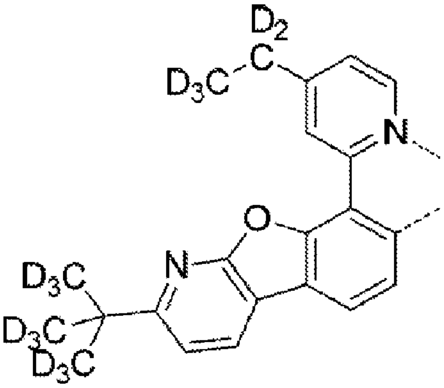 $L_{A220}$ --

Column 411, Lines 41-54, please delete
“ 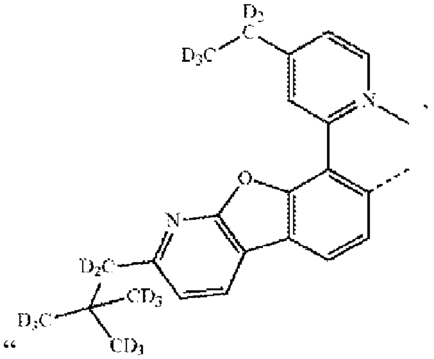 $L_{A221}$ ” and insert -- 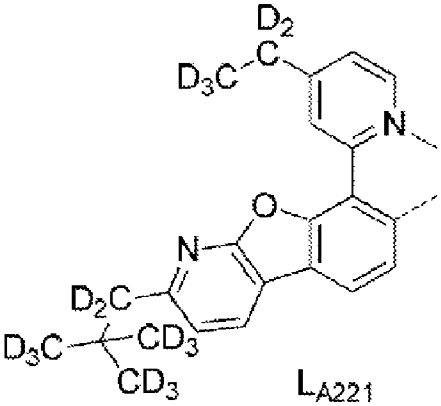 $L_{A221}$ --
Column 411, Lines 55-66, please delete
“ 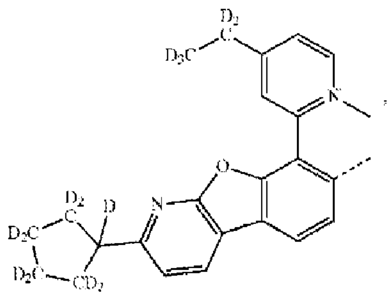 $L_{A222}$ ” and insert -- 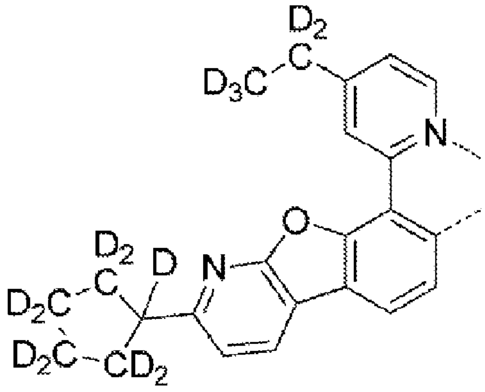 $L_{A222}$ --
Column 412, Lines 1-13, please delete
“ 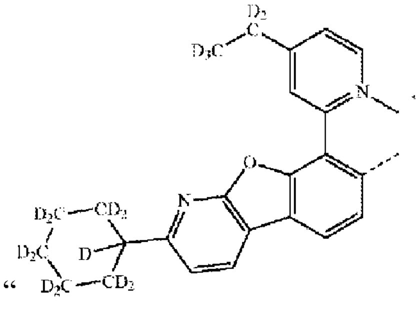 $L_{A223}$ ” and insert -- 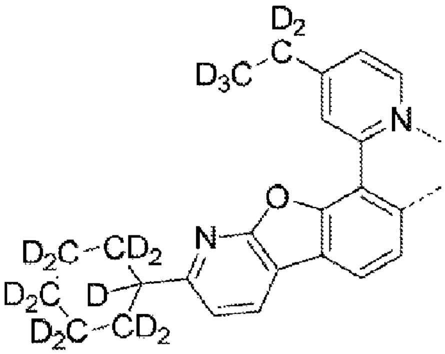 $L_{A223}$ --

Column 412, Lines 14-27, please delete
“ 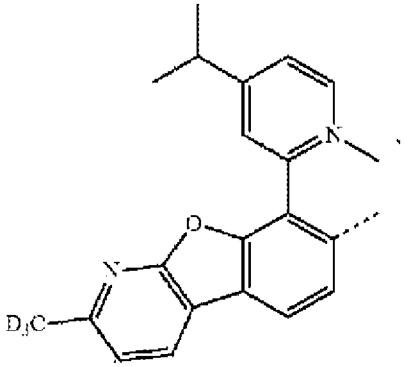 $L_{A224}$ ” and insert -- 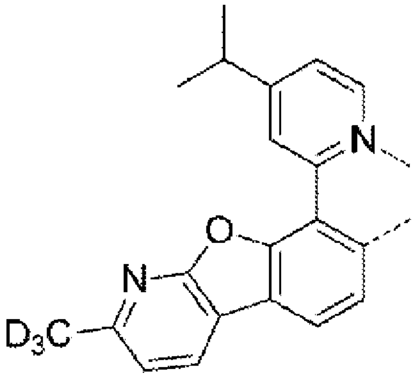 $L_{A224}$ --
Column 412, Lines 28-39, please delete
“ 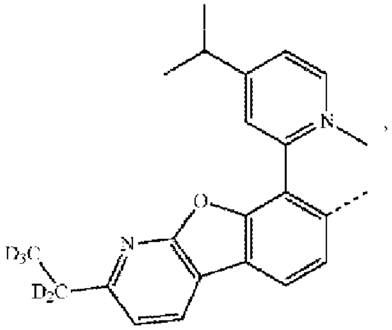 $L_{A225}$ ” and insert -- 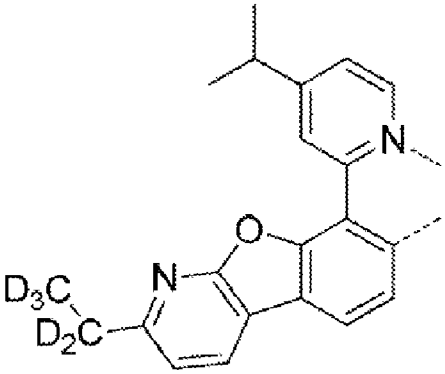 $L_{A225}$ --
Column 412, Lines 40-52, please delete
“ 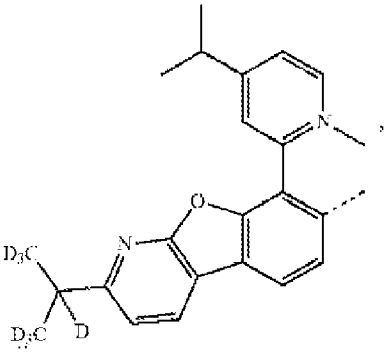 $L_{A226}$ ” and insert -- 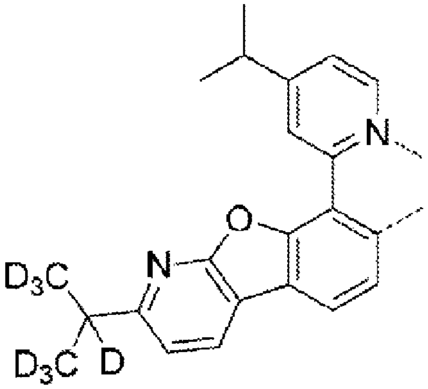 $L_{A226}$ --

Column 412, Lines 53-66, please delete
"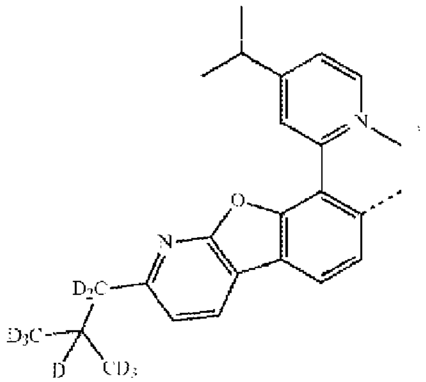 $L_{A227}$ " and insert -- 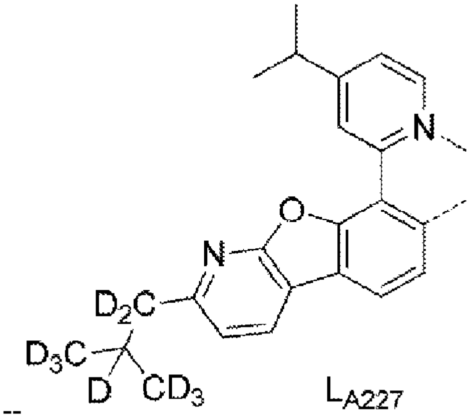 $L_{A227}$ --
Column 413, Lines 1-17, please delete
"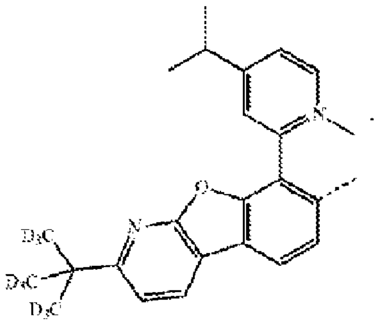 $L_{A228}$ " and insert -- 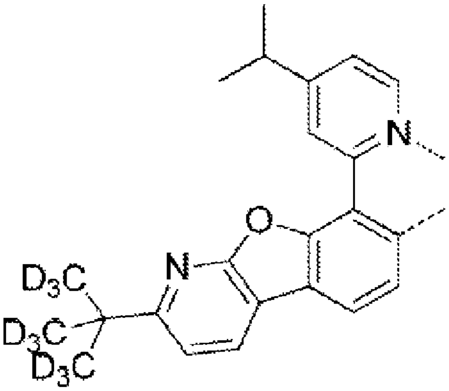 $L_{A228}$ --
Column 413, Lines 18-36, please delete
"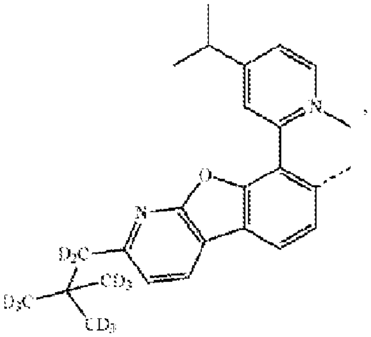 $L_{A229}$ " and insert -- 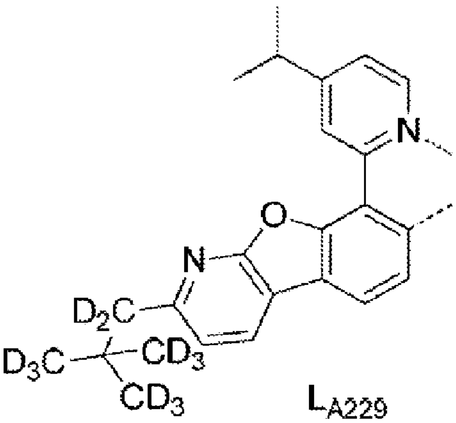 $L_{A229}$ --

Column 413, Lines 37-53, please delete
$L_{A230}$
“ 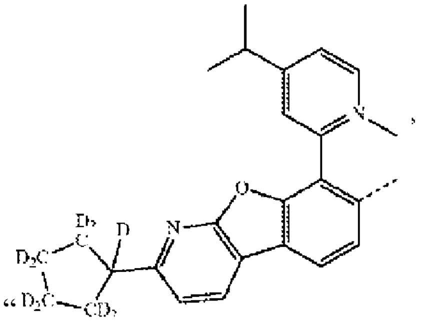 ” and insert -- 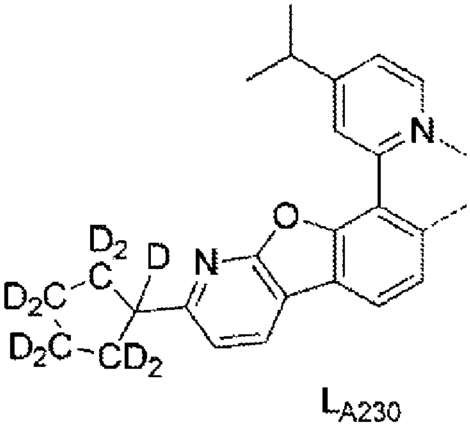 $L_{A230}$ --
Column 413, Lines 54-66, please delete
$L_{A231}$
“ 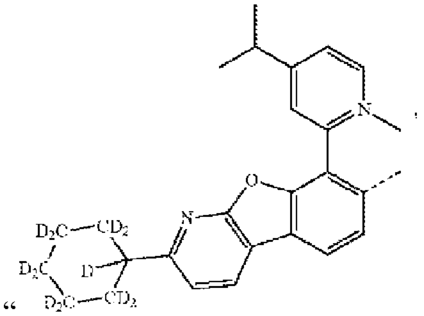 ” and insert -- 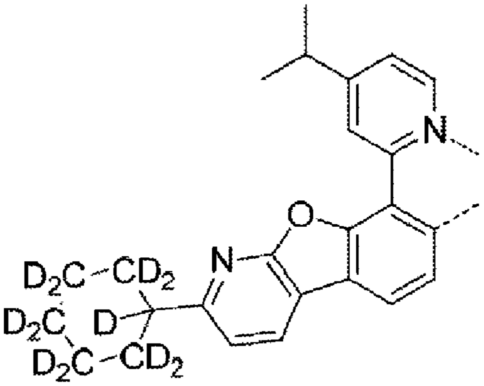 $L_{A231}$ --
Column 414, Lines 1-18, please delete
$L_{A232}$
“ 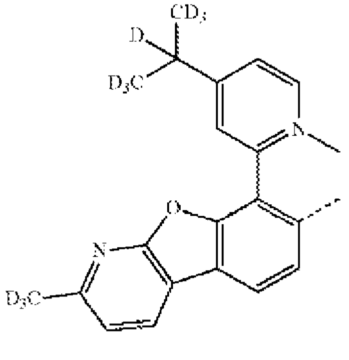 ” and insert -- 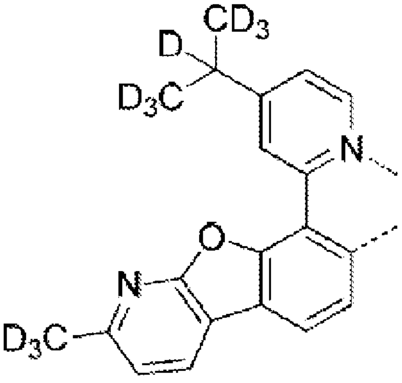 $L_{A232}$ --
Column 414, Lines 19-35, please delete " 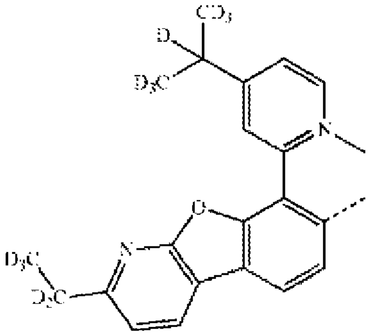 $L_{A233}$ " and insert -- 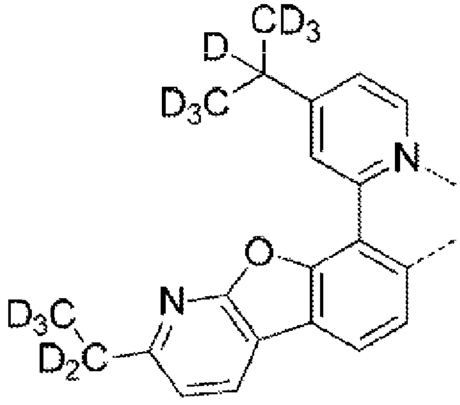 $L_{A233}$ --
Column 414, Lines 36-53, please delete
" 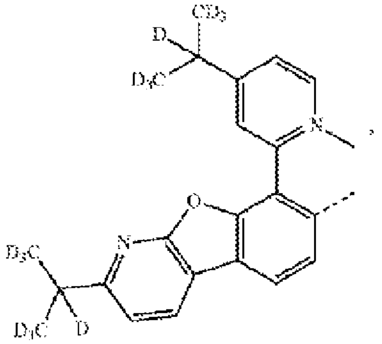 $L_{A234}$ " and insert -- 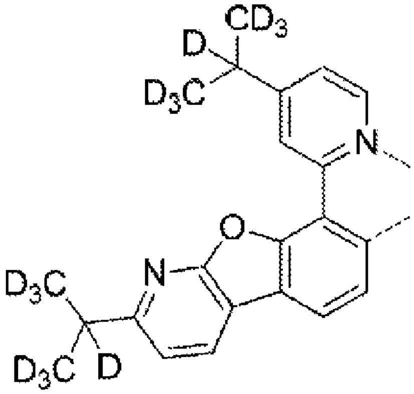 $L_{A234}$ --
Column 414, Lines 54-66, please delete
" 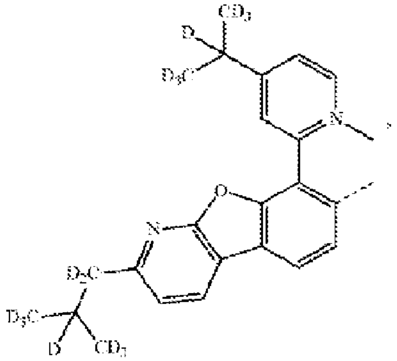 $L_{A235}$ " and insert -- 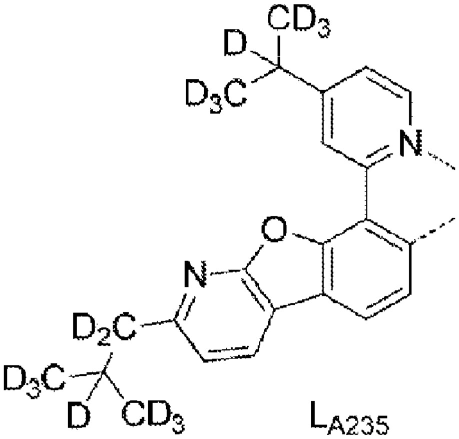 $L_{A235}$ , --
Column 415, Lines 1-17, please delete $L_{A236}$
" 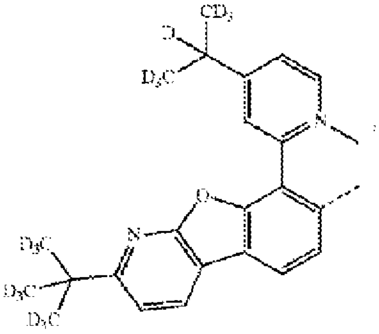 " and insert -- 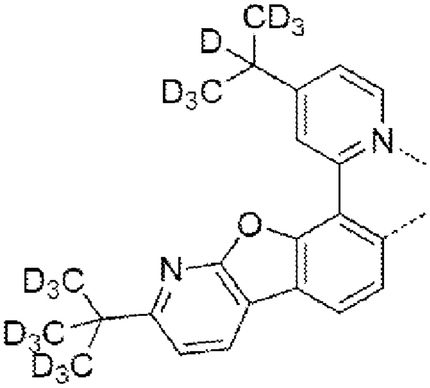 $L_{A236}$ --
Column 415, Lines 18-35, please delete
$L_{A237}$
" 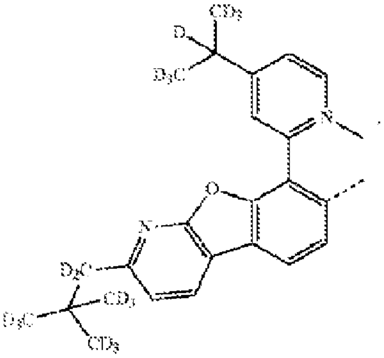 " and insert -- 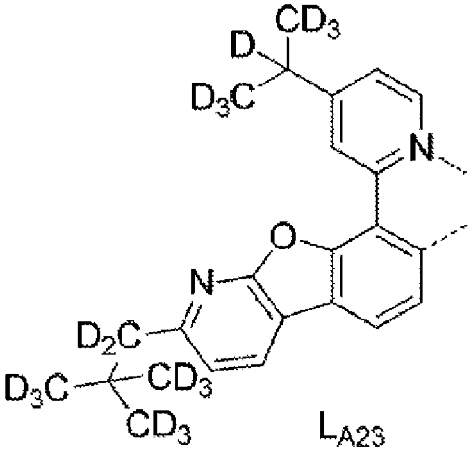 $L_{A23}$ 7 --
Column 415, Lines 36-52, please delete
$L_{A238}$
" 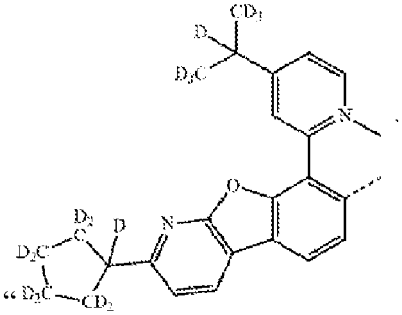 " and insert -- 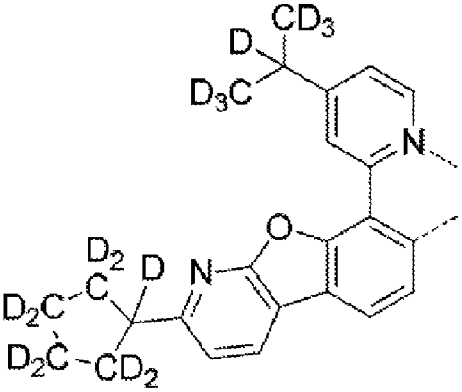 $L_{A238}$ --
Column 415, Lines 53-66, please delete “ 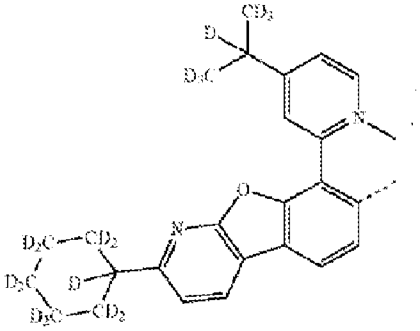 $L_{A239}$ ” and insert -- 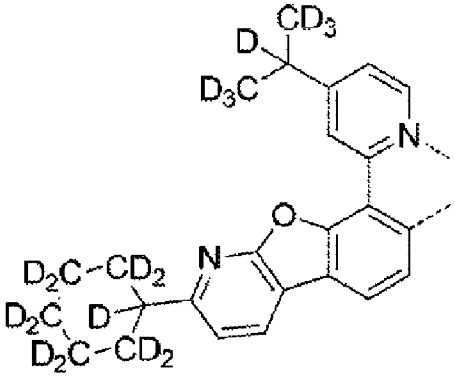 $L_{A239}$ --
Column 416, Lines 1-14, please delete
“ 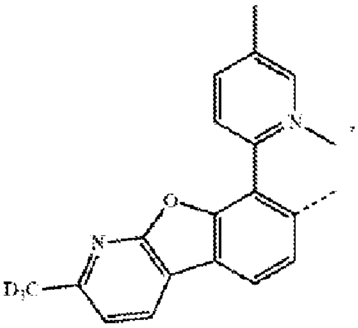 $L_{A240}$ ” and insert -- 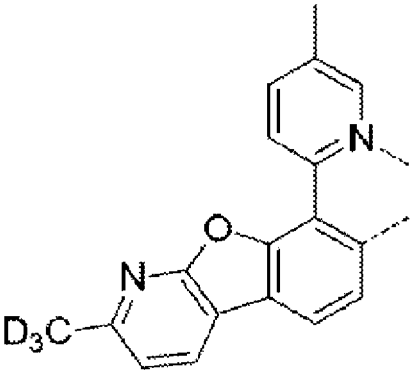 $L_{A240}$ --
Column 416, Lines 15-26, please delete
“ 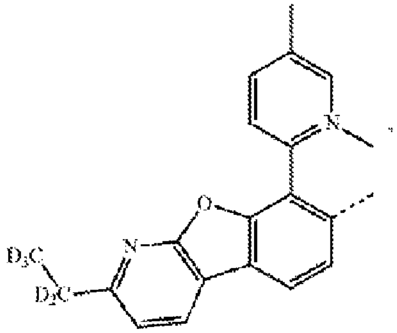 $L_{A241}$ ” and insert -- 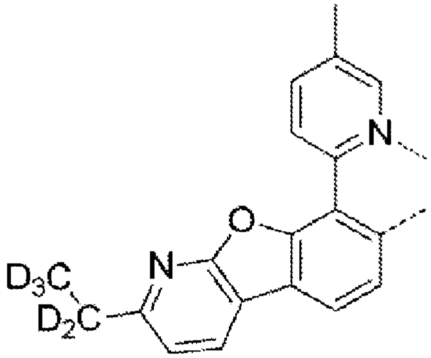 $L_{A241}$ --
Column 416, Lines 27-39, please delete “ 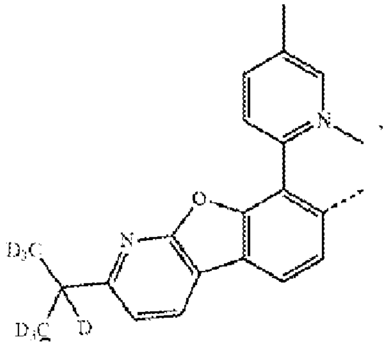 $L_{A242}$ ” and insert -- 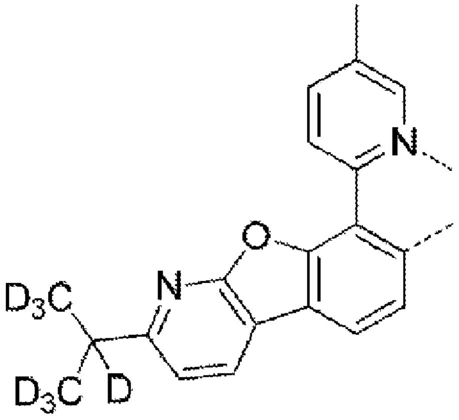 $L_{A242}$ --
Column 416, Lines 40-54, please delete
“ 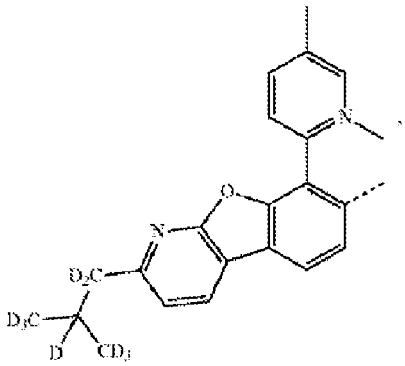 $L_{A243}$ ” and insert -- 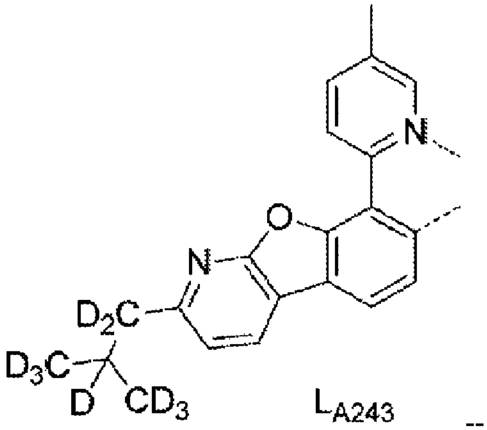 $L_{A243}$ --
Column 416, Lines 55-66, please delete
“ 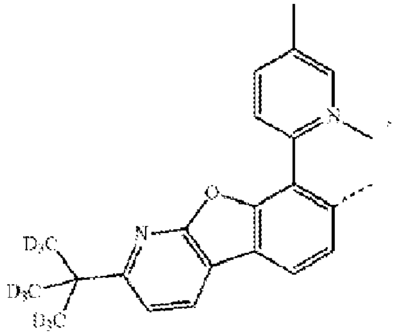 $L_{A244}$ ” and insert -- 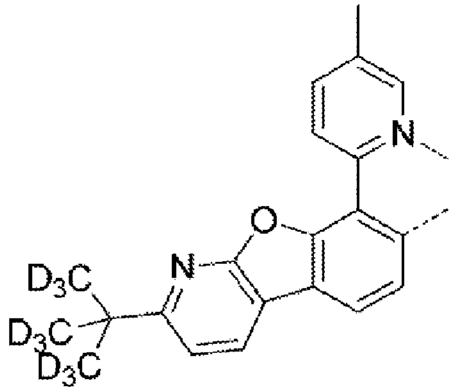 $L_{A244}$ --
Column 417, Lines 1-20, please delete “ 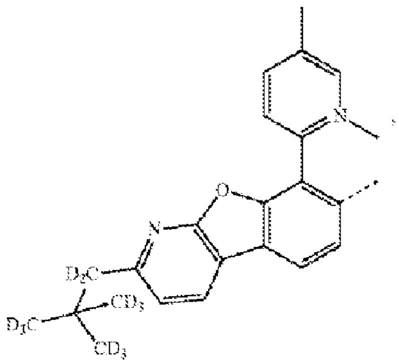 $L_{A245}$ ” and insert -- 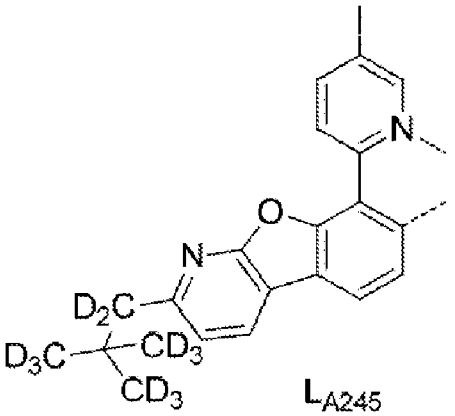 $L_{A245}$ --
Column 417, Lines 21-35, please delete
“ 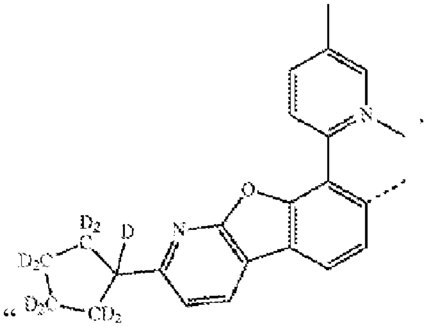 $L_{A246}$ ” and insert -- 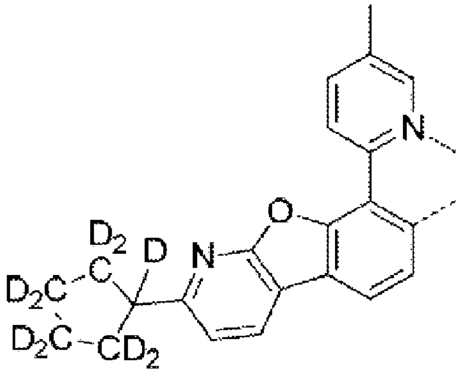 $L_{A246}$ --
Column 417, Lines 36-53, please delete
“ 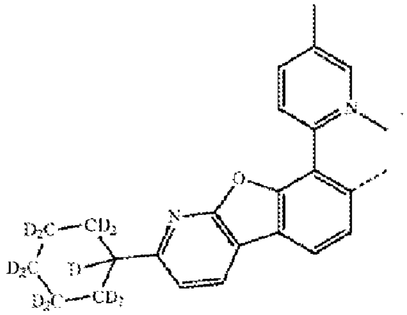 $L_{A247}$ ” and insert -- 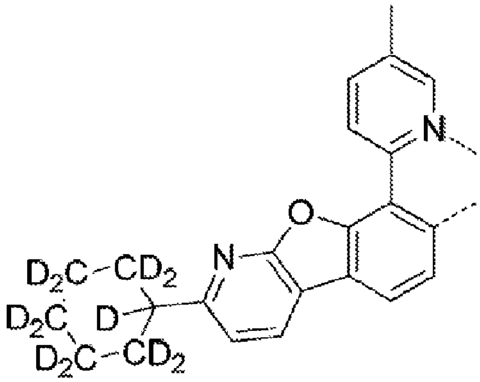 $L_{A247}$ --
Column 417, Lines 54-66, please delete “ 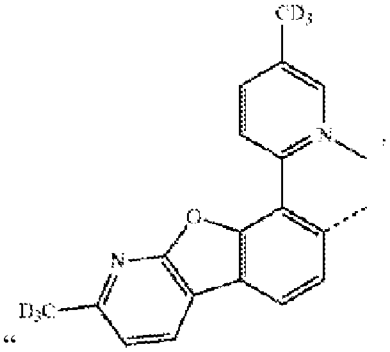 $L_{A248}$ ” and insert -- 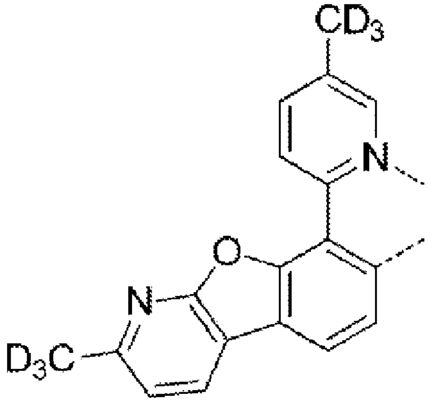 $L_{A248}$ --
Column 418, Lines 1-15, please delete
“ 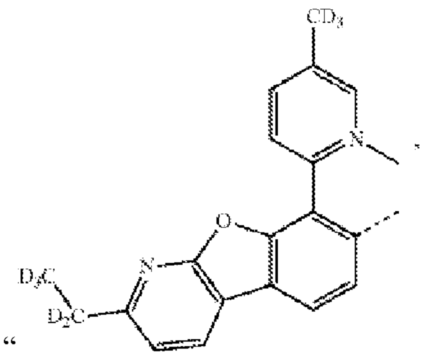 $L_{A249}$ ” and insert -- 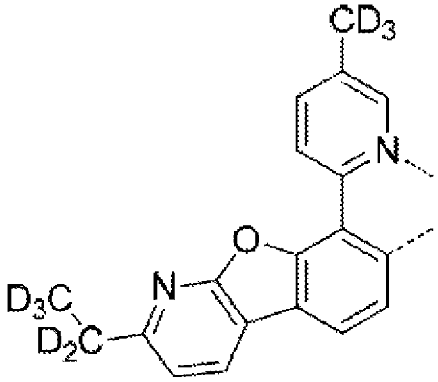 $L_{A249}$ --
Column 418, Lines 16-34, please delete
“ 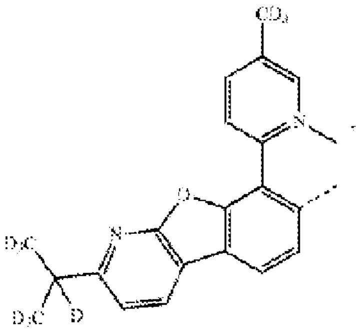 $L_{A250}$ ” and insert -- 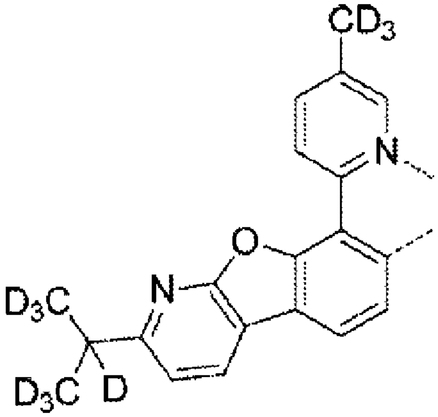 $L_{A250}$ --
Column 418, Lines 35-53, please delete “ 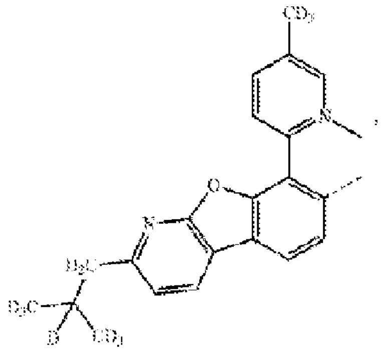 $L_{A251}$ ” and insert -- 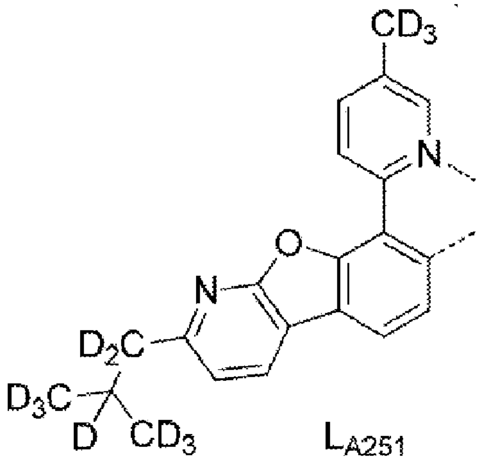 $L_{A251}$ --
Column 418, Lines 54-66, please delete
“ 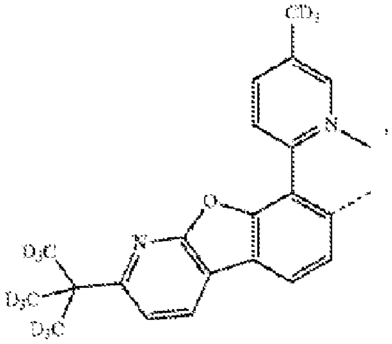 $L_{A252}$ ” and insert -- 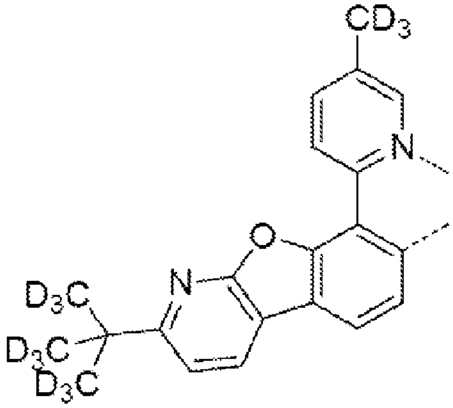 $L_{A252}$ --
Column 419, Lines 1-19, please delete
“ 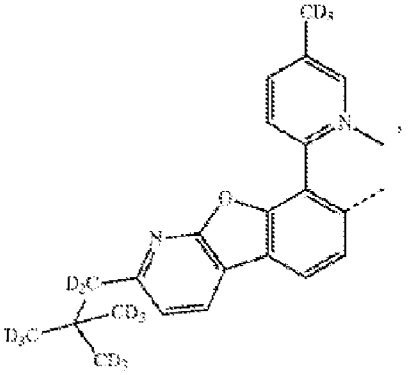 $L_{A253}$ ” and insert -- 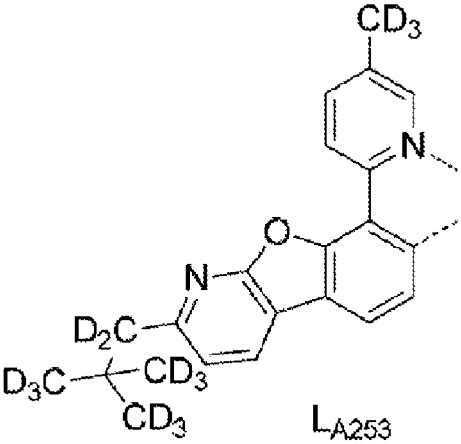 $L_{A253}$ --
Column 419, Lines 20-36, please delete $L_{A254}$
“ 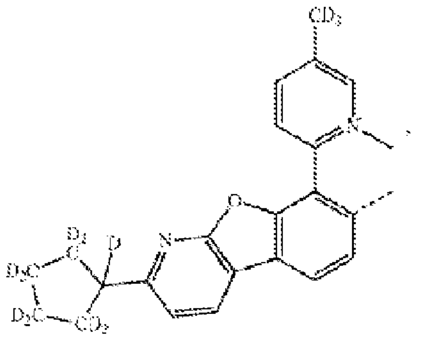 ” and insert -- 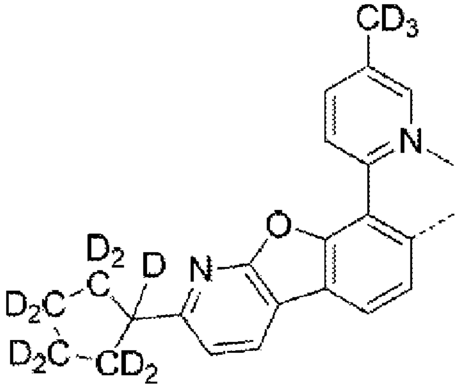 $L_{A254}$ --
Column 419, Lines 37-53, please delete
$L_{A255}$
“ 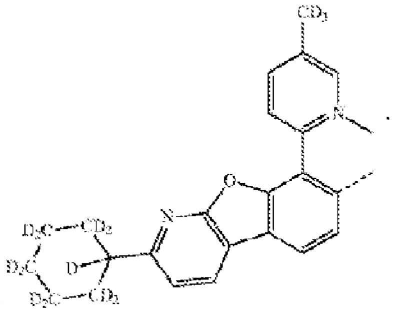 ” and insert -- 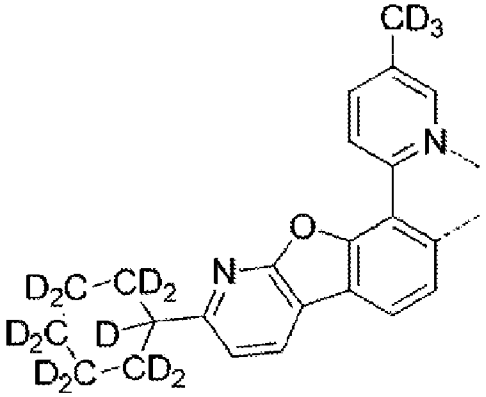 $L_{A255}$ --
Column 419, Lines 54-66, please delete
$L_{A256}$
“ 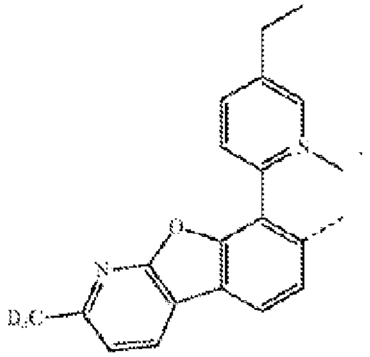 ” and insert -- 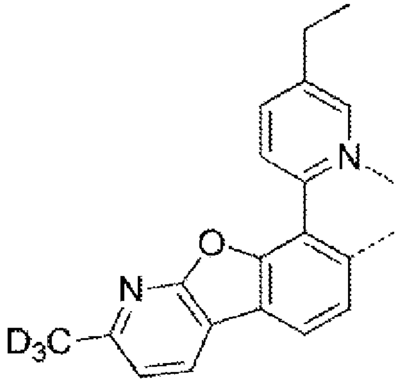 $L_{A256}$ --

Column 420, Lines 1-16, please delete
"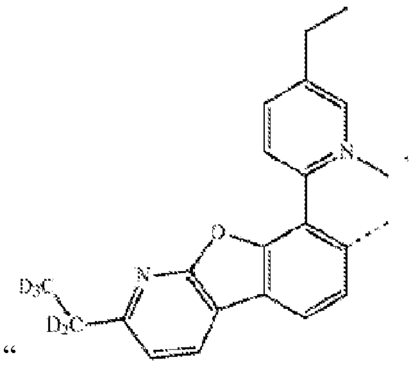 $L_{A257}$ " and insert -- 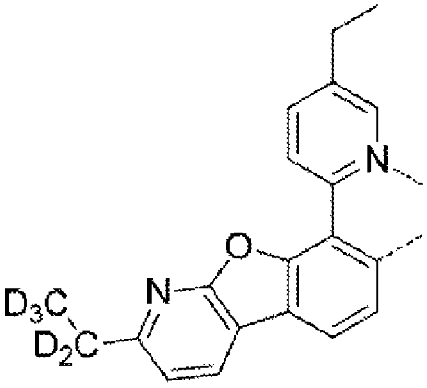 $L_{A257}$ --
Column 420, Lines 17-33, please delete
"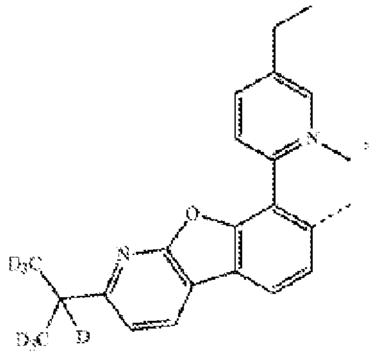 $L_{A258}$ " and insert -- 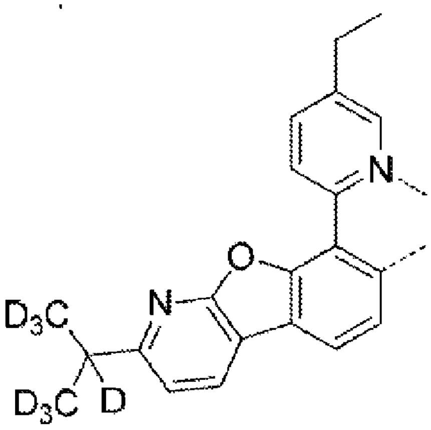 $L_{A258}$ --
Column 420, Lines 34-52, please delete
"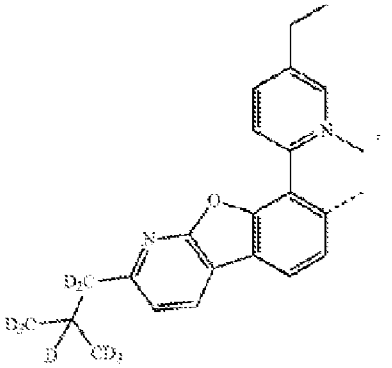 $L_{A259}$ " and insert -- 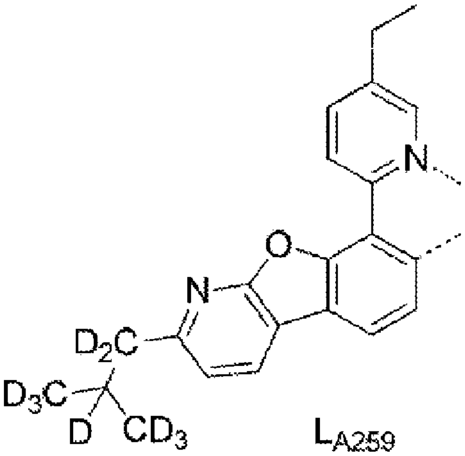 $L_{A259}$ --
Column 420, Lines 53-66, please delete “ 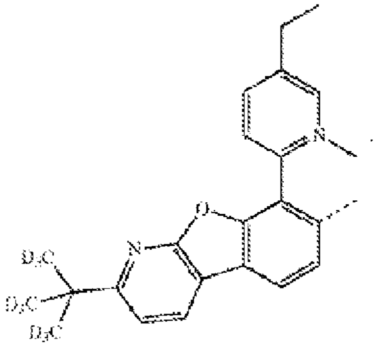 $L_{A260}$ ” and insert -- 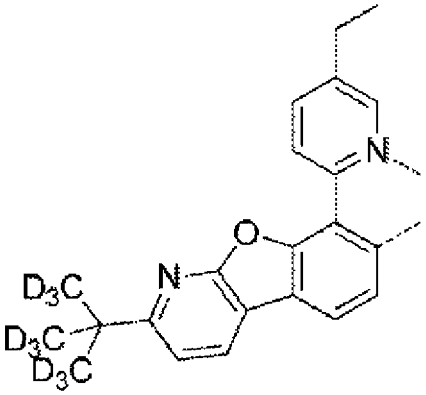 $L_{A260}$ --
Column 421, Lines 1-18, please delete
“ 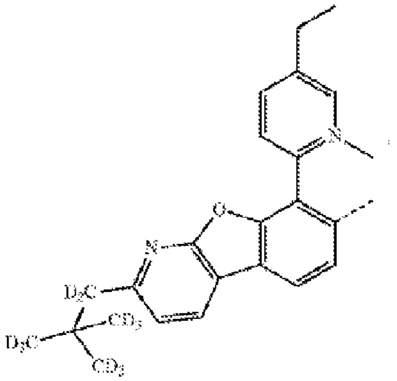 $L_{A261}$ ” and insert -- 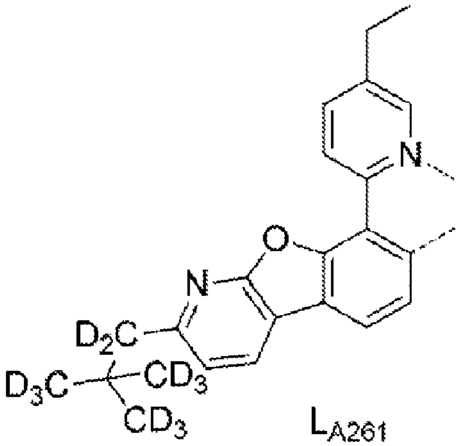 $L_{A261}$ --
Column 421, Lines 19-36, please delete
“ 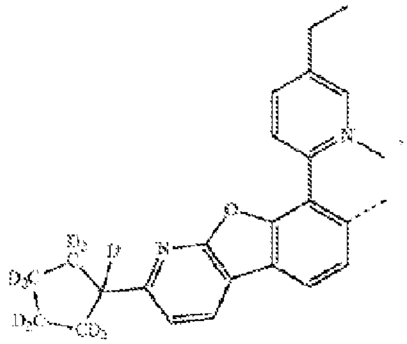 $L_{A262}$ ” and insert -- 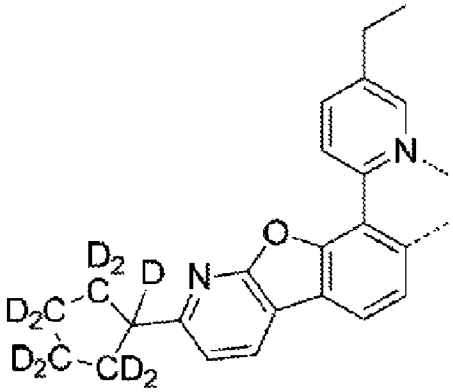 $L_{A262}$ --
Column 421, Lines 37-52, please delete ,
$L_{A262}$
“ 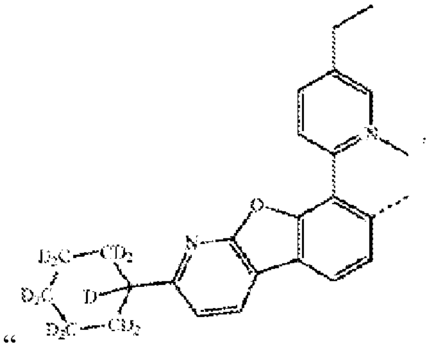 ” and insert -- 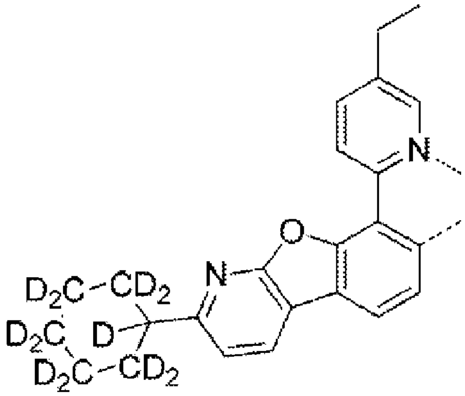 $L_{A263}$ --
Column 421, Lines 53-66, please delete
$L_{A264}$
“ 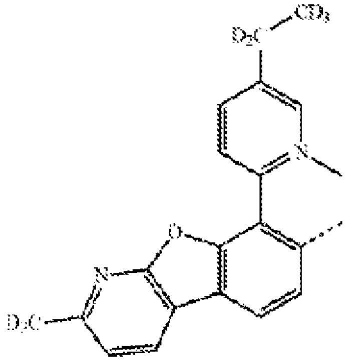 ” and insert -- 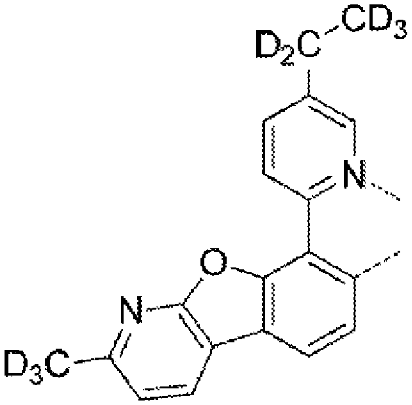 $L_{A264}$ --
Column 422, Lines 1-15, please delete
$L_{A265}$
“ 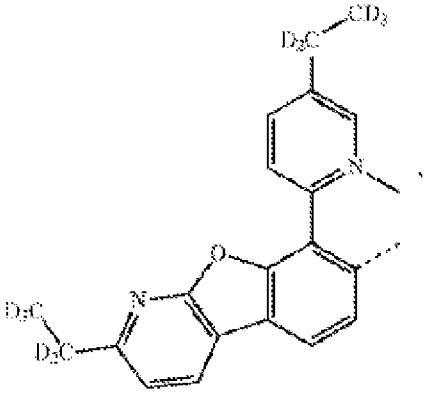 ” and insert -- 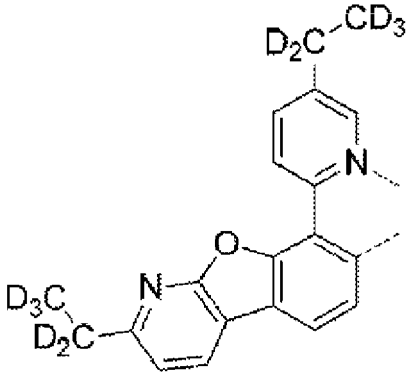 $L_{A265}$ --
Column 422, Lines 16-33, please delete $L_{A266}$
“ 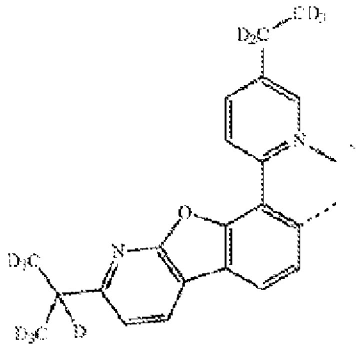 ” and insert -- 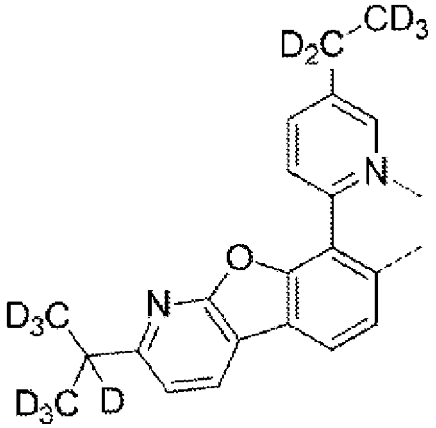 $L_{A266}$ --
Column 422, Lines 34-51, please delete
$L_{A267}$
“ 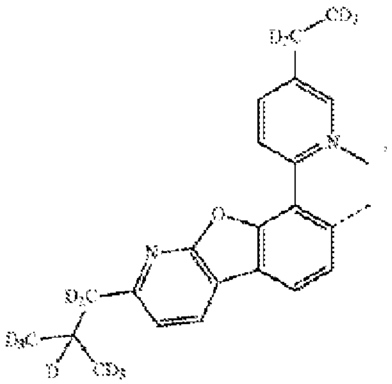 ” and insert -- 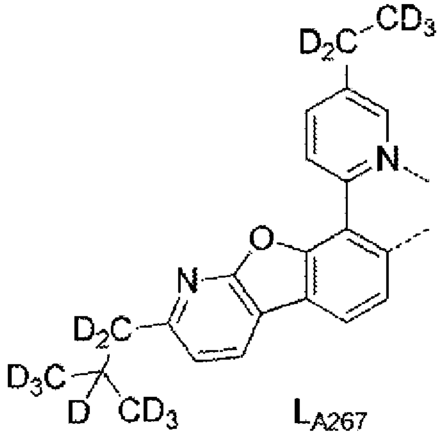 $L_{A267}$ --
Column 422, Lines 52-66, please delete
$L_{A268}$
“ 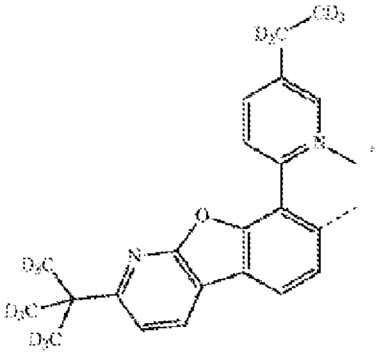 ” and insert -- 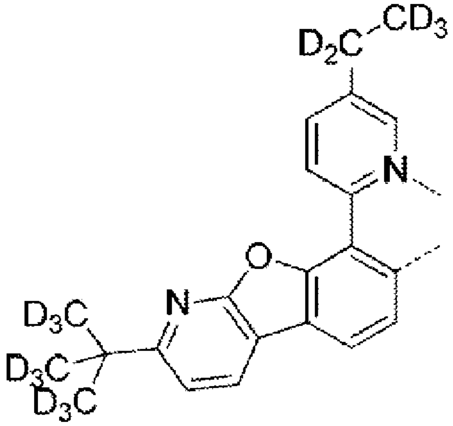 $L_{A268}$ --

Column 423, Lines 1-16, please delete
“ 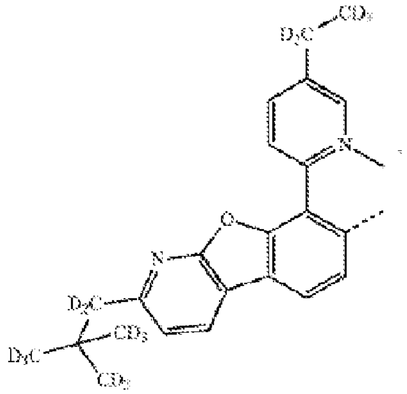 $L_{A269}$ ” and insert -- 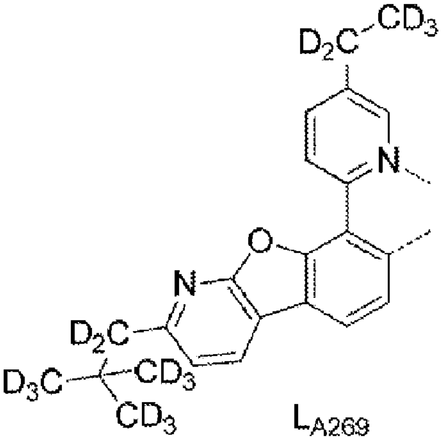 $L_{A269}$ --
Column 423, Lines 17-34, please delete
“ 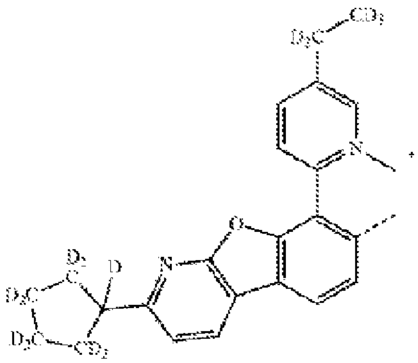 $L_{A270}$ ” and insert -- 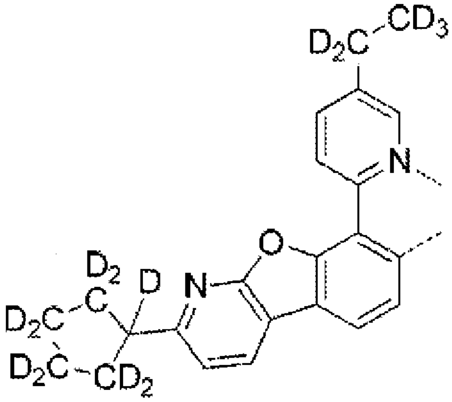 $L_{A270}$ --
Column 423, Lines 35-52, please delete
“ 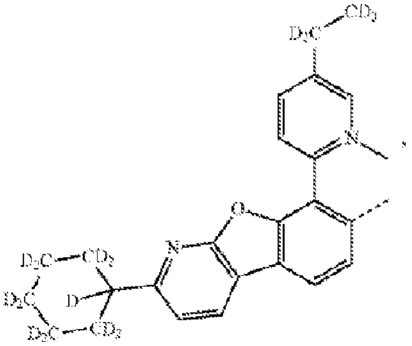 $L_{A271}$ ” and insert -- 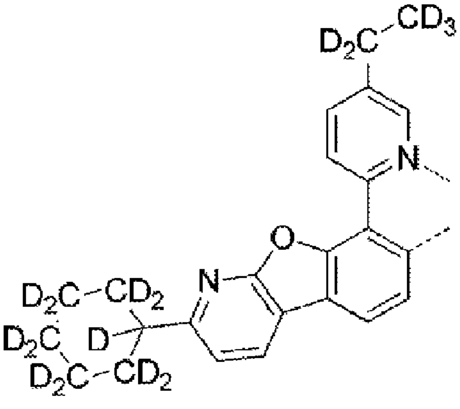 $L_{A271}$ --

Column 423, Lines 53-66, please delete
“ 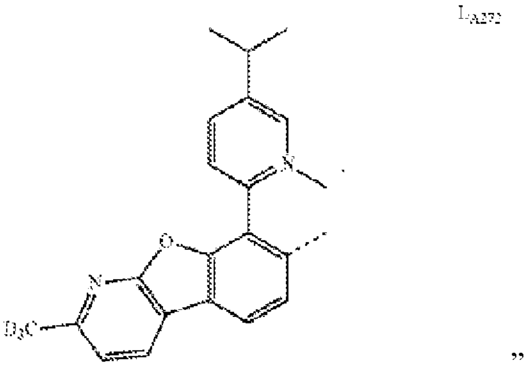 ” and insert -- 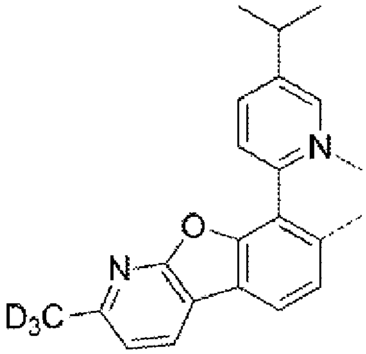 $L_{A272}$ --
Column 424, Lines 1-15, please delete
“ 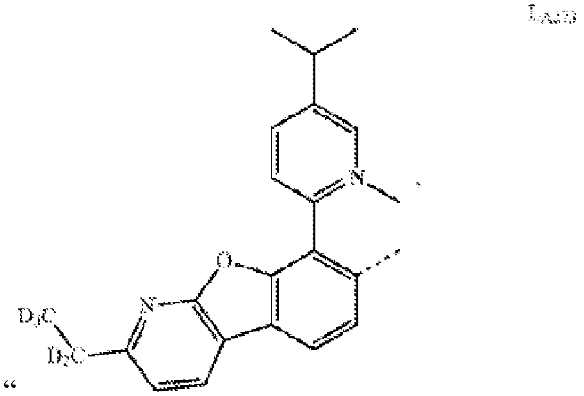 ” and insert -- 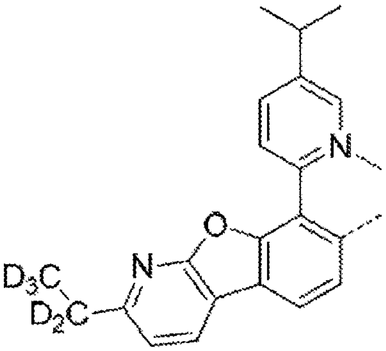 $L_{A273}$ . --
Column 424, Lines 16-34, please delete
“ 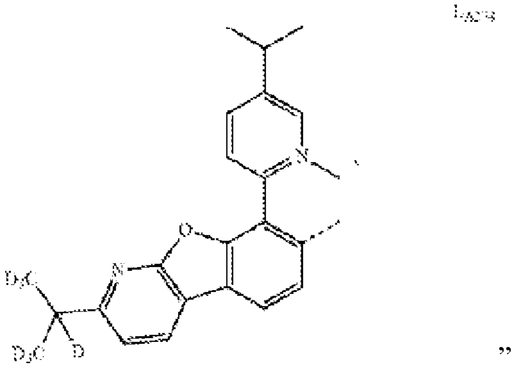 ” and insert -- 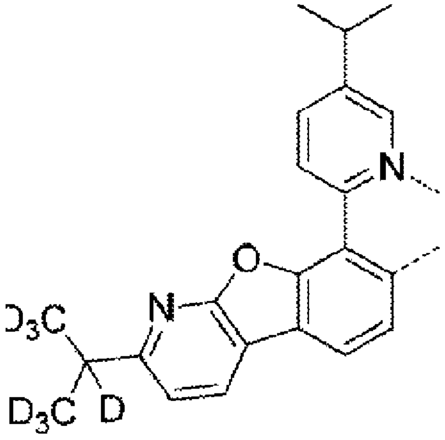 $L_{A274}$ --

Column 424, Lines 35-52, please delete
$L_{A275}$
“ 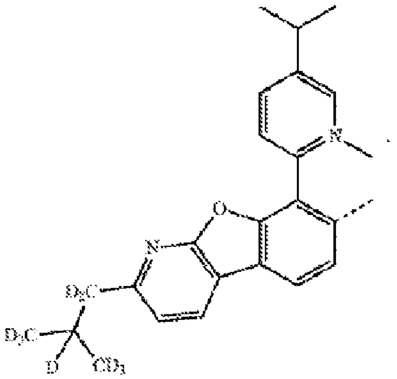 ” and insert -- 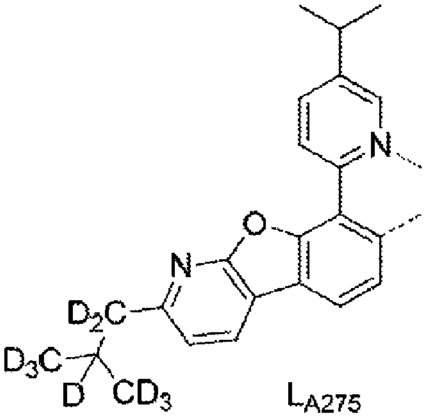 $L_{A275}$ --
Column 424, Lines 53-66, please delete
$L_{A276}$
“ 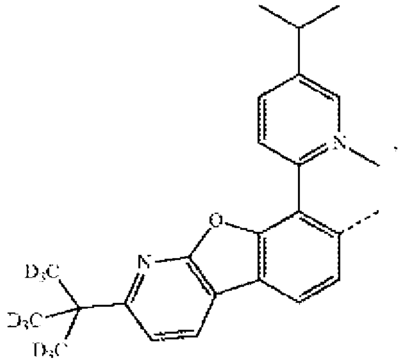 ” and insert -- 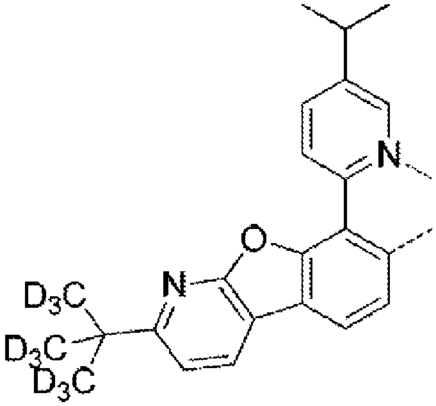 $L_{A276}$ --
Column 425, Lines 1-15, please delete
$L_{A277}$
“ 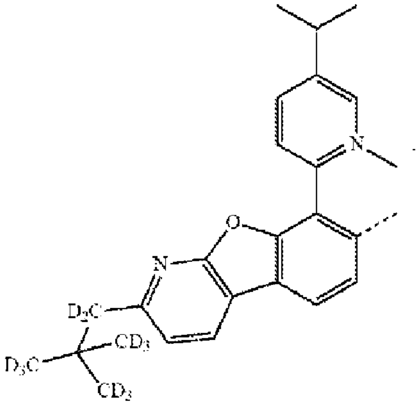 ” and insert -- 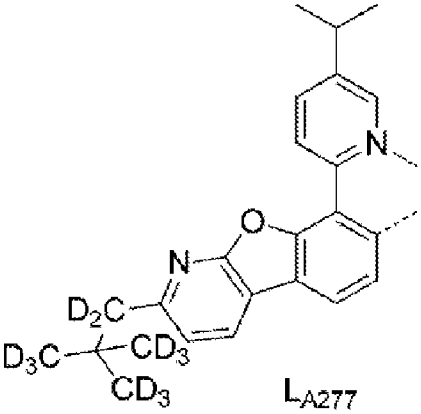 $L_{A277}$ --

Column 425, Lines 16-34, please delete
$L_{A278}$
“ 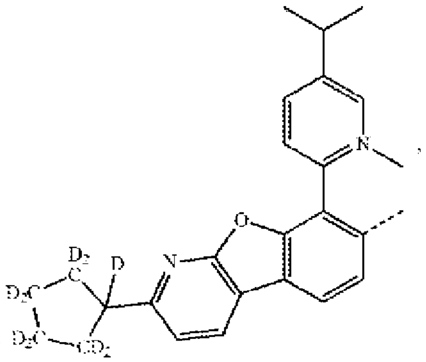 ” and insert -- 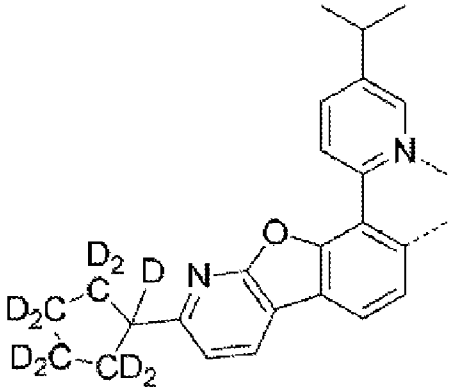
$L_{A278}$ --
Column 425, Lines 35-52, please delete
$L_{A279}$
“ 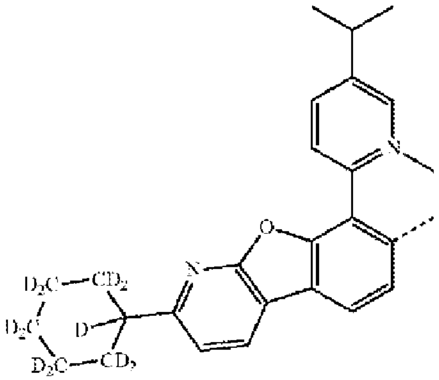 ” and insert -- 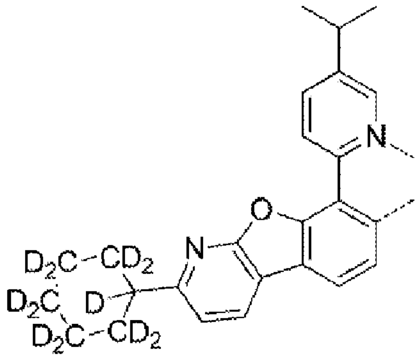
$L_{A279}$ --
Column 428, Lines 53-66, please delete
$L_{A280}$
“ 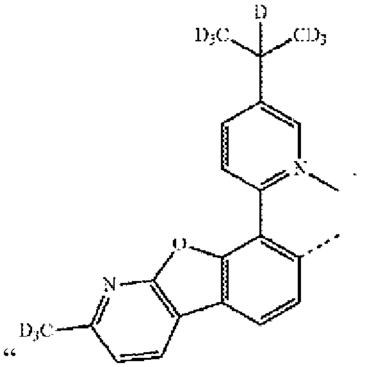 ” and insert -- 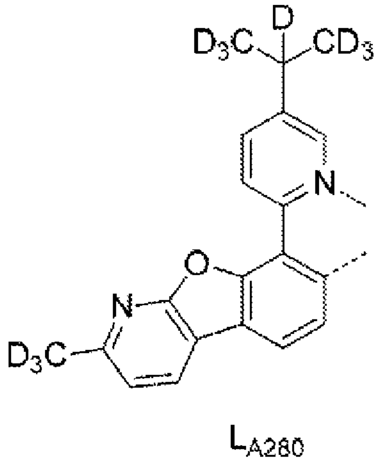
$L_{A280}$ --

Column 426, Lines 1-15, please delete
"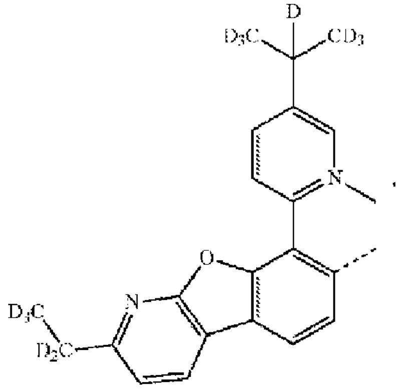 $L_{A281}$" and insert -- 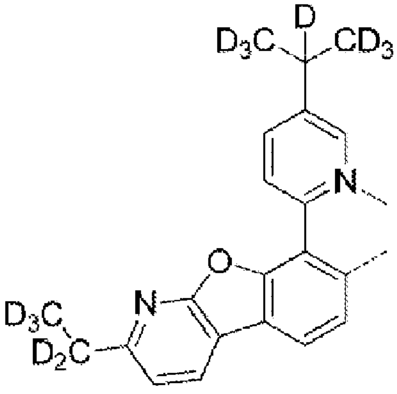 $L_{A281}$ --
Column 426, Lines 16-33, please delete
"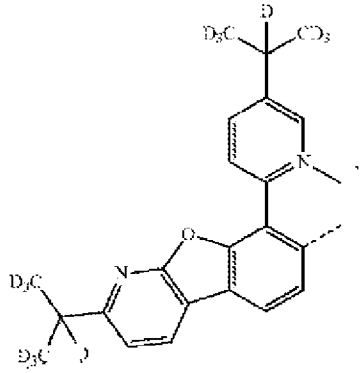 $L_{A282}$" and insert -- 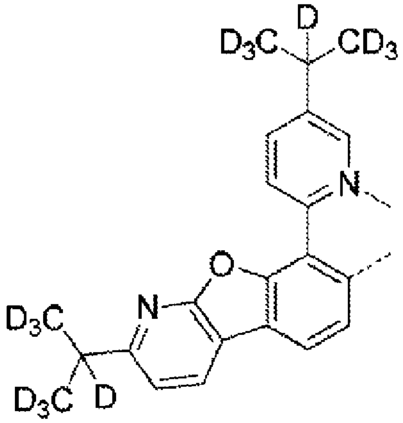 $L_{A282}$ --
Column 426, Lines 34-51, please delete
"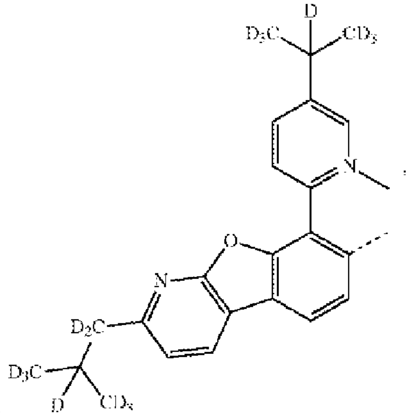 $L_{A283}$" and insert -- 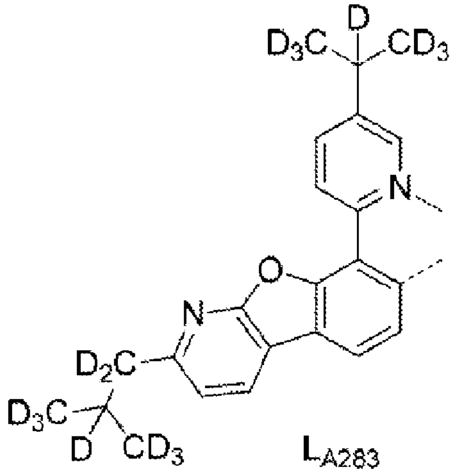 $L_{A283}$ --

Column 426, Lines 52-66, please delete
" 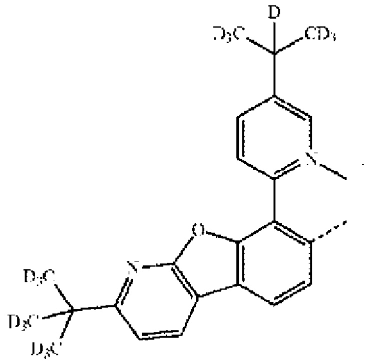 $L_{A284}$ " and insert -- 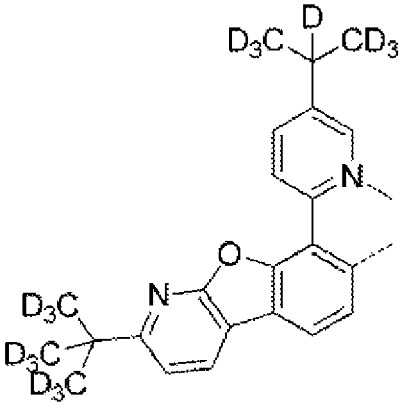 $L_{A284}$ --
Column 427, Lines 1-18, please delete
" 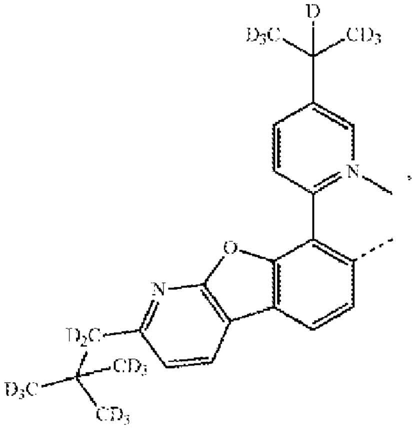 $L_{A285}$ " and insert -- 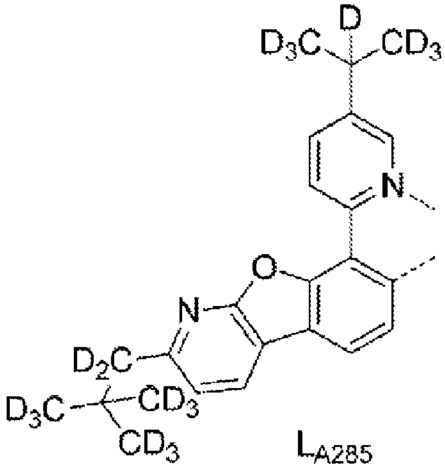 $L_{A285}$ --
Column 427, Lines 19-36, please delete
" 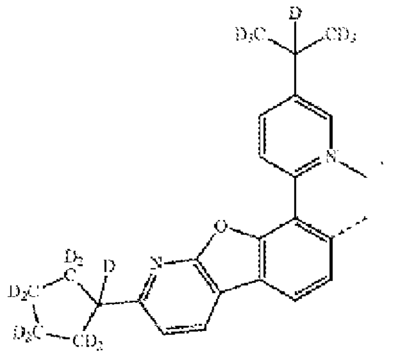 $L_{A286}$ " and insert -- 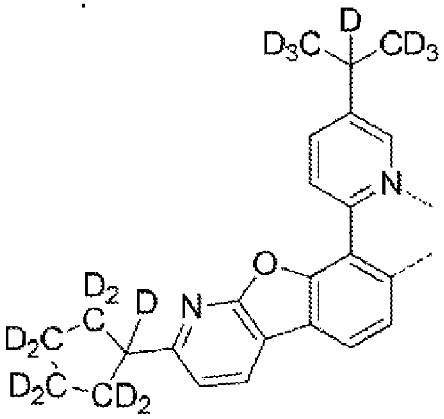 $L_{A286}$ --

Column 427, Lines 37-54, please delete
“ 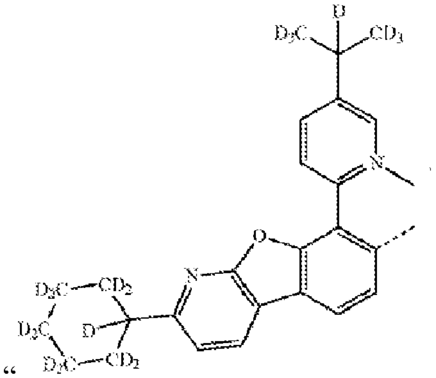 $L_{A287}$ ” and insert -- 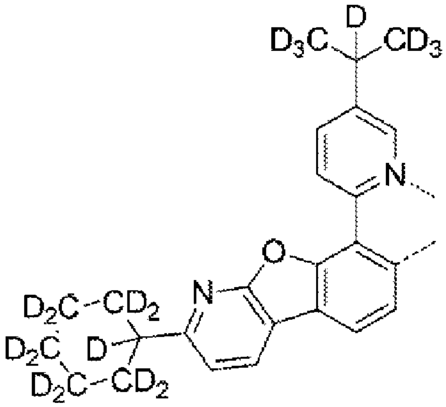
$L_{A287}$ --
Column 427, Lines 55-66, please delete
“ 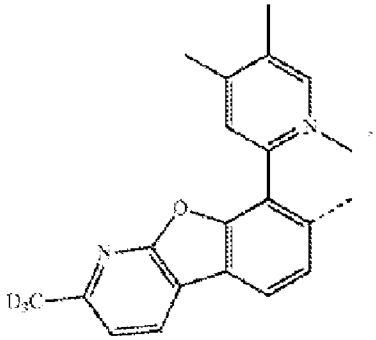 $L_{A288}$ ” and insert -- 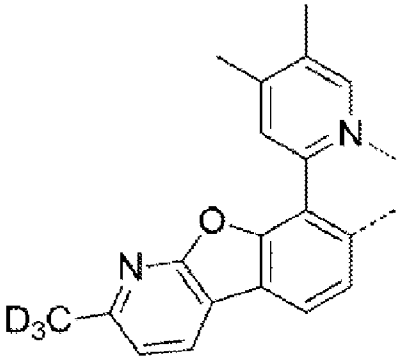
$L_{A288}$ ---
Column 428, Lines 1-16, please delete
“ 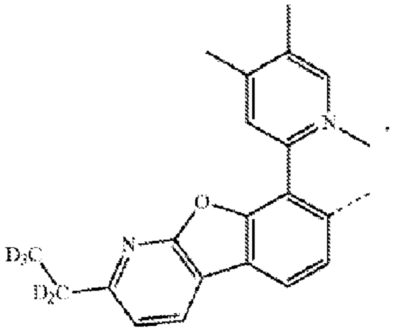 $L_{A289}$ ” and insert -- 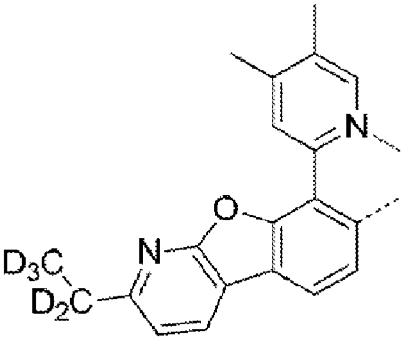
$L_{A289}$ . --

Column 428, Lines 17-34, please delete
“ 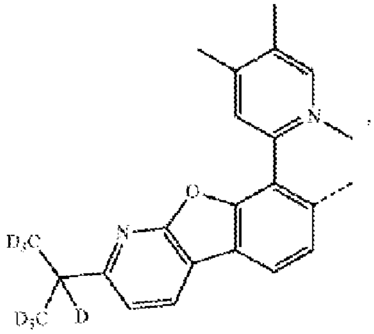 $L_{A290}$ ” and insert -- 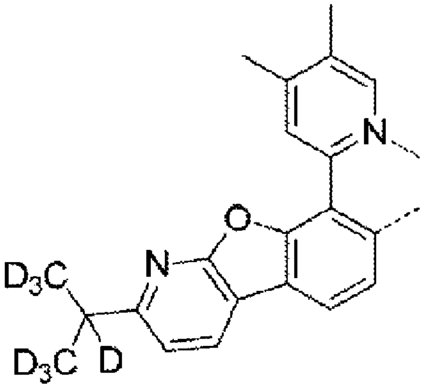 $L_{A290}$ --
Column 428, Lines 35-52, please delete
“ 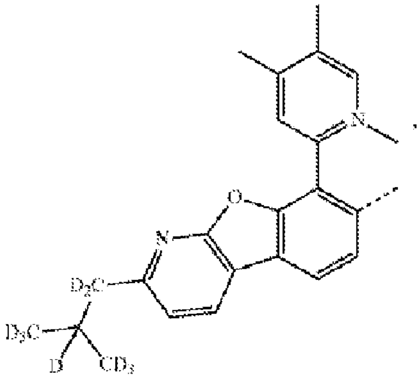 $L_{A291}$ ” and insert -- 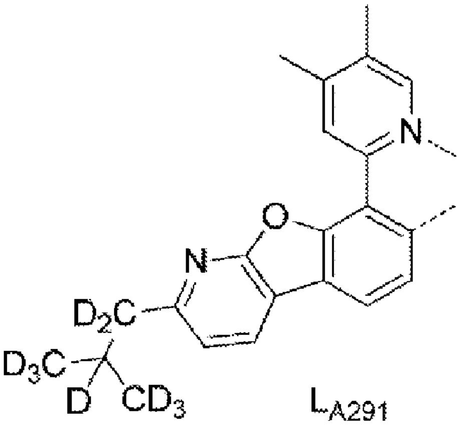 $L_{A291}$ --
Column 428, Lines 53-66, please delete
“ 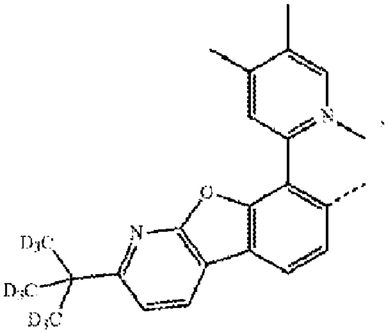 $L_{A292}$ ” and insert -- 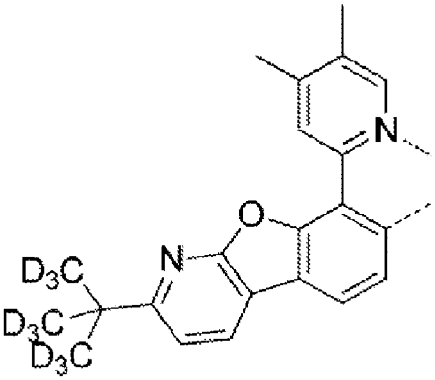 $L_{A292}$ --

Column 429, Lines 1-21, please delete
“ 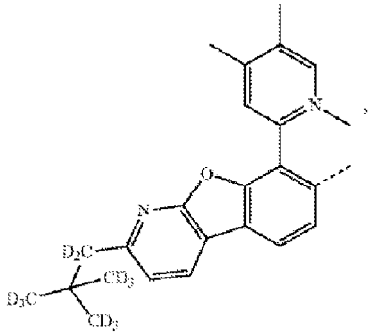 $L_{A293}$ ” and insert -- 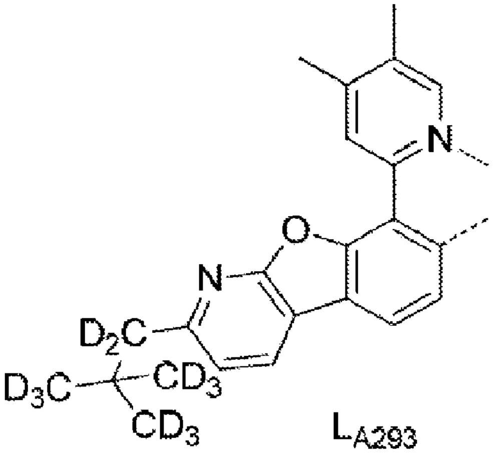 $L_{A293}$ --
Column 429, Lines 22-36, please delete
“ 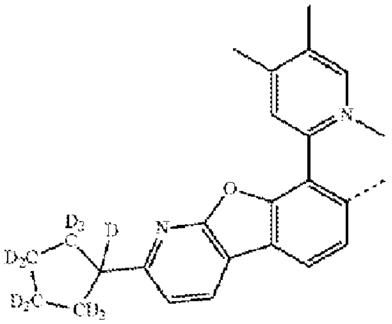 $L_{A294}$ ” and insert -- 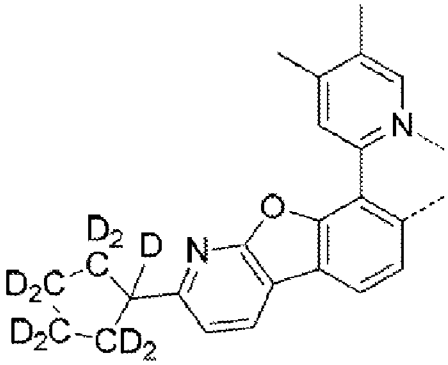 $L_{A294}$ --
Column 429, Lines 37-54, please delete
“ 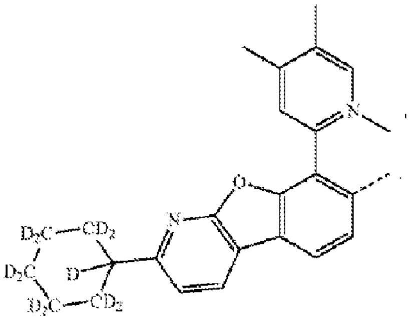 $L_{A295}$ ” and insert -- 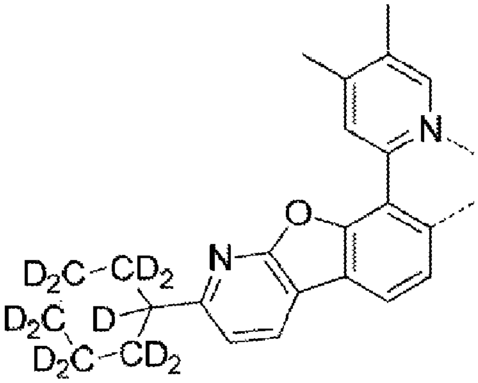 $L_{A295}$ --

Column 429, Lines 55-66, please delete
" 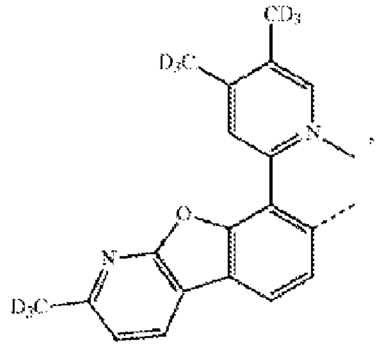 $L_{A296}$ " and insert -- 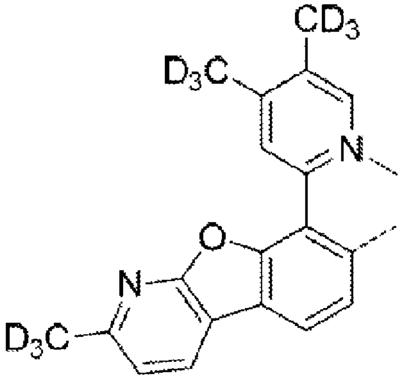 $L_{A296}$ --
Column 430, Lines 1-17, please delete
" 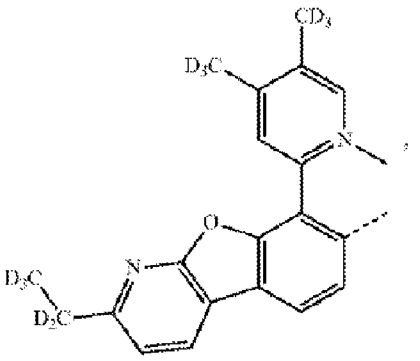 $L_{A297}$ " and insert -- 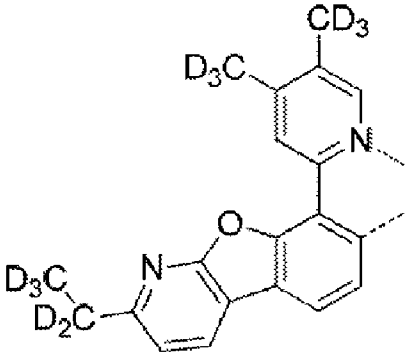 $L_{A297}$ --
Column 430, Lines 18-35, please delete
" 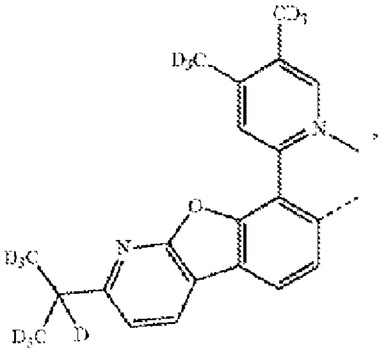 $L_{A298}$ " and insert -- 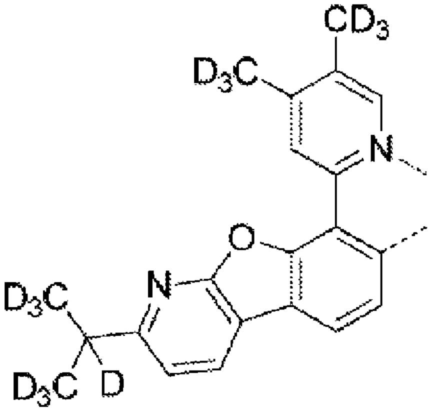 $L_{A298}$ --

Column 430, Lines 36-53, please delete
“ 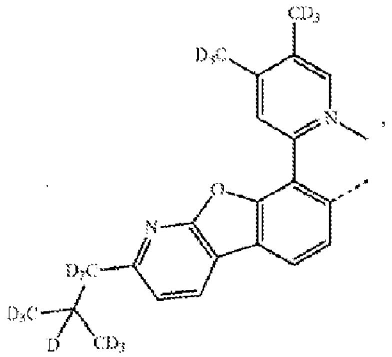 $L_{A299}$ ” and insert -- 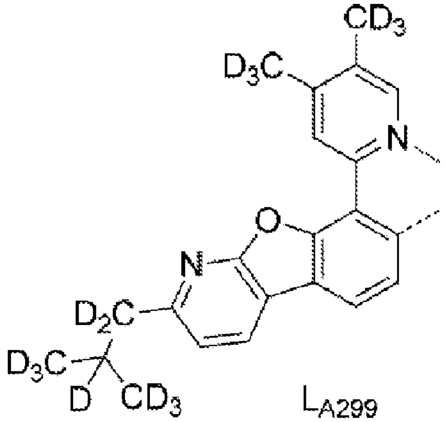 $L_{A299}$ , --
Column 430, Lines 54-66, please delete
“ 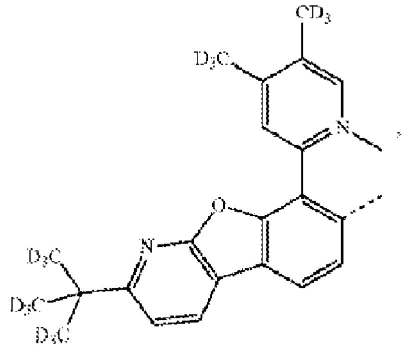 $L_{A300}$ ” and insert -- 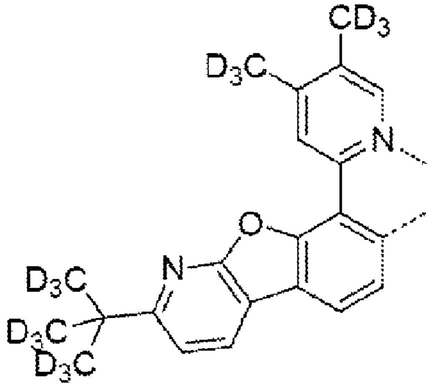 $L_{A300}$ --
Column 431, Lines 1-20, please delete
“ 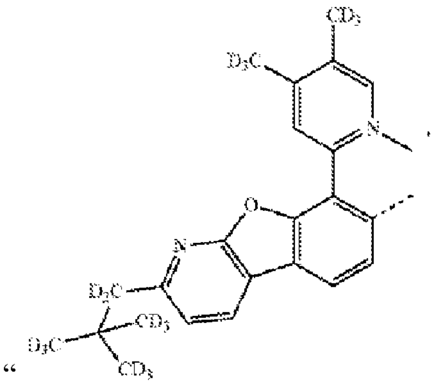 $L_{A301}$ ” and insert -- 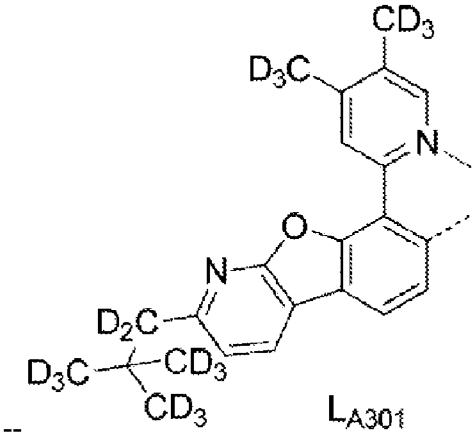 $L_{A301}$ --

Column 431, Lines 21-37, please delete
$L_{A302}$
" 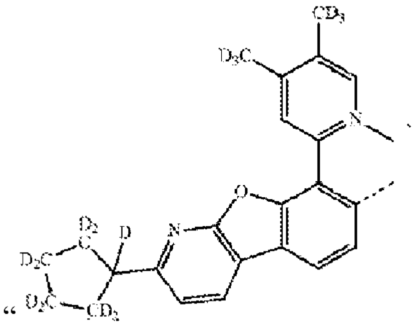 " and insert -- 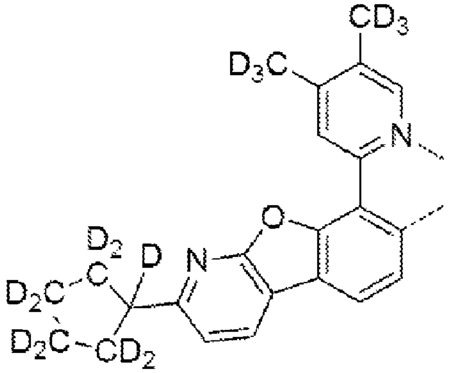
$L_{A302}$ --
Column 431, Lines 38-54, please delete
$L_{A303}$
" 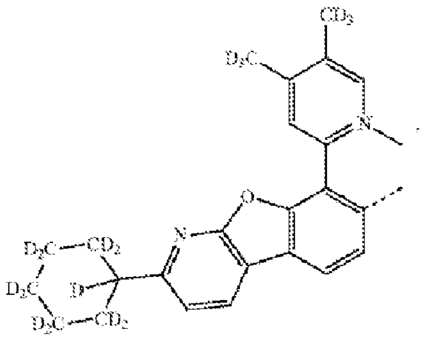 " and insert -- 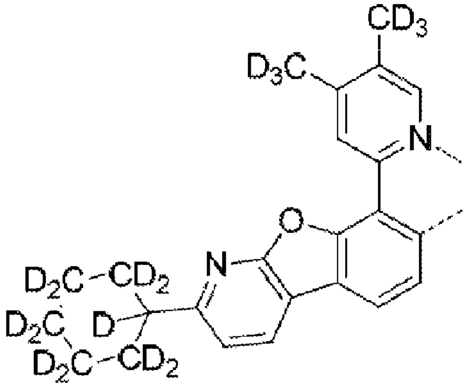
$L_{A303}$ --
Column 431, Lines 55-66, please delete
$L_{A304}$
" 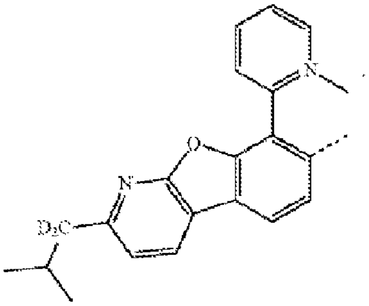 " and insert -- 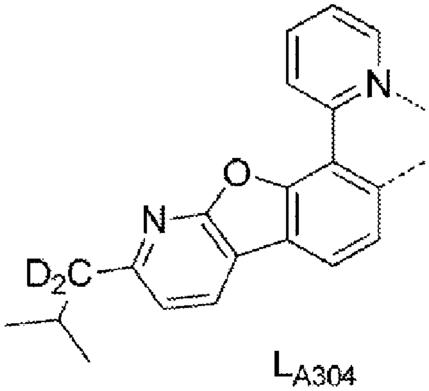
$L_{A304}$ --

Column 432, Lines 1-17, please delete
" 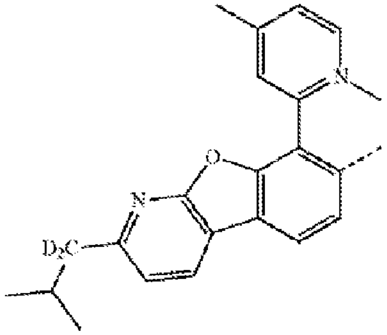 $L_{A305}$ " and insert -- 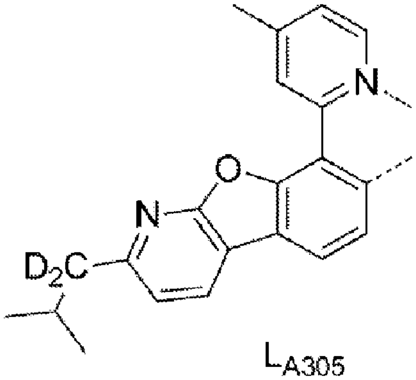 $L_{A305}$ --
Column 432, Lines 18-34, please delete
" 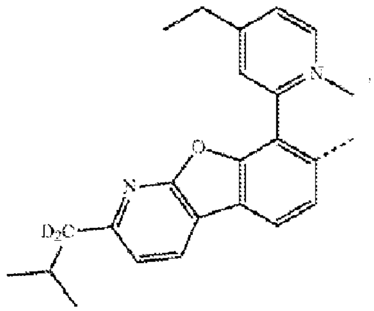 $L_{A306}$ " and insert -- 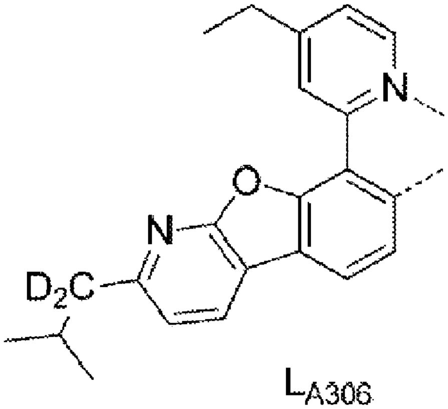 $L_{A306}$ --
Column 432, Lines 35-51, please delete
" 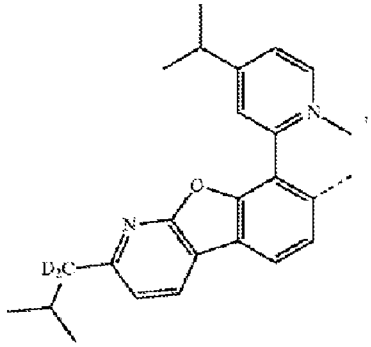 $L_{A307}$ " and insert -- 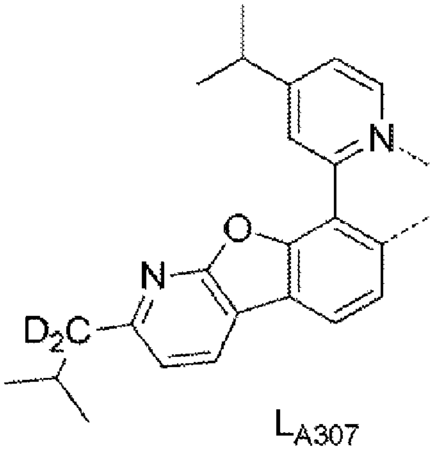 $L_{A307}$ --

Column 432, Lines 52-66, please delete
“ 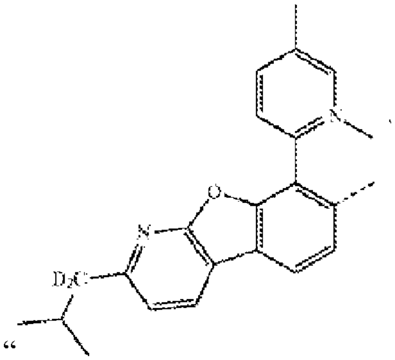 $L_{A308}$ ” and insert -- 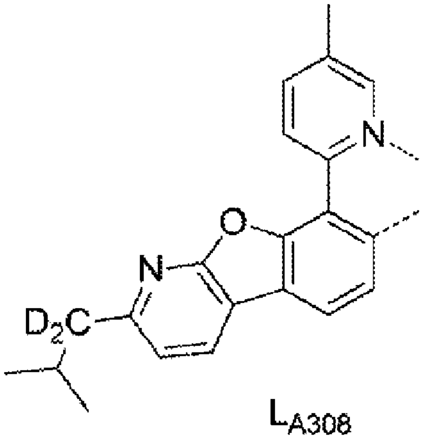 $L_{A308}$ --
Column 433, Lines 1-17, please delete
“ 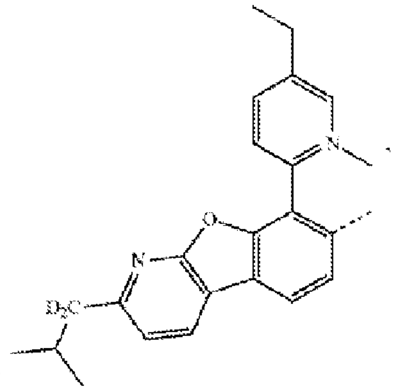 $L_{A309}$ ” and insert -- 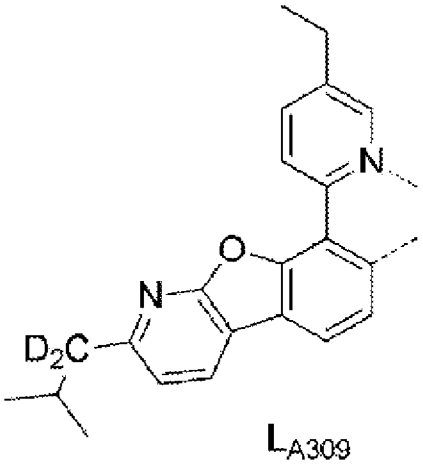 $L_{A309}$ --
Column 433, Lines 18-36, please delete
“ 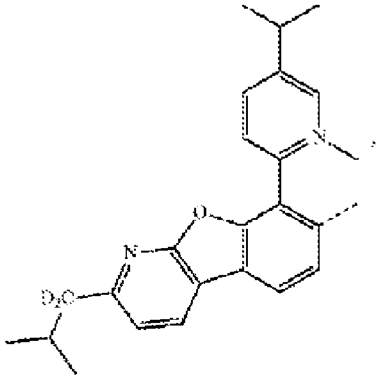 $L_{A310}$ ” and insert -- 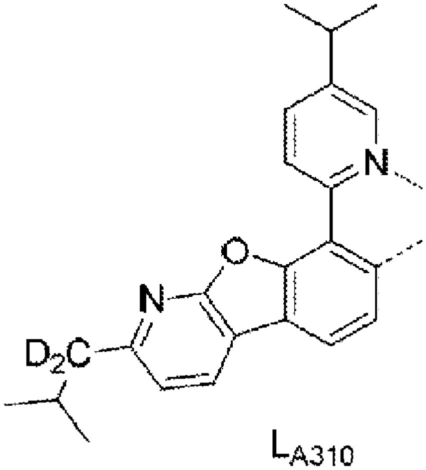 $L_{A310}$ --

Column 433, Lines 37-53, please delete
“ 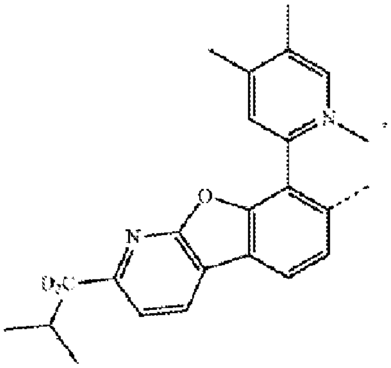 $L_{A311}$ ” and insert -- 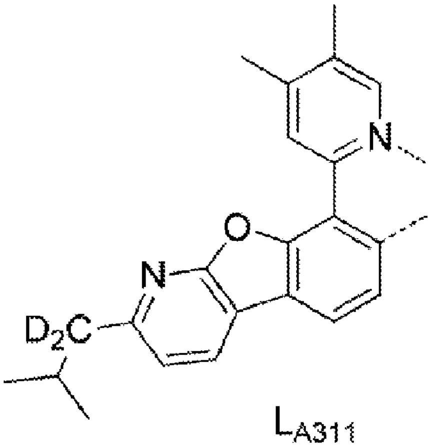 $L_{A311}$ --
Column 433, Lines 54-66, please delete
“ 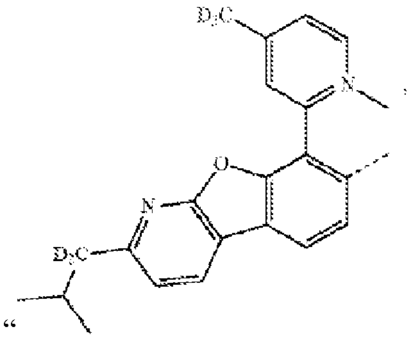 $L_{A312}$ ” and insert -- 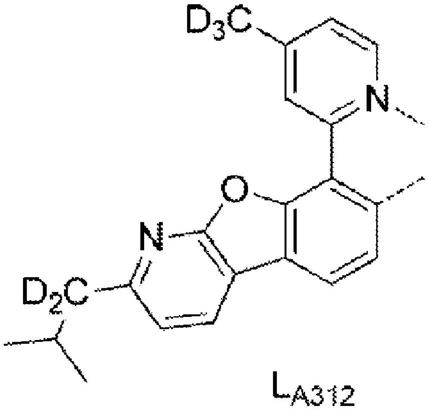 $L_{A312}$ --
Column 434, Lines 1-15, please delete
“ 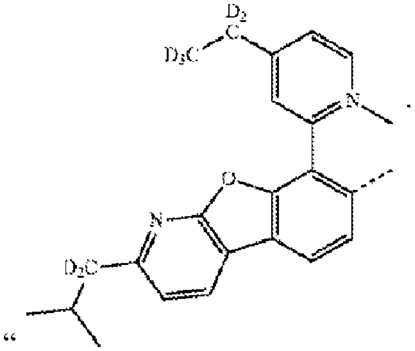 $L_{A313}$ ” and insert -- 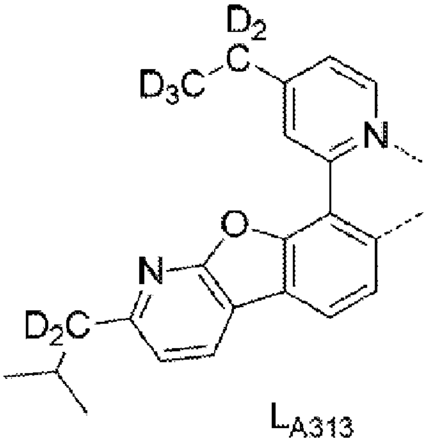 $L_{A313}$ --
Column 434, Lines 16-33, please delete “ 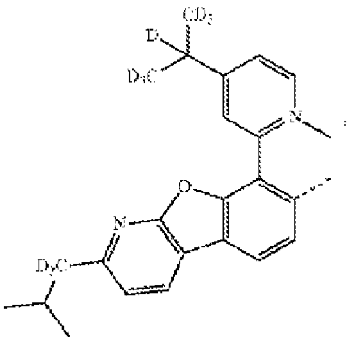 ; $L_{A314}$ ” and insert -- 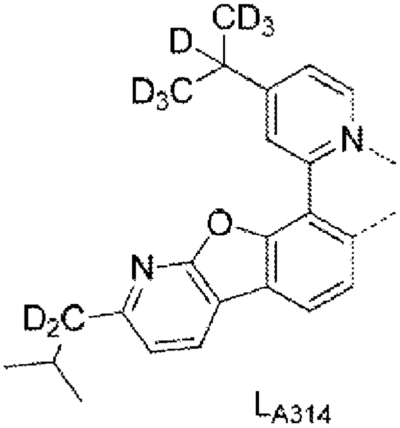 $L_{A314}$ --
Column 434, Lines 34-50, please delete
“ 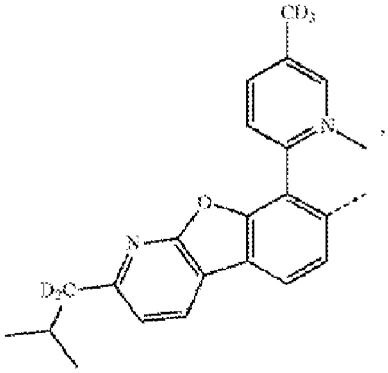 , $L_{A315}$ ” and insert -- 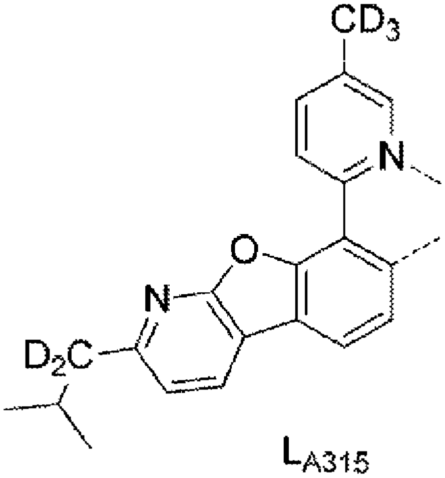 $L_{A315}$ --
Column 434, Lines 51-66, please delete
“ 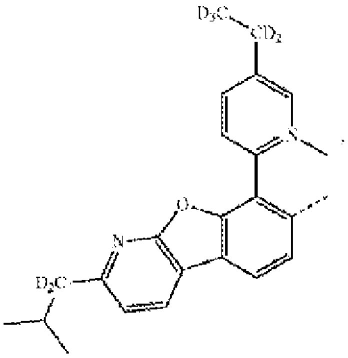 , and $L_{A316}$ ” and insert -- 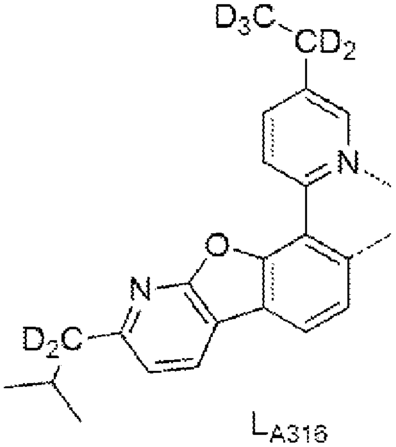 $L_{A316}$ --
Column 435, Lines 1-19, please delete " 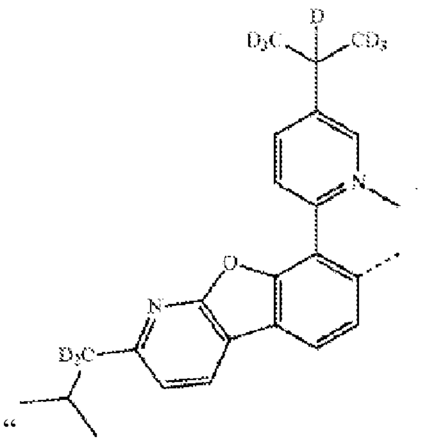 $L_{A317}$ " and insert -- 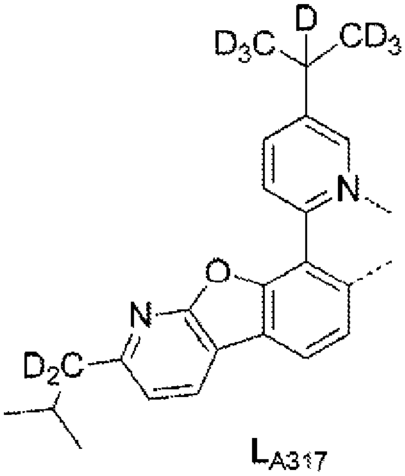 $L_{A317}$ ; --
Column 435, Lines 28-37, please delete
" 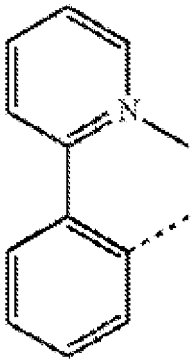 $L_{B1}$ " and insert -- 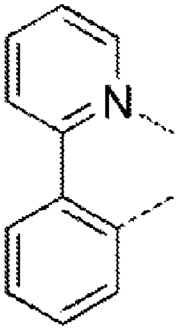 $L_{B1}$ --
Column 435, Lines 38-46, please delete
" 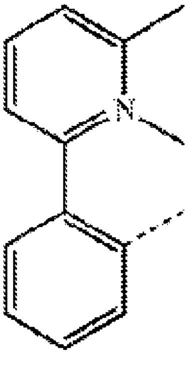 $L_{B2}$ " and insert -- 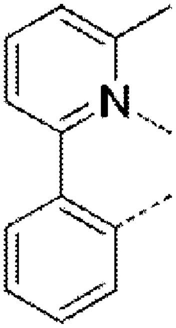 $L_{B2}$ --
Column 435, Lines 47-57, please delete “ 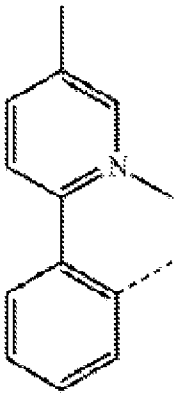 ” and insert -- 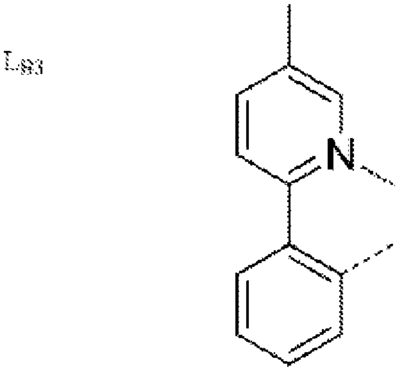 $L_{B3}$ --
Column 435, Lines 57-66, please delete
“ 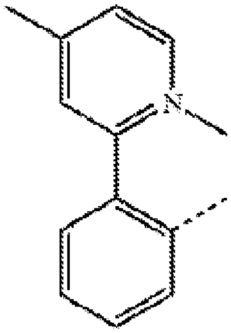 ” and insert -- 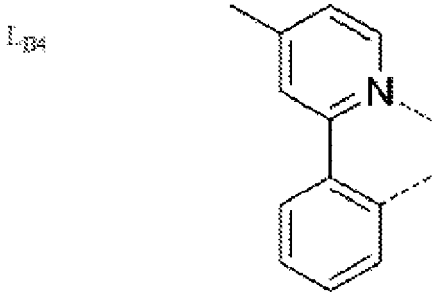 $L_{B4}$ --
Column 436, Lines 1-11, please delete
“ 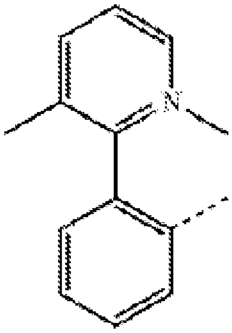 ” and insert -- 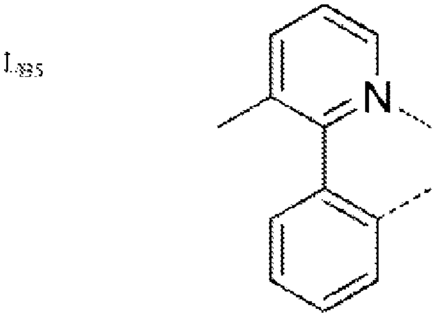 $L_{B5}$ --
Column 436, Lines 12-22, please delete “ 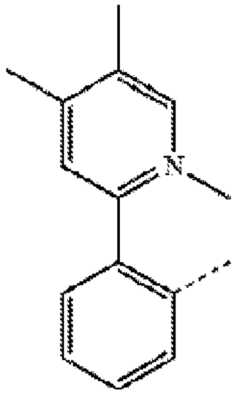 ” and insert -- $L_{B6}$ 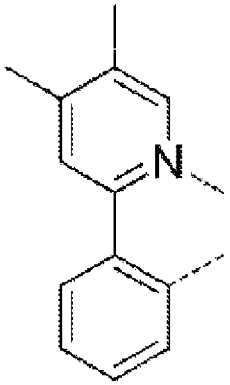 $L_{B6}$ --
Column 436, Lines 23-34, please delete
“ 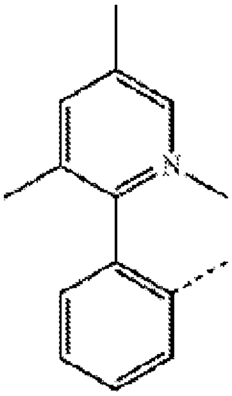 ” and insert -- $L_{B7}$ 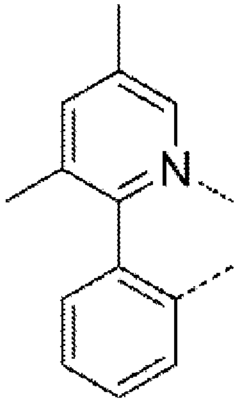 $L_{B7}$ --
Column 436, Lines 35-43, please delete
“ 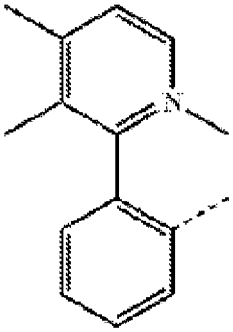 ” and insert -- $L_{B8}$ 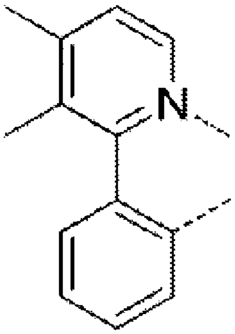 $L_{B8}$ --
Column 436, Lines 44-55, please delete “ 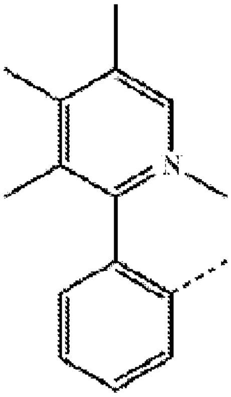 ” and insert -- $L_{B9}$ 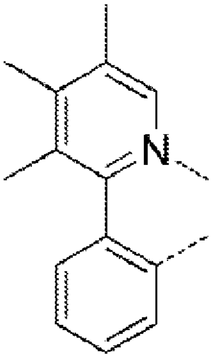 $L_{B9}$ --
Column 436, Lines 56-66, please delete
“ 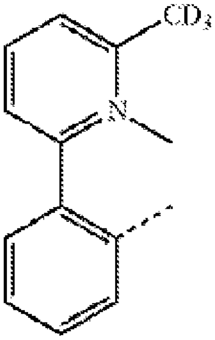 ” and insert -- $L_{B10}$ 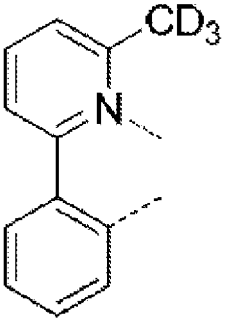 $L_{B10}$ --
Column 437, Lines 1-12, please delete
“ 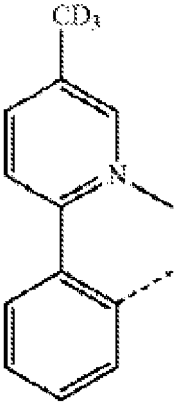 ” and insert -- $L_{B11}$ 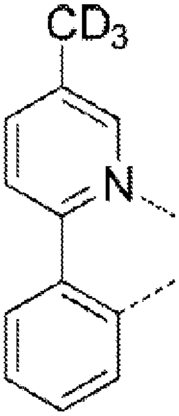 $L_{B11}$ --
Column 437, Lines 13-22, please delete “ 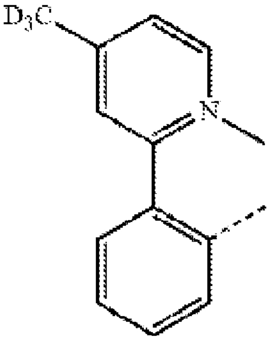 ” and insert -- $L_{B12}$ 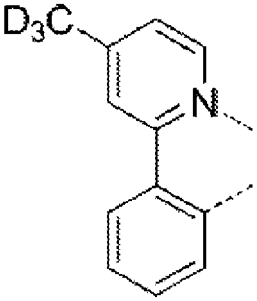 $L_{B12}$ --
Column 437, Lines 23-32, please delete
“ 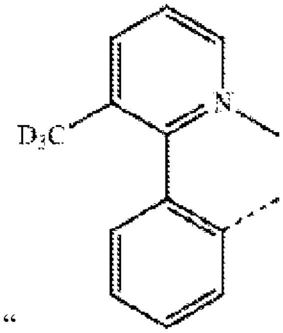 ” and insert -- $L_{B13}$ 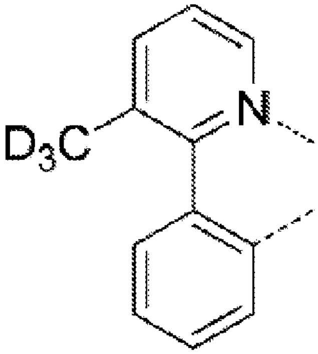 $L_{B13}$ --
Column 437, Lines 33-44, please delete
“ 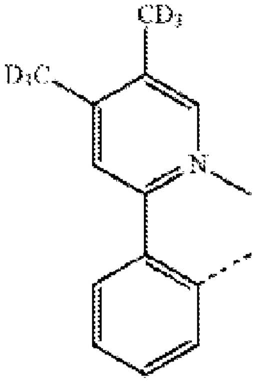 ” and insert -- $L_{B14}$ 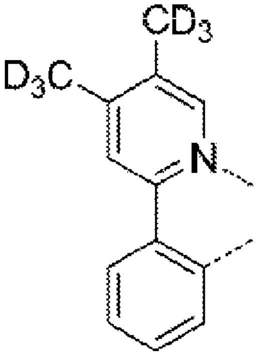 $L_{B14}$ --
Column 437, Lines 45-56, please delete “
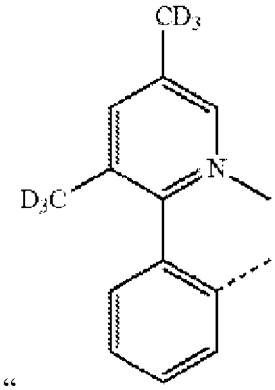
” and insert --
$L_{B15}$
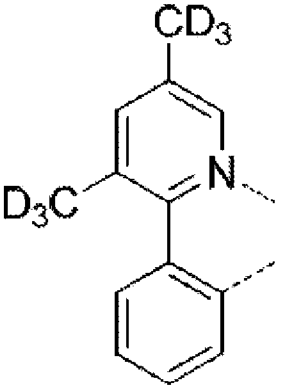
$L_{B15}$ --
Column 437, Lines 57-66 please delete
“
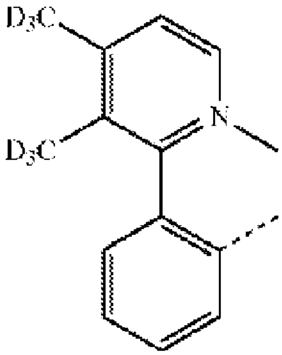
” and insert --
$L_{B16}$
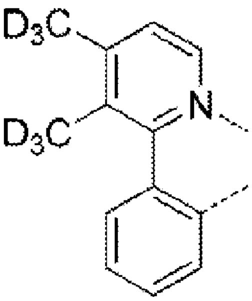
$L_{B16}$ --
Column 438, Lines 1-13, delete
“
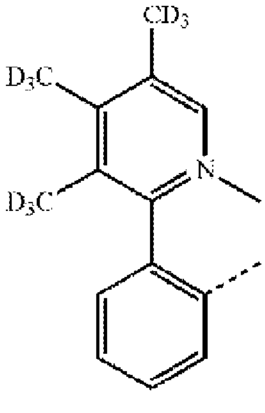
” and insert --
$L_{B17}$
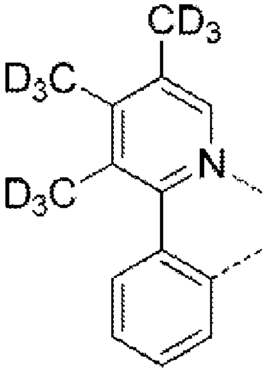
$L_{B17}$ --
Column 438, Lines 14-24, delete “ 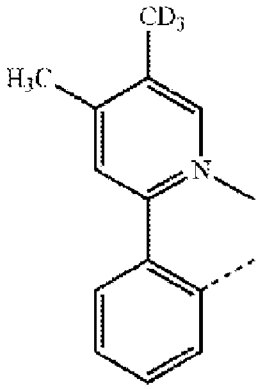 ” and insert -- $L_{B18}$ 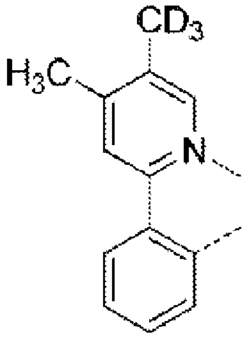 $L_{B18}$ --
Column 438, Lines 25-34, please delete
“ 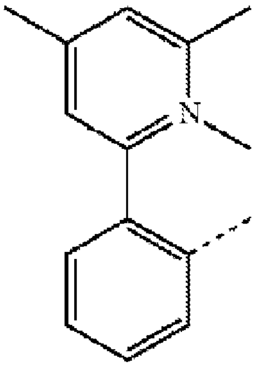 ” and insert -- $L_{B19}$ 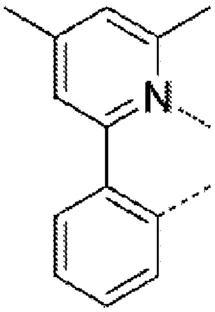 $L_{B19}$ --
Column 438, Lines 35-45, please delete
“ 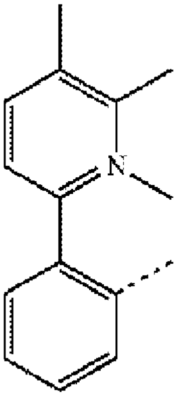 ” and insert -- $L_{B20}$ 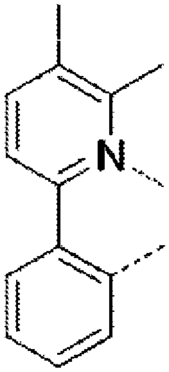 $L_{B20}$ --
Column 438, Lines 46-56, please delete “ 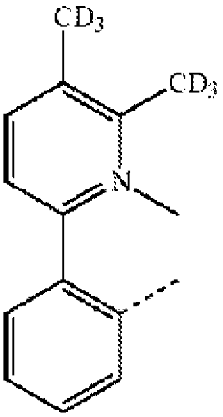 ” and insert -- $L_{B21}$ 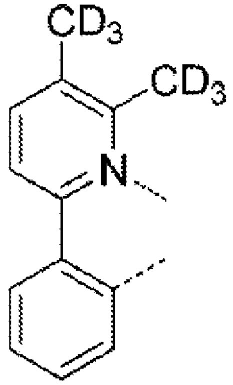 $L_{B21}$ --
Column 438, Lines 57-66, please delete
“ 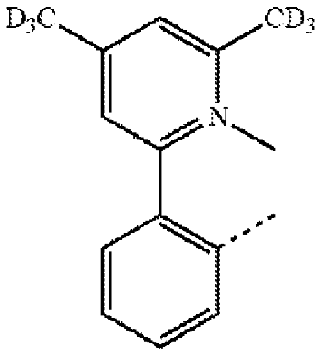 ” and insert -- $L_{B22}$ 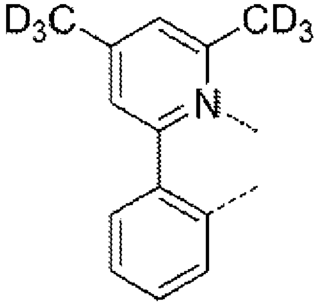 $L_{B22}$ --
Column 439, Lines 1-13, please delete
“ 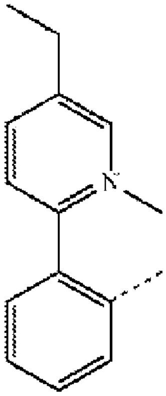 ” and insert -- $L_{B23}$ 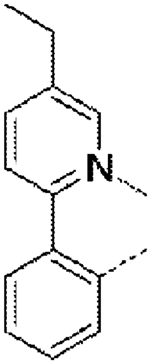 $L_{B23}$ --
Column 439, Lines 14-27, please delete “
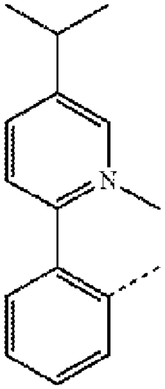
” and insert --
L-B24
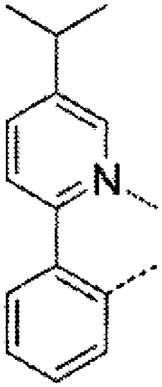
LB24 --
Column 439, Lines 28-41, please delete
“
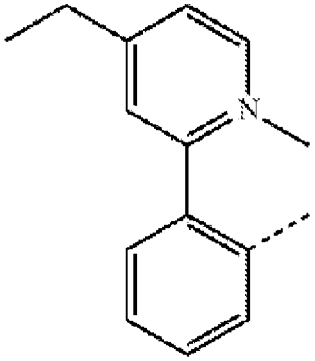
” and insert --
L-B25
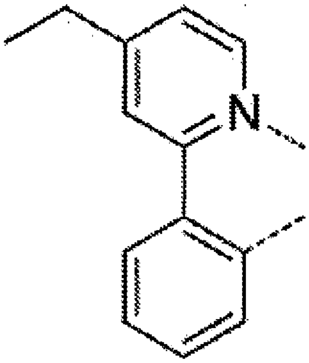
LB25 --
Column 439, Lines 42-54, please delete
“
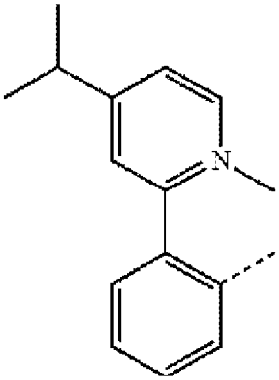
” and insert --
L-B26
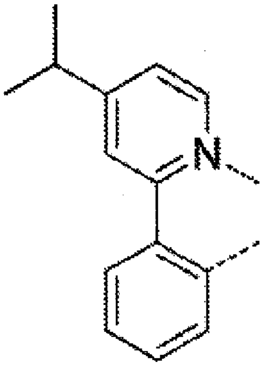
LB26 --
Column 439, Lines 55-66, please delete “ 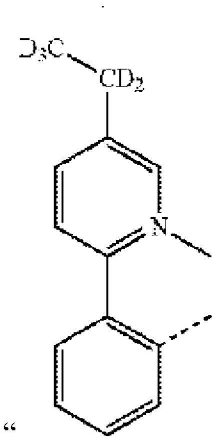 $L_{B27}$ ” and insert -- 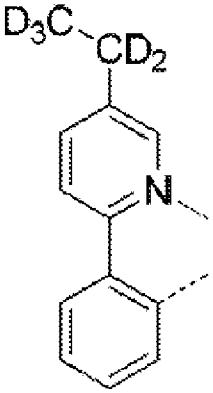 $L_{B27}$ --
Column 439, Lines 1-14, please delete
“ 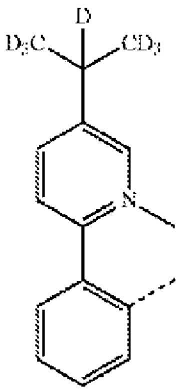 $L_{B28}$ ” and insert -- 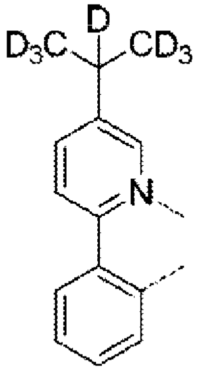 $L_{B28}$ --
Column 440, Lines 15-25, please delete
“ 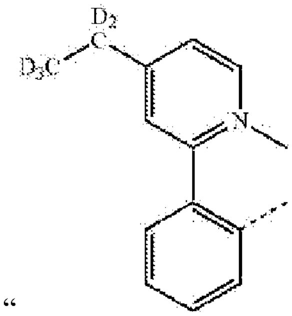 , and $L_{B29}$ ” and insert -- 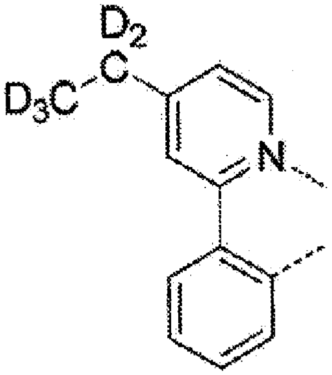 $L_{B29}$ --
Column 440, Lines 26-38, please delete " 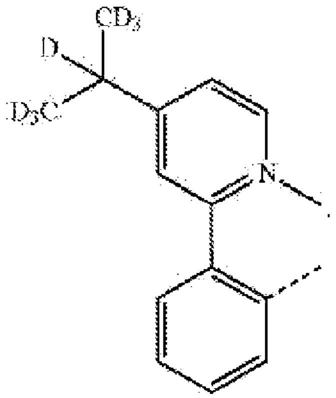 $L_{B30}$ " and insert -- 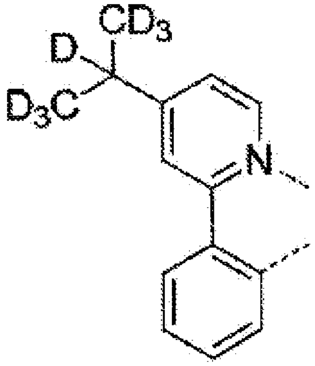 $L_{B30}$ --